US009828363B2

(12) United States Patent
Zhou et al.

(10) Patent No.: US 9,828,363 B2
(45) Date of Patent: Nov. 28, 2017

(54) FUSED PYRIMIDINES AS INHIBITORS OF P97 COMPLEX

(71) Applicant: Cleave Biosciences, Inc., Burlingame, CA (US)

(72) Inventors: Han-Jie Zhou, Foster City, CA (US); David Wustrow, Los Gatos, CA (US)

(73) Assignee: Cleave Biosciences, Inc., Burlingame, CA (US)

( * ) Notice: Subject to any disclaimer, the term of this patent is extended or adjusted under 35 U.S.C. 154(b) by 0 days.

(21) Appl. No.: 15/112,659

(22) PCT Filed: Jan. 19, 2015

(86) PCT No.: PCT/US2015/011921
§ 371 (c)(1),
(2) Date: Jul. 19, 2016

(87) PCT Pub. No.: WO2015/109285
PCT Pub. Date: Jul. 23, 2015

(65) Prior Publication Data
US 2016/0332990 A1    Nov. 17, 2016

Related U.S. Application Data

(60) Provisional application No. 61/929,382, filed on Jan. 20, 2014.

(51) Int. Cl.
*C07D 403/04* (2006.01)
*C07D 471/04* (2006.01)
*C07D 491/048* (2006.01)
*C07D 491/052* (2006.01)

(52) U.S. Cl.
CPC ......... *C07D 403/04* (2013.01); *C07D 471/04* (2013.01); *C07D 491/048* (2013.01); *C07D 491/052* (2013.01)

(58) Field of Classification Search
CPC  C07D 403/04; C07D 471/04; C07D 491/048; C07D 491/052
See application file for complete search history.

(56) References Cited

U.S. PATENT DOCUMENTS

| | | | |
|---|---|---|---|
| 2006/0030612 | A1 | 2/2006 | Steffan et al. |
| 2008/0085898 | A1 | 4/2008 | Lu et al. |
| 2011/0237590 | A1 | 9/2011 | Kitamura et al. |
| 2016/0304495 | A1 | 10/2016 | Wustrow et al. |

FOREIGN PATENT DOCUMENTS

| | | |
|---|---|---|
| CN | 106458996 A | 2/2017 |
| EP | 0640599 A1 | 3/1995 |
| EP | 2338888 A1 | 6/2011 |
| IN | 201617026874 A | 8/2016 |
| JP | 2004303057 A | 10/2004 |
| JP | 2017505812 A | 2/2017 |
| KR | 1020010091827 A | 10/2001 |
| KR | 1020020020316 A | 3/2002 |
| KR | 1020030009830 A | 2/2003 |
| TW | 201605832 A | 2/2016 |
| TW | 201605833 A | 2/2016 |
| WO | WO-2008040753 A1 | 4/2008 |
| WO | WO-2010072823 A1 | 7/2010 |
| WO | WO-2011101161 A1 | 8/2011 |
| WO | WO-2011115804 A1 | 9/2011 |
| WO | WO-2011140527 A2 | 11/2011 |
| WO | WO-2014015291 A1 | 1/2014 |
| WO | WO-2015089218 A1 | 6/2015 |
| WO | WO-2015109285 A1 | 7/2015 |

OTHER PUBLICATIONS

U.S. Appl. No. 15/103,828, Non Final Office Action dated Feb. 10, 2017, 22 pgs.
Australian Application Serial No. 2015206292, First Examiner Report dated Jan. 27, 2017, 4 pgs.
New Zealand Application Serial No. 722624, Office Action dated Feb. 15, 2017, 4 pgs.
Gura, T., "Systems for Identifying New Drugs Are Often Faulty", Science, 278, (Nov. 7, 1997), 1041-1042.
Johnson, et al., "Relationships between drug activity in NCI preclinical in vitro and in vivo models and early clinical trials", British Journal of Cancer, (2001), 1424-1431 pgs.
Pearce, et al., "Failure modes in anticancer drug discovery and development", Cancer Drug Design and Discovery, (2008), 424-435 pgs.
Simone, "Oncology: Introduction", Cecil Textbook of Medicine, 20th Edition, (1995), 1004-1010.
"5H-Pyrrolo[3,4-d]pyrimidin-4-amine,6,7-dihydro-2-(1H-indol-3-yl)-N-[(2-methoxyphenyl)methyl]-", Database Registry, RN: 1360239-22-0, Chemical Abstracts Service, Columbus, OH (Mar. 7, 2012), 1 pg.
International Application Serial No. PCT/US2014/069598; International Preliminary Report on Patentability dated Feb. 26, 2016, 10 pgs.
International Application Serial No. PCT/US2014/069598, International Search Report dated Mar. 4, 2015, 6 pgs.
International Application Serial No. PCT/US2014/069598, Written Opinion dated Mar. 4, 2015, 7 pgs.
International Application Serial No. PCT/US2014/069598, Written Opinion dated Nov. 11, 2015, 9 pgs.
International Application Serial No. PCT/US2015/0011921, International Preliminary Report on Patentability dated Apr. 11, 2016, 13 pgs.
International Application Serial No. PCT/US2015/011921, International Search Report dated Mar. 30, 2015, 6 pgs.
International Application Serial No. PCT/US2015/011921, Opinion dated Feb. 11, 2016, 8 pgs.

(Continued)

*Primary Examiner* — Bruck Kifle
(74) *Attorney, Agent, or Firm* — Schwegman Lundberg & Woessner, P.A.

(57) ABSTRACT

The present invention is directed to certain fused pyrimidines having a homo or hetero cyclopentyl, cyclohexyl or cycloheptyl ring as the pyrimidine fusion partner; having an amino benzyl or substituted amino benzyl group at the 4 position of the pyrimidine ring; and a 5:6 heterobicyclo ring with at least one N, O or S at the 2 position of the pyrimidine ring. These compounds are useful for treatment of cancer by inhibition of the p97 complex.

20 Claims, No Drawings

(56) References Cited

OTHER PUBLICATIONS

International Application Serial No. PCT/US2015/011921, Written Opinion dated Mar. 30, 2015, 9 pgs.
International Application Serial No. PCT/US2015/011921,Written Opinion dated Feb. 11, 2016, 8 pgs.
Taiwanese Application Serial No. 103143184, Notice of Preliminary Rejection dated Apr. 15, 2015, 7 pgs.
Chou, Tsui-Fen, et al., "Structure-Activity Relationship Study Reveals ML240 and ML241 as Potent and Selective Inhibitors of p97 ATPase", ChemMedChem, 8(2), Supporting Information: table S9; compound S164 [retrieved on Feb. 23, 2015]., Retrieved from the Internet: <URL: http://onlinelibrary.wiley.com/store/10.1002/cmdc.201200520/asset/supinfo/cmdc_201200520_sm_miscellaneous_information.pdf?v=1&s=7106b4bdbaf65d12e11c89ab243b44199f715810 >, (Jan. 11, 2013), 175 p.
Chou, Tsui-Fen, et al., "Structure-Activity Relationship Study Reveals ML240 and ML241 as Potent and Selective Inhibitors of p97 ATPase", ChemMedChem, 8(2), (2013), 297-312.
Australian Application Serial No. 2015206292, Office Action dated May 27, 2017, 2 pgs.
Australian Application Serial No. 2015206292, Response to First Examiner Report dated Apr. 20, 2017, 51 pgs.
European Application Serial No. 15705122.8 Response to Communication pursuant to Rules 161(1) and 162 EPC dated Apr. 5, 2017, 24 pgs.
Haines, D.S., "p97-Containing Complexes in Proliferation Control and Cancer: Emerging Culprits or Guilt by Association?", Genes & Cancer, 1(7), (2010), 753-763.
Vekaria, P.H., et al., "Targeting p97 to Disrupt Protein Homeostasis in Cancer", Frontiers in Oncology, 6, (Aug. 2016), 8 pgs.
U.S. Appl. No. 15/103,828, Notice of Allowance dated Sep. 13, 2017, 5 pgs.
U.S. Appl. No. 15/103,828, Response filed Aug. 30, 2017 to Final Office Action dated Jul. 13, 2017, 12 pgs.
Eurasian Application Serial No. 201691472, Office Action dated Aug. 7, 2017, W/ English Translation, 6 pgs.
Japanese Application Serial No. 2016-565125, Office Action dated Oct. 2, 2017.

FUSED PYRIMIDINES AS INHIBITORS OF P97 COMPLEX

This application is a U.S. National Stage Filing under 35 U.S.C. 371 from International Application No. PCT/US2015/011921, filed on Jan. 19, 2015, and published as WO 2015/109285 A1 on Jul. 23, 2015, which claims the benefit of priority under 35 U.S.C. § 119(e) to U.S. Provisional Patent Application No. 61/929,382, filed on Jan. 20, 2014, which are hereby incorporated by reference herein in their entireties.

BACKGROUND OF THE INVENTION

The AAA (ATPase Associated with a variety of Activities) ATPase p97 having the descriptive name, Valosin containing protein, is conserved across all eukaryotes and is essential for life in budding yeast (Giaever, G., et. al. *Nature* (2002) 418, 387-391) and mice (Muller, J. M. et al. *Biochem. Biophys. Res. Commun.* (2007) 354, 459-465). Humans bearing reduction-of-function alleles of p97 are afflicted with a syndrome that includes inclusion body myopathy and frontotemporal lobar degeneration (Weihl, C. et al. *Hum. Mol. Genet.* (2006) 15, 189-199). Loss-of-function studies in model organisms indicate that p97 plays a critical role in a broad array of cellular processes including Golgi membrane reassembly (Rabouille, C. et al. *Cell* (1995) 82, 905-914), membrane transport (Ye, Y. et al *Nature* (2001) 414, 652-656; Ye, Y. et al. *Nature* (2004) 429, 841-847) degradation of misfolded membrane and secretory proteins by the ubiquitin-proteasome system (UPS) (Golbik, R. et al. *Biol. Chem.* (1999) 380, 1049-1062; Richly, H. et al. *Cell* (2005) 120, 73-84), regulation of myofibril assembly (Janiesch, P. C. et al. *Nat. Cell Biol.* (2007) 9, 379-390), and cell division (Cao, K. et at *Cell* (2003) 115, 355-367). The broad range of cellular functions for this protein is thought to derive from its ability to unfold proteins or disassemble protein complexes. The mechanochemical activity of p97 is linked to substrate proteins by an array of at least 14 UBX domain adapters that bind p97, as well as the non-UBX domain adaptors Ufdl and Np14 (Meyer, H. H. et al. *EMBO J.* (2000) 19, 2181-2192).

The sequence of p97 reveals three domains (N-domain, D1 ATPase domain, and D2 ATPase domain) joined by linker regions. X-ray crystallography of p97 revealed that it forms a homohexamer of 97 kilodalton subunits that assemble to form two stacked rings. The two rings are formed by the ATPase domains (Huyton, T. et al., *Struct. Biol.* (2003) 144, 337-348; DeLaBarre, B. et al. *Nat. Struct. Biol.* (2003) 10, 856-863). The 'top' ring is formed by a hexamer of the D1 domains, whereas the 'bottom' ring is formed by a hexamer of the D2 domains. The N-domain extends outward from the D1 domain ring. Although it is clear that the D2 domain hydrolyzes ATP in vitro, the level of D1-specific ATPase activity reported by different investigators varies. Nevertheless, genetic studies in yeast suggest that ATP hydrolysis by both the D1 and D2 domains is essential for the function of p97 (Song, C. et al. *J. Biol. Chem.* (2003) 278, 3648-3655; Ye, Y. et al. *J. Cell Biol.* (2004) 162, 71-84). Binding of ATP to the D1 domain is also required for assembly of p97 (Wang, Q. et al. *Biochem. Biophys. Res. Commun.* (2003) 300, 253-260). Although ATP hydrolysis by the D2 domain is not required for assembly of p97 hexamer, it is thought that ATP hydrolysis by the D2 domain is a substrate conversion, resulting in their unfolding or dissociation from bound partners.

A prominent cellular function for p97 that has received considerable scrutiny is its role in the turnover of misfolded secretory proteins via the UPS (ubiquitin proteasome system). In this process, which is known as ERAD (for endoplasmic reticulum-associated degradation), proteins that fail to fold within the ER are retrotranslocated in a p97-dependent manner into the cytoplasm where they are degraded by the UPS (Ye, Y. et al. *Nature* (2004) 429, 841-847). In this process, p97 is thought to mediate extraction of substrates from the ER membrane. The complex p97 is also required for the turnover of cytosolic substrates of the UPS (Janiesch, P. C. et al. *Nat. Cell Biol.* (2007) 9, 379-390; Cao, K. et al. *Cell* (2003) 115, 355-367; Fu, X. et al. *J. Cell Biol.* (2003) 163, 21-26), although its role in turnover of cytosolic proteins is less understood.

The Valosin containing protein, p97, represents a suitable target for cancer therapeutics. The complex p97 and its function are essential for continued cellular viability, and so drugs that inhibit it should be antiproliferative. In other words, inhibition of p97 will cause undesirable protein concentration within the target cell. A consequential cellular reaction is often apoptosis or at least amelioration of cellular growth and mitosis. Also, p97 is known to be overproduced in multiple cancers (Yamamoto, S. et al. *Ann. Surg. Oncol.* (2005) 12, 925-934; Yamamoto, S. et al. *Clin. Cancer Res.* (2004) 10, 5558-5565; Yamamoto, S. et al. *Ann. Surg. Oncol.* (2004) 11, 697-704; Yamamoto, S. et al. *Ann. Surg. Oncol.* (2004) 11, 165-172) suggesting that its activity may be rate-limiting for the development of at least some cancers. p97 is known to be essential for ERAD (Carvalho, P. et al. *Cell* (2006) 126, 361-373), and recent studies suggest that cancer cells may be particularly dependent upon ERAD (Boelens, J. et al. *In Vivo* (2007) 21, 215-226). Furthermore, p97 has been linked to the turnover of IlcB and consequent activation of NF-kB (Dai, R. M. et al. *J. Biol. Chem.* (1998) 273, 3562-3573). NF-kB activity is important for the survival of some tumor cells, particularly in multiple myeloma (Keats, J. J. et. al. *Cancer Cell* (2007) 12, 131-144; Annunziata, C. M. et. al. *Cancer Cell* (2007) 12, 115-130). It has been suggested that bortezomib is active in multiple myeloma due to its ability to block turnover of proteins via the ERAD pathway and its ability to block turnover of 1 kB, thereby squelching the activity of NF-kB. Given that p97 is implicated in both ERAD and IlcB turnover but otherwise has a more restricted role in the UPS compared to the proteasome itself, drugs that target p97 may retain much of the efficacy of bortezomib but with less toxicity. In addition, compounds intersecting with the p97 complex are disclosed in PCT/US2011/035654, filed May 6, 2011 and published as WO2011/140527 on Nov. 10, 2011.

Goals of the Invention

Thus, there is a need to develop compounds suitable for inhibition of p97 activity and for methods of inhibiting the activity of p97 using such compounds. There is a need to develop such compounds for use in treatment of neoplastic malconditions.

SUMMARY OF THE INVENTION

These and other needs are met by aspects of the present invention, one of which is directed to a group of fused pyrimidine compounds having a cyclopentyl, cyclohexyl or cycloheptyl ring as the fusion partner of the fused pryimidine compounds. The fusion partner optionally contains a nitrogen, oxygen or sulfur heteroatom in its ring. The fused pyrimidine compounds have certain optionally substituted 5:6 heterocyclic rings substituted at the 2 position of the pyrimidine ring and an optionally substituted benzyl amine group substituted at the 4 position of the pyrimidine ring.

In a further aspect of the invention, the fused pyrimidine of the invention and their pharmaceutical compositions have an ability to inhibit Valosin containing protein p97 and to ameliorate, diminish, shrink, moderate and/or eliminate cells exhibiting neoplastic tendencies and/or abnormal function. In a further aspect of the invention, such compounds and compositions inhibit the ATPase activity of p97. Another aspect of the invention concerns treatment of malconditions and/or disease such as cancer through use of such compounds and compositions.

The first aspect of the invention is directed to fused pyrimidine compounds having a 5:6 heterocyclic ring at position 2 of the pyrimidine ring and an optionally substituted benzyl amine group at position 4 of the pyrimidine ring. Embodiments of the fused pyrimidine compounds of the invention have a structure represented by Formula I wherein Y is $CR^4$, NH, $NR^5$, O or S and C of $CR^4$ is an $sp^3$ carbon. The symbols m and n of Formula I are each independently an integer of 0, 1, 2, 3 or 4 and the sum of n and m is an integer of 2, 3 or 4. Ar is an optionally substituted aryl group and the moiety at the 2 position of the pyrimidine ring is a 5:6 heterobicyclic ring herein designated as HET.

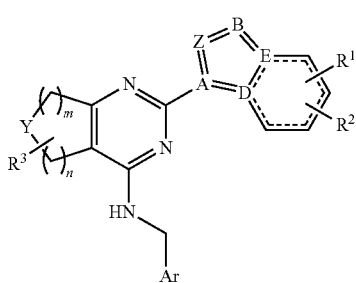

Formula I

The "scaffold" of Formula I is the fused pyrimidine ring alone and is represented by Formula II. Formula II presents embodiments of the fused pyrimidine ring without the -HET and —$NHCH_2Ar$ moieties. The scaffold (Formula II) is a fused pyrimidine in which the saturated ring fused to the pyrimidine is a 5, 6 or 7 membered ring and the Y group or atom is in any position around the saturated ring except at the positions shared by the pyrimidine ring. Preferred saturated rings of the scaffold are the five and six membered saturated rings in which Y is located at any position around the saturated ring except the fusion positions. Preferred locations of Y on the five and six membered saturated rings are the saturated ring positions adjacent to the fused positions. Further preferred scaffolds are the 5 and 6 membered saturated rings wherein Y is located at saturated ring positions other than adjacent to the fusion positions and when Het is other than an indole or benzimidazole moiety.

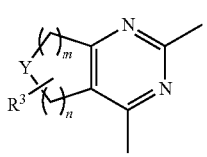

Formula II

The HET moiety of Formula I is represented by Formula HET wherein A, D, E, B and Z have the following designations. The following designations of A, D, E, B and Z also apply to the embodiments of the fused pyrimidine compounds of the invention represented by Formula I. The six membered ring of Formula HET is an aromatic ring while the five membered ring may be aromatic or partially saturated.

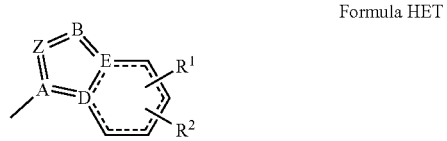

Formula HET

A, D and E of Formula HET (and hence of Formula I) are each independently C or N wherein C is an $sp^2$ carbon substituted by H or alkyl of one to four carbons when one of the C valences is not otherwise designated. Z and B are each independently $CR^6$, N, $NR^7$, O or S wherein C as $CR^6$ is an $sp^2$ carbon. Certain provisos apply to Formula HET when part of Formula I. These are:
1. At least one of D and E is C;
2. At least one of A, D, E, Z and B is other than C;
3. Z and B cannot both simultaneously be any of $NR^7$, O or S;
4. When one of D and E is N and A is C, then Z and B are each independently $CR^6$, N or $NR^7$;
5. When both of D and E are C and A is N, then Z and B are each independently $CR^6$ or N; and in this designation for D, E, A, Z and B, when Y is carbon and $R^3$ is hydrogen, or in this designation for D, E, A, Z and B when both of m and n are other than 0 (zero integer), then in either of these sub-designations, Z and B cannot both be $CR^6$ and B cannot be N;
6. When all of D, E and A are C, then Z and B are each independently $CR^6$, N, $NR^7$, O or S;
7. When one of Z and B is O or S, then the other is $CR^6$ or N, and A, D and E are all C;
8. When one of Z and B is $NR^7$, then the other is N or $CR^6$ and A, D and E are all C.

For proviso 5, a single primary designation and two secondary designations are present. When both of D and E are C and A is N, then the primary designation is that Z and B are each independently $CR^6$ or N. Under this primary designation, two secondary designations apply. Under the primary designation for Z and B when D and E are C and A is N, the first secondary designation is that when Y is carbon and the $R^3$ group attached to Y as C is hydrogen, then Z and B cannot both be $CR^6$ and B cannot be N. Also, under the primary designation for Z and B when D and E are C and A is N, the second secondary designation is that when both of m and n are other than 0 (i.e., m and n are independently an integer of 1-4) and $R^3$ is hydrogen, then Z and B cannot both be $CR^6$ and B cannot be N.

The substituents $R^1$, $R^2$, $R^3$, $R^4$, $R^5$, $R^6$ and $R^7$ may be each independently selected from hydrogen, an optionally substituted aliphatic group, an optionally substituted aromatic group and/or an optionally substituted functional group.

These designations of the substituent R groups are further described in the definition section below.

An additional aspect of the invention is directed to a pharmaceutical composition of a pharmaceutically acceptable carrier and the above described compounds of Formula I.

Another aspect of the invention is directed to a method of decreasing Valosin containing protein (p97) activity or decreasing degradation of a proteasome system substrate, especially a ubiquitin substrate, by administration to a patent in need an effective therapeutic amount of the one of the compounds of Formula I.

Yet another aspect of the invention is directed to the treatment of neoplastic malconditions, cancer and other malconditions associated with p97 by administration to a patient in need a compound of Formula I or the foregoing pharmaceutical composition.

The fused pyrimidine compounds and pharmaceutical compositions of the invention will inhibit or ameliorate the activity of the bioactive enzyme p97, show the physiological profile and will preferably show the desirable degree of inhibition or amelioration, especially with respect to the treatment of cancer and related malconditions.

DETAILED DESCRIPTION OF THE INVENTION

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "may" in the context of this application means "is permitted to" or "is able to" and is a synonym for the term "can." The term "may" as used herein does not mean possibility or chance.

The term "disease" or "disorder" or "malcondition" are used interchangeably, and are used to refer to diseases or conditions wherein X plays a role in the biochemical mechanisms involved in the disease or malcondition or symptom(s) thereof such that a therapeutically beneficial effect can be achieved by acting on X. "Acting on" X, or "modulating" X, can include binding to X and/or inhibiting the bioactivity of X and/or allosterically regulating the bioactivity of X in vivo.

The expression "effective amount", when used to describe therapy to an individual suffering from a disorder, refers to the amount of a drug, pharmaceutical agent or compound of the invention that will elicit the biological or medical response of a cell, tissue, system, animal or human that is being sought, for instance, by a researcher or clinician. Such responses include but are not limited to amelioration, inhibition or other action on a disorder, malcondition, disease, infection or other issue with or in the individual's tissues wherein the disorder, malcondition, disease and the like is active, wherein such inhibition or other action occurs to an extent sufficient to produce a beneficial therapeutic effect. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

In general, "substituted" refers to an organic group as defined herein in which one or more bonds to a hydrogen atom contained therein are replaced by one or more bonds to a non-hydrogen atom. More particularly, the term "chemical substituent" refers to any and all aliphatic, aromatic and functional groups listed in this section that can be appended to an organic molecule. A functional group is an inorganic moiety such as halogen, sulfate, nitro, amino and the like as well as monocarbon functional groups such as carboxyl, carbonyl, carboxamide that are ordinary and typical optional substituents of organic molecules. In the context of this invention, recitation of this term without indication of specific groups constitutes the definition given above. Recitation of this term in combination with a Markush recitation of specific groups constitutes a subgenus of the understanding conveyed by the foregoing definition. The term "substituent" generally means any appropriate group named below that has an "yl", "y" or "o" ending to designate that it is appended, attached or covalently bonded to another moiety such as but not limited to an aromatic framework. Examples include but are not limited to, a halogen (i.e., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

For all substituents, the first atom of the molecular formula of the substituent is the atom bonding the substituent to its corresponding moiety, eg, for the functional group, $N(R^a)C(O)R^a$, the N is bonded to the corresponding moiety substituted by this group. If the substituent is described in words, such as alkyenylamine, the phrase ending in "enyl" indicates the carbon atom bonding the substituent to its corresponding moiety. For substituents that display a single bonding site, such as carboxylic acid, sulfonic acid, fluoro, methyl and the like, the bonding arrangement is the expected arrangement.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

Unless stated otherwise specifically in the specification, an alkyl group is optionally substituted by one or more of substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$ where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

Unless stated otherwise specifically in the specification, an alkenyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, —$N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., C2-C10 alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., C2-C5 alkynyl). The alkynyl is attached to the rest of the molecule by a single bond, for example, ethynyl, propynyl, butynyl, pentynyl, hexynyl, and the like.

Unless stated otherwise specifically in the specification, an alkynyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)2, —C(O)R$^a$, —C(O)OR$^a$, —C(O)N(R$^a$)2, —C(O)N(R$^a$)2, —N(R$^a$)C(O)OR$^a$, —N(R$^a$)C(O)R$^a$, —N(R$^a$)C(O)N(R$^a$)2, N(R$^a$)C(NR$^a$)N(R$^a$)2, —N(R$^a$)S(O)$_t$R$^a$ (where t is 1 or 2), —S(O)$_t$OR$^a$ (where t is 1 or 2), —S(O)$_t$N(R$^a$)2 (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl. "Alkynyl-cycloalkyl" refers to refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., C$_2$-C$_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a C$_3$-C$_8$ cycloalkyl radical. In some embodiments, it is a C$_3$-C$_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

Unless stated otherwise specifically in the specification, a cycloalkyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Cycloalkyl-alkenyl" refers to a -(cycloalkyl) alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

"Alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, C$_1$-C$_4$ alkyl is an alkyl group which encompasses both straight and branched chain alkyls of from 1 to 4 carbon atoms.

"Substituted alkoxy" refers to alkoxy wherein the alkyl constituent is substituted (i.e., —O-(substituted alkyl)).

Unless stated otherwise specifically in the specification, the alkyl moiety of an alkoxy group is optionally substituted by one or more substituents as defined above. Such substituents further independently include: alkyl, hetero alkyl, alkenyl, alkynyl, cycloalkyl, heterocycloalkyl, aryl, arylalkyl, hetero aryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —C(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or hetero arylalkyl.

"Alkoxycarbonyl" refers to a group of the formula (alkoxy)(C═O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, C$_1$-C$_4$ alkoxy, is an alkoxy group which encompasses both straight and branched chain alkoxy groups of from 1 to 4 carbon atoms.

"Substituted alkoxycarbonyl" refers to the group (substituted alkyl)-O—C(O)— wherein the group is attached to the parent structure through the carbonyl functionality.

Unless stated otherwise specifically in the specification, the alkyl moiety of an alkoxycarbonyl group is optionally substituted by one or more substituents as defined above. Such substituents further independently include: alkyl, heteroalkyl, alkenyl, alkynyl, cycloalkyl, heterocycloalkyl, aryl, arylalkyl, hetero aryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or hetero arylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a C$_1$-C$_{10}$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms.

Unless stated otherwise specifically in the specification, the "R" of an acyloxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl. "Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms.

Unless stated otherwise specifically in the specification, the "R" of an acyloxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2-S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Amino" or "amine" refers to a —N($R^a$)$_2$ radical group, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl, unless stated otherwise specifically in the specification. When a —N($R^a$)$_2$ group has two Ra other than hydrogen they can be combined with the nitrogen atom to form a 4-, 5-, 6-, or 7-membered ring. For example, —N($R^a$)$_2$ is meant to include, but not be limited to, 1-pyrrolidinyl and 4-morpholinyl.

Unless stated otherwise specifically in the specification, an amino group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl and each of these moieties may be optionally substituted as defined herein.

"Substituted amino" also refers to N-oxides of the groups —NH$R^d$, and N$R^d R^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

"Aryl" refers to a conjugated pi radical with six or ten ring atoms which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or fused-ring polycyclic (i.e., rings which share adjacent pairs of ring atoms) groups.

Unless stated otherwise specifically in the specification, an aryl moiety is optionally substituted by one or more substituents as defined above. Such substituents further are independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Aralkyl" or "arylalkyl" refers to an (aryl)alkyl- radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

Unless stated otherwise specifically in the specification, an ester group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O) OR$^a$, —OC(O)N(R$^a$)$_2$, —C(O)N(R$^a$)$_2$, —N(R$^a$)C(O) OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Functional substituent, group or component" refers to a substituent capable of displaying functionality such as and including hydroxyl, ester, amide, amine, enamine, halogen, cyano, thio, oxidized sulfur, nitrogen or phosphorus groups, alkoxy, olefinic, aldehyde, ketone, carboxylic acid, anhydride, urethane, urea, imine, amidine, hydroxylimine, hydroxylamine, nitrile, organometallic, and any other group capable of displaying dipole interaction and/or reactivity. See *Basic Principles of Organic Chemistry*, Roberts & Casario, W. A. Benjamin, publisher New York, N.Y. 1965, Chapter 10. Additional examples include hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, C(O)N(R$^a$)$_2$, —C(O)N(R$^a$)$_2$, —N(R$^a$)C(O) OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —R$^a$—N(R$^a$)$_2$ or PO$_3$(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Hetero alkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the molecule may be through either a hetero atom or a carbon in the heteroalkyl chain.

A heteroalkyl group may be substituted with one or more substituents as defined above. Such substituents further independently include: alkyl, hetero alkyl, alkenyl, alkynyl, cycloalkyl, heterocycloalkyl, aryl, arylalkyl, hetero aryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively.

"Heteroalkylheterocycloalkyl" refers to an -(heteroalkyl) heterocycloalkyl radical where heteroalkyl and heteroaryl are as disclosed herein and which are optionally substituted by one or more of the substituents described as suitable substituents for heteroalkyl and heterocycloalkyl respectively.

"Heteroalkylcycloalkyl" refers to an -(heteroalkyl) cycloalkyl radical where heteroalkyl and cycloalkyl are as disclosed herein and which are optionally substituted by one or more of the substituents described as suitable substituents for heteroalkyl and cycloalkyl respectively.

"Heteroaryl" refers to a 5, 6 or 10-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocyclooctan[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1 H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Unless stated otherwise specifically in the specification, a heteraryl moiety is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

Substituted heteroaryl also includes ring systems substituted with one or more oxide (—O—) substituents, such as pyridinyl N-oxides.

"Heterocyclyl" refers to any monocyclic or polycyclic moiety comprising at least one heteroatom selected from nitrogen, oxygen and sulfur. As used herein, heterocyclyl moieties can be aromatic or nonaromatic.

Unless stated otherwise, heterocyclyl moieties are optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heteroarylalkyl" refers to a moiety having an aryl moiety, as described herein, connected to an alkylene moiety, as described herein, wherein the connection to the remainder of the molecule is through the alkylene group.

"Heterocyclylalkyl" refers to a stable 5, 6 or 10-membered non-aromatic ring radical having from one to six heteroatoms selected from nitrogen, oxygen and sulfur. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

Unless stated otherwise specifically in the specification, a heterocycloalkyl moiety is optionally substituted by one or more substituents as defined above. Such substituents further independently include: alkyl, hetero alkyl, alkenyl, alkynyl, cycloalkyl, heterocycloalkyl, aryl, arylalkyl, hetero aryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocyclylalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

The term "(C$_x$-C$_y$)perfluoroalkyl," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$.

The term "(C$_x$-C$_y$)perfluoroalkylene," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkylene, more preferred is —(C$_1$-C$_3$)perfluoroalkylene, most preferred is —CF$_2$—.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6-, or 7-membered ring. In some embodiments, it is a C$_1$-C$_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, hetero aryl respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

"Azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

"Urethane" ("carbamoyl" or "carbamyl") includes N- and O-urethane groups, i.e., —NRC(O)OR and —OC(O)NR$_2$ groups, respectively.

"Sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

"Amidine" or "amidino" includes groups of the formula —C(NR)NR$_2$. Typically, an amidino group is —C(NH)NH$_2$.

"Guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

At various places in the present specification substituents of compounds of the invention are disclosed in groups or in ranges. It is specifically intended that the invention include each and every individual subcombination of the members of such groups and ranges. For example, the term "C1-C6 alkyl" is specifically intended to individually disclose methyl, ethyl, propyl, isopropyl, n-butyl, sec-butyl, isobutyl, etc. For a number qualified by the term "about", a variance of 2%, 5%, 10% or even 20% is within the ambit of the qualified number.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

Compounds

The invention is directed to fused pyrimidine compounds that inhibit ATPase Associated with a variety of Activities (AAA), the ATPase having the descriptive name Valosin containing protein, also known as p97, as well as methods to treat or prevent a disease or condition in a subject that would benefit by inhibition of p97. The compounds embodying the first aspect of the invention are fused cyclohexyl-pyrimidines, cyclopentyl-pyrimidines and cycloheptyl-pyrimidines having an all carbon, aza, oxa or thia ring as the cyclopentyl, cyclohexyl or cycloheptyl fusion partner of the fused pyrimidine. The fused pyrimidines have a benzyl amino group or substituted benzyl amino group at the 4 position of the fused pyrimidine or pyrimidine ring and a Het group at the 2 position. The Het group is as defined above. Formula I provides a pictorial-structural understanding of the foregoing description of embodiments of the fused pyrimidine compounds of the invention.

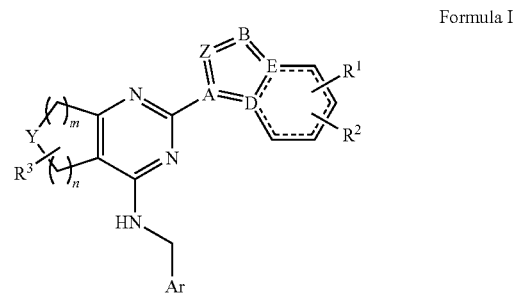

Formula I

The substituents $R^1$, $R^2$, $R^3$, $R^4$, $R^5$, $R^6$ and $R^7$ of Formula I are each independently selected from the group consisting of hydrogen, an optionally substituted aliphatic group, an optionally substituted aromatic group and an optionally substituted functional group as described above in the definitions section.

Preferred designations for A, D, E, B and Z for the fused pyrimidine compounds of Formula I independently and separately are those in which A is N or A is C.

Preferred designations for A, D, E, B and Z for the fused pyrimidine compounds of Formula I independently and separately are those in which D and E are both C and those in which one of D and E is N.

Preferred designations for A, D, E, B and Z for the fused pyrimidine compounds of Formula I independently and separately are those in which A is N and D and E are both C.

Preferred designations for A, D, E, B and Z for the fused pyrimidine compounds of Formula I independently and separately are those in which A, D and E are all C.

Preferred designations for A, D, E, B and Z for the fused pyrimidine compounds of Formula I independently and separately are those in which A and D are both C and B and E are both N.

Preferred designations for A, D, E, B and Z for the fused pyrimidine compounds of Formula I independently and separately are those in which A is C, one of D and E is N and the other is C, and Z and B are each independently N or $CR^6$.

A preferred designation for $R^3$ for the fused pyrimidine compounds of Formula I and for any of the foregoing preferred designations of A, B, D, E and Z is hydrogen or unsubstituted or substituted 1-4 carbon alkyl.

A preferred designation for Y for the fused pyrimidine compounds of Formula I and for any of the foregoing preferred designations of A, B, D, E and Z is $NR^5$ and $R^5$ is hydrogen or unsubstituted or substituted 1-4 carbon alkyl.

A preferred designation for Y for the fused pyrimidine compounds of Formula I and for any of the foregoing preferred designations of A, B, D, E and Z is O.

A preferred designation for Y for the fused pyrimidine compounds of Formula I and for any of the foregoing preferred designations of A, B, D, E and Z is S.

A preferred designation for Y for the fused pyrimidine compounds of Formula I and for any of the foregoing preferred designations of A, B, D, E and Z is $CR^4$.

Preferably, the substituents $R^1$, $R^2$, $R^3$, $R^4$, $R^5$, $R^6$ and $R^7$ of Formula I each are independently selected from the group consisting of hydrogen, halogen, alkyl, CN, OR', CN, SR', $SO_2R'$, NR'R'', C(O)R', C(O)NR'R'', C(O)OR', OC(O)R', OC(O) NR'R'', N(R')C(O)OR', N(R')C(O)R'', N(R')C(O)N (R''R), N(R')C(NR')N($RR^3$), N(R')S(O)$_2$R'', S(O)$_2$OR', S(O)$_2$N(R'R''), N($R^d$)$_2$, (CR'R'')$^t$N($RR^3$), (CR'R'')$^t$OR, $PO_3$ (R'R''), $CF_3$ wherein each R, $R^3$, R' and R'' each are independently hydrogen, alkyl, fluoroalkyl, carbocyclyl, carbocyclylalkyl, aryl, aralkyl, heterocyclyl, heterocyclylalkyl, heteroaryl, heteroarylalkyl alkenyl, alkynyl or any combination thereof; and wherein and each t is independently selected from the group of integers of 1 and 2.

More preferably, the substituents $R^1$, $R^2$, $R^3$, $R^4$, $R^5$, $R^6$ and $R^7$ of Formula I are each independently selected from hydrogen, halogen, linear, branched or cyclo alkyl of 1 to 6 carbons, carboxyl, carboxamide, substituted aminomethyl, sulfonyl, sulfonamide, amine, mono, di or trialkyl amine of 1 to 6 carbons, nitrile, halogen, N-alkyl carboxamide of 1 to 6 carbons in the alkyl group, perfluoroalkyl of 1 to 3 carbons, alkoxy of 1 to 6 carbons.

Especially preferably for Formula I, $R^1$ is substituted at the 4 position of the Het group. Also, especially preferably, the $R^2$ group is hydrogen. Also preferably, the fused pyrimidine compounds of Formula I may substituted with $R^3$ which may be selected from alkyl of 1 to 3 carbons, perfluoroalkyl of 1 to 3 carbons, alkoxy of 1 to 3 carbons, alkylsulfone of 1 to 3 carbons, aminomethyl (—$NHCH_3$), methylamine (—$CH_2NH_2$), methanol (—$CH_2OH$), nitrile or halogen. These substituents $R^1$, $R^2$ and $R^3$ of the fused pyrimidine compounds of Formula I can also preferably be hydrogen. Especially more preferably, these substituents $R^1$, $R^2$ and $R^3$ of Formula I are each independently hydrogen, methyl, trifluoromethyl, methoxy or chloro.

The group $R^1$ is a substituent of the benzo moiety of the HET group may especially preferably be:
1. carboxylic acid —$CO_2H$
2. carboxamide —$CONH_2$
3. methyl amine —$CH_2NH_2$
4. methyl alcohol —$CH_2OH$
5. acetic acid —$CH_2CO_2H$
6. acetamide —$CH_2CONH_2$
7. methyl acetamide —$CH_2NHCOCH_3$
8. methyl propanamide —$CH_2NHCOCH_2CH_3$
9. methyl-2-methylpropanamide —$CH_2NHCOCH(CH_3)CH_3$
10. methyl methanesulfonamide —$CH_2NHSO_2CH_3$
11. methyl ethanesulfonamide —$CH_2NHSO_2CH_2CH_3$
12. methyl-2-methylethanesulfonamide —$CH_2NHSO_2CH(CH_3)CH_3$
13. methyl propanesulfonamide —$CH_2NHSO_2CH_2CH_2CH_3$
14. methyl-1-methylpropanesulfonamide —$CH_2NHSO_2CH(CH_3)CH_2CH_3$
15. methyl-2-methylpropanesulfonamide —$CH_2NHSO_2CH_2CH(CH_3)CH_3$ The group $R^2$ is an optional substituent of the benzo moiety of the HET group and especially preferably may be hydrogen, alkyl of 1 to 3 carbons, nitrile, perfluoroalkyl of 1 to 3 carbons.

Embodiments of the scaffold (Formula II) and the HET moiety (Formula HET) include the following structures. In each of these embodiments and the preferred, more preferred, especially more preferred and most preferred combinations, the substituent groups $R^1$, $R^2$, $R^3$, $R^4$, $R^5$, $R^6$ and $R^7$ are included as provided by Formula I. For each of these embodiments and the preferred, more preferred, especially more preferred and most preferred combinations of Formula II and Formula HET forming preferences for Formula I, the preferred and more preferred designations given above for substituent groups $R^1$, $R^2$, $R^3$, $R^4$, $R^5$, $R^6$ and $R^7$ as well as the especially preferred designations for substituent groups $R^1$, $R^2$ and $R^3$ are preferences applied to these preferred combinations as well.

Embodiments of Formula II, the Scaffold (labeled as S for scaffold) are:

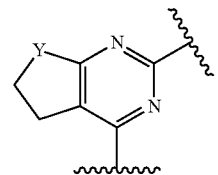

S1

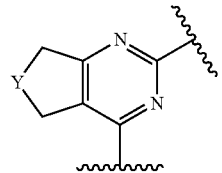

S2

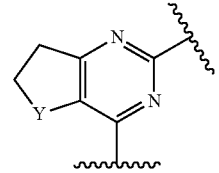

S3

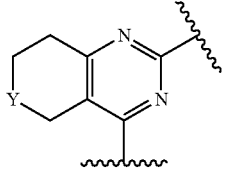

S4

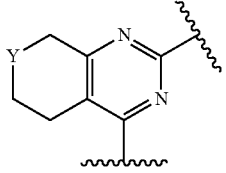

S5

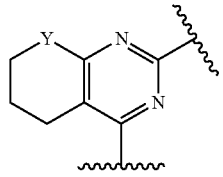

S6

S7
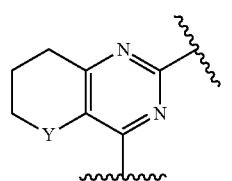

S8
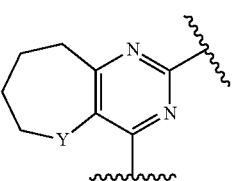

S9
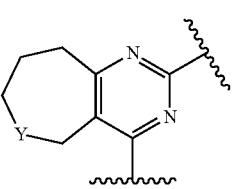

S10
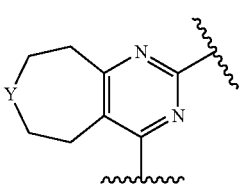

S11
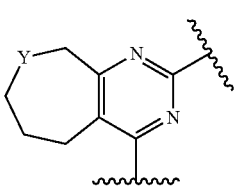

S12
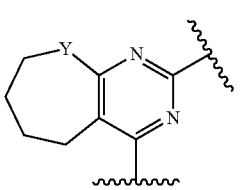

Preferred scaffold embodiments include S2, S3, S4, and S5 when the HET embodiments depicted below include any of the structures except H5 and H10. Especially preferred scaffold embodiments include S1, S3, S6 and S7 in combination with any of the HET embodiments depicted below.

Embodiments of Formula HET (labeled H for heterocyclic) wherein N— indicates the nitrogen of the group NR$^7$ are:

H1
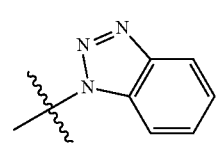

H2
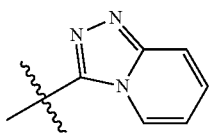

H3
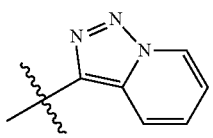

H4
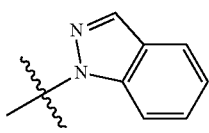

H5
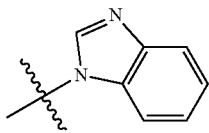

H6
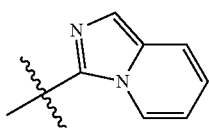

H7
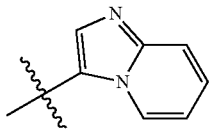

H8
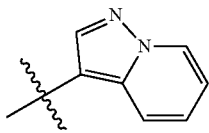

H9
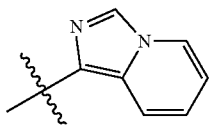

H10
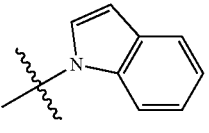

H11
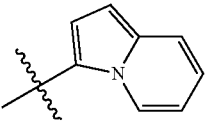

H12
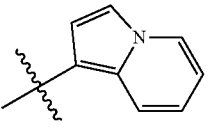

H13 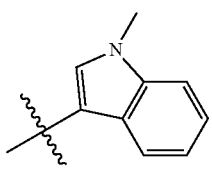

H14 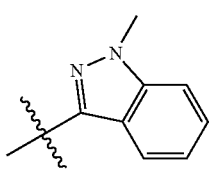

H15 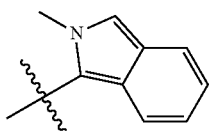

H16 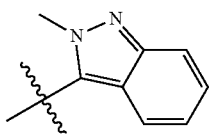

H17 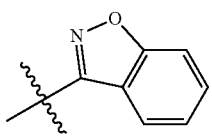

H18 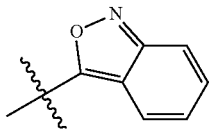

H19 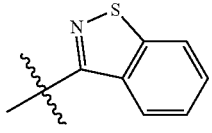

H20 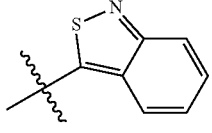

H21 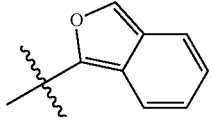

H22 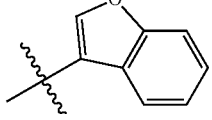

H23

H24

Especially preferred combinations of the scaffold and HET embodiments forming preferred embodiments of Formula I include each of S1, S2, S3, S4, S5, S6 and S7 bound with any one of H4, H5, H6, H7, H8, H9, H10, H11, H12, H13, H14, H17 and H22. According to the provisos set forth above for Formula I, H5 and H10 are not combined with S2, S4 and S5. As stated above, the substituent groups $R^1$, $R^2$, $R^3$, $R^4$, $R^5$, $R^6$ and $R^7$ are included as provided by Formula I. The preferred and more preferred designations given above for substituent groups $R^1$, $R^2$, $R^3$, $R^4$, $R^5$, $R^6$ and $R^7$ as well as the especially preferred designations for substituent groups $R^1$, $R^2$ and $R^3$ are preferences for these substituent groups as applied to the foregoing combinations of scaffold and HET embodiments for Formula I.

Especially preferred combinations of the scaffold and HET embodiments forming especially preferred embodiments of Formula I include each of S1, S2, S3, S4, S5, S6 and S7 bound with any one of H4, H5, H6, H7, H9, H10, H13 and H17. According to the provisos set forth above for Formula I, H5 and H10 are not combined with S2, S4 and S5. As stated above, the substituent groups $R^1$, $R^2$, $R^3$, $R^4$, $R^5$, $R^6$ and $R^7$ are included as provided by Formula I. The preferred and more preferred designations given above for substituent groups $R^1$, $R^2$, $R^3$, $R^4$, $R^5$, $R^6$ and $R^7$ as well as the especially preferred designations for substituent groups $R^1$, $R^2$ and $R^3$ are preferences for these substituent groups as applied to the foregoing combinations of scaffold and HET embodiments for Formula I.

Most preferred combinations of the scaffold embodiment and the HET embodiment forming most preferred embodiments of Formula I are chosen from S2, S4, S5, S9, S10 and S11 combined with H4. As stated above, this combination includes the substituents $R^1$, $R^2$, $R^3$, $R^4$, $R^5$, $R^6$ and $R^7$ as disclosed in Formula I. The preferred and more preferred designations given above for substituent groups $R^1$, $R^2$, $R^3$, $R^4$, $R^5$, $R^6$ and $R^7$ as well as the especially preferred designations for substituent groups $R^1$, $R^2$ and $R^3$ are preferences for these substituent groups as applied to the foregoing combinations of scaffold and HET embodiments for Formula I.

Most especially preferred combinations of the scaffold embodiment and the HET embodiment are chosen from S2, S4, S5, S9, S10 and S11 combined with H6, H7, H8, H9, H13, H17 and H22. As stated above, this combination includes the substituents $R^1$, $R^2$, $R^3$, $R^4$, $R^5$, $R^6$ and $R^7$ as disclosed in Formula I. The preferred and more preferred designations given above for substituent groups $R^1$, $R^2$, $R^3$, $R^4$, $R^5$, $R^6$ and $R^7$ as well as the especially preferred designations for substituent groups $R^1$, $R^2$ and $R^3$ are preferences for these substituent groups as applied to the foregoing combinations of scaffold and HET embodiments for Formula I.

Mechanism of Action and Medical Treatment

In certain embodiments, the invention is directed to methods of inhibiting p97. The fused pyrimidine compounds of the invention for use in the methods disclosed herein bind to the active site of p97, e.g., noncovalently or covalently. In certain such embodiments, the covalent binding may be reversible or irreversible.

The compounds of the invention and their pharmaceutical compositions are capable of acting as "inhibitors" of p97 which means that they are capable of blocking or reducing the activity of an enzyme, for example, inhibition of various activities of p97. An inhibitor can act with competitive, uncompetitive, or noncompetitive inhibition. An inhibitor can bind reversibly or irreversibly, and therefore the term includes compounds that are suicide the enzyme, or it can cause a conformational change elsewhere on the enzyme.

The compounds of the invention and their pharmaceutical compositions function as therapeutic agents in that they are capable of preventing, ameliorating, modifying and/or affecting a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The ability to prevent, ameliorate, modify and/or affect in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths population, and/or delaying the appearance of detectable cancerous growths in a treated population versus an untreated control population, e.g., by a statistically and/or clinically significant amount.

Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The compounds of the invention and their pharmaceutical compositions are capable of functioning prophylacticly and/or therapeutically and include administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The compounds of the invention and their pharmaceutical compositions are capable of prophylactic and/or therapeutic treatments. If a compound or pharmaceutical composition is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, the term "treating" or "treatment" includes reversing, reducing, or arresting the symptoms, clinical signs, and underlying pathology of a condition in manner to improve or stabilize a subject's condition.

The compounds of the invention and their pharmaceutical compositions can be administered in "therapeutically effective amounts" with respect to the subject method of treatment. The therapeutically effective amount is an amount of the compound(s) in a pharmaceutical composition which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

Administration

Compounds of the invention and their pharmaceutical compositions prepared as described herein can be administered in various forms, depending on the disorder to be treated and the age, condition, and body weight of the patient, as is well known in the art. As is consistent, recommended and required by medical authorities and the governmental registration authority for pharmaceuticals, administration is ultimately provided under the guidance and prescription of an attending physician whose wisdom, experience and knowledge control patient treatment.

For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route or other similar transmucosal route, they may be formulated as drops or ointments.

These formulations for administration orally or by a transmucosal route can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the gender of the patient, the nature and severity of the disorder to be treated or prevented, the route of administration and the form of the drug, in general, a daily dosage of from 0.0001 to 2000 mg, preferably 0.001 to 1000 mg, more preferably 0.001 to 500 mg, especially more preferably 0.001 to 250 mg, most preferably 0.001 to 150 mg of the compound is recommended for an adult human patient, and this may be administered in a single dose or in divided doses. Alternatively, a daily dose can be given according to body weight such as 1 nanogram/kg (ng/kg) to 200 mg/kg, preferably 10 ng/kg to 100 mg/kg, more preferably 10 ng/kg to 10 mg/kg, most preferably 10 ng/kg to 1 mg/kg. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutical Compositions Incorporating Formula I

The pharmaceutical compositions of the invention incorporate embodiments of a fused pyrimidine compound of Formula I of the invention and a pharmaceutically acceptable carrier. The nature of the pharmaceutical carrier and the dose of the fused pyrimidine compound of Formula I depend upon the route of administration chosen, the effective dose for such a route and the wisdom and experience of the attending physician.

A "pharmaceutically acceptable carrier" is a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted (3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound of the invention as an active ingredient. A composition may also be administered as a bolus, electuary, or paste.

In solid dosage form for oral administration (capsules, tablets, pills, dragees, powders, granules, and the like), a compound of the invention is mixed with one or more pharmaceutically acceptable carriers, such as sodium citrate or dicalcium phosphate, and/or any of the following:
  (1) fillers or extenders, such as starches, cyclodextrins, lactose, sucrose, glucose, mannitol, and/or silicic acid;
  (2) binders, such as, for example, carboxymethylcellulose, alginates, gelatin, polyvinyl pyrrolidone, sucrose, and/or acacia;
  (3) humectants, such as glycerol;
  (4) disintegrating agents, such as agar-agar, calcium carbonate, potato or tapioca starch, alginic acid, certain silicates, and sodium carbonate;
  (5) solution retarding agents, such as paraffin;
  (6) absorption accelerators, such as quaternary ammonium compounds;
  (7) wetting agents, such as, for example, acetyl alcohol and glycerol monostearate; (8) absorbents, such as kaolin and bentonite clay;
  (9) lubricants, such a talc, calcium stearate, magnesium stearate, solid polyethylene glycols, sodium lauryl sulfate, and mixtures thereof; and
  (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions which can be used include polymeric substances and waxes. A compound of the invention can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound of the invention can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of a compound of the invention together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more compounds of the invention in combination with one or more pharmaceutically acceptable sterile aqueous or nonaqueous solutions, dispersions, suspensions or emulsions, or sterile powders which may be reconstituted into sterile injectable solutions or dispersions just prior to isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound of the invention, it is desirable to slow the absorption of the compound from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The pharmaceutical compositions may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The pharmaceutical compositions of the invention may be "systemically administered" "administered systemically," "peripherally administered" and "administered peripherally" meaning the administration of a ligand, drug, or other material other than directly into the central nervous system, such that it enters the patient's system and thus, is subject to metabolism and other like processes, for example, subcutaneous administration.

The compound(s) of the invention may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compound(s) of the invention, which may be used in a suitable hydrated form, and/or the pharmaceutical compositions of the present invention, are formulated into pharmaceutically acceptable dosage forms by conventional methods known to those of skill in the art.

Actual dosage levels of the compound(s) of the invention in the pharmaceutical compositions of this invention may be varied so as to obtain an amount of the active ingredient which is effective to achieve the desired therapeutic response for a particular patient, composition, and mode of administration, without being toxic to the patient.

The concentration of a compound of the invention in a pharmaceutically acceptable mixture will vary depending on several factors, including the dosage of the compound to be administered, the pharmacokinetic characteristics of the compound(s) employed, and the route of administration.

In general, the compositions of this invention may be provided in an aqueous solution containing about 0.1-10% w/v of a compound disclosed herein, among other substances, for parenteral administration. Typical dose ranges are from about 0.001 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the compounds and compositions of the invention. Such conjoint treatment will achieve the same or similar treatment accounting for the additive effects of the conjoined therapeutic agents other than the compounds of the invention.

In certain embodiments, a compound of the invention can be conjointly administered with one or more proteasome inhibitor(s). In certain embodiments, a compound of the invention is conjointly administered with a chemotherapeutic. Suitable chemotherapeutics may include, natural products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycin, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, paramethasone, prednicarbate, prednisolone, prednisolone 25-diethylaminoacetate, prednisolone, sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

Treatment of Cancer

Exemplary forms of cancer which may be treated by the methods of the invention using the fused pyrimidine compounds of the invention and their pharmaceutical compositions include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer.

Additional exemplary forms of cancer which may be treated by the methods of the invention include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer.

The compounds of the present invention and their salts and solvates, thereof, may be employed alone or in combination with other therapeutic agents for the treatment of the diseases or conditions associated with inappropriate P97 activity.

Additional diseases that can be treated according to the methods of the invention include in addition to cancer, auto-immune disorders, metabolic diseases, infection diseases, neurological diseases, graft versus host disease and other hereditary diseases outlined here: abeta-lipoproteinema, acerulopasminemia, alpha-1-antichymotrypsin (ACT) deficiency, aspartylglucosaminuria, autosomal dominant retinitis pigmentosa, brugada syndrome, Charcot-Marie-Tooth syndrome, congenital adrenal hyperplasia, congenital chloride diarrhea, congenital hypothyroidism, congenital long QT syndrome, congenital nephritic syndrome, congenital sucrase-isomaltase deficiency, Crigler-Najjar type II, cystic fibrosis, diabetes mellitus, diastrophic displasia, DubinJohnson syndrome, Fabri disease, familial chylomicronemia, familial glucocorticoid deficiency, familial hypercholesterolemia, Gaucher disease, heavy chain disease, hereditary emphysema, hereditary emphysema with liver injury, hereditary hemochromatosis, hereditary hypofibrinogenemia, hereditary myeloperoxidase, hereditary spherocytosis, hirschprung disease, hypogonadotropic hypogonadism, infantile systemic hyalinosis, infentile neuronal ceroid lipofuscinosis, laron syndrome, liver failure, marfan syndrome, medullary cystic kidney disease, familial juvenile hyperuricemic nephropathy, Menkes disease, nephrogenic diabetes, neurohypophyseal diabetes insipidus, oculocutaneous albinism, osteogenesis imperfect, Pelizaeus-Merzbacher disease, Pendred syndrome, persistent hyperinsulinemic hypoglycemia of infancy, primary hypothyroidism, Protein C deficiency, pseudoachondropla with multiple epiphyseal dysplasia, severe congenital neutropenia, Stargardt-like macular dystrophy, steroid-resistant nephrotic syndrome, Tay-Sachs, Type I hereditary angioedema, tyroxine binding globulin deficiency, von Willebrand disease type IIA, X-linked Charot-Marie-Tooth disease, X-linked hypophosphatemia, Alzheimer disease autosomal recessive juvenile parkinsonism, combined factors V and VIII deficiency, cranio-lenticulo-sutural dysplasia, hypotonia and dysmorphism, inclusion body myopathy Paget's disease of the bone and frontotemporal dementia (IBMPFD), lipid absorption disorders, Marinesco-Sjoegren syndrome, Parkinson, polycystic liver disease, spondyloepiphyseal dysplasia tarda, Walcott-Rallison syndrome and Lou Gehrig's disease (ALS).

In various embodiments, compounds of the invention may be used to treat neoplastic growth, angiogenesis, infection, inflammation, immune-related diseases, ischemia and reperfusion injury, multiple sclerosis, rheumatoid arthritis, neurodegenerative conditions, or psoriasis.

Neoplastic growth may include cancer. Suitably, the present invention relates to a method for treating or lessening the severity of a cancer selected from: brain (gliomas), glioblastomas, breast, Wilm's tumor, Ewing's sarcoma, rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, Hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In various embodiments, the cancer is selected from brain cancer (gliomas), glioblastomas, breast cancer, colon cancer, head and neck cancer, kidney cancer, lung cancer, liver cancer, melanoma, ovarian cancer, pancreatic cancer, prostate cancer, sarcoma and thyroid cancer.

In various embodiments, the cancer to be treated is associated with the proteasome. See Voorhees et al., The Proteasome as a Target for Cancer Therapy, Clinical Cancer Research, vol. 9, 6316-6325, December 2003, incorporated by reference in its entirety. In various embodiments, the cancer is associated with a particular target, such as NFkB, p44/42 MAPK, P-gp, TopI, TopIIalpha.

In various embodiments, the cancer is a solid tumor. In various embodiments, the cancer is selected from multiple myeloma, metastatic breast cancer, non-small cell lung cancer, prostate cancer, advanced colorectal cancer, ovarian or primary peritoneal carcinoma, hormone refractory prostate cancer, squamous cell carcinoma of the head and neck, metastatic pancreatic adenocarcinoma, gastroesophageal junction or stomach, or non-Hodgkin's lymphoma.

A method of using the compounds described herein for treating a disorder characterized by an inappropriate level of proteasome activity, or in which a reduction of the normal level of proteasome activity yields a clinical benefit. This disorder can include cancer or immune disorders characterized by excessive cell proliferation or cellular signaling. Among cancers, this includes human cancers that overexpress c-Myc or express an oncogenic form of the K-Ras protein.

Neurodegenerative diseases and conditions may include without limitation stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, ALS, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis). Compounds of the invention may be used to treat Alzheimer's disease, including administering to a subject an effective amount of an agent or composition (e.g., pharmaceutical composition) disclosed herein.

Compounds of the invention may be used to treat cachexia and muscle-wasting diseases. Compounds of the invention may be used to treat such conditions wherein the condition is related to cancer, chronic infectious diseases, fever, muscle disuse (atrophy) and denervation, nerve injury, fasting, renal failure associated with acidosis, diabetes, and hepatic failure.

Compounds of the invention can be used to treat hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of burn victims is often hampered by fibrosis, thus, an additional embodiment of the application is the topical or systemic administration of the inhibitors to treat burns. Wound closure following surgery is often associated with disfiguring scars, which may be prevented by inhibition of fibrosis. Thus, in certain embodiments, the application relates to a method for the prevention or reduction of scarring.

Compounds of the invention can be used to treat ischemic conditions or reperfusion injury for example acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Compounds of the invention can be used for the inhibition of TNFalpha to prevent and/or treat septic shock.

Compounds of the invention can be used for inhibiting antigen presentation in a cell, including exposing the cell to an agent described herein. A compound of the invention may be used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for moedulating the immune system of a subject (e.g., inhibiting transplant rejection, allergies, auto-immune diseases, and asthma), including administering to the subject an effective amount of a compound of the invention.

Compounds of the invention can be used in methods for altering the repertoire of antigenic peptides produced by the proteasome or other protein assembly with multicatalytic activity.

Compounds of the invention can be used in methods for inhibiting IKB-alpha degradation, including contacting the cell with an agent identified herein. A further embodiment is a method for reducing the cellular content of NF-KB in a cell, muscle, organ, or subject, including contacting the cell, muscle, organ, or subject with a compound of the invention.

Compounds of the invention can be used in methods for affecting cyclin-dependent eukaryotic cell cycles. Compounds of the invention can be used in methods for treating a proliferative disease in a subject (e.g., cancer, psoriasis, or restenosis). Compounds of the invention can be used for treating cyclin-related inflammation in a subject.

One embodiment is a method for treating p53-related apoptosis, including administering to a subject an effective amount of a compound of the invention.

In another embodiment, the compounds of the present application are useful for the treatment of a parasitic infection, such as infections caused by protozoan parasites. In certain such embodiments, the agents are useful for the treatment of parasitic infections in humans caused by a protozoan parasite selected from *Plasmodium* sps., *Trypanosoma* sps., *Leishmania* sps., *Pneumocystis carinii, Toxoplasma gondii, Entamoeba histolytica, Entamoeba invadens*, and *Giardia lamblia*. In certain embodiments, the agents are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds useful as proteasome inhibitors in the treatment of parasitic diseases are described in WO 98/10779, which is incorporated herein in its entirety.

In particular, the methods of treatment include inhibiting, arresting, ameliorating, minimizing and/or eliminating malconditions associated with the inability of cells to metabolize, degrade or otherwise remove ubiquitin tagged proteins and peptides because the tag has been cleaved, degraded, removed or otherwise rendered disfunctional as a result of P97 metalloprotease domain activity. Included are methods in which a human disorder characterized by abnormal regulatory peptide degradation resulting in excessive cell proliferation or cell signaling. The methods are directed to administration of an effective amount of a compound or pharmaceutical formulation disclosed above so that the abnormal regulatory peptide degradation is ameliorated, reduced or inhibited. In particular, the human disorders include a cancer or immune disorder, a cancer resulting from overexpression of c-Myc or expression of an oncogenic form of the K-Ras protein. The methods also include inhibition or amelioration of P97 metalloprotease domain activity in a human patient suffering from abnormal P97 metalloprotease domain activity on ubiquitin modified proteins. As described above, these methods involve administering to the patient an effective amount of a compound or pharmaceutical formulation disclosed above so that the abnormal P97 metalloprotease domain activity is ameliorated, reduced or inhibited.

Diagnostics

Various cellular proteins are subject to proteolytic processing during maturation or activation. The compositions identified herein can also be useful as diagnostic agents (e.g., in diagnostic kits or for use in clinical laboratories) for screening for proteins (e.g., enzymes, transcription factors) processed by hydrolases, including the proteasome. The agents are also useful as research reagents for specifically binding the X/MB 1 subunit or alpha-chain and inhibiting the proteolytic activities associated with it. For example, the activity of (and specific inhibitors of) other subunits of the proteasome can be determined.

Compounds of the invention identified herein can be used to determine whether a cellular, developmental, or physiological process or output is regulated by proteolytic activity. One such method includes obtaining an organism, an intact cell preparation, or a cell extract; exposing the organism, cell preparation, or cell extract to an agent identified herein; exposing the agent-exposed organism, cell preparation, or cell extract to a signal, and monitoring the process or output. See, for example, U.S. Pat. No. 7,741,432.

The compounds of this invention may used as a part of a diagnostic assay. For instance cells from a patient may be obtained and an assay may be performed to determine whether the compounds of the invention are likely to be effective therapeutic compounds for that patient. The cells obtained from the patient can be for instance cancerous cells from a tumor. The cells can be cultured and compounds of the invention can be applied to determine how the cancerous cells respond.

The diagnostics aspect of the invention also includes an assay for the determination of inhibition of P97 activity. The assay involves combining a P97 enzymatic material with a protein substrate and determining whether a potential inhibitory candidate will function in this assay to lessen the enzymatic activity. The P97 enzymatic material is either a standard or taken from a patient's cells. The protein substrate similarly is either standard or taken from a patient's cells. In particular, the protein substrate is selected from the group consisting of a protein modified by a ubiquitin, a protein modified by a ubiquitin-like modifier and a protein modified by a ubiquitin chain that can be isolated from a patient's cells. The combination of the P97 enzymatic material and the protein substrate produces an enzymatic medium. For this medium, the protein substrate is modified with a tag that is detectable by measurement of molecular weight, spectroscopic interaction or chromatographic $R_f$ determination, Following the isolation and tagging, the enzymatic medium is manipulated to conduct a first measurement of the enzymatic medium relative to the protein substrate alone wherein the first measurement is made by a detection of the tag.

Following the first measurement procedure, a potential inhibitory candidate is combined with the tagged protein substrate and the P97 enzymatic material is added to produce a candidate medium.

The candidate medium is manipulated to conduct a second measurement of the candidate medium relative to the protein substrate alone wherein the second measurement is made by detection of the tag.

Finally, the ability of the inhibitory candidate to be effective treatment for the patient in need is assessed by comparing the first and second measurements to identify a candidate that demonstrates at least about a 50% inhibition at a concentration of no more than 500 micromolar in the candidate medium, the difference between the first and second measurements being at least about 50% with the second measurement being greater than the first measurement.

Specific Embodiments of the Fused Pyrimidine Compounds of Formula I

Embodiments of the fused pyrimidine compounds of Formula I include the specific compounds named in the following Table according to their IUPAC (International Union of Pure and Applied Chemistry) nomenclature. All compounds of these tables can be synthesized according to the synthetic schemes outlined below and will demonstrate appropriate biological activity in one or more Biological Assays described herein. Table I divides these embodiments into three groups: preferred, more preferred and most preferred.

Table I

List of Individual Compounds

Preferred 1-(4-((3,5-difluorobenzyl)amino)-6,7-dihydro-5H-pyrano[2,3-d]pyrimidin-2-yl)-2-methyl-1H-indole-4-carboxamide 1-(4-((3-fluorobenzyl)amino)-5,6,7,8-tetrahydropyrido[2,3-d]pyrimidin-2-yl)-1H-indazole-4-carboxamide 1-(4-((3-fluorobenzyl)amino)-5,6,7,8-tetrahydropyrido[2,3-d]pyrimidin-2-yl)-2-methoxy-1H-benzo[d]imidazole-4-carboxamide 1-(4-((3-fluorobenzyl)amino)-5,6,7,8-tetrahydropyrido[2,3-d]pyrimidin-2-yl)-2-methyl-1H-indole-4-carboxamide 1-(4-((3-fluorobenzyl)amino)-5,6,7,8-tetrahydropyrido[2,3-d]pyrimidin-2-yl)-6-fluoro-1H-indazole-4-carboxamide 1-(4-((3-fluorobenzyl)amino)-5,6,7,8-tetrahydropyrido[2,3-d]pyrimidin-2-yl)-6-fluoro-2-methoxy-1H-benzo[d]imidazole-4-carboxamide 1-(4-((3-fluorobenzyl)amino)-5,6,7,8-tetrahydropyrido[2,3-d]pyrimidin-2-yl)-6-fluoro-2-methyl-1H-indole-4-carboxamide 1-(4-((3-fluorobenzyl)amino)-5,6,7,8-tetrahydropyrido[3,2-d]pyrimidin-2-yl)-1H-indazole-4-carboxamide 1-(4-((3-fluorobenzyl)amino)-5,6,7,8-tetrahydropyrido[3,2-d]pyrimidin-2-yl)-2-methoxy-1H-benzo[d]imidazole-4-carboxamide 1-(4-((3-fluorobenzyl)amino)-5,6,7,8-tetrahydropyrido[3,2-d]pyrimidin-2-yl)-2-methyl-1H-indole-4-carboxamide 1-(4-((3-fluorobenzyl)amino)-5,6,7,8-tetrahydropyrido[3,2-d]pyrimidin-2-yl)-6-fluoro-1H-indazole-4-carboxamide 1-(4-((3-fluorobenzyl)amino)-5,6,7,8-tetrahydropyrido[3,2-d]pyrimidin-2-yl)-6-fluoro-2-methoxy-1H-benzo[d]imidazole-4-carboxamide 1-(4-((3-fluorobenzyl)amino)-5,6,7,8-tetrahydropyrido[3,2-d]pyrimidin-2-yl)-6-fluoro-2-methyl-1H-indole-4-carboxamide 1-(4-((3-fluorobenzyl)amino)-5,6,7,8-tetrahydropyrido[3,4-d]pyrimidin-2-yl)-1H-indazole-4-carboxamide 1-(4-((3-fluorobenzyl)amino)-5,6,7,8-tetrahydropyrido[3,4-d]pyrimidin-2-yl)-6-fluoro-1H-indazole-4-carboxamide 1-(4-((3-fluorobenzyl)amino)-5,6,7,8-tetrahydropyrido[4,3-d]pyrimidin-2-yl)-1H-indazole-4-carboxamide 1-(4-((3-fluorobenzyl)amino)-5,6,7,8-tetrahydropyrido[4,3-d]pyrimidin-2-yl)-6-fluoro-1H-indazole-4-carboxamide 1-(4-((3-fluorobenzyl)amino)-5,6,7,8-tetrahydroquinazolin-2-yl)-1H-indazole-4-carboxamide 1-(4-((3-fluorobenzyl)amino)-5,6,7,8-tetrahydroquinazolin-2-yl)-6-fluoro-1H-indazole-4-carboxamide 1-(4-((3-fluorobenzyl)amino)-5,6-dihydrofuro[2,3-d]pyrimidin-2-yl)-1H-indazole-4-carboxamide 1-(4-((3-fluorobenzyl)amino)-5,6-dihydrofuro[2,3-d]pyrimidin-2-yl)-2-methoxy-1H-benzo[d]imidazole-4-carboxamide 1-(4-((3-fluorobenzyl)amino)-5,6-dihydrofuro[2,3-d]pyrimidin-2-yl)-2-methyl-1H-indole-4-carboxamide 1-(4-((3-fluorobenzyl)amino)-5,6-dihydrofuro[2,3-d]pyrimidin-2-yl)-6-fluoro-1H-indazole-4-carboxamide 1-(4-((3-fluorobenzyl)amino)-5,6-dihydrofuro[2,3-d]pyrimidin-2-yl)-6-fluoro-2-methoxy-1H-benzo[d]imidazole-4-carboxamide 1-(4-((3-fluorobenzyl)amino)-5,6-dihydrofuro[2,3-d]pyrimidin-2-yl)-6-fluoro-2-methyl-1H-indole-4-carboxamide 1-(4-((3-fluorobenzyl)amino)-5,7-dihydrofuro[3,4-d]pyrimidin-2-yl)-1H-indazole-4-carboxamide 1-(4-((3-fluorobenzyl)amino)-5,7-dihydrofuro[3,4-d]pyrimidin-2-yl)-6-fluoro-1H-indazole-4-carboxamide 1-(4-((3-fluorobenzyl)amino)-5-methyl-5,6,7,8-tetrahydropyrido[3,2-d]pyrimidin-2-yl)-1H-indazole-4-carboxamide 1-(4-((3-fluorobenzyl)amino)-5-methyl-5,6,7,8-tetrahydropyrido[3,2-d]pyrimidin-2-yl)-2-methoxy-1H-benzo[d]imidazole-4-carboxamide 1-(4-((3-fluorobenzyl)amino)-5-methyl-5,6,7,8-tetrahydropyrido[3,2-d]pyrimidin-2-yl)-2-methyl-1H-indole-4-carboxamide 1-(4-((3-fluorobenzyl)amino)-5-methyl-5,6,7,8-tetrahydropyrido[3,2-d]pyrimidin-2-yl)-6-fluoro-1H-indazole-4-carboxamide 1-(4-((3-fluorobenzyl)amino)-5-methyl-5,6,7,8-tetrahydropyrido[3,2-d]pyrimidin-2-yl)-6-fluoro-2-methoxy-1H-benzo[d]imidazole-4-carboxamide 1-(4-((3-fluorobenzyl)amino)-5-methyl-5,6,7,8-tetrahydropyrido[3,2-d]pyrimidin-2-yl)-6-fluoro-2-methyl-1H-indole-4-carboxamide 1-(4-((3-fluorobenzyl)amino)-5-methyl-6,7-dihydro-5H-pyrrolo[3,2-d]pyrimidin-2-yl)-1H-indazole-4-carboxamide 1-(4-((3-fluorobenzyl)amino)-5-methyl-6,7-dihydro-5H-pyrrolo[3,2-d]pyrimidin-2-yl)-2-methoxy-1H-benzo[d]imidazole-4-carboxamide 1-(4-((3-fluorobenzyl)amino)-5-methyl-6,7-dihydro-5H-pyrrolo[3,2-d]pyrimidin-2-yl)-2-methyl-1H-indole-4-carboxamide 1-(4-((3-fluorobenzyl)amino)-5-methyl-6,7-dihydro-5H-pyrrolo[3,2-d]pyrimidin-2-yl)-6-fluoro-1H-indazole-4-carboxamide 1-(4-((3-fluorobenzyl)amino)-5-methyl-6,7-dihydro-5H-pyrrolo[3,2-d]pyrimidin-2-yl)-6-fluoro-2-methoxy-1H-benzo[d]imidazole-4-carboxamide 1-(4-((3-fluorobenzyl)amino)-5-methyl-6,7-dihydro-5H-pyrrolo[3,2-d]pyrimidin-2-yl)-6-fluoro-2-methyl-1H-indole-4-carboxamide 1-(4-((3-fluorobenzyl)amino)-6,7,8,9-tetrahydro-5H-cyclohepta[d]pyrimidin-2-yl)-1H-indazole-4-carboxamide 1-(4-((3-fluorobenzyl)amino)-6,7,8,9-tetrahydro-5H-cyclohepta[d]pyrimidin-2-yl)-6-fluoro-1H-indazole-4-carboxamide 1-(4-((3-fluorobenzyl)amino)-6,7-dihydro-5H-cyclopenta[d]pyrimidin-2-yl)-1H-indazole-4-carboxamide 1-(4-((3-fluorobenzyl)amino)-6,7-dihydro-5H-cyclopenta[d]pyrimidin-2-yl)-6-fluoro-1H-indazole-4-carboxamide 1-(4-((3-fluorobenzyl)amino)-6,7-dihydro-5H-pyrano[2,3-d]pyrimidin-2-yl)-1H-indazole-4-carboxamide 1-(4-((3-fluorobenzyl)amino)-6,7-dihydro-5H-pyrano[2,3-d]pyrimidin-2-yl)-2-methoxy-1H-benzo[d]imidazole-4-carboxamide 1-(4-((3-fluorobenzyl)amino)-6,7-dihydro-5H-pyrano[2,3-d]pyrimidin-2-yl)-2-methyl-1H-indole-4-carboxamide 1-(4-((3-fluorobenzyl)amino)-6,7-dihydro-5H-pyrano[2,3-d]pyrimidin-2-yl)-6-fluoro-1H-indazole-4-carboxamide 1-(4-((3-fluorobenzyl)amino)-6,7-dihydro-5H-pyrano[2,3-d]pyrimidin-2-yl)-6-fluoro-2-methoxy-1H-benzo[d]imidazole-4-carboxamide 1-(4-((3-fluorobenzyl)amino)-6,7-dihydro-5H-pyrano[2,3-d]pyrimidin-2-yl)-6-fluoro-2-methyl-1H-indole-4-carboxamide 1-(4-((3-fluorobenzyl)amino)-6,7-dihydro-5H-pyrrolo[2,3-d]pyrimidin-2-yl)-1H-indazole-4-carboxamide 1-(4-((3-fluorobenzyl)amino)-6,7-dihydro-5H-pyrrolo[2,3-d]pyrimidin-2-yl)-2-methoxy-1H-benzo[d]imidazole-4-carboxamide 1-(4-((3-fluorobenzyl)amino)-6,7-dihydro-5H-pyrrolo[2,3-d]pyrimidin-2-yl)-2-methyl-1H-indole-4-carboxamide 1-(4-((3-fluorobenzyl)amino)-6,7-dihydro-5H-pyrrolo[2,3-d]pyrimidin-2-yl)-6-fluoro-1H-indazole-4-carboxamide 1-(4-((3-fluorobenzyl)amino)-6,7-dihydro-5H-pyrrolo[2,3-d]pyrimidin-2-yl)-6-fluoro-2-methoxy-1H-benzo[d]imidazole-4-carboxamide 1-(4-((3-fluorobenzyl)amino)-6,7-dihydro-5H-pyrrolo[2,3-d]pyrimidin-2-yl)-6-fluoro-2-methyl-1H-indole-4-carboxamide 1-(4-((3-fluorobenzyl)amino)-6,7-dihydro-5H-pyrrolo[3,2-d]pyrimidin-2-yl)-1H-indazole-4-carboxamide 1-(4-((3-fluorobenzyl)amino)-6,7-dihydro-5H-pyrrolo[3,2-d]pyrimidin-2-yl)-2-methoxy-1H-benzo[d]imidazole-4-carboxamide 1-(4-((3-fluorobenzyl)amino)-6,7-dihydro-5H-pyrrolo[3,2-d]pyrimidin-2-yl)-2-methyl-1H-indole-4-carboxamide 1-(4-((3-fluorobenzyl)amino)-6,7-dihydro-5H-pyrrolo[3,2-d]pyrimidin-2-yl)-6-fluoro-1H-indazole-4-carboxamide 1-(4-((3-fluorobenzyl)amino)-6,7-dihydro-5H-pyrrolo[3,2-d]pyrimidin-2-yl)-6-fluoro-2-methoxy-1H-benzo[d]imidazole-4-carboxamide 1-(4-((3-fluorobenzyl)amino)-6,7-dihydro-5H-pyrrolo[3,2-d]pyrimidin-2-yl)-6-fluoro-2-methyl-1H-indole-4-carboxamide 1-(4-((3-fluorobenzyl)amino)-6,7-dihydro-5H-pyrrolo[3,4-d]pyrimidin-2-yl)-1H-indazole-4-carboxamide 1-(4-((3-fluorobenzyl)amino)-6,7-dihydro-5H-pyrrolo[3,4-d]pyrimidin-2-yl)-6-fluoro-1H-indazole-4-carboxamide 1-(4-((3-fluorobenzyl)amino)-6,8-dihydro-5H-pyrano[3,4-d]pyrimidin-2-yl)-1H-indazole-4-carboxamide 1-(4-((3-fluorobenzyl)amino)-6,8-dihydro-5H-pyrano[3,4-d]pyrimidin-2-yl)-6-fluoro-1H-indazole-4-carboxamide 1-(4-((3-fluorobenzyl)amino)-6-methyl-5,6,7,8-tetrahydropyrido[4,3-d]pyrimidin-2-yl)-1H-indazole-4-carboxamide 1-(4-((3-fluorobenzyl)amino)-6-methyl-5,6,7,8-tetrahydropyrido[4,3-d]pyrimidin-2-yl)-6-fluoro-1H-indazole-4-carboxamide 1-(4-((3-fluorobenzyl)amino)-6-methyl-6,7-dihydro-5H-pyrrolo[3,4-d]pyrimidin-2-yl)-1H-indazole-4-carboxamide 1-(4-((3-fluorobenzyl)amino)-6-methyl-6,7-dihydro-5H-pyrrolo[3,4-d]pyrimidin-2-yl)-6-fluoro-1H-indazole-4-carboxamide 1-(4-((3-fluorobenzyl)amino)-7,8-dihydro-5H-pyrano[4,3-d]pyrimidin-2-yl)-1H-indazole-4-carboxamide 1-(4-((3-fluorobenzyl)amino)-7,8-dihydro-5H-pyrano[4,3-d]pyrimidin-2-yl)-6-fluoro-1H-indazole-4-carboxamide 1-(4-((3-fluorobenzyl)amino)-7-methyl-5,6,7,8-tetrahydropyrido[3,4-d]pyrimidin-2-yl)-1H-indazole-4-carboxamide 1-(4-((3-fluorobenzyl)amino)-7-methyl-5,6,7,8-tetrahydropyrido[3,4-d]pyrimidin-2-yl)-6-fluoro-1H-indazole-4-carboxamide 1-(4-((3-fluorobenzyl)amino)-7-methyl-6,7-dihydro-5H-pyrrolo[2,3-d]pyrimidin-2-yl)-1H-indazole-4-carboxamide 1-(4-((3-fluorobenzyl)amino)-7-methyl-6,7-dihydro-5H-pyrrolo[2,3-d]pyrimidin-2-yl)-2-methoxy-1H-benzo[d]imidazole-4-carboxamide 1-(4-((3-fluorobenzyl)amino)-7-methyl-6,7-dihydro-5H-pyrrolo[2,3-d]pyrimidin-2-yl)-2-methyl-1H-indole-4-carboxamide 1-(4-((3-fluorobenzyl)amino)-7-methyl-6,7-dihydro-5H-pyrrolo[2,3-d]pyrimidin-2-yl)-6-fluoro-1H-indazole-4-carboxamide 1-(4-((3-fluorobenzyl)amino)-7-methyl-6,7-dihydro-5H-pyrrolo[2,3-d]pyrimidin-2-yl)-6-fluoro-2-methoxy-1H-benzo[d]imidazole-4-carboxamide 1-(4-((3-fluorobenzyl)amino)-7-methyl-6,7-dihydro-5H-pyrrolo[2,3-d]pyrimidin-2-yl)-6-fluoro-2-methyl-1H-indole-4-carboxamide 1-(4-((3-fluorobenzyl)amino)-8-methyl-5,6,7,8-tetrahydropyrido[2,3-d]pyrimidin-2-yl)-1H-indazole-4-carboxamide
1-(4-((3-fluorobenzyl)amino)-8-methyl-5,6,7,8-tetrahydropyrido[2,3-d]pyrimidin-2-yl)-2-methoxy-1H-benzo[d]imidazole-4-carboxamide
1-(4-((3-fluorobenzyl)amino)-8-methyl-5,6,7,8-tetrahydropyrido[2,3-d]pyrimidin-2-yl)-2-methyl-1H-indole-4-carboxamide
1-(4-((3-fluorobenzyl)amino)-8-methyl-5,6,7,8-tetrahydropyrido[2,3-d]pyrimidin-2-yl)-6-fluoro-1H-indazole-4-carboxamide
1-(4-((3-fluorobenzyl)amino)-8-methyl-5,6,7,8-tetrahydropyrido[2,3-d]pyrimidin-2-yl)-6-fluoro-2-methoxy-1H-benzo[d]imidazole-4-carboxamide
1-(4-((3-fluorobenzyl)amino)-8-methyl-5,6,7,8-tetrahydropyrido[2,3-d]pyrimidin-2-yl)-6-fluoro-2-methyl-1H-indole-4-carboxamide
1-(4-((thiophen-2-ylmethyl)amino)-5,6,7,8-tetrahydropyrido[2,3-d]pyrimidin-2-yl)-1H-indazole-4-carboxamide
1-(4-((thiophen-2-ylmethyl)amino)-5,6,7,8-tetrahydropyrido[2,3-d]pyrimidin-2-yl)-2-methoxy-1H-benzo[d]imidazole-4-carboxamide
1-(4-((thiophen-2-ylmethyl)amino)-5,6,7,8-tetrahydropyrido[2,3-d]pyrimidin-2-yl)-2-methyl-1H-indole-4-carboxamide
1-(4-((thiophen-2-ylmethyl)amino)-5,6,7,8-tetrahydropyrido[3,2-d]pyrimidin-2-yl)-1H-indazole-4-carboxamide
1-(4-((thiophen-2-ylmethyl)amino)-5,6,7,8-tetrahydropyrido[3,2-d]pyrimidin-2-yl)-2-methoxy-1H-benzo[d]imidazole-4-carboxamide
1-(4-((thiophen-2-ylmethyl)amino)-5,6,7,8-tetrahydropyrido[3,2-d]pyrimidin-2-yl)-2-methyl-1H-indole-4-carboxamide
1-(4-((thiophen-2-ylmethyl)amino)-5,6,7,8-tetrahydropyrido[3,4-d]pyrimidin-2-yl)-1H-indazole-4-carboxamide
1-(4-((thiophen-2-ylmethyl)amino)-5,6,7,8-tetrahydropyrido[4,3-d]pyrimidin-2-yl)-1H-indazole-4-carboxamide
1-(4-((thiophen-2-ylmethyl)amino)-5,6,7,8-tetrahydroquinazolin-2-yl)-1H-indazole-4-carboxamide
1-(4-((thiophen-2-ylmethyl)amino)-5,6-dihydrofuro[2,3-d]pyrimidin-2-yl)-1H-indazole-4-carboxamide
1-(4-((thiophen-2-ylmethyl)amino)-5,6-dihydrofuro[2,3-d]pyrimidin-2-yl)-2-methoxy-1H-benzo[d]imidazole-4-carboxamide
1-(4-((thiophen-2-ylmethyl)amino)-5,6-dihydrofuro[2,3-d]pyrimidin-2-yl)-2-methyl-1H-indole-4-carboxamide
1-(4-((thiophen-2-ylmethyl)amino)-5,7-dihydrofuro[3,4-d]pyrimidin-2-yl)-1H-indazole-4-carboxamide
1-(4-((thiophen-2-ylmethyl)amino)-5-methyl-5,6,7,8-tetrahydropyrido[3,2-d]pyrimidin-2-yl)-1H-indazole-4-carboxamide
1-(4-((thiophen-2-ylmethyl)amino)-5-methyl-5,6,7,8-tetrahydropyrido[3,2-d]pyrimidin-2-yl)-2-methoxy-1H-benzo[d]imidazole-4-carboxamide
1-(4-((thiophen-2-ylmethyl)amino)-5-methyl-5,6,7,8-tetrahydropyrido[3,2-d]pyrimidin-2-yl)-2-methyl-1H-indole-4-carboxamide
1-(4-((thiophen-2-ylmethyl)amino)-5-methyl-6,7-dihydro-5H-pyrrolo[3,2-d]pyrimidin-2-yl)-1H-indazole-4-carboxamide
1-(4-((thiophen-2-ylmethyl)amino)-5-methyl-6,7-dihydro-5H-pyrrolo[3,2-d]pyrimidin-2-yl)-2-methoxy-1H-benzo[d]imidazole-4-carboxamide
1-(4-((thiophen-2-ylmethyl)amino)-5-methyl-6,7-dihydro-5H-pyrrolo[3,2-d]pyrimidin-2-yl)-2-methyl-1H-indole-4-carboxamide
1-(4-((thiophen-2-ylmethyl)amino)-6,7,8,9-tetrahydro-5H-cyclohepta[d]pyrimidin-2-yl)-1H-indazole-4-carboxamide
1-(4-((thiophen-2-ylmethyl)amino)-6,7-dihydro-5H-cyclopenta[d]pyrimidin-2-yl)-1H-indazole-4-carboxamide
1-(4-((thiophen-2-ylmethyl)amino)-6,7-dihydro-5H-pyrano[2,3-d]pyrimidin-2-yl)-1H-indazole-4-carboxamide
1-(4-((thiophen-2-ylmethyl)amino)-6,7-dihydro-5H-pyrano[2,3-d]pyrimidin-2-yl)-2-methoxy-1H-benzo[d]imidazole-4-carboxamide
1-(4-((thiophen-2-ylmethyl)amino)-6,7-dihydro-5H-pyrano[2,3-d]pyrimidin-2-yl)-2-methyl-1H-indole-4-carboxamide
1-(4-((thiophen-2-ylmethyl)amino)-6,7-dihydro-5H-pyrrolo[2,3-d]pyrimidin-2-yl)-1H-indazole-4-carboxamide
1-(4-((thiophen-2-ylmethyl)amino)-6,7-dihydro-5H-pyrrolo[2,3-d]pyrimidin-2-yl)-2-methoxy-1H-benzo[d]imidazole-4-carboxamide
1-(4-((thiophen-2-ylmethyl)amino)-6,7-dihydro-5H-pyrrolo[2,3-d]pyrimidin-2-yl)-2-methyl-1H-indole-4-carboxamide
1-(4-((thiophen-2-ylmethyl)amino)-6,7-dihydro-5H-pyrrolo[3,2-d]pyrimidin-2-yl)-1H-indazole-4-carboxamide
1-(4-((thiophen-2-ylmethyl)amino)-6,7-dihydro-5H-pyrrolo[3,2-d]pyrimidin-2-yl)-2-methoxy-1H-benzo[d]imidazole-4-carboxamide
1-(4-((thiophen-2-ylmethyl)amino)-6,7-dihydro-5H-pyrrolo[3,2-d]pyrimidin-2-yl)-2-methyl-1H-indole-4-carboxamide
1-(4-((thiophen-2-ylmethyl)amino)-6,7-dihydro-5H-pyrrolo[3,4-d]pyrimidin-2-yl)-1H-indazole-4-carboxamide
1-(4-((thiophen-2-ylmethyl)amino)-6,8-dihydro-5H-pyrano[3,4-d]pyrimidin-2-yl)-1H-indazole-4-carboxamide
1-(4-((thiophen-2-ylmethyl)amino)-6-methyl-5,6,7,8-tetrahydropyrido[4,3-d]pyrimidin-2-yl)-1H-indazole-4-carboxamide
1-(4-((thiophen-2-ylmethyl)amino)-6-methyl-6,7-dihydro-5H-pyrrolo[3,4-d]pyrimidin-2-yl)-1H-indazole-4-carboxamide
1-(4-((thiophen-2-ylmethyl)amino)-7,8-dihydro-5H-pyrano[4,3-d]pyrimidin-2-yl)-1H-indazole-4-carboxamide
1-(4-((thiophen-2-ylmethyl)amino)-7-methyl-5,6,7,8-tetrahydropyrido[3,4-d]pyrimidin-2-yl)-1H-indazole-4-carboxamide
1-(4-((thiophen-2-ylmethyl)amino)-7-methyl-6,7-dihydro-5H-pyrrolo[2,3-d]pyrimidin-2-yl)-1H-indazole-4-carboxamide
1-(4-((thiophen-2-ylmethyl)amino)-7-methyl-6,7-dihydro-5H-pyrrolo[2,3-d]pyrimidin-2-yl)-2-methoxy-1H-benzo[d]imidazole-4-carboxamide
1-(4-((thiophen-2-ylmethyl)amino)-7-methyl-6,7-dihydro-5H-pyrrolo[2,3-d]pyrimidin-2-yl)-2-methyl-1H-indole-4-carboxamide
1-(4-((thiophen-2-ylmethyl)amino)-8-methyl-5,6,7,8-tetrahydropyrido[2,3-d]pyrimidin-2-yl)-1H-indazole-4-carboxamide
1-(4-((thiophen-2-ylmethyl)amino)-8-methyl-5,6,7,8-tetrahydropyrido[2,3-d]pyrimidin-2-yl)-2-methoxy-1H-benzo[d]imidazole-4-carboxamide 1-(4-((thiophen-2-ylmethyl)amino)-8-methyl-5,6,7,8-tetrahydropyrido[2,3-d]pyrimidin-2-yl)-2-methyl-1H-indole-4-carboxamide 1-(4-(benzylamino)-5,6,7,8-tetrahydropyrido[2,3-d]pyrimidin-2-yl)-1H-indazole-4-carboxamide 1-(4-(benzylamino)-5,6,7,8-tetrahydropyrido[2,3-d]pyrimidin-2-yl)-2-(hydroxymethyl)-1H-indole-4-carboxamide 1-(4-(benzylamino)-5,6,7,8-tetrahydropyrido[2,3-d]pyrimidin-2-yl)-2-methoxy-1H-benzo[d]imidazole-4-carboxamide 1-(4-(benzylamino)-5,6,7,8-tetrahydropyrido[2,3-d]pyrimidin-2-yl)-2-methyl-1H-indole-4-carboxamide 1-(4-(benzylamino)-5,6,7,8-tetrahydropyrido[2,3-d]pyrimidin-2-yl)-6-fluoro-1H-indazole-4-carboxamide 1-(4-(benzylamino)-5,6,7,8-tetrahydropyrido[2,3-d]pyrimidin-2-yl)-6-fluoro-2-methoxy-1H-benzo[d]imidazole-4-carboxamide 1-(4-(benzylamino)-5,6,7,8-tetrahydropyrido[2,3-d]pyrimidin-2-yl)-6-fluoro-2-methyl-1H-indole-4-carboxamide 1-(4-(benzylamino)-5,6,7,8-tetrahydropyrido[3,2-d]pyrimidin-2-yl)-1H-indazole-4-carboxamide 1-(4-(benzylamino)-5,6,7,8-tetrahydropyrido[3,2-d]pyrimidin-2-yl)-2-methoxy-1H-benzo[d]imidazole-4-carboxamide 1-(4-(benzylamino)-5,6,7,8-tetrahydropyrido[3,2-d]pyrimidin-2-yl)-2-methyl-1H-indole-4-carboxamide 1-(4-(benzylamino)-5,6,7,8-tetrahydropyrido[3,2-d]pyrimidin-2-yl)-6-fluoro-1H-indazole-4-carboxamide 1-(4-(benzylamino)-5,6,7,8-tetrahydropyrido[3,2-d]pyrimidin-2-yl)-6-fluoro-2-methoxy-1H-benzo[d]imidazole-4-carboxamide 1-(4-(benzylamino)-5,6,7,8-tetrahydropyrido[3,2-d]pyrimidin-2-yl)-6-fluoro-2-methyl-1H-indole-4-carboxamide 1-(4-(benzylamino)-5,6,7,8-tetrahydropyrido[3,4-d]pyrimidin-2-yl)-1H-indazole-4-carboxamide 1-(4-(benzylamino)-5,6,7,8-tetrahydropyrido[3,4-d]pyrimidin-2-yl)-6-fluoro-1H-indazole-4-carboxamide 1-(4-(benzylamino)-5,6,7,8-tetrahydropyrido[4,3-d]pyrimidin-2-yl)-1H-indazole-4-carboxamide 1-(4-(benzylamino)-5,6,7,8-tetrahydropyrido[4,3-d]pyrimidin-2-yl)-6-fluoro-1H-indazole-4-carboxamide 1-(4-(benzylamino)-5,6,7,8-tetrahydroquinazolin-2-yl)-1H-indazole-4-carboxamide 1-(4-(benzylamino)-5,6,7,8-tetrahydroquinazolin-2-yl)-6-fluoro-1H-indazole-4-carboxamide 1-(4-(benzylamino)-5,6-dihydrofuro[2,3-d]pyrimidin-2-yl)-1H-indazole-4-carboxamide 1-(4-(benzylamino)-5,6-dihydrofuro[2,3-d]pyrimidin-2-yl)-2-methoxy-1H-benzo[d]imidazole-4-carboxamide 1-(4-(benzylamino)-5,6-dihydrofuro[2,3-d]pyrimidin-2-yl)-2-methyl-1H-indole-4-carboxamide 1-(4-(benzylamino)-5,6-dihydrofuro[2,3-d]pyrimidin-2-yl)-6-fluoro-1H-indazole-4-carboxamide 1-(4-(benzylamino)-5,6-dihydrofuro[2,3-d]pyrimidin-2-yl)-6-fluoro-2-methoxy-1H-benzo[d]imidazole-4-carboxamide 1-(4-(benzylamino)-5,6-dihydrofuro[2,3-d]pyrimidin-2-yl)-6-fluoro-2-methyl-1H-indole-4-carboxamide 1-(4-(benzylamino)-5,7-dihydrofuro[3,4-d]pyrimidin-2-yl)-1H-indazole-4-carboxamide 1-(4-(benzylamino)-5,7-dihydrofuro[3,4-d]pyrimidin-2-yl)-6-fluoro-1H-indazole-4-carboxamide 1-(4-(benzylamino)-5,7-dimethyl-5,6,7,8-tetrahydropyrido[3,4-d]pyrimidin-2-yl)-1H-indazole-4-carboxamide 1-(4-(benzylamino)-5,7-dimethyl-5,6,7,8-tetrahydropyrido[3,4-d]pyrimidin-2-yl)-2-methoxy-1H-benzo[d]imidazole-4-carboxamide 1-(4-(benzylamino)-5,7-dimethyl-5,6,7,8-tetrahydropyrido[3,4-d]pyrimidin-2-yl)-2-methyl-1H-indole-4-carboxamide 1-(4-(benzylamino)-5-methyl-5,6,7,8-tetrahydropyrido[3,2-d]pyrimidin-2-yl)-1H-indazole-4-carboxamide 1-(4-(benzylamino)-5-methyl-5,6,7,8-tetrahydropyrido[3,2-d]pyrimidin-2-yl)-2-methoxy-1H-benzo[d]imidazole-4-carboxamide 1-(4-(benzylamino)-5-methyl-5,6,7,8-tetrahydropyrido[3,2-d]pyrimidin-2-yl)-2-methyl-1H-indole-4-carboxamide 1-(4-(benzylamino)-5-methyl-5,6,7,8-tetrahydropyrido[3,2-d]pyrimidin-2-yl)-6-fluoro-1H-indazole-4-carboxamide 1-(4-(benzylamino)-5-methyl-5,6,7,8-tetrahydropyrido[3,2-d]pyrimidin-2-yl)-6-fluoro-2-methoxy-1H-benzo[d]imidazole-4-carboxamide 1-(4-(benzylamino)-5-methyl-5,6,7,8-tetrahydropyrido[3,2-d]pyrimidin-2-yl)-6-fluoro-2-methyl-1H-indole-4-carboxamide 1-(4-(benzylamino)-5-methyl-5,6,7,8-tetrahydropyrido[3,4-d]pyrimidin-2-yl)-1H-indazole-4-carboxamide 1-(4-(benzylamino)-5-methyl-5,6,7,8-tetrahydropyrido[3,4-d]pyrimidin-2-yl)-2-methoxy-1H-benzo[d]imidazole-4-carboxamide 1-(4-(benzylamino)-5-methyl-5,6,7,8-tetrahydropyrido[3,4-d]pyrimidin-2-yl)-2-methyl-1H-indole-4-carboxamide 1-(4-(benzylamino)-5-methyl-5,6,7,8-tetrahydropyrido[4,3-d]pyrimidin-2-yl)-1H-indazole-4-carboxamide 1-(4-(benzylamino)-5-methyl-5,6,7,8-tetrahydropyrido[4,3-d]pyrimidin-2-yl)-2-methoxy-1H-benzo[d]imidazole-4-carboxamide 1-(4-(benzylamino)-5-methyl-5,6,7,8-tetrahydropyrido[4,3-d]pyrimidin-2-yl)-2-methyl-1H-indole-4-carboxamide 1-(4-(benzylamino)-5-methyl-5,6,7,8-tetrahydroquinazolin-2-yl)-1H-indazole-4-carboxamide 1-(4-(benzylamino)-5-methyl-5,6,7,8-tetrahydroquinazolin-2-yl)-2-methoxy-1H-benzo[d]imidazole-4-carboxamide 1-(4-(benzylamino)-5-methyl-5,6,7,8-tetrahydroquinazolin-2-yl)-2-methyl-1H-indole-4-carboxamide 1-(4-(benzylamino)-5-methyl-6,7-dihydro-5H-pyrrolo[3,2-d]pyrimidin-2-yl)-1H-indazole-4-carboxamide 1-(4-(benzylamino)-5-methyl-6,7-dihydro-5H-pyrrolo[3,2-d]pyrimidin-2-yl)-2-methoxy-1H-benzo[d]imidazole-4-carboxamide 1-(4-(benzylamino)-5-methyl-6,7-dihydro-5H-pyrrolo[3,2-d]pyrimidin-2-yl)-2-methyl-1H-indole-4-carboxamide 1-(4-(benzylamino)-5-methyl-6,7-dihydro-5H-pyrrolo[3,2-d]pyrimidin-2-yl)-6-fluoro-1H-indazole-4-carboxamide 1-(4-(benzylamino)-5-methyl-6,7-dihydro-5H-pyrrolo[3,2-d]pyrimidin-2-yl)-6-fluoro-2-methoxy-1H-benzo[d]imidazole-4-carboxamide 1-(4-(benzylamino)-5-methyl-6,7-dihydro-5H-pyrrolo[3,2-d]pyrimidin-2-yl)-6-fluoro-2-methyl-1H-indole-4-carboxamide 1-(4-(benzylamino)-5-methyl-6,8-dihydro-5H-pyrano[3,4-d]pyrimidin-2-yl)-1H-indazole-4-carboxamide 1-(4-(benzylamino)-5-methyl-6,8-dihydro-5H-pyrano[3,4-d]pyrimidin-2-yl)-2-methoxy-1H-benzo[d]imidazole-4-carboxamide 1-(4-(benzylamino)-5-methyl-6,8-dihydro-5H-pyrano[3,4-d]pyrimidin-2-yl)-2-methyl-1H-indole-4-carboxamide 1-(4-(benzylamino)-5-methyl-7,8-dihydro-5H-pyrano[4,3-d]pyrimidin-2-yl)-1H-indazole-4-carboxamide 1-(4-(benzylamino)-5-methyl-7,8-dihydro-5H-pyrano[4,3-d]pyrimidin-2-yl)-2-methoxy-1H-benzo[d]imidazole-4-carboxamide 1-(4-(benzylamino)-5-methyl-7,8-dihydro-5H-pyrano[4,3-d]pyrimidin-2-yl)-2-methyl-1H-indole-4-carboxamide 1-(4-(benzylamino)-6,7,8,9-tetrahydro-5H-cyclohepta[d]pyrimidin-2-yl)-1H-indazole-4-carboxamide
1-(4-(benzylamino)-6,7,8,9-tetrahydro-5H-cyclohepta[d]pyrimidin-2-yl)-6-fluoro-1H-indazole-4-carboxamide
1-(4-(benzylamino)-6,7,8,9-tetrahydro-5H-pyrimido[4,5-d]azepin-2-yl)-2-methyl-1H-indole-4-carboxamide
1-(4-(benzylamino)-6,7-dihydro-5H-cyclopenta[d]pyrimidin-2-yl)-1H-indazole-4-carboxamide
1-(4-(benzylamino)-6,7-dihydro-5H-cyclopenta[d]pyrimidin-2-yl)-6-fluoro-1H-indazole-4-carboxamide
1-(4-(benzylamino)-6,7-dihydro-5H-pyrano[2,3-d]pyrimidin-2-yl)-1H-indazole-4-carboxamide
1-(4-(benzylamino)-6,7-dihydro-5H-pyrano[2,3-d]pyrimidin-2-yl)-2-(hydroxymethyl)-1H-indole-4-carboxamide
1-(4-(benzylamino)-6,7-dihydro-5H-pyrano[2,3-d]pyrimidin-2-yl)-2-methoxy-1H-benzo[d]imidazole-4-carboxamide
1-(4-(benzylamino)-6,7-dihydro-5H-pyrano[2,3-d]pyrimidin-2-yl)-2-methyl-1H-indole-4-carboxamide
1-(4-(benzylamino)-6,7-dihydro-5H-pyrano[2,3-d]pyrimidin-2-yl)-6-fluoro-1H-indazole-4-carboxamide
1-(4-(benzylamino)-6,7-dihydro-5H-pyrano[2,3-d]pyrimidin-2-yl)-6-fluoro-2-methoxy-1H-benzo[d]imidazole-4-carboxamide
1-(4-(benzylamino)-6,7-dihydro-5H-pyrano[2,3-d]pyrimidin-2-yl)-6-fluoro-2-methyl-1H-indole-4-carboxamide
1-(4-(benzylamino)-6,7-dihydro-5H-pyrrolo[2,3-d]pyrimidin-2-yl)-1H-indazole-4-carboxamide
1-(4-(benzylamino)-6,7-dihydro-5H-pyrrolo[2,3-d]pyrimidin-2-yl)-2-methoxy-1H-benzo[d]imidazole-4-carboxamide
1-(4-(benzylamino)-6,7-dihydro-5H-pyrrolo[2,3-d]pyrimidin-2-yl)-2-methyl-1H-indole-4-carboxamide
1-(4-(benzylamino)-6,7-dihydro-5H-pyrrolo[2,3-d]pyrimidin-2-yl)-6-fluoro-1H-indazole-4-carboxamide
1-(4-(benzylamino)-6,7-dihydro-5H-pyrrolo[2,3-d]pyrimidin-2-yl)-6-fluoro-2-methoxy-1H-benzo[d]imidazole-4-carboxamide
1-(4-(benzylamino)-6,7-dihydro-5H-pyrrolo[2,3-d]pyrimidin-2-yl)-6-fluoro-2-methyl-1H-indole-4-carboxamide
1-(4-(benzylamino)-6,7-dihydro-5H-pyrrolo[3,2-d]pyrimidin-2-yl)-1H-indazole-4-carboxamide
1-(4-(benzylamino)-6,7-dihydro-5H-pyrrolo[3,2-d]pyrimidin-2-yl)-2-methoxy-1H-benzo[d]imidazole-4-carboxamide
1-(4-(benzylamino)-6,7-dihydro-5H-pyrrolo[3,2-d]pyrimidin-2-yl)-2-methyl-1H-indole-4-carboxamide
1-(4-(benzylamino)-6,7-dihydro-5H-pyrrolo[3,2-d]pyrimidin-2-yl)-6-fluoro-1H-indazole-4-carboxamide
1-(4-(benzylamino)-6,7-dihydro-5H-pyrrolo[3,2-d]pyrimidin-2-yl)-6-fluoro-2-methoxy-1H-benzo[d]imidazole-4-carboxamide
1-(4-(benzylamino)-6,7-dihydro-5H-pyrrolo[3,2-d]pyrimidin-2-yl)-6-fluoro-2-methyl-1H-indole-4-carboxamide
1-(4-(benzylamino)-6,7-dihydro-5H-pyrrolo[3,4-d]pyrimidin-2-yl)-1H-indazole-4-carboxamide
1-(4-(benzylamino)-6,7-dihydro-5H-pyrrolo[3,4-d]pyrimidin-2-yl)-6-fluoro-1H-indazole-4-carboxamide
1-(4-(benzylamino)-6,7-dimethyl-5,6,7,8-tetrahydropyrido[3,4-d]pyrimidin-2-yl)-1H-indazole-4-carboxamide
1-(4-(benzylamino)-6,7-dimethyl-5,6,7,8-tetrahydropyrido[3,4-d]pyrimidin-2-yl)-2-methoxy-1H-benzo[d]imidazole-4-carboxamide
1-(4-(benzylamino)-6,7-dimethyl-5,6,7,8-tetrahydropyrido[3,4-d]pyrimidin-2-yl)-2-methyl-1H-indole-4-carboxamide
1-(4-(benzylamino)-6,7-dimethyl-5,6,7,8-tetrahydropyrido[4,3-d]pyrimidin-2-yl)-1H-indazole-4-carboxamide
1-(4-(benzylamino)-6,7-dimethyl-5,6,7,8-tetrahydropyrido[4,3-d]pyrimidin-2-yl)-2-methoxy-1H-benzo[d]imidazole-4-carboxamide
1-(4-(benzylamino)-6,7-dimethyl-5,6,7,8-tetrahydropyrido[4,3-d]pyrimidin-2-yl)-2-methyl-1H-indole-4-carboxamide
1-(4-(benzylamino)-6,8-dihydro-5H-pyrano[3,4-d]pyrimidin-2-yl)-1H-indazole-4-carboxamide
1-(4-(benzylamino)-6,8-dihydro-5H-pyrano[3,4-d]pyrimidin-2-yl)-6-fluoro-1H-indazole-4-carboxamide
1-(4-(benzylamino)-6,8-dimethyl-5,6,7,8-tetrahydropyrido[4,3-d]pyrimidin-2-yl)-1H-indazole-4-carboxamide
1-(4-(benzylamino)-6,8-dimethyl-5,6,7,8-tetrahydropyrido[4,3-d]pyrimidin-2-yl)-2-methyl-1H-indole-4-carboxamide
1-(4-(benzylamino)-6-methyl-5,6,7,8-tetrahydropyrido[3,4-d]pyrimidin-2-yl)-1H-indazole-4-carboxamide
1-(4-(benzylamino)-6-methyl-5,6,7,8-tetrahydropyrido[3,4-d]pyrimidin-2-yl)-2-methoxy-1H-benzo[d]imidazole-4-carboxamide
1-(4-(benzylamino)-6-methyl-5,6,7,8-tetrahydropyrido[3,4-d]pyrimidin-2-yl)-2-methyl-1H-indole-4-carboxamide
1-(4-(benzylamino)-6-methyl-5,6,7,8-tetrahydropyrido[4,3-d]pyrimidin-2-yl)-1H-indazole-4-carboxamide
1-(4-(benzylamino)-6-methyl-5,6,7,8-tetrahydropyrido[4,3-d]pyrimidin-2-yl)-2-methoxy-1H-benzo[d]imidazole-4-carboxamide
1-(4-(benzylamino)-6-methyl-5,6,7,8-tetrahydropyrido[4,3-d]pyrimidin-2-yl)-6-fluoro-1H-indazole-4-carboxamide
1-(4-(benzylamino)-6-methyl-6,7-dihydro-5H-pyrrolo[3,4-d]pyrimidin-2-yl)-1H-indazole-4-carboxamide
1-(4-(benzylamino)-6-methyl-6,7-dihydro-5H-pyrrolo[3,4-d]pyrimidin-2-yl)-6-fluoro-1H-indazole-4-carboxamide
1-(4-(benzylamino)-6-methyl-6,8-dihydro-5H-pyrano[3,4-d]pyrimidin-2-yl)-1H-indazole-4-carboxamide
1-(4-(benzylamino)-6-methyl-6,8-dihydro-5H-pyrano[3,4-d]pyrimidin-2-yl)-2-methoxy-1H-benzo[d]imidazole-4-carboxamide
1-(4-(benzylamino)-6-methyl-6,8-dihydro-5H-pyrano[3,4-d]pyrimidin-2-yl)-2-methyl-1H-indole-4-carboxamide
1-(4-(benzylamino)-7,8-dihydro-5H-pyrano[4,3-d]pyrimidin-2-yl)-1H-indazole-4-carboxamide
1-(4-(benzylamino)-7,8-dihydro-5H-pyrano[4,3-d]pyrimidin-2-yl)-6-fluoro-1H-indazole-4-carboxamide
1-(4-(benzylamino)-7,8-dimethyl-5,6,7,8-tetrahydropyrido[3,4-d]pyrimidin-2-yl)-1H-indazole-4-carboxamide
1-(4-(benzylamino)-7,8-dimethyl-5,6,7,8-tetrahydropyrido[3,4-d]pyrimidin-2-yl)-2-methoxy-1H-benzo[d]imidazole-4-carboxamide
1-(4-(benzylamino)-7,8-dimethyl-5,6,7,8-tetrahydropyrido[3,4-d]pyrimidin-2-yl)-2-methyl-1H-indole-4-carboxamide
1-(4-(benzylamino)-7-methyl-5,6,7,8-tetrahydropyrido[3,4-d]pyrimidin-2-yl)-1H-indazole-4-carboxamide
1-(4-(benzylamino)-7-methyl-5,6,7,8-tetrahydropyrido[3,4-d]pyrimidin-2-yl)-6-fluoro-1H-indazole-4-carboxamide
1-(4-(benzylamino)-7-methyl-5,6,7,8-tetrahydropyrido[4,3-d]pyrimidin-2-yl)-1H-indazole-4-carboxamide
1-(4-(benzylamino)-7-methyl-5,6,7,8-tetrahydropyrido[4,3-d]pyrimidin-2-yl)-2-methoxy-1H-benzo[d]imidazole-4-carboxamide
1-(4-(benzylamino)-7-methyl-5,6,7,8-tetrahydropyrido[4,3-d]pyrimidin-2-yl)-2-methyl-1H-indole-4-carboxamide
1-(4-(benzylamino)-7-methyl-5,6,7,8-tetrahydroquinazolin-2-yl)-1H-indazole-4-carboxamide 1-(4-(benzylamino)-7-methyl-5,6,7,8-tetrahydroquinazolin-2-yl)-2-methoxy-1H-benzo[d]imidazole-4-carboxamide
1-(4-(benzylamino)-7-methyl-5,6,7,8-tetrahydroquinazolin-2-yl)-2-methyl-1H-indole-4-carboxamide
1-(4-(benzylamino)-7-methyl-6,7-dihydro-5H-pyrrolo[2,3-d]pyrimidin-2-yl)-1H-indazole-4-carboxamide
1-(4-(benzylamino)-7-methyl-6,7-dihydro-5H-pyrrolo[2,3-d]pyrimidin-2-yl)-2-methoxy-1H-benzo[d]imidazole-4-carboxamide
1-(4-(benzylamino)-7-methyl-6,7-dihydro-5H-pyrrolo[2,3-d]pyrimidin-2-yl)-2-methyl-1H-indole-4-carboxamide
1-(4-(benzylamino)-7-methyl-6,7-dihydro-5H-pyrrolo[2,3-d]pyrimidin-2-yl)-6-fluoro-1H-indazole-4-carboxamide
1-(4-(benzylamino)-7-methyl-6,7-dihydro-5H-pyrrolo[2,3-d]pyrimidin-2-yl)-6-fluoro-2-methoxy-1H-benzo[d]imidazole-4-carboxamide
1-(4-(benzylamino)-7-methyl-6,7-dihydro-5H-pyrrolo[2,3-d]pyrimidin-2-yl)-6-fluoro-2-methyl-1H-indole-4-carboxamide
1-(4-(benzylamino)-7-methyl-7,8-dihydro-5H-pyrano[4,3-d]pyrimidin-2-yl)-1H-indazole-4-carboxamide
1-(4-(benzylamino)-7-methyl-7,8-dihydro-5H-pyrano[4,3-d]pyrimidin-2-yl)-2-methoxy-1H-benzo[d]imidazole-4-carboxamide
1-(4-(benzylamino)-7-methyl-7,8-dihydro-5H-pyrano[4,3-d]pyrimidin-2-yl)-2-methyl-1H-indole-4-carboxamide
1-(4-(benzylamino)-8-methyl-5,6,7,8-tetrahydropyrido[2,3-d]pyrimidin-2-yl)-1H-indazole-4-carboxamide
1-(4-(benzylamino)-8-methyl-5,6,7,8-tetrahydropyrido[2,3-d]pyrimidin-2-yl)-2-methoxy-1H-benzo[d]imidazole-4-carboxamide
1-(4-(benzylamino)-8-methyl-5,6,7,8-tetrahydropyrido[2,3-d]pyrimidin-2-yl)-2-methyl-1H-indole-4-carboxamide
1-(4-(benzylamino)-8-methyl-5,6,7,8-tetrahydropyrido[2,3-d]pyrimidin-2-yl)-6-fluoro-1H-indazole-4-carboxamide
1-(4-(benzylamino)-8-methyl-5,6,7,8-tetrahydropyrido[2,3-d]pyrimidin-2-yl)-6-fluoro-2-methoxy-1H-benzo[d]imidazole-4-carboxamide
1-(4-(benzylamino)-8-methyl-5,6,7,8-tetrahydropyrido[2,3-d]pyrimidin-2-yl)-6-fluoro-2-methyl-1H-indole-4-carboxamide
1-(4-(benzylamino)-8-methyl-5,6,7,8-tetrahydropyrido[3,4-d]pyrimidin-2-yl)-1H-indazole-4-carboxamide
1-(4-(benzylamino)-8-methyl-5,6,7,8-tetrahydropyrido[3,4-d]pyrimidin-2-yl)-2-methoxy-1H-benzo[d]imidazole-4-carboxamide
1-(4-(benzylamino)-8-methyl-5,6,7,8-tetrahydropyrido[3,4-d]pyrimidin-2-yl)-2-methyl-1H-indole-4-carboxamide
1-(4-(benzylamino)-8-methyl-5,6,7,8-tetrahydropyrido[4,3-d]pyrimidin-2-yl)-1H-indazole-4-carboxamide
1-(4-(benzylamino)-8-methyl-5,6,7,8-tetrahydropyrido[4,3-d]pyrimidin-2-yl)-2-methoxy-1H-benzo[d]imidazole-4-carboxamide
1-(4-(benzylamino)-8-methyl-5,6,7,8-tetrahydropyrido[4,3-d]pyrimidin-2-yl)-2-methyl-1H-indole-4-carboxamide
1-(4-(benzylamino)-8-methyl-5,6,7,8-tetrahydroquinazolin-2-yl)-1H-indazole-4-carboxamide
1-(4-(benzylamino)-8-methyl-5,6,7,8-tetrahydroquinazolin-2-yl)-2-methoxy-1H-benzo[d]imidazole-4-carboxamide
1-(4-(benzylamino)-8-methyl-5,6,7,8-tetrahydroquinazolin-2-yl)-2-methyl-1H-indole-4-carboxamide
1-(4-(benzylamino)-8-methyl-6,8-dihydro-5H-pyrano[3,4-d]pyrimidin-2-yl)-1H-indazole-4-carboxamide
1-(4-(benzylamino)-8-methyl-6,8-dihydro-5H-pyrano[3,4-d]pyrimidin-2-yl)-2-methoxy-1H-benzo[d]imidazole-4-carboxamide
1-(4-(benzylamino)-8-methyl-6,8-dihydro-5H-pyrano[3,4-d]pyrimidin-2-yl)-2-methyl-1H-indole-4-carboxamide
1-(4-(benzylamino)-8-methyl-7,8-dihydro-5H-pyrano[4,3-d]pyrimidin-2-yl)-1H-indazole-4-carboxamide
1-(4-(benzylamino)-8-methyl-7,8-dihydro-5H-pyrano[4,3-d]pyrimidin-2-yl)-2-methoxy-1H-benzo[d]imidazole-4-carboxamide
1-(4-(benzylamino)-8-methyl-7,8-dihydro-5H-pyrano[4,3-d]pyrimidin-2-yl)-2-methyl-1H-indole-4-carboxamide
2-(4-(aminomethyl)-2-methyl-1H-indol-1-yl)-N-benzyl-6,7-dihydro-5H-pyrano[2,3-d]pyrimidin-4-amine
2-(aminomethyl)-1-(4-(benzylamino)-6,7-dihydro-5H-pyrano[2,3-d]pyrimidin-2-yl)-1H-indole-4-carboxamide
3-(4-((3-fluorobenzyl)amino)-5,6,7,8-tetrahydropyrido[2,3-d]pyrimidin-2-yl)-2-methyl-1H-indole-7-carboxamide
3-(4-((3-fluorobenzyl)amino)-5,6,7,8-tetrahydropyrido[3,2-d]pyrimidin-2-yl)-2-methyl-1H-indole-7-carboxamide
3-(4-((3-fluorobenzyl)amino)-5,6,7,8-tetrahydropyrido[3,4-d]pyrimidin-2-yl)-2-methyl-1H-indole-7-carboxamide
3-(4-((3-fluorobenzyl)amino)-5,6,7,8-tetrahydropyrido[4,3-d]pyrimidin-2-yl)-2-methyl-1H-indole-7-carboxamide
3-(4-((3-fluorobenzyl)amino)-5,6,7,8-tetrahydroquinazolin-2-yl)-2-methyl-1H-indole-7-carboxamide
3-(4-((3-fluorobenzyl)amino)-5,6-dihydrofuro[2,3-d]pyrimidin-2-yl)-2-methyl-1H-indole-7-carboxamide
3-(4-((3-fluorobenzyl)amino)-5,7-dihydrofuro[3,4-d]pyrimidin-2-yl)-2-methyl-1H-indole-7-carboxamide
3-(4-((3-fluorobenzyl)amino)-5-methyl-5,6,7,8-tetrahydropyrido[3,2-d]pyrimidin-2-yl)-2-methyl-1H-indole-7-carboxamide
3-(4-((3-fluorobenzyl)amino)-5-methyl-6,7-dihydro-5H-pyrrolo[3,2-d]pyrimidin-2-yl)-2-methyl-1H-indole-7-carboxamide
3-(4-((3-fluorobenzyl)amino)-6,7,8,9-tetrahydro-5H-cyclohepta[d]pyrimidin-2-yl)-2-methyl-1H-indole-7-carboxamide
3-(4-((3-fluorobenzyl)amino)-6,7-dihydro-5H-cyclopenta[d]pyrimidin-2-yl)-2-methyl-1H-indole-7-carboxamide
3-(4-((3-fluorobenzyl)amino)-6,7-dihydro-5H-pyrano[2,3-d]pyrimidin-2-yl)-2-methyl-1H-indole-7-carboxamide
3-(4-((3-fluorobenzyl)amino)-6,7-dihydro-5H-pyrrolo[2,3-d]pyrimidin-2-yl)-2-methyl-1H-indole-7-carboxamide
3-(4-((3-fluorobenzyl)amino)-6,7-dihydro-5H-pyrrolo[3,2-d]pyrimidin-2-yl)-2-methyl-1H-indole-7-carboxamide
3-(4-((3-fluorobenzyl)amino)-6,7-dihydro-5H-pyrrolo[3,4-d]pyrimidin-2-yl)-2-methyl-1H-indole-7-carboxamide
3-(4-((3-fluorobenzyl)amino)-6,8-dihydro-5H-pyrano[3,4-d]pyrimidin-2-yl)-2-methyl-1H-indole-7-carboxamide
3-(4-((3-fluorobenzyl)amino)-6-methyl-5,6,7,8-tetrahydropyrido[4,3-d]pyrimidin-2-yl)-2-methyl-1H-indole-7-carboxamide
3-(4-((3-fluorobenzyl)amino)-6-methyl-6,7-dihydro-5H-pyrrolo[3,4-d]pyrimidin-2-yl)-2-methyl-1H-indole-7-carboxamide
3-(4-((3-fluorobenzyl)amino)-7,8-dihydro-5H-pyrano[4,3-d]pyrimidin-2-yl)-2-methyl-1H-indole-7-carboxamide
3-(4-((3-fluorobenzyl)amino)-7,8-dihydro-5H-pyrano[4,3-d]pyrimidin-2-yl)-2-methylbenzofuran-7-carboxamide
3-(4-((3-fluorobenzyl)amino)-7-methyl-5,6,7,8-tetrahydropyrido[3,4-d]pyrimidin-2-yl)-2-methyl-1H-indole-7-carboxamide
3-(4-((3-fluorobenzyl)amino)-7-methyl-6,7-dihydro-5H-pyrrolo[2,3-d]pyrimidin-2-yl)-2-methyl-1H-indole-7-carboxamide
3-(4-((3-fluorobenzyl)amino)-8-methyl-5,6,7,8-tetrahydropyrido[2,3-d]pyrimidin-2-yl)-2-methyl-1H-indole-7-carboxamide 3-(4-(benzylamino)-5,6,7,8-tetrahydropyrido[2,3-d]pyrimidin-2-yl)-2-methyl-1H-indole-7-carboxamide
3-(4-(benzylamino)-5,6,7,8-tetrahydropyrido[3,2-d]pyrimidin-2-yl)-2-methyl-1H-indole-7-carboxamide
3-(4-(benzylamino)-5,6,7,8-tetrahydropyrido[3,4-d]pyrimidin-2-yl)-2-methyl-1H-indole-7-carboxamide
3-(4-(benzylamino)-5,6,7,8-tetrahydropyrido[4,3-d]pyrimidin-2-yl)-2-methyl-1H-indole-7-carboxamide
3-(4-(benzylamino)-5,6,7,8-tetrahydroquinazolin-2-yl)-1H-indazole-7-carboxamide
3-(4-(benzylamino)-5,6,7,8-tetrahydroquinazolin-2-yl)-2-methyl-1H-indole-7-carboxamide
3-(4-(benzylamino)-5,6,7,8-tetrahydroquinazolin-2-yl)-2-methylbenzofuran-7-carboxamide
3-(4-(benzylamino)-5,6-dihydrofuro[2,3-d]pyrimidin-2-yl)-2-methyl-1H-indole-7-carboxamide
3-(4-(benzylamino)-5,7-dihydrofuro[3,4-d]pyrimidin-2-yl)-2-methyl-1H-indole-7-carboxamide
3-(4-(benzylamino)-5-methyl-5,6,7,8-tetrahydropyrido[3,2-d]pyrimidin-2-yl)-2-methyl-1H-indole-7-carboxamide
3-(4-(benzylamino)-5-methyl-6,7-dihydro-5H-pyrrolo[3,2-d]pyrimidin-2-yl)-2-methyl-1H-indole-7-carboxamide
3-(4-(benzylamino)-6,7,8,9-tetrahydro-5H-cyclohepta[d]pyrimidin-2-yl)-2-methyl-1H-indole-7-carboxamide
3-(4-(benzylamino)-6,7-dihydro-5H-cyclopenta[d]pyrimidin-2-yl)-2-methyl-1H-indole-7-carboxamide
3-(4-(benzylamino)-6,7-dihydro-5H-pyrano[2,3-d]pyrimidin-2-yl)-2-methyl-1H-indole-7-carboxamide
3-(4-(benzylamino)-6,7-dihydro-5H-pyrrolo[2,3-d]pyrimidin-2-yl)-2-methyl-1H-indole-7-carboxamide
3-(4-(benzylamino)-6,7-dihydro-5H-pyrrolo[3,2-d]pyrimidin-2-yl)-2-methyl-1H-indole-7-carboxamide
3-(4-(benzylamino)-6,7-dihydro-5H-pyrrolo[3,4-d]pyrimidin-2-yl)-2-methyl-1H-indole-7-carboxamide
3-(4-(benzylamino)-6,8-dihydro-5H-pyrano[3,4-d]pyrimidin-2-yl)-2-methyl-1H-indole-7-carboxamide
3-(4-(benzylamino)-6-methyl-5,6,7,8-tetrahydropyrido[4,3-d]pyrimidin-2-yl)-2-methyl-1H-indole-7-carboxamide
3-(4-(benzylamino)-6-methyl-6,7-dihydro-5H-pyrrolo[3,4-d]pyrimidin-2-yl)-2-methyl-1H-indole-7-carboxamide
3-(4-(benzylamino)-7,8-dihydro-5H-pyrano[4,3-d]pyrimidin-2-yl)-2-methyl-1H-indole-7-carboxamide
3-(4-(benzylamino)-7-methyl-5,6,7,8-tetrahydropyrido[3,4-d]pyrimidin-2-yl)-2-methyl-1H-indole-7-carboxamide
3-(4-(benzylamino)-7-methyl-6,7-dihydro-5H-pyrrolo[2,3-d]pyrimidin-2-yl)-2-methyl-1H-indole-7-carboxamide
3-(4-(benzylamino)-8-methyl-5,6,7,8-tetrahydropyrido[2,3-d]pyrimidin-2-yl)-2-methyl-1H-indole-7-carboxamide
N-benzyl-2-(2-methyl-1H-indol-3-yl)-5,6,7,8-tetrahydroquinazolin-4-amine
(1-(4-(benzylamino)-5,6,7,8-tetrahydropyrido[3,4-d]pyrimidin-2-yl)-1H-indazol-4-yl)methanol
(1-(4-(benzylamino)-5,6,7,8-tetrahydropyrido[4,3-d]pyrimidin-2-yl)-1H-indazol-4-yl)methanol
(1-(4-(benzylamino)-5,6,7,8-tetrahydroquinazolin-2-yl)-1H-indazol-4-yl)methanol
(1-(4-(benzylamino)-6,8-dihydro-5H-pyrano[3,4-d]pyrimidin-2-yl)-1H-indazol-4-yl)methanol
(1-(4-(benzylamino)-7,8-dihydro-5H-pyrano[4,3-d]pyrimidin-2-yl)-1H-indazol-4-yl)methanol
(1-(4-((3-fluorobenzyl)amino)-5,6,7,8-tetrahydropyrido[3,4-d]pyrimidin-2-yl)-1H-indazol-4-yl)methanol
(1-(4-((3-fluorobenzyl)amino)-5,6,7,8-tetrahydropyrido[4,3-d]pyrimidin-2-yl)-1H-indazol-4-yl)methanol
(1-(4-((3-fluorobenzyl)amino)-5,6,7,8-tetrahydroquinazolin-2-yl)-1H-indazol-4-yl)methanol
(1-(4-((3-fluorobenzyl)amino)-5,6-dimethyl-pyrimidin-2-yl)-1H-indazol-4-yl)methanol
(1-(4-((3-fluorobenzyl)amino)-6,8-dihydro-5H-pyrano[3,4-d]pyrimidin-2-yl)-1H-indazol-4-yl)methanol
(1-(4-((3-fluorobenzyl)amino)-7,8-dihydro-5H-pyrano[4,3-d]pyrimidin-2-yl)-1H-indazol-4-yl)methanol
1-(4-(benzylamino)-5,6,7,8-tetrahydropyrido[3,4-d]pyrimidin-2-yl)-1H-indazole-4-carboxylic acid
1-(4-(benzylamino)-5,6,7,8-tetrahydropyrido[4,3-d]pyrimidin-2-yl)-1H-indazole-4-carboxylic acid
1-(4-(benzylamino)-5,6,7,8-tetrahydroquinazolin-2-yl)-1H-indazole-4-carboxylic acid
1-(4-(benzylamino)-6,8-dihydro-5H-pyrano[3,4-d]pyrimidin-2-yl)-1H-indazole-4-carboxylic acid
1-(4-(benzylamino)-7,8-dihydro-5H-pyrano[4,3-d]pyrimidin-2-yl)-1H-indazole-4-carboxylic acid
1-(4-((3-fluorobenzyl)amino)-5,6,7,8-tetrahydropyrido[3,4-d]pyrimidin-2-yl)-1H-indazole-4-carboxylic acid
1-(4-((3-fluorobenzyl)amino)-5,6,7,8-tetrahydropyrido[4,3-d]pyrimidin-2-yl)-1H-indazole-4-carboxylic acid
1-(4-((3-fluorobenzyl)amino)-5,6,7,8-tetrahydroquinazolin-2-yl)-1H-indazole-4-carboxylic acid
1-(4-((3-fluorobenzyl)amino)-6,8-dihydro-5H-pyrano[3,4-d]pyrimidin-2-yl)-1H-indazole-4-carboxylic acid
1-(4-((3-fluorobenzyl)amino)-7,8-dihydro-5H-pyrano[4,3-d]pyrimidin-2-yl)-1H-indazole-4-carboxylic acid
2-(4-(aminomethyl)-1H-indazol-1-yl)-N-(3-fluorobenzyl)-5,6,7,8-tetrahydropyrido[3,4-d]pyrimidin-4-amine
2-(4-(aminomethyl)-1H-indazol-1-yl)-N-(3-fluorobenzyl)-5,6,7,8-tetrahydropyrido[4,3-d]pyrimidin-4-amine
2-(4-(aminomethyl)-1H-indazol-1-yl)-N-(3-fluorobenzyl)-5,6,7,8-tetrahydroquinazolin-4-amine
2-(4-(aminomethyl)-1H-indazol-1-yl)-N-(3-fluorobenzyl)-6,8-dihydro-5H-pyrano[3,4-d]pyrimidin-4-amine
2-(4-(aminomethyl)-1H-indazol-1-yl)-N-(3-fluorobenzyl)-7,8-dihydro-5H-pyrano[4,3-d]pyrimidin-4-amine
2-(4-(aminomethyl)-1H-indazol-1-yl)-N-benzyl-5,6,7,8-tetrahydropyrido[3,4-d]pyrimidin-4-amine
2-(4-(aminomethyl)-1H-indazol-1-yl)-N-benzyl-5,6,7,8-tetrahydropyrido[4,3-d]pyrimidin-4-amine
2-(4-(aminomethyl)-1H-indazol-1-yl)-N-benzyl-5,6,7,8-tetrahydroquinazolin-4-amine
2-(4-(aminomethyl)-1H-indazol-1-yl)-N-benzyl-6,8-dihydro-5H-pyrano[3,4-d]pyrimidin-4-amine
2-(4-(aminomethyl)-1H-indazol-1-yl)-N-benzyl-7,8-dihydro-5H-pyrano[4,3-d]pyrimidin-4-amine
N-((1-(4-(benzylamino)-5,6,7,8-tetrahydropyrido[3,4-d]pyrimidin-2-yl)-1H-indazol-4-yl)methyl)-2-methyl-propanamide
N-((1-(4-(benzylamino)-5,6,7,8-tetrahydropyrido[3,4-d]pyrimidin-2-yl)-1H-indazol-4-yl)methyl)acetamide
N-((1-(4-(benzylamino)-5,6,7,8-tetrahydropyrido[3,4-d]pyrimidin-2-yl)-1H-indazol-4-yl)methyl)ethanesulfonamide
N-((1-(4-(benzylamino)-5,6,7,8-tetrahydropyrido[3,4-d]pyrimidin-2-yl)-1H-indazol-4-yl)methyl)methanesulfonamide
N-((1-(4-(benzylamino)-5,6,7,8-tetrahydropyrido[3,4-d]pyrimidin-2-yl)-1H-indazol-4-yl)methyl)propanamide
N-((1-(4-(benzylamino)-5,6,7,8-tetrahydropyrido[3,4-d]pyrimidin-2-yl)-1H-indazol-4-yl)methyl)propane-2-sulfonamide
N-((1-(4-(benzylamino)-5,6,7,8-tetrahydropyrido[4,3-d]pyrimidin-2-yl)-1H-indazol-4-yl)methyl)-2-methyl-propanamide
N-((1-(4-(benzylamino)-5,6,7,8-tetrahydropyrido[4,3-d]pyrimidin-2-yl)-1H-indazol-4-yl)methyl)acetamide N-((1-(4-(benzylamino)-5,6,7,8-tetrahydropyrido[4,3-d]pyrimidin-2-yl)-1H-indazol-4-yl)methyl)ethanesulfonamide
N-((1-(4-(benzylamino)-5,6,7,8-tetrahydropyrido[4,3-d]pyrimidin-2-yl)-1H-indazol-4-yl)methyl)methanesulfonamide
N-((1-(4-(benzylamino)-5,6,7,8-tetrahydropyrido[4,3-d]pyrimidin-2-yl)-1H-indazol-4-yl)methyl)propanamide
N-((1-(4-(benzylamino)-5,6,7,8-tetrahydropyrido[4,3-d]pyrimidin-2-yl)-1H-indazol-4-yl)methyl)propane-2-sulfonamide
N-((1-(4-(benzylamino)-5,6,7,8-tetrahydroquinazolin-2-yl)-1H-indazol-4-yl)methyl)-2-methyl-propanamide
N-((1-(4-(benzylamino)-5,6,7,8-tetrahydroquinazolin-2-yl)-1H-indazol-4-yl)methyl)acetamide
N-((1-(4-(benzylamino)-5,6,7,8-tetrahydroquinazolin-2-yl)-1H-indazol-4-yl)methyl)ethanesulfonamide
N-((1-(4-(benzylamino)-5,6,7,8-tetrahydroquinazolin-2-yl)-1H-indazol-4-yl)methyl)methanesulfonamide
N-((1-(4-(benzylamino)-5,6,7,8-tetrahydroquinazolin-2-yl)-1H-indazol-4-yl)methyl)propanamide
N-((1-(4-(benzylamino)-5,6,7,8-tetrahydroquinazolin-2-yl)-1H-indazol-4-yl)methyl)propane-2-sulfonamide
N-((1-(4-(benzylamino)-6,8-dihydro-5H-pyrano[3,4-d]pyrimidin-2-yl)-1H-indazol-4-yl)methyl)-2-methyl-propanamide
N-((1-(4-(benzylamino)-6,8-dihydro-5H-pyrano[3,4-d]pyrimidin-2-yl)-1H-indazol-4-yl)methyl)acetamide
N-((1-(4-(benzylamino)-6,8-dihydro-5H-pyrano[3,4-d]pyrimidin-2-yl)-1H-indazol-4-yl)methyl)ethanesulfonamide
N-((1-(4-(benzylamino)-6,8-dihydro-5H-pyrano[3,4-d]pyrimidin-2-yl)-1H-indazol-4-yl)methyl)methanesulfonamide
N-((1-(4-(benzylamino)-6,8-dihydro-5H-pyrano[3,4-d]pyrimidin-2-yl)-1H-indazol-4-yl)methyl)propanamide
N-((1-(4-(benzylamino)-6,8-dihydro-5H-pyrano[3,4-d]pyrimidin-2-yl)-1H-indazol-4-yl)methyl)propane-2-sulfonamide
N-((1-(4-(benzylamino)-7,8-dihydro-5H-pyrano[4,3-d]pyrimidin-2-yl)-1H-indazol-4-yl)methyl)-2-methyl-propanamide
N-((1-(4-(benzylamino)-7,8-dihydro-5H-pyrano[4,3-d]pyrimidin-2-yl)-1H-indazol-4-yl)methyl)acetamide
N-((1-(4-(benzylamino)-7,8-dihydro-5H-pyrano[4,3-d]pyrimidin-2-yl)-1H-indazol-4-yl)methyl)ethanesulfonamide
N-((1-(4-(benzylamino)-7,8-dihydro-5H-pyrano[4,3-d]pyrimidin-2-yl)-1H-indazol-4-yl)methyl)methanesulfonamide
N-((1-(4-(benzylamino)-7,8-dihydro-5H-pyrano[4,3-d]pyrimidin-2-yl)-1H-indazol-4-yl)methyl)propanamide
N-((1-(4-(benzylamino)-7,8-dihydro-5H-pyrano[4,3-d]pyrimidin-2-yl)-1H-indazol-4-yl)methyl)propane-2-sulfonamide
N-((1-(4-((3-fluorobenzyl)amino)-5,6,7,8-tetrahydropyrido[3,4-d]pyrimidin-2-yl)-1H-indazol-4-yl)methyl)-2-methyl-propanamide
N-((1-(4-((3-fluorobenzyl)amino)-5,6,7,8-tetrahydropyrido[3,4-d]pyrimidin-2-yl)-1H-indazol-4-yl)methyl)acetamide
N-((1-(4-((3-fluorobenzyl)amino)-5,6,7,8-tetrahydropyrido[3,4-d]pyrimidin-2-yl)-1H-indazol-4-yl)methyl)ethanesulfonamide
N-((1-(4-((3-fluorobenzyl)amino)-5,6,7,8-tetrahydropyrido[3,4-d]pyrimidin-2-yl)-1H-indazol-4-yl)methyl)methanesulfonamide
N-((1-(4-((3-fluorobenzyl)amino)-5,6,7,8-tetrahydropyrido[3,4-d]pyrimidin-2-yl)-1H-indazol-4-yl)methyl)propanamide
N-((1-(4-((3-fluorobenzyl)amino)-5,6,7,8-tetrahydropyrido[3,4-d]pyrimidin-2-yl)-1H-indazol-4-yl)methyl)propane-2-sulfonamide
N-((1-(4-((3-fluorobenzyl)amino)-5,6,7,8-tetrahydropyrido[4,3-d]pyrimidin-2-yl)-1H-indazol-4-yl)methyl)-2-methyl-propanamide
N-((1-(4-((3-fluorobenzyl)amino)-5,6,7,8-tetrahydropyrido[4,3-d]pyrimidin-2-yl)-1H-indazol-4-yl)methyl)acetamide
N-((1-(4-((3-fluorobenzyl)amino)-5,6,7,8-tetrahydropyrido[4,3-d]pyrimidin-2-yl)-1H-indazol-4-yl)methyl)ethanesulfonamide
N-((1-(4-((3-fluorobenzyl)amino)-5,6,7,8-tetrahydropyrido[4,3-d]pyrimidin-2-yl)-1H-indazol-4-yl)methyl)methanesulfonamide
N-((1-(4-((3-fluorobenzyl)amino)-5,6,7,8-tetrahydropyrido[4,3-d]pyrimidin-2-yl)-1H-indazol-4-yl)methyl)propanamide
N-((1-(4-((3-fluorobenzyl)amino)-5,6,7,8-tetrahydropyrido[4,3-d]pyrimidin-2-yl)-1H-indazol-4-yl)methyl)propane-2-sulfonamide
N-((1-(4-((3-fluorobenzyl)amino)-5,6,7,8-tetrahydroquinazolin-2-yl)-1H-indazol-4-yl)methyl)-2-methyl-propanamide
N-((1-(4-((3-fluorobenzyl)amino)-5,6,7,8-tetrahydroquinazolin-2-yl)-1H-indazol-4-yl)methyl)acetamide
N-((1-(4-((3-fluorobenzyl)amino)-5,6,7,8-tetrahydroquinazolin-2-yl)-1H-indazol-4-yl)methyl)ethanesulfonamide
N-((1-(4-((3-fluorobenzyl)amino)-5,6,7,8-tetrahydroquinazolin-2-yl)-1H-indazol-4-yl)methyl)methanesulfonamide
N-((1-(4-((3-fluorobenzyl)amino)-5,6,7,8-tetrahydroquinazolin-2-yl)-1H-indazol-4-yl)methyl)propanamide
N-((1-(4-((3-fluorobenzyl)amino)-5,6,7,8-tetrahydroquinazolin-2-yl)-1H-indazol-4-yl)methyl)propane-2-sulfonamide
N-((1-(4-((3-fluorobenzyl)amino)-6,8-dihydro-5H-pyrano[3,4-d]pyrimidin-2-yl)-1H-indazol-4-yl)methyl)-2-methyl-propanamide
N-((1-(4-((3-fluorobenzyl)amino)-6,8-dihydro-5H-pyrano[3,4-d]pyrimidin-2-yl)-1H-indazol-4-yl)methyl)acetamide
N-((1-(4-((3-fluorobenzyl)amino)-6,8-dihydro-5H-pyrano[3,4-d]pyrimidin-2-yl)-1H-indazol-4-yl)methyl)ethanesulfonamide
N-((1-(4-((3-fluorobenzyl)amino)-6,8-dihydro-5H-pyrano[3,4-d]pyrimidin-2-yl)-1H-indazol-4-yl)methyl)methanesulfonamide
N-((1-(4-((3-fluorobenzyl)amino)-6,8-dihydro-5H-pyrano[3,4-d]pyrimidin-2-yl)-1H-indazol-4-yl)methyl)propanamide
N-((1-(4-((3-fluorobenzyl)amino)-6,8-dihydro-5H-pyrano[3,4-d]pyrimidin-2-yl)-1H-indazol-4-yl)methyl)propane-2-sulfonamide
N-((1-(4-((3-fluorobenzyl)amino)-7,8-dihydro-5H-pyrano[4,3-d]pyrimidin-2-yl)-1H-indazol-4-yl)methyl)-2-methyl-propanamide
N-((1-(4-((3-fluorobenzyl)amino)-7,8-dihydro-5H-pyrano[4,3-d]pyrimidin-2-yl)-1H-indazol-4-yl)methyl)acetamide
N-((1-(4-((3-fluorobenzyl)amino)-7,8-dihydro-5H-pyrano[4,3-d]pyrimidin-2-yl)-1H-indazol-4-yl)methyl)ethanesulfonamide
N-((1-(4-((3-fluorobenzyl)amino)-7,8-dihydro-5H-pyrano[4,3-d]pyrimidin-2-yl)-1H-indazol-4-yl)methyl)methanesulfonamide N-((1-(4-((3-fluorobenzyl)amino)-7,8-dihydro-5H-pyrano[4,3-d]pyrimidin-2-yl)-1H-indazol-4-yl)methyl)propanamide N-((1-(4-((3-fluorobenzyl)amino)-7,8-dihydro-5H-pyrano[4,3-d]pyrimidin-2-yl)-1H-indazol-4-yl)methyl)propane-2-sulfonamide 1-(4-((3-fluorobenzyl)amino)-5,6,7,8-tetrahydrooxepino[2,3-d]pyrimidin-2-yl)-2-methoxy-1H-benzo[d]imidazole-4-carboxamide 1-(4-((3-fluorobenzyl)amino)-5,6,7,8-tetrahydrooxepino[2,3-d]pyrimidin-2-yl)-2-methyl-1H-indole-4-carboxamide 1-(4-((3-fluorobenzyl)amino)-5,6,7,8-tetrahydrooxepino[2,3-d]pyrimidin-2-yl)-6-fluoro-2-methoxy-1H-benzo[d]imidazole-4-carboxamide 1-(4-((3-fluorobenzyl)amino)-5,6,7,8-tetrahydrooxepino[2,3-d]pyrimidin-2-yl)-6-fluoro-2-methyl-1H-indole-4-carboxamide 1-(4-((3-fluorobenzyl)amino)-5,6,7,9-tetrahydrooxepino[3,4-d]pyrimidin-2-yl)-1H-indazole-4-carboxamide 1-(4-((3-fluorobenzyl)amino)-5,6,7,9-tetrahydrooxepino[3,4-d]pyrimidin-2-yl)-6-fluoro-1H-indazole-4-carboxamide 1-(4-((3-fluorobenzyl)amino)-5,6,8,9-tetrahydrooxepino[4,5-d]pyrimidin-2-yl)-1H-indazole-4-carboxamide 1-(4-((3-fluorobenzyl)amino)-5,6,8,9-tetrahydrooxepino[4,5-d]pyrimidin-2-yl)-6-fluoro-1H-indazole-4-carboxamide 1-(4-((3-fluorobenzyl)amino)-5,7,8,9-tetrahydrooxepino[4,3-d]pyrimidin-2-yl)-1H-indazole-4-carboxamide 1-(4-((3-fluorobenzyl)amino)-5,7,8,9-tetrahydrooxepino[4,3-d]pyrimidin-2-yl)-6-fluoro-1H-indazole-4-carboxamide 1-(4-((3-fluorobenzyl)amino)-5-methyl-6,7,8,9-tetrahydro-5H-pyrimido[5,4-b]azepin-2-yl)-1H-indazole-4-carboxamide 1-(4-((3-fluorobenzyl)amino)-5-methyl-6,7,8,9-tetrahydro-5H-pyrimido[5,4-b]azepin-2-yl)-2-methoxy-1H-benzo[d]imidazole-4-carboxamide 1-(4-((3-fluorobenzyl)amino)-5-methyl-6,7,8,9-tetrahydro-5H-pyrimido[5,4-b]azepin-2-yl)-2-methyl-1H-indole-4-carboxamide 1-(4-((3-fluorobenzyl)amino)-5-methyl-6,7,8,9-tetrahydro-5H-pyrimido[5,4-b]azepin-2-yl)-6-fluoro-1H-indazole-4-carboxamide 1-(4-((3-fluorobenzyl)amino)-5-methyl-6,7,8,9-tetrahydro-5H-pyrimido[5,4-b]azepin-2-yl)-6-fluoro-2-methoxy-1H-benzo[d]imidazole-4-carboxamide 1-(4-((3-fluorobenzyl)amino)-5-methyl-6,7,8,9-tetrahydro-5H-pyrimido[5,4-b]azepin-2-yl)-6-fluoro-2-methyl-1H-indole-4-carboxamide 1-(4-((3-fluorobenzyl)amino)-6,7,8,9-tetrahydro-5H-pyrimido[4,5-b]azepin-2-yl)-1H-indazole-4-carboxamide 1-(4-((3-fluorobenzyl)amino)-6,7,8,9-tetrahydro-5H-pyrimido[4,5-b]azepin-2-yl)-2-methoxy-1H-benzo[d]imidazole-4-carboxamide 1-(4-((3-fluorobenzyl)amino)-6,7,8,9-tetrahydro-5H-pyrimido[4,5-b]azepin-2-yl)-2-methyl-1H-indole-4-carboxamide 1-(4-((3-fluorobenzyl)amino)-6,7,8,9-tetrahydro-5H-pyrimido[4,5-b]azepin-2-yl)-6-fluoro-1H-indazole-4-carboxamide 1-(4-((3-fluorobenzyl)amino)-6,7,8,9-tetrahydro-5H-pyrimido[4,5-b]azepin-2-yl)-6-fluoro-2-methoxy-1H-benzo[d]imidazole-4-carboxamide 1-(4-((3-fluorobenzyl)amino)-6,7,8,9-tetrahydro-5H-pyrimido[4,5-b]azepin-2-yl)-6-fluoro-2-methyl-1H-indole-4-carboxamide 1-(4-((3-fluorobenzyl)amino)-6,7,8,9-tetrahydro-5H-pyrimido[4,5-c]azepin-2-yl)-1H-indazole-4-carboxamide 1-(4-((3-fluorobenzyl)amino)-6,7,8,9-tetrahydro-5H-pyrimido[4,5-c]azepin-2-yl)-6-fluoro-1H-indazole-4-carboxamide 1-(4-((3-fluorobenzyl)amino)-6,7,8,9-tetrahydro-5H-pyrimido[4,5-d]azepin-2-yl)-1H-indazole-4-carboxamide 1-(4-((3-fluorobenzyl)amino)-6,7,8,9-tetrahydro-5H-pyrimido[4,5-d]azepin-2-yl)-6-fluoro-1H-indazole-4-carboxamide 1-(4-((3-fluorobenzyl)amino)-6,7,8,9-tetrahydro-5H-pyrimido[5,4-b]azepin-2-yl)-1H-indazole-4-carboxamide 1-(4-((3-fluorobenzyl)amino)-6,7,8,9-tetrahydro-5H-pyrimido[5,4-b]azepin-2-yl)-2-methoxy-1H-benzo[d]imidazole-4-carboxamide 1-(4-((3-fluorobenzyl)amino)-6,7,8,9-tetrahydro-5H-pyrimido[5,4-b]azepin-2-yl)-2-methyl-1H-indole-4-carboxamide 1-(4-((3-fluorobenzyl)amino)-6,7,8,9-tetrahydro-5H-pyrimido[5,4-b]azepin-2-yl)-6-fluoro-1H-indazole-4-carboxamide 1-(4-((3-fluorobenzyl)amino)-6,7,8,9-tetrahydro-5H-pyrimido[5,4-b]azepin-2-yl)-6-fluoro-2-methoxy-1H-benzo[d]imidazole-4-carboxamide 1-(4-((3-fluorobenzyl)amino)-6,7,8,9-tetrahydro-5H-pyrimido[5,4-b]azepin-2-yl)-6-fluoro-2-methyl-1H-indole-4-carboxamide 1-(4-((3-fluorobenzyl)amino)-6,7,8,9-tetrahydro-5H-pyrimido[5,4-c]azepin-2-yl)-1H-indazole-4-carboxamide 1-(4-((3-fluorobenzyl)amino)-6,7,8,9-tetrahydro-5H-pyrimido[5,4-c]azepin-2-yl)-6-fluoro-1H-indazole-4-carboxamide 1-(4-((3-fluorobenzyl)amino)-6,7,8,9-tetrahydrooxepino[3,2-d]pyrimidin-2-yl)-1H-indazole-4-carboxamide 1-(4-((3-fluorobenzyl)amino)-6,7,8,9-tetrahydrooxepino[3,2-d]pyrimidin-2-yl)-2-methoxy-1H-benzo[d]imidazole-4-carboxamide 1-(4-((3-fluorobenzyl)amino)-6,7,8,9-tetrahydrooxepino[3,2-d]pyrimidin-2-yl)-2-methyl-1H-indole-4-carboxamide 1-(4-((3-fluorobenzyl)amino)-6,7,8,9-tetrahydrooxepino[3,2-d]pyrimidin-2-yl)-6-fluoro-1H-indazole-4-carboxamide 1-(4-((3-fluorobenzyl)amino)-6,7,8,9-tetrahydrooxepino[3,2-d]pyrimidin-2-yl)-6-fluoro-2-methoxy-1H-benzo[d]imidazole-4-carboxamide 1-(4-((3-fluorobenzyl)amino)-6,7,8,9-tetrahydrooxepino[3,2-d]pyrimidin-2-yl)-6-fluoro-2-methyl-1H-indole-4-carboxamide 1-(4-((3-fluorobenzyl)amino)-6,7-dihydrofuro[3,2-d]pyrimidin-2-yl)-1H-indazole-4-carboxamide 1-(4-((3-fluorobenzyl)amino)-6,7-dihydrofuro[3,2-d]pyrimidin-2-yl)-2-methoxy-1H-benzo[d]imidazole-4-carboxamide 1-(4-((3-fluorobenzyl)amino)-6,7-dihydrofuro[3,2-d]pyrimidin-2-yl)-2-methyl-1H-indole-4-carboxamide 1-(4-((3-fluorobenzyl)amino)-6,7-dihydrofuro[3,2-d]pyrimidin-2-yl)-6-fluoro-1H-indazole-4-carboxamide 1-(4-((3-fluorobenzyl)amino)-6,7-dihydrofuro[3,2-d]pyrimidin-2-yl)-6-fluoro-2-methoxy-1H-benzo[d]imidazole-4-carboxamide 1-(4-((3-fluorobenzyl)amino)-6,7-dihydrofuro[3,2-d]pyrimidin-2-yl)-6-fluoro-2-methyl-1H-indole-4-carboxamide 1-(4-((3-fluorobenzyl)amino)-6-methyl-6,7,8,9-tetrahydro-5H-pyrimido[5,4-c]azepin-2-yl)-1H-indazole-4-carboxamide 1-(4-((3-fluorobenzyl)amino)-6-methyl-6,7,8,9-tetrahydro-5H-pyrimido[5,4-c]azepin-2-yl)-6-fluoro-1H-indazole-4-carboxamide 1-(4-((3-fluorobenzyl)amino)-7,8-dihydro-6H-pyrano[3,2-d]pyrimidin-2-yl)-1H-indazole-4-carboxamide 1-(4-((3-fluorobenzyl)amino)-7,8-dihydro-6H-pyrano[3,2-d]pyrimidin-2-yl)-2-methoxy-1H-benzo[d]imidazole-4-carboxamide 1-(4-((3-fluorobenzyl)amino)-7,8-dihydro-6H-pyrano[3,2-d]pyrimidin-2-yl)-2-methyl-1H-indole-4-carboxamide 1-(4-((3-fluorobenzyl)amino)-7,8-dihydro-6H-pyrano[3,2-d]pyrimidin-2-yl)-6-fluoro-1H-indazole-4-carboxamide 1-(4-((3-fluorobenzyl)amino)-7,8-dihydro-6H-pyrano[3,2-d]pyrimidin-2-yl)-6-fluoro-2-methoxy-1H-benzo[d]imidazole-4-carboxamide 1-(4-((3-fluorobenzyl)amino)-7,8-dihydro-6H-pyrano[3,2-d]pyrimidin-2-yl)-6-fluoro-2-methyl-1H-indole-4-carboxamide 1-(4-((3-fluorobenzyl)amino)-8-methyl-6,7,8,9-tetrahydro-5H-pyrimido[4,5-c]azepin-2-yl)-1H-indazole-4-carboxamide 1-(4-((3-fluorobenzyl)amino)-8-methyl-6,7,8,9-tetrahydro-5H-pyrimido[4,5-c]azepin-2-yl)-6-fluoro-1H-indazole-4-carboxamide 1-(4-((3-fluorobenzyl)amino)-9-methyl-6,7,8,9-tetrahydro-5H-pyrimido[4,5-b]azepin-2-yl)-1H-indazole-4-carboxamide 1-(4-((3-fluorobenzyl)amino)-9-methyl-6,7,8,9-tetrahydro-5H-pyrimido[4,5-b]azepin-2-yl)-2-methoxy-1H-benzo[d]imidazole-4-carboxamide 1-(4-((3-fluorobenzyl)amino)-9-methyl-6,7,8,9-tetrahydro-5H-pyrimido[4,5-b]azepin-2-yl)-2-methyl-1H-indole-4-carboxamide 1-(4-((3-fluorobenzyl)amino)-9-methyl-6,7,8,9-tetrahydro-5H-pyrimido[4,5-b]azepin-2-yl)-6-fluoro-1H-indazole-4-carboxamide 1-(4-((3-fluorobenzyl)amino)-9-methyl-6,7,8,9-tetrahydro-5H-pyrimido[4,5-b]azepin-2-yl)-6-fluoro-2-methoxy-1H-benzo[d]imidazole-4-carboxamide 1-(4-((3-fluorobenzyl)amino)-9-methyl-6,7,8,9-tetrahydro-5H-pyrimido[4,5-b]azepin-2-yl)-6-fluoro-2-methyl-1H-indole-4-carboxamide 1-(4-((thiophen-2-ylmethyl)amino)-5,6,7,8-tetrahydrooxepino[2,3-d]pyrimidin-2-yl)-2-methoxy-1H-benzo[d]imidazole-4-carboxamide 1-(4-((thiophen-2-ylmethyl)amino)-5,6,7,8-tetrahydrooxepino[2,3-d]pyrimidin-2-yl)-2-methyl-1H-indole-4-carboxamide 1-(4-((thiophen-2-ylmethyl)amino)-5,6,7,9-tetrahydrooxepino[3,4-d]pyrimidin-2-yl)-1H-indazole-4-carboxamide 1-(4-((thiophen-2-ylmethyl)amino)-5,6,8,9-tetrahydrooxepino[4,5-d]pyrimidin-2-yl)-1H-indazole-4-carboxamide 1-(4-((thiophen-2-ylmethyl)amino)-5,7,8,9-tetrahydrooxepino[4,3-d]pyrimidin-2-yl)-1H-indazole-4-carboxamide 1-(4-((thiophen-2-ylmethyl)amino)-5-methyl-6,7,8,9-tetrahydro-5H-pyrimido[5,4-b]azepin-2-yl)-1H-indazole-4-carboxamide 1-(4-((thiophen-2-ylmethyl)amino)-5-methyl-6,7,8,9-tetrahydro-5H-pyrimido[5,4-b]azepin-2-yl)-2-methoxy-1H-benzo[d]imidazole-4-carboxamide 1-(4-((thiophen-2-ylmethyl)amino)-5-methyl-6,7,8,9-tetrahydro-5H-pyrimido[5,4-b]azepin-2-yl)-2-methyl-1H-indole-4-carboxamide 1-(4-((thiophen-2-ylmethyl)amino)-6,7,8,9-tetrahydro-5H-pyrimido[4,5-b]azepin-2-yl)-1H-indazole-4-carboxamide 1-(4-((thiophen-2-ylmethyl)amino)-6,7,8,9-tetrahydro-5H-pyrimido[4,5-b]azepin-2-yl)-2-methoxy-1H-benzo[d]imidazole-4-carboxamide 1-(4-((thiophen-2-ylmethyl)amino)-6,7,8,9-tetrahydro-5H-pyrimido[4,5-b]azepin-2-yl)-2-methyl-1H-indole-4-carboxamide 1-(4-((thiophen-2-ylmethyl)amino)-6,7,8,9-tetrahydro-5H-pyrimido[4,5-c]azepin-2-yl)-1H-indazole-4-carboxamide 1-(4-((thiophen-2-ylmethyl)amino)-6,7,8,9-tetrahydro-5H-pyrimido[4,5-d]azepin-2-yl)-1H-indazole-4-carboxamide 1-(4-((thiophen-2-ylmethyl)amino)-6,7,8,9-tetrahydro-5H-pyrimido[5,4-b]azepin-2-yl)-1H-indazole-4-carboxamide 1-(4-((thiophen-2-ylmethyl)amino)-6,7,8,9-tetrahydro-5H-pyrimido[5,4-b]azepin-2-yl)-2-methoxy-1H-benzo[d]imidazole-4-carboxamide 1-(4-((thiophen-2-ylmethyl)amino)-6,7,8,9-tetrahydro-5H-pyrimido[5,4-b]azepin-2-yl)-2-methyl-1H-indole-4-carboxamide 1-(4-((thiophen-2-ylmethyl)amino)-6,7,8,9-tetrahydro-5H-pyrimido[5,4-c]azepin-2-yl)-1H-indazole-4-carboxamide 1-(4-((thiophen-2-ylmethyl)amino)-6,7,8,9-tetrahydrooxepino[3,2-d]pyrimidin-2-yl)-1H-indazole-4-carboxamide 1-(4-((thiophen-2-ylmethyl)amino)-6,7,8,9-tetrahydrooxepino[3,2-d]pyrimidin-2-yl)-2-methoxy-1H-benzo[d]imidazole-4-carboxamide 1-(4-((thiophen-2-ylmethyl)amino)-6,7,8,9-tetrahydrooxepino[3,2-d]pyrimidin-2-yl)-2-methyl-1H-indole-4-carboxamide 1-(4-((thiophen-2-ylmethyl)amino)-6,7-dihydrofuro[3,2-d]pyrimidin-2-yl)-1H-indazole-4-carboxamide 1-(4-((thiophen-2-ylmethyl)amino)-6,7-dihydrofuro[3,2-d]pyrimidin-2-yl)-2-methoxy-1H-benzo[d]imidazole-4-carboxamide 1-(4-((thiophen-2-ylmethyl)amino)-6,7-dihydrofuro[3,2-d]pyrimidin-2-yl)-2-methyl-1H-indole-4-carboxamide 1-(4-((thiophen-2-ylmethyl)amino)-6-methyl-6,7,8,9-tetrahydro-5H-pyrimido[5,4-c]azepin-2-yl)-1H-indazole-4-carboxamide 1-(4-((thiophen-2-ylmethyl)amino)-7,8-dihydro-6H-pyrano[3,2-d]pyrimidin-2-yl)-1H-indazole-4-carboxamide 1-(4-((thiophen-2-ylmethyl)amino)-7,8-dihydro-6H-pyrano[3,2-d]pyrimidin-2-yl)-2-methoxy-1H-benzo[d]imidazole-4-carboxamide 1-(4-((thiophen-2-ylmethyl)amino)-7,8-dihydro-6H-pyrano[3,2-d]pyrimidin-2-yl)-2-methyl-1H-indole-4-carboxamide 1-(4-((thiophen-2-ylmethyl)amino)-8-methyl-6,7,8,9-tetrahydro-5H-pyrimido[4,5-c]azepin-2-yl)-1H-indazole-4-carboxamide 1-(4-((thiophen-2-ylmethyl)amino)-9-methyl-6,7,8,9-tetrahydro-5H-pyrimido[4,5-b]azepin-2-yl)-1H-indazole-4-carboxamide 1-(4-((thiophen-2-ylmethyl)amino)-9-methyl-6,7,8,9-tetrahydro-5H-pyrimido[4,5-b]azepin-2-yl)-2-methoxy-1H-benzo[d]imidazole-4-carboxamide 1-(4-((thiophen-2-ylmethyl)amino)-9-methyl-6,7,8,9-tetrahydro-5H-pyrimido[4,5-b]azepin-2-yl)-2-methyl-1H-indole-4-carboxamide 1-(4-(benzylamino)-5,6,7,8-tetrahydrooxepino[2,3-d]pyrimidin-2-yl)-1H-indazole-4-carboxamide 1-(4-(benzylamino)-5,6,7,8-tetrahydrooxepino[2,3-d]pyrimidin-2-yl)-2-methoxy-1H-benzo[d]imidazole-4-carboxamide 1-(4-(benzylamino)-5,6,7,8-tetrahydrooxepino[2,3-d]pyrimidin-2-yl)-2-methyl-1H-indole-4-carboxamide 1-(4-(benzylamino)-5,6,7,8-tetrahydrooxepino[2,3-d]pyrimidin-2-yl)-6-fluoro-2-methoxy-1H-benzo[d]imidazole-4-carboxamide
1-(4-(benzylamino)-5,6,7,8-tetrahydrooxepino[2,3-d]pyrimidin-2-yl)-6-fluoro-2-methyl-1H-indole-4-carboxamide
1-(4-(benzylamino)-5,6,7,8-tetrahydropyrido[2,3-d]pyrimidin-2-yl)imidazo[1,5-a]pyridine-5-carboxamide
1-(4-(benzylamino)-5,6,7,8-tetrahydropyrido[3,2-d]pyrimidin-2-yl)imidazo[1,5-a]pyridine-5-carboxamide
1-(4-(benzylamino)-5,6,7,8-tetrahydropyrido[3,4-d]pyrimidin-2-yl)imidazo[1,5-a]pyridine-5-carboxamide
1-(4-(benzylamino)-5,6,7,8-tetrahydropyrido[4,3-d]pyrimidin-2-yl)imidazo[1,5-a]pyridine-5-carboxamide
1-(4-(benzylamino)-5,6,7,8-tetrahydroquinazolin-2-yl)imidazo[1,5-a]pyridine-5-carboxamide
1-(4-(benzylamino)-5,6,7,9-tetrahydrooxepino[3,4-d]pyrimidin-2-yl)-1H-indazole-4-carboxamide
1-(4-(benzylamino)-5,6,7,9-tetrahydrooxepino[3,4-d]pyrimidin-2-yl)-6-fluoro-1H-indazole-4-carboxamide
1-(4-(benzylamino)-5,6,8,9-tetrahydrooxepino[4,5-d]pyrimidin-2-yl)-1H-indazole-4-carboxamide
1-(4-(benzylamino)-5,6,8,9-tetrahydrooxepino[4,5-d]pyrimidin-2-yl)-6-fluoro-1H-indazole-4-carboxamide
1-(4-(benzylamino)-5,7,8,9-tetrahydrooxepino[4,3-d]pyrimidin-2-yl)-1H-indazole-4-carboxamide
1-(4-(benzylamino)-5,7,8,9-tetrahydrooxepino[4,3-d]pyrimidin-2-yl)-6-fluoro-1H-indazole-4-carboxamide
1-(4-(benzylamino)-5-methyl-5,6,7,8-tetrahydropyrido[3,2-d]pyrimidin-2-yl)imidazo[1,5-a]pyridine-5-carboxamide
1-(4-(benzylamino)-5-methyl-6,7,8,9-tetrahydro-5H-pyrimido[5,4-b]azepin-2-yl)-1H-indazole-4-carboxamide
1-(4-(benzylamino)-5-methyl-6,7,8,9-tetrahydro-5H-pyrimido[5,4-b]azepin-2-yl)-2-methoxy-1H-benzo[d]imidazole-4-carboxamide
1-(4-(benzylamino)-5-methyl-6,7,8,9-tetrahydro-5H-pyrimido[5,4-b]azepin-2-yl)-2-methyl-1H-indole-4-carboxamide
1-(4-(benzylamino)-5-methyl-6,7,8,9-tetrahydro-5H-pyrimido[5,4-b]azepin-2-yl)-6-fluoro-1H-indazole-4-carboxamide
1-(4-(benzylamino)-5-methyl-6,7,8,9-tetrahydro-5H-pyrimido[5,4-b]azepin-2-yl)-6-fluoro-2-methoxy-1H-benzo[d]imidazole-4-carboxamide
1-(4-(benzylamino)-5-methyl-6,7,8,9-tetrahydro-5H-pyrimido[5,4-b]azepin-2-yl)-6-fluoro-2-methyl-1H-indole-4-carboxamide
1-(4-(benzylamino)-6,7,8,9-tetrahydro-5H-pyrimido[4,5-b]azepin-2-yl)-1H-indazole-4-carboxamide
1-(4-(benzylamino)-6,7,8,9-tetrahydro-5H-pyrimido[4,5-b]azepin-2-yl)-2-methoxy-1H-benzo[d]imidazole-4-carboxamide
1-(4-(benzylamino)-6,7,8,9-tetrahydro-5H-pyrimido[4,5-b]azepin-2-yl)-2-methyl-1H-indole-4-carboxamide
1-(4-(benzylamino)-6,7,8,9-tetrahydro-5H-pyrimido[4,5-b]azepin-2-yl)-6-fluoro-1H-indazole-4-carboxamide
1-(4-(benzylamino)-6,7,8,9-tetrahydro-5H-pyrimido[4,5-b]azepin-2-yl)-6-fluoro-2-methoxy-1H-benzo[d]imidazole-4-carboxamide
1-(4-(benzylamino)-6,7,8,9-tetrahydro-5H-pyrimido[4,5-b]azepin-2-yl)-6-fluoro-2-methyl-1H-indole-4-carboxamide
1-(4-(benzylamino)-6,7,8,9-tetrahydro-5H-pyrimido[4,5-c]azepin-2-yl)-1H-indazole-4-carboxamide
1-(4-(benzylamino)-6,7,8,9-tetrahydro-5H-pyrimido[4,5-c]azepin-2-yl)-6-fluoro-1H-indazole-4-carboxamide
1-(4-(benzylamino)-6,7,8,9-tetrahydro-5H-pyrimido[4,5-d]azepin-2-yl)-1H-indazole-4-carboxamide
1-(4-(benzylamino)-6,7,8,9-tetrahydro-5H-pyrimido[4,5-d]azepin-2-yl)-6-fluoro-1H-indazole-4-carboxamide
1-(4-(benzylamino)-6,7,8,9-tetrahydro-5H-pyrimido[5,4-b]azepin-2-yl)-1H-indazole-4-carboxamide
1-(4-(benzylamino)-6,7,8,9-tetrahydro-5H-pyrimido[5,4-b]azepin-2-yl)-2-methoxy-1H-benzo[d]imidazole-4-carboxamide
1-(4-(benzylamino)-6,7,8,9-tetrahydro-5H-pyrimido[5,4-b]azepin-2-yl)-2-methyl-1H-indole-4-carboxamide
1-(4-(benzylamino)-6,7,8,9-tetrahydro-5H-pyrimido[5,4-b]azepin-2-yl)-6-fluoro-1H-indazole-4-carboxamide
1-(4-(benzylamino)-6,7,8,9-tetrahydro-5H-pyrimido[5,4-b]azepin-2-yl)-6-fluoro-2-methoxy-1H-benzo[d]imidazole-4-carboxamide
1-(4-(benzylamino)-6,7,8,9-tetrahydro-5H-pyrimido[5,4-b]azepin-2-yl)-6-fluoro-2-methyl-1H-indole-4-carboxamide
1-(4-(benzylamino)-6,7,8,9-tetrahydro-5H-pyrimido[5,4-c]azepin-2-yl)-1H-indazole-4-carboxamide
1-(4-(benzylamino)-6,7,8,9-tetrahydro-5H-pyrimido[5,4-c]azepin-2-yl)-6-fluoro-1H-indazole-4-carboxamide
1-(4-(benzylamino)-6,7,8,9-tetrahydrooxepino[3,2-d]pyrimidin-2-yl)-1H-indazole-4-carboxamide
1-(4-(benzylamino)-6,7,8,9-tetrahydrooxepino[3,2-d]pyrimidin-2-yl)-2-methoxy-1H-benzo[d]imidazole-4-carboxamide
1-(4-(benzylamino)-6,7,8,9-tetrahydrooxepino[3,2-d]pyrimidin-2-yl)-2-methyl-1H-indole-4-carboxamide
1-(4-(benzylamino)-6,7,8,9-tetrahydrooxepino[3,2-d]pyrimidin-2-yl)-6-fluoro-1H-indazole-4-carboxamide
1-(4-(benzylamino)-6,7,8,9-tetrahydrooxepino[3,2-d]pyrimidin-2-yl)-6-fluoro-2-methoxy-1H-benzo[d]imidazole-4-carboxamide
1-(4-(benzylamino)-6,7,8,9-tetrahydrooxepino[3,2-d]pyrimidin-2-yl)-6-fluoro-2-methyl-1H-indole-4-carboxamide
1-(4-(benzylamino)-6,7-dihydro-5H-cyclopenta[d]pyrimidin-2-yl)imidazo[1,5-a]pyridine-5-carboxamide
1-(4-(benzylamino)-6,7-dihydro-5H-pyrano[2,3-d]pyrimidin-2-yl)imidazo[1,5-a]pyridine-5-carboxamide
1-(4-(benzylamino)-6,7-dihydrofuro[3,2-d]pyrimidin-2-yl)-1H-indazole-4-carboxamide
1-(4-(benzylamino)-6,7-dihydrofuro[3,2-d]pyrimidin-2-yl)-2-methoxy-1H-benzo[d]imidazole-4-carboxamide
1-(4-(benzylamino)-6,7-dihydrofuro[3,2-d]pyrimidin-2-yl)-2-methyl-1H-indole-4-carboxamide
1-(4-(benzylamino)-6,7-dihydrofuro[3,2-d]pyrimidin-2-yl)-6-fluoro-1H-indazole-4-carboxamide
1-(4-(benzylamino)-6,7-dihydrofuro[3,2-d]pyrimidin-2-yl)-6-fluoro-2-methoxy-1H-benzo[d]imidazole-4-carboxamide
1-(4-(benzylamino)-6,7-dihydrofuro[3,2-d]pyrimidin-2-yl)-6-fluoro-2-methyl-1H-indole-4-carboxamide
1-(4-(benzylamino)-6,8-dihydro-5H-pyrano[3,4-d]pyrimidin-2-yl)imidazo[1,5-a]pyridine-5-carboxamide
1-(4-(benzylamino)-6-methyl-5,6,7,8-tetrahydropyrido[4,3-d]pyrimidin-2-yl)imidazo[1,5-a]pyridine-5-carboxamide
1-(4-(benzylamino)-6-methyl-6,7,8,9-tetrahydro-5H-pyrimido[5,4-c]azepin-2-yl)-1H-indazole-4-carboxamide
1-(4-(benzylamino)-6-methyl-6,7,8,9-tetrahydro-5H-pyrimido[5,4-c]azepin-2-yl)-6-fluoro-1H-indazole-4-carboxamide
1-(4-(benzylamino)-7,8-dihydro-5H-pyrano[4,3-d]pyrimidin-2-yl)imidazo[1,5-a]pyridine-5-carboxamide 1-(4-(benzylamino)-7,8-dihydro-6H-pyrano[3,2-d]pyrimidin-2-yl)-1H-indazole-4-carboxamide
1-(4-(benzylamino)-7,8-dihydro-6H-pyrano[3,2-d]pyrimidin-2-yl)-2-methoxy-1H-benzo[d]imidazole-4-carboxamide
1-(4-(benzylamino)-7,8-dihydro-6H-pyrano[3,2-d]pyrimidin-2-yl)-2-methyl-1H-indole-4-carboxamide
1-(4-(benzylamino)-7,8-dihydro-6H-pyrano[3,2-d]pyrimidin-2-yl)-6-fluoro-1H-indazole-4-carboxamide
1-(4-(benzylamino)-7,8-dihydro-6H-pyrano[3,2-d]pyrimidin-2-yl)-6-fluoro-2-methoxy-1H-benzo[d]imidazole-4-carboxamide
1-(4-(benzylamino)-7,8-dihydro-6H-pyrano[3,2-d]pyrimidin-2-yl)-6-fluoro-2-methyl-1H-indole-4-carboxamide
1-(4-(benzylamino)-7-methyl-5,6,7,8-tetrahydropyrido[3,4-d]pyrimidin-2-yl)imidazo[1,5-a]pyridine-5-carboxamide
1-(4-(benzylamino)-8-methyl-5,6,7,8-tetrahydropyrido[2,3-d]pyrimidin-2-yl)imidazo[1,5-a]pyridine-5-carboxamide
1-(4-(benzylamino)-8-methyl-6,7,8,9-tetrahydro-5H-pyrimido[4,5-c]azepin-2-yl)-1H-indazole-4-carboxamide
1-(4-(benzylamino)-8-methyl-6,7,8,9-tetrahydro-5H-pyrimido[4,5-c]azepin-2-yl)-6-fluoro-1H-indazole-4-carboxamide
1-(4-(benzylamino)-9-methyl-6,7,8,9-tetrahydro-5H-pyrimido[4,5-b]azepin-2-yl)-1H-indazole-4-carboxamide
1-(4-(benzylamino)-9-methyl-6,7,8,9-tetrahydro-5H-pyrimido[4,5-b]azepin-2-yl)-2-methoxy-1H-benzo[d]imidazole-4-carboxamide
1-(4-(benzylamino)-9-methyl-6,7,8,9-tetrahydro-5H-pyrimido[4,5-b]azepin-2-yl)-2-methyl-1H-indole-4-carboxamide
1-(4-(benzylamino)-9-methyl-6,7,8,9-tetrahydro-5H-pyrimido[4,5-b]azepin-2-yl)-6-fluoro-1H-indazole-4-carboxamide
1-(4-(benzylamino)-9-methyl-6,7,8,9-tetrahydro-5H-pyrimido[4,5-b]azepin-2-yl)-6-fluoro-2-methoxy-1H-benzo[d]imidazole-4-carboxamide
1-(4-(benzylamino)-9-methyl-6,7,8,9-tetrahydro-5H-pyrimido[4,5-b]azepin-2-yl)-6-fluoro-2-methyl-1H-indole-4-carboxamide
3-(4-((3-fluorobenzyl)amino)-5,6,7,8-tetrahydrooxepino[2,3-d]pyrimidin-2-yl)-2-methyl-1H-indole-7-carboxamide
3-(4-((3-fluorobenzyl)amino)-5,6,7,8-tetrahydropyrido[2,3-d]pyrimidin-2-yl)-2-methylimidazo[1,2-a]pyridine-8-carboxamide
3-(4-((3-fluorobenzyl)amino)-5,6,7,8-tetrahydropyrido[2,3-d]pyrimidin-2-yl)imidazo[1,5-a]pyridine-8-carboxamide
3-(4-((3-fluorobenzyl)amino)-5,6,7,8-tetrahydropyrido[3,2-d]pyrimidin-2-yl)-2-methylimidazo[1,2-a]pyridine-8-carboxamide
3-(4-((3-fluorobenzyl)amino)-5,6,7,8-tetrahydropyrido[3,2-d]pyrimidin-2-yl)imidazo[1,5-a]pyridine-8-carboxamide
3-(4-((3-fluorobenzyl)amino)-5,6,7,8-tetrahydropyrido[3,4-d]pyrimidin-2-yl)-2-methylimidazo[1,2-a]pyridine-8-carboxamide
3-(4-((3-fluorobenzyl)amino)-5,6,7,8-tetrahydropyrido[3,4-d]pyrimidin-2-yl)imidazo[1,5-a]pyridine-8-carboxamide
3-(4-((3-fluorobenzyl)amino)-5,6,7,8-tetrahydropyrido[4,3-d]pyrimidin-2-yl)-2-methylimidazo[1,2-a]pyridine-8-carboxamide
3-(4-((3-fluorobenzyl)amino)-5,6,7,8-tetrahydropyrido[4,3-d]pyrimidin-2-yl)imidazo[1,5-a]pyridine-8-carboxamide
3-(4-((3-fluorobenzyl)amino)-5,6,7,8-tetrahydroquinazolin-2-yl)-2-methylimidazo[1,2-a]pyridine-8-carboxamide
3-(4-((3-fluorobenzyl)amino)-5,6,7,8-tetrahydroquinazolin-2-yl)imidazo[1,5-a]pyridine-8-carboxamide
3-(4-((3-fluorobenzyl)amino)-5,6,7,9-tetrahydrooxepino[3,4-d]pyrimidin-2-yl)-2-methyl-1H-indole-7-carboxamide
3-(4-((3-fluorobenzyl)amino)-5,6,8,9-tetrahydrooxepino[4,5-d]pyrimidin-2-yl)-2-methyl-1H-indole-7-carboxamide
3-(4-((3-fluorobenzyl)amino)-5-methyl-5,6,7,8-tetrahydropyrido[3,2-d]pyrimidin-2-yl)-2-methylimidazo[1,2-a]pyridine-8-carboxamide
3-(4-((3-fluorobenzyl)amino)-5-methyl-5,6,7,8-tetrahydropyrido[3,2-d]pyrimidin-2-yl)imidazo[1,5-a]pyridine-8-carboxamide
3-(4-((3-fluorobenzyl)amino)-6,7,8,9-tetrahydro-5H-pyrimido[4,5-b]azepin-2-yl)-2-methyl-1H-indole-7-carboxamide
3-(4-((3-fluorobenzyl)amino)-6,7,8,9-tetrahydro-5H-pyrimido[4,5-c]azepin-2-yl)-2-methyl-1H-indole-7-carboxamide
3-(4-((3-fluorobenzyl)amino)-6,7,8,9-tetrahydro-5H-pyrimido[4,5-d]azepin-2-yl)-2-methyl-1H-indole-7-carboxamide
3-(4-((3-fluorobenzyl)amino)-6,7-dihydro-5H-pyrano[2,3-d]pyrimidin-2-yl)-2-methylimidazo[1,2-a]pyridine-8-carboxamide
3-(4-((3-fluorobenzyl)amino)-6,7-dihydro-5H-pyrano[2,3-d]pyrimidin-2-yl)imidazo[1,5-a]pyridine-8-carboxamide
3-(4-((3-fluorobenzyl)amino)-6,7-dihydrofuro[3,2-d]pyrimidin-2-yl)-2-methyl-1H-indole-7-carboxamide
3-(4-((3-fluorobenzyl)amino)-6,8-dihydro-5H-pyrano[3,4-d]pyrimidin-2-yl)-2-methylimidazo[1,2-a]pyridine-8-carboxamide
3-(4-((3-fluorobenzyl)amino)-6,8-dihydro-5H-pyrano[3,4-d]pyrimidin-2-yl)imidazo[1,5-a]pyridine-8-carboxamide
3-(4-((3-fluorobenzyl)amino)-6-methyl-5,6,7,8-tetrahydropyrido[4,3-d]pyrimidin-2-yl)-2-methylimidazo[1,2-a]pyridine-8-carboxamide
3-(4-((3-fluorobenzyl)amino)-6-methyl-5,6,7,8-tetrahydropyrido[4,3-d]pyrimidin-2-yl)imidazo[1,5-a]pyridine-8-carboxamide
3-(4-((3-fluorobenzyl)amino)-7,8-dihydro-5H-pyrano[4,3-d]pyrimidin-2-yl)-2-methylimidazo[1,2-a]pyridine-8-carboxamide
3-(4-((3-fluorobenzyl)amino)-7,8-dihydro-5H-pyrano[4,3-d]pyrimidin-2-yl)imidazo[1,5-a]pyridine-8-carboxamide
3-(4-((3-fluorobenzyl)amino)-7,8-dihydro-6H-pyrano[3,2-d]pyrimidin-2-yl)-2-methyl-1H-indole-7-carboxamide
3-(4-((3-fluorobenzyl)amino)-7,8-dihydro-6H-pyrano[3,2-d]pyrimidin-2-yl)-2-methylimidazo[1,2-a]pyridine-8-carboxamide
3-(4-((3-fluorobenzyl)amino)-7,8-dihydro-6H-pyrano[3,2-d]pyrimidin-2-yl)imidazo[1,5-a]pyridine-8-carboxamide
3-(4-((3-fluorobenzyl)amino)-7-methyl-5,6,7,8-tetrahydropyrido[3,4-d]pyrimidin-2-yl)-2-methylimidazo[1,2-a]pyridine-8-carboxamide
3-(4-((3-fluorobenzyl)amino)-7-methyl-5,6,7,8-tetrahydropyrido[3,4-d]pyrimidin-2-yl)imidazo[1,5-a]pyridine-8-carboxamide
3-(4-((3-fluorobenzyl)amino)-8-methyl-5,6,7,8-tetrahydropyrido[2,3-d]pyrimidin-2-yl)-2-methylimidazo[1,2-a]pyridine-8-carboxamide
3-(4-((3-fluorobenzyl)amino)-8-methyl-5,6,7,8-tetrahydropyrido[2,3-d]pyrimidin-2-yl)imidazo[1,5-a]pyridine-8-carboxamide
3-(4-((3-fluorobenzyl)amino)-8-methyl-6,7,8,9-tetrahydro-5H-pyrimido[4,5-c]azepin-2-yl)-2-methyl-1H-indole-7-carboxamide
3-(4-((3-fluorobenzyl)amino)-9-methyl-6,7,8,9-tetrahydro-5H-pyrimido[4,5-b]azepin-2-yl)-2-methyl-1H-indole-7-carboxamide 3-(4-(benzylamino)-5,6,7,8-tetrahydrooxepino[2,3-d]pyrimidin-2-yl)-2-methyl-1H-indole-7-carboxamide
3-(4-(benzylamino)-5,6,7,8-tetrahydropyrido[2,3-d]pyrimidin-2-yl)-2-methylimidazo[1,2-a]pyridine-8-carboxamide
3-(4-(benzylamino)-5,6,7,8-tetrahydropyrido[2,3-d]pyrimidin-2-yl)-2-methylpyrazolo[1,5-a]pyridine-7-carboxamide
3-(4-(benzylamino)-5,6,7,8-tetrahydropyrido[2,3-d]pyrimidin-2-yl)imidazo[1,5-a]pyridine-8-carboxamide
3-(4-(benzylamino)-5,6,7,8-tetrahydropyrido[3,2-d]pyrimidin-2-yl)-2-methylimidazo[1,2-a]pyridine-8-carboxamide
3-(4-(benzylamino)-5,6,7,8-tetrahydropyrido[3,2-d]pyrimidin-2-yl)-2-methylpyrazolo[1,5-a]pyridine-7-carboxamide
3-(4-(benzylamino)-5,6,7,8-tetrahydropyrido[3,2-d]pyrimidin-2-yl)imidazo[1,5-a]pyridine-8-carboxamide
3-(4-(benzylamino)-5,6,7,8-tetrahydropyrido[3,4-d]pyrimidin-2-yl)-2-methylimidazo[1,2-a]pyridine-8-carboxamide
3-(4-(benzylamino)-5,6,7,8-tetrahydropyrido[3,4-d]pyrimidin-2-yl)-2-methylpyrazolo[1,5-a]pyridine-7-carboxamide
3-(4-(benzylamino)-5,6,7,8-tetrahydropyrido[3,4-d]pyrimidin-2-yl)imidazo[1,5-a]pyridine-8-carboxamide
3-(4-(benzylamino)-5,6,7,8-tetrahydropyrido[4,3-d]pyrimidin-2-yl)-2-methylimidazo[1,2-a]pyridine-8-carboxamide
3-(4-(benzylamino)-5,6,7,8-tetrahydropyrido[4,3-d]pyrimidin-2-yl)-2-methylpyrazolo[1,5-a]pyridine-7-carboxamide
3-(4-(benzylamino)-5,6,7,8-tetrahydropyrido[4,3-d]pyrimidin-2-yl)imidazo[1,5-a]pyridine-8-carboxamide
3-(4-(benzylamino)-5,6,7,8-tetrahydroquinazolin-2-yl)-2-methylimidazo[1,2-a]pyridine-8-carboxamide
3-(4-(benzylamino)-5,6,7,8-tetrahydroquinazolin-2-yl)-2-methylpyrazolo[1,5-a]pyridine-7-carboxamide
3-(4-(benzylamino)-5,6,7,8-tetrahydroquinazolin-2-yl)imidazo[1,5-a]pyridine-8-carboxamide
3-(4-(benzylamino)-5,6,7,9-tetrahydrooxepino[3,4-d]pyrimidin-2-yl)-2-methyl-1H-indole-7-carboxamide
3-(4-(benzylamino)-5,6,8,9-tetrahydrooxepino[4,5-d]pyrimidin-2-yl)-2-methyl-1H-indole-7-carboxamide
3-(4-(benzylamino)-5,7,8,9-tetrahydrooxepino[4,3-d]pyrimidin-2-yl)-2-methyl-1H-indole-7-carboxamide
3-(4-(benzylamino)-5,7-dimethyl-5,6,7,8-tetrahydropyrido[3,4-d]pyrimidin-2-yl)-2-methylimidazo[1,2-a]pyridine-8-carboxamide
3-(4-(benzylamino)-5,7-dimethyl-5,6,7,8-tetrahydropyrido[3,4-d]pyrimidin-2-yl)imidazo[1,5-a]pyridine-8-carboxamide
3-(4-(benzylamino)-5-methyl-5,6,7,8-tetrahydropyrido[3,2-d]pyrimidin-2-yl)-2-methylimidazo[1,2-a]pyridine-8-carboxamide
3-(4-(benzylamino)-5-methyl-5,6,7,8-tetrahydropyrido[3,2-d]pyrimidin-2-yl)-2-methylpyrazolo[1,5-a]pyridine-7-carboxamide
3-(4-(benzylamino)-5-methyl-5,6,7,8-tetrahydropyrido[3,2-d]pyrimidin-2-yl)imidazo[1,5-a]pyridine-8-carboxamide
3-(4-(benzylamino)-5-methyl-5,6,7,8-tetrahydropyrido[3,4-d]pyrimidin-2-yl)-2-methylimidazo[1,2-a]pyridine-8-carboxamide
3-(4-(benzylamino)-5-methyl-5,6,7,8-tetrahydropyrido[3,4-d]pyrimidin-2-yl)imidazo[1,5-a]pyridine-8-carboxamide
3-(4-(benzylamino)-5-methyl-5,6,7,8-tetrahydropyrido[4,3-d]pyrimidin-2-yl)-2-methylimidazo[1,2-a]pyridine-8-carboxamide
3-(4-(benzylamino)-5-methyl-5,6,7,8-tetrahydropyrido[4,3-d]pyrimidin-2-yl)imidazo[1,5-a]pyridine-8-carboxamide
3-(4-(benzylamino)-5-methyl-5,6,7,8-tetrahydroquinazolin-2-yl)-2-methylimidazo[1,2-a]pyridine-8-carboxamide
3-(4-(benzylamino)-5-methyl-5,6,7,8-tetrahydroquinazolin-2-yl)imidazo[1,5-a]pyridine-8-carboxamide
3-(4-(benzylamino)-5-methyl-6,7,8,9-tetrahydro-5H-pyrimido[5,4-b]azepin-2-yl)-2-methyl-1H-indole-7-carboxamide
3-(4-(benzylamino)-5-methyl-6,8-dihydro-5H-pyrano[3,4-d]pyrimidin-2-yl)-2-methylimidazo[1,2-a]pyridine-8-carboxamide
3-(4-(benzylamino)-5-methyl-6,8-dihydro-5H-pyrano[3,4-d]pyrimidin-2-yl)imidazo[1,5-a]pyridine-8-carboxamide
3-(4-(benzylamino)-5-methyl-7,8-dihydro-5H-pyrano[4,3-d]pyrimidin-2-yl)-2-methylimidazo[1,2-a]pyridine-8-carboxamide
3-(4-(benzylamino)-5-methyl-7,8-dihydro-5H-pyrano[4,3-d]pyrimidin-2-yl)imidazo[1,5-a]pyridine-8-carboxamide
3-(4-(benzylamino)-6,7,8,9-tetrahydro-5H-pyrimido[4,5-b]azepin-2-yl)-2-methyl-1H-indole-7-carboxamide
3-(4-(benzylamino)-6,7,8,9-tetrahydro-5H-pyrimido[4,5-c]azepin-2-yl)-2-methyl-1H-indole-7-carboxamide
3-(4-(benzylamino)-6,7,8,9-tetrahydro-5H-pyrimido[4,5-d]azepin-2-yl)-2-methyl-1H-indole-7-carboxamide
3-(4-(benzylamino)-6,7,8,9-tetrahydro-5H-pyrimido[5,4-b]azepin-2-yl)-2-methyl-1H-indole-7-carboxamide
3-(4-(benzylamino)-6,7,8,9-tetrahydro-5H-pyrimido[5,4-c]azepin-2-yl)-2-methyl-1H-indole-7-carboxamide
3-(4-(benzylamino)-6,7,8,9-tetrahydrooxepino[3,2-d]pyrimidin-2-yl)-2-methyl-1H-indole-7-carboxamide
3-(4-(benzylamino)-6,7-dihydro-5H-cyclopenta[d]pyrimidin-2-yl)-2-methylimidazo[1,2-a]pyridine-8-carboxamide
3-(4-(benzylamino)-6,7-dihydro-5H-cyclopenta[d]pyrimidin-2-yl)-2-methylpyrazolo[1,5-a]pyridine-7-carboxamide
3-(4-(benzylamino)-6,7-dihydro-5H-cyclopenta[d]pyrimidin-2-yl)imidazo[1,5-a]pyridine-8-carboxamide
3-(4-(benzylamino)-6,7-dihydro-5H-pyrano[2,3-d]pyrimidin-2-yl)-2-methylimidazo[1,2-a]pyridine-8-carboxamide
3-(4-(benzylamino)-6,7-dihydro-5H-pyrano[2,3-d]pyrimidin-2-yl)-2-methylpyrazolo[1,5-a]pyridine-7-carboxamide
3-(4-(benzylamino)-6,7-dihydro-5H-pyrano[2,3-d]pyrimidin-2-yl)imidazo[1,5-a]pyridine-8-carboxamide
3-(4-(benzylamino)-6,7-dihydrofuro[3,2-d]pyrimidin-2-yl)-2-methyl-1H-indole-7-carboxamide
3-(4-(benzylamino)-6,7-dimethyl-5,6,7,8-tetrahydropyrido[3,4-d]pyrimidin-2-yl)-2-methylimidazo[1,2-a]pyridine-8-carboxamide
3-(4-(benzylamino)-6,7-dimethyl-5,6,7,8-tetrahydropyrido[3,4-d]pyrimidin-2-yl)imidazo[1,5-a]pyridine-8-carboxamide
3-(4-(benzylamino)-6,7-dimethyl-5,6,7,8-tetrahydropyrido[4,3-d]pyrimidin-2-yl)-2-methylimidazo[1,2-a]pyridine-8-carboxamide
3-(4-(benzylamino)-6,7-dimethyl-5,6,7,8-tetrahydropyrido[4,3-d]pyrimidin-2-yl)imidazo[1,5-a]pyridine-8-carboxamide
3-(4-(benzylamino)-6,8-dihydro-5H-pyrano[3,4-d]pyrimidin-2-yl)-2-methylimidazo[1,2-a]pyridine-8-carboxamide 3-(4-(benzylamino)-6,8-dihydro-5H-pyrano[3,4-d]pyrimidin-2-yl)-2-methylpyrazolo[1,5-a]pyridine-7-carboxamide 3-(4-(benzylamino)-6,8-dihydro-5H-pyrano[3,4-d]pyrimidin-2-yl)imidazo[1,5-a]pyridine-8-carboxamide 3-(4-(benzylamino)-6-methyl-5,6,7,8-tetrahydropyrido[3,4-d]pyrimidin-2-yl)-2-methylimidazo[1,2-a]pyridine-8-carboxamide 3-(4-(benzylamino)-6-methyl-5,6,7,8-tetrahydropyrido[3,4-d]pyrimidin-2-yl)imidazo[1,5-a]pyridine-8-carboxamide 3-(4-(benzylamino)-6-methyl-5,6,7,8-tetrahydropyrido[4,3-d]pyrimidin-2-yl)-2-methylimidazo[1,2-a]pyridine-8-carboxamide 3-(4-(benzylamino)-6-methyl-5,6,7,8-tetrahydropyrido[4,3-d]pyrimidin-2-yl)-2-methylpyrazolo[1,5-a]pyridine-7-carboxamide 3-(4-(benzylamino)-6-methyl-5,6,7,8-tetrahydropyrido[4,3-d]pyrimidin-2-yl)imidazo[1,5-a]pyridine-8-carboxamide 3-(4-(benzylamino)-6-methyl-6,7,8,9-tetrahydro-5H-pyrimido[5,4-c]azepin-2-yl)-2-methyl-1H-indole-7-carboxamide 3-(4-(benzylamino)-6-methyl-6,8-dihydro-5H-pyrano[3,4-d]pyrimidin-2-yl)-2-methylimidazo[1,2-a]pyridine-8-carboxamide 3-(4-(benzylamino)-6-methyl-6,8-dihydro-5H-pyrano[3,4-d]pyrimidin-2-yl)imidazo[1,5-a]pyridine-8-carboxamide 3-(4-(benzylamino)-7,8-dihydro-5H-pyrano[4,3-d]pyrimidin-2-yl)-2-methylimidazo[1,2-a]pyridine-8-carboxamide 3-(4-(benzylamino)-7,8-dihydro-5H-pyrano[4,3-d]pyrimidin-2-yl)-2-methylpyrazolo[1,5-a]pyridine-7-carboxamide 3-(4-(benzylamino)-7,8-dihydro-5H-pyrano[4,3-d]pyrimidin-2-yl)imidazo[1,5-a]pyridine-8-carboxamide 3-(4-(benzylamino)-7,8-dihydro-6H-pyrano[3,2-d]pyrimidin-2-yl)-2-methyl-1H-indole-7-carboxamide 3-(4-(benzylamino)-7,8-dihydro-6H-pyrano[3,2-d]pyrimidin-2-yl)-2-methylimidazo[1,2-a]pyridine-8-carboxamide 3-(4-(benzylamino)-7,8-dihydro-6H-pyrano[3,2-d]pyrimidin-2-yl)imidazo[1,5-a]pyridine-8-carboxamide 3-(4-(benzylamino)-7,8-dimethyl-5,6,7,8-tetrahydropyrido[3,4-d]pyrimidin-2-yl)-2-methylimidazo[1,2-a]pyridine-8-carboxamide 3-(4-(benzylamino)-7,8-dimethyl-5,6,7,8-tetrahydropyrido[3,4-d]pyrimidin-2-yl)imidazo[1,5-a]pyridine-8-carboxamide 3-(4-(benzylamino)-7-methyl-5,6,7,8-tetrahydropyrido[3,4-d]pyrimidin-2-yl)-2-methylimidazo[1,2-a]pyridine-8-carboxamide 3-(4-(benzylamino)-7-methyl-5,6,7,8-tetrahydropyrido[3,4-d]pyrimidin-2-yl)-2-methylpyrazolo[1,5-a]pyridine-7-carboxamide 3-(4-(benzylamino)-7-methyl-5,6,7,8-tetrahydropyrido[3,4-d]pyrimidin-2-yl)imidazo[1,5-a]pyridine-8-carboxamide 3-(4-(benzylamino)-7-methyl-5,6,7,8-tetrahydropyrido[4,3-d]pyrimidin-2-yl)-2-methylimidazo[1,2-a]pyridine-8-carboxamide 3-(4-(benzylamino)-7-methyl-5,6,7,8-tetrahydropyrido[4,3-d]pyrimidin-2-yl)imidazo[1,5-a]pyridine-8-carboxamide 3-(4-(benzylamino)-7-methyl-5,6,7,8-tetrahydroquinazolin-2-yl)-2-methylimidazo[1,2-a]pyridine-8-carboxamide 3-(4-(benzylamino)-7-methyl-5,6,7,8-tetrahydroquinazolin-2-yl)imidazo[1,5-a]pyridine-8-carboxamide 3-(4-(benzylamino)-7-methyl-7,8-dihydro-5H-pyrano[4,3-d]pyrimidin-2-yl)-2-methylimidazo[1,2-a]pyridine-8-carboxamide 3-(4-(benzylamino)-7-methyl-7,8-dihydro-5H-pyrano[4,3-d]pyrimidin-2-yl)imidazo[1,5-a]pyridine-8-carboxamide 3-(4-(benzylamino)-8-methyl-5,6,7,8-tetrahydropyrido[2,3-d]pyrimidin-2-yl)-2-methylimidazo[1,2-a]pyridine-8-carboxamide 3-(4-(benzylamino)-8-methyl-5,6,7,8-tetrahydropyrido[2,3-d]pyrimidin-2-yl)-2-methylpyrazolo[1,5-a]pyridine-7-carboxamide 3-(4-(benzylamino)-8-methyl-5,6,7,8-tetrahydropyrido[2,3-d]pyrimidin-2-yl)imidazo[1,5-a]pyridine-8-carboxamide 3-(4-(benzylamino)-8-methyl-5,6,7,8-tetrahydropyrido[3,4-d]pyrimidin-2-yl)-2-methylimidazo[1,2-a]pyridine-8-carboxamide 3-(4-(benzylamino)-8-methyl-5,6,7,8-tetrahydropyrido[3,4-d]pyrimidin-2-yl)imidazo[1,5-a]pyridine-8-carboxamide 3-(4-(benzylamino)-8-methyl-5,6,7,8-tetrahydropyrido[4,3-d]pyrimidin-2-yl)-2-methylimidazo[1,2-a]pyridine-8-carboxamide 3-(4-(benzylamino)-8-methyl-5,6,7,8-tetrahydropyrido[4,3-d]pyrimidin-2-yl)imidazo[1,5-a]pyridine-8-carboxamide 3-(4-(benzylamino)-8-methyl-5,6,7,8-tetrahydroquinazolin-2-yl)-2-methylimidazo[1,2-a]pyridine-8-carboxamide 3-(4-(benzylamino)-8-methyl-5,6,7,8-tetrahydroquinazolin-2-yl)imidazo[1,5-a]pyridine-8-carboxamide 3-(4-(benzylamino)-8-methyl-6,7,8,9-tetrahydro-5H-pyrimido[4,5-c]azepin-2-yl)-2-methyl-1H-indole-7-carboxamide 3-(4-(benzylamino)-8-methyl-6,8-dihydro-5H-pyrano[3,4-d]pyrimidin-2-yl)-2-methylimidazo[1,2-a]pyridine-8-carboxamide 3-(4-(benzylamino)-8-methyl-6,8-dihydro-5H-pyrano[3,4-d]pyrimidin-2-yl)imidazo[1,5-a]pyridine-8-carboxamide 3-(4-(benzylamino)-8-methyl-7,8-dihydro-5H-pyrano[4,3-d]pyrimidin-2-yl)-2-methylimidazo[1,2-a]pyridine-8-carboxamide 3-(4-(benzylamino)-8-methyl-7,8-dihydro-5H-pyrano[4,3-d]pyrimidin-2-yl)imidazo[1,5-a]pyridine-8-carboxamide 3-(4-(benzylamino)-9-methyl-6,7,8,9-tetrahydro-5H-pyrimido[4,5-b]azepin-2-yl)-2-methyl-1H-indole-7-carboxamide 1-(4-(benzylamino)-5,6,7,8-tetrahydrooxepino[2,3-d]pyrimidin-2-yl)-2H-isoindole-4-carboxamide 1-(4-(benzylamino)-5,6,7,8-tetrahydrooxepino[2,3-d]pyrimidin-2-yl)-2-methylindolizine-5-carboxamide 1-(4-(benzylamino)-5,6,7,8-tetrahydrooxepino[2,3-d]pyrimidin-2-yl)benzo[c]thiophene-4-carboxamide 1-(4-(benzylamino)-5,6,7,8-tetrahydrooxepino[2,3-d]pyrimidin-2-yl)imidazo[1,5-a]pyridine-5-carboxamide 1-(4-(benzylamino)-5,6,7,8-tetrahydrooxepino[2,3-d]pyrimidin-2-yl)isobenzofuran-4-carboxamide 1-(4-(benzylamino)-5,6,7,8-tetrahydropyrido[2,3-d]pyrimidin-2-yl)-2H-isoindole-4-carboxamide 1-(4-(benzylamino)-5,6,7,8-tetrahydropyrido[2,3-d]pyrimidin-2-yl)-2-methylindolizine-5-carboxamide 1-(4-(benzylamino)-5,6,7,8-tetrahydropyrido[2,3-d]pyrimidin-2-yl)benzo[c]thiophene-4-carboxamide 1-(4-(benzylamino)-5,6,7,8-tetrahydropyrido[2,3-d]pyrimidin-2-yl)isobenzofuran-4-carboxamide 1-(4-(benzylamino)-5,6,7,8-tetrahydropyrido[3,2-d]pyrimidin-2-yl)-2H-isoindole-4-carboxamide 1-(4-(benzylamino)-5,6,7,8-tetrahydropyrido[3,2-d]pyrimidin-2-yl)-2-methylindolizine-5-carboxamide 1-(4-(benzylamino)-5,6,7,8-tetrahydropyrido[3,2-d]pyrimidin-2-yl)benzo[c]thiophene-4-carboxamide 1-(4-(benzylamino)-5,6,7,8-tetrahydropyrido[3,2-d]pyrimidin-2-yl)isobenzofuran-4-carboxamide 1-(4-(benzylamino)-5,6,7,8-tetrahydropyrido[3,4-d]pyrimidin-2-yl)-2H-isoindole-4-carboxamide
1-(4-(benzylamino)-5,6,7,8-tetrahydropyrido[3,4-d]pyrimidin-2-yl)-2-methylindolizine-5-carboxamide
1-(4-(benzylamino)-5,6,7,8-tetrahydropyrido[3,4-d]pyrimidin-2-yl)benzo[c]thiophene-4-carboxamide
1-(4-(benzylamino)-5,6,7,8-tetrahydropyrido[3,4-d]pyrimidin-2-yl)isobenzofuran-4-carboxamide
1-(4-(benzylamino)-5,6,7,8-tetrahydropyrido[4,3-d]pyrimidin-2-yl)-2H-isoindole-4-carboxamide
1-(4-(benzylamino)-5,6,7,8-tetrahydropyrido[4,3-d]pyrimidin-2-yl)-2-methylindolizine-5-carboxamide
1-(4-(benzylamino)-5,6,7,8-tetrahydropyrido[4,3-d]pyrimidin-2-yl)benzo[c]thiophene-4-carboxamide
1-(4-(benzylamino)-5,6,7,8-tetrahydropyrido[4,3-d]pyrimidin-2-yl)isobenzofuran-4-carboxamide
1-(4-(benzylamino)-5,6,7,8-tetrahydroquinazolin-2-yl)-1H-benzo[d][1,2,3]triazole-4-carboxamide
1-(4-(benzylamino)-5,6,7,8-tetrahydroquinazolin-2-yl)-2H-isoindole-4-carboxamide
1-(4-(benzylamino)-5,6,7,8-tetrahydroquinazolin-2-yl)-2-methylindolizine-5-carboxamide
1-(4-(benzylamino)-5,6,7,8-tetrahydroquinazolin-2-yl)benzo[c]thiophene-4-carboxamide
1-(4-(benzylamino)-5,6,7,8-tetrahydroquinazolin-2-yl)isobenzofuran-4-carboxamide
1-(4-(benzylamino)-5,6,7,9-tetrahydrooxepino[3,4-d]pyrimidin-2-yl)-2H-isoindole-4-carboxamide
1-(4-(benzylamino)-5,6,7,9-tetrahydrooxepino[3,4-d]pyrimidin-2-yl)-2-methylindolizine-5-carboxamide
1-(4-(benzylamino)-5,6,7,9-tetrahydrooxepino[3,4-d]pyrimidin-2-yl)benzo[c]thiophene-4-carboxamide
1-(4-(benzylamino)-5,6,7,9-tetrahydrooxepino[3,4-d]pyrimidin-2-yl)imidazo[1,5-a]pyridine-5-carboxamide
1-(4-(benzylamino)-5,6,7,9-tetrahydrooxepino[3,4-d]pyrimidin-2-yl)isobenzofuran-4-carboxamide
1-(4-(benzylamino)-5,6,8,9-tetrahydrooxepino[4,5-d]pyrimidin-2-yl)-2H-isoindole-4-carboxamide
1-(4-(benzylamino)-5,6,8,9-tetrahydrooxepino[4,5-d]pyrimidin-2-yl)-2-methylindolizine-5-carboxamide
1-(4-(benzylamino)-5,6,8,9-tetrahydrooxepino[4,5-d]pyrimidin-2-yl)benzo[c]thiophene-4-carboxamide
1-(4-(benzylamino)-5,6,8,9-tetrahydrooxepino[4,5-d]pyrimidin-2-yl)imidazo[1,5-a]pyridine-5-carboxamide
1-(4-(benzylamino)-5,6,8,9-tetrahydrooxepino[4,5-d]pyrimidin-2-yl)isobenzofuran-4-carboxamide
1-(4-(benzylamino)-5,6-dihydrofuro[2,3-d]pyrimidin-2-yl)-1H-benzo[d][1,2,3]triazole-4-carboxamide
1-(4-(benzylamino)-5,6-dihydrofuro[2,3-d]pyrimidin-2-yl)-2H-isoindole-4-carboxamide
1-(4-(benzylamino)-5,6-dihydrofuro[2,3-d]pyrimidin-2-yl)-2-methylindolizine-5-carboxamide
1-(4-(benzylamino)-5,6-dihydrofuro[2,3-d]pyrimidin-2-yl)benzo[c]thiophene-4-carboxamide
1-(4-(benzylamino)-5,6-dihydrofuro[2,3-d]pyrimidin-2-yl)imidazo[1,5-a]pyridine-5-carboxamide
1-(4-(benzylamino)-5,6-dihydrofuro[2,3-d]pyrimidin-2-yl)isobenzofuran-4-carboxamide
1-(4-(benzylamino)-5,7,8,9-tetrahydrooxepino[4,3-d]pyrimidin-2-yl)-2H-isoindole-4-carboxamide
1-(4-(benzylamino)-5,7,8,9-tetrahydrooxepino[4,3-d]pyrimidin-2-yl)-2-methylindolizine-5-carboxamide
1-(4-(benzylamino)-5,7,8,9-tetrahydrooxepino[4,3-d]pyrimidin-2-yl)benzo[c]thiophene-4-carboxamide
1-(4-(benzylamino)-5,7,8,9-tetrahydrooxepino[4,3-d]pyrimidin-2-yl)imidazo[1,5-a]pyridine-5-carboxamide
1-(4-(benzylamino)-5,7,8,9-tetrahydrooxepino[4,3-d]pyrimidin-2-yl)isobenzofuran-4-carboxamide
1-(4-(benzylamino)-5,7-dihydrofuro[3,4-d]pyrimidin-2-yl)-1H-benzo[d][1,2,3]triazole-4-carboxamide
1-(4-(benzylamino)-5,7-dihydrofuro[3,4-d]pyrimidin-2-yl)-2H-isoindole-4-carboxamide
1-(4-(benzylamino)-5,7-dihydrofuro[3,4-d]pyrimidin-2-yl)-2-methylindolizine-5-carboxamide
1-(4-(benzylamino)-5,7-dihydrofuro[3,4-d]pyrimidin-2-yl)benzo[c]thiophene-4-carboxamide
1-(4-(benzylamino)-5,7-dihydrofuro[3,4-d]pyrimidin-2-yl)imidazo[1,5-a]pyridine-5-carboxamide
1-(4-(benzylamino)-5,7-dihydrofuro[3,4-d]pyrimidin-2-yl)isobenzofuran-4-carboxamide
1-(4-(benzylamino)-5-methyl-5,6,7,8-tetrahydropyrido[3,2-d]pyrimidin-2-yl)-2H-isoindole-4-carboxamide
1-(4-(benzylamino)-5-methyl-5,6,7,8-tetrahydropyrido[3,2-d]pyrimidin-2-yl)-2-methylindolizine-5-carboxamide
1-(4-(benzylamino)-5-methyl-5,6,7,8-tetrahydropyrido[3,2-d]pyrimidin-2-yl)benzo[c]thiophene-4-carboxamide
1-(4-(benzylamino)-5-methyl-5,6,7,8-tetrahydropyrido[3,2-d]pyrimidin-2-yl)isobenzofuran-4-carboxamide
1-(4-(benzylamino)-5-methyl-6,7,8,9-tetrahydro-5H-pyrimido[5,4-b]azepin-2-yl)-2H-isoindole-4-carboxamide
1-(4-(benzylamino)-5-methyl-6,7,8,9-tetrahydro-5H-pyrimido[5,4-b]azepin-2-yl)-2-methylindolizine-5-carboxamide
1-(4-(benzylamino)-5-methyl-6,7,8,9-tetrahydro-5H-pyrimido[5,4-b]azepin-2-yl)benzo[c]thiophene-4-carboxamide
1-(4-(benzylamino)-5-methyl-6,7,8,9-tetrahydro-5H-pyrimido[5,4-b]azepin-2-yl)imidazo[1,5-a]pyridine-5-carboxamide
1-(4-(benzylamino)-5-methyl-6,7,8,9-tetrahydro-5H-pyrimido[5,4-b]azepin-2-yl)isobenzofuran-4-carboxamide
1-(4-(benzylamino)-5-methyl-6,7-dihydro-5H-pyrrolo[3,2-d]pyrimidin-2-yl)-2H-isoindole-4-carboxamide
1-(4-(benzylamino)-5-methyl-6,7-dihydro-5H-pyrrolo[3,2-d]pyrimidin-2-yl)-2-methylindolizine-5-carboxamide
1-(4-(benzylamino)-5-methyl-6,7-dihydro-5H-pyrrolo[3,2-d]pyrimidin-2-yl)benzo[c]thiophene-4-carboxamide
1-(4-(benzylamino)-5-methyl-6,7-dihydro-5H-pyrrolo[3,2-d]pyrimidin-2-yl)imidazo[1,5-a]pyridine-5-carboxamide
1-(4-(benzylamino)-5-methyl-6,7-dihydro-5H-pyrrolo[3,2-d]pyrimidin-2-yl)isobenzofuran-4-carboxamide
1-(4-(benzylamino)-6,7,8,9-tetrahydro-5H-cyclohepta[d]pyrimidin-2-yl)-1H-benzo[d][1,2,3]triazole-4-carboxamide
1-(4-(benzylamino)-6,7,8,9-tetrahydro-5H-cyclohepta[d]pyrimidin-2-yl)-2H-isoindole-4-carboxamide
1-(4-(benzylamino)-6,7,8,9-tetrahydro-5H-cyclohepta[d]pyrimidin-2-yl)-2-methylindolizine-5-carboxamide
1-(4-(benzylamino)-6,7,8,9-tetrahydro-5H-cyclohepta[d]pyrimidin-2-yl)benzo[c]thiophene-4-carboxamide
1-(4-(benzylamino)-6,7,8,9-tetrahydro-5H-cyclohepta[d]pyrimidin-2-yl)imidazo[1,5-a]pyridine-5-carboxamide
1-(4-(benzylamino)-6,7,8,9-tetrahydro-5H-cyclohepta[d]pyrimidin-2-yl)isobenzofuran-4-carboxamide
1-(4-(benzylamino)-6,7,8,9-tetrahydro-5H-pyrimido[4,5-b]azepin-2-yl)-2H-isoindole-4-carboxamide
1-(4-(benzylamino)-6,7,8,9-tetrahydro-5H-pyrimido[4,5-b]azepin-2-yl)-2-methylindolizine-5-carboxamide
1-(4-(benzylamino)-6,7,8,9-tetrahydro-5H-pyrimido[4,5-b]azepin-2-yl)benzo[c]thiophene-4-carboxamide
1-(4-(benzylamino)-6,7,8,9-tetrahydro-5H-pyrimido[4,5-b]azepin-2-yl)imidazo[1,5-a]pyridine-5-carboxamide 1-(4-(benzylamino)-6,7,8,9-tetrahydro-5H-pyrimido[4,5-b]
azepin-2-yl)isobenzofuran-4-carboxamide
1-(4-(benzylamino)-6,7,8,9-tetrahydro-5H-pyrimido[4,5-c]
azepin-2-yl)-2H-isoindole-4-carboxamide
1-(4-(benzylamino)-6,7,8,9-tetrahydro-5H-pyrimido[4,5-c]
azepin-2-yl)-2-methylindolizine-5-carboxamide
1-(4-(benzylamino)-6,7,8,9-tetrahydro-5H-pyrimido[4,5-c]
azepin-2-yl)benzo[c]thiophene-4-carboxamide
1-(4-(benzylamino)-6,7,8,9-tetrahydro-5H-pyrimido[4,5-c]
azepin-2-yl)imidazo[1,5-a]pyridine-5-carboxamide
1-(4-(benzylamino)-6,7,8,9-tetrahydro-5H-pyrimido[4,5-c]
azepin-2-yl)isobenzofuran-4-carboxamide
1-(4-(benzylamino)-6,7,8,9-tetrahydro-5H-pyrimido[4,5-d]
azepin-2-yl)-2H-isoindole-4-carboxamide
1-(4-(benzylamino)-6,7,8,9-tetrahydro-5H-pyrimido[4,5-d]
azepin-2-yl)-2-methylindolizine-5-carboxamide
1-(4-(benzylamino)-6,7,8,9-tetrahydro-5H-pyrimido[4,5-d]
azepin-2-yl)benzo[c]thiophene-4-carboxamide
1-(4-(benzylamino)-6,7,8,9-tetrahydro-5H-pyrimido[4,5-d]
azepin-2-yl)imidazo[1,5-a]pyridine-5-carboxamide
1-(4-(benzylamino)-6,7,8,9-tetrahydro-5H-pyrimido[4,5-d]
azepin-2-yl)isobenzofuran-4-carboxamide
1-(4-(benzylamino)-6,7,8,9-tetrahydro-5H-pyrimido[5,4-b]
azepin-2-yl)-2H-isoindole-4-carboxamide
1-(4-(benzylamino)-6,7,8,9-tetrahydro-5H-pyrimido[5,4-b]
azepin-2-yl)-2-methylindolizine-5-carboxamide
1-(4-(benzylamino)-6,7,8,9-tetrahydro-5H-pyrimido[5,4-b]
azepin-2-yl)benzo[c]thiophene-4-carboxamide
1-(4-(benzylamino)-6,7,8,9-tetrahydro-5H-pyrimido[5,4-b]
azepin-2-yl)imidazo[1,5-a]pyridine-5-carboxamide
1-(4-(benzylamino)-6,7,8,9-tetrahydro-5H-pyrimido[5,4-b]
azepin-2-yl)isobenzofuran-4-carboxamide
1-(4-(benzylamino)-6,7,8,9-tetrahydro-5H-pyrimido[5,4-c]
azepin-2-yl)-2H-isoindole-4-carboxamide
1-(4-(benzylamino)-6,7,8,9-tetrahydro-5H-pyrimido[5,4-c]
azepin-2-yl)-2-methylindolizine-5-carboxamide
1-(4-(benzylamino)-6,7,8,9-tetrahydro-5H-pyrimido[5,4-c]
azepin-2-yl)benzo[c]thiophene-4-carboxamide
1-(4-(benzylamino)-6,7,8,9-tetrahydro-5H-pyrimido[5,4-c]
azepin-2-yl)imidazo[1,5-a]pyridine-5-carboxamide
1-(4-(benzylamino)-6,7,8,9-tetrahydro-5H-pyrimido[5,4-c]
azepin-2-yl)isobenzofuran-4-carboxamide
1-(4-(benzylamino)-6,7,8,9-tetrahydrooxepino[3,2-d]py-
rimidin-2-yl)-2H-isoindole-4-carboxamide
1-(4-(benzylamino)-6,7,8,9-tetrahydrooxepino[3,2-d]py-
rimidin-2-yl)-2-methylindolizine-5-carboxamide
1-(4-(benzylamino)-6,7,8,9-tetrahydrooxepino[3,2-d]py-
rimidin-2-yl)benzo[c]thiophene-4-carboxamide
1-(4-(benzylamino)-6,7,8,9-tetrahydrooxepino[3,2-d]py-
rimidin-2-yl)imidazo[1,5-a]pyridine-5-carboxamide
1-(4-(benzylamino)-6,7,8,9-tetrahydrooxepino[3,2-d]py-
rimidin-2-yl)isobenzofuran-4-carboxamide
1-(4-(benzylamino)-6,7-dihydro-5H-cyclopenta[d]pyrimi-
din-2-yl)-1H-benzo[d][1,2,3]triazole-4-carboxamide
1-(4-(benzylamino)-6,7-dihydro-5H-cyclopenta[d]pyrimi-
din-2-yl)-2H-isoindole-4-carboxamide
1-(4-(benzylamino)-6,7-dihydro-5H-cyclopenta[d]pyrimi-
din-2-yl)-2-methylindolizine-5-carboxamide
1-(4-(benzylamino)-6,7-dihydro-5H-cyclopenta[d]pyrimi-
din-2-yl)benzo[c]thiophene-4-carboxamide
1-(4-(benzylamino)-6,7-dihydro-5H-cyclopenta[d]pyrimi-
din-2-yl)isobenzofuran-4-carboxamide
1-(4-(benzylamino)-6,7-dihydro-5H-pyrano[2,3-d]pyrimi-
din-2-yl)-1H-benzo[d][1,2,3]triazole-4-carboxamide
1-(4-(benzylamino)-6,7-dihydro-5H-pyrano[2,3-d]pyrimi-
din-2-yl)-2H-isoindole-4-carboxamide
1-(4-(benzylamino)-6,7-dihydro-5H-pyrano[2,3-d]pyrimi-
din-2-yl)-2-methylindolizine-5-carboxamide
1-(4-(benzylamino)-6,7-dihydro-5H-pyrano[2,3-d]pyrimi-
din-2-yl)benzo[c]thiophene-4-carboxamide
1-(4-(benzylamino)-6,7-dihydro-5H-pyrano[2,3-d]pyrimi-
din-2-yl)isobenzofuran-4-carboxamide
1-(4-(benzylamino)-6,7-dihydro-5H-pyrrolo[2,3-d]pyrimi-
din-2-yl)-2H-isoindole-4-carboxamide
1-(4-(benzylamino)-6,7-dihydro-5H-pyrrolo[2,3-d]pyrimi-
din-2-yl)-2-methylindolizine-5-carboxamide
1-(4-(benzylamino)-6,7-dihydro-5H-pyrrolo[2,3-d]pyrimi-
din-2-yl)benzo[c]thiophene-4-carboxamide
1-(4-(benzylamino)-6,7-dihydro-5H-pyrrolo[2,3-d]pyrimi-
din-2-yl)imidazo[1,5-a]pyridine-5-carboxamide
1-(4-(benzylamino)-6,7-dihydro-5H-pyrrolo[2,3-d]pyrimi-
din-2-yl)isobenzofuran-4-carboxamide
1-(4-(benzylamino)-6,7-dihydro-5H-pyrrolo[3,2-d]pyrimi-
din-2-yl)-2H-isoindole-4-carboxamide
1-(4-(benzylamino)-6,7-dihydro-5H-pyrrolo[3,2-d]pyrimi-
din-2-yl)-2-methylindolizine-5-carboxamide
1-(4-(benzylamino)-6,7-dihydro-5H-pyrrolo[3,2-d]pyrimi-
din-2-yl)benzo[c]thiophene-4-carboxamide
1-(4-(benzylamino)-6,7-dihydro-5H-pyrrolo[3,2-d]pyrimi-
din-2-yl)imidazo[1,5-a]pyridine-5-carboxamide
1-(4-(benzylamino)-6,7-dihydro-5H-pyrrolo[3,2-d]pyrimi-
din-2-yl)isobenzofuran-4-carboxamide
1-(4-(benzylamino)-6,7-dihydro-5H-pyrrolo[3,4-d]pyrimi-
din-2-yl)-2H-isoindole-4-carboxamide
1-(4-(benzylamino)-6,7-dihydro-5H-pyrrolo[3,4-d]pyrimi-
din-2-yl)-2-methylindolizine-5-carboxamide
1-(4-(benzylamino)-6,7-dihydro-5H-pyrrolo[3,4-d]pyrimi-
din-2-yl)benzo[c]thiophene-4-carboxamide
1-(4-(benzylamino)-6,7-dihydro-5H-pyrrolo[3,4-d]pyrimi-
din-2-yl)imidazo[1,5-a]pyridine-5-carboxamide
1-(4-(benzylamino)-6,7-dihydro-5H-pyrrolo[3,4-d]pyrimi-
din-2-yl)isobenzofuran-4-carboxamide
1-(4-(benzylamino)-6,7-dihydrofuro[3,2-d]pyrimidin-2-yl)-
1H-benzo[d][1,2,3]triazole-4-carboxamide
1-(4-(benzylamino)-6,7-dihydrofuro[3,2-d]pyrimidin-2-yl)-
2H-isoindole-4-carboxamide
1-(4-(benzylamino)-6,7-dihydrofuro[3,2-d]pyrimidin-2-yl)-
2-methylindolizine-5-carboxamide
1-(4-(benzylamino)-6,7-dihydrofuro[3,2-d]pyrimidin-2-yl)
benzo[c]thiophene-4-carboxamide
1-(4-(benzylamino)-6,7-dihydrofuro[3,2-d]pyrimidin-2-yl)
imidazo[1,5-a]pyridine-5-carboxamide
1-(4-(benzylamino)-6,7-dihydrofuro[3,2-d]pyrimidin-2-yl)
isobenzofuran-4-carboxamide
1-(4-(benzylamino)-6,8-dihydro-5H-pyrano[3,4-d]pyrimi-
din-2-yl)-1H-benzo[d][1,2,3]triazole-4-carboxamide
1-(4-(benzylamino)-6,8-dihydro-5H-pyrano[3,4-d]pyrimi-
din-2-yl)-2H-isoindole-4-carboxamide
1-(4-(benzylamino)-6,8-dihydro-5H-pyrano[3,4-d]pyrimi-
din-2-yl)-2-methylindolizine-5-carboxamide
1-(4-(benzylamino)-6,8-dihydro-5H-pyrano[3,4-d]pyrimi-
din-2-yl)benzo[c]thiophene-4-carboxamide
1-(4-(benzylamino)-6,8-dihydro-5H-pyrano[3,4-d]pyrimi-
din-2-yl)isobenzofuran-4-carboxamide
1-(4-(benzylamino)-6-methyl-5,6,7,8-tetrahydropyrido[4,3-
d]pyrimidin-2-yl)-2H-isoindole-4-carboxamide
1-(4-(benzylamino)-6-methyl-5,6,7,8-tetrahydropyrido[4,3-
d]pyrimidin-2-yl)-2-methylindolizine-5-carboxamide
1-(4-(benzylamino)-6-methyl-5,6,7,8-tetrahydropyrido[4,3-
d]pyrimidin-2-yl)benzo[c]thiophene-4-carboxamide
1-(4-(benzylamino)-6-methyl-5,6,7,8-tetrahydropyrido[4,3-
d]pyrimidin-2-yl)isobenzofuran-4-carboxamide 1-(4-(benzylamino)-6-methyl-6,7,8,9-tetrahydro-5H-pyrimido[5,4-c]azepin-2-yl)-2H-isoindole-4-carboxamide
1-(4-(benzylamino)-6-methyl-6,7,8,9-tetrahydro-5H-pyrimido[5,4-c]azepin-2-yl)-2-methylindolizine-5-carboxamide
1-(4-(benzylamino)-6-methyl-6,7,8,9-tetrahydro-5H-pyrimido[5,4-c]azepin-2-yl)benzo[c]thiophene-4-carboxamide
1-(4-(benzylamino)-6-methyl-6,7,8,9-tetrahydro-5H-pyrimido[5,4-c]azepin-2-yl)imidazo[1,5-a]pyridine-5-carboxamide
1-(4-(benzylamino)-6-methyl-6,7,8,9-tetrahydro-5H-pyrimido[5,4-c]azepin-2-yl)isobenzofuran-4-carboxamide
1-(4-(benzylamino)-6-methyl-6,7-dihydro-5H-pyrrolo[3,4-d]pyrimidin-2-yl)-2H-isoindole-4-carboxamide
1-(4-(benzylamino)-6-methyl-6,7-dihydro-5H-pyrrolo[3,4-d]pyrimidin-2-yl)-2-methylindolizine-5-carboxamide
1-(4-(benzylamino)-6-methyl-6,7-dihydro-5H-pyrrolo[3,4-d]pyrimidin-2-yl)benzo[c]thiophene-4-carboxamide
1-(4-(benzylamino)-6-methyl-6,7-dihydro-5H-pyrrolo[3,4-d]pyrimidin-2-yl)imidazo[1,5-a]pyridine-5-carboxamide
1-(4-(benzylamino)-6-methyl-6,7-dihydro-5H-pyrrolo[3,4-d]pyrimidin-2-yl)isobenzofuran-4-carboxamide
1-(4-(benzylamino)-7,8-dihydro-5H-pyrano[4,3-d]pyrimidin-2-yl)-1H-benzo[d][1,2,3]triazole-4-carboxamide
1-(4-(benzylamino)-7,8-dihydro-5H-pyrano[4,3-d]pyrimidin-2-yl)-2H-isoindole-4-carboxamide
1-(4-(benzylamino)-7,8-dihydro-5H-pyrano[4,3-d]pyrimidin-2-yl)-2-methylindolizine-5-carboxamide
1-(4-(benzylamino)-7,8-dihydro-5H-pyrano[4,3-d]pyrimidin-2-yl)benzo[c]thiophene-4-carboxamide
1-(4-(benzylamino)-7,8-dihydro-5H-pyrano[4,3-d]pyrimidin-2-yl)isobenzofuran-4-carboxamide
1-(4-(benzylamino)-7,8-dihydro-6H-pyrano[3,2-d]pyrimidin-2-yl)-1H-benzo[d][1,2,3]triazole-4-carboxamide
1-(4-(benzylamino)-7,8-dihydro-6H-pyrano[3,2-d]pyrimidin-2-yl)-2H-isoindole-4-carboxamide
1-(4-(benzylamino)-7,8-dihydro-6H-pyrano[3,2-d]pyrimidin-2-yl)-2-methylindolizine-5-carboxamide
1-(4-(benzylamino)-7,8-dihydro-6H-pyrano[3,2-d]pyrimidin-2-yl)benzo[c]thiophene-4-carboxamide
1-(4-(benzylamino)-7,8-dihydro-6H-pyrano[3,2-d]pyrimidin-2-yl)imidazo[1,5-a]pyridine-5-carboxamide
1-(4-(benzylamino)-7,8-dihydro-6H-pyrano[3,2-d]pyrimidin-2-yl)isobenzofuran-4-carboxamide
1-(4-(benzylamino)-7-methyl-5,6,7,8-tetrahydropyrido[3,4-d]pyrimidin-2-yl)-2H-isoindole-4-carboxamide
1-(4-(benzylamino)-7-methyl-5,6,7,8-tetrahydropyrido[3,4-d]pyrimidin-2-yl)-2-methylindolizine-5-carboxamide
1-(4-(benzylamino)-7-methyl-5,6,7,8-tetrahydropyrido[3,4-d]pyrimidin-2-yl)benzo[c]thiophene-4-carboxamide
1-(4-(benzylamino)-7-methyl-5,6,7,8-tetrahydropyrido[3,4-d]pyrimidin-2-yl)isobenzofuran-4-carboxamide
1-(4-(benzylamino)-7-methyl-6,7-dihydro-5H-pyrrolo[2,3-d]pyrimidin-2-yl)-2H-isoindole-4-carboxamide
1-(4-(benzylamino)-7-methyl-6,7-dihydro-5H-pyrrolo[2,3-d]pyrimidin-2-yl)-2-methylindolizine-5-carboxamide
1-(4-(benzylamino)-7-methyl-6,7-dihydro-5H-pyrrolo[2,3-d]pyrimidin-2-yl)benzo[c]thiophene-4-carboxamide
1-(4-(benzylamino)-7-methyl-6,7-dihydro-5H-pyrrolo[2,3-d]pyrimidin-2-yl)imidazo[1,5-a]pyridine-5-carboxamide
1-(4-(benzylamino)-7-methyl-6,7-dihydro-5H-pyrrolo[2,3-d]pyrimidin-2-yl)isobenzofuran-4-carboxamide
1-(4-(benzylamino)-8-methyl-5,6,7,8-tetrahydropyrido[2,3-d]pyrimidin-2-yl)-2H-isoindole-4-carboxamide
1-(4-(benzylamino)-8-methyl-5,6,7,8-tetrahydropyrido[2,3-d]pyrimidin-2-yl)-2-methylindolizine-5-carboxamide
1-(4-(benzylamino)-8-methyl-5,6,7,8-tetrahydropyrido[2,3-d]pyrimidin-2-yl)benzo[c]thiophene-4-carboxamide
1-(4-(benzylamino)-8-methyl-5,6,7,8-tetrahydropyrido[2,3-d]pyrimidin-2-yl)isobenzofuran-4-carboxamide
1-(4-(benzylamino)-8-methyl-6,7,8,9-tetrahydro-5H-pyrimido[4,5-c]azepin-2-yl)-2H-isoindole-4-carboxamide
1-(4-(benzylamino)-8-methyl-6,7,8,9-tetrahydro-5H-pyrimido[4,5-c]azepin-2-yl)-2-methylindolizine-5-carboxamide
1-(4-(benzylamino)-8-methyl-6,7,8,9-tetrahydro-5H-pyrimido[4,5-c]azepin-2-yl)benzo[c]thiophene-4-carboxamide
1-(4-(benzylamino)-8-methyl-6,7,8,9-tetrahydro-5H-pyrimido[4,5-c]azepin-2-yl)imidazo[1,5-a]pyridine-5-carboxamide
1-(4-(benzylamino)-8-methyl-6,7,8,9-tetrahydro-5H-pyrimido[4,5-c]azepin-2-yl)isobenzofuran-4-carboxamide
1-(4-(benzylamino)-9-methyl-6,7,8,9-tetrahydro-5H-pyrimido[4,5-b]azepin-2-yl)-2H-isoindole-4-carboxamide
1-(4-(benzylamino)-9-methyl-6,7,8,9-tetrahydro-5H-pyrimido[4,5-b]azepin-2-yl)-2-methylindolizine-5-carboxamide
1-(4-(benzylamino)-9-methyl-6,7,8,9-tetrahydro-5H-pyrimido[4,5-b]azepin-2-yl)benzo[c]thiophene-4-carboxamide
1-(4-(benzylamino)-9-methyl-6,7,8,9-tetrahydro-5H-pyrimido[4,5-b]azepin-2-yl)imidazo[1,5-a]pyridine-5-carboxamide
1-(4-(benzylamino)-9-methyl-6,7,8,9-tetrahydro-5H-pyrimido[4,5-b]azepin-2-yl)isobenzofuran-4-carboxamide
3-(4-((3-fluorobenzyl)amino)-5,6,7,8-tetrahydrooxepino[2,3-d]pyrimidin-2-yl)-2-methylimidazo[1,2-a]pyridine-8-carboxamide
3-(4-((3-fluorobenzyl)amino)-5,6,7,8-tetrahydrooxepino[2,3-d]pyrimidin-2-yl)imidazo[1,5-a]pyridine-8-carboxamide
3-(4-((3-fluorobenzyl)amino)-5,6,7,9-tetrahydrooxepino[3,4-d]pyrimidin-2-yl)-2-methylimidazo[1,2-a]pyridine-8-carboxamide
3-(4-((3-fluorobenzyl)amino)-5,6,7,9-tetrahydrooxepino[3,4-d]pyrimidin-2-yl)imidazo[1,5-a]pyridine-8-carboxamide
3-(4-((3-fluorobenzyl)amino)-5,6,8,9-tetrahydrooxepino[4,5-d]pyrimidin-2-yl)-2-methylimidazo[1,2-a]pyridine-8-carboxamide
3-(4-((3-fluorobenzyl)amino)-5,6,8,9-tetrahydrooxepino[4,5-d]pyrimidin-2-yl)imidazo[1,5-a]pyridine-8-carboxamide
3-(4-((3-fluorobenzyl)amino)-5,6-dihydrofuro[2,3-d]pyrimidin-2-yl)-2-methylimidazo[1,2-a]pyridine-8-carboxamide
3-(4-((3-fluorobenzyl)amino)-5,6-dihydrofuro[2,3-d]pyrimidin-2-yl)imidazo[1,5-a]pyridine-8-carboxamide
3-(4-((3-fluorobenzyl)amino)-5,7,8,9-tetrahydrooxepino[4,3-d]pyrimidin-2-yl)-2-methylimidazo[1,2-a]pyridine-8-carboxamide
3-(4-((3-fluorobenzyl)amino)-5,7,8,9-tetrahydrooxepino[4,3-d]pyrimidin-2-yl)imidazo[1,5-a]pyridine-8-carboxamide
3-(4-((3-fluorobenzyl)amino)-5,7-dihydrofuro[3,4-d]pyrimidin-2-yl)-2-methylimidazo[1,2-a]pyridine-8-carboxamide
3-(4-((3-fluorobenzyl)amino)-5,7-dihydrofuro[3,4-d]pyrimidin-2-yl)imidazo[1,5-a]pyridine-8-carboxamide
3-(4-((3-fluorobenzyl)amino)-5-methyl-6,7,8,9-tetrahydro-5H-pyrimido[5,4-b]azepin-2-yl)-2-methylimidazo[1,2-a]pyridine-8-carboxamide 3-(4-((3-fluorobenzyl)amino)-5-methyl-6,7,8,9-tetrahydro-5H-pyrimido[5,4-b]azepin-2-yl)imidazo[1,5-a]pyridine-8-carboxamide 3-(4-((3-fluorobenzyl)amino)-5-methyl-6,7-dihydro-5H-pyrrolo[3,2-d]pyrimidin-2-yl)-2-methylimidazo[1,2-a]pyridine-8-carboxamide 3-(4-((3-fluorobenzyl)amino)-5-methyl-6,7-dihydro-5H-pyrrolo[3,2-d]pyrimidin-2-yl)imidazo[1,5-a]pyridine-8-carboxamide 3-(4-((3-fluorobenzyl)amino)-6,7,8,9-tetrahydro-5H-cyclohepta[d]pyrimidin-2-yl)-2-methylimidazo[1,2-a]pyridine-8-carboxamide 3-(4-((3-fluorobenzyl)amino)-6,7,8,9-tetrahydro-5H-cyclohepta[d]pyrimidin-2-yl)imidazo[1,5-a]pyridine-8-carboxamide 3-(4-((3-fluorobenzyl)amino)-6,7,8,9-tetrahydro-5H-pyrimido[4,5-b]azepin-2-yl)-2-methylimidazo[1,2-a]pyridine-8-carboxamide 3-(4-((3-fluorobenzyl)amino)-6,7,8,9-tetrahydro-5H-pyrimido[4,5-b]azepin-2-yl)imidazo[1,5-a]pyridine-8-carboxamide 3-(4-((3-fluorobenzyl)amino)-6,7,8,9-tetrahydro-5H-pyrimido[4,5-c]azepin-2-yl)-2-methylimidazo[1,2-a]pyridine-8-carboxamide 3-(4-((3-fluorobenzyl)amino)-6,7,8,9-tetrahydro-5H-pyrimido[4,5-c]azepin-2-yl)imidazo[1,5-a]pyridine-8-carboxamide 3-(4-((3-fluorobenzyl)amino)-6,7,8,9-tetrahydro-5H-pyrimido[4,5-d]azepin-2-yl)-2-methylimidazo[1,2-a]pyridine-8-carboxamide 3-(4-((3-fluorobenzyl)amino)-6,7,8,9-tetrahydro-5H-pyrimido[4,5-d]azepin-2-yl)imidazo[1,5-a]pyridine-8-carboxamide 3-(4-((3-fluorobenzyl)amino)-6,7,8,9-tetrahydro-5H-pyrimido[5,4-b]azepin-2-yl)-2-methylimidazo[1,2-a]pyridine-8-carboxamide 3-(4-((3-fluorobenzyl)amino)-6,7,8,9-tetrahydro-5H-pyrimido[5,4-b]azepin-2-yl)imidazo[1,5-a]pyridine-8-carboxamide 3-(4-((3-fluorobenzyl)amino)-6,7,8,9-tetrahydro-5H-pyrimido[5,4-c]azepin-2-yl)-2-methylimidazo[1,2-a]pyridine-8-carboxamide 3-(4-((3-fluorobenzyl)amino)-6,7,8,9-tetrahydro-5H-pyrimido[5,4-c]azepin-2-yl)imidazo[1,5-a]pyridine-8-carboxamide 3-(4-((3-fluorobenzyl)amino)-6,7,8,9-tetrahydrooxepino[3,2-d]pyrimidin-2-yl)-2-methylimidazo[1,2-a]pyridine-8-carboxamide 3-(4-((3-fluorobenzyl)amino)-6,7,8,9-tetrahydrooxepino[3,2-d]pyrimidin-2-yl)imidazo[1,5-a]pyridine-8-carboxamide 3-(4-((3-fluorobenzyl)amino)-6,7-dihydro-5H-cyclopenta[d]pyrimidin-2-yl)-2-methylimidazo[1,2-a]pyridine-8-carboxamide 3-(4-((3-fluorobenzyl)amino)-6,7-dihydro-5H-cyclopenta[d]pyrimidin-2-yl)imidazo[1,5-a]pyridine-8-carboxamide 3-(4-((3-fluorobenzyl)amino)-6,7-dihydro-5H-pyrrolo[2,3-d]pyrimidin-2-yl)-2-methylimidazo[1,2-a]pyridine-8-carboxamide 3-(4-((3-fluorobenzyl)amino)-6,7-dihydro-5H-pyrrolo[2,3-d]pyrimidin-2-yl)imidazo[1,5-a]pyridine-8-carboxamide 3-(4-((3-fluorobenzyl)amino)-6,7-dihydro-5H-pyrrolo[3,2-d]pyrimidin-2-yl)-2-methylimidazo[1,2-a]pyridine-8-carboxamide 3-(4-((3-fluorobenzyl)amino)-6,7-dihydro-5H-pyrrolo[3,2-d]pyrimidin-2-yl)imidazo[1,5-a]pyridine-8-carboxamide 3-(4-((3-fluorobenzyl)amino)-6,7-dihydro-5H-pyrrolo[3,4-d]pyrimidin-2-yl)-2-methylimidazo[1,2-a]pyridine-8-carboxamide 3-(4-((3-fluorobenzyl)amino)-6,7-dihydro-5H-pyrrolo[3,4-d]pyrimidin-2-yl)imidazo[1,5-a]pyridine-8-carboxamide 3-(4-((3-fluorobenzyl)amino)-6,7-dihydrofuro[3,2-d]pyrimidin-2-yl)-2-methylimidazo[1,2-a]pyridine-8-carboxamide 3-(4-((3-fluorobenzyl)amino)-6,7-dihydrofuro[3,2-d]pyrimidin-2-yl)imidazo[1,5-a]pyridine-8-carboxamide 3-(4-((3-fluorobenzyl)amino)-6-methyl-6,7,8,9-tetrahydro-5H-pyrimido[5,4-c]azepin-2-yl)-2-methylimidazo[1,2-a]pyridine-8-carboxamide 3-(4-((3-fluorobenzyl)amino)-6-methyl-6,7,8,9-tetrahydro-5H-pyrimido[5,4-c]azepin-2-yl)imidazo[1,5-a]pyridine-8-carboxamide 3-(4-((3-fluorobenzyl)amino)-6-methyl-6,7-dihydro-5H-pyrrolo[3,4-d]pyrimidin-2-yl)-2-methylimidazo[1,2-a]pyridine-8-carboxamide 3-(4-((3-fluorobenzyl)amino)-6-methyl-6,7-dihydro-5H-pyrrolo[3,4-d]pyrimidin-2-yl)imidazo[1,5-a]pyridine-8-carboxamide 3-(4-((3-fluorobenzyl)amino)-7-methyl-6,7-dihydro-5H-pyrrolo[2,3-d]pyrimidin-2-yl)-2-methylimidazo[1,2-a]pyridine-8-carboxamide 3-(4-((3-fluorobenzyl)amino)-7-methyl-6,7-dihydro-5H-pyrrolo[2,3-d]pyrimidin-2-yl)imidazo[1,5-a]pyridine-8-carboxamide 3-(4-((3-fluorobenzyl)amino)-8-methyl-6,7,8,9-tetrahydro-5H-pyrimido[4,5-c]azepin-2-yl)-2-methylimidazo[1,2-a]pyridine-8-carboxamide 3-(4-((3-fluorobenzyl)amino)-8-methyl-6,7,8,9-tetrahydro-5H-pyrimido[4,5-c]azepin-2-yl)imidazo[1,5-a]pyridine-8-carboxamide 3-(4-((3-fluorobenzyl)amino)-9-methyl-6,7,8,9-tetrahydro-5H-pyrimido[4,5-b]azepin-2-yl)-2-methylimidazo[1,2-a]pyridine-8-carboxamide 3-(4-((3-fluorobenzyl)amino)-9-methyl-6,7,8,9-tetrahydro-5H-pyrimido[4,5-b]azepin-2-yl)imidazo[1,5-a]pyridine-8-carboxamide 3-(4-((thiophen-2-ylmethyl)amino)-5,6,7,8-tetrahydrooxepino[2,3-d]pyrimidin-2-yl)-2-methylimidazo[1,2-a]pyridine-8-carboxamide 3-(4-((thiophen-2-ylmethyl)amino)-5,6,7,8-tetrahydrooxepino[2,3-d]pyrimidin-2-yl)imidazo[1,5-a]pyridine-8-carboxamide 3-(4-((thiophen-2-ylmethyl)amino)-5,6,7,8-tetrahydropyrido[2,3-d]pyrimidin-2-yl)-2-methylimidazo[1,2-a]pyridine-8-carboxamide 3-(4-((thiophen-2-ylmethyl)amino)-5,6,7,8-tetrahydropyrido[2,3-d]pyrimidin-2-yl)imidazo[1,5-a]pyridine-8-carboxamide 3-(4-((thiophen-2-ylmethyl)amino)-5,6,7,8-tetrahydropyrido[3,2-d]pyrimidin-2-yl)-2-methylimidazo[1,2-a]pyridine-8-carboxamide 3-(4-((thiophen-2-ylmethyl)amino)-5,6,7,8-tetrahydropyrido[3,2-d]pyrimidin-2-yl)imidazo[1,5-a]pyridine-8-carboxamide 3-(4-((thiophen-2-ylmethyl)amino)-5,6,7,8-tetrahydropyrido[3,4-d]pyrimidin-2-yl)-2-methylimidazo[1,2-a]pyridine-8-carboxamide 3-(4-((thiophen-2-ylmethyl)amino)-5,6,7,8-tetrahydropyrido[3,4-d]pyrimidin-2-yl)imidazo[1,5-a]pyridine-8-carboxamide 3-(4-((thiophen-2-ylmethyl)amino)-5,6,7,8-tetrahydropyrido[4,3-d]pyrimidin-2-yl)-2-methylimidazo[1,2-a]pyridine-8-carboxamide 3-(4-((thiophen-2-ylmethyl)amino)-5,6,7,8-tetrahydropyrido[4,3-d]pyrimidin-2-yl)imidazo[1,5-a]pyridine-8-carboxamide 3-(4-((thiophen-2-ylmethyl)amino)-5,6,7,8-tetrahydroquinazolin-2-yl)-2-methylimidazo[1,2-a]pyridine-8-carboxamide 3-(4-((thiophen-2-ylmethyl)amino)-5,6,7,8-tetrahydroquinazolin-2-yl)imidazo[1,5-a]pyridine-8-carboxamide 3-(4-((thiophen-2-ylmethyl)amino)-5,6,7,9-tetrahydrooxepino[3,4-d]pyrimidin-2-yl)-2-methylimidazo[1,2-a]pyridine-8-carboxamide 3-(4-((thiophen-2-ylmethyl)amino)-5,6,7,9-tetrahydrooxepino[3,4-d]pyrimidin-2-yl)imidazo[1,5-a]pyridine-8-carboxamide 3-(4-((thiophen-2-ylmethyl)amino)-5,6,8,9-tetrahydrooxepino[4,5-d]pyrimidin-2-yl)-2-methylimidazo[1,2-a]pyridine-8-carboxamide 3-(4-((thiophen-2-ylmethyl)amino)-5,6,8,9-tetrahydrooxepino[4,5-d]pyrimidin-2-yl)imidazo[1,5-a]pyridine-8-carboxamide 3-(4-((thiophen-2-ylmethyl)amino)-5,6-dihydrofuro[2,3-d]pyrimidin-2-yl)-2-methylimidazo[1,2-a]pyridine-8-carboxamide 3-(4-((thiophen-2-ylmethyl)amino)-5,6-dihydrofuro[2,3-d]pyrimidin-2-yl)imidazo[1,5-a]pyridine-8-carboxamide 3-(4-((thiophen-2-ylmethyl)amino)-5,7,8,9-tetrahydrooxepino[4,3-d]pyrimidin-2-yl)-2-methylimidazo[1,2-a]pyridine-8-carboxamide 3-(4-((thiophen-2-ylmethyl)amino)-5,7,8,9-tetrahydrooxepino[4,3-d]pyrimidin-2-yl)imidazo[1,5-a]pyridine-8-carboxamide 3-(4-((thiophen-2-ylmethyl)amino)-5,7-dihydrofuro[3,4-d]pyrimidin-2-yl)-2-methylimidazo[1,2-a]pyridine-8-carboxamide 3-(4-((thiophen-2-ylmethyl)amino)-5,7-dihydrofuro[3,4-d]pyrimidin-2-yl)imidazo[1,5-a]pyridine-8-carboxamide 3-(4-((thiophen-2-ylmethyl)amino)-5-methyl-5,6,7,8-tetrahydropyrido[3,2-d]pyrimidin-2-yl)-2-methylimidazo[1,2-a]pyridine-8-carboxamide 3-(4-((thiophen-2-ylmethyl)amino)-5-methyl-5,6,7,8-tetrahydropyrido[3,2-d]pyrimidin-2-yl)imidazo[1,5-a]pyridine-8-carboxamide 3-(4-((thiophen-2-ylmethyl)amino)-5-methyl-6,7,8,9-tetrahydro-5H-pyrimido[5,4-b]azepin-2-yl)-2-methylimidazo[1,2-a]pyridine-8-carboxamide 3-(4-((thiophen-2-ylmethyl)amino)-5-methyl-6,7,8,9-tetrahydro-5H-pyrimido[5,4-b]azepin-2-yl)imidazo[1,5-a]pyridine-8-carboxamide 3-(4-((thiophen-2-ylmethyl)amino)-5-methyl-6,7-dihydro-5H-pyrrolo[3,2-d]pyrimidin-2-yl)-2-methylimidazo[1,2-a]pyridine-8-carboxamide 3-(4-((thiophen-2-ylmethyl)amino)-5-methyl-6,7-dihydro-5H-pyrrolo[3,2-d]pyrimidin-2-yl)imidazo[1,5-a]pyridine-8-carboxamide 3-(4-((thiophen-2-ylmethyl)amino)-6,7,8,9-tetrahydro-5H-cyclohept a[d]pyrimidin-2-yl)-2-methylimidazo[1,2-a]pyridine-8-carboxamide 3-(4-((thiophen-2-ylmethyl)amino)-6,7,8,9-tetrahydro-5H-cyclohepta[d]pyrimidin-2-yl)imidazo[1,5-a]pyridine-8-carboxamide 3-(4-((thiophen-2-ylmethyl)amino)-6,7,8,9-tetrahydro-5H-pyrimido[4,5-b]azepin-2-yl)-2-methylimidazo[1,2-a]pyridine-8-carboxamide 3-(4-((thiophen-2-ylmethyl)amino)-6,7,8,9-tetrahydro-5H-pyrimido[4,5-b]azepin-2-yl)imidazo[1,5-a]pyridine-8-carboxamide 3-(4-((thiophen-2-ylmethyl)amino)-6,7,8,9-tetrahydro-5H-pyrimido[4,5-c]azepin-2-yl)-2-methylimidazo[1,2-a]pyridine-8-carboxamide 3-(4-((thiophen-2-ylmethyl)amino)-6,7,8,9-tetrahydro-5H-pyrimido[4,5-c]azepin-2-yl)imidazo[1,5-a]pyridine-8-carboxamide 3-(4-((thiophen-2-ylmethyl)amino)-6,7,8,9-tetrahydro-5H-pyrimido[4,5-d]azepin-2-yl)-2-methylimidazo[1,2-a]pyridine-8-carboxamide 3-(4-((thiophen-2-ylmethyl)amino)-6,7,8,9-tetrahydro-5H-pyrimido[4,5-d]azepin-2-yl)imidazo[1,5-a]pyridine-8-carboxamide 3-(4-((thiophen-2-ylmethyl)amino)-6,7,8,9-tetrahydro-5H-pyrimido[5,4-b]azepin-2-yl)-2-methylimidazo[1,2-a]pyridine-8-carboxamide 3-(4-((thiophen-2-ylmethyl)amino)-6,7,8,9-tetrahydro-5H-pyrimido[5,4-b]azepin-2-yl)imidazo[1,5-a]pyridine-8-carboxamide 3-(4-((thiophen-2-ylmethyl)amino)-6,7,8,9-tetrahydro-5H-pyrimido[5,4-c]azepin-2-yl)-2-methylimidazo[1,2-a]pyridine-8-carboxamide 3-(4-((thiophen-2-ylmethyl)amino)-6,7,8,9-tetrahydro-5H-pyrimido[5,4-c]azepin-2-yl)imidazo[1,5-a]pyridine-8-carboxamide 3-(4-((thiophen-2-ylmethyl)amino)-6,7,8,9-tetrahydrooxepino[3,2-d]pyrimidin-2-yl)-2-methylimidazo[1,2-a]pyridine-8-carboxamide 3-(4-((thiophen-2-ylmethyl)amino)-6,7,8,9-tetrahydrooxepino[3,2-d]pyrimidin-2-yl)imidazo[1,5-a]pyridine-8-carboxamide 3-(4-((thiophen-2-ylmethyl)amino)-6,7-dihydro-5H-cyclopenta[d]pyrimidin-2-yl)-2-methylimidazo[1,2-a]pyridine-8-carboxamide 3-(4-((thiophen-2-ylmethyl)amino)-6,7-dihydro-5H-cyclopenta[d]pyrimidin-2-yl)imidazo[1,5-a]pyridine-8-carboxamide 3-(4-((thiophen-2-ylmethyl)amino)-6,7-dihydro-5H-pyrano[2,3-d]pyrimidin-2-yl)-2-methylimidazo[1,2-a]pyridine-8-carboxamide 3-(4-((thiophen-2-ylmethyl)amino)-6,7-dihydro-5H-pyrano[2,3-d]pyrimidin-2-yl)imidazo[1,5-a]pyridine-8-carboxamide 3-(4-((thiophen-2-ylmethyl)amino)-6,7-dihydro-5H-pyrrolo[2,3-d]pyrimidin-2-yl)-2-methylimidazo[1,2-a]pyridine-8-carboxamide 3-(4-((thiophen-2-ylmethyl)amino)-6,7-dihydro-5H-pyrrolo[2,3-d]pyrimidin-2-yl)imidazo[1,5-a]pyridine-8-carboxamide 3-(4-((thiophen-2-ylmethyl)amino)-6,7-dihydro-5H-pyrrolo[3,2-d]pyrimidin-2-yl)-2-methylimidazo[1,2-a]pyridine-8-carboxamide 3-(4-((thiophen-2-ylmethyl)amino)-6,7-dihydro-5H-pyrrolo[3,2-d]pyrimidin-2-yl)imidazo[1,5-a]pyridine-8-carboxamide 3-(4-((thiophen-2-ylmethyl)amino)-6,7-dihydro-5H-pyrrolo[3,4-d]pyrimidin-2-yl)-2-methylimidazo[1,2-a]pyridine-8-carboxamide 3-(4-((thiophen-2-ylmethyl)amino)-6,7-dihydro-5H-pyrrolo[3,4-d]pyrimidin-2-yl)imidazo[1,5-a]pyridine-8-carboxamide 3-(4-((thiophen-2-ylmethyl)amino)-6,7-dihydrofuro[3,2-d]pyrimidin-2-yl)-2-methylimidazo[1,2-a]pyridine-8-carboxamide 3-(4-((thiophen-2-ylmethyl)amino)-6,7-dihydrofuro[3,2-d]pyrimidin-2-yl)imidazo[1,5-a]pyridine-8-carboxamide 3-(4-((thiophen-2-ylmethyl)amino)-6,8-dihydro-5H-pyrano[3,4-d]pyrimidin-2-yl)-2-methylimidazo[1,2-a]pyridine-8-carboxamide 3-(4-((thiophen-2-ylmethyl)amino)-6,8-dihydro-5H-pyrano[3,4-d]pyrimidin-2-yl)imidazo[1,5-a]pyridine-8-carboxamide 3-(4-((thiophen-2-ylmethyl)amino)-6-methyl-5,6,7,8-tetrahydropyrido[4,3-d]pyrimidin-2-yl)-2-methylimidazo[1,2-a]pyridine-8-carboxamide 3-(4-((thiophen-2-ylmethyl)amino)-6-methyl-5,6,7,8-tetrahydropyrido[4,3-d]pyrimidin-2-yl)imidazo[1,5-a]pyridine-8-carboxamide 3-(4-((thiophen-2-ylmethyl)amino)-6-methyl-6,7,8,9-tetrahydro-5H-pyrimido[5,4-c]azepin-2-yl)-2-methylimidazo[1,2-a]pyridine-8-carboxamide 3-(4-((thiophen-2-ylmethyl)amino)-6-methyl-6,7,8,9-tetrahydro-5H-pyrimido[5,4-c]azepin-2-yl)imidazo[1,5-a]pyridine-8-carboxamide 3-(4-((thiophen-2-ylmethyl)amino)-6-methyl-6,7-dihydro-5H-pyrrolo[3,4-d]pyrimidin-2-yl)-2-methylimidazo[1,2-a]pyridine-8-carboxamide 3-(4-((thiophen-2-ylmethyl)amino)-6-methyl-6,7-dihydro-5H-pyrrolo[3,4-d]pyrimidin-2-yl)imidazo[1,5-a]pyridine-8-carboxamide 3-(4-((thiophen-2-ylmethyl)amino)-7,8-dihydro-5H-pyrano[4,3-d]pyrimidin-2-yl)-2-methylimidazo[1,2-a]pyridine-8-carboxamide 3-(4-((thiophen-2-ylmethyl)amino)-7,8-dihydro-5H-pyrano[4,3-d]pyrimidin-2-yl)imidazo[1,5-a]pyridine-8-carboxamide 3-(4-((thiophen-2-ylmethyl)amino)-7,8-dihydro-6H-pyrano[3,2-d]pyrimidin-2-yl)-2-methylimidazo[1,2-a]pyridine-8-carboxamide 3-(4-((thiophen-2-ylmethyl)amino)-7,8-dihydro-6H-pyrano[3,2-d]pyrimidin-2-yl)imidazo[1,5-a]pyridine-8-carboxamide 3-(4-((thiophen-2-ylmethyl)amino)-7-methyl-5,6,7,8-tetrahydropyrido[3,4-d]pyrimidin-2-yl)-2-methylimidazo[1,2-a]pyridine-8-carboxamide 3-(4-((thiophen-2-ylmethyl)amino)-7-methyl-5,6,7,8-tetrahydropyrido[3,4-d]pyrimidin-2-yl)imidazo[1,5-a]pyridine-8-carboxamide 3-(4-((thiophen-2-ylmethyl)amino)-7-methyl-6,7-dihydro-5H-pyrrolo[2,3-d]pyrimidin-2-yl)-2-methylimidazo[1,2-a]pyridine-8-carboxamide 3-(4-((thiophen-2-ylmethyl)amino)-7-methyl-6,7-dihydro-5H-pyrrolo[2,3-d]pyrimidin-2-yl)imidazo[1,5-a]pyridine-8-carboxamide 3-(4-((thiophen-2-ylmethyl)amino)-8-methyl-5,6,7,8-tetrahydropyrido[2,3-d]pyrimidin-2-yl)-2-methylimidazo[1,2-a]pyridine-8-carboxamide 3-(4-((thiophen-2-ylmethyl)amino)-8-methyl-5,6,7,8-tetrahydropyrido[2,3-d]pyrimidin-2-yl)imidazo[1,5-a]pyridine-8-carboxamide 3-(4-((thiophen-2-ylmethyl)amino)-8-methyl-6,7,8,9-tetrahydro-5H-pyrimido[4,5-c]azepin-2-yl)-2-methylimidazo[1,2-a]pyridine-8-carboxamide 3-(4-((thiophen-2-ylmethyl)amino)-8-methyl-6,7,8,9-tetrahydro-5H-pyrimido[4,5-c]azepin-2-yl)imidazo[1,5-a]pyridine-8-carboxamide 3-(4-((thiophen-2-ylmethyl)amino)-9-methyl-6,7,8,9-tetrahydro-5H-pyrimido[4,5-b]azepin-2-yl)-2-methylimidazo[1,2-a]pyridine-8-carboxamide 3-(4-((thiophen-2-ylmethyl)amino)-9-methyl-6,7,8,9-tetrahydro-5H-pyrimido[4,5-b]azepin-2-yl)imidazo[1,5-a]pyridine-8-carboxamide 3-(4-(benzylamino)-5,6,7,8-tetrahydrooxepino[2,3-d]pyrimidin-2-yl)-1H-indazole-7-carboxamide 3-(4-(benzylamino)-5,6,7,8-tetrahydrooxepino[2,3-d]pyrimidin-2-yl)-2-methylbenzo[b]thiophene-7-carboxamide 3-(4-(benzylamino)-5,6,7,8-tetrahydrooxepino[2,3-d]pyrimidin-2-yl)-2-methylbenzofuran-7-carboxamide 3-(4-(benzylamino)-5,6,7,8-tetrahydrooxepino[2,3-d]pyrimidin-2-yl)-2-methylimidazo[1,2-a]pyridine-8-carboxamide 3-(4-(benzylamino)-5,6,7,8-tetrahydrooxepino[2,3-d]pyrimidin-2-yl)-2-methylindolizine-8-carboxamide 3-(4-(benzylamino)-5,6,7,8-tetrahydrooxepino[2,3-d]pyrimidin-2-yl)-2-methylpyrazolo[1,5-a]pyridine-7-carboxamide 3-(4-(benzylamino)-5,6,7,8-tetrahydrooxepino[2,3-d]pyrimidin-2-yl)benzo[c]isothiazole-7-carboxamide 3-(4-(benzylamino)-5,6,7,8-tetrahydrooxepino[2,3-d]pyrimidin-2-yl)benzo[c]isoxazole-7-carboxamide 3-(4-(benzylamino)-5,6,7,8-tetrahydrooxepino[2,3-d]pyrimidin-2-yl)benzo[d]isothiazole-7-carboxamide 3-(4-(benzylamino)-5,6,7,8-tetrahydrooxepino[2,3-d]pyrimidin-2-yl)benzo[d]isoxazole-7-carboxamide 3-(4-(benzylamino)-5,6,7,8-tetrahydrooxepino[2,3-d]pyrimidin-2-yl)imidazo[1,5-a]pyridine-8-carboxamide 3-(4-(benzylamino)-5,6,7,8-tetrahydropyrido[2,3-d]pyrimidin-2-yl)-1H-indazole-7-carboxamide 3-(4-(benzylamino)-5,6,7,8-tetrahydropyrido[2,3-d]pyrimidin-2-yl)-2-methylbenzo[b]thiophene-7-carboxamide 3-(4-(benzylamino)-5,6,7,8-tetrahydropyrido[2,3-d]pyrimidin-2-yl)-2-methylbenzofuran-7-carboxamide 3-(4-(benzylamino)-5,6,7,8-tetrahydropyrido[2,3-d]pyrimidin-2-yl)-2-methylindolizine-8-carboxamide 3-(4-(benzylamino)-5,6,7,8-tetrahydropyrido[2,3-d]pyrimidin-2-yl)benzo[c]isothiazole-7-carboxamide 3-(4-(benzylamino)-5,6,7,8-tetrahydropyrido[2,3-d]pyrimidin-2-yl)benzo[c]isoxazole-7-carboxamide 3-(4-(benzylamino)-5,6,7,8-tetrahydropyrido[2,3-d]pyrimidin-2-yl)benzo[d]isothiazole-7-carboxamide 3-(4-(benzylamino)-5,6,7,8-tetrahydropyrido[2,3-d]pyrimidin-2-yl)benzo[d]isoxazole-7-carboxamide 3-(4-(benzylamino)-5,6,7,8-tetrahydropyrido[3,2-d]pyrimidin-2-yl)-1H-indazole-7-carboxamide 3-(4-(benzylamino)-5,6,7,8-tetrahydropyrido[3,2-d]pyrimidin-2-yl)-2-methylbenzo[b]thiophene-7-carboxamide 3-(4-(benzylamino)-5,6,7,8-tetrahydropyrido[3,2-d]pyrimidin-2-yl)-2-methylbenzofuran-7-carboxamide 3-(4-(benzylamino)-5,6,7,8-tetrahydropyrido[3,2-d]pyrimidin-2-yl)-2-methylindolizine-8-carboxamide 3-(4-(benzylamino)-5,6,7,8-tetrahydropyrido[3,2-d]pyrimidin-2-yl)benzo[c]isothiazole-7-carboxamide 3-(4-(benzylamino)-5,6,7,8-tetrahydropyrido[3,2-d]pyrimidin-2-yl)benzo[c]isoxazole-7-carboxamide 3-(4-(benzylamino)-5,6,7,8-tetrahydropyrido[3,2-d]pyrimidin-2-yl)benzo[d]isothiazole-7-carboxamide 3-(4-(benzylamino)-5,6,7,8-tetrahydropyrido[3,2-d]pyrimidin-2-yl)benzo[d]isoxazole-7-carboxamide 3-(4-(benzylamino)-5,6,7,8-tetrahydropyrido[3,4-d]pyrimidin-2-yl)-1H-indazole-7-carboxamide 3-(4-(benzylamino)-5,6,7,8-tetrahydropyrido[3,4-d]pyrimidin-2-yl)-2-methylbenzo[b]thiophene-7-carboxamide 3-(4-(benzylamino)-5,6,7,8-tetrahydropyrido[3,4-d]pyrimidin-2-yl)-2-methylbenzofuran-7-carboxamide 3-(4-(benzylamino)-5,6,7,8-tetrahydropyrido[3,4-d]pyrimidin-2-yl)-2-methylindolizine-8-carboxamide 3-(4-(benzylamino)-5,6,7,8-tetrahydropyrido[3,4-d]pyrimidin-2-yl)benzo[c]isothiazole-7-carboxamide 3-(4-(benzylamino)-5,6,7,8-tetrahydropyrido[3,4-d]pyrimidin-2-yl)benzo[c]isoxazole-7-carboxamide
3-(4-(benzylamino)-5,6,7,8-tetrahydropyrido[3,4-d]pyrimidin-2-yl)benzo[d]isothiazole-7-carboxamide
3-(4-(benzylamino)-5,6,7,8-tetrahydropyrido[3,4-d]pyrimidin-2-yl)benzo[d]isoxazole-7-carboxamide
3-(4-(benzylamino)-5,6,7,8-tetrahydropyrido[4,3-d]pyrimidin-2-yl)-1H-indazole-7-carboxamide
3-(4-(benzylamino)-5,6,7,8-tetrahydropyrido[4,3-d]pyrimidin-2-yl)-2-methylbenzo[b]thiophene-7-carboxamide
3-(4-(benzylamino)-5,6,7,8-tetrahydropyrido[4,3-d]pyrimidin-2-yl)-2-methylbenzofuran-7-carboxamide
3-(4-(benzylamino)-5,6,7,8-tetrahydropyrido[4,3-d]pyrimidin-2-yl)-2-methylindolizine-8-carboxamide
3-(4-(benzylamino)-5,6,7,8-tetrahydropyrido[4,3-d]pyrimidin-2-yl)benzo[c]isothiazole-7-carboxamide
3-(4-(benzylamino)-5,6,7,8-tetrahydropyrido[4,3-d]pyrimidin-2-yl)benzo[c]isoxazole-7-carboxamide
3-(4-(benzylamino)-5,6,7,8-tetrahydropyrido[4,3-d]pyrimidin-2-yl)benzo[d]isothiazole-7-carboxamide
3-(4-(benzylamino)-5,6,7,8-tetrahydropyrido[4,3-d]pyrimidin-2-yl)benzo[d]isoxazole-7-carboxamide
3-(4-(benzylamino)-5,6,7,8-tetrahydroquinazolin-2-yl)-[1,2,3]triazolo[1,5-a]pyridine-7-carboxamide
3-(4-(benzylamino)-5,6,7,8-tetrahydroquinazolin-2-yl)-[1,2,4]triazolo[4,3-a]pyridine-8-carboxamide
3-(4-(benzylamino)-5,6,7,8-tetrahydroquinazolin-2-yl)-2-methylbenzo[b]thiophene-7-carboxamide
3-(4-(benzylamino)-5,6,7,8-tetrahydroquinazolin-2-yl)-2-methylindolizine-8-carboxamide
3-(4-(benzylamino)-5,6,7,8-tetrahydroquinazolin-2-yl)benzo[c]isothiazole-7-carboxamide
3-(4-(benzylamino)-5,6,7,8-tetrahydroquinazolin-2-yl)benzo[c]isoxazole-7-carboxamide
3-(4-(benzylamino)-5,6,7,8-tetrahydroquinazolin-2-yl)benzo[d]isothiazole-7-carboxamide
3-(4-(benzylamino)-5,6,7,8-tetrahydroquinazolin-2-yl)benzo[d]isoxazole-7-carboxamide
3-(4-(benzylamino)-5,6,7,9-tetrahydrooxepino[3,4-d]pyrimidin-2-yl)-1H-indazole-7-carboxamide
3-(4-(benzylamino)-5,6,7,9-tetrahydrooxepino[3,4-d]pyrimidin-2-yl)-2-methylbenzo[b]thiophene-7-carboxamide
3-(4-(benzylamino)-5,6,7,9-tetrahydrooxepino[3,4-d]pyrimidin-2-yl)-2-methylbenzofuran-7-carboxamide
3-(4-(benzylamino)-5,6,7,9-tetrahydrooxepino[3,4-d]pyrimidin-2-yl)-2-methylimidazo[1,2-a]pyridine-8-carboxamide
3-(4-(benzylamino)-5,6,7,9-tetrahydrooxepino[3,4-d]pyrimidin-2-yl)-2-methylindolizine-8-carboxamide
3-(4-(benzylamino)-5,6,7,9-tetrahydrooxepino[3,4-d]pyrimidin-2-yl)-2-methylpyrazolo[1,5-a]pyridine-7-carboxamide
3-(4-(benzylamino)-5,6,7,9-tetrahydrooxepino[3,4-d]pyrimidin-2-yl)benzo[c]isothiazole-7-carboxamide
3-(4-(benzylamino)-5,6,7,9-tetrahydrooxepino[3,4-d]pyrimidin-2-yl)benzo[c]isoxazole-7-carboxamide
3-(4-(benzylamino)-5,6,7,9-tetrahydrooxepino[3,4-d]pyrimidin-2-yl)benzo[d]isothiazole-7-carboxamide
3-(4-(benzylamino)-5,6,7,9-tetrahydrooxepino[3,4-d]pyrimidin-2-yl)benzo[d]isoxazole-7-carboxamide
3-(4-(benzylamino)-5,6,7,9-tetrahydrooxepino[3,4-d]pyrimidin-2-yl)imidazo[1,5-a]pyridine-8-carboxamide
3-(4-(benzylamino)-5,6,8,9-tetrahydrooxepino[4,5-d]pyrimidin-2-yl)-1H-indazole-7-carboxamide
3-(4-(benzylamino)-5,6,8,9-tetrahydrooxepino[4,5-d]pyrimidin-2-yl)-2-methylbenzo[b]thiophene-7-carboxamide
3-(4-(benzylamino)-5,6,8,9-tetrahydrooxepino[4,5-d]pyrimidin-2-yl)-2-methylbenzofuran-7-carboxamide
3-(4-(benzylamino)-5,6,8,9-tetrahydrooxepino[4,5-d]pyrimidin-2-yl)-2-methylimidazo[1,2-a]pyridine-8-carboxamide
3-(4-(benzylamino)-5,6,8,9-tetrahydrooxepino[4,5-d]pyrimidin-2-yl)-2-methylindolizine-8-carboxamide
3-(4-(benzylamino)-5,6,8,9-tetrahydrooxepino[4,5-d]pyrimidin-2-yl)-2-methylpyrazolo[1,5-a]pyridine-7-carboxamide
3-(4-(benzylamino)-5,6,8,9-tetrahydrooxepino[4,5-d]pyrimidin-2-yl)benzo[c]isothiazole-7-carboxamide
3-(4-(benzylamino)-5,6,8,9-tetrahydrooxepino[4,5-d]pyrimidin-2-yl)benzo[c]isoxazole-7-carboxamide
3-(4-(benzylamino)-5,6,8,9-tetrahydrooxepino[4,5-d]pyrimidin-2-yl)benzo[d]isothiazole-7-carboxamide
3-(4-(benzylamino)-5,6,8,9-tetrahydrooxepino[4,5-d]pyrimidin-2-yl)benzo[d]isoxazole-7-carboxamide
3-(4-(benzylamino)-5,6,8,9-tetrahydrooxepino[4,5-d]pyrimidin-2-yl)imidazo[1,5-a]pyridine-8-carboxamide
3-(4-(benzylamino)-5,6-dihydrofuro[2,3-d]pyrimidin-2-yl)-[1,2,3]triazolo[1,5-a]pyridine-7-carboxamide
3-(4-(benzylamino)-5,6-dihydrofuro[2,3-d]pyrimidin-2-yl)-[1,2,4]triazolo[4,3-a]pyridine-8-carboxamide
3-(4-(benzylamino)-5,6-dihydrofuro[2,3-d]pyrimidin-2-yl)-1H-indazole-7-carboxamide
3-(4-(benzylamino)-5,6-dihydrofuro[2,3-d]pyrimidin-2-yl)-2-methylbenzo[b]thiophene-7-carboxamide
3-(4-(benzylamino)-5,6-dihydrofuro[2,3-d]pyrimidin-2-yl)-2-methylbenzofuran-7-carboxamide
3-(4-(benzylamino)-5,6-dihydrofuro[2,3-d]pyrimidin-2-yl)-2-methylimidazo[1,2-a]pyridine-8-carboxamide
3-(4-(benzylamino)-5,6-dihydrofuro[2,3-d]pyrimidin-2-yl)-2-methylindolizine-8-carboxamide
3-(4-(benzylamino)-5,6-dihydrofuro[2,3-d]pyrimidin-2-yl)-2-methylpyrazolo[1,5-a]pyridine-7-carboxamide
3-(4-(benzylamino)-5,6-dihydrofuro[2,3-d]pyrimidin-2-yl)benzo[c]isothiazole-7-carboxamide
3-(4-(benzylamino)-5,6-dihydrofuro[2,3-d]pyrimidin-2-yl)benzo[c]isoxazole-7-carboxamide
3-(4-(benzylamino)-5,6-dihydrofuro[2,3-d]pyrimidin-2-yl)benzo[d]isothiazole-7-carboxamide
3-(4-(benzylamino)-5,6-dihydrofuro[2,3-d]pyrimidin-2-yl)benzo[d]isoxazole-7-carboxamide
3-(4-(benzylamino)-5,6-dihydrofuro[2,3-d]pyrimidin-2-yl)imidazo[1,5-a]pyridine-8-carboxamide
3-(4-(benzylamino)-5,7,8,9-tetrahydrooxepino[4,3-d]pyrimidin-2-yl)-1H-indazole-7-carboxamide
3-(4-(benzylamino)-5,7,8,9-tetrahydrooxepino[4,3-d]pyrimidin-2-yl)-2-methylbenzo[b]thiophene-7-carboxamide
3-(4-(benzylamino)-5,7,8,9-tetrahydrooxepino[4,3-d]pyrimidin-2-yl)-2-methylbenzofuran-7-carboxamide
3-(4-(benzylamino)-5,7,8,9-tetrahydrooxepino[4,3-d]pyrimidin-2-yl)-2-methylimidazo[1,2-a]pyridine-8-carboxamide
3-(4-(benzylamino)-5,7,8,9-tetrahydrooxepino[4,3-d]pyrimidin-2-yl)-2-methylindolizine-8-carboxamide
3-(4-(benzylamino)-5,7,8,9-tetrahydrooxepino[4,3-d]pyrimidin-2-yl)-2-methylpyrazolo[1,5-a]pyridine-7-carboxamide
3-(4-(benzylamino)-5,7,8,9-tetrahydrooxepino[4,3-d]pyrimidin-2-yl)benzo[c]isothiazole-7-carboxamide
3-(4-(benzylamino)-5,7,8,9-tetrahydrooxepino[4,3-d]pyrimidin-2-yl)benzo[c]isoxazole-7-carboxamide
3-(4-(benzylamino)-5,7,8,9-tetrahydrooxepino[4,3-d]pyrimidin-2-yl)benzo[d]isothiazole-7-carboxamide 3-(4-(benzylamino)-5,7,8,9-tetrahydrooxepino[4,3-d]pyrimidin-2-yl)benzo[d]isoxazole-7-carboxamide
3-(4-(benzylamino)-5,7,8,9-tetrahydrooxepino[4,3-d]pyrimidin-2-yl)imidazo[1,5-a]pyridine-8-carboxamide
3-(4-(benzylamino)-5,7-dihydrofuro[3,4-d]pyrimidin-2-yl)-[1,2,3]triazolo[1,5-a]pyridine-7-carboxamide
3-(4-(benzylamino)-5,7-dihydrofuro[3,4-d]pyrimidin-2-yl)-[1,2,4]triazolo[4,3-a]pyridine-8-carboxamide
3-(4-(benzylamino)-5,7-dihydrofuro[3,4-d]pyrimidin-2-yl)-1H-indazole-7-carboxamide
3-(4-(benzylamino)-5,7-dihydrofuro[3,4-d]pyrimidin-2-yl)-2-methylbenzo[b]thiophene-7-carboxamide
3-(4-(benzylamino)-5,7-dihydrofuro[3,4-d]pyrimidin-2-yl)-2-methylbenzofuran-7-carboxamide
3-(4-(benzylamino)-5,7-dihydrofuro[3,4-d]pyrimidin-2-yl)-2-methylimidazo[1,2-a]pyridine-8-carboxamide
3-(4-(benzylamino)-5,7-dihydrofuro[3,4-d]pyrimidin-2-yl)-2-methylindolizine-8-carboxamide
3-(4-(benzylamino)-5,7-dihydrofuro[3,4-d]pyrimidin-2-yl)-2-methylpyrazolo[1,5-a]pyridine-7-carboxamide
3-(4-(benzylamino)-5,7-dihydrofuro[3,4-d]pyrimidin-2-yl)benzo[c]isothiazole-7-carboxamide
3-(4-(benzylamino)-5,7-dihydrofuro[3,4-d]pyrimidin-2-yl)benzo[c]isoxazole-7-carboxamide
3-(4-(benzylamino)-5,7-dihydrofuro[3,4-d]pyrimidin-2-yl)benzo[d]isothiazole-7-carboxamide
3-(4-(benzylamino)-5,7-dihydrofuro[3,4-d]pyrimidin-2-yl)benzo[d]isoxazole-7-carboxamide
3-(4-(benzylamino)-5,7-dihydrofuro[3,4-d]pyrimidin-2-yl)imidazo[1,5-a]pyridine-8-carboxamide
3-(4-(benzylamino)-5-methyl-5,6,7,8-tetrahydropyrido[3,2-d]pyrimidin-2-yl)-1H-indazole-7-carboxamide
3-(4-(benzylamino)-5-methyl-5,6,7,8-tetrahydropyrido[3,2-d]pyrimidin-2-yl)-2-methylbenzo[b]thiophene-7-carboxamide
3-(4-(benzylamino)-5-methyl-5,6,7,8-tetrahydropyrido[3,2-d]pyrimidin-2-yl)-2-methylbenzofuran-7-carboxamide
3-(4-(benzylamino)-5-methyl-5,6,7,8-tetrahydropyrido[3,2-d]pyrimidin-2-yl)-2-methylindolizine-8-carboxamide
3-(4-(benzylamino)-5-methyl-5,6,7,8-tetrahydropyrido[3,2-d]pyrimidin-2-yl)benzo[c]isothiazole-7-carboxamide
3-(4-(benzylamino)-5-methyl-5,6,7,8-tetrahydropyrido[3,2-d]pyrimidin-2-yl)benzo[c]isoxazole-7-carboxamide
3-(4-(benzylamino)-5-methyl-5,6,7,8-tetrahydropyrido[3,2-d]pyrimidin-2-yl)benzo[d]isothiazole-7-carboxamide
3-(4-(benzylamino)-5-methyl-5,6,7,8-tetrahydropyrido[3,2-d]pyrimidin-2-yl)benzo[d]isoxazole-7-carboxamide
3-(4-(benzylamino)-5-methyl-6,7,8,9-tetrahydro-5H-pyrimido[5,4-b]azepin-2-yl)-1H-indazole-7-carboxamide
3-(4-(benzylamino)-5-methyl-6,7,8,9-tetrahydro-5H-pyrimido[5,4-b]azepin-2-yl)-2-methylbenzo[b]thiophene-7-carboxamide
3-(4-(benzylamino)-5-methyl-6,7,8,9-tetrahydro-5H-pyrimido[5,4-b]azepin-2-yl)-2-methylbenzofuran-7-carboxamide
3-(4-(benzylamino)-5-methyl-6,7,8,9-tetrahydro-5H-pyrimido[5,4-b]azepin-2-yl)-2-methylimidazo[1,2-a]pyridine-8-carboxamide
3-(4-(benzylamino)-5-methyl-6,7,8,9-tetrahydro-5H-pyrimido[5,4-b]azepin-2-yl)-2-methylindolizine-8-carboxamide
3-(4-(benzylamino)-5-methyl-6,7,8,9-tetrahydro-5H-pyrimido[5,4-b]azepin-2-yl)-2-methylpyrazolo[1,5-a]pyridine-7-carboxamide
3-(4-(benzylamino)-5-methyl-6,7,8,9-tetrahydro-5H-pyrimido[5,4-b]azepin-2-yl)benzo[c]isothiazole-7-carboxamide
3-(4-(benzylamino)-5-methyl-6,7,8,9-tetrahydro-5H-pyrimido[5,4-b]azepin-2-yl)benzo[c]isoxazole-7-carboxamide
3-(4-(benzylamino)-5-methyl-6,7,8,9-tetrahydro-5H-pyrimido[5,4-b]azepin-2-yl)benzo[d]isothiazole-7-carboxamide
3-(4-(benzylamino)-5-methyl-6,7,8,9-tetrahydro-5H-pyrimido[5,4-b]azepin-2-yl)benzo[d]isoxazole-7-carboxamide
3-(4-(benzylamino)-5-methyl-6,7,8,9-tetrahydro-5H-pyrimido[5,4-b]azepin-2-yl)imidazo[1,5-a]pyridine-8-carboxamide
3-(4-(benzylamino)-5-methyl-6,7-dihydro-5H-pyrrolo[3,2-d]pyrimidin-2-yl)-1H-indazole-7-carboxamide
3-(4-(benzylamino)-5-methyl-6,7-dihydro-5H-pyrrolo[3,2-d]pyrimidin-2-yl)-2-methylbenzo[b]thiophene-7-carboxamide
3-(4-(benzylamino)-5-methyl-6,7-dihydro-5H-pyrrolo[3,2-d]pyrimidin-2-yl)-2-methylbenzofuran-7-carboxamide
3-(4-(benzylamino)-5-methyl-6,7-dihydro-5H-pyrrolo[3,2-d]pyrimidin-2-yl)-2-methylimidazo[1,2-a]pyridine-8-carboxamide
3-(4-(benzylamino)-5-methyl-6,7-dihydro-5H-pyrrolo[3,2-d]pyrimidin-2-yl)-2-methylindolizine-8-carboxamide
3-(4-(benzylamino)-5-methyl-6,7-dihydro-5H-pyrrolo[3,2-d]pyrimidin-2-yl)-2-methylpyrazolo[1,5-a]pyridine-7-carboxamide
3-(4-(benzylamino)-5-methyl-6,7-dihydro-5H-pyrrolo[3,2-d]pyrimidin-2-yl)benzo[c]isothiazole-7-carboxamide
3-(4-(benzylamino)-5-methyl-6,7-dihydro-5H-pyrrolo[3,2-d]pyrimidin-2-yl)benzo[c]isoxazole-7-carboxamide
3-(4-(benzylamino)-5-methyl-6,7-dihydro-5H-pyrrolo[3,2-d]pyrimidin-2-yl)benzo[d]isothiazole-7-carboxamide
3-(4-(benzylamino)-5-methyl-6,7-dihydro-5H-pyrrolo[3,2-d]pyrimidin-2-yl)benzo[d]isoxazole-7-carboxamide
3-(4-(benzylamino)-5-methyl-6,7-dihydro-5H-pyrrolo[3,2-d]pyrimidin-2-yl)imidazo[1,5-a]pyridine-8-carboxamide
3-(4-(benzylamino)-6,7,8,9-tetrahydro-5H-cyclohepta[d]pyrimidin-2-yl)-[1,2,3]triazolo[1,5-a]pyridine-7-carboxamide
3-(4-(benzylamino)-6,7,8,9-tetrahydro-5H-cyclohepta[d]pyrimidin-2-yl)-[1,2,4]triazolo[4,3-a]pyridine-8-carboxamide
3-(4-(benzylamino)-6,7,8,9-tetrahydro-5H-cyclohepta[d]pyrimidin-2-yl)-1H-indazole-7-carboxamide
3-(4-(benzylamino)-6,7,8,9-tetrahydro-5H-cyclohepta[d]pyrimidin-2-yl)-2-methylbenzo[b]thiophene-7-carboxamide
3-(4-(benzylamino)-6,7,8,9-tetrahydro-5H-cyclohepta[d]pyrimidin-2-yl)-2-methylbenzofuran-7-carboxamide
3-(4-(benzylamino)-6,7,8,9-tetrahydro-5H-cyclohepta[d]pyrimidin-2-yl)-2-methylimidazo[1,2-a]pyridine-8-carboxamide
3-(4-(benzylamino)-6,7,8,9-tetrahydro-5H-cyclohepta[d]pyrimidin-2-yl)-2-methylindolizine-8-carboxamide
3-(4-(benzylamino)-6,7,8,9-tetrahydro-5H-cyclohepta[d]pyrimidin-2-yl)-2-methylpyrazolo[1,5-a]pyridine-7-carboxamide
3-(4-(benzylamino)-6,7,8,9-tetrahydro-5H-cyclohepta[d]pyrimidin-2-yl)benzo[c]isothiazole-7-carboxamide
3-(4-(benzylamino)-6,7,8,9-tetrahydro-5H-cyclohepta[d]pyrimidin-2-yl)benzo[c]isoxazole-7-carboxamide
3-(4-(benzylamino)-6,7,8,9-tetrahydro-5H-cyclohepta[d]pyrimidin-2-yl)benzo[d]isothiazole-7-carboxamide
3-(4-(benzylamino)-6,7,8,9-tetrahydro-5H-cyclohepta[d]pyrimidin-2-yl)benzo[d]isoxazole-7-carboxamide 3-(4-(benzylamino)-6,7,8,9-tetrahydro-5H-cyclohepta[d]pyrimidin-2-yl)imidazo[1,5-a]pyridine-8-carboxamide
3-(4-(benzylamino)-6,7,8,9-tetrahydro-5H-pyrimido[4,5-b]azepin-2-yl)-1H-indazole-7-carboxamide
3-(4-(benzylamino)-6,7,8,9-tetrahydro-5H-pyrimido[4,5-b]azepin-2-yl)-2-methylbenzo[b]thiophene-7-carboxamide
3-(4-(benzylamino)-6,7,8,9-tetrahydro-5H-pyrimido[4,5-b]azepin-2-yl)-2-methylbenzofuran-7-carboxamide
3-(4-(benzylamino)-6,7,8,9-tetrahydro-5H-pyrimido[4,5-b]azepin-2-yl)-2-methylimidazo[1,2-a]pyridine-8-carboxamide
3-(4-(benzylamino)-6,7,8,9-tetrahydro-5H-pyrimido[4,5-b]azepin-2-yl)-2-methylindolizine-8-carboxamide
3-(4-(benzylamino)-6,7,8,9-tetrahydro-5H-pyrimido[4,5-b]azepin-2-yl)-2-methylpyrazolo[1,5-a]pyridine-7-carboxamide
3-(4-(benzylamino)-6,7,8,9-tetrahydro-5H-pyrimido[4,5-b]azepin-2-yl)benzo[c]isothiazole-7-carboxamide
3-(4-(benzylamino)-6,7,8,9-tetrahydro-5H-pyrimido[4,5-b]azepin-2-yl)benzo[c]isoxazole-7-carboxamide
3-(4-(benzylamino)-6,7,8,9-tetrahydro-5H-pyrimido[4,5-b]azepin-2-yl)benzo[d]isothiazole-7-carboxamide
3-(4-(benzylamino)-6,7,8,9-tetrahydro-5H-pyrimido[4,5-b]azepin-2-yl)benzo[d]isoxazole-7-carboxamide
3-(4-(benzylamino)-6,7,8,9-tetrahydro-5H-pyrimido[4,5-b]azepin-2-yl)imidazo[1,5-a]pyridine-8-carboxamide
3-(4-(benzylamino)-6,7,8,9-tetrahydro-5H-pyrimido[4,5-c]azepin-2-yl)-1H-indazole-7-carboxamide
3-(4-(benzylamino)-6,7,8,9-tetrahydro-5H-pyrimido[4,5-c]azepin-2-yl)-2-methylbenzo[b]thiophene-7-carboxamide
3-(4-(benzylamino)-6,7,8,9-tetrahydro-5H-pyrimido[4,5-c]azepin-2-yl)-2-methylbenzofuran-7-carboxamide
3-(4-(benzylamino)-6,7,8,9-tetrahydro-5H-pyrimido[4,5-c]azepin-2-yl)-2-methylimidazo[1,2-a]pyridine-8-carboxamide
3-(4-(benzylamino)-6,7,8,9-tetrahydro-5H-pyrimido[4,5-c]azepin-2-yl)-2-methylindolizine-8-carboxamide
3-(4-(benzylamino)-6,7,8,9-tetrahydro-5H-pyrimido[4,5-c]azepin-2-yl)-2-methylpyrazolo[1,5-a]pyridine-7-carboxamide
3-(4-(benzylamino)-6,7,8,9-tetrahydro-5H-pyrimido[4,5-c]azepin-2-yl)benzo[c]isothiazole-7-carboxamide
3-(4-(benzylamino)-6,7,8,9-tetrahydro-5H-pyrimido[4,5-c]azepin-2-yl)benzo[c]isoxazole-7-carboxamide
3-(4-(benzylamino)-6,7,8,9-tetrahydro-5H-pyrimido[4,5-c]azepin-2-yl)benzo[d]isothiazole-7-carboxamide
3-(4-(benzylamino)-6,7,8,9-tetrahydro-5H-pyrimido[4,5-c]azepin-2-yl)benzo[d]isoxazole-7-carboxamide
3-(4-(benzylamino)-6,7,8,9-tetrahydro-5H-pyrimido[4,5-c]azepin-2-yl)imidazo[1,5-a]pyridine-8-carboxamide
3-(4-(benzylamino)-6,7,8,9-tetrahydro-5H-pyrimido[4,5-d]azepin-2-yl)-1H-indazole-7-carboxamide
3-(4-(benzylamino)-6,7,8,9-tetrahydro-5H-pyrimido[4,5-d]azepin-2-yl)-2-methylbenzo[b]thiophene-7-carboxamide
3-(4-(benzylamino)-6,7,8,9-tetrahydro-5H-pyrimido[4,5-d]azepin-2-yl)-2-methylbenzofuran-7-carboxamide
3-(4-(benzylamino)-6,7,8,9-tetrahydro-5H-pyrimido[4,5-d]azepin-2-yl)-2-methylimidazo[1,2-a]pyridine-8-carboxamide
3-(4-(benzylamino)-6,7,8,9-tetrahydro-5H-pyrimido[4,5-d]azepin-2-yl)-2-methylindolizine-8-carboxamide
3-(4-(benzylamino)-6,7,8,9-tetrahydro-5H-pyrimido[4,5-d]azepin-2-yl)-2-methylpyrazolo[1,5-a]pyridine-7-carboxamide
3-(4-(benzylamino)-6,7,8,9-tetrahydro-5H-pyrimido[4,5-d]azepin-2-yl)benzo[c]isothiazole-7-carboxamide
3-(4-(benzylamino)-6,7,8,9-tetrahydro-5H-pyrimido[4,5-d]azepin-2-yl)benzo[c]isoxazole-7-carboxamide
3-(4-(benzylamino)-6,7,8,9-tetrahydro-5H-pyrimido[4,5-d]azepin-2-yl)benzo[d]isothiazole-7-carboxamide
3-(4-(benzylamino)-6,7,8,9-tetrahydro-5H-pyrimido[4,5-d]azepin-2-yl)benzo[d]isoxazole-7-carboxamide
3-(4-(benzylamino)-6,7,8,9-tetrahydro-5H-pyrimido[4,5-d]azepin-2-yl)imidazo[1,5-a]pyridine-8-carboxamide
3-(4-(benzylamino)-6,7,8,9-tetrahydro-5H-pyrimido[5,4-b]azepin-2-yl)-1H-indazole-7-carboxamide
3-(4-(benzylamino)-6,7,8,9-tetrahydro-5H-pyrimido[5,4-b]azepin-2-yl)-2-methylbenzo[b]thiophene-7-carboxamide
3-(4-(benzylamino)-6,7,8,9-tetrahydro-5H-pyrimido[5,4-b]azepin-2-yl)-2-methylbenzofuran-7-carboxamide
3-(4-(benzylamino)-6,7,8,9-tetrahydro-5H-pyrimido[5,4-b]azepin-2-yl)-2-methylimidazo[1,2-a]pyridine-8-carboxamide
3-(4-(benzylamino)-6,7,8,9-tetrahydro-5H-pyrimido[5,4-b]azepin-2-yl)-2-methylindolizine-8-carboxamide
3-(4-(benzylamino)-6,7,8,9-tetrahydro-5H-pyrimido[5,4-b]azepin-2-yl)-2-methylpyrazolo[1,5-a]pyridine-7-carboxamide
3-(4-(benzylamino)-6,7,8,9-tetrahydro-5H-pyrimido[5,4-b]azepin-2-yl)benzo[c]isothiazole-7-carboxamide
3-(4-(benzylamino)-6,7,8,9-tetrahydro-5H-pyrimido[5,4-b]azepin-2-yl)benzo[c]isoxazole-7-carboxamide
3-(4-(benzylamino)-6,7,8,9-tetrahydro-5H-pyrimido[5,4-b]azepin-2-yl)benzo[d]isothiazole-7-carboxamide
3-(4-(benzylamino)-6,7,8,9-tetrahydro-5H-pyrimido[5,4-b]azepin-2-yl)benzo[d]isoxazole-7-carboxamide
3-(4-(benzylamino)-6,7,8,9-tetrahydro-5H-pyrimido[5,4-b]azepin-2-yl)imidazo[1,5-a]pyridine-8-carboxamide
3-(4-(benzylamino)-6,7,8,9-tetrahydro-5H-pyrimido[5,4-c]azepin-2-yl)-1H-indazole-7-carboxamide
3-(4-(benzylamino)-6,7,8,9-tetrahydro-5H-pyrimido[5,4-c]azepin-2-yl)-2-methylbenzo[b]thiophene-7-carboxamide
3-(4-(benzylamino)-6,7,8,9-tetrahydro-5H-pyrimido[5,4-c]azepin-2-yl)-2-methylbenzofuran-7-carboxamide
3-(4-(benzylamino)-6,7,8,9-tetrahydro-5H-pyrimido[5,4-c]azepin-2-yl)-2-methylimidazo[1,2-a]pyridine-8-carboxamide
3-(4-(benzylamino)-6,7,8,9-tetrahydro-5H-pyrimido[5,4-c]azepin-2-yl)-2-methylindolizine-8-carboxamide
3-(4-(benzylamino)-6,7,8,9-tetrahydro-5H-pyrimido[5,4-c]azepin-2-yl)-2-methylpyrazolo[1,5-a]pyridine-7-carboxamide
3-(4-(benzylamino)-6,7,8,9-tetrahydro-5H-pyrimido[5,4-c]azepin-2-yl)benzo[c]isothiazole-7-carboxamide
3-(4-(benzylamino)-6,7,8,9-tetrahydro-5H-pyrimido[5,4-c]azepin-2-yl)benzo[c]isoxazole-7-carboxamide
3-(4-(benzylamino)-6,7,8,9-tetrahydro-5H-pyrimido[5,4-c]azepin-2-yl)benzo[d]isothiazole-7-carboxamide
3-(4-(benzylamino)-6,7,8,9-tetrahydro-5H-pyrimido[5,4-c]azepin-2-yl)benzo[d]isoxazole-7-carboxamide
3-(4-(benzylamino)-6,7,8,9-tetrahydro-5H-pyrimido[5,4-c]azepin-2-yl)imidazo[1,5-a]pyridine-8-carboxamide
3-(4-(benzylamino)-6,7,8,9-tetrahydrooxepino[3,2-d]pyrimidin-2-yl)-1H-indazole-7-carboxamide
3-(4-(benzylamino)-6,7,8,9-tetrahydrooxepino[3,2-d]pyrimidin-2-yl)-2-methylbenzo[b]thiophene-7-carboxamide
3-(4-(benzylamino)-6,7,8,9-tetrahydrooxepino[3,2-d]pyrimidin-2-yl)-2-methylbenzofuran-7-carboxamide
3-(4-(benzylamino)-6,7,8,9-tetrahydrooxepino[3,2-d]pyrimidin-2-yl)-2-methylimidazo[1,2-a]pyridine-8-carboxamide
3-(4-(benzylamino)-6,7,8,9-tetrahydrooxepino[3,2-d]pyrimidin-2-yl)-2-methylindolizine-8-carboxamide 3-(4-(benzylamino)-6,7,8,9-tetrahydrooxepino[3,2-d]pyrimidin-2-yl)-2-methylpyrazolo[1,5-a]pyridine-7-carboxamide
3-(4-(benzylamino)-6,7,8,9-tetrahydrooxepino[3,2-d]pyrimidin-2-yl)benzo[c]isothiazole-7-carboxamide
3-(4-(benzylamino)-6,7,8,9-tetrahydrooxepino[3,2-d]pyrimidin-2-yl)benzo[c]isoxazole-7-carboxamide
3-(4-(benzylamino)-6,7,8,9-tetrahydrooxepino[3,2-d]pyrimidin-2-yl)benzo[d]isothiazole-7-carboxamide
3-(4-(benzylamino)-6,7,8,9-tetrahydrooxepino[3,2-d]pyrimidin-2-yl)benzo[d]isoxazole-7-carboxamide
3-(4-(benzylamino)-6,7,8,9-tetrahydrooxepino[3,2-d]pyrimidin-2-yl)imidazo[1,5-a]pyridine-8-carboxamide
3-(4-(benzylamino)-6,7-dihydro-5H-cyclopenta[d]pyrimidin-2-yl)-[1,2,3]triazolo[1,5-a]pyridine-7-carboxamide
3-(4-(benzylamino)-6,7-dihydro-5H-cyclopenta[d]pyrimidin-2-yl)-[1,2,4]triazolo[4,3-a]pyridine-8-carboxamide
3-(4-(benzylamino)-6,7-dihydro-5H-cyclopenta[d]pyrimidin-2-yl)-1H-indazole-7-carboxamide
3-(4-(benzylamino)-6,7-dihydro-5H-cyclopenta[d]pyrimidin-2-yl)-2-methylbenzo[b]thiophene-7-carboxamide
3-(4-(benzylamino)-6,7-dihydro-5H-cyclopenta[d]pyrimidin-2-yl)-2-methylbenzofuran-7-carboxamide
3-(4-(benzylamino)-6,7-dihydro-5H-cyclopenta[d]pyrimidin-2-yl)-2-methylindolizine-8-carboxamide
3-(4-(benzylamino)-6,7-dihydro-5H-cyclopenta[d]pyrimidin-2-yl)benzo[c]isothiazole-7-carboxamide
3-(4-(benzylamino)-6,7-dihydro-5H-cyclopenta[d]pyrimidin-2-yl)benzo[c]isoxazole-7-carboxamide
3-(4-(benzylamino)-6,7-dihydro-5H-cyclopenta[d]pyrimidin-2-yl)benzo[d]isothiazole-7-carboxamide
3-(4-(benzylamino)-6,7-dihydro-5H-cyclopenta[d]pyrimidin-2-yl)benzo[d]isoxazole-7-carboxamide
3-(4-(benzylamino)-6,7-dihydro-5H-pyrano[2,3-d]pyrimidin-2-yl)-[1,2,3]triazolo[1,5-a]pyridine-7-carboxamide
3-(4-(benzylamino)-6,7-dihydro-5H-pyrano[2,3-d]pyrimidin-2-yl)-[1,2,4]triazolo[4,3-a]pyridine-8-carboxamide
3-(4-(benzylamino)-6,7-dihydro-5H-pyrano[2,3-d]pyrimidin-2-yl)-1H-indazole-7-carboxamide
3-(4-(benzylamino)-6,7-dihydro-5H-pyrano[2,3-d]pyrimidin-2-yl)-2-methylbenzo[b]thiophene-7-carboxamide
3-(4-(benzylamino)-6,7-dihydro-5H-pyrano[2,3-d]pyrimidin-2-yl)-2-methylbenzofuran-7-carboxamide
3-(4-(benzylamino)-6,7-dihydro-5H-pyrano[2,3-d]pyrimidin-2-yl)-2-methylindolizine-8-carboxamide
3-(4-(benzylamino)-6,7-dihydro-5H-pyrano[2,3-d]pyrimidin-2-yl)benzo[c]isothiazole-7-carboxamide
3-(4-(benzylamino)-6,7-dihydro-5H-pyrano[2,3-d]pyrimidin-2-yl)benzo[c]isoxazole-7-carboxamide
3-(4-(benzylamino)-6,7-dihydro-5H-pyrano[2,3-d]pyrimidin-2-yl)benzo[d]isothiazole-7-carboxamide
3-(4-(benzylamino)-6,7-dihydro-5H-pyrano[2,3-d]pyrimidin-2-yl)benzo[d]isoxazole-7-carboxamide
3-(4-(benzylamino)-6,7-dihydro-5H-pyrrolo[2,3-d]pyrimidin-2-yl)-1H-indazole-7-carboxamide
3-(4-(benzylamino)-6,7-dihydro-5H-pyrrolo[2,3-d]pyrimidin-2-yl)-2-methylbenzo[b]thiophene-7-carboxamide
3-(4-(benzylamino)-6,7-dihydro-5H-pyrrolo[2,3-d]pyrimidin-2-yl)-2-methylbenzofuran-7-carboxamide
3-(4-(benzylamino)-6,7-dihydro-5H-pyrrolo[2,3-d]pyrimidin-2-yl)-2-methylimidazo[1,2-a]pyridine-8-carboxamide
3-(4-(benzylamino)-6,7-dihydro-5H-pyrrolo[2,3-d]pyrimidin-2-yl)-2-methylindolizine-8-carboxamide
3-(4-(benzylamino)-6,7-dihydro-5H-pyrrolo[2,3-d]pyrimidin-2-yl)-2-methylpyrazolo[1,5-a]pyridine-7-carboxamide
3-(4-(benzylamino)-6,7-dihydro-5H-pyrrolo[2,3-d]pyrimidin-2-yl)benzo[c]isothiazole-7-carboxamide
3-(4-(benzylamino)-6,7-dihydro-5H-pyrrolo[2,3-d]pyrimidin-2-yl)benzo[c]isoxazole-7-carboxamide
3-(4-(benzylamino)-6,7-dihydro-5H-pyrrolo[2,3-d]pyrimidin-2-yl)benzo[d]isothiazole-7-carboxamide
3-(4-(benzylamino)-6,7-dihydro-5H-pyrrolo[2,3-d]pyrimidin-2-yl)benzo[d]isoxazole-7-carboxamide
3-(4-(benzylamino)-6,7-dihydro-5H-pyrrolo[2,3-d]pyrimidin-2-yl)imidazo[1,5-a]pyridine-8-carboxamide
3-(4-(benzylamino)-6,7-dihydro-5H-pyrrolo[3,2-d]pyrimidin-2-yl)-1H-indazole-7-carboxamide
3-(4-(benzylamino)-6,7-dihydro-5H-pyrrolo[3,2-d]pyrimidin-2-yl)-2-methylbenzo[b]thiophene-7-carboxamide
3-(4-(benzylamino)-6,7-dihydro-5H-pyrrolo[3,2-d]pyrimidin-2-yl)-2-methylbenzofuran-7-carboxamide
3-(4-(benzylamino)-6,7-dihydro-5H-pyrrolo[3,2-d]pyrimidin-2-yl)-2-methylimidazo[1,2-a]pyridine-8-carboxamide
3-(4-(benzylamino)-6,7-dihydro-5H-pyrrolo[3,2-d]pyrimidin-2-yl)-2-methylindolizine-8-carboxamide
3-(4-(benzylamino)-6,7-dihydro-5H-pyrrolo[3,2-d]pyrimidin-2-yl)-2-methylpyrazolo[1,5-a]pyridine-7-carboxamide
3-(4-(benzylamino)-6,7-dihydro-5H-pyrrolo[3,2-d]pyrimidin-2-yl)benzo[c]isothiazole-7-carboxamide
3-(4-(benzylamino)-6,7-dihydro-5H-pyrrolo[3,2-d]pyrimidin-2-yl)benzo[c]isoxazole-7-carboxamide
3-(4-(benzylamino)-6,7-dihydro-5H-pyrrolo[3,2-d]pyrimidin-2-yl)benzo[d]isothiazole-7-carboxamide
3-(4-(benzylamino)-6,7-dihydro-5H-pyrrolo[3,2-d]pyrimidin-2-yl)benzo[d]isoxazole-7-carboxamide
3-(4-(benzylamino)-6,7-dihydro-5H-pyrrolo[3,2-d]pyrimidin-2-yl)imidazo[1,5-a]pyridine-8-carboxamide
3-(4-(benzylamino)-6,7-dihydro-5H-pyrrolo[3,4-d]pyrimidin-2-yl)-1H-indazole-7-carboxamide
3-(4-(benzylamino)-6,7-dihydro-5H-pyrrolo[3,4-d]pyrimidin-2-yl)-2-methylbenzo[b]thiophene-7-carboxamide
3-(4-(benzylamino)-6,7-dihydro-5H-pyrrolo[3,4-d]pyrimidin-2-yl)-2-methylbenzofuran-7-carboxamide
3-(4-(benzylamino)-6,7-dihydro-5H-pyrrolo[3,4-d]pyrimidin-2-yl)-2-methylimidazo[1,2-a]pyridine-8-carboxamide
3-(4-(benzylamino)-6,7-dihydro-5H-pyrrolo[3,4-d]pyrimidin-2-yl)-2-methylindolizine-8-carboxamide
3-(4-(benzylamino)-6,7-dihydro-5H-pyrrolo[3,4-d]pyrimidin-2-yl)-2-methylpyrazolo[1,5-a]pyridine-7-carboxamide
3-(4-(benzylamino)-6,7-dihydro-5H-pyrrolo[3,4-d]pyrimidin-2-yl)benzo[c]isothiazole-7-carboxamide
3-(4-(benzylamino)-6,7-dihydro-5H-pyrrolo[3,4-d]pyrimidin-2-yl)benzo[c]isoxazole-7-carboxamide
3-(4-(benzylamino)-6,7-dihydro-5H-pyrrolo[3,4-d]pyrimidin-2-yl)benzo[d]isothiazole-7-carboxamide
3-(4-(benzylamino)-6,7-dihydro-5H-pyrrolo[3,4-d]pyrimidin-2-yl)benzo[d]isoxazole-7-carboxamide
3-(4-(benzylamino)-6,7-dihydro-5H-pyrrolo[3,4-d]pyrimidin-2-yl)imidazo[1,5-a]pyridine-8-carboxamide
3-(4-(benzylamino)-6,7-dihydrofuro[3,2-d]pyrimidin-2-yl)-[1,2,3]triazolo[1,5-a]pyridine-7-carboxamide
3-(4-(benzylamino)-6,7-dihydrofuro[3,2-d]pyrimidin-2-yl)-[1,2,4]triazolo[4,3-a]pyridine-8-carboxamide
3-(4-(benzylamino)-6,7-dihydrofuro[3,2-d]pyrimidin-2-yl)-1H-indazole-7-carboxamide
3-(4-(benzylamino)-6,7-dihydrofuro[3,2-d]pyrimidin-2-yl)-2-methylbenzo[b]thiophene-7-carboxamide 3-(4-(benzylamino)-6,7-dihydrofuro[3,2-d]pyrimidin-2-yl)-2-methylbenzofuran-7-carboxamide
3-(4-(benzylamino)-6,7-dihydrofuro[3,2-d]pyrimidin-2-yl)-2-methylimidazo[1,2-a]pyridine-8-carboxamide
3-(4-(benzylamino)-6,7-dihydrofuro[3,2-d]pyrimidin-2-yl)-2-methylindolizine-8-carboxamide
3-(4-(benzylamino)-6,7-dihydrofuro[3,2-d]pyrimidin-2-yl)-2-methylpyrazolo[1,5-a]pyridine-7-carboxamide
3-(4-(benzylamino)-6,7-dihydrofuro[3,2-d]pyrimidin-2-yl)benzo[c]isothiazole-7-carboxamide
3-(4-(benzylamino)-6,7-dihydrofuro[3,2-d]pyrimidin-2-yl)benzo[c]isoxazole-7-carboxamide
3-(4-(benzylamino)-6,7-dihydrofuro[3,2-d]pyrimidin-2-yl)benzo[d]isothiazole-7-carboxamide
3-(4-(benzylamino)-6,7-dihydrofuro[3,2-d]pyrimidin-2-yl)benzo[d]isoxazole-7-carboxamide
3-(4-(benzylamino)-6,7-dihydrofuro[3,2-d]pyrimidin-2-yl)imidazo[1,5-a]pyridine-8-carboxamide
3-(4-(benzylamino)-6,8-dihydro-5H-pyrano[3,4-d]pyrimidin-2-yl)-[1,2,3]triazolo[1,5-a]pyridine-7-carboxamide
3-(4-(benzylamino)-6,8-dihydro-5H-pyrano[3,4-d]pyrimidin-2-yl)-[1,2,4]triazolo[4,3-a]pyridine-8-carboxamide
3-(4-(benzylamino)-6,8-dihydro-5H-pyrano[3,4-d]pyrimidin-2-yl)-1H-indazole-7-carboxamide
3-(4-(benzylamino)-6,8-dihydro-5H-pyrano[3,4-d]pyrimidin-2-yl)-2-methylbenzo[b]thiophene-7-carboxamide
3-(4-(benzylamino)-6,8-dihydro-5H-pyrano[3,4-d]pyrimidin-2-yl)-2-methylbenzofuran-7-carboxamide
3-(4-(benzylamino)-6,8-dihydro-5H-pyrano[3,4-d]pyrimidin-2-yl)-2-methylindolizine-8-carboxamide
3-(4-(benzylamino)-6,8-dihydro-5H-pyrano[3,4-d]pyrimidin-2-yl)benzo[c]isothiazole-7-carboxamide
3-(4-(benzylamino)-6,8-dihydro-5H-pyrano[3,4-d]pyrimidin-2-yl)benzo[c]isoxazole-7-carboxamide
3-(4-(benzylamino)-6,8-dihydro-5H-pyrano[3,4-d]pyrimidin-2-yl)benzo[d]isothiazole-7-carboxamide
3-(4-(benzylamino)-6,8-dihydro-5H-pyrano[3,4-d]pyrimidin-2-yl)benzo[d]isoxazole-7-carboxamide
3-(4-(benzylamino)-6-methyl-5,6,7,8-tetrahydropyrido[4,3-d]pyrimidin-2-yl)-1H-indazole-7-carboxamide
3-(4-(benzylamino)-6-methyl-5,6,7,8-tetrahydropyrido[4,3-d]pyrimidin-2-yl)-2-methylbenzo[b]thiophene-7-carboxamide
3-(4-(benzylamino)-6-methyl-5,6,7,8-tetrahydropyrido[4,3-d]pyrimidin-2-yl)-2-methylbenzofuran-7-carboxamide
3-(4-(benzylamino)-6-methyl-5,6,7,8-tetrahydropyrido[4,3-d]pyrimidin-2-yl)-2-methylindolizine-8-carboxamide
3-(4-(benzylamino)-6-methyl-5,6,7,8-tetrahydropyrido[4,3-d]pyrimidin-2-yl)benzo[c]isothiazole-7-carboxamide
3-(4-(benzylamino)-6-methyl-5,6,7,8-tetrahydropyrido[4,3-d]pyrimidin-2-yl)benzo[c]isoxazole-7-carboxamide
3-(4-(benzylamino)-6-methyl-5,6,7,8-tetrahydropyrido[4,3-d]pyrimidin-2-yl)benzo[d]isothiazole-7-carboxamide
3-(4-(benzylamino)-6-methyl-5,6,7,8-tetrahydropyrido[4,3-d]pyrimidin-2-yl)benzo[d]isoxazole-7-carboxamide
3-(4-(benzylamino)-6-methyl-6,7,8,9-tetrahydro-5H-pyrimido[5,4-c]azepin-2-yl)-1H-indazole-7-carboxamide
3-(4-(benzylamino)-6-methyl-6,7,8,9-tetrahydro-5H-pyrimido[5,4-c]azepin-2-yl)-2-methylbenzo[b]thiophene-7-carboxamide
3-(4-(benzylamino)-6-methyl-6,7,8,9-tetrahydro-5H-pyrimido[5,4-c]azepin-2-yl)-2-methylbenzofuran-7-carboxamide
3-(4-(benzylamino)-6-methyl-6,7,8,9-tetrahydro-5H-pyrimido[5,4-c]azepin-2-yl)-2-methylimidazo[1,2-a]pyridine-8-carboxamide
3-(4-(benzylamino)-6-methyl-6,7,8,9-tetrahydro-5H-pyrimido[5,4-c]azepin-2-yl)-2-methylindolizine-8-carboxamide
3-(4-(benzylamino)-6-methyl-6,7,8,9-tetrahydro-5H-pyrimido[5,4-c]azepin-2-yl)-2-methylpyrazolo[1,5-a]pyridine-7-carboxamide
3-(4-(benzylamino)-6-methyl-6,7,8,9-tetrahydro-5H-pyrimido[5,4-c]azepin-2-yl)benzo[c]isothiazole-7-carboxamide
3-(4-(benzylamino)-6-methyl-6,7,8,9-tetrahydro-5H-pyrimido[5,4-c]azepin-2-yl)benzo[c]isoxazole-7-carboxamide
3-(4-(benzylamino)-6-methyl-6,7,8,9-tetrahydro-5H-pyrimido[5,4-c]azepin-2-yl)benzo[d]isothiazole-7-carboxamide
3-(4-(benzylamino)-6-methyl-6,7,8,9-tetrahydro-5H-pyrimido[5,4-c]azepin-2-yl)benzo[d]isoxazole-7-carboxamide
3-(4-(benzylamino)-6-methyl-6,7,8,9-tetrahydro-5H-pyrimido[5,4-c]azepin-2-yl)imidazo[1,5-a]pyridine-8-carboxamide
3-(4-(benzylamino)-6-methyl-6,7-dihydro-5H-pyrrolo[3,4-d]pyrimidin-2-yl)-1H-indazole-7-carboxamide
3-(4-(benzylamino)-6-methyl-6,7-dihydro-5H-pyrrolo[3,4-d]pyrimidin-2-yl)-2-methylbenzo[b]thiophene-7-carboxamide
3-(4-(benzylamino)-6-methyl-6,7-dihydro-5H-pyrrolo[3,4-d]pyrimidin-2-yl)-2-methylbenzofuran-7-carboxamide
3-(4-(benzylamino)-6-methyl-6,7-dihydro-5H-pyrrolo[3,4-d]pyrimidin-2-yl)-2-methylimidazo[1,2-a]pyridine-8-carboxamide
3-(4-(benzylamino)-6-methyl-6,7-dihydro-5H-pyrrolo[3,4-d]pyrimidin-2-yl)-2-methylindolizine-8-carboxamide
3-(4-(benzylamino)-6-methyl-6,7-dihydro-5H-pyrrolo[3,4-d]pyrimidin-2-yl)-2-methylpyrazolo[1,5-a]pyridine-7-carboxamide
3-(4-(benzylamino)-6-methyl-6,7-dihydro-5H-pyrrolo[3,4-d]pyrimidin-2-yl)benzo[c]isothiazole-7-carboxamide
3-(4-(benzylamino)-6-methyl-6,7-dihydro-5H-pyrrolo[3,4-d]pyrimidin-2-yl)benzo[c]isoxazole-7-carboxamide
3-(4-(benzylamino)-6-methyl-6,7-dihydro-5H-pyrrolo[3,4-d]pyrimidin-2-yl)benzo[d]isothiazole-7-carboxamide
3-(4-(benzylamino)-6-methyl-6,7-dihydro-5H-pyrrolo[3,4-d]pyrimidin-2-yl)benzo[d]isoxazole-7-carboxamide
3-(4-(benzylamino)-6-methyl-6,7-dihydro-5H-pyrrolo[3,4-d]pyrimidin-2-yl)imidazo[1,5-a]pyridine-8-carboxamide
3-(4-(benzylamino)-7,8-dihydro-5H-pyrano[4,3-d]pyrimidin-2-yl)-[1,2,3]triazolo[1,5-a]pyridine-7-carboxamide
3-(4-(benzylamino)-7,8-dihydro-5H-pyrano[4,3-d]pyrimidin-2-yl)-[1,2,4]triazolo[4,3-a]pyridine-8-carboxamide
3-(4-(benzylamino)-7,8-dihydro-5H-pyrano[4,3-d]pyrimidin-2-yl)-1H-indazole-7-carboxamide
3-(4-(benzylamino)-7,8-dihydro-5H-pyrano[4,3-d]pyrimidin-2-yl)-2-methylbenzo[b]thiophene-7-carboxamide
3-(4-(benzylamino)-7,8-dihydro-5H-pyrano[4,3-d]pyrimidin-2-yl)-2-methylbenzofuran-7-carboxamide
3-(4-(benzylamino)-7,8-dihydro-5H-pyrano[4,3-d]pyrimidin-2-yl)-2-methylindolizine-8-carboxamide
3-(4-(benzylamino)-7,8-dihydro-5H-pyrano[4,3-d]pyrimidin-2-yl)benzo[c]isothiazole-7-carboxamide
3-(4-(benzylamino)-7,8-dihydro-5H-pyrano[4,3-d]pyrimidin-2-yl)benzo[c]isoxazole-7-carboxamide
3-(4-(benzylamino)-7,8-dihydro-5H-pyrano[4,3-d]pyrimidin-2-yl)benzo[d]isothiazole-7-carboxamide
3-(4-(benzylamino)-7,8-dihydro-5H-pyrano[4,3-d]pyrimidin-2-yl)benzo[d]isoxazole-7-carboxamide 3-(4-(benzylamino)-7,8-dihydro-6H-pyrano[3,2-d]pyrimidin-2-yl)-[1,2,3]triazolo[1,5-a]pyridine-7-carboxamide
3-(4-(benzylamino)-7,8-dihydro-6H-pyrano[3,2-d]pyrimidin-2-yl)-[1,2,4]triazolo[4,3-a]pyridine-8-carboxamide
3-(4-(benzylamino)-7,8-dihydro-6H-pyrano[3,2-d]pyrimidin-2-yl)-1H-indazole-7-carboxamide
3-(4-(benzylamino)-7,8-dihydro-6H-pyrano[3,2-d]pyrimidin-2-yl)-2-methylbenzo[b]thiophene-7-carboxamide
3-(4-(benzylamino)-7,8-dihydro-6H-pyrano[3,2-d]pyrimidin-2-yl)-2-methylbenzofuran-7-carboxamide
3-(4-(benzylamino)-7,8-dihydro-6H-pyrano[3,2-d]pyrimidin-2-yl)-2-methylindolizine-8-carboxamide
3-(4-(benzylamino)-7,8-dihydro-6H-pyrano[3,2-d]pyrimidin-2-yl)-2-methylpyrazolo[1,5-a]pyridine-7-carboxamide
3-(4-(benzylamino)-7,8-dihydro-6H-pyrano[3,2-d]pyrimidin-2-yl)benzo[c]isothiazole-7-carboxamide
3-(4-(benzylamino)-7,8-dihydro-6H-pyrano[3,2-d]pyrimidin-2-yl)benzo[c]isoxazole-7-carboxamide
3-(4-(benzylamino)-7,8-dihydro-6H-pyrano[3,2-d]pyrimidin-2-yl)benzo[d]isothiazole-7-carboxamide
3-(4-(benzylamino)-7,8-dihydro-6H-pyrano[3,2-d]pyrimidin-2-yl)benzo[d]isoxazole-7-carboxamide
3-(4-(benzylamino)-7-methyl-5,6,7,8-tetrahydropyrido[3,4-d]pyrimidin-2-yl)-1H-indazole-7-carboxamide
3-(4-(benzylamino)-7-methyl-5,6,7,8-tetrahydropyrido[3,4-d]pyrimidin-2-yl)-2-methylbenzo[b]thiophene-7-carboxamide
3-(4-(benzylamino)-7-methyl-5,6,7,8-tetrahydropyrido[3,4-d]pyrimidin-2-yl)-2-methylbenzofuran-7-carboxamide
3-(4-(benzylamino)-7-methyl-5,6,7,8-tetrahydropyrido[3,4-d]pyrimidin-2-yl)-2-methylindolizine-8-carboxamide
3-(4-(benzylamino)-7-methyl-5,6,7,8-tetrahydropyrido[3,4-d]pyrimidin-2-yl)benzo[c]isothiazole-7-carboxamide
3-(4-(benzylamino)-7-methyl-5,6,7,8-tetrahydropyrido[3,4-d]pyrimidin-2-yl)benzo[c]isoxazole-7-carboxamide
3-(4-(benzylamino)-7-methyl-5,6,7,8-tetrahydropyrido[3,4-d]pyrimidin-2-yl)benzo[d]isothiazole-7-carboxamide
3-(4-(benzylamino)-7-methyl-5,6,7,8-tetrahydropyrido[3,4-d]pyrimidin-2-yl)benzo[d]isoxazole-7-carboxamide
3-(4-(benzylamino)-7-methyl-6,7-dihydro-5H-pyrrolo[2,3-d]pyrimidin-2-yl)-1H-indazole-7-carboxamide
3-(4-(benzylamino)-7-methyl-6,7-dihydro-5H-pyrrolo[2,3-d]pyrimidin-2-yl)-2-methylbenzo[b]thiophene-7-carboxamide
3-(4-(benzylamino)-7-methyl-6,7-dihydro-5H-pyrrolo[2,3-d]pyrimidin-2-yl)-2-methylbenzofuran-7-carboxamide
3-(4-(benzylamino)-7-methyl-6,7-dihydro-5H-pyrrolo[2,3-d]pyrimidin-2-yl)-2-methylimidazo[1,2-a]pyridine-8-carboxamide
3-(4-(benzylamino)-7-methyl-6,7-dihydro-5H-pyrrolo[2,3-d]pyrimidin-2-yl)-2-methylindolizine-8-carboxamide
3-(4-(benzylamino)-7-methyl-6,7-dihydro-5H-pyrrolo[2,3-d]pyrimidin-2-yl)-2-methylpyrazolo[1,5-a]pyridine-7-carboxamide
3-(4-(benzylamino)-7-methyl-6,7-dihydro-5H-pyrrolo[2,3-d]pyrimidin-2-yl)benzo[c]isothiazole-7-carboxamide
3-(4-(benzylamino)-7-methyl-6,7-dihydro-5H-pyrrolo[2,3-d]pyrimidin-2-yl)benzo[c]isoxazole-7-carboxamide
3-(4-(benzylamino)-7-methyl-6,7-dihydro-5H-pyrrolo[2,3-d]pyrimidin-2-yl)benzo[d]isothiazole-7-carboxamide
3-(4-(benzylamino)-7-methyl-6,7-dihydro-5H-pyrrolo[2,3-d]pyrimidin-2-yl)benzo[d]isoxazole-7-carboxamide
3-(4-(benzylamino)-7-methyl-6,7-dihydro-5H-pyrrolo[2,3-d]pyrimidin-2-yl)imidazo[1,5-a]pyridine-8-carboxamide
3-(4-(benzylamino)-8-methyl-5,6,7,8-tetrahydropyrido[2,3-d]pyrimidin-2-yl)-1H-indazole-7-carboxamide
3-(4-(benzylamino)-8-methyl-5,6,7,8-tetrahydropyrido[2,3-d]pyrimidin-2-yl)-2-methylbenzo[b]thiophene-7-carboxamide
3-(4-(benzylamino)-8-methyl-5,6,7,8-tetrahydropyrido[2,3-d]pyrimidin-2-yl)-2-methylbenzofuran-7-carboxamide
3-(4-(benzylamino)-8-methyl-5,6,7,8-tetrahydropyrido[2,3-d]pyrimidin-2-yl)-2-methylindolizine-8-carboxamide
3-(4-(benzylamino)-8-methyl-5,6,7,8-tetrahydropyrido[2,3-d]pyrimidin-2-yl)benzo[c]isothiazole-7-carboxamide
3-(4-(benzylamino)-8-methyl-5,6,7,8-tetrahydropyrido[2,3-d]pyrimidin-2-yl)benzo[c]isoxazole-7-carboxamide
3-(4-(benzylamino)-8-methyl-5,6,7,8-tetrahydropyrido[2,3-d]pyrimidin-2-yl)benzo[d]isothiazole-7-carboxamide
3-(4-(benzylamino)-8-methyl-5,6,7,8-tetrahydropyrido[2,3-d]pyrimidin-2-yl)benzo[d]isoxazole-7-carboxamide
3-(4-(benzylamino)-8-methyl-6,7,8,9-tetrahydro-5H-pyrimido[4,5-c]azepin-2-yl)-1H-indazole-7-carboxamide
3-(4-(benzylamino)-8-methyl-6,7,8,9-tetrahydro-5H-pyrimido[4,5-c]azepin-2-yl)-2-methylbenzo[b]thiophene-7-carboxamide
3-(4-(benzylamino)-8-methyl-6,7,8,9-tetrahydro-5H-pyrimido[4,5-c]azepin-2-yl)-2-methylbenzofuran-7-carboxamide
3-(4-(benzylamino)-8-methyl-6,7,8,9-tetrahydro-5H-pyrimido[4,5-c]azepin-2-yl)-2-methylimidazo[1,2-a]pyridine-8-carboxamide
3-(4-(benzylamino)-8-methyl-6,7,8,9-tetrahydro-5H-pyrimido[4,5-c]azepin-2-yl)-2-methylindolizine-8-carboxamide
3-(4-(benzylamino)-8-methyl-6,7,8,9-tetrahydro-5H-pyrimido[4,5-c]azepin-2-yl)-2-methylpyrazolo[1,5-a]pyridine-7-carboxamide
3-(4-(benzylamino)-8-methyl-6,7,8,9-tetrahydro-5H-pyrimido[4,5-c]azepin-2-yl)benzo[c]isothiazole-7-carboxamide
3-(4-(benzylamino)-8-methyl-6,7,8,9-tetrahydro-5H-pyrimido[4,5-c]azepin-2-yl)benzo[c]isoxazole-7-carboxamide
3-(4-(benzylamino)-8-methyl-6,7,8,9-tetrahydro-5H-pyrimido[4,5-c]azepin-2-yl)benzo[d]isothiazole-7-carboxamide
3-(4-(benzylamino)-8-methyl-6,7,8,9-tetrahydro-5H-pyrimido[4,5-c]azepin-2-yl)benzo[d]isoxazole-7-carboxamide
3-(4-(benzylamino)-8-methyl-6,7,8,9-tetrahydro-5H-pyrimido[4,5-c]azepin-2-yl)imidazo[1,5-a]pyridine-8-carboxamide
3-(4-(benzylamino)-9-methyl-6,7,8,9-tetrahydro-5H-pyrimido[4,5-b]azepin-2-yl)-1H-indazole-7-carboxamide
3-(4-(benzylamino)-9-methyl-6,7,8,9-tetrahydro-5H-pyrimido[4,5-b]azepin-2-yl)-2-methylbenzo[b]thiophene-7-carboxamide
3-(4-(benzylamino)-9-methyl-6,7,8,9-tetrahydro-5H-pyrimido[4,5-b]azepin-2-yl)-2-methylbenzofuran-7-carboxamide
3-(4-(benzylamino)-9-methyl-6,7,8,9-tetrahydro-5H-pyrimido[4,5-b]azepin-2-yl)-2-methylimidazo[1,2-a]pyridine-8-carboxamide
3-(4-(benzylamino)-9-methyl-6,7,8,9-tetrahydro-5H-pyrimido[4,5-b]azepin-2-yl)-2-methylindolizine-8-carboxamide
3-(4-(benzylamino)-9-methyl-6,7,8,9-tetrahydro-5H-pyrimido[4,5-b]azepin-2-yl)-2-methylpyrazolo[1,5-a]pyridine-7-carboxamide
3-(4-(benzylamino)-9-methyl-6,7,8,9-tetrahydro-5H-pyrimido[4,5-b]azepin-2-yl)benzo[c]isothiazole-7-carboxamide 3-(4-(benzylamino)-9-methyl-6,7,8,9-tetrahydro-5H-pyrimido[4,5-b]azepin-2-yl)benzo[c]isoxazole-7-carboxamide 3-(4-(benzylamino)-9-methyl-6,7,8,9-tetrahydro-5H-pyrimido[4,5-b]azepin-2-yl)benzo[d]isothiazole-7-carboxamide 3-(4-(benzylamino)-9-methyl-6,7,8,9-tetrahydro-5H-pyrimido[4,5-b]azepin-2-yl)benzo[d]isoxazole-7-carboxamide 3-(4-(benzylamino)-9-methyl-6,7,8,9-tetrahydro-5H-pyrimido[4,5-b]azepin-2-yl)imidazo[1,5-a]pyridine-8-carboxamide More Preferred:

1-(4-((3,5-difluorobenzyl)amino)-6,7-dihydro-5H-pyrano[2,3-d]pyrimidin-2-yl)-2-methyl-1H-indole-4-carboxamide 1-(4-((3-fluorobenzyl)amino)-5,6,7,8-tetrahydropyrido[2,3-d]pyrimidin-2-yl)-1H-indazole-4-carboxamide 1-(4-((3-fluorobenzyl)amino)-5,6,7,8-tetrahydropyrido[2,3-d]pyrimidin-2-yl)-2-methoxy-1H-benzo[d]imidazole-4-carboxamide 1-(4-((3-fluorobenzyl)amino)-5,6,7,8-tetrahydropyrido[2,3-d]pyrimidin-2-yl)-2-methyl-1H-indole-4-carboxamide 1-(4-((3-fluorobenzyl)amino)-5,6,7,8-tetrahydropyrido[2,3-d]pyrimidin-2-yl)-6-fluoro-1H-indazole-4-carboxamide 1-(4-((3-fluorobenzyl)amino)-5,6,7,8-tetrahydropyrido[2,3-d]pyrimidin-2-yl)-6-fluoro-2-methoxy-1H-benzo[d]imidazole-4-carboxamide 1-(4-((3-fluorobenzyl)amino)-5,6,7,8-tetrahydropyrido[2,3-d]pyrimidin-2-yl)-6-fluoro-2-methyl-1H-indole-4-carboxamide 1-(4-((3-fluorobenzyl)amino)-5,6,7,8-tetrahydropyrido[3,2-d]pyrimidin-2-yl)-1H-indazole-4-carboxamide 1-(4-((3-fluorobenzyl)amino)-5,6,7,8-tetrahydropyrido[3,2-d]pyrimidin-2-yl)-2-methoxy-1H-benzo[d]imidazole-4-carboxamide 1-(4-((3-fluorobenzyl)amino)-5,6,7,8-tetrahydropyrido[3,2-d]pyrimidin-2-yl)-2-methyl-1H-indole-4-carboxamide 1-(4-((3-fluorobenzyl)amino)-5,6,7,8-tetrahydropyrido[3,2-d]pyrimidin-2-yl)-6-fluoro-1H-indazole-4-carboxamide 1-(4-((3-fluorobenzyl)amino)-5,6,7,8-tetrahydropyrido[3,2-d]pyrimidin-2-yl)-6-fluoro-2-methoxy-1H-benzo[d]imidazole-4-carboxamide 1-(4-((3-fluorobenzyl)amino)-5,6,7,8-tetrahydropyrido[3,2-d]pyrimidin-2-yl)-6-fluoro-2-methyl-1H-indole-4-carboxamide 1-(4-((3-fluorobenzyl)amino)-5,6,7,8-tetrahydropyrido[3,4-d]pyrimidin-2-yl)-1H-indazole-4-carboxamide 1-(4-((3-fluorobenzyl)amino)-5,6,7,8-tetrahydropyrido[3,4-d]pyrimidin-2-yl)-6-fluoro-1H-indazole-4-carboxamide 1-(4-((3-fluorobenzyl)amino)-5,6,7,8-tetrahydropyrido[4,3-d]pyrimidin-2-yl)-1H-indazole-4-carboxamide 1-(4-((3-fluorobenzyl)amino)-5,6,7,8-tetrahydropyrido[4,3-d]pyrimidin-2-yl)-6-fluoro-1H-indazole-4-carboxamide 1-(4-((3-fluorobenzyl)amino)-5,6,7,8-tetrahydroquinazolin-2-yl)-1H-indazole-4-carboxamide 1-(4-((3-fluorobenzyl)amino)-5,6,7,8-tetrahydroquinazolin-2-yl)-6-fluoro-1H-indazole-4-carboxamide 1-(4-((3-fluorobenzyl)amino)-5,6-dihydrofuro[2,3-d]pyrimidin-2-yl)-1H-indazole-4-carboxamide 1-(4-((3-fluorobenzyl)amino)-5,6-dihydrofuro[2,3-d]pyrimidin-2-yl)-2-methoxy-1H-benzo[d]imidazole-4-carboxamide 1-(4-((3-fluorobenzyl)amino)-5,6-dihydrofuro[2,3-d]pyrimidin-2-yl)-2-methyl-1H-indole-4-carboxamide 1-(4-((3-fluorobenzyl)amino)-5,6-dihydrofuro[2,3-d]pyrimidin-2-yl)-6-fluoro-1H-indazole-4-carboxamide 1-(4-((3-fluorobenzyl)amino)-5,6-dihydrofuro[2,3-d]pyrimidin-2-yl)-6-fluoro-2-methoxy-1H-benzo[d]imidazole-4-carboxamide 1-(4-((3-fluorobenzyl)amino)-5,6-dihydrofuro[2,3-d]pyrimidin-2-yl)-6-fluoro-2-methyl-1H-indole-4-carboxamide 1-(4-((3-fluorobenzyl)amino)-5,7-dihydrofuro[3,4-d]pyrimidin-2-yl)-1H-indazole-4-carboxamide 1-(4-((3-fluorobenzyl)amino)-5,7-dihydrofuro[3,4-d]pyrimidin-2-yl)-6-fluoro-1H-indazole-4-carboxamide 1-(4-((3-fluorobenzyl)amino)-5-methyl-5,6,7,8-tetrahydropyrido[3,2-d]pyrimidin-2-yl)-1H-indazole-4-carboxamide 1-(4-((3-fluorobenzyl)amino)-5-methyl-5,6,7,8-tetrahydropyrido[3,2-d]pyrimidin-2-yl)-2-methoxy-1H-benzo[d]imidazole-4-carboxamide 1-(4-((3-fluorobenzyl)amino)-5-methyl-5,6,7,8-tetrahydropyrido[3,2-d]pyrimidin-2-yl)-2-methyl-1H-indole-4-carboxamide 1-(4-((3-fluorobenzyl)amino)-5-methyl-5,6,7,8-tetrahydropyrido[3,2-d]pyrimidin-2-yl)-6-fluoro-1H-indazole-4-carboxamide 1-(4-((3-fluorobenzyl)amino)-5-methyl-5,6,7,8-tetrahydropyrido[3,2-d]pyrimidin-2-yl)-6-fluoro-2-methoxy-1H-benzo[d]imidazole-4-carboxamide 1-(4-((3-fluorobenzyl)amino)-5-methyl-5,6,7,8-tetrahydropyrido[3,2-d]pyrimidin-2-yl)-6-fluoro-2-methyl-1H-indole-4-carboxamide 1-(4-((3-fluorobenzyl)amino)-5-methyl-6,7-dihydro-5H-pyrrolo[3,2-d]pyrimidin-2-yl)-1H-indazole-4-carboxamide 1-(4-((3-fluorobenzyl)amino)-5-methyl-6,7-dihydro-5H-pyrrolo[3,2-d]pyrimidin-2-yl)-2-methoxy-1H-benzo[d]imidazole-4-carboxamide 1-(4-((3-fluorobenzyl)amino)-5-methyl-6,7-dihydro-5H-pyrrolo[3,2-d]pyrimidin-2-yl)-2-methyl-1H-indole-4-carboxamide 1-(4-((3-fluorobenzyl)amino)-5-methyl-6,7-dihydro-5H-pyrrolo[3,2-d]pyrimidin-2-yl)-6-fluoro-1H-indazole-4-carboxamide 1-(4-((3-fluorobenzyl)amino)-5-methyl-6,7-dihydro-5H-pyrrolo[3,2-d]pyrimidin-2-yl)-6-fluoro-2-methoxy-1H-benzo[d]imidazole-4-carboxamide 1-(4-((3-fluorobenzyl)amino)-5-methyl-6,7-dihydro-5H-pyrrolo[3,2-d]pyrimidin-2-yl)-6-fluoro-2-methyl-1H-indole-4-carboxamide 1-(4-((3-fluorobenzyl)amino)-6,7,8,9-tetrahydro-5H-cyclohepta[d]pyrimidin-2-yl)-1H-indazole-4-carboxamide 1-(4-((3-fluorobenzyl)amino)-6,7,8,9-tetrahydro-5H-cyclohepta[d]pyrimidin-2-yl)-6-fluoro-1H-indazole-4-carboxamide 1-(4-((3-fluorobenzyl)amino)-6,7-dihydro-5H-cyclopenta[d]pyrimidin-2-yl)-1H-indazole-4-carboxamide 1-(4-((3-fluorobenzyl)amino)-6,7-dihydro-5H-cyclopenta[d]pyrimidin-2-yl)-6-fluoro-1H-indazole-4-carboxamide 1-(4-((3-fluorobenzyl)amino)-6,7-dihydro-5H-pyrano[2,3-d]pyrimidin-2-yl)-1H-indazole-4-carboxamide 1-(4-((3-fluorobenzyl)amino)-6,7-dihydro-5H-pyrano[2,3-d]pyrimidin-2-yl)-2-methoxy-1H-benzo[d]imidazole-4-carboxamide 1-(4-((3-fluorobenzyl)amino)-6,7-dihydro-5H-pyrano[2,3-d]pyrimidin-2-yl)-2-methyl-1H-indole-4-carboxamide 1-(4-((3-fluorobenzyl)amino)-6,7-dihydro-5H-pyrano[2,3-d]pyrimidin-2-yl)-6-fluoro-1H-indazole-4-carboxamide 1-(4-((3-fluorobenzyl)amino)-6,7-dihydro-5H-pyrano[2,3-d]pyrimidin-2-yl)-6-fluoro-2-methoxy-1H-benzo[d]imidazole-4-carboxamide 1-(4-((3-fluorobenzyl)amino)-6,7-dihydro-5H-pyrano[2,3-d]pyrimidin-2-yl)-6-fluoro-2-methyl-1H-indole-4-carboxamide 1-(4-((3-fluorobenzyl)amino)-6,7-dihydro-5H-pyrrolo[2,3-d]pyrimidin-2-yl)-1H-indazole-4-carboxamide 1-(4-((3-fluorobenzyl)amino)-6,7-dihydro-5H-pyrrolo[2,3-d]pyrimidin-2-yl)-2-methoxy-1H-benzo[d]imidazole-4-carboxamide 1-(4-((3-fluorobenzyl)amino)-6,7-dihydro-5H-pyrrolo[2,3-d]pyrimidin-2-yl)-2-methyl-1H-indole-4-carboxamide 1-(4-((3-fluorobenzyl)amino)-6,7-dihydro-5H-pyrrolo[2,3-d]pyrimidin-2-yl)-6-fluoro-1H-indazole-4-carboxamide 1-(4-((3-fluorobenzyl)amino)-6,7-dihydro-5H-pyrrolo[2,3-d]pyrimidin-2-yl)-6-fluoro-2-methoxy-1H-benzo[d]imidazole-4-carboxamide 1-(4-((3-fluorobenzyl)amino)-6,7-dihydro-5H-pyrrolo[2,3-d]pyrimidin-2-yl)-6-fluoro-2-methyl-1H-indole-4-carboxamide 1-(4-((3-fluorobenzyl)amino)-6,7-dihydro-5H-pyrrolo[3,2-d]pyrimidin-2-yl)-1H-indazole-4-carboxamide 1-(4-((3-fluorobenzyl)amino)-6,7-dihydro-5H-pyrrolo[3,2-d]pyrimidin-2-yl)-2-methoxy-1H-benzo[d]imidazole-4-carboxamide 1-(4-((3-fluorobenzyl)amino)-6,7-dihydro-5H-pyrrolo[3,2-d]pyrimidin-2-yl)-2-methyl-1H-indole-4-carboxamide 1-(4-((3-fluorobenzyl)amino)-6,7-dihydro-5H-pyrrolo[3,2-d]pyrimidin-2-yl)-6-fluoro-1H-indazole-4-carboxamide 1-(4-((3-fluorobenzyl)amino)-6,7-dihydro-5H-pyrrolo[3,2-d]pyrimidin-2-yl)-6-fluoro-2-methoxy-1H-benzo[d]imidazole-4-carboxamide 1-(4-((3-fluorobenzyl)amino)-6,7-dihydro-5H-pyrrolo[3,2-d]pyrimidin-2-yl)-6-fluoro-2-methyl-1H-indole-4-carboxamide 1-(4-((3-fluorobenzyl)amino)-6,7-dihydro-5H-pyrrolo[3,4-d]pyrimidin-2-yl)-1H-indazole-4-carboxamide 1-(4-((3-fluorobenzyl)amino)-6,7-dihydro-5H-pyrrolo[3,4-d]pyrimidin-2-yl)-6-fluoro-1H-indazole-4-carboxamide 1-(4-((3-fluorobenzyl)amino)-6,8-dihydro-5H-pyrano[3,4-d]pyrimidin-2-yl)-1H-indazole-4-carboxamide 1-(4-((3-fluorobenzyl)amino)-6,8-dihydro-5H-pyrano[3,4-d]pyrimidin-2-yl)-6-fluoro-1H-indazole-4-carboxamide 1-(4-((3-fluorobenzyl)amino)-6-methyl-5,6,7,8-tetrahydropyrido[4,3-d]pyrimidin-2-yl)-1H-indazole-4-carboxamide 1-(4-((3-fluorobenzyl)amino)-6-methyl-5,6,7,8-tetrahydropyrido[4,3-d]pyrimidin-2-yl)-6-fluoro-1H-indazole-4-carboxamide 1-(4-((3-fluorobenzyl)amino)-6-methyl-6,7-dihydro-5H-pyrrolo[3,4-d]pyrimidin-2-yl)-1H-indazole-4-carboxamide 1-(4-((3-fluorobenzyl)amino)-6-methyl-6,7-dihydro-5H-pyrrolo[3,4-d]pyrimidin-2-yl)-6-fluoro-1H-indazole-4-carboxamide 1-(4-((3-fluorobenzyl)amino)-7,8-dihydro-5H-pyrano[4,3-d]pyrimidin-2-yl)-1H-indazole-4-carboxamide 1-(4-((3-fluorobenzyl)amino)-7,8-dihydro-5H-pyrano[4,3-d]pyrimidin-2-yl)-6-fluoro-1H-indazole-4-carboxamide 1-(4-((3-fluorobenzyl)amino)-7-methyl-5,6,7,8-tetrahydropyrido[3,4-d]pyrimidin-2-yl)-1H-indazole-4-carboxamide 1-(4-((3-fluorobenzyl)amino)-7-methyl-5,6,7,8-tetrahydropyrido[3,4-d]pyrimidin-2-yl)-6-fluoro-1H-indazole-4-carboxamide 1-(4-((3-fluorobenzyl)amino)-7-methyl-6,7-dihydro-5H-pyrrolo[2,3-d]pyrimidin-2-yl)-1H-indazole-4-carboxamide 1-(4-((3-fluorobenzyl)amino)-7-methyl-6,7-dihydro-5H-pyrrolo[2,3-d]pyrimidin-2-yl)-2-methoxy-1H-benzo[d]imidazole-4-carboxamide 1-(4-((3-fluorobenzyl)amino)-7-methyl-6,7-dihydro-5H-pyrrolo[2,3-d]pyrimidin-2-yl)-2-methyl-1H-indole-4-carboxamide 1-(4-((3-fluorobenzyl)amino)-7-methyl-6,7-dihydro-5H-pyrrolo[2,3-d]pyrimidin-2-yl)-6-fluoro-1H-indazole-4-carboxamide 1-(4-((3-fluorobenzyl)amino)-7-methyl-6,7-dihydro-5H-pyrrolo[2,3-d]pyrimidin-2-yl)-6-fluoro-2-methoxy-1H-benzo[d]imidazole-4-carboxamide 1-(4-((3-fluorobenzyl)amino)-7-methyl-6,7-dihydro-5H-pyrrolo[2,3-d]pyrimidin-2-yl)-6-fluoro-2-methyl-1H-indole-4-carboxamide 1-(4-((3-fluorobenzyl)amino)-8-methyl-5,6,7,8-tetrahydropyrido[2,3-d]pyrimidin-2-yl)-1H-indazole-4-carboxamide 1-(4-((3-fluorobenzyl)amino)-8-methyl-5,6,7,8-tetrahydropyrido[2,3-d]pyrimidin-2-yl)-2-methoxy-1H-benzo[d]imidazole-4-carboxamide 1-(4-((3-fluorobenzyl)amino)-8-methyl-5,6,7,8-tetrahydropyrido[2,3-d]pyrimidin-2-yl)-2-methyl-1H-indole-4-carboxamide 1-(4-((3-fluorobenzyl)amino)-8-methyl-5,6,7,8-tetrahydropyrido[2,3-d]pyrimidin-2-yl)-6-fluoro-1H-indazole-4-carboxamide 1-(4-((3-fluorobenzyl)amino)-8-methyl-5,6,7,8-tetrahydropyrido[2,3-d]pyrimidin-2-yl)-6-fluoro-2-methoxy-1H-benzo[d]imidazole-4-carboxamide 1-(4-((3-fluorobenzyl)amino)-8-methyl-5,6,7,8-tetrahydropyrido[2,3-d]pyrimidin-2-yl)-6-fluoro-2-methyl-1H-indole-4-carboxamide 1-(4-((thiophen-2-ylmethyl)amino)-5,6,7,8-tetrahydropyrido[2,3-d]pyrimidin-2-yl)-1H-indazole-4-carboxamide 1-(4-((thiophen-2-ylmethyl)amino)-5,6,7,8-tetrahydropyrido[2,3-d]pyrimidin-2-yl)-2-methoxy-1H-benzo[d]imidazole-4-carboxamide 1-(4-((thiophen-2-ylmethyl)amino)-5,6,7,8-tetrahydropyrido[2,3-d]pyrimidin-2-yl)-2-methyl-1H-indole-4-carboxamide 1-(4-((thiophen-2-ylmethyl)amino)-5,6,7,8-tetrahydropyrido[3,2-d]pyrimidin-2-yl)-1H-indazole-4-carboxamide 1-(4-((thiophen-2-ylmethyl)amino)-5,6,7,8-tetrahydropyrido[3,2-d]pyrimidin-2-yl)-2-methoxy-1H-benzo[d]imidazole-4-carboxamide 1-(4-((thiophen-2-ylmethyl)amino)-5,6,7,8-tetrahydropyrido[3,2-d]pyrimidin-2-yl)-2-methyl-1H-indole-4-carboxamide 1-(4-((thiophen-2-ylmethyl)amino)-5,6,7,8-tetrahydropyrido[3,4-d]pyrimidin-2-yl)-1H-indazole-4-carboxamide 1-(4-((thiophen-2-ylmethyl)amino)-5,6,7,8-tetrahydropyrido[4,3-d]pyrimidin-2-yl)-1H-indazole-4-carboxamide 1-(4-((thiophen-2-ylmethyl)amino)-5,6,7,8-tetrahydroquinazolin-2-yl)-1H-indazole-4-carboxamide 1-(4-((thiophen-2-ylmethyl)amino)-5,6-dihydrofuro[2,3-d]pyrimidin-2-yl)-1H-indazole-4-carboxamide 1-(4-((thiophen-2-ylmethyl)amino)-5,6-dihydrofuro[2,3-d]pyrimidin-2-yl)-2-methoxy-1H-benzo[d]imidazole-4-carboxamide 1-(4-((thiophen-2-ylmethyl)amino)-5,6-dihydrofuro[2,3-d]pyrimidin-2-yl)-2-methyl-1H-indole-4-carboxamide 1-(4-((thiophen-2-ylmethyl)amino)-5,7-dihydrofuro[3,4-d]pyrimidin-2-yl)-1H-indazole-4-carboxamide
1-(4-((thiophen-2-ylmethyl)amino)-5-methyl-5,6,7,8-tetrahydropyrido[3,2-d]pyrimidin-2-yl)-1H-indazole-4-carboxamide
1-(4-((thiophen-2-ylmethyl)amino)-5-methyl-5,6,7,8-tetrahydropyrido[3,2-d]pyrimidin-2-yl)-2-methoxy-1H-benzo[d]imidazole-4-carboxamide
1-(4-((thiophen-2-ylmethyl)amino)-5-methyl-5,6,7,8-tetrahydropyrido[3,2-d]pyrimidin-2-yl)-2-methyl-1H-indole-4-carboxamide
1-(4-((thiophen-2-ylmethyl)amino)-5-methyl-6,7-dihydro-5H-pyrrolo[3,2-d]pyrimidin-2-yl)-1H-indazole-4-carboxamide
1-(4-((thiophen-2-ylmethyl)amino)-5-methyl-6,7-dihydro-5H-pyrrolo[3,2-d]pyrimidin-2-yl)-2-methoxy-1H-benzo[d]imidazole-4-carboxamide
1-(4-((thiophen-2-ylmethyl)amino)-5-methyl-6,7-dihydro-5H-pyrrolo[3,2-d]pyrimidin-2-yl)-2-methyl-1H-indole-4-carboxamide
1-(4-((thiophen-2-ylmethyl)amino)-6,7,8,9-tetrahydro-5H-cyclohepta[d]pyrimidin-2-yl)-1H-indazole-4-carboxamide
1-(4-((thiophen-2-ylmethyl)amino)-6,7-dihydro-5H-cyclopenta[d]pyrimidin-2-yl)-1H-indazole-4-carboxamide
1-(4-((thiophen-2-ylmethyl)amino)-6,7-dihydro-5H-pyrano[2,3-d]pyrimidin-2-yl)-1H-indazole-4-carboxamide
1-(4-((thiophen-2-ylmethyl)amino)-6,7-dihydro-5H-pyrano[2,3-d]pyrimidin-2-yl)-2-methoxy-1H-benzo[d]imidazole-4-carboxamide
1-(4-((thiophen-2-ylmethyl)amino)-6,7-dihydro-5H-pyrano[2,3-d]pyrimidin-2-yl)-2-methyl-1H-indole-4-carboxamide
1-(4-((thiophen-2-ylmethyl)amino)-6,7-dihydro-5H-pyrrolo[2,3-d]pyrimidin-2-yl)-1H-indazole-4-carboxamide
1-(4-((thiophen-2-ylmethyl)amino)-6,7-dihydro-5H-pyrrolo[2,3-d]pyrimidin-2-yl)-2-methoxy-1H-benzo[d]imidazole-4-carboxamide
1-(4-((thiophen-2-ylmethyl)amino)-6,7-dihydro-5H-pyrrolo[2,3-d]pyrimidin-2-yl)-2-methyl-1H-indole-4-carboxamide
1-(4-((thiophen-2-ylmethyl)amino)-6,7-dihydro-5H-pyrrolo[3,2-d]pyrimidin-2-yl)-1H-indazole-4-carboxamide
1-(4-((thiophen-2-ylmethyl)amino)-6,7-dihydro-5H-pyrrolo[3,2-d]pyrimidin-2-yl)-2-methoxy-1H-benzo[d]imidazole-4-carboxamide
1-(4-((thiophen-2-ylmethyl)amino)-6,7-dihydro-5H-pyrrolo[3,2-d]pyrimidin-2-yl)-2-methyl-1H-indole-4-carboxamide
1-(4-((thiophen-2-ylmethyl)amino)-6,7-dihydro-5H-pyrrolo[3,4-d]pyrimidin-2-yl)-1H-indazole-4-carboxamide
1-(4-((thiophen-2-ylmethyl)amino)-6,8-dihydro-5H-pyrano[3,4-d]pyrimidin-2-yl)-1H-indazole-4-carboxamide
1-(4-((thiophen-2-ylmethyl)amino)-6-methyl-5,6,7,8-tetrahydropyrido[4,3-d]pyrimidin-2-yl)-1H-indazole-4-carboxamide
1-(4-((thiophen-2-ylmethyl)amino)-6-methyl-6,7-dihydro-5H-pyrrolo[3,4-d]pyrimidin-2-yl)-1H-indazole-4-carboxamide
1-(4-((thiophen-2-ylmethyl)amino)-7,8-dihydro-5H-pyrano[4,3-d]pyrimidin-2-yl)-1H-indazole-4-carboxamide
1-(4-((thiophen-2-ylmethyl)amino)-7-methyl-5,6,7,8-tetrahydropyrido[3,4-d]pyrimidin-2-yl)-1H-indazole-4-carboxamide
1-(4-((thiophen-2-ylmethyl)amino)-7-methyl-6,7-dihydro-5H-pyrrolo[2,3-d]pyrimidin-2-yl)-1H-indazole-4-carboxamide
1-(4-((thiophen-2-ylmethyl)amino)-7-methyl-6,7-dihydro-5H-pyrrolo[2,3-d]pyrimidin-2-yl)-2-methoxy-1H-benzo[d]imidazole-4-carboxamide
1-(4-((thiophen-2-ylmethyl)amino)-7-methyl-6,7-dihydro-5H-pyrrolo[2,3-d]pyrimidin-2-yl)-2-methyl-1H-indole-4-carboxamide
1-(4-((thiophen-2-ylmethyl)amino)-8-methyl-5,6,7,8-tetrahydropyrido[2,3-d]pyrimidin-2-yl)-1H-indazole-4-carboxamide
1-(4-((thiophen-2-ylmethyl)amino)-8-methyl-5,6,7,8-tetrahydropyrido[2,3-d]pyrimidin-2-yl)-2-methoxy-1H-benzo[d]imidazole-4-carboxamide
1-(4-((thiophen-2-ylmethyl)amino)-8-methyl-5,6,7,8-tetrahydropyrido[2,3-d]pyrimidin-2-yl)-2-methyl-1H-indole-4-carboxamide
1-(4-(benzylamino)-5,6,7,8-tetrahydropyrido[2,3-d]pyrimidin-2-yl)-1H-indazole-4-carboxamide
1-(4-(benzylamino)-5,6,7,8-tetrahydropyrido[2,3-d]pyrimidin-2-yl)-2-(hydroxymethyl)-1H-indole-4-carboxamide
1-(4-(benzylamino)-5,6,7,8-tetrahydropyrido[2,3-d]pyrimidin-2-yl)-2-methoxy-1H-benzo[d]imidazole-4-carboxamide
1-(4-(benzylamino)-5,6,7,8-tetrahydropyrido[2,3-d]pyrimidin-2-yl)-2-methyl-1H-indole-4-carboxamide
1-(4-(benzylamino)-5,6,7,8-tetrahydropyrido[2,3-d]pyrimidin-2-yl)-6-fluoro-1H-indazole-4-carboxamide
1-(4-(benzylamino)-5,6,7,8-tetrahydropyrido[2,3-d]pyrimidin-2-yl)-6-fluoro-2-methoxy-1H-benzo[d]imidazole-4-carboxamide
1-(4-(benzylamino)-5,6,7,8-tetrahydropyrido[2,3-d]pyrimidin-2-yl)-6-fluoro-2-methyl-1H-indole-4-carboxamide
1-(4-(benzylamino)-5,6,7,8-tetrahydropyrido[3,2-d]pyrimidin-2-yl)-1H-indazole-4-carboxamide
1-(4-(benzylamino)-5,6,7,8-tetrahydropyrido[3,2-d]pyrimidin-2-yl)-2-methoxy-1H-benzo[d]imidazole-4-carboxamide
1-(4-(benzylamino)-5,6,7,8-tetrahydropyrido[3,2-d]pyrimidin-2-yl)-2-methyl-1H-indole-4-carboxamide
1-(4-(benzylamino)-5,6,7,8-tetrahydropyrido[3,2-d]pyrimidin-2-yl)-6-fluoro-1H-indazole-4-carboxamide
1-(4-(benzylamino)-5,6,7,8-tetrahydropyrido[3,2-d]pyrimidin-2-yl)-6-fluoro-2-methoxy-1H-benzo[d]imidazole-4-carboxamide
1-(4-(benzylamino)-5,6,7,8-tetrahydropyrido[3,2-d]pyrimidin-2-yl)-6-fluoro-2-methyl-1H-indole-4-carboxamide
1-(4-(benzylamino)-5,6,7,8-tetrahydropyrido[3,4-d]pyrimidin-2-yl)-1H-indazole-4-carboxamide
1-(4-(benzylamino)-5,6,7,8-tetrahydropyrido[3,4-d]pyrimidin-2-yl)-6-fluoro-1H-indazole-4-carboxamide
1-(4-(benzylamino)-5,6,7,8-tetrahydropyrido[4,3-d]pyrimidin-2-yl)-1H-indazole-4-carboxamide
1-(4-(benzylamino)-5,6,7,8-tetrahydropyrido[4,3-d]pyrimidin-2-yl)-6-fluoro-1H-indazole-4-carboxamide
1-(4-(benzylamino)-5,6,7,8-tetrahydroquinazolin-2-yl)-1H-indazole-4-carboxamide
1-(4-(benzylamino)-5,6,7,8-tetrahydroquinazolin-2-yl)-6-fluoro-1H-indazole-4-carboxamide
1-(4-(benzylamino)-5,6-dihydrofuro[2,3-d]pyrimidin-2-yl)-1H-indazole-4-carboxamide
1-(4-(benzylamino)-5,6-dihydrofuro[2,3-d]pyrimidin-2-yl)-2-methoxy-1H-benzo[d]imidazole-4-carboxamide
1-(4-(benzylamino)-5,6-dihydrofuro[2,3-d]pyrimidin-2-yl)-2-methyl-1H-indole-4-carboxamide
1-(4-(benzylamino)-5,6-dihydrofuro[2,3-d]pyrimidin-2-yl)-6-fluoro-1H-indazole-4-carboxamide 1-(4-(benzylamino)-5,6-dihydrofuro[2,3-d]pyrimidin-2-yl)-6-fluoro-2-methoxy-1H-benzo[d]imidazole-4-carboxamide
1-(4-(benzylamino)-5,6-dihydrofuro[2,3-d]pyrimidin-2-yl)-6-fluoro-2-methyl-1H-indole-4-carboxamide
1-(4-(benzylamino)-5,7-dihydrofuro[3,4-d]pyrimidin-2-yl)-1H-indazole-4-carboxamide
1-(4-(benzylamino)-5,7-dihydrofuro[3,4-d]pyrimidin-2-yl)-6-fluoro-1H-indazole-4-carboxamide
1-(4-(benzylamino)-5,7-dimethyl-5,6,7,8-tetrahydropyrido[3,4-d]pyrimidin-2-yl)-1H-indazole-4-carboxamide
1-(4-(benzylamino)-5,7-dimethyl-5,6,7,8-tetrahydropyrido[3,4-d]pyrimidin-2-yl)-2-methoxy-1H-benzo[d]imidazole-4-carboxamide
1-(4-(benzylamino)-5,7-dimethyl-5,6,7,8-tetrahydropyrido[3,4-d]pyrimidin-2-yl)-2-methyl-1H-indole-4-carboxamide
1-(4-(benzylamino)-5-methyl-5,6,7,8-tetrahydropyrido[3,2-d]pyrimidin-2-yl)-1H-indazole-4-carboxamide
1-(4-(benzylamino)-5-methyl-5,6,7,8-tetrahydropyrido[3,2-d]pyrimidin-2-yl)-2-methoxy-1H-benzo[d]imidazole-4-carboxamide
1-(4-(benzylamino)-5-methyl-5,6,7,8-tetrahydropyrido[3,2-d]pyrimidin-2-yl)-2-methyl-1H-indole-4-carboxamide
1-(4-(benzylamino)-5-methyl-5,6,7,8-tetrahydropyrido[3,2-d]pyrimidin-2-yl)-6-fluoro-1H-indazole-4-carboxamide
1-(4-(benzylamino)-5-methyl-5,6,7,8-tetrahydropyrido[3,2-d]pyrimidin-2-yl)-6-fluoro-2-methoxy-1H-benzo[d]imidazole-4-carboxamide
1-(4-(benzylamino)-5-methyl-5,6,7,8-tetrahydropyrido[3,2-d]pyrimidin-2-yl)-6-fluoro-2-methyl-1H-indole-4-carboxamide
1-(4-(benzylamino)-5-methyl-5,6,7,8-tetrahydropyrido[3,4-d]pyrimidin-2-yl)-1H-indazole-4-carboxamide
1-(4-(benzylamino)-5-methyl-5,6,7,8-tetrahydropyrido[3,4-d]pyrimidin-2-yl)-2-methoxy-1H-benzo[d]imidazole-4-carboxamide
1-(4-(benzylamino)-5-methyl-5,6,7,8-tetrahydropyrido[3,4-d]pyrimidin-2-yl)-2-methyl-1H-indole-4-carboxamide
1-(4-(benzylamino)-5-methyl-5,6,7,8-tetrahydropyrido[4,3-d]pyrimidin-2-yl)-1H-indazole-4-carboxamide
1-(4-(benzylamino)-5-methyl-5,6,7,8-tetrahydropyrido[4,3-d]pyrimidin-2-yl)-2-methoxy-1H-benzo[d]imidazole-4-carboxamide
1-(4-(benzylamino)-5-methyl-5,6,7,8-tetrahydropyrido[4,3-d]pyrimidin-2-yl)-2-methyl-1H-indole-4-carboxamide
1-(4-(benzylamino)-5-methyl-5,6,7,8-tetrahydroquinazolin-2-yl)-1H-indazole-4-carboxamide
1-(4-(benzylamino)-5-methyl-5,6,7,8-tetrahydroquinazolin-2-yl)-2-methoxy-1H-benzo[d]imidazole-4-carboxamide
1-(4-(benzylamino)-5-methyl-5,6,7,8-tetrahydroquinazolin-2-yl)-2-methyl-1H-indole-4-carboxamide
1-(4-(benzylamino)-5-methyl-6,7-dihydro-5H-pyrrolo[3,2-d]pyrimidin-2-yl)-1H-indazole-4-carboxamide
1-(4-(benzylamino)-5-methyl-6,7-dihydro-5H-pyrrolo[3,2-d]pyrimidin-2-yl)-2-methoxy-1H-benzo[d]imidazole-4-carboxamide
1-(4-(benzylamino)-5-methyl-6,7-dihydro-5H-pyrrolo[3,2-d]pyrimidin-2-yl)-2-methyl-1H-indole-4-carboxamide
1-(4-(benzylamino)-5-methyl-6,7-dihydro-5H-pyrrolo[3,2-d]pyrimidin-2-yl)-6-fluoro-1H-indazole-4-carboxamide
1-(4-(benzylamino)-5-methyl-6,7-dihydro-5H-pyrrolo[3,2-d]pyrimidin-2-yl)-6-fluoro-2-methoxy-1H-benzo[d]imidazole-4-carboxamide
1-(4-(benzylamino)-5-methyl-6,7-dihydro-5H-pyrrolo[3,2-d]pyrimidin-2-yl)-6-fluoro-2-methyl-1H-indole-4-carboxamide
1-(4-(benzylamino)-5-methyl-6,8-dihydro-5H-pyrano[3,4-d]pyrimidin-2-yl)-1H-indazole-4-carboxamide
1-(4-(benzylamino)-5-methyl-6,8-dihydro-5H-pyrano[3,4-d]pyrimidin-2-yl)-2-methoxy-1H-benzo[d]imidazole-4-carboxamide
1-(4-(benzylamino)-5-methyl-6,8-dihydro-5H-pyrano[3,4-d]pyrimidin-2-yl)-2-methyl-1H-indole-4-carboxamide
1-(4-(benzylamino)-5-methyl-7,8-dihydro-5H-pyrano[4,3-d]pyrimidin-2-yl)-1H-indazole-4-carboxamide
1-(4-(benzylamino)-5-methyl-7,8-dihydro-5H-pyrano[4,3-d]pyrimidin-2-yl)-2-methoxy-1H-benzo[d]imidazole-4-carboxamide
1-(4-(benzylamino)-5-methyl-7,8-dihydro-5H-pyrano[4,3-d]pyrimidin-2-yl)-2-methyl-1H-indole-4-carboxamide
1-(4-(benzylamino)-6,7,8,9-tetrahydro-5H-cyclohepta[d]pyrimidin-2-yl)-1H-indazole-4-carboxamide
1-(4-(benzylamino)-6,7,8,9-tetrahydro-5H-cyclohepta[d]pyrimidin-2-yl)-6-fluoro-1H-indazole-4-carboxamide
1-(4-(benzylamino)-6,7,8,9-tetrahydro-5H-pyrimido[4,5-d]azepin-2-yl)-2-methyl-1H-indole-4-carboxamide
1-(4-(benzylamino)-6,7-dihydro-5H-cyclopenta[d]pyrimidin-2-yl)-1H-indazole-4-carboxamide
1-(4-(benzylamino)-6,7-dihydro-5H-cyclopenta[d]pyrimidin-2-yl)-6-fluoro-1H-indazole-4-carboxamide
1-(4-(benzylamino)-6,7-dihydro-5H-pyrano[2,3-d]pyrimidin-2-yl)-1H-indazole-4-carboxamide
1-(4-(benzylamino)-6,7-dihydro-5H-pyrano[2,3-d]pyrimidin-2-yl)-2-(hydroxymethyl)-1H-indole-4-carboxamide
1-(4-(benzylamino)-6,7-dihydro-5H-pyrano[2,3-d]pyrimidin-2-yl)-2-methoxy-1H-benzo[d]imidazole-4-carboxamide
1-(4-(benzylamino)-6,7-dihydro-5H-pyrano[2,3-d]pyrimidin-2-yl)-2-methyl-1H-indole-4-carboxamide
1-(4-(benzylamino)-6,7-dihydro-5H-pyrano[2,3-d]pyrimidin-2-yl)-6-fluoro-1H-indazole-4-carboxamide
1-(4-(benzylamino)-6,7-dihydro-5H-pyrano[2,3-d]pyrimidin-2-yl)-6-fluoro-2-methoxy-1H-benzo[d]imidazole-4-carboxamide
1-(4-(benzylamino)-6,7-dihydro-5H-pyrano[2,3-d]pyrimidin-2-yl)-6-fluoro-2-methyl-1H-indole-4-carboxamide
1-(4-(benzylamino)-6,7-dihydro-5H-pyrrolo[2,3-d]pyrimidin-2-yl)-1H-indazole-4-carboxamide
1-(4-(benzylamino)-6,7-dihydro-5H-pyrrolo[2,3-d]pyrimidin-2-yl)-2-methoxy-1H-benzo[d]imidazole-4-carboxamide
1-(4-(benzylamino)-6,7-dihydro-5H-pyrrolo[2,3-d]pyrimidin-2-yl)-2-methyl-1H-indole-4-carboxamide
1-(4-(benzylamino)-6,7-dihydro-5H-pyrrolo[2,3-d]pyrimidin-2-yl)-6-fluoro-1H-indazole-4-carboxamide
1-(4-(benzylamino)-6,7-dihydro-5H-pyrrolo[2,3-d]pyrimidin-2-yl)-6-fluoro-2-methoxy-1H-benzo[d]imidazole-4-carboxamide
1-(4-(benzylamino)-6,7-dihydro-5H-pyrrolo[2,3-d]pyrimidin-2-yl)-6-fluoro-2-methyl-1H-indole-4-carboxamide
1-(4-(benzylamino)-6,7-dihydro-5H-pyrrolo[3,2-d]pyrimidin-2-yl)-1H-indazole-4-carboxamide
1-(4-(benzylamino)-6,7-dihydro-5H-pyrrolo[3,2-d]pyrimidin-2-yl)-2-methoxy-1H-benzo[d]imidazole-4-carboxamide
1-(4-(benzylamino)-6,7-dihydro-5H-pyrrolo[3,2-d]pyrimidin-2-yl)-2-methyl-1H-indole-4-carboxamide
1-(4-(benzylamino)-6,7-dihydro-5H-pyrrolo[3,2-d]pyrimidin-2-yl)-6-fluoro-1H-indazole-4-carboxamide
1-(4-(benzylamino)-6,7-dihydro-5H-pyrrolo[3,2-d]pyrimidin-2-yl)-6-fluoro-2-methoxy-1H-benzo[d]imidazole-4-carboxamide 1-(4-(benzylamino)-6,7-dihydro-5H-pyrrolo[3,2-d]pyrimidin-2-yl)-6-fluoro-2-methyl-1H-indole-4-carboxamide
1-(4-(benzylamino)-6,7-dihydro-5H-pyrrolo[3,4-d]pyrimidin-2-yl)-1H-indazole-4-carboxamide
1-(4-(benzylamino)-6,7-dihydro-5H-pyrrolo[3,4-d]pyrimidin-2-yl)-6-fluoro-1H-indazole-4-carboxamide
1-(4-(benzylamino)-6,7-dimethyl-5,6,7,8-tetrahydropyrido[3,4-d]pyrimidin-2-yl)-1H-indazole-4-carboxamide
1-(4-(benzylamino)-6,7-dimethyl-5,6,7,8-tetrahydropyrido[3,4-d]pyrimidin-2-yl)-2-methoxy-1H-benzo[d]imidazole-4-carboxamide
1-(4-(benzylamino)-6,7-dimethyl-5,6,7,8-tetrahydropyrido[3,4-d]pyrimidin-2-yl)-2-methyl-1H-indole-4-carboxamide
1-(4-(benzylamino)-6,7-dimethyl-5,6,7,8-tetrahydropyrido[4,3-d]pyrimidin-2-yl)-1H-indazole-4-carboxamide
1-(4-(benzylamino)-6,7-dimethyl-5,6,7,8-tetrahydropyrido[4,3-d]pyrimidin-2-yl)-2-methoxy-1H-benzo[d]imidazole-4-carboxamide
1-(4-(benzylamino)-6,7-dimethyl-5,6,7,8-tetrahydropyrido[4,3-d]pyrimidin-2-yl)-2-methyl-1H-indole-4-carboxamide
1-(4-(benzylamino)-6,8-dihydro-5H-pyrano[3,4-d]pyrimidin-2-yl)-1H-indazole-4-carboxamide
1-(4-(benzylamino)-6,8-dihydro-5H-pyrano[3,4-d]pyrimidin-2-yl)-6-fluoro-1H-indazole-4-carboxamide
1-(4-(benzylamino)-6,8-dimethyl-5,6,7,8-tetrahydropyrido[4,3-d]pyrimidin-2-yl)-1H-indazole-4-carboxamide
1-(4-(benzylamino)-6,8-dimethyl-5,6,7,8-tetrahydropyrido[4,3-d]pyrimidin-2-yl)-2-methyl-1H-indole-4-carboxamide
1-(4-(benzylamino)-6-methyl-5,6,7,8-tetrahydropyrido[3,4-d]pyrimidin-2-yl)-1H-indazole-4-carboxamide
1-(4-(benzylamino)-6-methyl-5,6,7,8-tetrahydropyrido[3,4-d]pyrimidin-2-yl)-2-methoxy-1H-benzo[d]imidazole-4-carboxamide
1-(4-(benzylamino)-6-methyl-5,6,7,8-tetrahydropyrido[3,4-d]pyrimidin-2-yl)-2-methyl-1H-indole-4-carboxamide
1-(4-(benzylamino)-6-methyl-5,6,7,8-tetrahydropyrido[4,3-d]pyrimidin-2-yl)-1H-indazole-4-carboxamide
1-(4-(benzylamino)-6-methyl-5,6,7,8-tetrahydropyrido[4,3-d]pyrimidin-2-yl)-2-methoxy-1H-benzo[d]imidazole-4-carboxamide
1-(4-(benzylamino)-6-methyl-5,6,7,8-tetrahydropyrido[4,3-d]pyrimidin-2-yl)-6-fluoro-1H-indazole-4-carboxamide
1-(4-(benzylamino)-6-methyl-6,7-dihydro-5H-pyrrolo[3,4-d]pyrimidin-2-yl)-1H-indazole-4-carboxamide
1-(4-(benzylamino)-6-methyl-6,7-dihydro-5H-pyrrolo[3,4-d]pyrimidin-2-yl)-6-fluoro-1H-indazole-4-carboxamide
1-(4-(benzylamino)-6-methyl-6,8-dihydro-5H-pyrano[3,4-d]pyrimidin-2-yl)-1H-indazole-4-carboxamide
1-(4-(benzylamino)-6-methyl-6,8-dihydro-5H-pyrano[3,4-d]pyrimidin-2-yl)-2-methoxy-1H-benzo[d]imidazole-4-carboxamide
1-(4-(benzylamino)-6-methyl-6,8-dihydro-5H-pyrano[3,4-d]pyrimidin-2-yl)-2-methyl-1H-indole-4-carboxamide
1-(4-(benzylamino)-7,8-dihydro-5H-pyrano[4,3-d]pyrimidin-2-yl)-1H-indazole-4-carboxamide
1-(4-(benzylamino)-7,8-dihydro-5H-pyrano[4,3-d]pyrimidin-2-yl)-6-fluoro-1H-indazole-4-carboxamide
1-(4-(benzylamino)-7,8-dimethyl-5,6,7,8-tetrahydropyrido[3,4-d]pyrimidin-2-yl)-1H-indazole-4-carboxamide
1-(4-(benzylamino)-7,8-dimethyl-5,6,7,8-tetrahydropyrido[3,4-d]pyrimidin-2-yl)-2-methoxy-1H-benzo[d]imidazole-4-carboxamide
1-(4-(benzylamino)-7,8-dimethyl-5,6,7,8-tetrahydropyrido[3,4-d]pyrimidin-2-yl)-2-methyl-1H-indole-4-carboxamide
1-(4-(benzylamino)-7-methyl-5,6,7,8-tetrahydropyrido[3,4-d]pyrimidin-2-yl)-1H-indazole-4-carboxamide
1-(4-(benzylamino)-7-methyl-5,6,7,8-tetrahydropyrido[3,4-d]pyrimidin-2-yl)-6-fluoro-1H-indazole-4-carboxamide
1-(4-(benzylamino)-7-methyl-5,6,7,8-tetrahydropyrido[4,3-d]pyrimidin-2-yl)-1H-indazole-4-carboxamide
1-(4-(benzylamino)-7-methyl-5,6,7,8-tetrahydropyrido[4,3-d]pyrimidin-2-yl)-2-methoxy-1H-benzo[d]imidazole-4-carboxamide
1-(4-(benzylamino)-7-methyl-5,6,7,8-tetrahydropyrido[4,3-d]pyrimidin-2-yl)-2-methyl-1H-indole-4-carboxamide
1-(4-(benzylamino)-7-methyl-5,6,7,8-tetrahydroquinazolin-2-yl)-1H-indazole-4-carboxamide
1-(4-(benzylamino)-7-methyl-5,6,7,8-tetrahydroquinazolin-2-yl)-2-methoxy-1H-benzo[d]imidazole-4-carboxamide
1-(4-(benzylamino)-7-methyl-5,6,7,8-tetrahydroquinazolin-2-yl)-2-methyl-1H-indole-4-carboxamide
1-(4-(benzylamino)-7-methyl-6,7-dihydro-5H-pyrrolo[2,3-d]pyrimidin-2-yl)-1H-indazole-4-carboxamide
1-(4-(benzylamino)-7-methyl-6,7-dihydro-5H-pyrrolo[2,3-d]pyrimidin-2-yl)-2-methoxy-1H-benzo[d]imidazole-4-carboxamide
1-(4-(benzylamino)-7-methyl-6,7-dihydro-5H-pyrrolo[2,3-d]pyrimidin-2-yl)-2-methyl-1H-indole-4-carboxamide
1-(4-(benzylamino)-7-methyl-6,7-dihydro-5H-pyrrolo[2,3-d]pyrimidin-2-yl)-6-fluoro-1H-indazole-4-carboxamide
1-(4-(benzylamino)-7-methyl-6,7-dihydro-5H-pyrrolo[2,3-d]pyrimidin-2-yl)-6-fluoro-2-methoxy-1H-benzo[d]imidazole-4-carboxamide
1-(4-(benzylamino)-7-methyl-6,7-dihydro-5H-pyrrolo[2,3-d]pyrimidin-2-yl)-6-fluoro-2-methyl-1H-indole-4-carboxamide
1-(4-(benzylamino)-7-methyl-7,8-dihydro-5H-pyrano[4,3-d]pyrimidin-2-yl)-1H-indazole-4-carboxamide
1-(4-(benzylamino)-7-methyl-7,8-dihydro-5H-pyrano[4,3-d]pyrimidin-2-yl)-2-methoxy-1H-benzo[d]imidazole-4-carboxamide
1-(4-(benzylamino)-7-methyl-7,8-dihydro-5H-pyrano[4,3-d]pyrimidin-2-yl)-2-methyl-1H-indole-4-carboxamide
1-(4-(benzylamino)-8-methyl-5,6,7,8-tetrahydropyrido[2,3-d]pyrimidin-2-yl)-1H-indazole-4-carboxamide
1-(4-(benzylamino)-8-methyl-5,6,7,8-tetrahydropyrido[2,3-d]pyrimidin-2-yl)-2-methoxy-1H-benzo[d]imidazole-4-carboxamide
1-(4-(benzylamino)-8-methyl-5,6,7,8-tetrahydropyrido[2,3-d]pyrimidin-2-yl)-2-methyl-1H-indole-4-carboxamide
1-(4-(benzylamino)-8-methyl-5,6,7,8-tetrahydropyrido[2,3-d]pyrimidin-2-yl)-6-fluoro-1H-indazole-4-carboxamide
1-(4-(benzylamino)-8-methyl-5,6,7,8-tetrahydropyrido[2,3-d]pyrimidin-2-yl)-6-fluoro-2-methoxy-1H-benzo[d]imidazole-4-carboxamide
1-(4-(benzylamino)-8-methyl-5,6,7,8-tetrahydropyrido[2,3-d]pyrimidin-2-yl)-6-fluoro-2-methyl-1H-indole-4-carboxamide
1-(4-(benzylamino)-8-methyl-5,6,7,8-tetrahydropyrido[3,4-d]pyrimidin-2-yl)-1H-indazole-4-carboxamide
1-(4-(benzylamino)-8-methyl-5,6,7,8-tetrahydropyrido[3,4-d]pyrimidin-2-yl)-2-methoxy-1H-benzo[d]imidazole-4-carboxamide
1-(4-(benzylamino)-8-methyl-5,6,7,8-tetrahydropyrido[3,4-d]pyrimidin-2-yl)-2-methyl-1H-indole-4-carboxamide
1-(4-(benzylamino)-8-methyl-5,6,7,8-tetrahydropyrido[4,3-d]pyrimidin-2-yl)-1H-indazole-4-carboxamide 1-(4-(benzylamino)-8-methyl-5,6,7,8-tetrahydropyrido[4,3-d]pyrimidin-2-yl)-2-methoxy-1H-benzo[d]imidazole-4-carboxamide
1-(4-(benzylamino)-8-methyl-5,6,7,8-tetrahydropyrido[4,3-d]pyrimidin-2-yl)-2-methyl-1H-indole-4-carboxamide
1-(4-(benzylamino)-8-methyl-5,6,7,8-tetrahydroquinazolin-2-yl)-1H-indazole-4-carboxamide
1-(4-(benzylamino)-8-methyl-5,6,7,8-tetrahydroquinazolin-2-yl)-2-methoxy-1H-benzo[d]imidazole-4-carboxamide
1-(4-(benzylamino)-8-methyl-5,6,7,8-tetrahydroquinazolin-2-yl)-2-methyl-1H-indole-4-carboxamide
1-(4-(benzylamino)-8-methyl-6,8-dihydro-5H-pyrano[3,4-d]pyrimidin-2-yl)-1H-indazole-4-carboxamide
1-(4-(benzylamino)-8-methyl-6,8-dihydro-5H-pyrano[3,4-d]pyrimidin-2-yl)-2-methoxy-1H-benzo[d]imidazole-4-carboxamide
1-(4-(benzylamino)-8-methyl-6,8-dihydro-5H-pyrano[3,4-d]pyrimidin-2-yl)-2-methyl-1H-indole-4-carboxamide
1-(4-(benzylamino)-8-methyl-7,8-dihydro-5H-pyrano[4,3-d]pyrimidin-2-yl)-1H-indazole-4-carboxamide
1-(4-(benzylamino)-8-methyl-7,8-dihydro-5H-pyrano[4,3-d]pyrimidin-2-yl)-2-methoxy-1H-benzo[d]imidazole-4-carboxamide
1-(4-(benzylamino)-8-methyl-7,8-dihydro-5H-pyrano[4,3-d]pyrimidin-2-yl)-2-methyl-1H-indole-4-carboxamide
2-(4-(aminomethyl)-2-methyl-1H-indol-1-yl)-N-benzyl-6,7-dihydro-5H-pyrano[2,3-d]pyrimidin-4-amine
2-(aminomethyl)-1-(4-(benzylamino)-6,7-dihydro-5H-pyrano[2,3-d]pyrimidin-2-yl)-1H-indole-4-carboxamide
3-(4-((3-fluorobenzyl)amino)-5,6,7,8-tetrahydropyrido[2,3-d]pyrimidin-2-yl)-2-methyl-1H-indole-7-carboxamide
3-(4-((3-fluorobenzyl)amino)-5,6,7,8-tetrahydropyrido[3,2-d]pyrimidin-2-yl)-2-methyl-1H-indole-7-carboxamide
3-(4-((3-fluorobenzyl)amino)-5,6,7,8-tetrahydropyrido[3,4-d]pyrimidin-2-yl)-2-methyl-1H-indole-7-carboxamide
3-(4-((3-fluorobenzyl)amino)-5,6,7,8-tetrahydropyrido[4,3-d]pyrimidin-2-yl)-2-methyl-1H-indole-7-carboxamide
3-(4-((3-fluorobenzyl)amino)-5,6,7,8-tetrahydroquinazolin-2-yl)-2-methyl-1H-indole-7-carboxamide
3-(4-((3-fluorobenzyl)amino)-5,6-dihydrofuro[2,3-d]pyrimidin-2-yl)-2-methyl-1H-indole-7-carboxamide
3-(4-((3-fluorobenzyl)amino)-5,7-dihydrofuro[3,4-d]pyrimidin-2-yl)-2-methyl-1H-indole-7-carboxamide
3-(4-((3-fluorobenzyl)amino)-5-methyl-5,6,7,8-tetrahydropyrido[3,2-d]pyrimidin-2-yl)-2-methyl-1H-indole-7-carboxamide
3-(4-((3-fluorobenzyl)amino)-5-methyl-6,7-dihydro-5H-pyrrolo[3,2-d]pyrimidin-2-yl)-2-methyl-1H-indole-7-carboxamide
3-(4-((3-fluorobenzyl)amino)-6,7,8,9-tetrahydro-5H-cyclohepta[d]pyrimidin-2-yl)-2-methyl-1H-indole-7-carboxamide
3-(4-((3-fluorobenzyl)amino)-6,7-dihydro-5H-cyclopenta[d]pyrimidin-2-yl)-2-methyl-1H-indole-7-carboxamide
3-(4-((3-fluorobenzyl)amino)-6,7-dihydro-5H-pyrano[2,3-d]pyrimidin-2-yl)-2-methyl-1H-indole-7-carboxamide
3-(4-((3-fluorobenzyl)amino)-6,7-dihydro-5H-pyrrolo[2,3-d]pyrimidin-2-yl)-2-methyl-1H-indole-7-carboxamide
3-(4-((3-fluorobenzyl)amino)-6,7-dihydro-5H-pyrrolo[3,2-d]pyrimidin-2-yl)-2-methyl-1H-indole-7-carboxamide
3-(4-((3-fluorobenzyl)amino)-6,7-dihydro-5H-pyrrolo[3,4-d]pyrimidin-2-yl)-2-methyl-1H-indole-7-carboxamide
3-(4-((3-fluorobenzyl)amino)-6,8-dihydro-5H-pyrano[3,4-d]pyrimidin-2-yl)-2-methyl-1H-indole-7-carboxamide
3-(4-((3-fluorobenzyl)amino)-6-methyl-5,6,7,8-tetrahydropyrido[4,3-d]pyrimidin-2-yl)-2-methyl-1H-indole-7-carboxamide
3-(4-((3-fluorobenzyl)amino)-6-methyl-6,7-dihydro-5H-pyrrolo[3,4-d]pyrimidin-2-yl)-2-methyl-1H-indole-7-carboxamide
3-(4-((3-fluorobenzyl)amino)-7,8-dihydro-5H-pyrano[4,3-d]pyrimidin-2-yl)-2-methyl-1H-indole-7-carboxamide
3-(4-((3-fluorobenzyl)amino)-7,8-dihydro-5H-pyrano[4,3-d]pyrimidin-2-yl)-2-methylbenzofuran-7-carboxamide
3-(4-((3-fluorobenzyl)amino)-7-methyl-5,6,7,8-tetrahydropyrido[3,4-d]pyrimidin-2-yl)-2-methyl-1H-indole-7-carboxamide
3-(4-((3-fluorobenzyl)amino)-7-methyl-6,7-dihydro-5H-pyrrolo[2,3-d]pyrimidin-2-yl)-2-methyl-1H-indole-7-carboxamide
3-(4-((3-fluorobenzyl)amino)-8-methyl-5,6,7,8-tetrahydropyrido[2,3-d]pyrimidin-2-yl)-2-methyl-1H-indole-7-carboxamide
3-(4-(benzylamino)-5,6,7,8-tetrahydropyrido[2,3-d]pyrimidin-2-yl)-2-methyl-1H-indole-7-carboxamide
3-(4-(benzylamino)-5,6,7,8-tetrahydropyrido[3,2-d]pyrimidin-2-yl)-2-methyl-1H-indole-7-carboxamide
3-(4-(benzylamino)-5,6,7,8-tetrahydropyrido[3,4-d]pyrimidin-2-yl)-2-methyl-1H-indole-7-carboxamide
3-(4-(benzylamino)-5,6,7,8-tetrahydropyrido[4,3-d]pyrimidin-2-yl)-2-methyl-1H-indole-7-carboxamide
3-(4-(benzylamino)-5,6,7,8-tetrahydroquinazolin-2-yl)-1H-indazole-7-carboxamide
3-(4-(benzylamino)-5,6,7,8-tetrahydroquinazolin-2-yl)-2-methyl-1H-indole-7-carboxamide
3-(4-(benzylamino)-5,6,7,8-tetrahydroquinazolin-2-yl)-2-methylbenzofuran-7-carboxamide
3-(4-(benzylamino)-5,6-dihydrofuro[2,3-d]pyrimidin-2-yl)-2-methyl-1H-indole-7-carboxamide
3-(4-(benzylamino)-5,7-dihydrofuro[3,4-d]pyrimidin-2-yl)-2-methyl-1H-indole-7-carboxamide
3-(4-(benzylamino)-5-methyl-5,6,7,8-tetrahydropyrido[3,2-d]pyrimidin-2-yl)-2-methyl-1H-indole-7-carboxamide
3-(4-(benzylamino)-5-methyl-6,7-dihydro-5H-pyrrolo[3,2-d]pyrimidin-2-yl)-2-methyl-1H-indole-7-carboxamide
3-(4-(benzylamino)-6,7,8,9-tetrahydro-5H-cyclohepta[d]pyrimidin-2-yl)-2-methyl-1H-indole-7-carboxamide
3-(4-(benzylamino)-6,7-dihydro-5H-cyclopenta[d]pyrimidin-2-yl)-2-methyl-1H-indole-7-carboxamide
3-(4-(benzylamino)-6,7-dihydro-5H-pyrano[2,3-d]pyrimidin-2-yl)-2-methyl-1H-indole-7-carboxamide
3-(4-(benzylamino)-6,7-dihydro-5H-pyrrolo[2,3-d]pyrimidin-2-yl)-2-methyl-1H-indole-7-carboxamide
3-(4-(benzylamino)-6,7-dihydro-5H-pyrrolo[3,2-d]pyrimidin-2-yl)-2-methyl-1H-indole-7-carboxamide
3-(4-(benzylamino)-6,7-dihydro-5H-pyrrolo[3,4-d]pyrimidin-2-yl)-2-methyl-1H-indole-7-carboxamide
3-(4-(benzylamino)-6,8-dihydro-5H-pyrano[3,4-d]pyrimidin-2-yl)-2-methyl-1H-indole-7-carboxamide
3-(4-(benzylamino)-6-methyl-5,6,7,8-tetrahydropyrido[4,3-d]pyrimidin-2-yl)-2-methyl-1H-indole-7-carboxamide
3-(4-(benzylamino)-6-methyl-6,7-dihydro-5H-pyrrolo[3,4-d]pyrimidin-2-yl)-2-methyl-1H-indole-7-carboxamide
3-(4-(benzylamino)-7,8-dihydro-5H-pyrano[4,3-d]pyrimidin-2-yl)-2-methyl-1H-indole-7-carboxamide
3-(4-(benzylamino)-7-methyl-5,6,7,8-tetrahydropyrido[3,4-d]pyrimidin-2-yl)-2-methyl-1H-indole-7-carboxamide
3-(4-(benzylamino)-7-methyl-6,7-dihydro-5H-pyrrolo[2,3-d]pyrimidin-2-yl)-2-methyl-1H-indole-7-carboxamide
3-(4-(benzylamino)-8-methyl-5,6,7,8-tetrahydropyrido[2,3-d]pyrimidin-2-yl)-2-methyl-1H-indole-7-carboxamide
N-benzyl-2-(2-methyl-1H-indol-3-yl)-5,6,7,8-tetrahydroquinazolin-4-amine (1-(4-(benzylamino)-5,6,7,8-tetrahydropyrido[3,4-d]pyrimidin-2-yl)-1H-indazol-4-yl)methanol
(1-(4-(benzylamino)-5,6,7,8-tetrahydropyrido[4,3-d]pyrimidin-2-yl)-1H-indazol-4-yl)methanol
(1-(4-(benzylamino)-5,6,7,8-tetrahydroquinazolin-2-yl)-1H-indazol-4-yl)methanol
(1-(4-(benzylamino)-6,8-dihydro-5H-pyrano[3,4-d]pyrimidin-2-yl)-1H-indazol-4-yl)methanol
(1-(4-(benzylamino)-7,8-dihydro-5H-pyrano[4,3-d]pyrimidin-2-yl)-1H-indazol-4-yl)methanol
(1-(4-((3-fluorobenzyl)amino)-5,6,7,8-tetrahydropyrido[3,4-d]pyrimidin-2-yl)-1H-indazol-4-yl)methanol
(1-(4-((3-fluorobenzyl)amino)-5,6,7,8-tetrahydropyrido[4,3-d]pyrimidin-2-yl)-1H-indazol-4-yl)methanol
(1-(4-((3-fluorobenzyl)amino)-5,6,7,8-tetrahydroquinazolin-2-yl)-1H-indazol-4-yl)methanol
(1-(4-((3-fluorobenzyl)amino)-5,6-dimethyl-pyrimidin-2-yl)-1H-indazol-4-yl)methanol
(1-(4-((3-fluorobenzyl)amino)-6,8-dihydro-5H-pyrano[3,4-d]pyrimidin-2-yl)-1H-indazol-4-yl)methanol
(1-(4-((3-fluorobenzyl)amino)-7,8-dihydro-5H-pyrano[4,3-d]pyrimidin-2-yl)-1H-indazol-4-yl)methanol
1-(4-(benzylamino)-5,6,7,8-tetrahydropyrido[3,4-d]pyrimidin-2-yl)-1H-indazole-4-carboxylic acid
1-(4-(benzylamino)-5,6,7,8-tetrahydropyrido[4,3-d]pyrimidin-2-yl)-1H-indazole-4-carboxylic acid
1-(4-(benzylamino)-5,6,7,8-tetrahydroquinazolin-2-yl)-1H-indazole-4-carboxylic acid
1-(4-(benzylamino)-6,8-dihydro-5H-pyrano[3,4-d]pyrimidin-2-yl)-1H-indazole-4-carboxylic acid
1-(4-(benzylamino)-7,8-dihydro-5H-pyrano[4,3-d]pyrimidin-2-yl)-1H-indazole-4-carboxylic acid
1-(4-((3-fluorobenzyl)amino)-5,6,7,8-tetrahydropyrido[3,4-d]pyrimidin-2-yl)-1H-indazole-4-carboxylic acid
1-(4-((3-fluorobenzyl)amino)-5,6,7,8-tetrahydropyrido[4,3-d]pyrimidin-2-yl)-1H-indazole-4-carboxylic acid
1-(4-((3-fluorobenzyl)amino)-5,6,7,8-tetrahydroquinazolin-2-yl)-1H-indazole-4-carboxylic acid
1-(4-((3-fluorobenzyl)amino)-6,8-dihydro-5H-pyrano[3,4-d]pyrimidin-2-yl)-1H-indazole-4-carboxylic acid
1-(4-((3-fluorobenzyl)amino)-7,8-dihydro-5H-pyrano[4,3-d]pyrimidin-2-yl)-1H-indazole-4-carboxylic acid
2-(4-(aminomethyl)-1H-indazol-1-yl)-N-(3-fluorobenzyl)-5,6,7,8-tetrahydropyrido[3,4-d]pyrimidin-4-amine
2-(4-(aminomethyl)-1H-indazol-1-yl)-N-(3-fluorobenzyl)-5,6,7,8-tetrahydropyrido[4,3-d]pyrimidin-4-amine
2-(4-(aminomethyl)-1H-indazol-1-yl)-N-(3-fluorobenzyl)-5,6,7,8-tetrahydroquinazolin-4-amine
2-(4-(aminomethyl)-1H-indazol-1-yl)-N-(3-fluorobenzyl)-6,8-dihydro-5H-pyrano[3,4-d]pyrimidin-4-amine
2-(4-(aminomethyl)-1H-indazol-1-yl)-N-(3-fluorobenzyl)-7,8-dihydro-5H-pyrano[4,3-d]pyrimidin-4-amine
2-(4-(aminomethyl)-1H-indazol-1-yl)-N-benzyl-5,6,7,8-tetrahydropyrido[3,4-d]pyrimidin-4-amine
2-(4-(aminomethyl)-1H-indazol-1-yl)-N-benzyl-5,6,7,8-tetrahydropyrido[4,3-d]pyrimidin-4-amine
2-(4-(aminomethyl)-1H-indazol-1-yl)-N-benzyl-5,6,7,8-tetrahydroquinazolin-4-amine
2-(4-(aminomethyl)-1H-indazol-1-yl)-N-benzyl-6,8-dihydro-5H-pyrano[3,4-d]pyrimidin-4-amine
2-(4-(aminomethyl)-1H-indazol-1-yl)-N-benzyl-7,8-dihydro-5H-pyrano[4,3-d]pyrimidin-4-amine
N-((1-(4-(benzylamino)-5,6,7,8-tetrahydropyrido[3,4-d]pyrimidin-2-yl)-1H-indazol-4-yl)methyl)-2-methyl-propanamide
N-((1-(4-(benzylamino)-5,6,7,8-tetrahydropyrido[3,4-d]pyrimidin-2-yl)-1H-indazol-4-yl)methyl)acetamide
N-((1-(4-(benzylamino)-5,6,7,8-tetrahydropyrido[3,4-d]pyrimidin-2-yl)-1H-indazol-4-yl)methyl)ethanesulfonamide
N-((1-(4-(benzylamino)-5,6,7,8-tetrahydropyrido[3,4-d]pyrimidin-2-yl)-1H-indazol-4-yl)methyl)methanesulfonamide
N-((1-(4-(benzylamino)-5,6,7,8-tetrahydropyrido[3,4-d]pyrimidin-2-yl)-1H-indazol-4-yl)methyl)propanamide
N-((1-(4-(benzylamino)-5,6,7,8-tetrahydropyrido[3,4-d]pyrimidin-2-yl)-1H-indazol-4-yl)methyl)propane-2-sulfonamide
N-((1-(4-(benzylamino)-5,6,7,8-tetrahydropyrido[4,3-d]pyrimidin-2-yl)-1H-indazol-4-yl)methyl)-2-methyl-propanamide
N-((1-(4-(benzylamino)-5,6,7,8-tetrahydropyrido[4,3-d]pyrimidin-2-yl)-1H-indazol-4-yl)methyl)acetamide
N-((1-(4-(benzylamino)-5,6,7,8-tetrahydropyrido[4,3-d]pyrimidin-2-yl)-1H-indazol-4-yl)methyl)ethanesulfonamide
N-((1-(4-(benzylamino)-5,6,7,8-tetrahydropyrido[4,3-d]pyrimidin-2-yl)-1H-indazol-4-yl)methyl)methanesulfonamide
N-((1-(4-(benzylamino)-5,6,7,8-tetrahydropyrido[4,3-d]pyrimidin-2-yl)-1H-indazol-4-yl)methyl)propanamide
N-((1-(4-(benzylamino)-5,6,7,8-tetrahydropyrido[4,3-d]pyrimidin-2-yl)-1H-indazol-4-yl)methyl)propane-2-sulfonamide
N-((1-(4-(benzylamino)-5,6,7,8-tetrahydroquinazolin-2-yl)-1H-indazol-4-yl)methyl)-2-methyl-propanamide
N-((1-(4-(benzylamino)-5,6,7,8-tetrahydroquinazolin-2-yl)-1H-indazol-4-yl)methyl)acetamide
N-((1-(4-(benzylamino)-5,6,7,8-tetrahydroquinazolin-2-yl)-1H-indazol-4-yl)methyl)ethanesulfonamide
N-((1-(4-(benzylamino)-5,6,7,8-tetrahydroquinazolin-2-yl)-1H-indazol-4-yl)methyl)methanesulfonamide
N-((1-(4-(benzylamino)-5,6,7,8-tetrahydroquinazolin-2-yl)-1H-indazol-4-yl)methyl)propanamide
N-((1-(4-(benzylamino)-5,6,7,8-tetrahydroquinazolin-2-yl)-1H-indazol-4-yl)methyl)propane-2-sulfonamide
N-((1-(4-(benzylamino)-6,8-dihydro-5H-pyrano[3,4-d]pyrimidin-2-yl)-1H-indazol-4-yl)methyl)-2-methyl-propanamide
N-((1-(4-(benzylamino)-6,8-dihydro-5H-pyrano[3,4-d]pyrimidin-2-yl)-1H-indazol-4-yl)methyl)acetamide
N-((1-(4-(benzylamino)-6,8-dihydro-5H-pyrano[3,4-d]pyrimidin-2-yl)-1H-indazol-4-yl)methyl)ethanesulfonamide
N-((1-(4-(benzylamino)-6,8-dihydro-5H-pyrano[3,4-d]pyrimidin-2-yl)-1H-indazol-4-yl)methyl)methanesulfonamide
N-((1-(4-(benzylamino)-6,8-dihydro-5H-pyrano[3,4-d]pyrimidin-2-yl)-1H-indazol-4-yl)methyl)propanamide
N-((1-(4-(benzylamino)-6,8-dihydro-5H-pyrano[3,4-d]pyrimidin-2-yl)-1H-indazol-4-yl)methyl)propane-2-sulfonamide
N-((1-(4-(benzylamino)-7,8-dihydro-5H-pyrano[4,3-d]pyrimidin-2-yl)-1H-indazol-4-yl)methyl)-2-methyl-propanamide
N-((1-(4-(benzylamino)-7,8-dihydro-5H-pyrano[4,3-d]pyrimidin-2-yl)-1H-indazol-4-yl)methyl)acetamide
N-((1-(4-(benzylamino)-7,8-dihydro-5H-pyrano[4,3-d]pyrimidin-2-yl)-1H-indazol-4-yl)methyl)ethanesulfonamide
N-((1-(4-(benzylamino)-7,8-dihydro-5H-pyrano[4,3-d]pyrimidin-2-yl)-1H-indazol-4-yl)methyl)methanesulfonamide
N-((1-(4-(benzylamino)-7,8-dihydro-5H-pyrano[4,3-d]pyrimidin-2-yl)-1H-indazol-4-yl)methyl)propanamide
N-((1-(4-(benzylamino)-7,8-dihydro-5H-pyrano[4,3-d]pyrimidin-2-yl)-1H-indazol-4-yl)methyl)propane-2-sulfonamide N-((1-(4-((3-fluorobenzyl)amino)-5,6,7,8-tetrahydropyrido[3,4-d]pyrimidin-2-yl)-1H-indazol-4-yl)methyl)-2-methyl-propanamide N-((1-(4-((3-fluorobenzyl)amino)-5,6,7,8-tetrahydropyrido[3,4-d]pyrimidin-2-yl)-1H-indazol-4-yl)methyl)acetamide N-((1-(4-((3-fluorobenzyl)amino)-5,6,7,8-tetrahydropyrido[3,4-d]pyrimidin-2-yl)-1H-indazol-4-yl)methyl)ethanesulfonamide N-((1-(4-((3-fluorobenzyl)amino)-5,6,7,8-tetrahydropyrido[3,4-d]pyrimidin-2-yl)-1H-indazol-4-yl)methyl)methanesulfonamide N-((1-(4-((3-fluorobenzyl)amino)-5,6,7,8-tetrahydropyrido[3,4-d]pyrimidin-2-yl)-1H-indazol-4-yl)methyl)propanamide N-((1-(4-((3-fluorobenzyl)amino)-5,6,7,8-tetrahydropyrido[3,4-d]pyrimidin-2-yl)-1H-indazol-4-yl)methyl)propane-2-sulfonamide N-((1-(4-((3-fluorobenzyl)amino)-5,6,7,8-tetrahydropyrido[4,3-d]pyrimidin-2-yl)-1H-indazol-4-yl)methyl)-2-methyl-propanamide N-((1-(4-((3-fluorobenzyl)amino)-5,6,7,8-tetrahydropyrido[4,3-d]pyrimidin-2-yl)-1H-indazol-4-yl)methyl)acetamide N-((1-(4-((3-fluorobenzyl)amino)-5,6,7,8-tetrahydropyrido[4,3-d]pyrimidin-2-yl)-1H-indazol-4-yl)methyl)ethanesulfonamide N-((1-(4-((3-fluorobenzyl)amino)-5,6,7,8-tetrahydropyrido[4,3-d]pyrimidin-2-yl)-1H-indazol-4-yl)methyl)methanesulfonamide N-((1-(4-((3-fluorobenzyl)amino)-5,6,7,8-tetrahydropyrido[4,3-d]pyrimidin-2-yl)-1H-indazol-4-yl)methyl)propanamide N-((1-(4-((3-fluorobenzyl)amino)-5,6,7,8-tetrahydropyrido[4,3-d]pyrimidin-2-yl)-1H-indazol-4-yl)methyl)propane-2-sulfonamide N-((1-(4-((3-fluorobenzyl)amino)-5,6,7,8-tetrahydroquinazolin-2-yl)-1H-indazol-4-yl)methyl)-2-methyl-propanamide N-((1-(4-((3-fluorobenzyl)amino)-5,6,7,8-tetrahydroquinazolin-2-yl)-1H-indazol-4-yl)methyl)acetamide N-((1-(4-((3-fluorobenzyl)amino)-5,6,7,8-tetrahydroquinazolin-2-yl)-1H-indazol-4-yl)methyl)ethanesulfonamide N-((1-(4-((3-fluorobenzyl)amino)-5,6,7,8-tetrahydroquinazolin-2-yl)-1H-indazol-4-yl)methyl)methanesulfonamide N-((1-(4-((3-fluorobenzyl)amino)-5,6,7,8-tetrahydroquinazolin-2-yl)-1H-indazol-4-yl)methyl)propanamide N-((1-(4-((3-fluorobenzyl)amino)-5,6,7,8-tetrahydroquinazolin-2-yl)-1H-indazol-4-yl)methyl)propane-2-sulfonamide N-((1-(4-((3-fluorobenzyl)amino)-6,8-dihydro-5H-pyrano[3,4-d]pyrimidin-2-yl)-1H-indazol-4-yl)methyl)-2-methyl-propanamide N-((1-(4-((3-fluorobenzyl)amino)-6,8-dihydro-5H-pyrano[3,4-d]pyrimidin-2-yl)-1H-indazol-4-yl)methyl)acetamide N-((1-(4-((3-fluorobenzyl)amino)-6,8-dihydro-5H-pyrano[3,4-d]pyrimidin-2-yl)-1H-indazol-4-yl)methyl)ethanesulfonamide N-((1-(4-((3-fluorobenzyl)amino)-6,8-dihydro-5H-pyrano[3,4-d]pyrimidin-2-yl)-1H-indazol-4-yl)methyl)methanesulfonamide N-((1-(4-((3-fluorobenzyl)amino)-6,8-dihydro-5H-pyrano[3,4-d]pyrimidin-2-yl)-1H-indazol-4-yl)methyl)propanamide N-((1-(4-((3-fluorobenzyl)amino)-6,8-dihydro-5H-pyrano[3,4-d]pyrimidin-2-yl)-1H-indazol-4-yl)methyl)propane-2-sulfonamide N-((1-(4-((3-fluorobenzyl)amino)-7,8-dihydro-5H-pyrano[4,3-d]pyrimidin-2-yl)-1H-indazol-4-yl)methyl)-2-methyl-propanamide N-((1-(4-((3-fluorobenzyl)amino)-7,8-dihydro-5H-pyrano[4,3-d]pyrimidin-2-yl)-1H-indazol-4-yl)methyl)acetamide N-((1-(4-((3-fluorobenzyl)amino)-7,8-dihydro-5H-pyrano[4,3-d]pyrimidin-2-yl)-1H-indazol-4-yl)methyl)ethanesulfonamide N-((1-(4-((3-fluorobenzyl)amino)-7,8-dihydro-5H-pyrano[4,3-d]pyrimidin-2-yl)-1H-indazol-4-yl)methyl)methanesulfonamide N-((1-(4-((3-fluorobenzyl)amino)-7,8-dihydro-5H-pyrano[4,3-d]pyrimidin-2-yl)-1H-indazol-4-yl)methyl)propanamide N-((1-(4-((3-fluorobenzyl)amino)-7,8-dihydro-5H-pyrano[4,3-d]pyrimidin-2-yl)-1H-indazol-4-yl)methyl)propane-2-sulfonamide 1-(4-((3-fluorobenzyl)amino)-5,6,7,8-tetrahydrooxepino[2,3-d]pyrimidin-2-yl)-2-methoxy-1H-benzo[d]imidazole-4-carboxamide 1-(4-((3-fluorobenzyl)amino)-5,6,7,8-tetrahydrooxepino[2,3-d]pyrimidin-2-yl)-2-methyl-1H-indole-4-carboxamide 1-(4-((3-fluorobenzyl)amino)-5,6,7,8-tetrahydrooxepino[2,3-d]pyrimidin-2-yl)-6-fluoro-2-methoxy-1H-benzo[d]imidazole-4-carboxamide 1-(4-((3-fluorobenzyl)amino)-5,6,7,8-tetrahydrooxepino[2,3-d]pyrimidin-2-yl)-6-fluoro-2-methyl-1H-indole-4-carboxamide 1-(4-((3-fluorobenzyl)amino)-5,6,7,9-tetrahydrooxepino[3,4-d]pyrimidin-2-yl)-1H-indazole-4-carboxamide 1-(4-((3-fluorobenzyl)amino)-5,6,7,9-tetrahydrooxepino[3,4-d]pyrimidin-2-yl)-6-fluoro-1H-indazole-4-carboxamide 1-(4-((3-fluorobenzyl)amino)-5,6,8,9-tetrahydrooxepino[4,5-d]pyrimidin-2-yl)-1H-indazole-4-carboxamide 1-(4-((3-fluorobenzyl)amino)-5,6,8,9-tetrahydrooxepino[4,5-d]pyrimidin-2-yl)-6-fluoro-1H-indazole-4-carboxamide 1-(4-((3-fluorobenzyl)amino)-5,7,8,9-tetrahydrooxepino[4,3-d]pyrimidin-2-yl)-1H-indazole-4-carboxamide 1-(4-((3-fluorobenzyl)amino)-5,7,8,9-tetrahydrooxepino[4,3-d]pyrimidin-2-yl)-6-fluoro-1H-indazole-4-carboxamide 1-(4-((3-fluorobenzyl)amino)-5-methyl-6,7,8,9-tetrahydro-5H-pyrimido[5,4-b]azepin-2-yl)-1H-indazole-4-carboxamide 1-(4-((3-fluorobenzyl)amino)-5-methyl-6,7,8,9-tetrahydro-5H-pyrimido[5,4-b]azepin-2-yl)-2-methoxy-1H-benzo[d]imidazole-4-carboxamide 1-(4-((3-fluorobenzyl)amino)-5-methyl-6,7,8,9-tetrahydro-5H-pyrimido[5,4-b]azepin-2-yl)-2-methyl-1H-indole-4-carboxamide 1-(4-((3-fluorobenzyl)amino)-5-methyl-6,7,8,9-tetrahydro-5H-pyrimido[5,4-b]azepin-2-yl)-6-fluoro-1H-indazole-4-carboxamide 1-(4-((3-fluorobenzyl)amino)-5-methyl-6,7,8,9-tetrahydro-5H-pyrimido[5,4-b]azepin-2-yl)-6-fluoro-2-methoxy-1H-benzo[d]imidazole-4-carboxamide 1-(4-((3-fluorobenzyl)amino)-5-methyl-6,7,8,9-tetrahydro-5H-pyrimido[5,4-b]azepin-2-yl)-6-fluoro-2-methyl-1H-indole-4-carboxamide 1-(4-((3-fluorobenzyl)amino)-6,7,8,9-tetrahydro-5H-pyrimido[4,5-b]azepin-2-yl)-1H-indazole-4-carboxamide 1-(4-((3-fluorobenzyl)amino)-6,7,8,9-tetrahydro-5H-pyrimido[4,5-b]azepin-2-yl)-2-methoxy-1H-benzo[d]imidazole-4-carboxamide
1-(4-((3-fluorobenzyl)amino)-6,7,8,9-tetrahydro-5H-pyrimido[4,5-b]azepin-2-yl)-2-methyl-1H-indole-4-carboxamide
1-(4-((3-fluorobenzyl)amino)-6,7,8,9-tetrahydro-5H-pyrimido[4,5-b]azepin-2-yl)-6-fluoro-1H-indazole-4-carboxamide
1-(4-((3-fluorobenzyl)amino)-6,7,8,9-tetrahydro-5H-pyrimido[4,5-b]azepin-2-yl)-6-fluoro-2-methoxy-1H-benzo[d]imidazole-4-carboxamide
1-(4-((3-fluorobenzyl)amino)-6,7,8,9-tetrahydro-5H-pyrimido[4,5-b]azepin-2-yl)-6-fluoro-2-methyl-1H-indole-4-carboxamide
1-(4-((3-fluorobenzyl)amino)-6,7,8,9-tetrahydro-5H-pyrimido[4,5-c]azepin-2-yl)-1H-indazole-4-carboxamide
1-(4-((3-fluorobenzyl)amino)-6,7,8,9-tetrahydro-5H-pyrimido[4,5-c]azepin-2-yl)-6-fluoro-1H-indazole-4-carboxamide
1-(4-((3-fluorobenzyl)amino)-6,7,8,9-tetrahydro-5H-pyrimido[4,5-d]azepin-2-yl)-1H-indazole-4-carboxamide
1-(4-((3-fluorobenzyl)amino)-6,7,8,9-tetrahydro-5H-pyrimido[4,5-d]azepin-2-yl)-6-fluoro-1H-indazole-4-carboxamide
1-(4-((3-fluorobenzyl)amino)-6,7,8,9-tetrahydro-5H-pyrimido[5,4-b]azepin-2-yl)-1H-indazole-4-carboxamide
1-(4-((3-fluorobenzyl)amino)-6,7,8,9-tetrahydro-5H-pyrimido[5,4-b]azepin-2-yl)-2-methoxy-1H-benzo[d]imidazole-4-carboxamide
1-(4-((3-fluorobenzyl)amino)-6,7,8,9-tetrahydro-5H-pyrimido[5,4-b]azepin-2-yl)-2-methyl-1H-indole-4-carboxamide
1-(4-((3-fluorobenzyl)amino)-6,7,8,9-tetrahydro-5H-pyrimido[5,4-b]azepin-2-yl)-6-fluoro-1H-indazole-4-carboxamide
1-(4-((3-fluorobenzyl)amino)-6,7,8,9-tetrahydro-5H-pyrimido[5,4-b]azepin-2-yl)-6-fluoro-2-methoxy-1H-benzo[d]imidazole-4-carboxamide
1-(4-((3-fluorobenzyl)amino)-6,7,8,9-tetrahydro-5H-pyrimido[5,4-b]azepin-2-yl)-6-fluoro-2-methyl-1H-indole-4-carboxamide
1-(4-((3-fluorobenzyl)amino)-6,7,8,9-tetrahydro-5H-pyrimido[5,4-c]azepin-2-yl)-1H-indazole-4-carboxamide
1-(4-((3-fluorobenzyl)amino)-6,7,8,9-tetrahydro-5H-pyrimido[5,4-c]azepin-2-yl)-6-fluoro-1H-indazole-4-carboxamide
1-(4-((3-fluorobenzyl)amino)-6,7,8,9-tetrahydrooxepino[3,2-d]pyrimidin-2-yl)-1H-indazole-4-carboxamide
1-(4-((3-fluorobenzyl)amino)-6,7,8,9-tetrahydrooxepino[3,2-d]pyrimidin-2-yl)-2-methoxy-1H-benzo[d]imidazole-4-carboxamide
1-(4-((3-fluorobenzyl)amino)-6,7,8,9-tetrahydrooxepino[3,2-d]pyrimidin-2-yl)-2-methyl-1H-indole-4-carboxamide
1-(4-((3-fluorobenzyl)amino)-6,7,8,9-tetrahydrooxepino[3,2-d]pyrimidin-2-yl)-6-fluoro-1H-indazole-4-carboxamide
1-(4-((3-fluorobenzyl)amino)-6,7,8,9-tetrahydrooxepino[3,2-d]pyrimidin-2-yl)-6-fluoro-2-methoxy-1H-benzo[d]imidazole-4-carboxamide
1-(4-((3-fluorobenzyl)amino)-6,7,8,9-tetrahydrooxepino[3,2-d]pyrimidin-2-yl)-6-fluoro-2-methyl-1H-indole-4-carboxamide
1-(4-((3-fluorobenzyl)amino)-6,7-dihydrofuro[3,2-d]pyrimidin-2-yl)-1H-indazole-4-carboxamide
1-(4-((3-fluorobenzyl)amino)-6,7-dihydrofuro[3,2-d]pyrimidin-2-yl)-2-methoxy-1H-benzo[d]imidazole-4-carboxamide
1-(4-((3-fluorobenzyl)amino)-6,7-dihydrofuro[3,2-d]pyrimidin-2-yl)-2-methyl-1H-indole-4-carboxamide
1-(4-((3-fluorobenzyl)amino)-6,7-dihydrofuro[3,2-d]pyrimidin-2-yl)-6-fluoro-1H-indazole-4-carboxamide
1-(4-((3-fluorobenzyl)amino)-6,7-dihydrofuro[3,2-d]pyrimidin-2-yl)-6-fluoro-2-methoxy-1H-benzo[d]imidazole-4-carboxamide
1-(4-((3-fluorobenzyl)amino)-6,7-dihydrofuro[3,2-d]pyrimidin-2-yl)-6-fluoro-2-methyl-1H-indole-4-carboxamide
1-(4-((3-fluorobenzyl)amino)-6-methyl-6,7,8,9-tetrahydro-5H-pyrimido[5,4-c]azepin-2-yl)-1H-indazole-4-carboxamide
1-(4-((3-fluorobenzyl)amino)-6-methyl-6,7,8,9-tetrahydro-5H-pyrimido[5,4-c]azepin-2-yl)-6-fluoro-1H-indazole-4-carboxamide
1-(4-((3-fluorobenzyl)amino)-7,8-dihydro-6H-pyrano[3,2-d]pyrimidin-2-yl)-1H-indazole-4-carboxamide
1-(4-((3-fluorobenzyl)amino)-7,8-dihydro-6H-pyrano[3,2-d]pyrimidin-2-yl)-2-methoxy-1H-benzo[d]imidazole-4-carboxamide
1-(4-((3-fluorobenzyl)amino)-7,8-dihydro-6H-pyrano[3,2-d]pyrimidin-2-yl)-2-methyl-1H-indole-4-carboxamide
1-(4-((3-fluorobenzyl)amino)-7,8-dihydro-6H-pyrano[3,2-d]pyrimidin-2-yl)-6-fluoro-1H-indazole-4-carboxamide
1-(4-((3-fluorobenzyl)amino)-7,8-dihydro-6H-pyrano[3,2-d]pyrimidin-2-yl)-6-fluoro-2-methoxy-1H-benzo[d]imidazole-4-carboxamide
1-(4-((3-fluorobenzyl)amino)-7,8-dihydro-6H-pyrano[3,2-d]pyrimidin-2-yl)-6-fluoro-2-methyl-1H-indole-4-carboxamide
1-(4-((3-fluorobenzyl)amino)-8-methyl-6,7,8,9-tetrahydro-5H-pyrimido[4,5-c]azepin-2-yl)-1H-indazole-4-carboxamide
1-(4-((3-fluorobenzyl)amino)-8-methyl-6,7,8,9-tetrahydro-5H-pyrimido[4,5-c]azepin-2-yl)-6-fluoro-1H-indazole-4-carboxamide
1-(4-((3-fluorobenzyl)amino)-9-methyl-6,7,8,9-tetrahydro-5H-pyrimido[4,5-b]azepin-2-yl)-1H-indazole-4-carboxamide
1-(4-((3-fluorobenzyl)amino)-9-methyl-6,7,8,9-tetrahydro-5H-pyrimido[4,5-b]azepin-2-yl)-2-methoxy-1H-benzo[d]imidazole-4-carboxamide
1-(4-((3-fluorobenzyl)amino)-9-methyl-6,7,8,9-tetrahydro-5H-pyrimido[4,5-b]azepin-2-yl)-2-methyl-1H-indole-4-carboxamide
1-(4-((3-fluorobenzyl)amino)-9-methyl-6,7,8,9-tetrahydro-5H-pyrimido[4,5-b]azepin-2-yl)-6-fluoro-1H-indazole-4-carboxamide
1-(4-((3-fluorobenzyl)amino)-9-methyl-6,7,8,9-tetrahydro-5H-pyrimido[4,5-b]azepin-2-yl)-6-fluoro-2-methoxy-1H-benzo[d]imidazole-4-carboxamide
1-(4-((3-fluorobenzyl)amino)-9-methyl-6,7,8,9-tetrahydro-5H-pyrimido[4,5-b]azepin-2-yl)-6-fluoro-2-methyl-1H-indole-4-carboxamide
1-(4-((thiophen-2-ylmethyl)amino)-5,6,7,8-tetrahydrooxepino[2,3-d]pyrimidin-2-yl)-2-methoxy-1H-benzo[d]imidazole-4-carboxamide
1-(4-((thiophen-2-ylmethyl)amino)-5,6,7,8-tetrahydrooxepino[2,3-d]pyrimidin-2-yl)-2-methyl-1H-indole-4-carboxamide
1-(4-((thiophen-2-ylmethyl)amino)-5,6,7,9-tetrahydrooxepino[3,4-d]pyrimidin-2-yl)-1H-indazole-4-carboxamide 1-(4-((thiophen-2-ylmethyl)amino)-5,6,8,9-tetrahydrooxepino[4,5-d]pyrimidin-2-yl)-1H-indazole-4-carboxamide
1-(4-((thiophen-2-ylmethyl)amino)-5,7,8,9-tetrahydrooxepino[4,3-d]pyrimidin-2-yl)-1H-indazole-4-carboxamide
1-(4-((thiophen-2-ylmethyl)amino)-5-methyl-6,7,8,9-tetrahydro-5H-pyrimido[5,4-b]azepin-2-yl)-1H-indazole-4-carboxamide
1-(4-((thiophen-2-ylmethyl)amino)-5-methyl-6,7,8,9-tetrahydro-5H-pyrimido[5,4-b]azepin-2-yl)-2-methoxy-1H-benzo[d]imidazole-4-carboxamide
1-(4-((thiophen-2-ylmethyl)amino)-5-methyl-6,7,8,9-tetrahydro-5H-pyrimido[5,4-b]azepin-2-yl)-2-methyl-1H-indole-4-carboxamide
1-(4-((thiophen-2-ylmethyl)amino)-6,7,8,9-tetrahydro-5H-pyrimido[4,5-b]azepin-2-yl)-1H-indazole-4-carboxamide
1-(4-((thiophen-2-ylmethyl)amino)-6,7,8,9-tetrahydro-5H-pyrimido[4,5-b]azepin-2-yl)-2-methoxy-1H-benzo[d]imidazole-4-carboxamide
1-(4-((thiophen-2-ylmethyl)amino)-6,7,8,9-tetrahydro-5H-pyrimido[4,5-b]azepin-2-yl)-2-methyl-1H-indole-4-carboxamide
1-(4-((thiophen-2-ylmethyl)amino)-6,7,8,9-tetrahydro-5H-pyrimido[4,5-c]azepin-2-yl)-1H-indazole-4-carboxamide
1-(4-((thiophen-2-ylmethyl)amino)-6,7,8,9-tetrahydro-5H-pyrimido[4,5-d]azepin-2-yl)-1H-indazole-4-carboxamide
1-(4-((thiophen-2-ylmethyl)amino)-6,7,8,9-tetrahydro-5H-pyrimido[5,4-b]azepin-2-yl)-1H-indazole-4-carboxamide
1-(4-((thiophen-2-ylmethyl)amino)-6,7,8,9-tetrahydro-5H-pyrimido[5,4-b]azepin-2-yl)-2-methoxy-1H-benzo[d]imidazole-4-carboxamide
1-(4-((thiophen-2-ylmethyl)amino)-6,7,8,9-tetrahydro-5H-pyrimido[5,4-b]azepin-2-yl)-2-methyl-1H-indole-4-carboxamide
1-(4-((thiophen-2-ylmethyl)amino)-6,7,8,9-tetrahydro-5H-pyrimido[5,4-c]azepin-2-yl)-1H-indazole-4-carboxamide
1-(4-((thiophen-2-ylmethyl)amino)-6,7,8,9-tetrahydrooxepino[3,2-d]pyrimidin-2-yl)-1H-indazole-4-carboxamide
1-(4-((thiophen-2-ylmethyl)amino)-6,7,8,9-tetrahydrooxepino[3,2-d]pyrimidin-2-yl)-2-methoxy-1H-benzo[d]imidazole-4-carboxamide
1-(4-((thiophen-2-ylmethyl)amino)-6,7,8,9-tetrahydrooxepino[3,2-d]pyrimidin-2-yl)-2-methyl-1H-indole-4-carboxamide
1-(4-((thiophen-2-ylmethyl)amino)-6,7-dihydrofuro[3,2-d]pyrimidin-2-yl)-1H-indazole-4-carboxamide
1-(4-((thiophen-2-ylmethyl)amino)-6,7-dihydrofuro[3,2-d]pyrimidin-2-yl)-2-methoxy-1H-benzo[d]imidazole-4-carboxamide
1-(4-((thiophen-2-ylmethyl)amino)-6,7-dihydrofuro[3,2-d]pyrimidin-2-yl)-2-methyl-1H-indole-4-carboxamide
1-(4-((thiophen-2-ylmethyl)amino)-6-methyl-6,7,8,9-tetrahydro-5H-pyrimido[5,4-c]azepin-2-yl)-1H-indazole-4-carboxamide
1-(4-((thiophen-2-ylmethyl)amino)-7,8-dihydro-6H-pyrano[3,2-d]pyrimidin-2-yl)-1H-indazole-4-carboxamide
1-(4-((thiophen-2-ylmethyl)amino)-7,8-dihydro-6H-pyrano[3,2-d]pyrimidin-2-yl)-2-methoxy-1H-benzo[d]imidazole-4-carboxamide
1-(4-((thiophen-2-ylmethyl)amino)-7,8-dihydro-6H-pyrano[3,2-d]pyrimidin-2-yl)-2-methyl-1H-indole-4-carboxamide
1-(4-((thiophen-2-ylmethyl)amino)-8-methyl-6,7,8,9-tetrahydro-5H-pyrimido[4,5-c]azepin-2-yl)-1H-indazole-4-carboxamide
1-(4-((thiophen-2-ylmethyl)amino)-9-methyl-6,7,8,9-tetrahydro-5H-pyrimido[4,5-b]azepin-2-yl)-1H-indazole-4-carboxamide
1-(4-((thiophen-2-ylmethyl)amino)-9-methyl-6,7,8,9-tetrahydro-5H-pyrimido[4,5-b]azepin-2-yl)-2-methoxy-1H-benzo[d]imidazole-4-carboxamide
1-(4-((thiophen-2-ylmethyl)amino)-9-methyl-6,7,8,9-tetrahydro-5H-pyrimido[4,5-b]azepin-2-yl)-2-methyl-1H-indole-4-carboxamide
1-(4-(benzylamino)-5,6,7,8-tetrahydrooxepino[2,3-d]pyrimidin-2-yl)-1H-indazole-4-carboxamide
1-(4-(benzylamino)-5,6,7,8-tetrahydrooxepino[2,3-d]pyrimidin-2-yl)-2-methoxy-1H-benzo[d]imidazole-4-carboxamide
1-(4-(benzylamino)-5,6,7,8-tetrahydrooxepino[2,3-d]pyrimidin-2-yl)-2-methyl-1H-indole-4-carboxamide
1-(4-(benzylamino)-5,6,7,8-tetrahydrooxepino[2,3-d]pyrimidin-2-yl)-6-fluoro-2-methoxy-1H-benzo[d]imidazole-4-carboxamide
1-(4-(benzylamino)-5,6,7,8-tetrahydrooxepino[2,3-d]pyrimidin-2-yl)-6-fluoro-2-methyl-1H-indole-4-carboxamide
1-(4-(benzylamino)-5,6,7,8-tetrahydropyrido[2,3-d]pyrimidin-2-yl)imidazo[1,5-a]pyridine-5-carboxamide
1-(4-(benzylamino)-5,6,7,8-tetrahydropyrido[3,2-d]pyrimidin-2-yl)imidazo[1,5-a]pyridine-5-carboxamide
1-(4-(benzylamino)-5,6,7,8-tetrahydropyrido[3,4-d]pyrimidin-2-yl)imidazo[1,5-a]pyridine-5-carboxamide
1-(4-(benzylamino)-5,6,7,8-tetrahydropyrido[4,3-d]pyrimidin-2-yl)imidazo[1,5-a]pyridine-5-carboxamide
1-(4-(benzylamino)-5,6,7,8-tetrahydroquinazolin-2-yl)imidazo[1,5-a]pyridine-5-carboxamide
1-(4-(benzylamino)-5,6,7,9-tetrahydrooxepino[3,4-d]pyrimidin-2-yl)-1H-indazole-4-carboxamide
1-(4-(benzylamino)-5,6,7,9-tetrahydrooxepino[3,4-d]pyrimidin-2-yl)-6-fluoro-1H-indazole-4-carboxamide
1-(4-(benzylamino)-5,6,8,9-tetrahydrooxepino[4,5-d]pyrimidin-2-yl)-1H-indazole-4-carboxamide
1-(4-(benzylamino)-5,6,8,9-tetrahydrooxepino[4,5-d]pyrimidin-2-yl)-6-fluoro-1H-indazole-4-carboxamide
1-(4-(benzylamino)-5,7,8,9-tetrahydrooxepino[4,3-d]pyrimidin-2-yl)-1H-indazole-4-carboxamide
1-(4-(benzylamino)-5,7,8,9-tetrahydrooxepino[4,3-d]pyrimidin-2-yl)-6-fluoro-1H-indazole-4-carboxamide
1-(4-(benzylamino)-5-methyl-5,6,7,8-tetrahydropyrido[3,2-d]pyrimidin-2-yl)imidazo[1,5-a]pyridine-5-carboxamide
1-(4-(benzylamino)-5-methyl-6,7,8,9-tetrahydro-5H-pyrimido[5,4-b]azepin-2-yl)-1H-indazole-4-carboxamide
1-(4-(benzylamino)-5-methyl-6,7,8,9-tetrahydro-5H-pyrimido[5,4-b]azepin-2-yl)-2-methoxy-1H-benzo[d]imidazole-4-carboxamide
1-(4-(benzylamino)-5-methyl-6,7,8,9-tetrahydro-5H-pyrimido[5,4-b]azepin-2-yl)-2-methyl-1H-indole-4-carboxamide
1-(4-(benzylamino)-5-methyl-6,7,8,9-tetrahydro-5H-pyrimido[5,4-b]azepin-2-yl)-6-fluoro-1H-indazole-4-carboxamide
1-(4-(benzylamino)-5-methyl-6,7,8,9-tetrahydro-5H-pyrimido[5,4-b]azepin-2-yl)-6-fluoro-2-methoxy-1H-benzo[d]imidazole-4-carboxamide
1-(4-(benzylamino)-5-methyl-6,7,8,9-tetrahydro-5H-pyrimido[5,4-b]azepin-2-yl)-6-fluoro-2-methyl-1H-indole-4-carboxamide
1-(4-(benzylamino)-6,7,8,9-tetrahydro-5H-pyrimido[4,5-b]azepin-2-yl)-1H-indazole-4-carboxamide
1-(4-(benzylamino)-6,7,8,9-tetrahydro-5H-pyrimido[4,5-b]azepin-2-yl)-2-methoxy-1H-benzo[d]imidazole-4-carboxamide
1-(4-(benzylamino)-6,7,8,9-tetrahydro-5H-pyrimido[4,5-b]azepin-2-yl)-2-methyl-1H-indole-4-carboxamide 1-(4-(benzylamino)-6,7,8,9-tetrahydro-5H-pyrimido[4,5-b]
  azepin-2-yl)-6-fluoro-1H-indazole-4-carboxamide
1-(4-(benzylamino)-6,7,8,9-tetrahydro-5H-pyrimido[4,5-b]
  azepin-2-yl)-6-fluoro-2-methoxy-1H-benzo[d]imidazole-
  4-carboxamide
1-(4-(benzylamino)-6,7,8,9-tetrahydro-5H-pyrimido[4,5-b]
  azepin-2-yl)-6-fluoro-2-methyl-1H-indole-4-carboxamide
1-(4-(benzylamino)-6,7,8,9-tetrahydro-5H-pyrimido[4,5-c]
  azepin-2-yl)-1H-indazole-4-carboxamide
1-(4-(benzylamino)-6,7,8,9-tetrahydro-5H-pyrimido[4,5-c]
  azepin-2-yl)-6-fluoro-1H-indazole-4-carboxamide
1-(4-(benzylamino)-6,7,8,9-tetrahydro-5H-pyrimido[4,5-d]
  azepin-2-yl)-1H-indazole-4-carboxamide
1-(4-(benzylamino)-6,7,8,9-tetrahydro-5H-pyrimido[4,5-d]
  azepin-2-yl)-6-fluoro-1H-indazole-4-carboxamide
1-(4-(benzylamino)-6,7,8,9-tetrahydro-5H-pyrimido[5,4-b]
  azepin-2-yl)-1H-indazole-4-carboxamide
1-(4-(benzylamino)-6,7,8,9-tetrahydro-5H-pyrimido[5,4-b]
  azepin-2-yl)-2-methoxy-1H-benzo[d]imidazole-4-carboxamide
1-(4-(benzylamino)-6,7,8,9-tetrahydro-5H-pyrimido[5,4-b]
  azepin-2-yl)-2-methyl-1H-indole-4-carboxamide
1-(4-(benzylamino)-6,7,8,9-tetrahydro-5H-pyrimido[5,4-b]
  azepin-2-yl)-6-fluoro-1H-indazole-4-carboxamide
1-(4-(benzylamino)-6,7,8,9-tetrahydro-5H-pyrimido[5,4-b]
  azepin-2-yl)-6-fluoro-2-methoxy-1H-benzo[d]imidazole-
  4-carboxamide
1-(4-(benzylamino)-6,7,8,9-tetrahydro-5H-pyrimido[5,4-b]
  azepin-2-yl)-6-fluoro-2-methyl-1H-indole-4-carboxamide
1-(4-(benzylamino)-6,7,8,9-tetrahydro-5H-pyrimido[5,4-c]
  azepin-2-yl)-1H-indazole-4-carboxamide
1-(4-(benzylamino)-6,7,8,9-tetrahydro-5H-pyrimido[5,4-c]
  azepin-2-yl)-6-fluoro-1H-indazole-4-carboxamide
1-(4-(benzylamino)-6,7,8,9-tetrahydrooxepino[3,2-d]pyrimidin-2-yl)-1H-indazole-4-carboxamide
1-(4-(benzylamino)-6,7,8,9-tetrahydrooxepino[3,2-d]pyrimidin-2-yl)-2-methoxy-1H-benzo[d]imidazole-4-carboxamide
1-(4-(benzylamino)-6,7,8,9-tetrahydrooxepino[3,2-d]pyrimidin-2-yl)-2-methyl-1H-indole-4-carboxamide
1-(4-(benzylamino)-6,7,8,9-tetrahydrooxepino[3,2-d]pyrimidin-2-yl)-6-fluoro-1H-indazole-4-carboxamide
1-(4-(benzylamino)-6,7,8,9-tetrahydrooxepino[3,2-d]pyrimidin-2-yl)-6-fluoro-2-methoxy-1H-benzo[d]imidazole-4-carboxamide
1-(4-(benzylamino)-6,7,8,9-tetrahydrooxepino[3,2-d]pyrimidin-2-yl)-6-fluoro-2-methyl-1H-indole-4-carboxamide
1-(4-(benzylamino)-6,7-dihydro-5H-cyclopenta[d]pyrimidin-2-yl)imidazo[1,5-a]pyridine-5-carboxamide
1-(4-(benzylamino)-6,7-dihydro-5H-pyrano[2,3-d]pyrimidin-2-yl)imidazo[1,5-a]pyridine-5-carboxamide
1-(4-(benzylamino)-6,7-dihydrofuro[3,2-d]pyrimidin-2-yl)-1H-indazole-4-carboxamide
1-(4-(benzylamino)-6,7-dihydrofuro[3,2-d]pyrimidin-2-yl)-2-methoxy-1H-benzo[d]imidazole-4-carboxamide
1-(4-(benzylamino)-6,7-dihydrofuro[3,2-d]pyrimidin-2-yl)-2-methyl-1H-indole-4-carboxamide
1-(4-(benzylamino)-6,7-dihydrofuro[3,2-d]pyrimidin-2-yl)-6-fluoro-1H-indazole-4-carboxamide
1-(4-(benzylamino)-6,7-dihydrofuro[3,2-d]pyrimidin-2-yl)-6-fluoro-2-methoxy-1H-benzo[d]imidazole-4-carboxamide
1-(4-(benzylamino)-6,7-dihydrofuro[3,2-d]pyrimidin-2-yl)-6-fluoro-2-methyl-1H-indole-4-carboxamide
1-(4-(benzylamino)-6,8-dihydro-5H-pyrano[3,4-d]pyrimidin-2-yl)imidazo[1,5-a]pyridine-5-carboxamide
1-(4-(benzylamino)-6-methyl-5,6,7,8-tetrahydropyrido[4,3-d]pyrimidin-2-yl)imidazo[1,5-a]pyridine-5-carboxamide
1-(4-(benzylamino)-6-methyl-6,7,8,9-tetrahydro-5H-pyrimido[5,4-c]azepin-2-yl)-1H-indazole-4-carboxamide
1-(4-(benzylamino)-6-methyl-6,7,8,9-tetrahydro-5H-pyrimido[5,4-c]azepin-2-yl)-6-fluoro-1H-indazole-4-carboxamide
1-(4-(benzylamino)-7,8-dihydro-5H-pyrano[4,3-d]pyrimidin-2-yl)imidazo[1,5-a]pyridine-5-carboxamide
1-(4-(benzylamino)-7,8-dihydro-6H-pyrano[3,2-d]pyrimidin-2-yl)-1H-indazole-4-carboxamide
1-(4-(benzylamino)-7,8-dihydro-6H-pyrano[3,2-d]pyrimidin-2-yl)-2-methoxy-1H-benzo[d]imidazole-4-carboxamide
1-(4-(benzylamino)-7,8-dihydro-6H-pyrano[3,2-d]pyrimidin-2-yl)-2-methyl-1H-indole-4-carboxamide
1-(4-(benzylamino)-7,8-dihydro-6H-pyrano[3,2-d]pyrimidin-2-yl)-6-fluoro-1H-indazole-4-carboxamide
1-(4-(benzylamino)-7,8-dihydro-6H-pyrano[3,2-d]pyrimidin-2-yl)-6-fluoro-2-methoxy-1H-benzo[d]imidazole-4-carboxamide
1-(4-(benzylamino)-7,8-dihydro-6H-pyrano[3,2-d]pyrimidin-2-yl)-6-fluoro-2-methyl-1H-indole-4-carboxamide
1-(4-(benzylamino)-7-methyl-5,6,7,8-tetrahydropyrido[3,4-d]pyrimidin-2-yl)imidazo[1,5-a]pyridine-5-carboxamide
1-(4-(benzylamino)-8-methyl-5,6,7,8-tetrahydropyrido[2,3-d]pyrimidin-2-yl)imidazo[1,5-a]pyridine-5-carboxamide
1-(4-(benzylamino)-8-methyl-6,7,8,9-tetrahydro-5H-pyrimido[4,5-c]azepin-2-yl)-1H-indazole-4-carboxamide
1-(4-(benzylamino)-8-methyl-6,7,8,9-tetrahydro-5H-pyrimido[4,5-c]azepin-2-yl)-6-fluoro-1H-indazole-4-carboxamide
1-(4-(benzylamino)-9-methyl-6,7,8,9-tetrahydro-5H-pyrimido[4,5-b]azepin-2-yl)-1H-indazole-4-carboxamide
1-(4-(benzylamino)-9-methyl-6,7,8,9-tetrahydro-5H-pyrimido[4,5-b]azepin-2-yl)-2-methoxy-1H-benzo[d]imidazole-4-carboxamide
1-(4-(benzylamino)-9-methyl-6,7,8,9-tetrahydro-5H-pyrimido[4,5-b]azepin-2-yl)-2-methyl-1H-indole-4-carboxamide
1-(4-(benzylamino)-9-methyl-6,7,8,9-tetrahydro-5H-pyrimido[4,5-b]azepin-2-yl)-6-fluoro-1H-indazole-4-carboxamide
1-(4-(benzylamino)-9-methyl-6,7,8,9-tetrahydro-5H-pyrimido[4,5-b]azepin-2-yl)-6-fluoro-2-methoxy-1H-benzo[d]imidazole-4-carboxamide
1-(4-(benzylamino)-9-methyl-6,7,8,9-tetrahydro-5H-pyrimido[4,5-b]azepin-2-yl)-6-fluoro-2-methyl-1H-indole-4-carboxamide
3-(4-((3-fluorobenzyl)amino)-5,6,7,8-tetrahydrooxepino[2,3-d]pyrimidin-2-yl)-2-methyl-1H-indole-7-carboxamide
3-(4-((3-fluorobenzyl)amino)-5,6,7,8-tetrahydropyrido[2,3-d]pyrimidin-2-yl)-2-methylimidazo[1,2-a]pyridine-8-carboxamide
3-(4-((3-fluorobenzyl)amino)-5,6,7,8-tetrahydropyrido[2,3-d]pyrimidin-2-yl)imidazo[1,5-a]pyridine-8-carboxamide
3-(4-((3-fluorobenzyl)amino)-5,6,7,8-tetrahydropyrido[3,2-d]pyrimidin-2-yl)-2-methylimidazo[1,2-a]pyridine-8-carboxamide
3-(4-((3-fluorobenzyl)amino)-5,6,7,8-tetrahydropyrido[3,2-d]pyrimidin-2-yl)imidazo[1,5-a]pyridine-8-carboxamide
3-(4-((3-fluorobenzyl)amino)-5,6,7,8-tetrahydropyrido[3,4-d]pyrimidin-2-yl)-2-methylimidazo[1,2-a]pyridine-8-carboxamide 3-(4-((3-fluorobenzyl)amino)-5,6,7,8-tetrahydropyrido[3,4-d]pyrimidin-2-yl)imidazo[1,5-a]pyridine-8-carboxamide
3-(4-((3-fluorobenzyl)amino)-5,6,7,8-tetrahydropyrido[4,3-d]pyrimidin-2-yl)-2-methylimidazo[1,2-a]pyridine-8-carboxamide
3-(4-((3-fluorobenzyl)amino)-5,6,7,8-tetrahydropyrido[4,3-d]pyrimidin-2-yl)imidazo[1,5-a]pyridine-8-carboxamide
3-(4-((3-fluorobenzyl)amino)-5,6,7,8-tetrahydroquinazolin-2-yl)-2-methylimidazo[1,2-a]pyridine-8-carboxamide
3-(4-((3-fluorobenzyl)amino)-5,6,7,8-tetrahydroquinazolin-2-yl)imidazo[1,5-a]pyridine-8-carboxamide
3-(4-((3-fluorobenzyl)amino)-5,6,7,9-tetrahydrooxepino[3,4-d]pyrimidin-2-yl)-2-methyl-1H-indole-7-carboxamide
3-(4-((3-fluorobenzyl)amino)-5,6,8,9-tetrahydrooxepino[4,5-d]pyrimidin-2-yl)-2-methyl-1H-indole-7-carboxamide
3-(4-((3-fluorobenzyl)amino)-5-methyl-5,6,7,8-tetrahydropyrido[3,2-d]pyrimidin-2-yl)-2-methylimidazo[1,2-a]pyridine-8-carboxamide
3-(4-((3-fluorobenzyl)amino)-5-methyl-5,6,7,8-tetrahydropyrido[3,2-d]pyrimidin-2-yl)imidazo[1,5-a]pyridine-8-carboxamide
3-(4-((3-fluorobenzyl)amino)-6,7,8,9-tetrahydro-5H-pyrimido[4,5-b]azepin-2-yl)-2-methyl-1H-indole-7-carboxamide
3-(4-((3-fluorobenzyl)amino)-6,7,8,9-tetrahydro-5H-pyrimido[4,5-c]azepin-2-yl)-2-methyl-1H-indole-7-carboxamide
3-(4-((3-fluorobenzyl)amino)-6,7,8,9-tetrahydro-5H-pyrimido[4,5-d]azepin-2-yl)-2-methyl-1H-indole-7-carboxamide
3-(4-((3-fluorobenzyl)amino)-6,7-dihydro-5H-pyrano[2,3-d]pyrimidin-2-yl)-2-methylimidazo[1,2-a]pyridine-8-carboxamide
3-(4-((3-fluorobenzyl)amino)-6,7-dihydro-5H-pyrano[2,3-d]pyrimidin-2-yl)imidazo[1,5-a]pyridine-8-carboxamide
3-(4-((3-fluorobenzyl)amino)-6,7-dihydrofuro[3,2-d]pyrimidin-2-yl)-2-methyl-1H-indole-7-carboxamide
3-(4-((3-fluorobenzyl)amino)-6,8-dihydro-5H-pyrano[3,4-d]pyrimidin-2-yl)-2-methylimidazo[1,2-a]pyridine-8-carboxamide
3-(4-((3-fluorobenzyl)amino)-6,8-dihydro-5H-pyrano[3,4-d]pyrimidin-2-yl)imidazo[1,5-a]pyridine-8-carboxamide
3-(4-((3-fluorobenzyl)amino)-6-methyl-5,6,7,8-tetrahydropyrido[4,3-d]pyrimidin-2-yl)-2-methylimidazo[1,2-a]pyridine-8-carboxamide
3-(4-((3-fluorobenzyl)amino)-6-methyl-5,6,7,8-tetrahydropyrido[4,3-d]pyrimidin-2-yl)imidazo[1,5-a]pyridine-8-carboxamide
3-(4-((3-fluorobenzyl)amino)-7,8-dihydro-5H-pyrano[4,3-d]pyrimidin-2-yl)-2-methylimidazo[1,2-a]pyridine-8-carboxamide
3-(4-((3-fluorobenzyl)amino)-7,8-dihydro-5H-pyrano[4,3-d]pyrimidin-2-yl)imidazo[1,5-a]pyridine-8-carboxamide
3-(4-((3-fluorobenzyl)amino)-7,8-dihydro-6H-pyrano[3,2-d]pyrimidin-2-yl)-2-methyl-1H-indole-7-carboxamide
3-(4-((3-fluorobenzyl)amino)-7,8-dihydro-6H-pyrano[3,2-d]pyrimidin-2-yl)-2-methylimidazo[1,2-a]pyridine-8-carboxamide
3-(4-((3-fluorobenzyl)amino)-7,8-dihydro-6H-pyrano[3,2-d]pyrimidin-2-yl)imidazo[1,5-a]pyridine-8-carboxamide
3-(4-((3-fluorobenzyl)amino)-7-methyl-5,6,7,8-tetrahydropyrido[3,4-d]pyrimidin-2-yl)-2-methylimidazo[1,2-a]pyridine-8-carboxamide
3-(4-((3-fluorobenzyl)amino)-7-methyl-5,6,7,8-tetrahydropyrido[3,4-d]pyrimidin-2-yl)imidazo[1,5-a]pyridine-8-carboxamide
3-(4-((3-fluorobenzyl)amino)-8-methyl-5,6,7,8-tetrahydropyrido[2,3-d]pyrimidin-2-yl)-2-methylimidazo[1,2-a]pyridine-8-carboxamide
3-(4-((3-fluorobenzyl)amino)-8-methyl-5,6,7,8-tetrahydropyrido[2,3-d]pyrimidin-2-yl)imidazo[1,5-a]pyridine-8-carboxamide
3-(4-((3-fluorobenzyl)amino)-8-methyl-6,7,8,9-tetrahydro-5H-pyrimido[4,5-c]azepin-2-yl)-2-methyl-1H-indole-7-carboxamide
3-(4-((3-fluorobenzyl)amino)-9-methyl-6,7,8,9-tetrahydro-5H-pyrimido[4,5-b]azepin-2-yl)-2-methyl-1H-indole-7-carboxamide
3-(4-(benzylamino)-5,6,7,8-tetrahydrooxepino[2,3-d]pyrimidin-2-yl)-2-methyl-1H-indole-7-carboxamide
3-(4-(benzylamino)-5,6,7,8-tetrahydropyrido[2,3-d]pyrimidin-2-yl)-2-methylimidazo[1,2-a]pyridine-8-carboxamide
3-(4-(benzylamino)-5,6,7,8-tetrahydropyrido[2,3-d]pyrimidin-2-yl)-2-methylpyrazolo[1,5-a]pyridine-7-carboxamide
3-(4-(benzylamino)-5,6,7,8-tetrahydropyrido[2,3-d]pyrimidin-2-yl)imidazo[1,5-a]pyridine-8-carboxamide
3-(4-(benzylamino)-5,6,7,8-tetrahydropyrido[3,2-d]pyrimidin-2-yl)-2-methylimidazo[1,2-a]pyridine-8-carboxamide
3-(4-(benzylamino)-5,6,7,8-tetrahydropyrido[3,2-d]pyrimidin-2-yl)-2-methylpyrazolo[1,5-a]pyridine-7-carboxamide
3-(4-(benzylamino)-5,6,7,8-tetrahydropyrido[3,2-d]pyrimidin-2-yl)imidazo[1,5-a]pyridine-8-carboxamide
3-(4-(benzylamino)-5,6,7,8-tetrahydropyrido[3,4-d]pyrimidin-2-yl)-2-methylimidazo[1,2-a]pyridine-8-carboxamide
3-(4-(benzylamino)-5,6,7,8-tetrahydropyrido[3,4-d]pyrimidin-2-yl)-2-methylpyrazolo[1,5-a]pyridine-7-carboxamide
3-(4-(benzylamino)-5,6,7,8-tetrahydropyrido[3,4-d]pyrimidin-2-yl)imidazo[1,5-a]pyridine-8-carboxamide
3-(4-(benzylamino)-5,6,7,8-tetrahydropyrido[4,3-d]pyrimidin-2-yl)-2-methylimidazo[1,2-a]pyridine-8-carboxamide
3-(4-(benzylamino)-5,6,7,8-tetrahydropyrido[4,3-d]pyrimidin-2-yl)-2-methylpyrazolo[1,5-a]pyridine-7-carboxamide
3-(4-(benzylamino)-5,6,7,8-tetrahydropyrido[4,3-d]pyrimidin-2-yl)imidazo[1,5-a]pyridine-8-carboxamide
3-(4-(benzylamino)-5,6,7,8-tetrahydroquinazolin-2-yl)-2-methylimidazo[1,2-a]pyridine-8-carboxamide
3-(4-(benzylamino)-5,6,7,8-tetrahydroquinazolin-2-yl)-2-methylpyrazolo[1,5-a]pyridine-7-carboxamide
3-(4-(benzylamino)-5,6,7,8-tetrahydroquinazolin-2-yl)imidazo[1,5-a]pyridine-8-carboxamide
3-(4-(benzylamino)-5,6,7,9-tetrahydrooxepino[3,4-d]pyrimidin-2-yl)-2-methyl-1H-indole-7-carboxamide
3-(4-(benzylamino)-5,6,8,9-tetrahydrooxepino[4,5-d]pyrimidin-2-yl)-2-methyl-1H-indole-7-carboxamide
3-(4-(benzylamino)-5,7,8,9-tetrahydrooxepino[4,3-d]pyrimidin-2-yl)-2-methyl-1H-indole-7-carboxamide
3-(4-(benzylamino)-5,7-dimethyl-5,6,7,8-tetrahydropyrido[3,4-d]pyrimidin-2-yl)-2-methylimidazo[1,2-a]pyridine-8-carboxamide
3-(4-(benzylamino)-5,7-dimethyl-5,6,7,8-tetrahydropyrido[3,4-d]pyrimidin-2-yl)imidazo[1,5-a]pyridine-8-carboxamide
3-(4-(benzylamino)-5-methyl-5,6,7,8-tetrahydropyrido[3,2-d]pyrimidin-2-yl)-2-methylimidazo[1,2-a]pyridine-8-carboxamide 3-(4-(benzylamino)-5-methyl-5,6,7,8-tetrahydropyrido[3,2-d]pyrimidin-2-yl)-2-methylpyrazolo[1,5-a]pyridine-7-carboxamide 3-(4-(benzylamino)-5-methyl-5,6,7,8-tetrahydropyrido[3,2-d]pyrimidin-2-yl)imidazo[1,5-a]pyridine-8-carboxamide 3-(4-(benzylamino)-5-methyl-5,6,7,8-tetrahydropyrido[3,4-d]pyrimidin-2-yl)-2-methylimidazo[1,2-a]pyridine-8-carboxamide 3-(4-(benzylamino)-5-methyl-5,6,7,8-tetrahydropyrido[3,4-d]pyrimidin-2-yl)imidazo[1,5-a]pyridine-8-carboxamide 3-(4-(benzylamino)-5-methyl-5,6,7,8-tetrahydropyrido[4,3-d]pyrimidin-2-yl)-2-methylimidazo[1,2-a]pyridine-8-carboxamide 3-(4-(benzylamino)-5-methyl-5,6,7,8-tetrahydropyrido[4,3-d]pyrimidin-2-yl)imidazo[1,5-a]pyridine-8-carboxamide 3-(4-(benzylamino)-5-methyl-5,6,7,8-tetrahydroquinazolin-2-yl)-2-methylimidazo[1,2-a]pyridine-8-carboxamide 3-(4-(benzylamino)-5-methyl-5,6,7,8-tetrahydroquinazolin-2-yl)imidazo[1,5-a]pyridine-8-carboxamide 3-(4-(benzylamino)-5-methyl-6,7,8,9-tetrahydro-5H-pyrimido[5,4-b]azepin-2-yl)-2-methyl-1H-indole-7-carboxamide 3-(4-(benzylamino)-5-methyl-6,8-dihydro-5H-pyrano[3,4-d]pyrimidin-2-yl)-2-methylimidazo[1,2-a]pyridine-8-carboxamide 3-(4-(benzylamino)-5-methyl-6,8-dihydro-5H-pyrano[3,4-d]pyrimidin-2-yl)imidazo[1,5-a]pyridine-8-carboxamide 3-(4-(benzylamino)-5-methyl-7,8-dihydro-5H-pyrano[4,3-d]pyrimidin-2-yl)-2-methylimidazo[1,2-a]pyridine-8-carboxamide 3-(4-(benzylamino)-5-methyl-7,8-dihydro-5H-pyrano[4,3-d]pyrimidin-2-yl)imidazo[1,5-a]pyridine-8-carboxamide 3-(4-(benzylamino)-6,7,8,9-tetrahydro-5H-pyrimido[4,5-b]azepin-2-yl)-2-methyl-1H-indole-7-carboxamide 3-(4-(benzylamino)-6,7,8,9-tetrahydro-5H-pyrimido[4,5-c]azepin-2-yl)-2-methyl-1H-indole-7-carboxamide 3-(4-(benzylamino)-6,7,8,9-tetrahydro-5H-pyrimido[4,5-d]azepin-2-yl)-2-methyl-1H-indole-7-carboxamide 3-(4-(benzylamino)-6,7,8,9-tetrahydro-5H-pyrimido[5,4-b]azepin-2-yl)-2-methyl-1H-indole-7-carboxamide 3-(4-(benzylamino)-6,7,8,9-tetrahydro-5H-pyrimido[5,4-c]azepin-2-yl)-2-methyl-1H-indole-7-carboxamide 3-(4-(benzylamino)-6,7,8,9-tetrahydrooxepino[3,2-d]pyrimidin-2-yl)-2-methyl-1H-indole-7-carboxamide 3-(4-(benzylamino)-6,7-dihydro-5H-cyclopenta[d]pyrimidin-2-yl)-2-methylimidazo[1,2-a]pyridine-8-carboxamide 3-(4-(benzylamino)-6,7-dihydro-5H-cyclopenta[d]pyrimidin-2-yl)-2-methylpyrazolo[1,5-a]pyridine-7-carboxamide 3-(4-(benzylamino)-6,7-dihydro-5H-cyclopenta[d]pyrimidin-2-yl)imidazo[1,5-a]pyridine-8-carboxamide 3-(4-(benzylamino)-6,7-dihydro-5H-pyrano[2,3-d]pyrimidin-2-yl)-2-methylimidazo[1,2-a]pyridine-8-carboxamide 3-(4-(benzylamino)-6,7-dihydro-5H-pyrano[2,3-d]pyrimidin-2-yl)-2-methylpyrazolo[1,5-a]pyridine-7-carboxamide 3-(4-(benzylamino)-6,7-dihydro-5H-pyrano[2,3-d]pyrimidin-2-yl)imidazo[1,5-a]pyridine-8-carboxamide 3-(4-(benzylamino)-6,7-dihydrofuro[3,2-d]pyrimidin-2-yl)-2-methyl-1H-indole-7-carboxamide 3-(4-(benzylamino)-6,7-dimethyl-5,6,7,8-tetrahydropyrido[3,4-d]pyrimidin-2-yl)-2-methylimidazo[1,2-a]pyridine-8-carboxamide 3-(4-(benzylamino)-6,7-dimethyl-5,6,7,8-tetrahydropyrido[3,4-d]pyrimidin-2-yl)imidazo[1,5-a]pyridine-8-carboxamide 3-(4-(benzylamino)-6,7-dimethyl-5,6,7,8-tetrahydropyrido[4,3-d]pyrimidin-2-yl)-2-methylimidazo[1,2-a]pyridine-8-carboxamide 3-(4-(benzylamino)-6,7-dimethyl-5,6,7,8-tetrahydropyrido[4,3-d]pyrimidin-2-yl)imidazo[1,5-a]pyridine-8-carboxamide 3-(4-(benzylamino)-6,8-dihydro-5H-pyrano[3,4-d]pyrimidin-2-yl)-2-methylimidazo[1,2-a]pyridine-8-carboxamide 3-(4-(benzylamino)-6,8-dihydro-5H-pyrano[3,4-d]pyrimidin-2-yl)-2-methylpyrazolo[1,5-a]pyridine-7-carboxamide 3-(4-(benzylamino)-6,8-dihydro-5H-pyrano[3,4-d]pyrimidin-2-yl)imidazo[1,5-a]pyridine-8-carboxamide 3-(4-(benzylamino)-6-methyl-5,6,7,8-tetrahydropyrido[3,4-d]pyrimidin-2-yl)-2-methylimidazo[1,2-a]pyridine-8-carboxamide 3-(4-(benzylamino)-6-methyl-5,6,7,8-tetrahydropyrido[3,4-d]pyrimidin-2-yl)imidazo[1,5-a]pyridine-8-carboxamide 3-(4-(benzylamino)-6-methyl-5,6,7,8-tetrahydropyrido[4,3-d]pyrimidin-2-yl)-2-methylimidazo[1,2-a]pyridine-8-carboxamide 3-(4-(benzylamino)-6-methyl-5,6,7,8-tetrahydropyrido[4,3-d]pyrimidin-2-yl)-2-methylpyrazolo[1,5-a]pyridine-7-carboxamide 3-(4-(benzylamino)-6-methyl-5,6,7,8-tetrahydropyrido[4,3-d]pyrimidin-2-yl)imidazo[1,5-a]pyridine-8-carboxamide 3-(4-(benzylamino)-6-methyl-6,7,8,9-tetrahydro-5H-pyrimido[5,4-c]azepin-2-yl)-2-methyl-1H-indole-7-carboxamide 3-(4-(benzylamino)-6-methyl-6,8-dihydro-5H-pyrano[3,4-d]pyrimidin-2-yl)-2-methylimidazo[1,2-a]pyridine-8-carboxamide 3-(4-(benzylamino)-6-methyl-6,8-dihydro-5H-pyrano[3,4-d]pyrimidin-2-yl)imidazo[1,5-a]pyridine-8-carboxamide 3-(4-(benzylamino)-7,8-dihydro-5H-pyrano[4,3-d]pyrimidin-2-yl)-2-methylimidazo[1,2-a]pyridine-8-carboxamide 3-(4-(benzylamino)-7,8-dihydro-5H-pyrano[4,3-d]pyrimidin-2-yl)-2-methylpyrazolo[1,5-a]pyridine-7-carboxamide 3-(4-(benzylamino)-7,8-dihydro-5H-pyrano[4,3-d]pyrimidin-2-yl)imidazo[1,5-a]pyridine-8-carboxamide 3-(4-(benzylamino)-7,8-dihydro-6H-pyrano[3,2-d]pyrimidin-2-yl)-2-methyl-1H-indole-7-carboxamide 3-(4-(benzylamino)-7,8-dihydro-6H-pyrano[3,2-d]pyrimidin-2-yl)-2-methylimidazo[1,2-a]pyridine-8-carboxamide 3-(4-(benzylamino)-7,8-dihydro-6H-pyrano[3,2-d]pyrimidin-2-yl)imidazo[1,5-a]pyridine-8-carboxamide 3-(4-(benzylamino)-7,8-dimethyl-5,6,7,8-tetrahydropyrido[3,4-d]pyrimidin-2-yl)-2-methylimidazo[1,2-a]pyridine-8-carboxamide 3-(4-(benzylamino)-7,8-dimethyl-5,6,7,8-tetrahydropyrido[3,4-d]pyrimidin-2-yl)imidazo[1,5-a]pyridine-8-carboxamide 3-(4-(benzylamino)-7-methyl-5,6,7,8-tetrahydropyrido[3,4-d]pyrimidin-2-yl)-2-methylimidazo[1,2-a]pyridine-8-carboxamide 3-(4-(benzylamino)-7-methyl-5,6,7,8-tetrahydropyrido[3,4-d]pyrimidin-2-yl)-2-methylpyrazolo[1,5-a]pyridine-7-carboxamide 3-(4-(benzylamino)-7-methyl-5,6,7,8-tetrahydropyrido[3,4-d]pyrimidin-2-yl)imidazo[1,5-a]pyridine-8-carboxamide 3-(4-(benzylamino)-7-methyl-5,6,7,8-tetrahydropyrido[4,3-d]pyrimidin-2-yl)-2-methylimidazo[1,2-a]pyridine-8-carboxamide 3-(4-(benzylamino)-7-methyl-5,6,7,8-tetrahydropyrido[4,3-d]pyrimidin-2-yl)imidazo[1,5-a]pyridine-8-carboxamide 3-(4-(benzylamino)-7-methyl-5,6,7,8-tetrahydroquinazolin-2-yl)-2-methylimidazo[1,2-a]pyridine-8-carboxamide 3-(4-(benzylamino)-7-methyl-5,6,7,8-tetrahydroquinazolin-2-yl)imidazo[1,5-a]pyridine-8-carboxamide 3-(4-(benzylamino)-7-methyl-7,8-dihydro-5H-pyrano[4,3-d]pyrimidin-2-yl)-2-methylimidazo[1,2-a]pyridine-8-carboxamide 3-(4-(benzylamino)-7-methyl-7,8-dihydro-5H-pyrano[4,3-d]pyrimidin-2-yl)imidazo[1,5-a]pyridine-8-carboxamide 3-(4-(benzylamino)-8-methyl-5,6,7,8-tetrahydropyrido[2,3-d]pyrimidin-2-yl)-2-methylimidazo[1,2-a]pyridine-8-carboxamide 3-(4-(benzylamino)-8-methyl-5,6,7,8-tetrahydropyrido[2,3-d]pyrimidin-2-yl)-2-methylpyrazolo[1,5-a]pyridine-7-carboxamide 3-(4-(benzylamino)-8-methyl-5,6,7,8-tetrahydropyrido[2,3-d]pyrimidin-2-yl)imidazo[1,5-a]pyridine-8-carboxamide 3-(4-(benzylamino)-8-methyl-5,6,7,8-tetrahydropyrido[3,4-d]pyrimidin-2-yl)-2-methylimidazo[1,2-a]pyridine-8-carboxamide 3-(4-(benzylamino)-8-methyl-5,6,7,8-tetrahydropyrido[3,4-d]pyrimidin-2-yl)imidazo[1,5-a]pyridine-8-carboxamide 3-(4-(benzylamino)-8-methyl-5,6,7,8-tetrahydropyrido[4,3-d]pyrimidin-2-yl)-2-methylimidazo[1,2-a]pyridine-8-carboxamide 3-(4-(benzylamino)-8-methyl-5,6,7,8-tetrahydropyrido[4,3-d]pyrimidin-2-yl)imidazo[1,5-a]pyridine-8-carboxamide 3-(4-(benzylamino)-8-methyl-5,6,7,8-tetrahydroquinazolin-2-yl)-2-methylimidazo[1,2-a]pyridine-8-carboxamide 3-(4-(benzylamino)-8-methyl-5,6,7,8-tetrahydroquinazolin-2-yl)imidazo[1,5-a]pyridine-8-carboxamide 3-(4-(benzylamino)-8-methyl-6,7,8,9-tetrahydro-5H-pyrimido[4,5-c]azepin-2-yl)-2-methyl-1H-indole-7-carboxamide 3-(4-(benzylamino)-8-methyl-6,8-dihydro-5H-pyrano[3,4-d]pyrimidin-2-yl)-2-methylimidazo[1,2-a]pyridine-8-carboxamide 3-(4-(benzylamino)-8-methyl-6,8-dihydro-5H-pyrano[3,4-d]pyrimidin-2-yl)imidazo[1,5-a]pyridine-8-carboxamide 3-(4-(benzylamino)-8-methyl-7,8-dihydro-5H-pyrano[4,3-d]pyrimidin-2-yl)-2-methylimidazo[1,2-a]pyridine-8-carboxamide 3-(4-(benzylamino)-8-methyl-7,8-dihydro-5H-pyrano[4,3-d]pyrimidin-2-yl)imidazo[1,5-a]pyridine-8-carboxamide 3-(4-(benzylamino)-9-methyl-6,7,8,9-tetrahydro-5H-pyrimido[4,5-b]azepin-2-yl)-2-methyl-1H-indole-7-carboxamide Most Preferred:

1-(4-((3,5-difluorobenzyl)amino)-6,7-dihydro-5H-pyrano[2,3-d]pyrimidin-2-yl)-2-methyl-1H-indole-4-carboxamide 1-(4-((3-fluorobenzyl)amino)-5,6,7,8-tetrahydropyrido[2,3-d]pyrimidin-2-yl)-1H-indazole-4-carboxamide 1-(4-((3-fluorobenzyl)amino)-5,6,7,8-tetrahydropyrido[2,3-d]pyrimidin-2-yl)-2-methoxy-1H-benzo[d]imidazole-4-carboxamide 1-(4-((3-fluorobenzyl)amino)-5,6,7,8-tetrahydropyrido[2,3-d]pyrimidin-2-yl)-2-methyl-1H-indole-4-carboxamide 1-(4-((3-fluorobenzyl)amino)-5,6,7,8-tetrahydropyrido[2,3-d]pyrimidin-2-yl)-6-fluoro-1H-indazole-4-carboxamide 1-(4-((3-fluorobenzyl)amino)-5,6,7,8-tetrahydropyrido[2,3-d]pyrimidin-2-yl)-6-fluoro-2-methoxy-1H-benzo[d]imidazole-4-carboxamide 1-(4-((3-fluorobenzyl)amino)-5,6,7,8-tetrahydropyrido[2,3-d]pyrimidin-2-yl)-6-fluoro-2-methyl-1H-indole-4-carboxamide 1-(4-((3-fluorobenzyl)amino)-5,6,7,8-tetrahydropyrido[3,2-d]pyrimidin-2-yl)-1H-indazole-4-carboxamide 1-(4-((3-fluorobenzyl)amino)-5,6,7,8-tetrahydropyrido[3,2-d]pyrimidin-2-yl)-2-methoxy-1H-benzo[d]imidazole-4-carboxamide 1-(4-((3-fluorobenzyl)amino)-5,6,7,8-tetrahydropyrido[3,2-d]pyrimidin-2-yl)-2-methyl-1H-indole-4-carboxamide 1-(4-((3-fluorobenzyl)amino)-5,6,7,8-tetrahydropyrido[3,2-d]pyrimidin-2-yl)-6-fluoro-1H-indazole-4-carboxamide 1-(4-((3-fluorobenzyl)amino)-5,6,7,8-tetrahydropyrido[3,2-d]pyrimidin-2-yl)-6-fluoro-2-methoxy-1H-benzo[d]imidazole-4-carboxamide 1-(4-((3-fluorobenzyl)amino)-5,6,7,8-tetrahydropyrido[3,2-d]pyrimidin-2-yl)-6-fluoro-2-methyl-1H-indole-4-carboxamide 1-(4-((3-fluorobenzyl)amino)-5,6,7,8-tetrahydropyrido[3,4-d]pyrimidin-2-yl)-1H-indazole-4-carboxamide 1-(4-((3-fluorobenzyl)amino)-5,6,7,8-tetrahydropyrido[3,4-d]pyrimidin-2-yl)-6-fluoro-1H-indazole-4-carboxamide 1-(4-((3-fluorobenzyl)amino)-5,6,7,8-tetrahydropyrido[4,3-d]pyrimidin-2-yl)-1H-indazole-4-carboxamide 1-(4-((3-fluorobenzyl)amino)-5,6,7,8-tetrahydropyrido[4,3-d]pyrimidin-2-yl)-6-fluoro-1H-indazole-4-carboxamide 1-(4-((3-fluorobenzyl)amino)-5,6,7,8-tetrahydroquinazolin-2-yl)-1H-indazole-4-carboxamide 1-(4-((3-fluorobenzyl)amino)-5,6,7,8-tetrahydroquinazolin-2-yl)-6-fluoro-1H-indazole-4-carboxamide 1-(4-((3-fluorobenzyl)amino)-5,6-dihydrofuro[2,3-d]pyrimidin-2-yl)-1H-indazole-4-carboxamide 1-(4-((3-fluorobenzyl)amino)-5,6-dihydrofuro[2,3-d]pyrimidin-2-yl)-2-methoxy-1H-benzo[d]imidazole-4-carboxamide 1-(4-((3-fluorobenzyl)amino)-5,6-dihydrofuro[2,3-d]pyrimidin-2-yl)-2-methyl-1H-indole-4-carboxamide 1-(4-((3-fluorobenzyl)amino)-5,6-dihydrofuro[2,3-d]pyrimidin-2-yl)-6-fluoro-1H-indazole-4-carboxamide 1-(4-((3-fluorobenzyl)amino)-5,6-dihydrofuro[2,3-d]pyrimidin-2-yl)-6-fluoro-2-methoxy-1H-benzo[d]imidazole-4-carboxamide 1-(4-((3-fluorobenzyl)amino)-5,6-dihydrofuro[2,3-d]pyrimidin-2-yl)-6-fluoro-2-methyl-1H-indole-4-carboxamide 1-(4-((3-fluorobenzyl)amino)-5,7-dihydrofuro[3,4-d]pyrimidin-2-yl)-1H-indazole-4-carboxamide 1-(4-((3-fluorobenzyl)amino)-5,7-dihydrofuro[3,4-d]pyrimidin-2-yl)-6-fluoro-1H-indazole-4-carboxamide 1-(4-((3-fluorobenzyl)amino)-5-methyl-5,6,7,8-tetrahydropyrido[3,2-d]pyrimidin-2-yl)-1H-indazole-4-carboxamide 1-(4-((3-fluorobenzyl)amino)-5-methyl-5,6,7,8-tetrahydropyrido[3,2-d]pyrimidin-2-yl)-2-methoxy-1H-benzo[d]imidazole-4-carboxamide 1-(4-((3-fluorobenzyl)amino)-5-methyl-5,6,7,8-tetrahydropyrido[3,2-d]pyrimidin-2-yl)-2-methyl-1H-indole-4-carboxamide 1-(4-((3-fluorobenzyl)amino)-5-methyl-5,6,7,8-tetrahydropyrido[3,2-d]pyrimidin-2-yl)-6-fluoro-1H-indazole-4-carboxamide 1-(4-((3-fluorobenzyl)amino)-5-methyl-5,6,7,8-tetrahydropyrido[3,2-d]pyrimidin-2-yl)-6-fluoro-2-methoxy-1H-benzo[d]imidazole-4-carboxamide 1-(4-((3-fluorobenzyl)amino)-5-methyl-5,6,7,8-tetrahydropyrido[3,2-d]pyrimidin-2-yl)-6-fluoro-2-methyl-1H-indole-4-carboxamide 1-(4-((3-fluorobenzyl)amino)-5-methyl-6,7-dihydro-5H-pyrrolo[3,2-d]pyrimidin-2-yl)-1H-indazole-4-carboxamide 1-(4-((3-fluorobenzyl)amino)-5-methyl-6,7-dihydro-5H-pyrrolo[3,2-d]pyrimidin-2-yl)-2-methoxy-1H-benzo[d]imidazole-4-carboxamide 1-(4-((3-fluorobenzyl)amino)-5-methyl-6,7-dihydro-5H-pyrrolo[3,2-d]pyrimidin-2-yl)-2-methyl-1H-indole-4-carboxamide 1-(4-((3-fluorobenzyl)amino)-5-methyl-6,7-dihydro-5H-pyrrolo[3,2-d]pyrimidin-2-yl)-6-fluoro-1H-indazole-4-carboxamide 1-(4-((3-fluorobenzyl)amino)-5-methyl-6,7-dihydro-5H-pyrrolo[3,2-d]pyrimidin-2-yl)-6-fluoro-2-methoxy-1H-benzo[d]imidazole-4-carboxamide 1-(4-((3-fluorobenzyl)amino)-5-methyl-6,7-dihydro-5H-pyrrolo[3,2-d]pyrimidin-2-yl)-6-fluoro-2-methyl-1H-indole-4-carboxamide 1-(4-((3-fluorobenzyl)amino)-6,7,8,9-tetrahydro-5H-cyclohepta[d]pyrimidin-2-yl)-1H-indazole-4-carboxamide 1-(4-((3-fluorobenzyl)amino)-6,7,8,9-tetrahydro-5H-cyclohepta[d]pyrimidin-2-yl)-6-fluoro-1H-indazole-4-carboxamide 1-(4-((3-fluorobenzyl)amino)-6,7-dihydro-5H-cyclopenta[d]pyrimidin-2-yl)-1H-indazole-4-carboxamide 1-(4-((3-fluorobenzyl)amino)-6,7-dihydro-5H-cyclopenta[d]pyrimidin-2-yl)-6-fluoro-1H-indazole-4-carboxamide 1-(4-((3-fluorobenzyl)amino)-6,7-dihydro-5H-pyrano[2,3-d]pyrimidin-2-yl)-1H-indazole-4-carboxamide 1-(4-((3-fluorobenzyl)amino)-6,7-dihydro-5H-pyrano[2,3-d]pyrimidin-2-yl)-2-methoxy-1H-benzo[d]imidazole-4-carboxamide 1-(4-((3-fluorobenzyl)amino)-6,7-dihydro-5H-pyrano[2,3-d]pyrimidin-2-yl)-2-methyl-1H-indole-4-carboxamide 1-(4-((3-fluorobenzyl)amino)-6,7-dihydro-5H-pyrano[2,3-d]pyrimidin-2-yl)-6-fluoro-1H-indazole-4-carboxamide 1-(4-((3-fluorobenzyl)amino)-6,7-dihydro-5H-pyrano[2,3-d]pyrimidin-2-yl)-6-fluoro-2-methoxy-1H-benzo[d]imidazole-4-carboxamide 1-(4-((3-fluorobenzyl)amino)-6,7-dihydro-5H-pyrano[2,3-d]pyrimidin-2-yl)-6-fluoro-2-methyl-1H-indole-4-carboxamide 1-(4-((3-fluorobenzyl)amino)-6,7-dihydro-5H-pyrrolo[2,3-d]pyrimidin-2-yl)-1H-indazole-4-carboxamide 1-(4-((3-fluorobenzyl)amino)-6,7-dihydro-5H-pyrrolo[2,3-d]pyrimidin-2-yl)-2-methoxy-1H-benzo[d]imidazole-4-carboxamide 1-(4-((3-fluorobenzyl)amino)-6,7-dihydro-5H-pyrrolo[2,3-d]pyrimidin-2-yl)-2-methyl-1H-indole-4-carboxamide 1-(4-((3-fluorobenzyl)amino)-6,7-dihydro-5H-pyrrolo[2,3-d]pyrimidin-2-yl)-6-fluoro-1H-indazole-4-carboxamide 1-(4-((3-fluorobenzyl)amino)-6,7-dihydro-5H-pyrrolo[2,3-d]pyrimidin-2-yl)-6-fluoro-2-methoxy-1H-benzo[d]imidazole-4-carboxamide 1-(4-((3-fluorobenzyl)amino)-6,7-dihydro-5H-pyrrolo[2,3-d]pyrimidin-2-yl)-6-fluoro-2-methyl-1H-indole-4-carboxamide 1-(4-((3-fluorobenzyl)amino)-6,7-dihydro-5H-pyrrolo[3,2-d]pyrimidin-2-yl)-1H-indazole-4-carboxamide 1-(4-((3-fluorobenzyl)amino)-6,7-dihydro-5H-pyrrolo[3,2-d]pyrimidin-2-yl)-2-methoxy-1H-benzo[d]imidazole-4-carboxamide 1-(4-((3-fluorobenzyl)amino)-6,7-dihydro-5H-pyrrolo[3,2-d]pyrimidin-2-yl)-2-methyl-1H-indole-4-carboxamide 1-(4-((3-fluorobenzyl)amino)-6,7-dihydro-5H-pyrrolo[3,2-d]pyrimidin-2-yl)-6-fluoro-1H-indazole-4-carboxamide 1-(4-((3-fluorobenzyl)amino)-6,7-dihydro-5H-pyrrolo[3,2-d]pyrimidin-2-yl)-6-fluoro-2-methoxy-1H-benzo[d]imidazole-4-carboxamide 1-(4-((3-fluorobenzyl)amino)-6,7-dihydro-5H-pyrrolo[3,2-d]pyrimidin-2-yl)-6-fluoro-2-methyl-1H-indole-4-carboxamide 1-(4-((3-fluorobenzyl)amino)-6,7-dihydro-5H-pyrrolo[3,4-d]pyrimidin-2-yl)-1H-indazole-4-carboxamide 1-(4-((3-fluorobenzyl)amino)-6,7-dihydro-5H-pyrrolo[3,4-d]pyrimidin-2-yl)-6-fluoro-1H-indazole-4-carboxamide 1-(4-((3-fluorobenzyl)amino)-6,8-dihydro-5H-pyrano[3,4-d]pyrimidin-2-yl)-1H-indazole-4-carboxamide 1-(4-((3-fluorobenzyl)amino)-6,8-dihydro-5H-pyrano[3,4-d]pyrimidin-2-yl)-6-fluoro-1H-indazole-4-carboxamide 1-(4-((3-fluorobenzyl)amino)-6-methyl-5,6,7,8-tetrahydropyrido[4,3-d]pyrimidin-2-yl)-1H-indazole-4-carboxamide 1-(4-((3-fluorobenzyl)amino)-6-methyl-5,6,7,8-tetrahydropyrido[4,3-d]pyrimidin-2-yl)-6-fluoro-1H-indazole-4-carboxamide 1-(4-((3-fluorobenzyl)amino)-6-methyl-6,7-dihydro-5H-pyrrolo[3,4-d]pyrimidin-2-yl)-1H-indazole-4-carboxamide 1-(4-((3-fluorobenzyl)amino)-6-methyl-6,7-dihydro-5H-pyrrolo[3,4-d]pyrimidin-2-yl)-6-fluoro-1H-indazole-4-carboxamide 1-(4-((3-fluorobenzyl)amino)-7,8-dihydro-5H-pyrano[4,3-d]pyrimidin-2-yl)-1H-indazole-4-carboxamide 1-(4-((3-fluorobenzyl)amino)-7,8-dihydro-5H-pyrano[4,3-d]pyrimidin-2-yl)-6-fluoro-1H-indazole-4-carboxamide 1-(4-((3-fluorobenzyl)amino)-7-methyl-5,6,7,8-tetrahydropyrido[3,4-d]pyrimidin-2-yl)-1H-indazole-4-carboxamide 1-(4-((3-fluorobenzyl)amino)-7-methyl-5,6,7,8-tetrahydropyrido[3,4-d]pyrimidin-2-yl)-6-fluoro-1H-indazole-4-carboxamide 1-(4-((3-fluorobenzyl)amino)-7-methyl-6,7-dihydro-5H-pyrrolo[2,3-d]pyrimidin-2-yl)-1H-indazole-4-carboxamide 1-(4-((3-fluorobenzyl)amino)-7-methyl-6,7-dihydro-5H-pyrrolo[2,3-d]pyrimidin-2-yl)-2-methoxy-1H-benzo[d]imidazole-4-carboxamide 1-(4-((3-fluorobenzyl)amino)-7-methyl-6,7-dihydro-5H-pyrrolo[2,3-d]pyrimidin-2-yl)-2-methyl-1H-indole-4-carboxamide 1-(4-((3-fluorobenzyl)amino)-7-methyl-6,7-dihydro-5H-pyrrolo[2,3-d]pyrimidin-2-yl)-6-fluoro-1H-indazole-4-carboxamide 1-(4-((3-fluorobenzyl)amino)-7-methyl-6,7-dihydro-5H-pyrrolo[2,3-d]pyrimidin-2-yl)-6-fluoro-2-methoxy-1H-benzo[d]imidazole-4-carboxamide 1-(4-((3-fluorobenzyl)amino)-7-methyl-6,7-dihydro-5H-pyrrolo[2,3-d]pyrimidin-2-yl)-6-fluoro-2-methyl-1H-indole-4-carboxamide 1-(4-((3-fluorobenzyl)amino)-8-methyl-5,6,7,8-tetrahydropyrido[2,3-d]pyrimidin-2-yl)-1H-indazole-4-carboxamide 1-(4-((3-fluorobenzyl)amino)-8-methyl-5,6,7,8-tetrahydropyrido[2,3-d]pyrimidin-2-yl)-2-methoxy-1H-benzo[d]imidazole-4-carboxamide 1-(4-((3-fluorobenzyl)amino)-8-methyl-5,6,7,8-tetrahydropyrido[2,3-d]pyrimidin-2-yl)-2-methyl-1H-indole-4-carboxamide 1-(4-((3-fluorobenzyl)amino)-8-methyl-5,6,7,8-tetrahydropyrido[2,3-d]pyrimidin-2-yl)-6-fluoro-1H-indazole-4-carboxamide
1-(4-((3-fluorobenzyl)amino)-8-methyl-5,6,7,8-tetrahydropyrido[2,3-d]pyrimidin-2-yl)-6-fluoro-2-methoxy-1H-benzo[d]imidazole-4-carboxamide
1-(4-((3-fluorobenzyl)amino)-8-methyl-5,6,7,8-tetrahydropyrido[2,3-d]pyrimidin-2-yl)-6-fluoro-2-methyl-1H-indole-4-carboxamide
1-(4-((thiophen-2-ylmethyl)amino)-5,6,7,8-tetrahydropyrido[2,3-d]pyrimidin-2-yl)-1H-indazole-4-carboxamide
1-(4-((thiophen-2-ylmethyl)amino)-5,6,7,8-tetrahydropyrido[2,3-d]pyrimidin-2-yl)-2-methoxy-1H-benzo[d]imidazole-4-carboxamide
1-(4-((thiophen-2-ylmethyl)amino)-5,6,7,8-tetrahydropyrido[2,3-d]pyrimidin-2-yl)-2-methyl-1H-indole-4-carboxamide
1-(4-((thiophen-2-ylmethyl)amino)-5,6,7,8-tetrahydropyrido[3,2-d]pyrimidin-2-yl)-1H-indazole-4-carboxamide
1-(4-((thiophen-2-ylmethyl)amino)-5,6,7,8-tetrahydropyrido[3,2-d]pyrimidin-2-yl)-2-methoxy-1H-benzo[d]imidazole-4-carboxamide
1-(4-((thiophen-2-ylmethyl)amino)-5,6,7,8-tetrahydropyrido[3,2-d]pyrimidin-2-yl)-2-methyl-1H-indole-4-carboxamide
1-(4-((thiophen-2-ylmethyl)amino)-5,6,7,8-tetrahydropyrido[3,4-d]pyrimidin-2-yl)-1H-indazole-4-carboxamide
1-(4-((thiophen-2-ylmethyl)amino)-5,6,7,8-tetrahydropyrido[4,3-d]pyrimidin-2-yl)-1H-indazole-4-carboxamide
1-(4-((thiophen-2-ylmethyl)amino)-5,6,7,8-tetrahydroquinazolin-2-yl)-1H-indazole-4-carboxamide
1-(4-((thiophen-2-ylmethyl)amino)-5,6-dihydrofuro[2,3-d]pyrimidin-2-yl)-1H-indazole-4-carboxamide
1-(4-((thiophen-2-ylmethyl)amino)-5,6-dihydrofuro[2,3-d]pyrimidin-2-yl)-2-methoxy-1H-benzo[d]imidazole-4-carboxamide
1-(4-((thiophen-2-ylmethyl)amino)-5,6-dihydrofuro[2,3-d]pyrimidin-2-yl)-2-methyl-1H-indole-4-carboxamide
1-(4-((thiophen-2-ylmethyl)amino)-5,7-dihydrofuro[3,4-d]pyrimidin-2-yl)-1H-indazole-4-carboxamide
1-(4-((thiophen-2-ylmethyl)amino)-5-methyl-5,6,7,8-tetrahydropyrido[3,2-d]pyrimidin-2-yl)-1H-indazole-4-carboxamide
1-(4-((thiophen-2-ylmethyl)amino)-5-methyl-5,6,7,8-tetrahydropyrido[3,2-d]pyrimidin-2-yl)-2-methoxy-1H-benzo[d]imidazole-4-carboxamide
1-(4-((thiophen-2-ylmethyl)amino)-5-methyl-5,6,7,8-tetrahydropyrido[3,2-d]pyrimidin-2-yl)-2-methyl-1H-indole-4-carboxamide
1-(4-((thiophen-2-ylmethyl)amino)-5-methyl-6,7-dihydro-5H-pyrrolo[3,2-d]pyrimidin-2-yl)-1H-indazole-4-carboxamide
1-(4-((thiophen-2-ylmethyl)amino)-5-methyl-6,7-dihydro-5H-pyrrolo[3,2-d]pyrimidin-2-yl)-2-methoxy-1H-benzo[d]imidazole-4-carboxamide
1-(4-((thiophen-2-ylmethyl)amino)-5-methyl-6,7-dihydro-5H-pyrrolo[3,2-d]pyrimidin-2-yl)-2-methyl-1H-indole-4-carboxamide
1-(4-((thiophen-2-ylmethyl)amino)-6,7,8,9-tetrahydro-5H-cyclohepta[d]pyrimidin-2-yl)-1H-indazole-4-carboxamide
1-(4-((thiophen-2-ylmethyl)amino)-6,7-dihydro-5H-cyclopenta[d]pyrimidin-2-yl)-1H-indazole-4-carboxamide
1-(4-((thiophen-2-ylmethyl)amino)-6,7-dihydro-5H-pyrano[2,3-d]pyrimidin-2-yl)-1H-indazole-4-carboxamide
1-(4-((thiophen-2-ylmethyl)amino)-6,7-dihydro-5H-pyrano[2,3-d]pyrimidin-2-yl)-2-methoxy-1H-benzo[d]imidazole-4-carboxamide
1-(4-((thiophen-2-ylmethyl)amino)-6,7-dihydro-5H-pyrano[2,3-d]pyrimidin-2-yl)-2-methyl-1H-indole-4-carboxamide
1-(4-((thiophen-2-ylmethyl)amino)-6,7-dihydro-5H-pyrrolo[2,3-d]pyrimidin-2-yl)-1H-indazole-4-carboxamide
1-(4-((thiophen-2-ylmethyl)amino)-6,7-dihydro-5H-pyrrolo[2,3-d]pyrimidin-2-yl)-2-methoxy-1H-benzo[d]imidazole-4-carboxamide
1-(4-((thiophen-2-ylmethyl)amino)-6,7-dihydro-5H-pyrrolo[2,3-d]pyrimidin-2-yl)-2-methyl-1H-indole-4-carboxamide
1-(4-((thiophen-2-ylmethyl)amino)-6,7-dihydro-5H-pyrrolo[3,2-d]pyrimidin-2-yl)-1H-indazole-4-carboxamide
1-(4-((thiophen-2-ylmethyl)amino)-6,7-dihydro-5H-pyrrolo[3,2-d]pyrimidin-2-yl)-2-methoxy-1H-benzo[d]imidazole-4-carboxamide
1-(4-((thiophen-2-ylmethyl)amino)-6,7-dihydro-5H-pyrrolo[3,2-d]pyrimidin-2-yl)-2-methyl-1H-indole-4-carboxamide
1-(4-((thiophen-2-ylmethyl)amino)-6,7-dihydro-5H-pyrrolo[3,4-d]pyrimidin-2-yl)-1H-indazole-4-carboxamide
1-(4-((thiophen-2-ylmethyl)amino)-6,8-dihydro-5H-pyrano[3,4-d]pyrimidin-2-yl)-1H-indazole-4-carboxamide
1-(4-((thiophen-2-ylmethyl)amino)-6-methyl-5,6,7,8-tetrahydropyrido[4,3-d]pyrimidin-2-yl)-1H-indazole-4-carboxamide
1-(4-((thiophen-2-ylmethyl)amino)-6-methyl-6,7-dihydro-5H-pyrrolo[3,4-d]pyrimidin-2-yl)-1H-indazole-4-carboxamide
1-(4-((thiophen-2-ylmethyl)amino)-7,8-dihydro-5H-pyrano[4,3-d]pyrimidin-2-yl)-1H-indazole-4-carboxamide
1-(4-((thiophen-2-ylmethyl)amino)-7-methyl-5,6,7,8-tetrahydropyrido[3,4-d]pyrimidin-2-yl)-1H-indazole-4-carboxamide
1-(4-((thiophen-2-ylmethyl)amino)-7-methyl-6,7-dihydro-5H-pyrrolo[2,3-d]pyrimidin-2-yl)-1H-indazole-4-carboxamide
1-(4-((thiophen-2-ylmethyl)amino)-7-methyl-6,7-dihydro-5H-pyrrolo[2,3-d]pyrimidin-2-yl)-2-methoxy-1H-benzo[d]imidazole-4-carboxamide
1-(4-((thiophen-2-ylmethyl)amino)-7-methyl-6,7-dihydro-5H-pyrrolo[2,3-d]pyrimidin-2-yl)-2-methyl-1H-indole-4-carboxamide
1-(4-((thiophen-2-ylmethyl)amino)-8-methyl-5,6,7,8-tetrahydropyrido[2,3-d]pyrimidin-2-yl)-1H-indazole-4-carboxamide
1-(4-((thiophen-2-ylmethyl)amino)-8-methyl-5,6,7,8-tetrahydropyrido[2,3-d]pyrimidin-2-yl)-2-methoxy-1H-benzo[d]imidazole-4-carboxamide
1-(4-((thiophen-2-ylmethyl)amino)-8-methyl-5,6,7,8-tetrahydropyrido[2,3-d]pyrimidin-2-yl)-2-methyl-1H-indole-4-carboxamide
1-(4-(benzylamino)-5,6,7,8-tetrahydropyrido[2,3-d]pyrimidin-2-yl)-1H-indazole-4-carboxamide
1-(4-(benzylamino)-5,6,7,8-tetrahydropyrido[2,3-d]pyrimidin-2-yl)-2-(hydroxymethyl)-1H-indole-4-carboxamide
1-(4-(benzylamino)-5,6,7,8-tetrahydropyrido[2,3-d]pyrimidin-2-yl)-2-methoxy-1H-benzo[d]imidazole-4-carboxamide
1-(4-(benzylamino)-5,6,7,8-tetrahydropyrido[2,3-d]pyrimidin-2-yl)-2-methyl-1H-indole-4-carboxamide 1-(4-(benzylamino)-5,6,7,8-tetrahydropyrido[2,3-d]pyrimidin-2-yl)-6-fluoro-1H-indazole-4-carboxamide
1-(4-(benzylamino)-5,6,7,8-tetrahydropyrido[2,3-d]pyrimidin-2-yl)-6-fluoro-2-methoxy-1H-benzo[d]imidazole-4-carboxamide
1-(4-(benzylamino)-5,6,7,8-tetrahydropyrido[2,3-d]pyrimidin-2-yl)-6-fluoro-2-methyl-1H-indole-4-carboxamide
1-(4-(benzylamino)-5,6,7,8-tetrahydropyrido[3,2-d]pyrimidin-2-yl)-1H-indazole-4-carboxamide
1-(4-(benzylamino)-5,6,7,8-tetrahydropyrido[3,2-d]pyrimidin-2-yl)-2-methoxy-1H-benzo[d]imidazole-4-carboxamide
1-(4-(benzylamino)-5,6,7,8-tetrahydropyrido[3,2-d]pyrimidin-2-yl)-2-methyl-1H-indole-4-carboxamide
1-(4-(benzylamino)-5,6,7,8-tetrahydropyrido[3,2-d]pyrimidin-2-yl)-6-fluoro-1H-indazole-4-carboxamide
1-(4-(benzylamino)-5,6,7,8-tetrahydropyrido[3,2-d]pyrimidin-2-yl)-6-fluoro-2-methoxy-1H-benzo[d]imidazole-4-carboxamide
1-(4-(benzylamino)-5,6,7,8-tetrahydropyrido[3,2-d]pyrimidin-2-yl)-6-fluoro-2-methyl-1H-indole-4-carboxamide
1-(4-(benzylamino)-5,6,7,8-tetrahydropyrido[3,4-d]pyrimidin-2-yl)-1H-indazole-4-carboxamide
1-(4-(benzylamino)-5,6,7,8-tetrahydropyrido[3,4-d]pyrimidin-2-yl)-6-fluoro-1H-indazole-4-carboxamide
1-(4-(benzylamino)-5,6,7,8-tetrahydropyrido[4,3-d]pyrimidin-2-yl)-1H-indazole-4-carboxamide
1-(4-(benzylamino)-5,6,7,8-tetrahydropyrido[4,3-d]pyrimidin-2-yl)-6-fluoro-1H-indazole-4-carboxamide
1-(4-(benzylamino)-5,6,7,8-tetrahydroquinazolin-2-yl)-1H-indazole-4-carboxamide
1-(4-(benzylamino)-5,6,7,8-tetrahydroquinazolin-2-yl)-6-fluoro-1H-indazole-4-carboxamide
1-(4-(benzylamino)-5,6-dihydrofuro[2,3-d]pyrimidin-2-yl)-1H-indazole-4-carboxamide
1-(4-(benzylamino)-5,6-dihydrofuro[2,3-d]pyrimidin-2-yl)-2-methoxy-1H-benzo[d]imidazole-4-carboxamide
1-(4-(benzylamino)-5,6-dihydrofuro[2,3-d]pyrimidin-2-yl)-2-methyl-1H-indole-4-carboxamide
1-(4-(benzylamino)-5,6-dihydrofuro[2,3-d]pyrimidin-2-yl)-6-fluoro-1H-indazole-4-carboxamide
1-(4-(benzylamino)-5,6-dihydrofuro[2,3-d]pyrimidin-2-yl)-6-fluoro-2-methoxy-1H-benzo[d]imidazole-4-carboxamide
1-(4-(benzylamino)-5,6-dihydrofuro[2,3-d]pyrimidin-2-yl)-6-fluoro-2-methyl-1H-indole-4-carboxamide
1-(4-(benzylamino)-5,7-dihydrofuro[3,4-d]pyrimidin-2-yl)-1H-indazole-4-carboxamide
1-(4-(benzylamino)-5,7-dihydrofuro[3,4-d]pyrimidin-2-yl)-6-fluoro-1H-indazole-4-carboxamide
1-(4-(benzylamino)-5,7-dimethyl-5,6,7,8-tetrahydropyrido[3,4-d]pyrimidin-2-yl)-1H-indazole-4-carboxamide
1-(4-(benzylamino)-5,7-dimethyl-5,6,7,8-tetrahydropyrido[3,4-d]pyrimidin-2-yl)-2-methoxy-1H-benzo[d]imidazole-4-carboxamide
1-(4-(benzylamino)-5,7-dimethyl-5,6,7,8-tetrahydropyrido[3,4-d]pyrimidin-2-yl)-2-methyl-1H-indole-4-carboxamide
1-(4-(benzylamino)-5-methyl-5,6,7,8-tetrahydropyrido[3,2-d]pyrimidin-2-yl)-1H-indazole-4-carboxamide
1-(4-(benzylamino)-5-methyl-5,6,7,8-tetrahydropyrido[3,2-d]pyrimidin-2-yl)-2-methoxy-1H-benzo[d]imidazole-4-carboxamide
1-(4-(benzylamino)-5-methyl-5,6,7,8-tetrahydropyrido[3,2-d]pyrimidin-2-yl)-2-methyl-1H-indole-4-carboxamide
1-(4-(benzylamino)-5-methyl-5,6,7,8-tetrahydropyrido[3,2-d]pyrimidin-2-yl)-6-fluoro-1H-indazole-4-carboxamide
1-(4-(benzylamino)-5-methyl-5,6,7,8-tetrahydropyrido[3,2-d]pyrimidin-2-yl)-6-fluoro-2-methoxy-1H-benzo[d]imidazole-4-carboxamide
1-(4-(benzylamino)-5-methyl-5,6,7,8-tetrahydropyrido[3,2-d]pyrimidin-2-yl)-6-fluoro-2-methyl-1H-indole-4-carboxamide
1-(4-(benzylamino)-5-methyl-5,6,7,8-tetrahydropyrido[3,4-d]pyrimidin-2-yl)-1H-indazole-4-carboxamide
1-(4-(benzylamino)-5-methyl-5,6,7,8-tetrahydropyrido[3,4-d]pyrimidin-2-yl)-2-methoxy-1H-benzo[d]imidazole-4-carboxamide
1-(4-(benzylamino)-5-methyl-5,6,7,8-tetrahydropyrido[3,4-d]pyrimidin-2-yl)-2-methyl-1H-indole-4-carboxamide
1-(4-(benzylamino)-5-methyl-5,6,7,8-tetrahydropyrido[4,3-d]pyrimidin-2-yl)-1H-indazole-4-carboxamide
1-(4-(benzylamino)-5-methyl-5,6,7,8-tetrahydropyrido[4,3-d]pyrimidin-2-yl)-2-methoxy-1H-benzo[d]imidazole-4-carboxamide
1-(4-(benzylamino)-5-methyl-5,6,7,8-tetrahydropyrido[4,3-d]pyrimidin-2-yl)-2-methyl-1H-indole-4-carboxamide
1-(4-(benzylamino)-5-methyl-5,6,7,8-tetrahydroquinazolin-2-yl)-1H-indazole-4-carboxamide
1-(4-(benzylamino)-5-methyl-5,6,7,8-tetrahydroquinazolin-2-yl)-2-methoxy-1H-benzo[d]imidazole-4-carboxamide
1-(4-(benzylamino)-5-methyl-5,6,7,8-tetrahydroquinazolin-2-yl)-2-methyl-1H-indole-4-carboxamide
1-(4-(benzylamino)-5-methyl-6,7-dihydro-5H-pyrrolo[3,2-d]pyrimidin-2-yl)-1H-indazole-4-carboxamide
1-(4-(benzylamino)-5-methyl-6,7-dihydro-5H-pyrrolo[3,2-d]pyrimidin-2-yl)-2-methoxy-1H-benzo[d]imidazole-4-carboxamide
1-(4-(benzylamino)-5-methyl-6,7-dihydro-5H-pyrrolo[3,2-d]pyrimidin-2-yl)-2-methyl-1H-indole-4-carboxamide
1-(4-(benzylamino)-5-methyl-6,7-dihydro-5H-pyrrolo[3,2-d]pyrimidin-2-yl)-6-fluoro-1H-indazole-4-carboxamide
1-(4-(benzylamino)-5-methyl-6,7-dihydro-5H-pyrrolo[3,2-d]pyrimidin-2-yl)-6-fluoro-2-methoxy-1H-benzo[d]imidazole-4-carboxamide
1-(4-(benzylamino)-5-methyl-6,7-dihydro-5H-pyrrolo[3,2-d]pyrimidin-2-yl)-6-fluoro-2-methyl-1H-indole-4-carboxamide
1-(4-(benzylamino)-5-methyl-6,8-dihydro-5H-pyrano[3,4-d]pyrimidin-2-yl)-1H-indazole-4-carboxamide
1-(4-(benzylamino)-5-methyl-6,8-dihydro-5H-pyrano[3,4-d]pyrimidin-2-yl)-2-methoxy-1H-benzo[d]imidazole-4-carboxamide
1-(4-(benzylamino)-5-methyl-6,8-dihydro-5H-pyrano[3,4-d]pyrimidin-2-yl)-2-methyl-1H-indole-4-carboxamide
1-(4-(benzylamino)-5-methyl-7,8-dihydro-5H-pyrano[4,3-d]pyrimidin-2-yl)-1H-indazole-4-carboxamide
1-(4-(benzylamino)-5-methyl-7,8-dihydro-5H-pyrano[4,3-d]pyrimidin-2-yl)-2-methoxy-1H-benzo[d]imidazole-4-carboxamide
1-(4-(benzylamino)-5-methyl-7,8-dihydro-5H-pyrano[4,3-d]pyrimidin-2-yl)-2-methyl-1H-indole-4-carboxamide
1-(4-(benzylamino)-6,7,8,9-tetrahydro-5H-cyclohepta[d]pyrimidin-2-yl)-1H-indazole-4-carboxamide
1-(4-(benzylamino)-6,7,8,9-tetrahydro-5H-cyclohepta[d]pyrimidin-2-yl)-6-fluoro-1H-indazole-4-carboxamide
1-(4-(benzylamino)-6,7,8,9-tetrahydro-5H-pyrimido[4,5-d]azepin-2-yl)-2-methyl-1H-indole-4-carboxamide
1-(4-(benzylamino)-6,7-dihydro-5H-cyclopenta[d]pyrimidin-2-yl)-1H-indazole-4-carboxamide
1-(4-(benzylamino)-6,7-dihydro-5H-cyclopenta[d]pyrimidin-2-yl)-6-fluoro-1H-indazole-4-carboxamide
1-(4-(benzylamino)-6,7-dihydro-5H-pyrano[2,3-d]pyrimidin-2-yl)-1H-indazole-4-carboxamide 1-(4-(benzylamino)-6,7-dihydro-5H-pyrano[2,3-d]pyrimidin-2-yl)-2-(hydroxymethyl)-1H-indole-4-carboxamide
1-(4-(benzylamino)-6,7-dihydro-5H-pyrano[2,3-d]pyrimidin-2-yl)-2-methoxy-1H-benzo[d]imidazole-4-carboxamide
1-(4-(benzylamino)-6,7-dihydro-5H-pyrano[2,3-d]pyrimidin-2-yl)-2-methyl-1H-indole-4-carboxamide
1-(4-(benzylamino)-6,7-dihydro-5H-pyrano[2,3-d]pyrimidin-2-yl)-6-fluoro-1H-indazole-4-carboxamide
1-(4-(benzylamino)-6,7-dihydro-5H-pyrano[2,3-d]pyrimidin-2-yl)-6-fluoro-2-methoxy-1H-benzo[d]imidazole-4-carboxamide
1-(4-(benzylamino)-6,7-dihydro-5H-pyrano[2,3-d]pyrimidin-2-yl)-6-fluoro-2-methyl-1H-indole-4-carboxamide
1-(4-(benzylamino)-6,7-dihydro-5H-pyrrolo[2,3-d]pyrimidin-2-yl)-1H-indazole-4-carboxamide
1-(4-(benzylamino)-6,7-dihydro-5H-pyrrolo[2,3-d]pyrimidin-2-yl)-2-methoxy-1H-benzo[d]imidazole-4-carboxamide
1-(4-(benzylamino)-6,7-dihydro-5H-pyrrolo[2,3-d]pyrimidin-2-yl)-2-methyl-1H-indole-4-carboxamide
1-(4-(benzylamino)-6,7-dihydro-5H-pyrrolo[2,3-d]pyrimidin-2-yl)-6-fluoro-1H-indazole-4-carboxamide
1-(4-(benzylamino)-6,7-dihydro-5H-pyrrolo[2,3-d]pyrimidin-2-yl)-6-fluoro-2-methoxy-1H-benzo[d]imidazole-4-carboxamide
1-(4-(benzylamino)-6,7-dihydro-5H-pyrrolo[2,3-d]pyrimidin-2-yl)-6-fluoro-2-methyl-1H-indole-4-carboxamide
1-(4-(benzylamino)-6,7-dihydro-5H-pyrrolo[3,2-d]pyrimidin-2-yl)-1H-indazole-4-carboxamide
1-(4-(benzylamino)-6,7-dihydro-5H-pyrrolo[3,2-d]pyrimidin-2-yl)-2-methoxy-1H-benzo[d]imidazole-4-carboxamide
1-(4-(benzylamino)-6,7-dihydro-5H-pyrrolo[3,2-d]pyrimidin-2-yl)-2-methyl-1H-indole-4-carboxamide
1-(4-(benzylamino)-6,7-dihydro-5H-pyrrolo[3,2-d]pyrimidin-2-yl)-6-fluoro-1H-indazole-4-carboxamide
1-(4-(benzylamino)-6,7-dihydro-5H-pyrrolo[3,2-d]pyrimidin-2-yl)-6-fluoro-2-methoxy-1H-benzo[d]imidazole-4-carboxamide
1-(4-(benzylamino)-6,7-dihydro-5H-pyrrolo[3,2-d]pyrimidin-2-yl)-6-fluoro-2-methyl-1H-indole-4-carboxamide
1-(4-(benzylamino)-6,7-dihydro-5H-pyrrolo[3,4-d]pyrimidin-2-yl)-1H-indazole-4-carboxamide
1-(4-(benzylamino)-6,7-dihydro-5H-pyrrolo[3,4-d]pyrimidin-2-yl)-6-fluoro-1H-indazole-4-carboxamide
1-(4-(benzylamino)-6,7-dimethyl-5,6,7,8-tetrahydropyrido[3,4-d]pyrimidin-2-yl)-1H-indazole-4-carboxamide
1-(4-(benzylamino)-6,7-dimethyl-5,6,7,8-tetrahydropyrido[3,4-d]pyrimidin-2-yl)-2-methoxy-1H-benzo[d]imidazole-4-carboxamide
1-(4-(benzylamino)-6,7-dimethyl-5,6,7,8-tetrahydropyrido[3,4-d]pyrimidin-2-yl)-2-methyl-1H-indole-4-carboxamide
1-(4-(benzylamino)-6,7-dimethyl-5,6,7,8-tetrahydropyrido[4,3-d]pyrimidin-2-yl)-1H-indazole-4-carboxamide
1-(4-(benzylamino)-6,7-dimethyl-5,6,7,8-tetrahydropyrido[4,3-d]pyrimidin-2-yl)-2-methoxy-1H-benzo[d]imidazole-4-carboxamide
1-(4-(benzylamino)-6,7-dimethyl-5,6,7,8-tetrahydropyrido[4,3-d]pyrimidin-2-yl)-2-methyl-1H-indole-4-carboxamide
1-(4-(benzylamino)-6,8-dihydro-5H-pyrano[3,4-d]pyrimidin-2-yl)-1H-indazole-4-carboxamide
1-(4-(benzylamino)-6,8-dihydro-5H-pyrano[3,4-d]pyrimidin-2-yl)-6-fluoro-1H-indazole-4-carboxamide
1-(4-(benzylamino)-6,8-dimethyl-5,6,7,8-tetrahydropyrido[4,3-d]pyrimidin-2-yl)-1H-indazole-4-carboxamide
1-(4-(benzylamino)-6,8-dimethyl-5,6,7,8-tetrahydropyrido[4,3-d]pyrimidin-2-yl)-2-methyl-1H-indole-4-carboxamide
1-(4-(benzylamino)-6-methyl-5,6,7,8-tetrahydropyrido[3,4-d]pyrimidin-2-yl)-1H-indazole-4-carboxamide
1-(4-(benzylamino)-6-methyl-5,6,7,8-tetrahydropyrido[3,4-d]pyrimidin-2-yl)-2-methoxy-1H-benzo[d]imidazole-4-carboxamide
1-(4-(benzylamino)-6-methyl-5,6,7,8-tetrahydropyrido[3,4-d]pyrimidin-2-yl)-2-methyl-1H-indole-4-carboxamide
1-(4-(benzylamino)-6-methyl-5,6,7,8-tetrahydropyrido[4,3-d]pyrimidin-2-yl)-1H-indazole-4-carboxamide
1-(4-(benzylamino)-6-methyl-5,6,7,8-tetrahydropyrido[4,3-d]pyrimidin-2-yl)-2-methoxy-1H-benzo[d]imidazole-4-carboxamide
1-(4-(benzylamino)-6-methyl-5,6,7,8-tetrahydropyrido[4,3-d]pyrimidin-2-yl)-6-fluoro-1H-indazole-4-carboxamide
1-(4-(benzylamino)-6-methyl-6,7-dihydro-5H-pyrrolo[3,4-d]pyrimidin-2-yl)-1H-indazole-4-carboxamide
1-(4-(benzylamino)-6-methyl-6,7-dihydro-5H-pyrrolo[3,4-d]pyrimidin-2-yl)-6-fluoro-1H-indazole-4-carboxamide
1-(4-(benzylamino)-6-methyl-6,8-dihydro-5H-pyrano[3,4-d]pyrimidin-2-yl)-1H-indazole-4-carboxamide
1-(4-(benzylamino)-6-methyl-6,8-dihydro-5H-pyrano[3,4-d]pyrimidin-2-yl)-2-methoxy-1H-benzo[d]imidazole-4-carboxamide
1-(4-(benzylamino)-6-methyl-6,8-dihydro-5H-pyrano[3,4-d]pyrimidin-2-yl)-2-methyl-1H-indole-4-carboxamide
1-(4-(benzylamino)-7,8-dihydro-5H-pyrano[4,3-d]pyrimidin-2-yl)-1H-indazole-4-carboxamide
1-(4-(benzylamino)-7,8-dihydro-5H-pyrano[4,3-d]pyrimidin-2-yl)-6-fluoro-1H-indazole-4-carboxamide
1-(4-(benzylamino)-7,8-dimethyl-5,6,7,8-tetrahydropyrido[3,4-d]pyrimidin-2-yl)-1H-indazole-4-carboxamide
1-(4-(benzylamino)-7,8-dimethyl-5,6,7,8-tetrahydropyrido[3,4-d]pyrimidin-2-yl)-2-methoxy-1H-benzo[d]imidazole-4-carboxamide
1-(4-(benzylamino)-7,8-dimethyl-5,6,7,8-tetrahydropyrido[3,4-d]pyrimidin-2-yl)-2-methyl-1H-indole-4-carboxamide
1-(4-(benzylamino)-7-methyl-5,6,7,8-tetrahydropyrido[3,4-d]pyrimidin-2-yl)-1H-indazole-4-carboxamide
1-(4-(benzylamino)-7-methyl-5,6,7,8-tetrahydropyrido[3,4-d]pyrimidin-2-yl)-6-fluoro-1H-indazole-4-carboxamide
1-(4-(benzylamino)-7-methyl-5,6,7,8-tetrahydropyrido[4,3-d]pyrimidin-2-yl)-1H-indazole-4-carboxamide
1-(4-(benzylamino)-7-methyl-5,6,7,8-tetrahydropyrido[4,3-d]pyrimidin-2-yl)-2-methoxy-1H-benzo[d]imidazole-4-carboxamide
1-(4-(benzylamino)-7-methyl-5,6,7,8-tetrahydropyrido[4,3-d]pyrimidin-2-yl)-2-methyl-1H-indole-4-carboxamide
1-(4-(benzylamino)-7-methyl-5,6,7,8-tetrahydroquinazolin-2-yl)-1H-indazole-4-carboxamide
1-(4-(benzylamino)-7-methyl-5,6,7,8-tetrahydroquinazolin-2-yl)-2-methoxy-1H-benzo[d]imidazole-4-carboxamide
1-(4-(benzylamino)-7-methyl-5,6,7,8-tetrahydroquinazolin-2-yl)-2-methyl-1H-indole-4-carboxamide
1-(4-(benzylamino)-7-methyl-6,7-dihydro-5H-pyrrolo[2,3-d]pyrimidin-2-yl)-1H-indazole-4-carboxamide
1-(4-(benzylamino)-7-methyl-6,7-dihydro-5H-pyrrolo[2,3-d]pyrimidin-2-yl)-2-methoxy-1H-benzo[d]imidazole-4-carboxamide
1-(4-(benzylamino)-7-methyl-6,7-dihydro-5H-pyrrolo[2,3-d]pyrimidin-2-yl)-2-methyl-1H-indole-4-carboxamide 1-(4-(benzylamino)-7-methyl-6,7-dihydro-5H-pyrrolo[2,3-d]pyrimidin-2-yl)-6-fluoro-1H-indazole-4-carboxamide
1-(4-(benzylamino)-7-methyl-6,7-dihydro-5H-pyrrolo[2,3-d]pyrimidin-2-yl)-6-fluoro-2-methoxy-1H-benzo[d]imidazole-4-carboxamide
1-(4-(benzylamino)-7-methyl-6,7-dihydro-5H-pyrrolo[2,3-d]pyrimidin-2-yl)-6-fluoro-2-methyl-1H-indole-4-carboxamide
1-(4-(benzylamino)-7-methyl-7,8-dihydro-5H-pyrano[4,3-d]pyrimidin-2-yl)-1H-indazole-4-carboxamide
1-(4-(benzylamino)-7-methyl-7,8-dihydro-5H-pyrano[4,3-d]pyrimidin-2-yl)-2-methoxy-1H-benzo[d]imidazole-4-carboxamide
1-(4-(benzylamino)-7-methyl-7,8-dihydro-5H-pyrano[4,3-d]pyrimidin-2-yl)-2-methyl-1H-indole-4-carboxamide
1-(4-(benzylamino)-8-methyl-5,6,7,8-tetrahydropyrido[2,3-d]pyrimidin-2-yl)-1H-indazole-4-carboxamide
1-(4-(benzylamino)-8-methyl-5,6,7,8-tetrahydropyrido[2,3-d]pyrimidin-2-yl)-2-methoxy-1H-benzo[d]imidazole-4-carboxamide
1-(4-(benzylamino)-8-methyl-5,6,7,8-tetrahydropyrido[2,3-d]pyrimidin-2-yl)-2-methyl-1H-indole-4-carboxamide
1-(4-(benzylamino)-8-methyl-5,6,7,8-tetrahydropyrido[2,3-d]pyrimidin-2-yl)-6-fluoro-1H-indazole-4-carboxamide
1-(4-(benzylamino)-8-methyl-5,6,7,8-tetrahydropyrido[2,3-d]pyrimidin-2-yl)-6-fluoro-2-methoxy-1H-benzo[d]imidazole-4-carboxamide
1-(4-(benzylamino)-8-methyl-5,6,7,8-tetrahydropyrido[2,3-d]pyrimidin-2-yl)-6-fluoro-2-methyl-1H-indole-4-carboxamide
1-(4-(benzylamino)-8-methyl-5,6,7,8-tetrahydropyrido[3,4-d]pyrimidin-2-yl)-1H-indazole-4-carboxamide
1-(4-(benzylamino)-8-methyl-5,6,7,8-tetrahydropyrido[3,4-d]pyrimidin-2-yl)-2-methoxy-1H-benzo[d]imidazole-4-carboxamide
1-(4-(benzylamino)-8-methyl-5,6,7,8-tetrahydropyrido[3,4-d]pyrimidin-2-yl)-2-methyl-1H-indole-4-carboxamide
1-(4-(benzylamino)-8-methyl-5,6,7,8-tetrahydropyrido[4,3-d]pyrimidin-2-yl)-1H-indazole-4-carboxamide
1-(4-(benzylamino)-8-methyl-5,6,7,8-tetrahydropyrido[4,3-d]pyrimidin-2-yl)-2-methoxy-1H-benzo[d]imidazole-4-carboxamide
1-(4-(benzylamino)-8-methyl-5,6,7,8-tetrahydropyrido[4,3-d]pyrimidin-2-yl)-2-methyl-1H-indole-4-carboxamide
1-(4-(benzylamino)-8-methyl-5,6,7,8-tetrahydroquinazolin-2-yl)-1H-indazole-4-carboxamide
1-(4-(benzylamino)-8-methyl-5,6,7,8-tetrahydroquinazolin-2-yl)-2-methoxy-1H-benzo[d]imidazole-4-carboxamide
1-(4-(benzylamino)-8-methyl-5,6,7,8-tetrahydroquinazolin-2-yl)-2-methyl-1H-indole-4-carboxamide
1-(4-(benzylamino)-8-methyl-6,8-dihydro-5H-pyrano[3,4-d]pyrimidin-2-yl)-1H-indazole-4-carboxamide
1-(4-(benzylamino)-8-methyl-6,8-dihydro-5H-pyrano[3,4-d]pyrimidin-2-yl)-2-methoxy-1H-benzo[d]imidazole-4-carboxamide
1-(4-(benzylamino)-8-methyl-6,8-dihydro-5H-pyrano[3,4-d]pyrimidin-2-yl)-2-methyl-1H-indole-4-carboxamide
1-(4-(benzylamino)-8-methyl-7,8-dihydro-5H-pyrano[4,3-d]pyrimidin-2-yl)-1H-indazole-4-carboxamide
1-(4-(benzylamino)-8-methyl-7,8-dihydro-5H-pyrano[4,3-d]pyrimidin-2-yl)-2-methoxy-1H-benzo[d]imidazole-4-carboxamide
1-(4-(benzylamino)-8-methyl-7,8-dihydro-5H-pyrano[4,3-d]pyrimidin-2-yl)-2-methyl-1H-indole-4-carboxamide
2-(4-(aminomethyl)-2-methyl-1H-indol-1-yl)-N-benzyl-6,7-dihydro-5H-pyrano[2,3-d]pyrimidin-4-amine
2-(aminomethyl)-1-(4-(benzylamino)-6,7-dihydro-5H-pyrano[2,3-d]pyrimidin-2-yl)-1H-indole-4-carboxamide
3-(4-((3-fluorobenzyl)amino)-5,6,7,8-tetrahydropyrido[2,3-d]pyrimidin-2-yl)-2-methyl-1H-indole-7-carboxamide
3-(4-((3-fluorobenzyl)amino)-5,6,7,8-tetrahydropyrido[3,2-d]pyrimidin-2-yl)-2-methyl-1H-indole-7-carboxamide
3-(4-((3-fluorobenzyl)amino)-5,6,7,8-tetrahydropyrido[3,4-d]pyrimidin-2-yl)-2-methyl-1H-indole-7-carboxamide
3-(4-((3-fluorobenzyl)amino)-5,6,7,8-tetrahydropyrido[4,3-d]pyrimidin-2-yl)-2-methyl-1H-indole-7-carboxamide
3-(4-((3-fluorobenzyl)amino)-5,6,7,8-tetrahydroquinazolin-2-yl)-2-methyl-1H-indole-7-carboxamide
3-(4-((3-fluorobenzyl)amino)-5,6-dihydrofuro[2,3-d]pyrimidin-2-yl)-2-methyl-1H-indole-7-carboxamide
3-(4-((3-fluorobenzyl)amino)-5,7-dihydrofuro[3,4-d]pyrimidin-2-yl)-2-methyl-1H-indole-7-carboxamide
3-(4-((3-fluorobenzyl)amino)-5-methyl-5,6,7,8-tetrahydropyrido[3,2-d]pyrimidin-2-yl)-2-methyl-1H-indole-7-carboxamide
3-(4-((3-fluorobenzyl)amino)-5-methyl-6,7-dihydro-5H-pyrrolo[3,2-d]pyrimidin-2-yl)-2-methyl-1H-indole-7-carboxamide
3-(4-((3-fluorobenzyl)amino)-6,7,8,9-tetrahydro-5H-cyclohepta[d]pyrimidin-2-yl)-2-methyl-1H-indole-7-carboxamide
3-(4-((3-fluorobenzyl)amino)-6,7-dihydro-5H-cyclopenta[d]pyrimidin-2-yl)-2-methyl-1H-indole-7-carboxamide
3-(4-((3-fluorobenzyl)amino)-6,7-dihydro-5H-pyrano[2,3-d]pyrimidin-2-yl)-2-methyl-1H-indole-7-carboxamide
3-(4-((3-fluorobenzyl)amino)-6,7-dihydro-5H-pyrrolo[2,3-d]pyrimidin-2-yl)-2-methyl-1H-indole-7-carboxamide
3-(4-((3-fluorobenzyl)amino)-6,7-dihydro-5H-pyrrolo[3,2-d]pyrimidin-2-yl)-2-methyl-1H-indole-7-carboxamide
3-(4-((3-fluorobenzyl)amino)-6,7-dihydro-5H-pyrrolo[3,4-d]pyrimidin-2-yl)-2-methyl-1H-indole-7-carboxamide
3-(4-((3-fluorobenzyl)amino)-6,8-dihydro-5H-pyrano[3,4-d]pyrimidin-2-yl)-2-methyl-1H-indole-7-carboxamide
3-(4-((3-fluorobenzyl)amino)-6-methyl-5,6,7,8-tetrahydropyrido[4,3-d]pyrimidin-2-yl)-2-methyl-1H-indole-7-carboxamide
3-(4-((3-fluorobenzyl)amino)-6-methyl-6,7-dihydro-5H-pyrrolo[3,4-d]pyrimidin-2-yl)-2-methyl-1H-indole-7-carboxamide
3-(4-((3-fluorobenzyl)amino)-7,8-dihydro-5H-pyrano[4,3-d]pyrimidin-2-yl)-2-methyl-1H-indole-7-carboxamide
3-(4-((3-fluorobenzyl)amino)-7,8-dihydro-5H-pyrano[4,3-d]pyrimidin-2-yl)-2-methylbenzofuran-7-carboxamide
3-(4-((3-fluorobenzyl)amino)-7-methyl-5,6,7,8-tetrahydropyrido[3,4-d]pyrimidin-2-yl)-2-methyl-1H-indole-7-carboxamide
3-(4-((3-fluorobenzyl)amino)-7-methyl-6,7-dihydro-5H-pyrrolo[2,3-d]pyrimidin-2-yl)-2-methyl-1H-indole-7-carboxamide
3-(4-((3-fluorobenzyl)amino)-8-methyl-5,6,7,8-tetrahydropyrido[2,3-d]pyrimidin-2-yl)-2-methyl-1H-indole-7-carboxamide
3-(4-(benzylamino)-5,6,7,8-tetrahydropyrido[2,3-d]pyrimidin-2-yl)-2-methyl-1H-indole-7-carboxamide
3-(4-(benzylamino)-5,6,7,8-tetrahydropyrido[3,2-d]pyrimidin-2-yl)-2-methyl-1H-indole-7-carboxamide
3-(4-(benzylamino)-5,6,7,8-tetrahydropyrido[3,4-d]pyrimidin-2-yl)-2-methyl-1H-indole-7-carboxamide
3-(4-(benzylamino)-5,6,7,8-tetrahydropyrido[4,3-d]pyrimidin-2-yl)-2-methyl-1H-indole-7-carboxamide
3-(4-(benzylamino)-5,6,7,8-tetrahydroquinazolin-2-yl)-1H-indazole-7-carboxamide 3-(4-(benzylamino)-5,6,7,8-tetrahydroquinazolin-2-yl)-2-methyl-1H-indole-7-carboxamide
3-(4-(benzylamino)-5,6,7,8-tetrahydroquinazolin-2-yl)-2-methylbenzofuran-7-carboxamide
3-(4-(benzylamino)-5,6-dihydrofuro[2,3-d]pyrimidin-2-yl)-2-methyl-1H-indole-7-carboxamide
3-(4-(benzylamino)-5,7-dihydrofuro[3,4-d]pyrimidin-2-yl)-2-methyl-1H-indole-7-carboxamide
3-(4-(benzylamino)-5-methyl-5,6,7,8-tetrahydropyrido[3,2-d]pyrimidin-2-yl)-2-methyl-1H-indole-7-carboxamide
3-(4-(benzylamino)-5-methyl-6,7-dihydro-5H-pyrrolo[3,2-d]pyrimidin-2-yl)-2-methyl-1H-indole-7-carboxamide
3-(4-(benzylamino)-6,7,8,9-tetrahydro-5H-cyclohepta[d]pyrimidin-2-yl)-2-methyl-1H-indole-7-carboxamide
3-(4-(benzylamino)-6,7-dihydro-5H-cyclopenta[d]pyrimidin-2-yl)-2-methyl-1H-indole-7-carboxamide
3-(4-(benzylamino)-6,7-dihydro-5H-pyrano[2,3-d]pyrimidin-2-yl)-2-methyl-1H-indole-7-carboxamide
3-(4-(benzylamino)-6,7-dihydro-5H-pyrrolo[2,3-d]pyrimidin-2-yl)-2-methyl-1H-indole-7-carboxamide
3-(4-(benzylamino)-6,7-dihydro-5H-pyrrolo[3,2-d]pyrimidin-2-yl)-2-methyl-1H-indole-7-carboxamide
3-(4-(benzylamino)-6,7-dihydro-5H-pyrrolo[3,4-d]pyrimidin-2-yl)-2-methyl-1H-indole-7-carboxamide
3-(4-(benzylamino)-6,8-dihydro-5H-pyrano[3,4-d]pyrimidin-2-yl)-2-methyl-1H-indole-7-carboxamide
3-(4-(benzylamino)-6-methyl-5,6,7,8-tetrahydropyrido[4,3-d]pyrimidin-2-yl)-2-methyl-1H-indole-7-carboxamide
3-(4-(benzylamino)-6-methyl-6,7-dihydro-5H-pyrrolo[3,4-d]pyrimidin-2-yl)-2-methyl-1H-indole-7-carboxamide
3-(4-(benzylamino)-7,8-dihydro-5H-pyrano[4,3-d]pyrimidin-2-yl)-2-methyl-1H-indole-7-carboxamide
3-(4-(benzylamino)-7-methyl-5,6,7,8-tetrahydropyrido[3,4-d]pyrimidin-2-yl)-2-methyl-1H-indole-7-carboxamide
3-(4-(benzylamino)-7-methyl-6,7-dihydro-5H-pyrrolo[2,3-d]pyrimidin-2-yl)-2-methyl-1H-indole-7-carboxamide
3-(4-(benzylamino)-8-methyl-5,6,7,8-tetrahydropyrido[2,3-d]pyrimidin-2-yl)-2-methyl-1H-indole-7-carboxamide
N-benzyl-2-(2-methyl-1H-indol-3-yl)-5,6,7,8-tetrahydroquinazolin-4-amine
(1-(4-(benzylamino)-5,6,7,8-tetrahydropyrido[3,4-d]pyrimidin-2-yl)-1H-indazol-4-yl)methanol
(1-(4-(benzylamino)-5,6,7,8-tetrahydropyrido[4,3-d]pyrimidin-2-yl)-1H-indazol-4-yl)methanol
(1-(4-(benzylamino)-5,6,7,8-tetrahydroquinazolin-2-yl)-1H-indazol-4-yl)methanol
(1-(4-(benzylamino)-6,8-dihydro-5H-pyrano[3,4-d]pyrimidin-2-yl)-1H-indazol-4-yl)methanol
(1-(4-(benzylamino)-7,8-dihydro-5H-pyrano[4,3-d]pyrimidin-2-yl)-1H-indazol-4-yl)methanol
(1-(4-((3-fluorobenzyl)amino)-5,6,7,8-tetrahydropyrido[3,4-d]pyrimidin-2-yl)-1H-indazol-4-yl)methanol
(1-(4-((3-fluorobenzyl)amino)-5,6,7,8-tetrahydropyrido[4,3-d]pyrimidin-2-yl)-1H-indazol-4-yl)methanol
(1-(4-((3-fluorobenzyl)amino)-5,6,7,8-tetrahydroquinazolin-2-yl)-1H-indazol-4-yl)methanol
(1-(4-((3-fluorobenzyl)amino)-5,6-dimethyl-pyrimidin-2-yl)-1H-indazol-4-yl)methanol
(1-(4-((3-fluorobenzyl)amino)-6,8-dihydro-5H-pyrano[3,4-d]pyrimidin-2-yl)-1H-indazol-4-yl)methanol
(1-(4-((3-fluorobenzyl)amino)-7,8-dihydro-5H-pyrano[4,3-d]pyrimidin-2-yl)-1H-indazol-4-yl)methanol
1-(4-(benzylamino)-5,6,7,8-tetrahydropyrido[3,4-d]pyrimidin-2-yl)-1H-indazole-4-carboxylic acid
1-(4-(benzylamino)-5,6,7,8-tetrahydropyrido[4,3-d]pyrimidin-2-yl)-1H-indazole-4-carboxylic acid
1-(4-(benzylamino)-5,6,7,8-tetrahydroquinazolin-2-yl)-1H-indazole-4-carboxylic acid
1-(4-(benzylamino)-6,8-dihydro-5H-pyrano[3,4-d]pyrimidin-2-yl)-1H-indazole-4-carboxylic acid
1-(4-(benzylamino)-7,8-dihydro-5H-pyrano[4,3-d]pyrimidin-2-yl)-1H-indazole-4-carboxylic acid
1-(4-((3-fluorobenzyl)amino)-5,6,7,8-tetrahydropyrido[3,4-d]pyrimidin-2-yl)-1H-indazole-4-carboxylic acid
1-(4-((3-fluorobenzyl)amino)-5,6,7,8-tetrahydropyrido[4,3-d]pyrimidin-2-yl)-1H-indazole-4-carboxylic acid
1-(4-((3-fluorobenzyl)amino)-5,6,7,8-tetrahydroquinazolin-2-yl)-1H-indazole-4-carboxylic acid
1-(4-((3-fluorobenzyl)amino)-6,8-dihydro-5H-pyrano[3,4-d]pyrimidin-2-yl)-1H-indazole-4-carboxylic acid
1-(4-((3-fluorobenzyl)amino)-7,8-dihydro-5H-pyrano[4,3-d]pyrimidin-2-yl)-1H-indazole-4-carboxylic acid
2-(4-(aminomethyl)-1H-indazol-1-yl)-N-(3-fluorobenzyl)-5,6,7,8-tetrahydropyrido[3,4-d]pyrimidin-4-amine
2-(4-(aminomethyl)-1H-indazol-1-yl)-N-(3-fluorobenzyl)-5,6,7,8-tetrahydropyrido[4,3-d]pyrimidin-4-amine
2-(4-(aminomethyl)-1H-indazol-1-yl)-N-(3-fluorobenzyl)-5,6,7,8-tetrahydroquinazolin-4-amine
2-(4-(aminomethyl)-1H-indazol-1-yl)-N-(3-fluorobenzyl)-6,8-dihydro-5H-pyrano[3,4-d]pyrimidin-4-amine
2-(4-(aminomethyl)-1H-indazol-1-yl)-N-(3-fluorobenzyl)-7,8-dihydro-5H-pyrano[4,3-d]pyrimidin-4-amine
2-(4-(aminomethyl)-1H-indazol-1-yl)-N-benzyl-5,6,7,8-tetrahydropyrido[3,4-d]pyrimidin-4-amine
2-(4-(aminomethyl)-1H-indazol-1-yl)-N-benzyl-5,6,7,8-tetrahydropyrido[4,3-d]pyrimidin-4-amine
2-(4-(aminomethyl)-1H-indazol-1-yl)-N-benzyl-5,6,7,8-tetrahydroquinazolin-4-amine
2-(4-(aminomethyl)-1H-indazol-1-yl)-N-benzyl-6,8-dihydro-5H-pyrano[3,4-d]pyrimidin-4-amine
2-(4-(aminomethyl)-1H-indazol-1-yl)-N-benzyl-7,8-dihydro-5H-pyrano[4,3-d]pyrimidin-4-amine
N-((1-(4-(benzylamino)-5,6,7,8-tetrahydropyrido[3,4-d]pyrimidin-2-yl)-1H-indazol-4-yl)methyl)-2-methyl-propanamide
N-((1-(4-(benzylamino)-5,6,7,8-tetrahydropyrido[3,4-d]pyrimidin-2-yl)-1H-indazol-4-yl)methyl)acetamide
N-((1-(4-(benzylamino)-5,6,7,8-tetrahydropyrido[3,4-d]pyrimidin-2-yl)-1H-indazol-4-yl)methyl)ethanesulfonamide
N-((1-(4-(benzylamino)-5,6,7,8-tetrahydropyrido[3,4-d]pyrimidin-2-yl)-1H-indazol-4-yl)methyl)methanesulfonamide
N-((1-(4-(benzylamino)-5,6,7,8-tetrahydropyrido[3,4-d]pyrimidin-2-yl)-1H-indazol-4-yl)methyl)propanamide
N-((1-(4-(benzylamino)-5,6,7,8-tetrahydropyrido[3,4-d]pyrimidin-2-yl)-1H-indazol-4-yl)methyl)propane-2-sulfonamide
N-((1-(4-(benzylamino)-5,6,7,8-tetrahydropyrido[4,3-d]pyrimidin-2-yl)-1H-indazol-4-yl)methyl)-2-methyl-propanamide
N-((1-(4-(benzylamino)-5,6,7,8-tetrahydropyrido[4,3-d]pyrimidin-2-yl)-1H-indazol-4-yl)methyl)acetamide
N-((1-(4-(benzylamino)-5,6,7,8-tetrahydropyrido[4,3-d]pyrimidin-2-yl)-1H-indazol-4-yl)methyl)ethanesulfonamide
N-((1-(4-(benzylamino)-5,6,7,8-tetrahydropyrido[4,3-d]pyrimidin-2-yl)-1H-indazol-4-yl)methyl)methanesulfonamide
N-((1-(4-(benzylamino)-5,6,7,8-tetrahydropyrido[4,3-d]pyrimidin-2-yl)-1H-indazol-4-yl)methyl)propanamide
N-((1-(4-(benzylamino)-5,6,7,8-tetrahydropyrido[4,3-d]pyrimidin-2-yl)-1H-indazol-4-yl)methyl)propane-2-sulfonamide N-((1-(4-(benzylamino)-5,6,7,8-tetrahydroquinazolin-2-yl)-1H-indazol-4-yl)methyl)-2-methyl-propanamide
N-((1-(4-(benzylamino)-5,6,7,8-tetrahydroquinazolin-2-yl)-1H-indazol-4-yl)methyl)acetamide
N-((1-(4-(benzylamino)-5,6,7,8-tetrahydroquinazolin-2-yl)-1H-indazol-4-yl)methyl)ethanesulfonamide
N-((1-(4-(benzylamino)-5,6,7,8-tetrahydroquinazolin-2-yl)-1H-indazol-4-yl)methyl)methanesulfonamide
N-((1-(4-(benzylamino)-5,6,7,8-tetrahydroquinazolin-2-yl)-1H-indazol-4-yl)methyl)propanamide
N-((1-(4-(benzylamino)-5,6,7,8-tetrahydroquinazolin-2-yl)-1H-indazol-4-yl)methyl)propane-2-sulfonamide
N-((1-(4-(benzylamino)-6,8-dihydro-5H-pyrano[3,4-d]pyrimidin-2-yl)-1H-indazol-4-yl)methyl)-2-methyl-propanamide
N-((1-(4-(benzylamino)-6,8-dihydro-5H-pyrano[3,4-d]pyrimidin-2-yl)-1H-indazol-4-yl)methyl)acetamide
N-((1-(4-(benzylamino)-6,8-dihydro-5H-pyrano[3,4-d]pyrimidin-2-yl)-1H-indazol-4-yl)methyl)ethanesulfonamide
N-((1-(4-(benzylamino)-6,8-dihydro-5H-pyrano[3,4-d]pyrimidin-2-yl)-1H-indazol-4-yl)methyl)methanesulfonamide
N-((1-(4-(benzylamino)-6,8-dihydro-5H-pyrano[3,4-d]pyrimidin-2-yl)-1H-indazol-4-yl)methyl)propanamide
N-((1-(4-(benzylamino)-6,8-dihydro-5H-pyrano[3,4-d]pyrimidin-2-yl)-1H-indazol-4-yl)methyl)propane-2-sulfonamide
N-((1-(4-(benzylamino)-7,8-dihydro-5H-pyrano[4,3-d]pyrimidin-2-yl)-1H-indazol-4-yl)methyl)-2-methyl-propanamide
N-((1-(4-(benzylamino)-7,8-dihydro-5H-pyrano[4,3-d]pyrimidin-2-yl)-1H-indazol-4-yl)methyl)acetamide
N-((1-(4-(benzylamino)-7,8-dihydro-5H-pyrano[4,3-d]pyrimidin-2-yl)-1H-indazol-4-yl)methyl)ethanesulfonamide
N-((1-(4-(benzylamino)-7,8-dihydro-5H-pyrano[4,3-d]pyrimidin-2-yl)-1H-indazol-4-yl)methyl)methanesulfonamide
N-((1-(4-(benzylamino)-7,8-dihydro-5H-pyrano[4,3-d]pyrimidin-2-yl)-1H-indazol-4-yl)methyl)propanamide
N-((1-(4-(benzylamino)-7,8-dihydro-5H-pyrano[4,3-d]pyrimidin-2-yl)-1H-indazol-4-yl)methyl)propane-2-sulfonamide
N-((1-(4-((3-fluorobenzyl)amino)-5,6,7,8-tetrahydropyrido[3,4-d]pyrimidin-2-yl)-1H-indazol-4-yl)methyl)-2-methyl-propanamide
N-((1-(4-((3-fluorobenzyl)amino)-5,6,7,8-tetrahydropyrido[3,4-d]pyrimidin-2-yl)-1H-indazol-4-yl)methyl)acetamide
N-((1-(4-((3-fluorobenzyl)amino)-5,6,7,8-tetrahydropyrido[3,4-d]pyrimidin-2-yl)-1H-indazol-4-yl)methyl)ethanesulfonamide
N-((1-(4-((3-fluorobenzyl)amino)-5,6,7,8-tetrahydropyrido[3,4-d]pyrimidin-2-yl)-1H-indazol-4-yl)methyl)methanesulfonamide
N-((1-(4-((3-fluorobenzyl)amino)-5,6,7,8-tetrahydropyrido[3,4-d]pyrimidin-2-yl)-1H-indazol-4-yl)methyl)propanamide
N-((1-(4-((3-fluorobenzyl)amino)-5,6,7,8-tetrahydropyrido[3,4-d]pyrimidin-2-yl)-1H-indazol-4-yl)methyl)propane-2-sulfonamide
N-((1-(4-((3-fluorobenzyl)amino)-5,6,7,8-tetrahydropyrido[4,3-d]pyrimidin-2-yl)-1H-indazol-4-yl)methyl)-2-methyl-propanamide
N-((1-(4-((3-fluorobenzyl)amino)-5,6,7,8-tetrahydropyrido[4,3-d]pyrimidin-2-yl)-1H-indazol-4-yl)methyl)acetamide
N-((1-(4-((3-fluorobenzyl)amino)-5,6,7,8-tetrahydropyrido[4,3-d]pyrimidin-2-yl)-1H-indazol-4-yl)methyl)ethanesulfonamide
N-((1-(4-((3-fluorobenzyl)amino)-5,6,7,8-tetrahydropyrido[4,3-d]pyrimidin-2-yl)-1H-indazol-4-yl)methyl)methanesulfonamide
N-((1-(4-((3-fluorobenzyl)amino)-5,6,7,8-tetrahydropyrido[4,3-d]pyrimidin-2-yl)-1H-indazol-4-yl)methyl)propanamide
N-((1-(4-((3-fluorobenzyl)amino)-5,6,7,8-tetrahydropyrido[4,3-d]pyrimidin-2-yl)-1H-indazol-4-yl)methyl)propane-2-sulfonamide
N-((1-(4-((3-fluorobenzyl)amino)-5,6,7,8-tetrahydroquinazolin-2-yl)-1H-indazol-4-yl)methyl)-2-methyl-propanamide
N-((1-(4-((3-fluorobenzyl)amino)-5,6,7,8-tetrahydroquinazolin-2-yl)-1H-indazol-4-yl)methyl)acetamide
N-((1-(4-((3-fluorobenzyl)amino)-5,6,7,8-tetrahydroquinazolin-2-yl)-1H-indazol-4-yl)methyl)ethanesulfonamide
N-((1-(4-((3-fluorobenzyl)amino)-5,6,7,8-tetrahydroquinazolin-2-yl)-1H-indazol-4-yl)methyl)methanesulfonamide
N-((1-(4-((3-fluorobenzyl)amino)-5,6,7,8-tetrahydroquinazolin-2-yl)-1H-indazol-4-yl)methyl)propanamide
N-((1-(4-((3-fluorobenzyl)amino)-5,6,7,8-tetrahydroquinazolin-2-yl)-1H-indazol-4-yl)methyl)propane-2-sulfonamide
N-((1-(4-((3-fluorobenzyl)amino)-6,8-dihydro-5H-pyrano[3,4-d]pyrimidin-2-yl)-1H-indazol-4-yl)methyl)-2-methyl-propanamide
N-((1-(4-((3-fluorobenzyl)amino)-6,8-dihydro-5H-pyrano[3,4-d]pyrimidin-2-yl)-1H-indazol-4-yl)methyl)acetamide
N-((1-(4-((3-fluorobenzyl)amino)-6,8-dihydro-5H-pyrano[3,4-d]pyrimidin-2-yl)-1H-indazol-4-yl)methyl)ethanesulfonamide
N-((1-(4-((3-fluorobenzyl)amino)-6,8-dihydro-5H-pyrano[3,4-d]pyrimidin-2-yl)-1H-indazol-4-yl)methyl)methanesulfonamide
N-((1-(4-((3-fluorobenzyl)amino)-6,8-dihydro-5H-pyrano[3,4-d]pyrimidin-2-yl)-1H-indazol-4-yl)methyl)propanamide
N-((1-(4-((3-fluorobenzyl)amino)-6,8-dihydro-5H-pyrano[3,4-d]pyrimidin-2-yl)-1H-indazol-4-yl)methyl)propane-2-sulfonamide
N-((1-(4-((3-fluorobenzyl)amino)-7,8-dihydro-5H-pyrano[4,3-d]pyrimidin-2-yl)-1H-indazol-4-yl)methyl)-2-methyl-propanamide
N-((1-(4-((3-fluorobenzyl)amino)-7,8-dihydro-5H-pyrano[4,3-d]pyrimidin-2-yl)-1H-indazol-4-yl)methyl)acetamide
N-((1-(4-((3-fluorobenzyl)amino)-7,8-dihydro-5H-pyrano[4,3-d]pyrimidin-2-yl)-1H-indazol-4-yl)methyl)ethanesulfonamide
N-((1-(4-((3-fluorobenzyl)amino)-7,8-dihydro-5H-pyrano[4,3-d]pyrimidin-2-yl)-1H-indazol-4-yl)methyl)methanesulfonamide
N-((1-(4-((3-fluorobenzyl)amino)-7,8-dihydro-5H-pyrano[4,3-d]pyrimidin-2-yl)-1H-indazol-4-yl)methyl)propanamide
N-((1-(4-((3-fluorobenzyl)amino)-7,8-dihydro-5H-pyrano[4,3-d]pyrimidin-2-yl)-1H-indazol-4-yl)methyl)propane-2-sulfonamide Synthetic Methods The following section describes the preparation of representative compounds of the invention in greater detail. The following examples are offered for illustrative purposes, and are not intended to limit the invention in any manner. Those of skill in the art will readily recognize a variety of non-critical parameters which can be changed or modified to yield essentially the same results.

Those skilled in the art will recognize, or be able to ascertain using no more than routine experimentation, numerous equivalents to the syntheses of the compounds and methods of use thereof described herein. Although certain exemplary embodiments are depicted and described herein, it will be appreciated that compound of the invention can be prepared according to the methods generally available to one of ordinary skill in the art. All of the above-cited references and publications are hereby incorporated by reference.

Synthetic Preparation

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the alt. The chemistry of protecting groups can be found, for example, in Greene and Wuts, *Protective Groups in Organic Synthesis*, 44th. Ed., Wiley & Sons, 2006, as well as in Jerry March, *Advanced Organic Chemistry*, 4$^{th}$ edition, John Wiley & Sons, publisher, New York, 1992 which are incorporated herein by reference in their entirety.

The fused pyrimidine scaffolds can be prepared by the literature methods cited in the following text. The following schemes depict established, known syntheses of these scaffolds.

The Het moiety and the amine substituents of the fused pyrimidine scaffolds can be synthesized and attached to these scaffolds by the literature methods cited in the following text. The following schemes depict the known techniques for accomplishing this joinder.

General Synthetic Schemes for Fused Pyrmidines

Compounds of the present invention can be synthesized using the following methods. General reaction conditions are given and reaction products can be purified by general known methods including crystallization, silica gel chromatography using various organic solvents such as hexane, cyclohexane, ethyl acetate, methanol and the like, preparative high pressure liquid chromatography or preparative reverse phase high pressure liquid chromatography.

Scheme 01: general synthetic routes to prepare 2-chloro-substituted fused cycloalkylpyrimidines (Y is a sp$^3$ carbon)

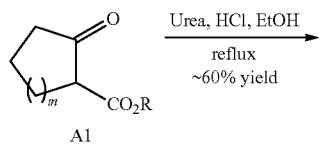

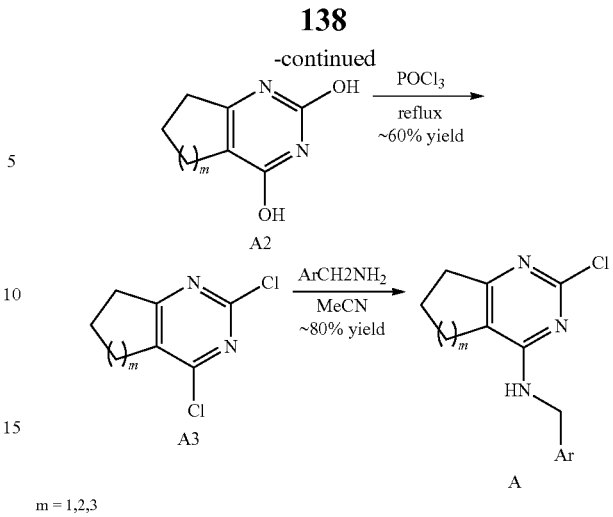

m = 1,2,3

A cyclic ketoester of the general structure A1 can be reacted with urea in the presence of acid such as HCl in a solvent such as ethanol at refluxing temperature for 2 to 24 hours to give the pyrimidine dione A2. Pyrimidinedione A2 can be reacted with an excess of POCl$_3$ at reflux for 3-12 hours optionally in the presence of a teriary amine such as triethyl amine to give the fused dicholorpyrmidine of the general structure A3. Other chlorinating agents such as thionyl chloride or PCl$_5$ can be substituted for POCl$_3$. A3 can be reacted with excess amounts of various substituted amines at temperatures ranging from room temperature to reflux in a solvent such as acetonitrile or dimethylformamide to give 4-amino-2-chloro fused pyrimidines of the general structure A.

Scheme 02: general synthetic routes to prepare 2-chloro-substituted fused dihydrofuropyrimidines or tetrahydropyranopyrimidines (Y is oxygen)

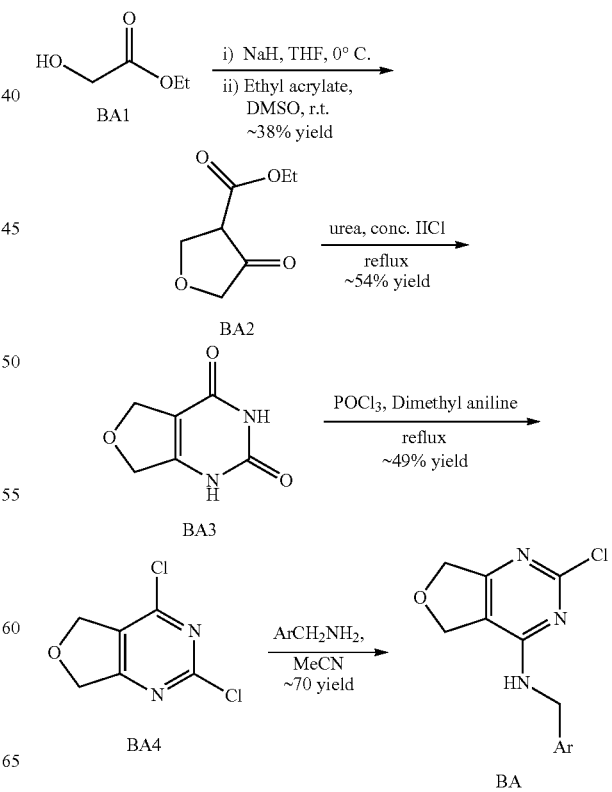

Similarly, 2-Cl-5,7-dihydrofuro[3,4-d]pyrimidin-4-amines BA can be prepared for the corresponding ketoester BA2, the later can be made from treatment 2-hydroxyacetate with ethyl acrylate in the presence of a strong base such as sodium hydride.

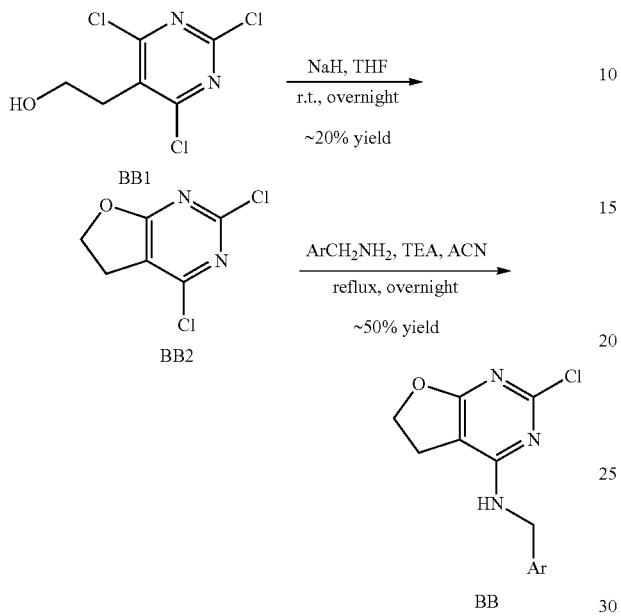

2-(2,4,6-trichloropyrimidin-5-yl)ethanol BB1 can be converted into the dichloride BB2 through intramolecular cyclization in the presence of a strong base such as sodium hydride at room temperature. Similarly, the latter can react with amines to yield 2-chloro-5,6-dihydrofuro[2,3-d]pyrimidin-4-amines BB.

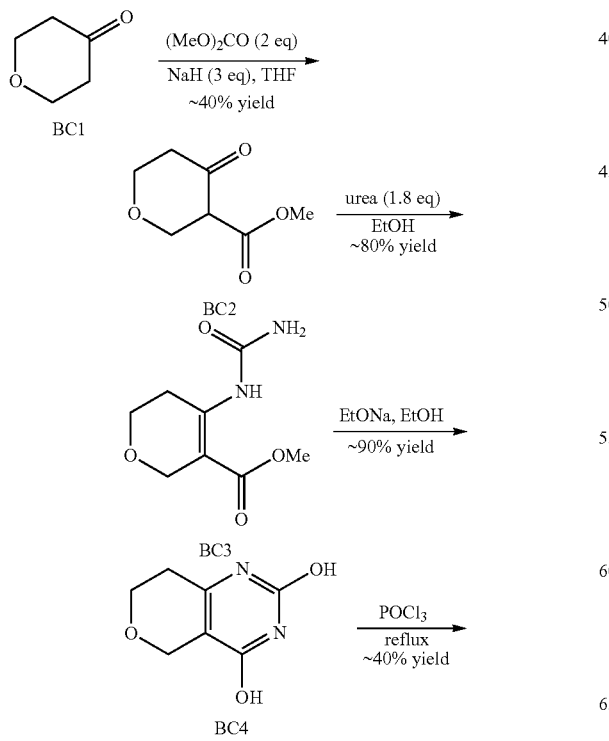

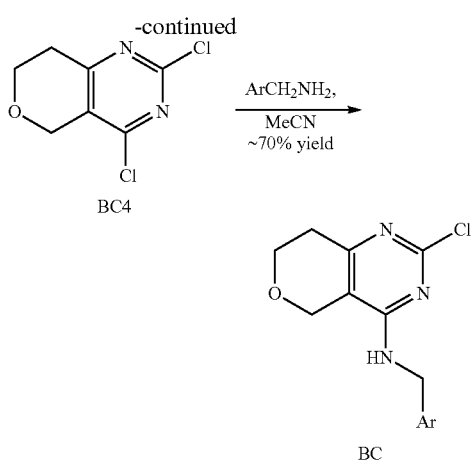

Tetrahydropyran-4-one BC1 can react with dimethylcarbonate in the presence of sodium hydride to 4-oxotetrahydro-2H-pyran-3-carboxylate BC2, the latter can be then converted into the corresponding diol BC4 in a two-step procedure through the intermediate of 4-ureido-5,6-dihydro-2H-pyran-3-carboxylate BC3. Similarly, the diol can be converted into 2-chloro-7,8-dihydro-5H-pyrano[4,3-d]pyrimidin-4-amines BC.

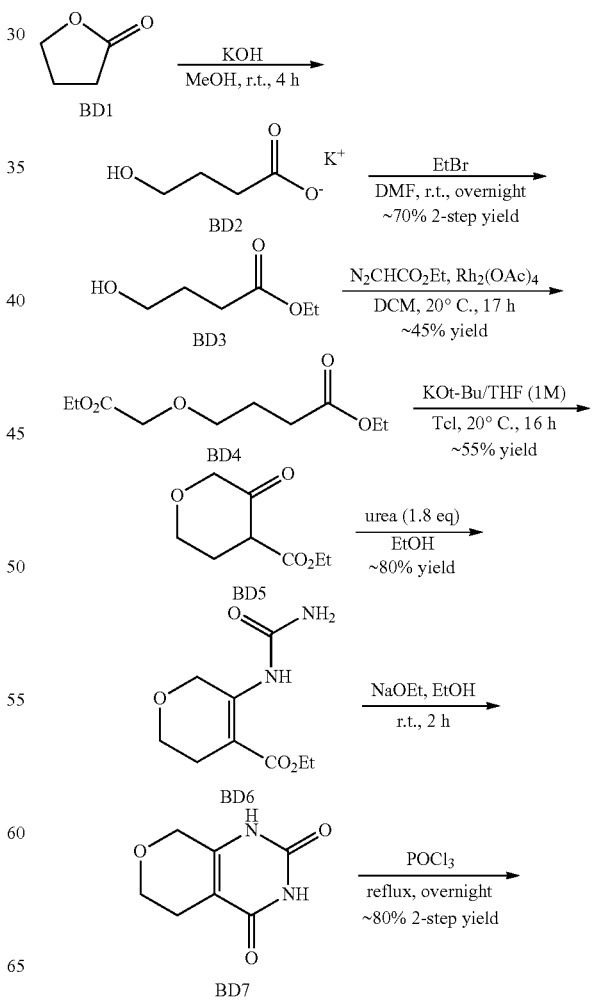

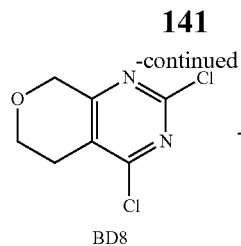

BD8

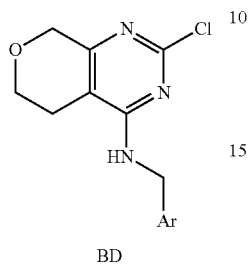

BD

Dihydrofuran-2(3H)-one BD1 can be converted into 4-hydroxybutanoate BD3 by hydrolysis using a strong base such as potassium hydroxide followed by treatment with an alkylbromide. It can react with 2-propionyldiazenecarbaldehyde in the presence of $Rh_2(OAc)_4$ to yield 4-(2-ethoxy-2-oxoethoxy)butanoate BD4, the latter can be converted into 3-oxotetrahydro-2H-pyran-4-carboxylate BD5 by treatment with potassium tert-butoxide. Then similar approach as used in preparation of BC can transfer the ketoester into 2-chloro-6,8-dihydro-5H-pyrano[3,4-d]pyrimidin-4-amines BD.

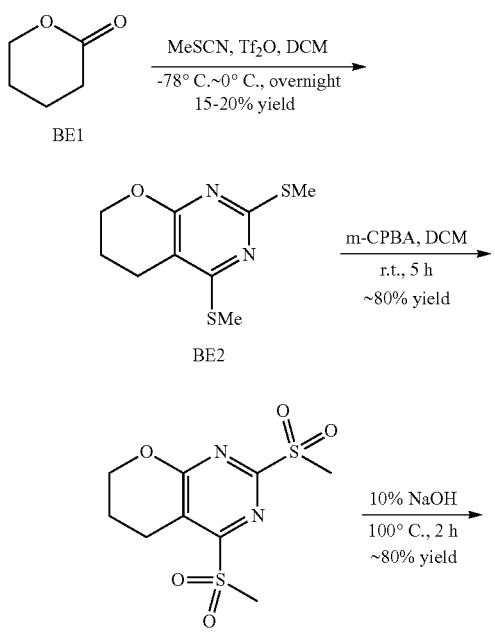

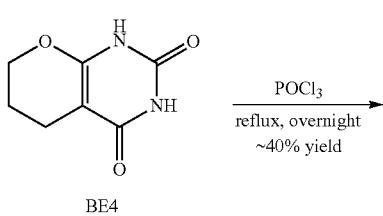

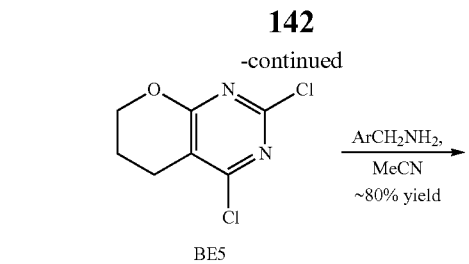

BE5

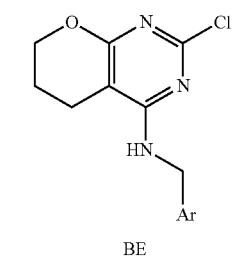

BE

Tetrahydro-2H-pyran-2-one BE1 can be converted into 2,4-bis(methylthio)-pyrimidine BE2 by a single step reaction with thiocyanatomethane in the presence of TFA though its yield is relatively low. The latter is then oxidized by m-CPBA into disulfone BE3. The sulfone can be hydrolysized into the diol BE4 using aqueous sodium hydroxide solution. Similarly, it can be then converted into 2-chloro-6,7-dihydro-5H-pyrano[2,3-d]pyrimidin-4-amines BE.

Scheme 03: general synthetic routes to prepare 2-chloro-substituted fused dihydropyrrolopyrimidines or tetrahydropyridopyrimidines (Y is nitrogen)

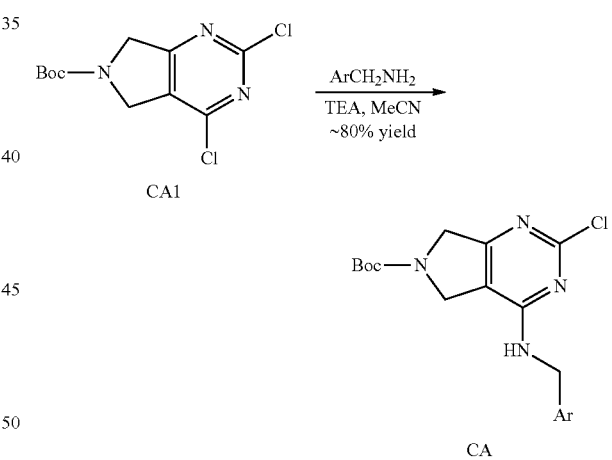

CA

Commercially available Boc-protected 2,4-dichloro-5H-pyrrolo[3,4-d]pyrimidine CA1 can be converted into the corresponding 2-chloro-6,7-dihydro-5H-pyrrolo[3,4-d]pyrimidin-4-amines CA in a similarly approach.

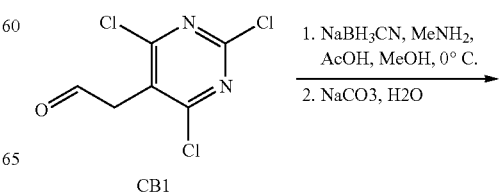

CB1

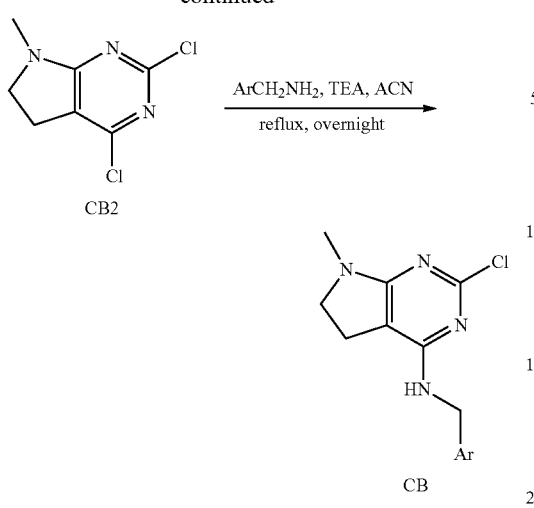

2-(2,4,6-trichloropyrimidin-5-yl)acetaldehyde CB1 can react with amines such as methylamine through reductive amination in the presence of NaBH3CN to yield 2,4-dichloride CB2 according to PCT Int. Appl., 2011152485, the latter can be easily converted into 2-chloro-6,7-dihydro-5H-pyrrolo[2,3-d]pyrimidin-4-amines CB in the aforementioned approach.

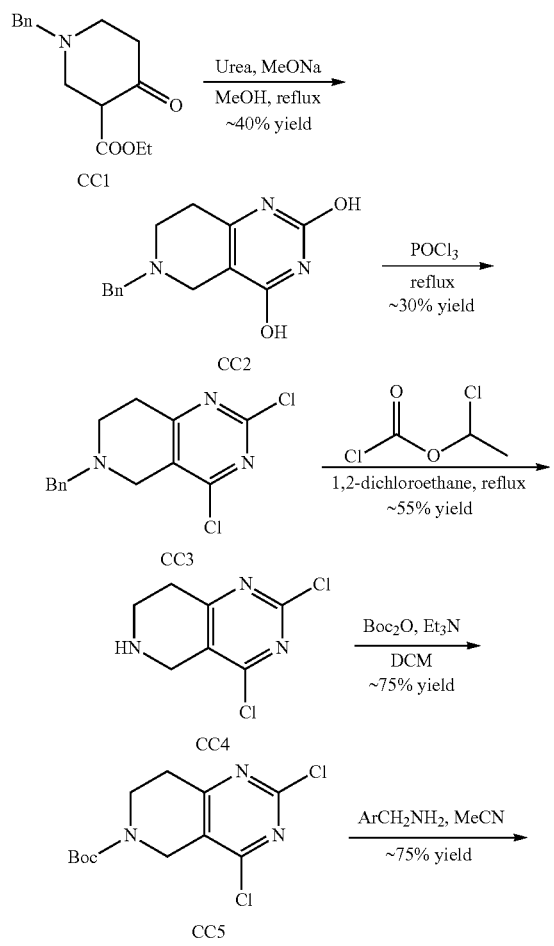

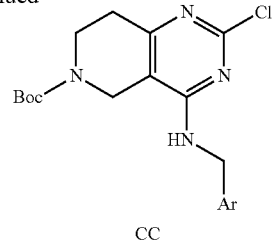

Benzyl protected 4-oxopiperidine-3-carboxylate CC1 can be converted into its diol CC2 by treatment with urea under basic conditions such as sodium methoxide. It is then transferred into the dichloride CC3 prior to switch protection group from benzyl group into Boc group considering it'd be challenge to remove benzyl group selectively once aromaticmethylamino group at 4-position of the pyrimidine. Similarly, Boc-protected dichloride CC5 can react with amines to yield Boc-protected 2-chloro-5,6,7,8-tetrahydropyrido[4,3-d]pyrimidin-4-amines CC.

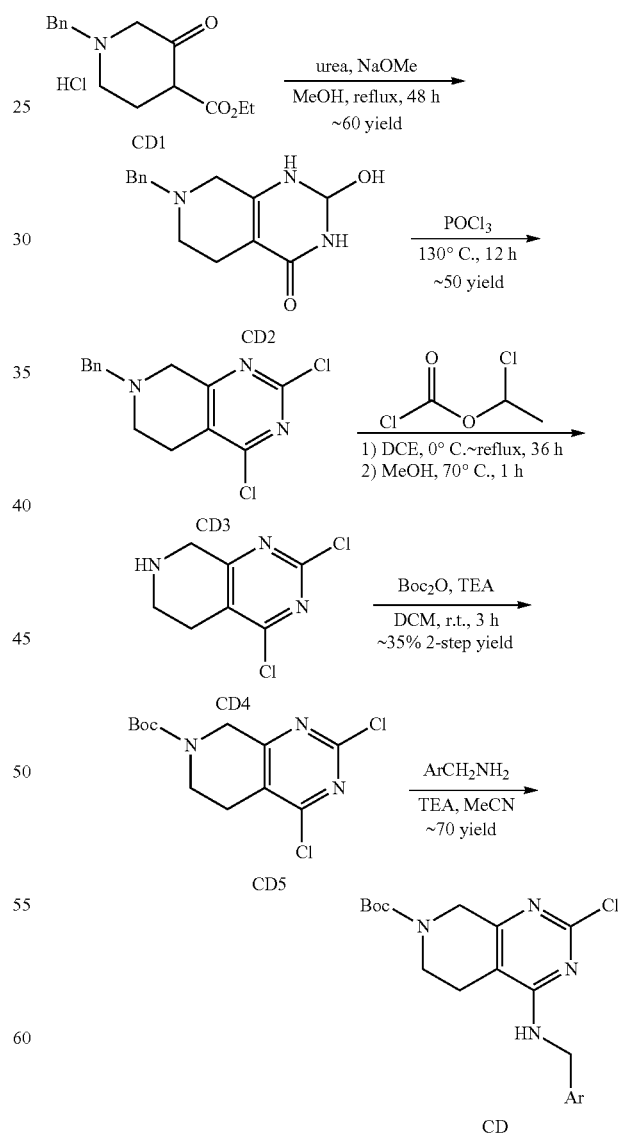

Similarly, Boc-protected 2-chloro-5,6,7,8-tetrahydropyrido[3,4-d]pyrimidin-4-amines CD can be prepared from 1-benzyl-3-oxopiperidine-4-carboxylate CD1.

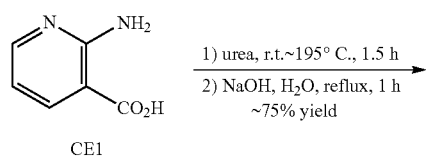
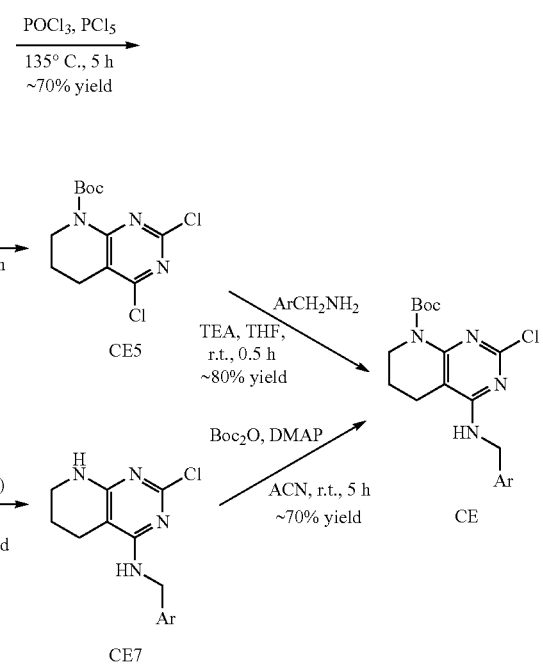

Region isomers CE, 2-chloro-5,6,7,8-tetrahydropyrido[2,3-d]pyrimidin-4-amines, can be prepared in couple of different approaches. 2-aminonicotinic acid CE1 can react with urea followed by hydrolysis to yield pyrido[2,3-d]pyrimidine-2,4-diol CE2, the latter can be easily converted into the dichloride CE3. CE3 can be selectively reduced into 2,4-dichloro-5,6,7,8-tetrahydropyrido[2,3-d]pyrimidine CE4 under hydrogen of one atmosphere pressure in the presence of $PtO_2$, thought the yield in general is relatively poor. Then introduction of Boc protection group on the amino group and replacement of 4-chloride with amines can yield CE. Alternatively, treatment CE3 with amines first followed by reduction by hydrogen of higher pressure can achieve better yield.

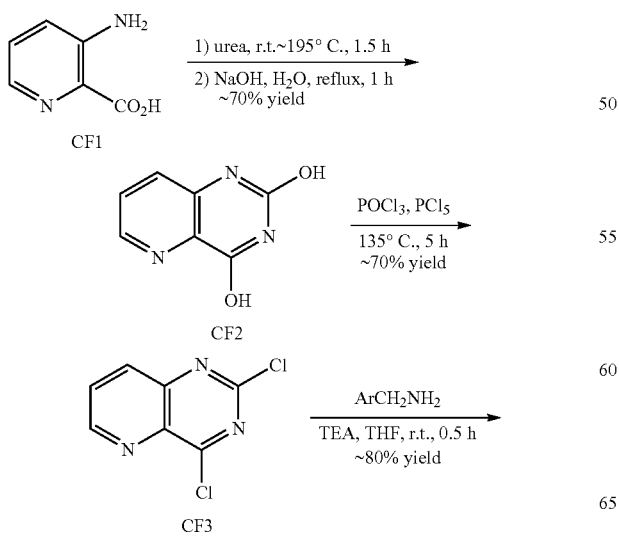

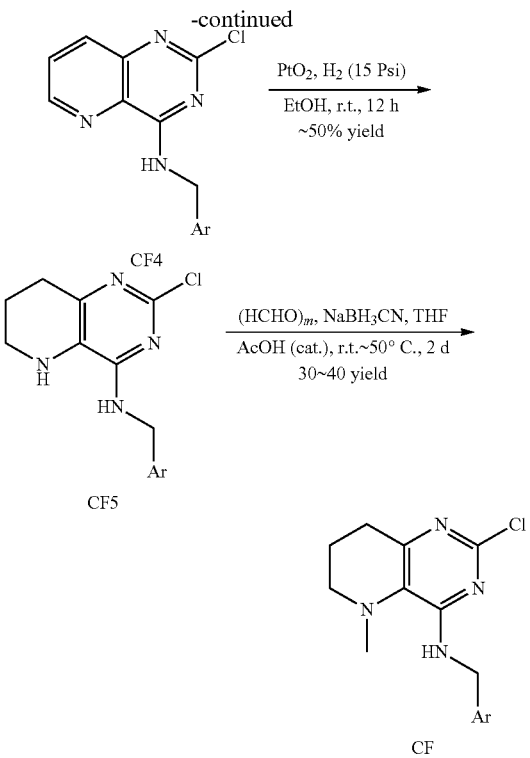

A similar approach can be utilized to prepare another set of region isomers, 2-chloro-5,6,7,8-tetrahydropyrido[3,2-d]pyrimidin-4-amines CF. 3-aminopicolinic acid CF1 is the starting material. Due to substitution on 4-position of the pyrimidine, it can be challenge to introduce protection groups such as Boc to protect the amino group in a reasonable yield, instead, small alkyl groups such as methyl can be easily inserted.

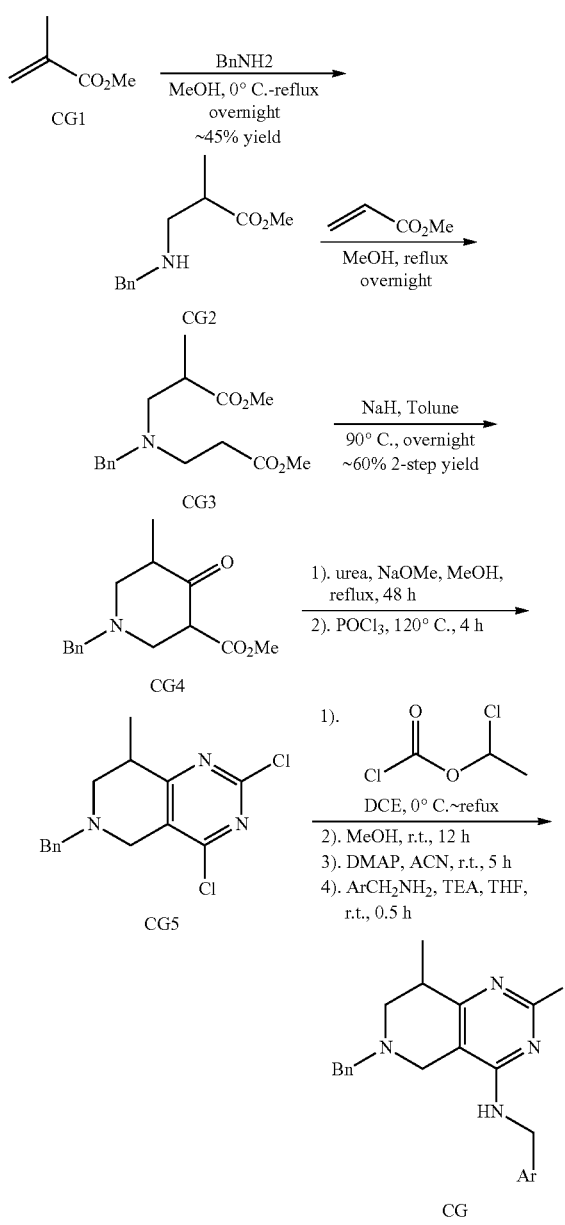

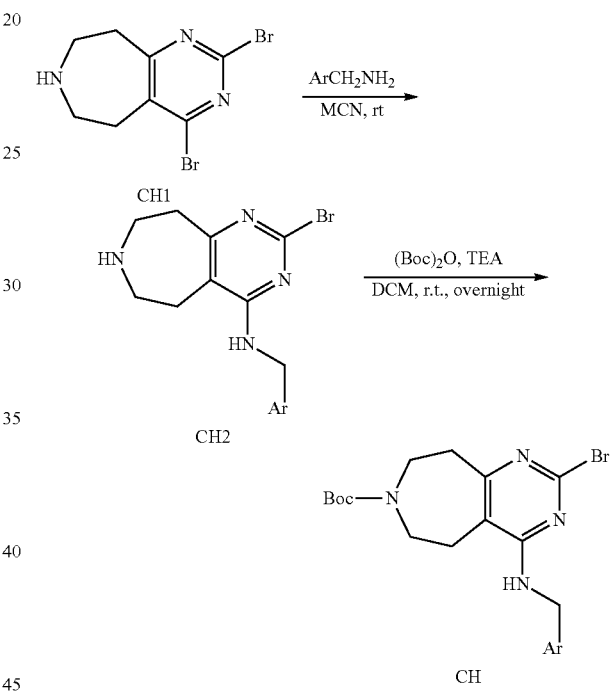

prepared using the aforementioned approaches as long as their corresponding ketoester can be prepared. For example, 1-benzyl-5-methyl-4-oxopiperidine-3-carboxylate can be prepared in a three-step procedure from methyl methacrylate CG1. 3-(benzylamino)-2-methylpropanoate can be prepared from Michael addition between methacrylate CG1 and benzylamine, similarly one more Michael addition with acrylate can yield 3-(benzyl(3-methoxy-3-oxopropyl)amino)-2-methylpropanoate CG3. An intramolecular cyclization of CG3 in presence of sodium hydride at reflux can yield 1-benzyl-5-methyl-4-oxopiperidine-3-carboxylate CG4. Then a similar route as aforementioned can achieve 2-chloro-8-methyl-5,6,7,8-tetrahydropyrido[4,3-d]pyrimidin-4-amines CG. Similar strategy can be utilized to prepare tetrahydropyridopyrimidin-4-amines with alkyl group substituted on other positions or chiral derivatives if chiral acrylates were used as starting material.

2,4-Dibromo-6,7,8,9-tetrahydro-5H-pyrimido[4,5-d]azepine CH1 can be reacted with an amine to selectively yield the intermediate CH2, the later can be Boc-protected by reaction with Boca hydride to yield CH.

5,6,7,8-tetrahydropyridopyrimidin-4-amines with alkyl group on their carbon of the saturated ring can also be Scheme 04: general synthetic routes to prepare 2-(1H-benzo[d]imidazol-1-yl)-substituted saturated fused pyrimidines (DA)

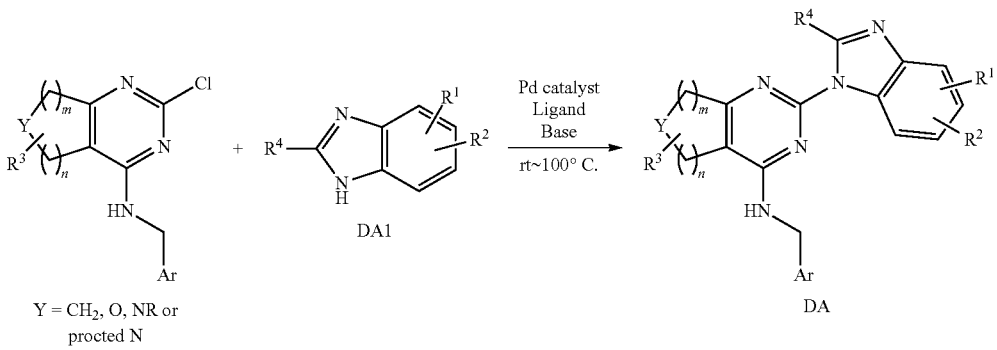

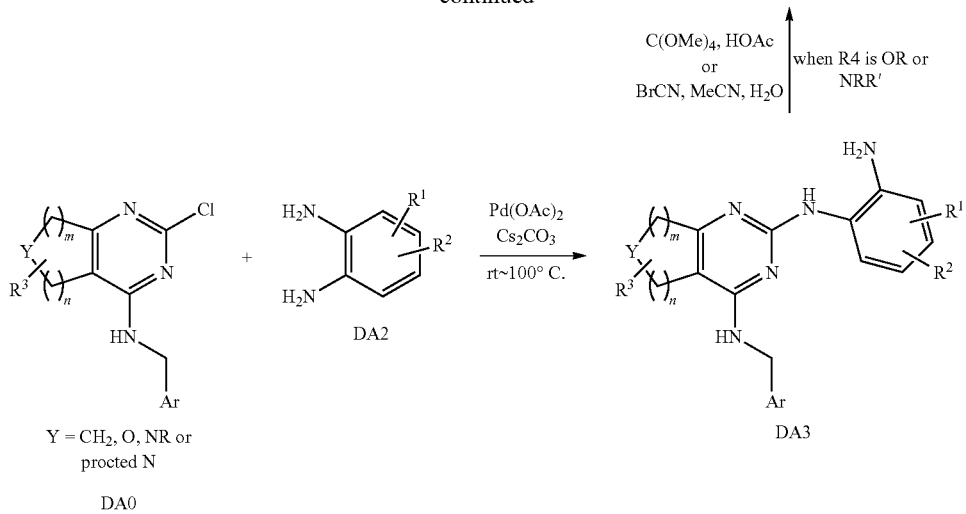

A general synthetic approach to install benzo[d]imidazole DA1 through its 1-position into the 2-position of fused pyrimidine to yield the desired molecules DA is Pd-based coupling reaction. A common condition is Pd(dba)$_2$ as a transition metal catalyst and X-phos as a ligand and cesium carbonate as a base and dioxane an organic solvent. The reaction temperature varies from the room temperature to reflux. For example if Y is Boc-protected nitrogen, an extra step to deBoc can be achieved. For example if R$^1$ is a nitrile (CN) it can be converted to an amide in the presence of urea hydrogen peroxide (UHP). Alternatively, in some cases of R$^4$ is alkoxy or amino groups, coupling reaction can be take place between the 2-chloro-pyrimidine DA0 and benzene-1,2-diamines DA2 suing Pd(OAc)$_2$ as the catalyst and CsCO$_3$ as the base, then cyclization can occur with either bromocyanide or tetramethoxymethane.

Scheme 05: general synthetic routes to prepare 2-(1H-indol-1-yl or 1H-indazol-1-yl)-substituted saturated fused pyrimidines (DB)

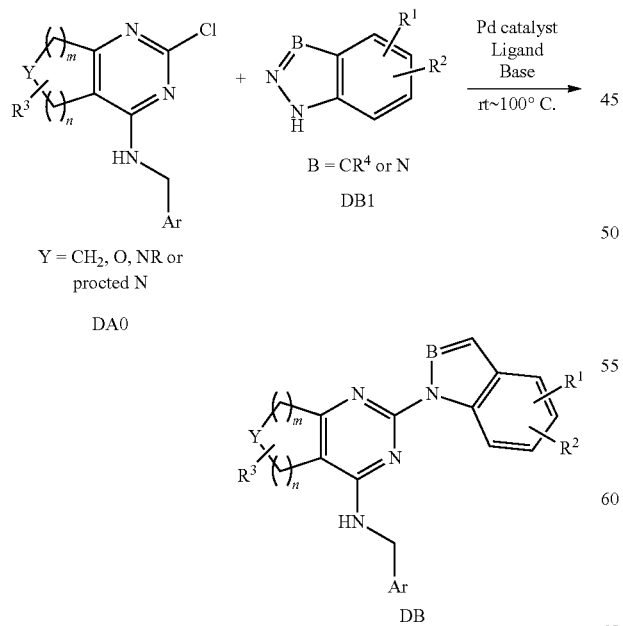

Coupling to a solution of the substituted pyrimidine DA0 with an indole or inadazole DB1 can be effective to achieve the desired molecules DB using methods similar to that described in Zhou, H.-J. et. al. WO 2014015291. To a solution of substituted pyrimidine such as compound DA0 is added a indole or a substituted ones such as compound DB1 and a base such as sodium carbonate or cesium carbonate, in the presence of a palladium catalyst such as Pd(OAc)$_2$ and a ligand such as triphenylphosphine in a solvent such as dioxane and the reaction can optionally be heated to reflux for up to 48 hours.

Scheme 06: general synthetic routes to prepare 2-(1H-benzo[d][1,2,3] triazol-1-yl)-substituted saturated fused pyrimidines (DC)

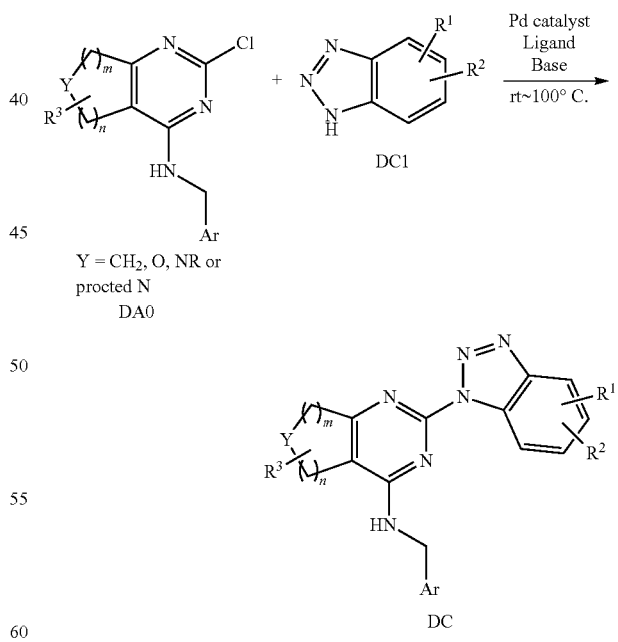

Compounds containing the structure of 1-pyrimidin-2-yl-1,2,3-benzotriazoles DC can be produced using methods similar to those described in Zhou, H.-J. et. al. WO 2014015291 and Ohlmeyer, Michael J. et al WO 2008060301 and as described above by using a substituted 1,2,3-benzotriazole DC1.

Scheme 07: general synthetic routes to prepare 2-(1H-indol-3-yl or benzofuran-3-yl or benzo[b]thiophen-3-yl)-substituted saturated fused pyrimidines (DD)

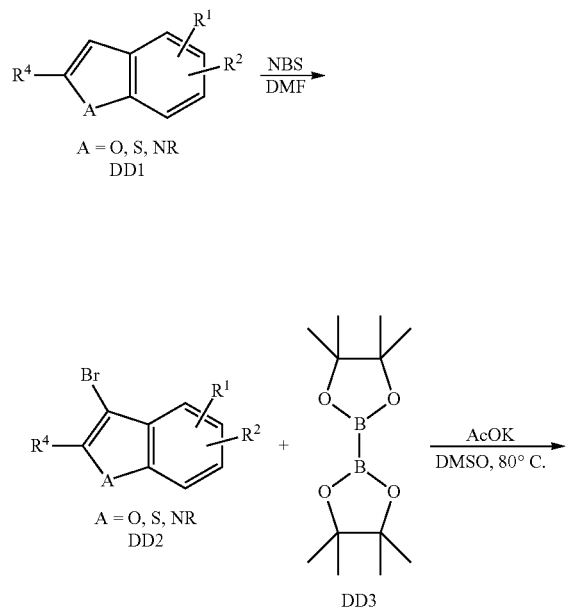

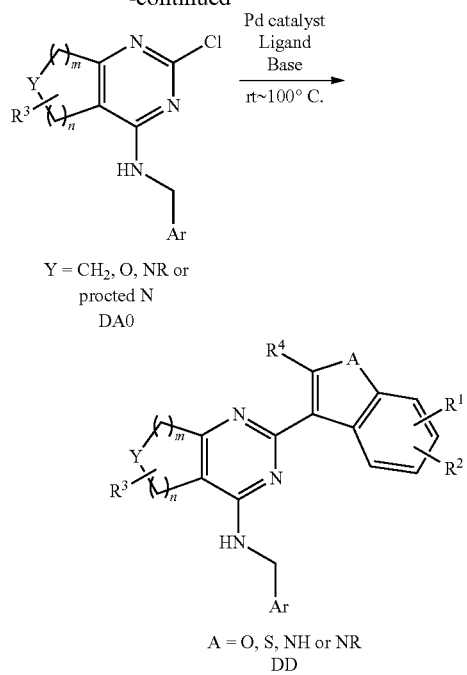

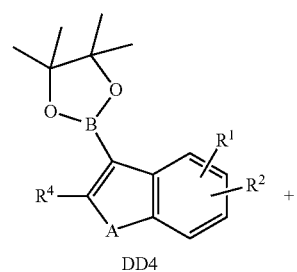

Under various conditions such as NBS in DMF, bromination of 3-unsubstituted intermediates DD1 (X=O, S, either substituted or properly protected nitrogen) would take place region-selectively on their 3-position to yield 3-Br-substituted intermediates DD2. They then can be converted into boronic esters DD4 by treatment with boronic ester DD3 under various conditions. Then Pd-based coupling reaction similar to those described in Zhou, H.-J. et. al. WO 2014015291 between intermediates DD4 and DA0 provided the desired molecules. For example if Y or A is protected nitrogen, an extra step to deprotection can be achieved using reported conditions.

Scheme 08: general synthetic routes to prepare 2-(benzo[d]isoxazol-3-yl or benzo[d]isothiazol-3-yl, 1H-indazol-3-yl)-substituted saturated fused pyrimidines (DE)

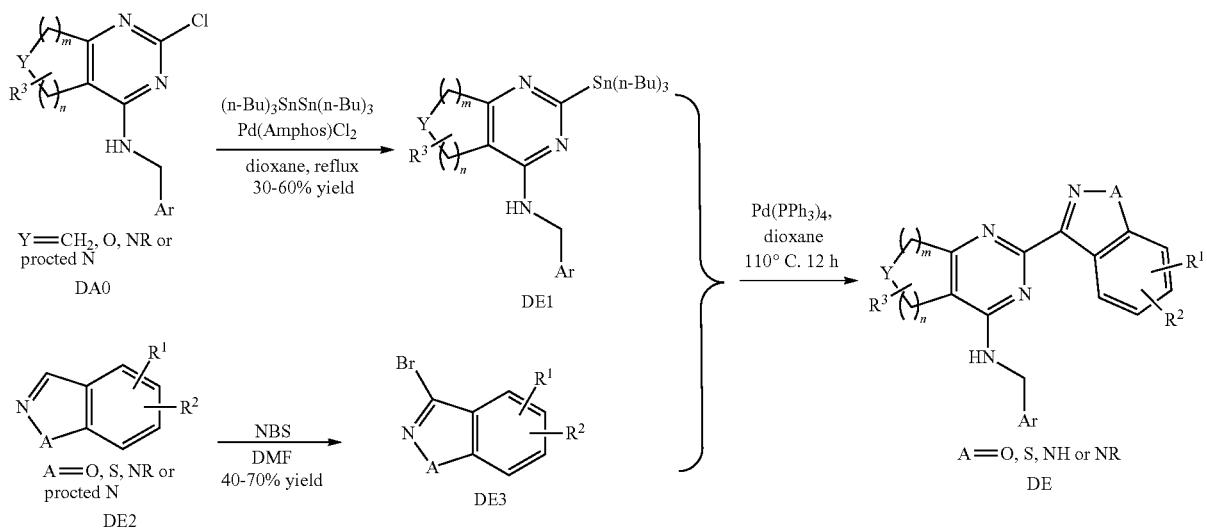

The key intermediate DE1, tributyl-2-pyrmidinyltin can be prepared from the intermediates DA0 following the similar procedure in the reference (Castanedo, Georgette et al, PCT Int. Appl., 2010138589). Bromonation can occur selectively into the 3-position of these 5,6-bicycloaromatic rings. Then Pd-based coupling reaction similar to those described in Zhou, H.-J. et. al. WO 2014015291 between intermediates DE1 and DE2 provided the desired molecules DE. For example if Y or A is protected nitrogen, an extra step to deprotection can be achieved using reported conditions.

Scheme 09: general synthetic routes to prepare 2-(imidazo[1,5-a]pyridin-1-yl)-substituted saturated fused pyrimidines (DF)

Method A:

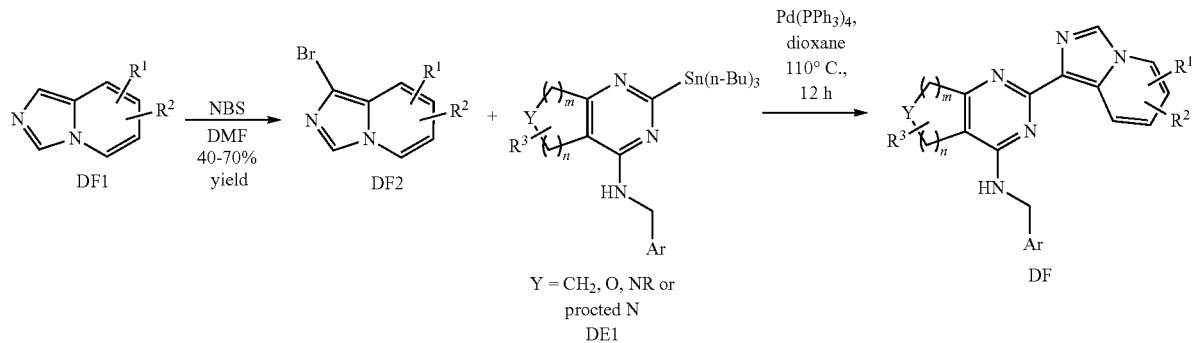

Method B:

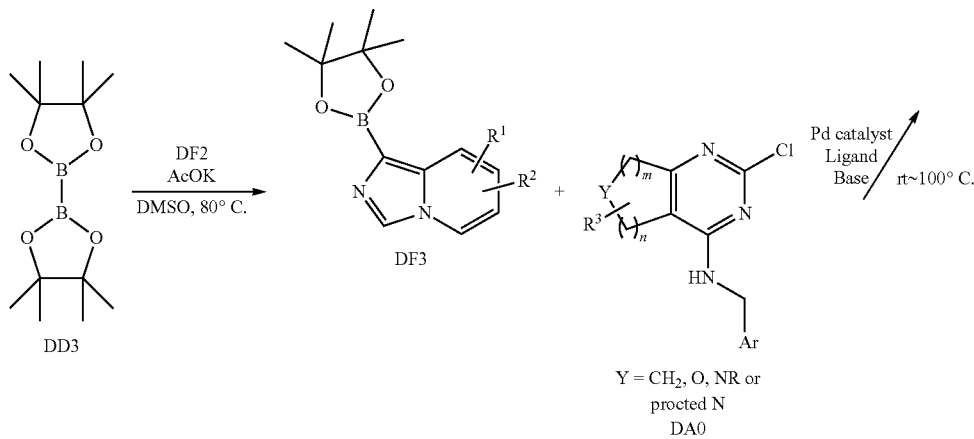

Bromonation can occur selectively into the 3-position of imidazo[1,5-a]pyridine DF1. Then Pd-based coupling reaction similar to those described above between intermediates DE1 and DF2 provided the desired molecules DF. For example if Y is protected nitrogen, an extra step to deprotection can be achieved using reported conditions.

Alternatively, bromides DF2 can be converted into boronic esters DF3 by treatment with boronic ester DD3 under various conditions. Then Pd-based coupling reaction similar to those described above between intermediates DF3 and DA0 provided the desired molecules. For example if Y or A is protected nitrogen, an extra step to deprotection can be achieved using reported conditions.

Scheme 10: general synthetic routes to prepare 2-(imidazo[1,5-a]pyridin-1-yl)-substituted saturated fused pyrimidines (DG)
Method A:
Method B:
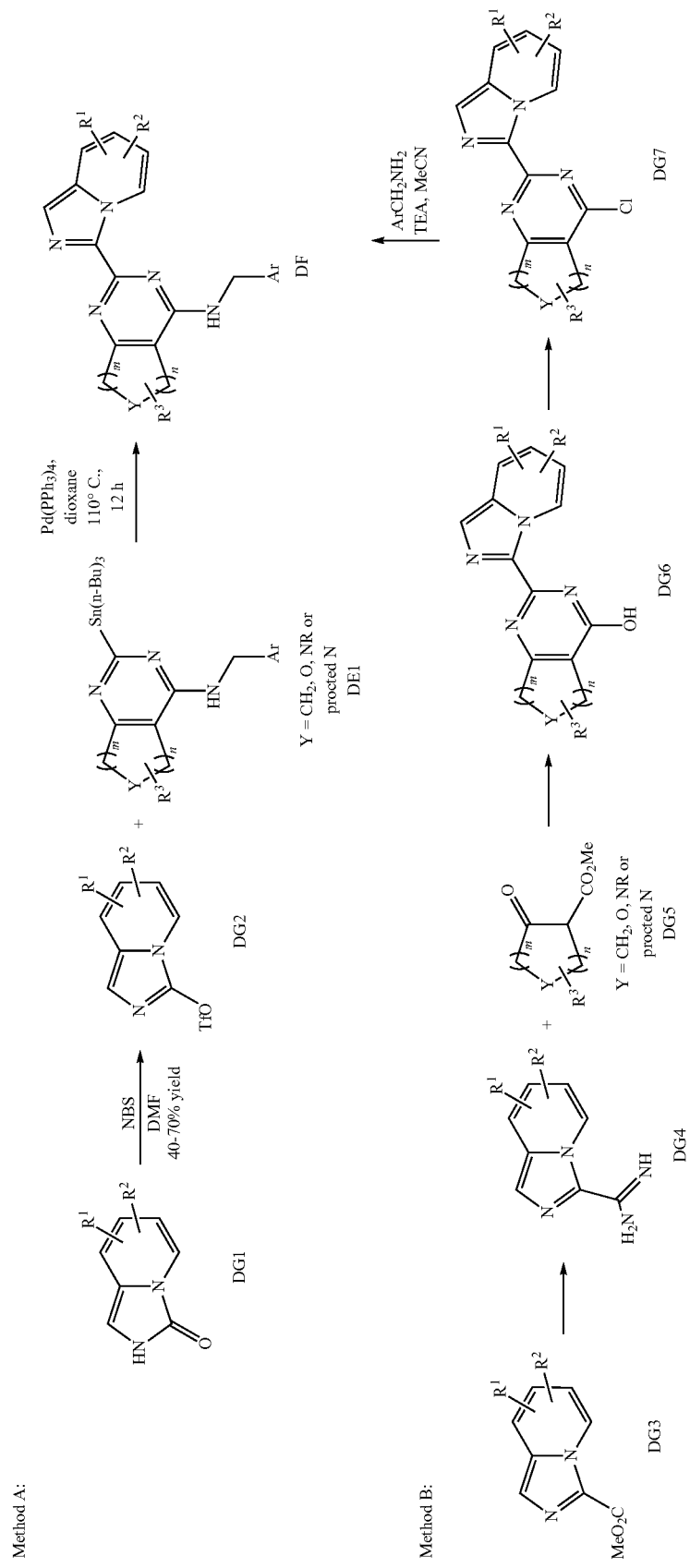

Imidazo[1,5-a]pyridin-3(2H)-one DG1 can be converted into its triflate DG2. Then Pd-based coupling reaction similar to those described above between intermediates DE1 and DG2 provided the desired molecules DG. For example if Y is protected nitrogen, an extra step to deprotection can be achieved using reported conditions.

Alternatively, substituted imidazo[1,5-a]pyridine-3-carboxylate esters DG3 can be prepared by various methods including those outlined in Chen, Shaoqing et al WO 2013030138, Bilodeau, and Mark T. et al WO 2008085302. An imidazo[1,5-a]pyridine-3-carboxylate ester DG3 can be converted into the corresponding amidine DG4 using aminochloromethyl aluminum in an organic solvent such as toluene at a temperate between ambient and 100° C. as described in Brockunier L. et. al. WO 2010065275 and Gargiapati R. S. Tetrahedron Letters 1990, 31, 1969. The resulting imidazo[1,5-a]pyridine-3-carboxamidine DG4 can be reacted with the aforementioned ketoesters DG5 in the presence of a catalytic amount of a base such as sodium ethoxide in ethanol at reflux to give the pyrimidin-4-ol DG6. The latter can be converted into the desired molecules DG using the methods described above.

Scheme 11: general synthetic routes to prepare 2-(imidazo[1,2-a]pyridin-3-yl)-, or 2-([1,2,4]triazolo[4,3,-a]pyridin-3-yl)-substituted saturated fused pyrimidines (DH)

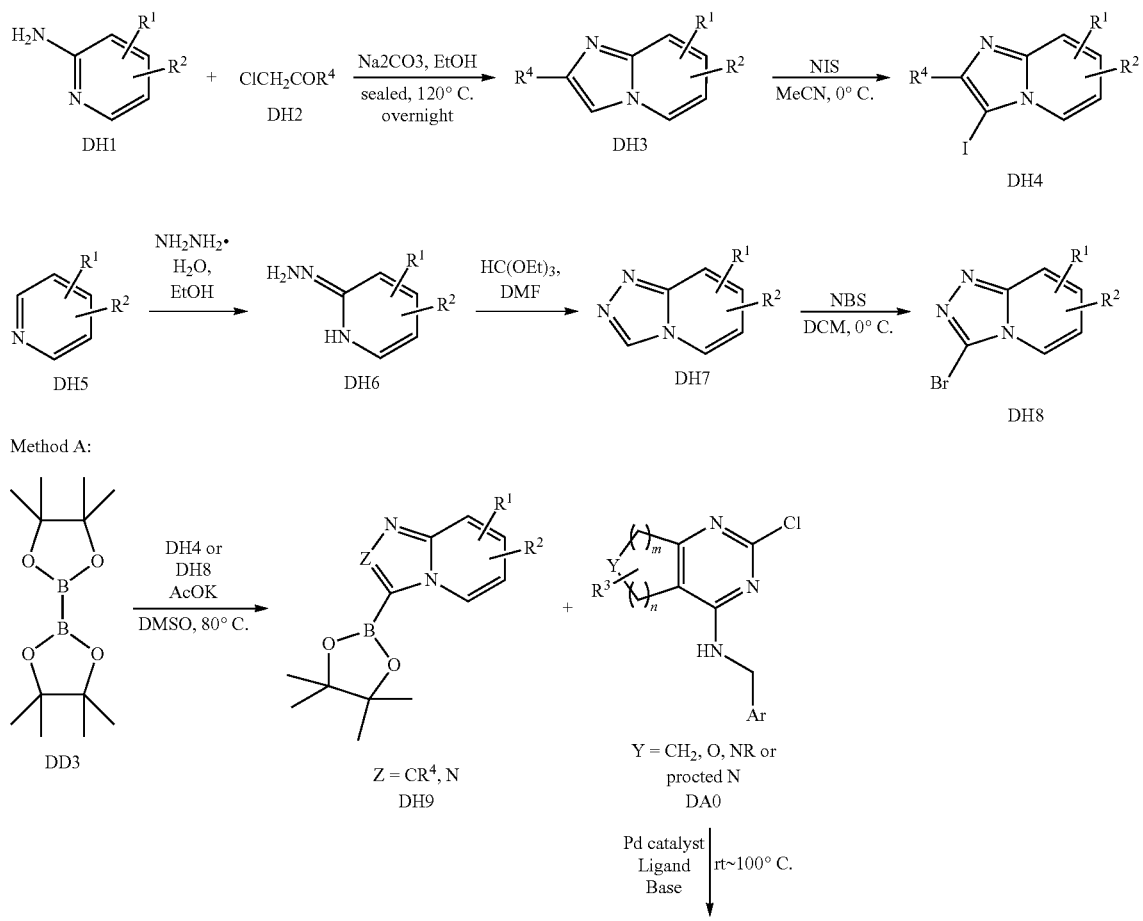

Method B:

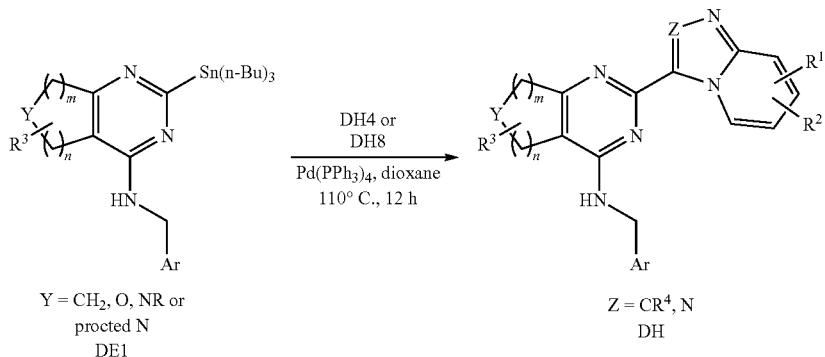

Imidazo[1,2-a]pyridine DH3 can be prepared by treatment 2-aminopyridine DH1 with aldehydes or ketones DH2 by a method similar to those described in described in the references such as Ebetino, Frank Hallock et al. PCT Int. Appl., 2010033978. Iodination with NIS can yield 3-I-Imidazo[1,2-a]pyridine DH4 by a method similar to those described in described in the references such as Bifulco, Neil, Jr. et al. PCT Int. Appl., 2014011900. [1,2,4]triazolo[4,3-a]pyridine-8-carbonitrile DH7 can be prepared by substituted pyridine DH5 in a two-step procedures, reaction with hydrazine followed by treatment with triethoxymethane by a method similar to those described in described in the references such as such as Allen, Shelley et al, PCT Int. Appl., 2010022076; Potts, K. T. and Burton, H. R., Journal of Organic Chemistry, 31(1), 251-60; 1966. Then bromination with NBS can yield the intermediate DH8. DH4 or DH8 can be converted into boronic esters DH9 then by treatment with boronic ester DD3 under various conditions. Then Pd-based coupling reaction similar to those described above between intermediates DH9 and DA0 provided the desired molecules DH. Alternatively, Pd-based coupling reaction similar to those described above between intermediates DE1 and DH4 or DH8 provided the desired molecules DH as well. For example if Y is protected nitrogen, an extra step to deprotection can be achieved using reported conditions.

Scheme 12: general synthetic routes to prepare 2-(pyrazolo[1,5-a]pyridin-3-yl)- or 2-([1,2,3]triazolo[1,5-a]pyridin-3-yl)-substituted saturated fused pyrimidines (DI)

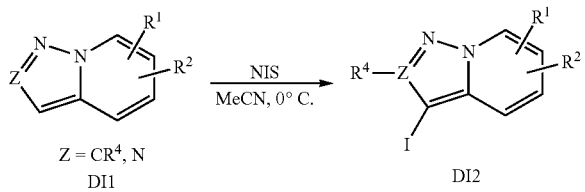

Method A:

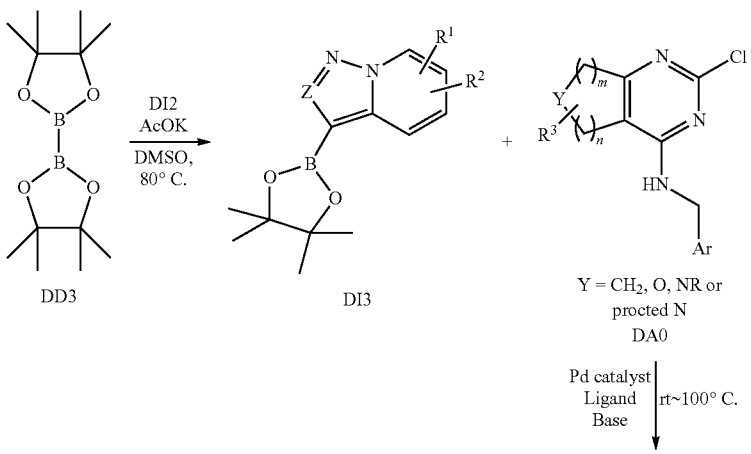

Method B:

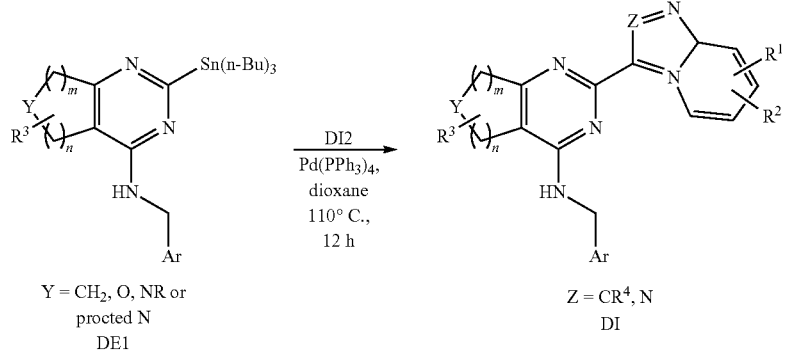

Various methods can be used to prepare substituted 3-pyrimidin-2-ylpyrazolo[1,5-a]pyridines DI1 (Z=$CR^4$) as outlined in Tsuchiya, et. al. Chemical & Pharmaceutical Bulletin 1983, 31, 4568; Hajos, G. and Riedl, Z. Science of Synthesis, 2002, 12, 613 and Aboul-Fadl, T. et al. Synthesis, 2000, 12, 1727-1732. Various methods can be used to prepare substituted [1,2,3]triazolo[1,5-a]pyridine DI1

(Z=N) as outlined in Latham, Elliot J. and Stanforth, Stephen P. Journal of Heterocyclic Chemistry, 32(3), 787-9; 199; Sheng et al, Organic Letters, 14(14), 3744-3747; 2012 and Prakash, Om et al, Synthetic Communications, 30(3), 417-425; 2000. Iodination with NIS can yield 3-iodo-pyrazolo[1,5-a]pyridine DI2 by a method similar to those described in described in the references such as Bifulco, Neil, Jr. et al. PCT Int. Appl., 2014011900; Wan, Huixin et al, PCT Int. Appl., 2013170774, 21 Nov. 2013. DI2 can be then converted into boronic esters DI3 then by treatment with boronic ester DD3 under various conditions. Then Pd-based coupling reaction similar to those described above between intermediates DI3 and DA0 provided the desired molecules DI. Alternatively, Pd-based coupling reaction similar to those described above between intermediates DE1 and DI2 provided the desired molecules DI as well. For example if Y is protected nitrogen, an extra step to deprotection can be achieved using reported conditions.

Scheme 13: general synthetic routes to prepare 2-(2-methylindolizin-1-yl)-substituted saturated fused pyrimidines (DJ)

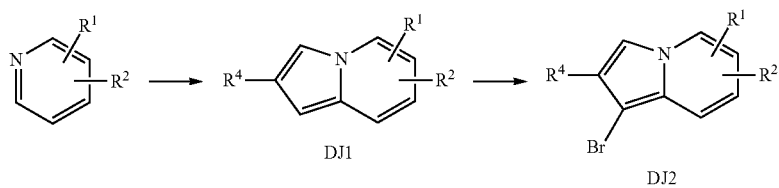

Method A:

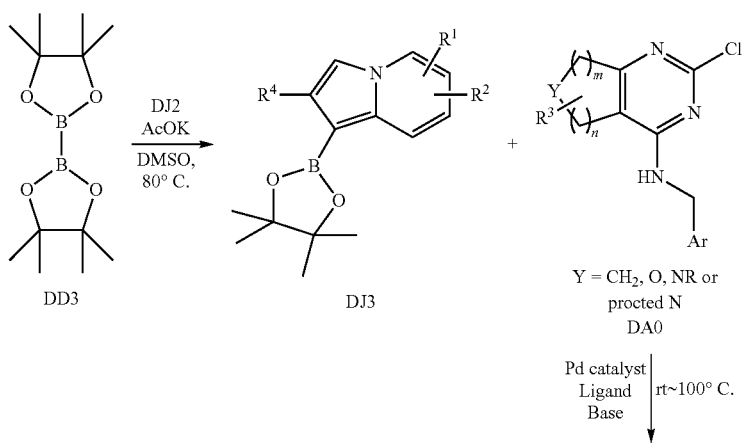

Method B:

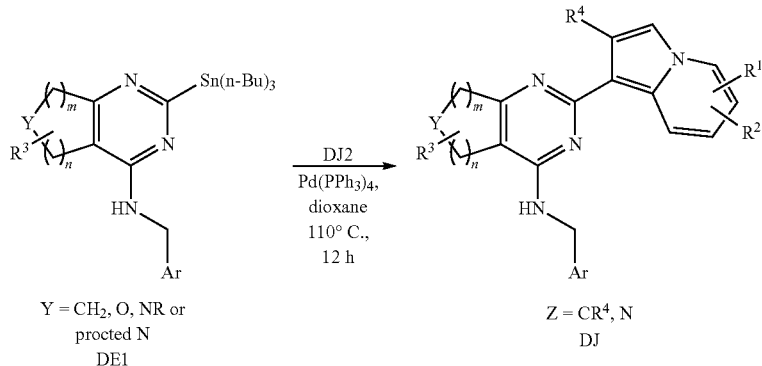

1-Bromo-lindolizine DJ2 can be prepare from substituted pyridine using methods as outlined in Iizuka, Masato and Shimizu, Kazuo, PCT Int. Appl., 2012043638. DJ2 can be then converted into boronic esters DI3 then by treatment with boronic ester DD3 under various conditions. Then Pd-based coupling reaction similar to those described above between intermediates DJ3 and DA0 provided the desired molecules DJ. Alternatively, Pd-based coupling reaction similar to those described above between intermediates DE1 and DJ2 provided the desired molecules DI as well. For example if Y is protected nitrogen, an extra step to deprotection can be achieved using reported conditions.

Scheme 14: general synthetic routes to prepare 2-(indolizin-3-yl)-substituted saturated fused pyrimidines (DK)

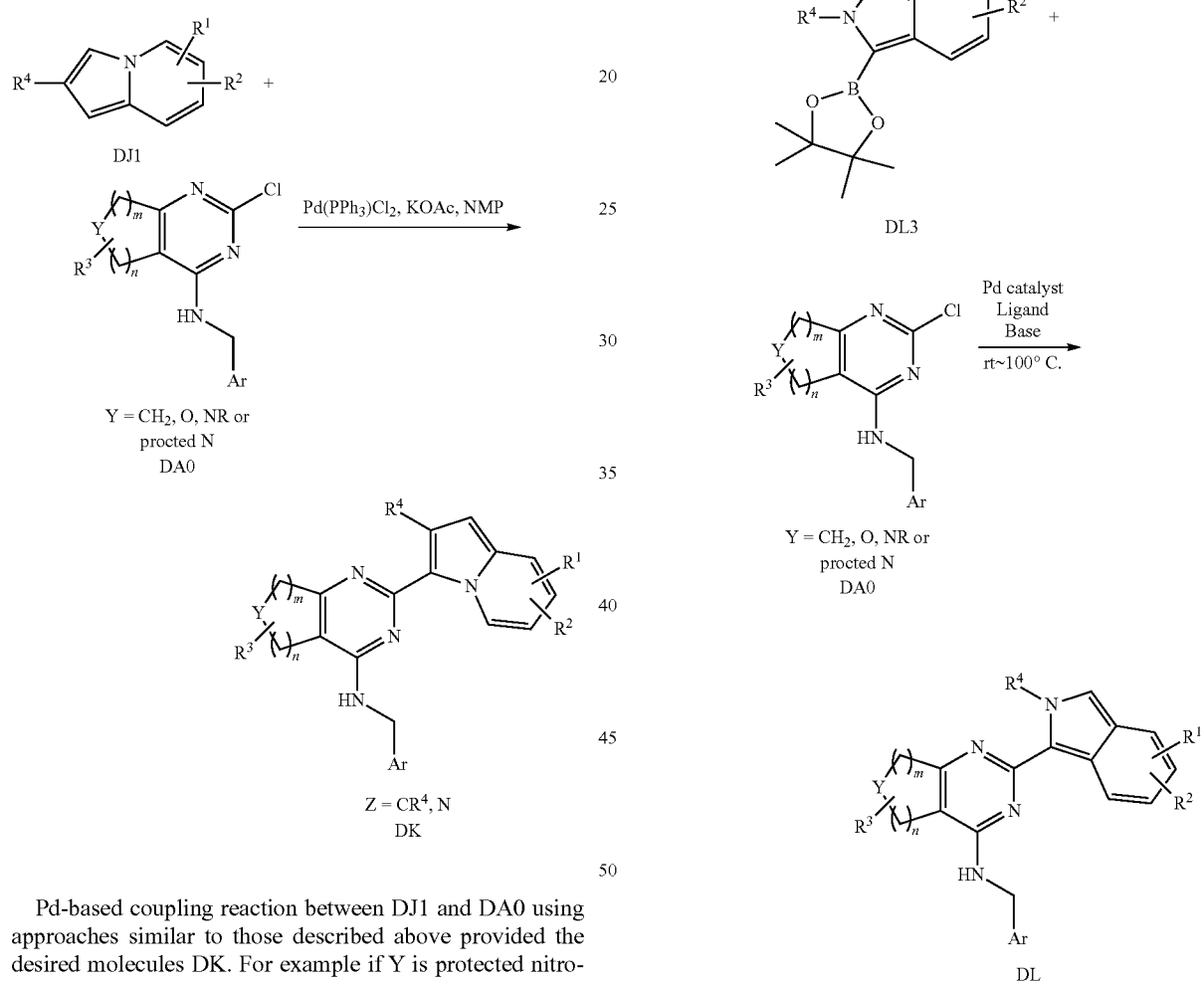

Pd-based coupling reaction between DJ1 and DA0 using approaches similar to those described above provided the desired molecules DK. For example if Y is protected nitrogen, an extra step to deprotection can be achieved using reported conditions.

Scheme 15: general synthetic routes to prepare 2-(2H-isoindol-1-yl)-substituted saturated fused pyrimidines (DL)

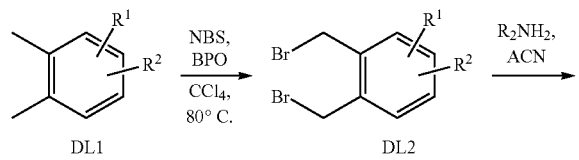

The boronic ester of 2H-isoindole DL3 can prepared from substituted 1,2-dimethylbenzene DL1 following the procedure in the reference (Ohmura, Toshimichi et al Journal of the American Chemical Society, 131(17), 6070-6071; 2009). Then Pd-based coupling reaction similar to those described above between intermediates DL3 and DA0 provided the desired molecules DL. For example if Y is protected nitrogen, an extra step to deprotection can be achieved using reported conditions.

Scheme 16: general synthetic routes to prepare 2-(benzo[c]thiophen-1-yl)-substituted saturated fused pyrimidines (DM)

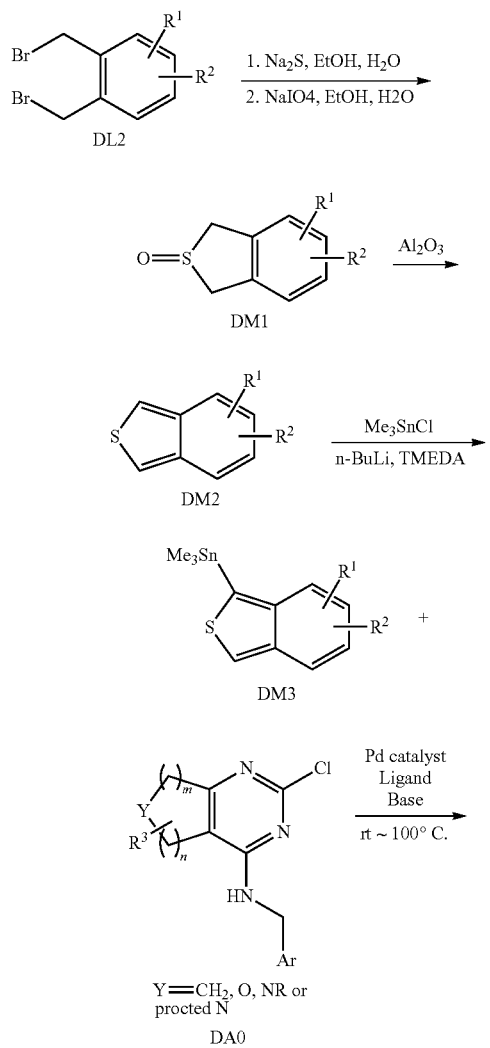

Scheme 17: general synthetic routes to prepare 2-(isobenzofuran-1-yl)-substituted saturated fused pyrimidines (DN)

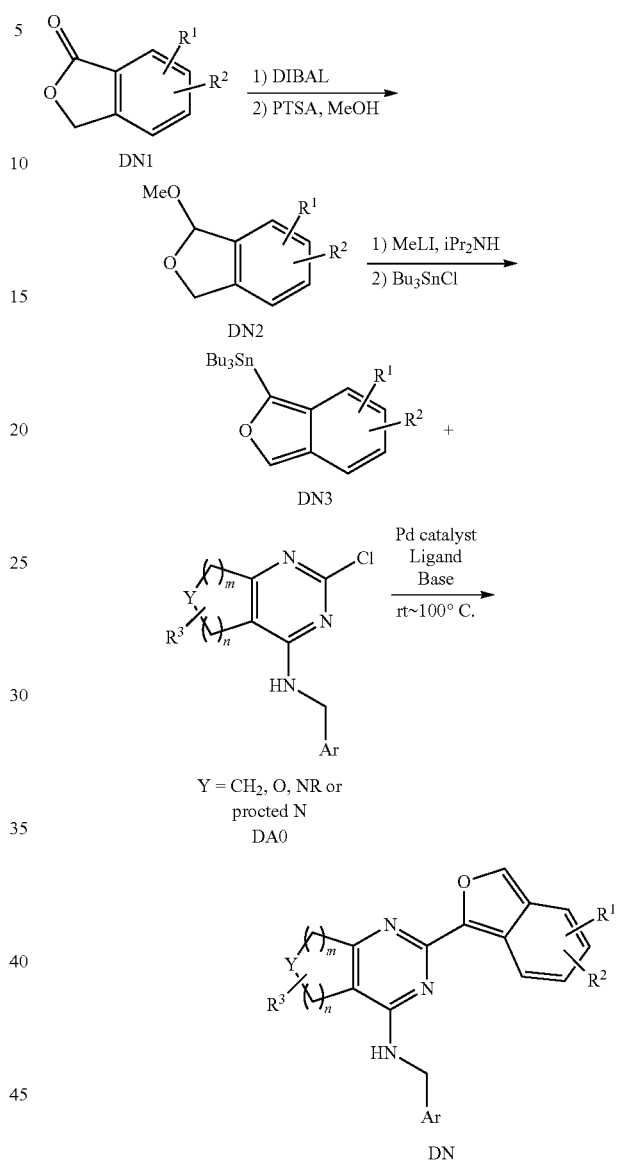

The key intermediates DN3, tributyliisobenzofuran-1-yl) stannane can prepared from the intermediates DN2, which can be prepared from lactone DN1. Then Pd-based coupling reaction similar to those described above between intermediates DN3 and DA0 provided the desired molecules DN. For example if Y is protected nitrogen, an extra step to deprotection can be achieved using reported conditions.

The key intermediates DM3, benzo[c]thiophen-1-yltrimethylstannane can prepared from the intermediates DL2 following the similar procedure in the reference (Kawabata, Kohsuke and Goto, Hiromasa, Journal of Materials Chemistry, 22(44), 23514-23524; 2012). Then Pd-based coupling reaction similar to those described above between intermediates DM3 and DA0 provided the desired molecules DM. For example if Y is protected nitrogen, an extra step to deprotection can be achieved using reported conditions.

Scheme 18: general synthetic routes to prepare 2-(benzo[c]isoxazol-3-yl) or 2-(benzo[c]isothiazol-3-yl)-substituted saturated fused pyrimidines DO

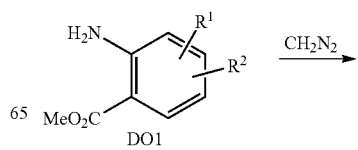

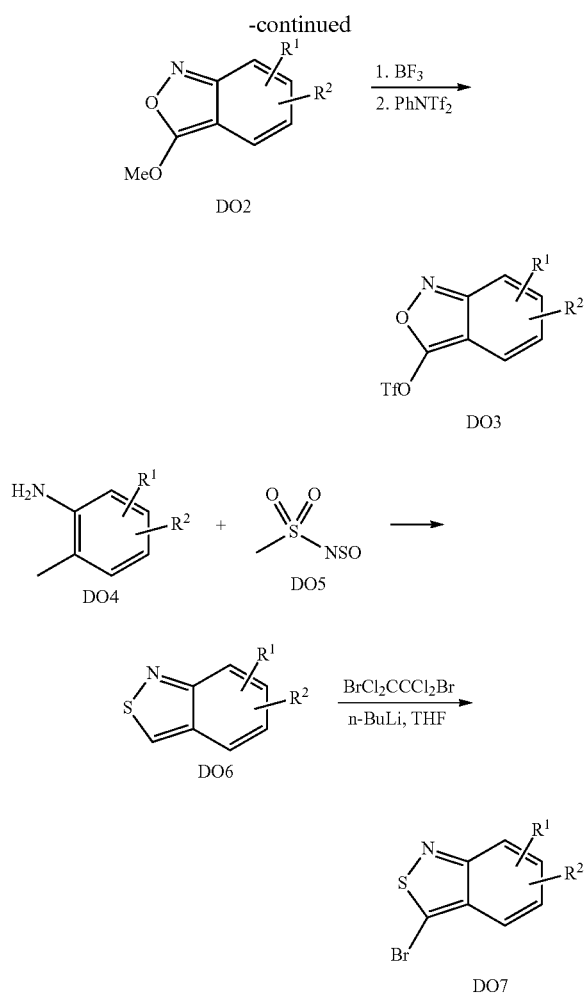

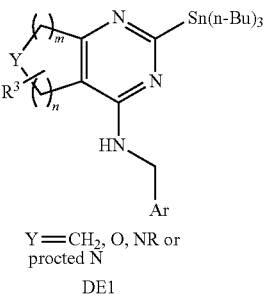

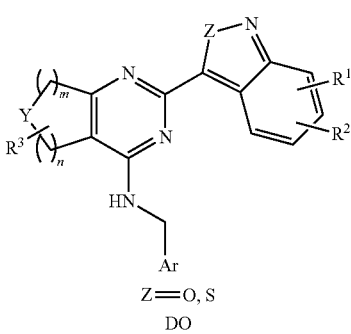

Substituted 3-methoxybenzo[c]isoxazoles DO2 can prepared from 2-aminobenzoates DO1 following the similar procedure in the references such as Chauhan, Mohinder S. and McKinnon, David M., Canadian Journal of Chemistry, 53(9), 1336-42; Smalley, R. K., Science of Synthesis, 11, 337-382; 2002. Then demethylation and conversion hydroxyl into triflate group can yield the intermediate DO3. Substituted benzo[c]isothiazole DO6 can prepared from substituted o-toluidine DO4 following the similar procedure in the references such as Puetz, Claudia et al, Eur. Pat. Appl., 1352910. Then bromination with BNS can selectively into Br into its position DO7. Then Pd-based coupling reaction similar to those described above between intermediates DO3 or DO7 and DA0 provided the desired molecules DO. For example if Y is protected nitrogen, an extra step to deprotection can be achieved using reported conditions.

Scheme 19: Conversion of nitriles into amides DP2

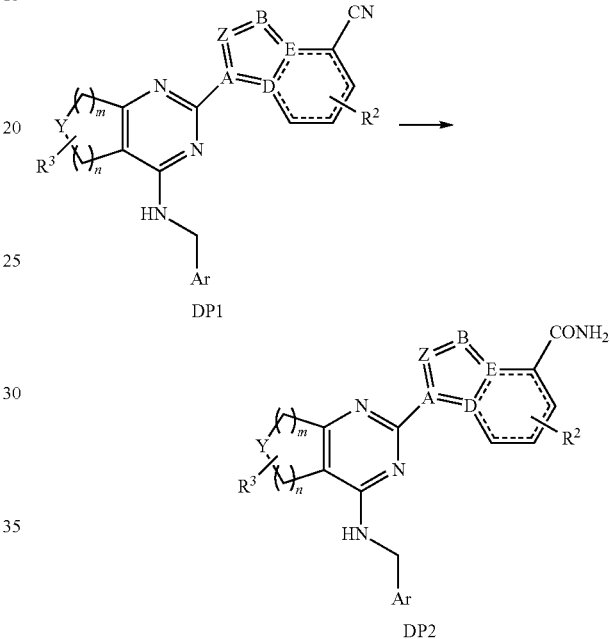

In some cases the desired compounds DP1 prepared in Schemes 5-18 above can have a nitrile substitution at the position indicated in Scheme 19. This substituent can be converted to the corresponding carboxamide. Nitriles DP1 are dissolved in a 1/10 ratio of water/DMSO and treated with urea-hydrogen peroxide (UHP) and a base such as potassium carbonate. Reaction mixture is stirred at room temperature for up to 18 hours and then is poured into ice water and stirred for two hours. The resulting solid is filtered, dried and if necessary purified by column chromatography to give the desired amides DP2.

Scheme 20: Conversion of nitriles into amino methylamines DP3

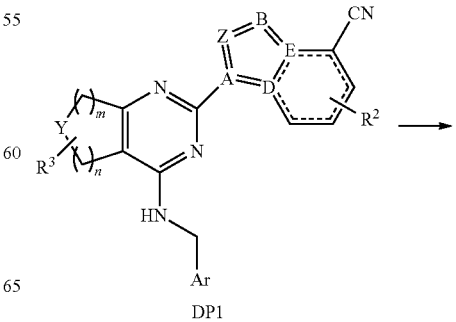

-continued

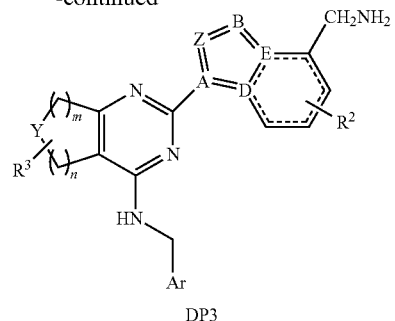
DP3

In some cases the desired compounds DP1 prepared in Schemes 1-18 above can have a nitrile substitution at the position indicated in Scheme 20. This substituent can be converted to the corresponding methylamines DP3. A solution of nitrile DP1 in an aprotic organic solvent such as THF is treated with LAH and the resulting mixture is stirred for up to 18 hours. The reaction mixture is treated with 15% NaOH in water and the reaction is stirred for one hour and is then filtered. The THF is removed under reduced pressure to give the product DP3 which can be further purified by column chromatography.

Scheme 21: Conversion of esters into acids DP4 or amides DP5

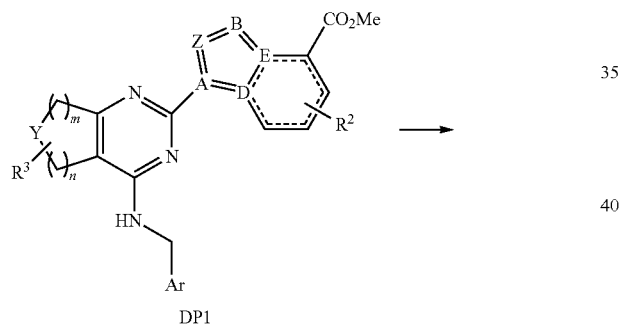
DP1

-continued

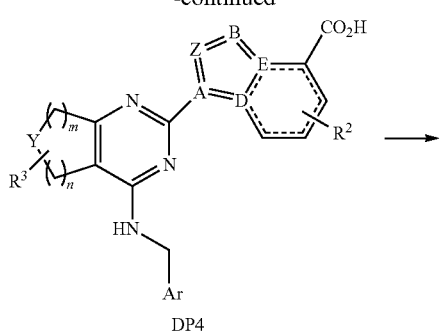
DP4

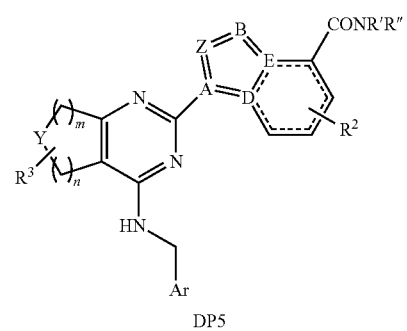
DP5

In some cases the desired compounds DP1 prepared in Schemes 5-18 above can have a carboxylate ester at the position indicated in Scheme 21. This functionality can be readily converted to the corresponding acids DP4 or substituted amides DP5 using standard methodology.

Scheme 22: Conversion of aldehydes DP6 into amines DP7 or methyl alcohols or ethers DP8

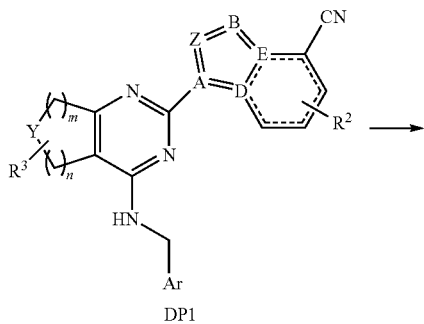
DP1

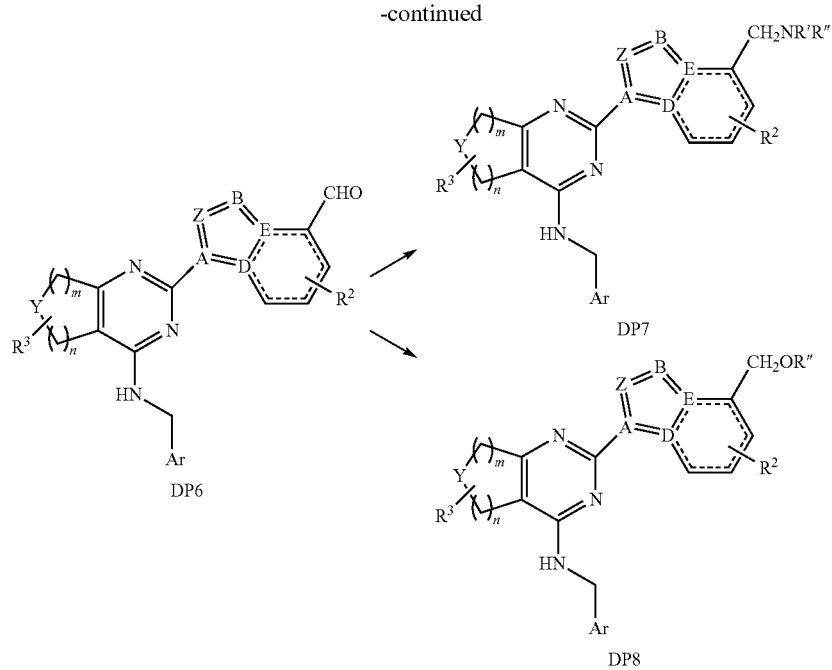

In some cases the desired compounds DP1 prepared in Schemes 5-18 above can have a nitrile at the position indicated in Scheme 22. This functionality can be readily converted to the corresponding amines DP7 or alcohols or ethers DP8 using standard methodology through the intermediate—aldehydes DP6.

Scheme 23: Conversion of aldehydes DP9 into methyl alcohols or ethers DP10 OR amines DP11

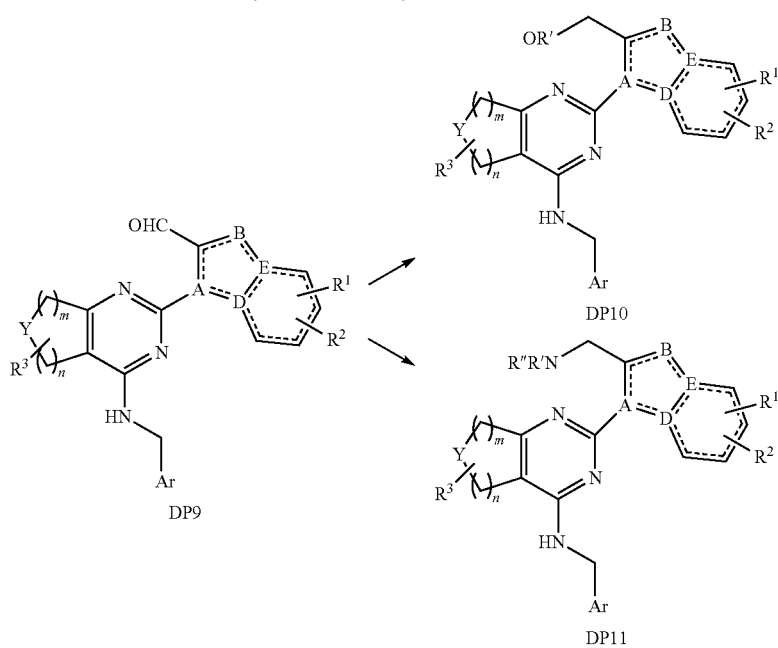

In some cases the desired compounds DP9 prepared in Schemes 5-18 above can have an aldehyde at the position indicated in Scheme 23. This functionality can be readily converted to the corresponding alcohols or ethers DP10 or amines DP11 or using standard methodology.

Biological Assays

The biological activities of the fused pyrimidine compounds of the invention can be determined by their examination in in vitro and cellular assays using protocols well established to identify and select compounds that will exhibit anti-cancer activity. The present invention focuses upon the ability of the fused pyrimidine compounds to intersect with the p97 proteosome complex. As described in the Background, the function of the p97 complex is essential for continued cellular viability. Inhibition of the activity of the complex will cause protein build-up in the cell and consequent apoptosis. The biological assays allow an assessment of the biological activities of the fused pyrimidine compounds of the invention.

The primary biological analyses are in vitro assays and cellular based assays for determining the inhibitory capability of the fused pyrimidine compounds of the invention of the invention against Valosin-containing protein, i.e., p97. The assays also provide a primary indication of bioavailability of the fused pyrimidine compounds of the invention.

The ability to inhibit the p97 complex is studied through use of a p97 in vitro assay using a tagged p97 substrate pursuant to the method of Christianson in Nat Cell Biol. (2011) 14:93 for a p97 cell-based assay. A cell based assay is used to test the anti-tumor effects of inhibitors on cultured cancer cells. This anti-tumor assay is based upon cultured cancer cells using the commercially available cell titer glo assay provided by Promega. Additional assays enable assessment of bioavailability through art recognized model studies designed to demonstrate the ability of the compounds of the invention to reach target cells in vivo. While all compounds tested displayed a degree of anti-tumor activity, the assays also allowed identification of fused pyrimidine compounds as candidates that may be selected for further examined by in vivo anti-tumor testing in mouse, guinea pig and dog models. The selected candidates were shown to have highly desirable pharmacokinetic properties in these in vitro assays.

P97 ATPase Biochemical Assay

The ATPase assay is performed according the following protocol: Purified enzyme (20 nM p97), substrate (20 μM ATP) and a dose titration of compounds are mixed in buffer (50 mM TRIS pH 7.5, 20 mM $MgCl_2$, 0.02% TX-100, 1 mM DTT, 0.2% (v/v) glycerol) and incubated at 37° C. for 15 minutes. The reaction is terminated and the level of product generated is measured using the ADP Glo Assay Kit (Promega, Madison Wis.). Plotting product generated versus compound concentration and using a four-parameter fit model generates an IC50 value for each compounds.

P97 Cell-Based Assay

On target cell-based effects of compounds of the invention are monitored using the reporter cell line HEK-293 TCRα-GFP as described in Christianson et al. Nat. Cell Biol. (2011) 14:93. Inhibition of turnover of the TCRα-GFP reporter is a hallmark of p97 inhibition. The protocol for TCRα-GFP monitoring reporter turnover is as follows: Reporter cells are seeded and incubated with proteasome inhibitor MG132 to accumulate TCRα-GFP. Subsequently, MG132-containing media is removed and a dose titration of compound plus cycloheximide is incubated with the cells. At the end of the incubation, compound and media are removed, cells are fixed and GFP fluorescence is measured by standard epifluorescent microscopy techniques. Plotting fluorescence versus compound concentration and using a four-parameter fit model generates an IC50 value for each compound.

Image-analysis is used to generate quantitative data from these assays that can be fit to a four-parameter sigmoid curve to derive IC50 values. Substrates of the ubiquitin-proteasome system, such as p53, are monitored after tumor cell lines are incubated with compounds for several hours. Accumulation of these proteins indicates an inhibition of proteasome-mediated degradation. Accumulation of lysine-48 chain linkage of poly-ubiquitin is also monitored by immunofluorescence as an indicator of ubiquitin-proteasome system inhibition. Both LC3 and SQSTM1 are mediators of autophagy. The localization and amounts of these proteins are monitored by immunofluorescence and report on the activity and inhibition of autophagy in response to p97 inhibition.

Cultured Cancer Cell Assay

Anti-tumor effects are monitored in cultured cancer cells after several days of compound treatment. The cell titer glo assay (Promega) measures the amount of ATP present as a proxy for cellular viability. Cellular counting is done using high-content microscopy followed by image analysis. A hanging drop 3D-culture system (3D Biomatrix) is used followed by cell titer glo to measure growth in a tumor-like environment.

Absorption Assay

The ability of compounds to be absorbed from the lumen of the gastrointestinal tract after oral administration was assessed by measuring their permeability through Caco-2 cell monolayers. SunD, et al., Curr. Opin. Drug Discov. Develop [(2004) 75. The in vitro permeability of compound (2 μM in Kreb's buffer or HBSS buffer with n=2) was determined using 21-day old Caco-2 cell monolayers. The permeation coefficient was determined for both Apical to Basolateral (A to B) and Basolateral to Apical (B to A) after 120 min at 37° C. The efflux ratio was calculated based on the ratio of permeation coefficient of B to A vs. A to B to determine the potential of compound as substrate for efflux pump (e.g. Pgp). The protocol for this Caco-2 assay and the corresponding detailed description are provided in the following experimental section.

Metabolic Stability Assay

Metabolic stability of compounds can be assessed by measuring their half lives in liver microsomal preparations. Roserts, Sa, et al., Xenobiotica (2001) 37:557. Compounds are applied to a preparation of mouse liver microsomes in the presence of NADPH and their half lives are determined by measuring the rate of disappearance of the compounds from the preparation by determining the concentration at 0, 15, 30 and 60 minutes using LCMS/MS. The protocol for determining metabolic stability in a mouse liver assay and the corresponding detailed description are provided in the following experimental section.

Nonspecific Binding Assay

Many compounds are known to bind nonspecifically to proteins found in high abundance in the plasma. The fraction of unbound drug (free fraction) is available for interaction with targets found in tissues. Banker, M. J. et al., Curr. Drug Metab. (2008) 9:854. The ability of compounds to escape a chamber containing blood plasma to a chamber containing only buffer can be assessed by measuring the concentration that appears in the buffer chamber and the concentration that remains in the plasma chamber. These measurements can be used to determine the fraction of compound bound to plasma proteins and its free fraction (100-percent bound to plasma proteins). The protocol for determining non-specific protein binding in a plasma protein binding assay and the corresponding detailed description are provided in the following experimental section.

The results of the primary assay conducted with selected fused pyrimidine compounds of the invention show that the fused pyrimidine compounds of the invention display significant inhibitory activity ($IC_{50}$) against the enzymatic action of p97 toward its natural substrate. Some of these compounds also have greater potency in cell based assays and have in vitro pharmacokinetic properties consistent with good oral bioavailability. These results are provided below in Table II.

EXAMPLES

The following describes the preparation of representative compounds of the invention in greater detail. The following examples are offered for illustrative purposes, and are not intended to limit the invention in any manner. Those of skill in the art will readily recognize a variety of noncritical parameters which can be changed or modified to yield essentially the same results.

Those skilled in the art will recognize, or be able to ascertain using no more than routine experimentation, numerous equivalents to the syntheses of the compounds and methods of use thereof described herein. Although certain exemplary embodiments are depicted and dscribed herein, it will be appreciated that compound of the invention can be prepared according to the methods generally available to one of ordinary skill in the art. All of the above-cited references and publications are hereby incorporated by reference.

Unless otherwise noted, all solvents, chemicals, and reagents were obtained commercially and used without purification. The 1H NMR spectra were obtained in CDCl3, d6-DMSO, CD3OD, or d6-acetone at 25° C. at 300 MHz on an OXFORD (Varian) spectrometer with chemical shift (δ, ppm) reported relative to TMS as an internal standard. HPLC-MS chromatograms and mass spectra were obtained with Shimadzu LC-MS-2020 system. The prep-HPLC instruments used to purify some compounds were either a Gilson GX-281(Gilson) or a P230 Preparative Gradient System (Elite). Preparative chira HPLC seperations were performed using an Elite P230 Preparative Gradient System, a Thar Prep-80 or Thar SFC X-5. Reactions using microwave irriadation were performed on a CEM Discover SP instrument.

Synthesis of 1-(4-(benzylamino)-5,6,7,8-tetrahydroquinazolin-2-yl)-1H-indazole-4-carboxamide FF03

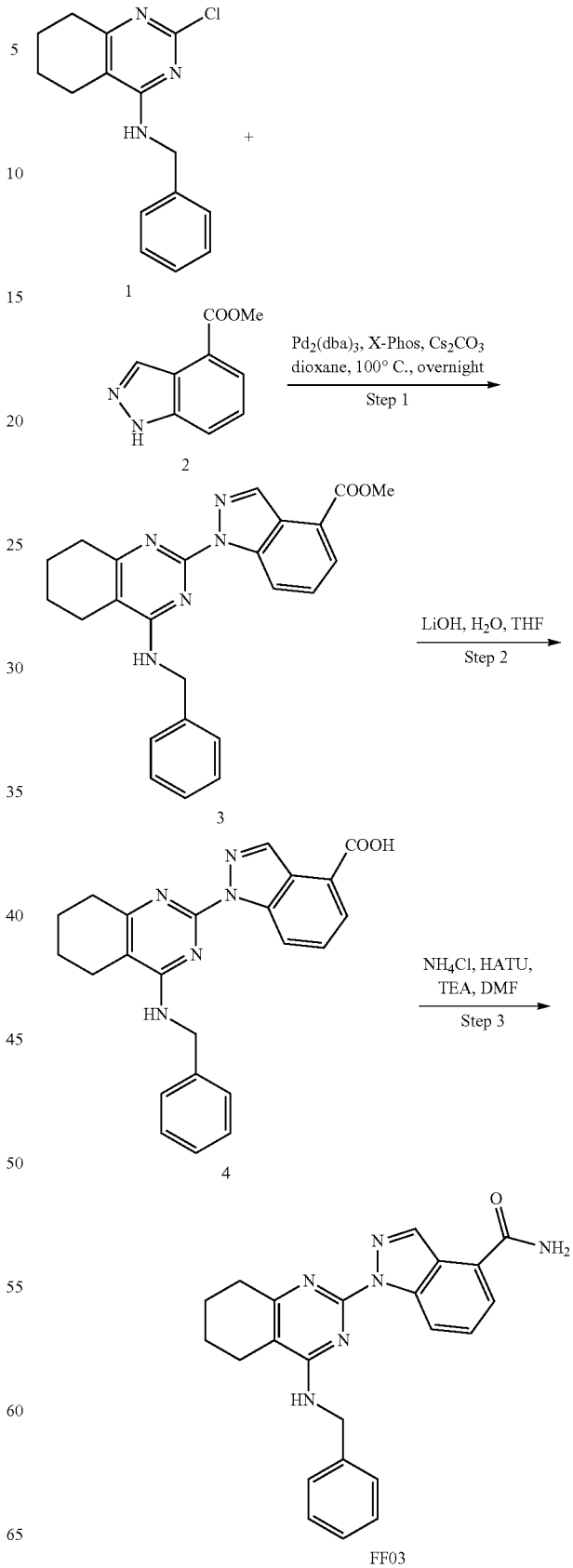

To a solution of methyl 1H-indazole-4-carboxylate 2 (2.6 g, 14.7 mmol) and N-benzyl-2-chloro-5,6,7,8-tetrahydroquinazolin-4-amine 1 (4 g, 14.7 mmol) in dioxane (150 mL) was added Pd$_2$(dba)$_3$ (2.7 g, 2.94 mmol), X-Phos (2.8 g, 5.88 mmol) and Cs$_2$CO$_3$ (9.6 g, 29.4 mmol). The mixture was degassed for 3 times, and then stirred at 100° C. for 12 hours. The resulting mixture was concentrated in vacuo and the residue was purified by column chromatography (silica gel, petroleum ether/ethyl acetate=3:1) to give methyl 1-(4-(benzylamino)-5,6,7,8-tetrahydroquinazolin-2-yl)-1H-indazole-4-carboxylate 3 (2.74 g, 45%). LRMS (M+H+) m/z: calcd 414.47; found 414.

To a solution of methyl 1-(4-(benzylamino)-5,6,7,8-tetrahydroquinazolin-2-yl)-1H-indazole-4-carboxylate 3 (2.74 g, 6.63 mmol) in THF (12 mL), MeOH (4 mL) and H$_2$O (4 mL) was added LiOH (836 mg, 19.9 mmol). Then the mixture was stirred at room temperature for 3 h. The solvent was removed and the solid was resolved with water, neutralized with HCl (1M) to pH=2~3, the solid was filtered and dried to give 1-(4-(benzylamino)-5,6,7,8-tetrahydroquinazolin-2-yl)-1H-indazole-4-carboxylic acid 4 (2.3 g, 87%) which was used for next step without further purification. LRMS (M+H$^+$) m/z: calcd 400.45; found 400.

To a solution of 1-(4-(benzylamino)-5,6,7,8-tetrahydroquinazolin-2-yl)-1H-indazole-4-carboxylic acid 4 (2.3 g, 5.76 mmol) in DMF (60 mL) was added NR$_4$Cl (930 mg, 17.3 mmol), HATU (3.3 g, 8.64 mmol) and Et$_3$N (2.4 mL, 17.3 mmol). Then the reaction solution was stirred at room temperature overnight. Water was added to the resulting solution and the solid was filtered, dried and purified by Combiflash (dichloromethane/methanol=20:1) to give 1-(4-(benzylamino)-5,6,7,8-tetrahydroquinazolin-2-yl)-1H-indazole-4-carboxamide FF03 (1.6 g, 70%). LRMS (M+H$^+$) m/z: calcd 399.46; found 399. HPLC purity (214 nm): 100%. $^1$HNMR (300 MHz, DMSO): δ 8.61 (s, 1H), 8.38 (d, J=8.4 Hz, 1H), 8.09 (s, 1H), 7.70-7.68 (m, 2H), 7.54 (s, 1H), 7.42-7.32 (m, 5H), 7.24-7.23 (m, 1H), 4.74 (d, J=5.6 Hz, 2H), 2.70-2.68 (m, 2H), 2.50-2.48 (m, 2H), 1.83-1.82 (m, 2H).

Synthesis of 1-(4-(benzylamino)-7,8-dihydro-5H-pyrano[4,3-d]pyrimidin-2-yl)-1H-indazole-4-carboxamide Compound FF04

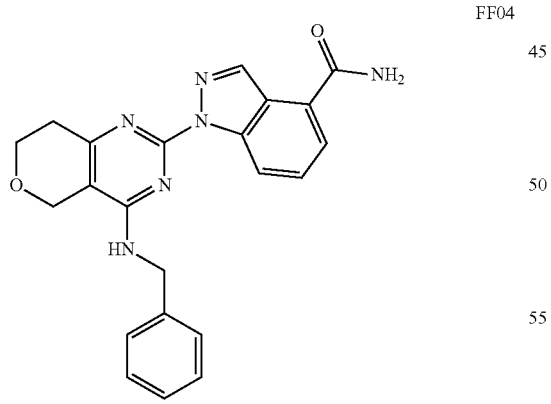

FF04

Similar procedure was utilized to the desired molecule FF04, 1-(4-(benzylamino)-7,8-dihydro-5H-pyrano[4,3-d]pyrimidin-2-yl)-1H-indazole-4-carboxamide as white solid (60 mg, 52%). LRMS (M+H$^+$) m/z: calcd 400.16; found 401. HPLC purity (214 nm): 98%. $^1$HNMR (400 MHz, DMSO): δ 8.63 (s, 1H), 8.39 (d, J=5.4 Hz, 1H), 8.11 (br, 1H), 7.69 (d, J=4.5 Hz, 2H), 7.56 (br, 1H), 7.41-7.20 (m, 5H), 4.73 (d, J=5.4 Hz, 2H), 4.58 (s, 2H), 4.00-3.96 (m, 2H), 2.77 (t, J=0.3 Hz, 2H)

Synthesis of 3-(4-(benzylamino)-5,6,7,8-tetrahydroquinazolin-2-yl)-2-methyl-1H-indole-7-carboxamide FF05

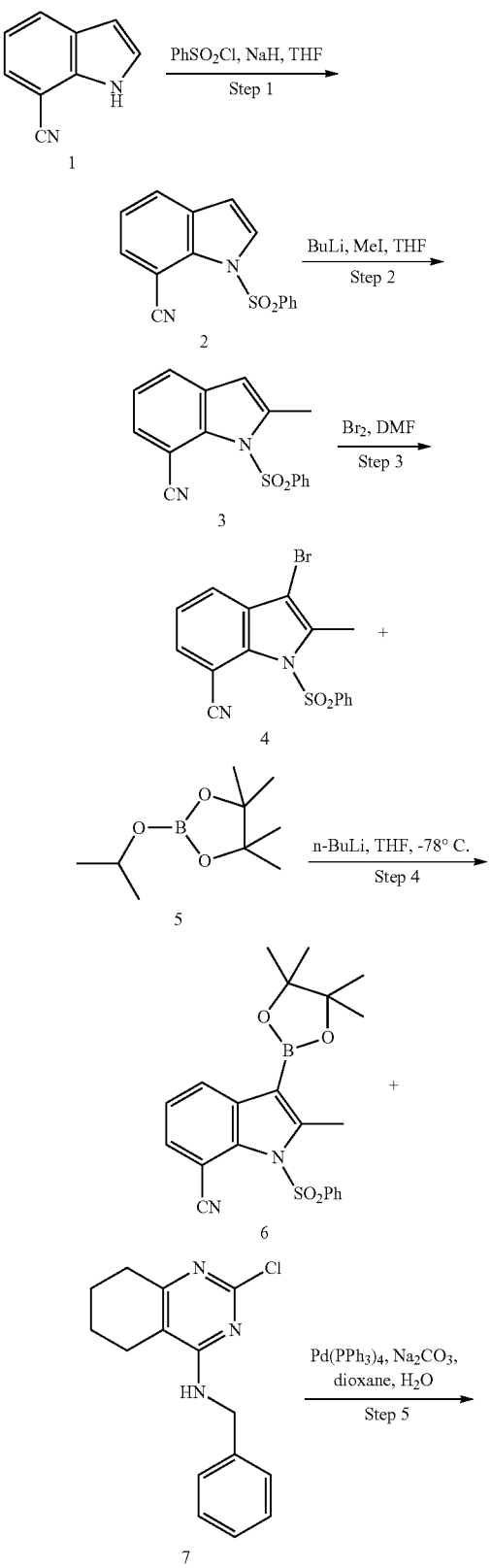

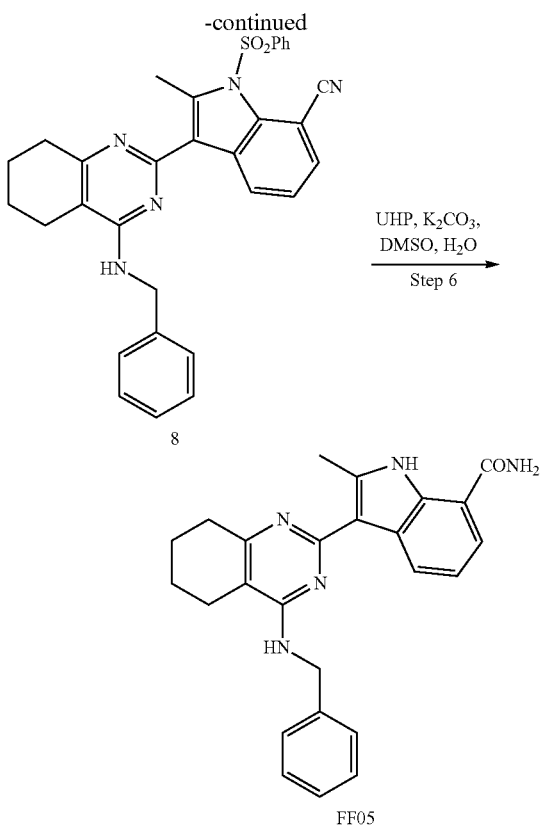

To a solution of 1H-indole-7-carbonitrile 1 (1.0 g, 7.04 mmol) in THF (30 mL) was added NaH (0.36 g, 9.15 mmol, 60%) at 0° C., and the reaction mixture was stirred at 20° C. for 30 min. Then benzenesulfonyl chloride (1.49 g, 8.44 mmol) was added. The mixture was stirred at r.t. for 2 hours. The solution was quenched by adding a.q. $NH_4Cl$ and extracted with EtOAc (300 mL×2), dried over $Na_2SO_4$ and concentrated under vacuum. The residue was purified by flash chromatography (PE:EA=3:1) to afford 1-(phenylsulfonyl)-1H-indole-7-carbonitrile 2 (1.83 g, 92%). LRMS (M+H$^+$) m/z: calcd 282.32; found 282.

To a solution of 1-(phenylsulfonyl)-1H-indole-7-carbonitrile 2 (1.83 g, 6.49 mmol) in THF (30 mL) at −80° C. was added n-BuLi (3 mL, 7.14 mmol, 2.4 N), the reaction mixture was stirred at −60° C. for 1 h. Then iodomethane (1.38 g, 9.73 mmol) was added. The reaction mixture was stirred at ambient for 1 hour. The reaction was quenched by aq. $NH_4Cl$ and extracted with EA (200 mL×2), dried over $Na_2SO_4$ and concentrated under vacuum. The residue was purified by flash chromatography (PE:EA=3:1) to afford 2-methyl-1-(phenylsulfonyl)-1H-indole-7-carbonitrile 3 (1.83 g, 95%). LRMS (M+H$^+$) m/z: calcd 296.34; found 296.

To a solution of 2-methyl-1-(phenylsulfonyl)-1H-indole-7-carbonitrile 3 (1.6 g, 5.67 mmol) in DCM (15 mL) was added $Br_2$ (1.81 g, 11.34 mmol), the reaction mixture was stirred at ambient for 2 h. The reaction was quenched by adding aq. $NaHCO_3$ and extracted with EA (60 ml×2), dried over $Na_2SO_4$ and concentrated under vacuum. The residue was purified by flash chromatography (PE:EA=3:1) to afford 3-bromo-2-methyl-1-(phenylsulfonyl)-1H-indole-7-carbonitrile 4 (1.8 g, 85%). LRMS (M+H$^+$) m/z: calcd 375.24; found 375. $^1$HNMR (300 MHz, CD$_3$OD): δ 7.66-7.84 (m, 5H), 7.46-7.58 (m, 3H), 2.66 (s, 3H).

To a solution of 3-bromo-2-methyl-1-(phenylsulfonyl)-1H-indole-7-carbonitrile 4 (900 mg, 2.4 mmol) and 2-isopropoxy-4,4,5,5-tetramethyl-1,3,2-dioxaborolane 5 (450 mg, 2.4 mmol) in THF (15 mL) at −78° C. was added n-BuLi (1 mL, 2.4 mmol, 2.4 N), and the reaction mixture was stirred at −78° C. for 1 h. Then the solution was allowed to warm to r.t. and stirred for 1 hour. The reaction was quenched by aq. $NH_4Cl$ and extracted with EA (50 mL×2), dried over $Na_2SO_4$ and concentrated under vacuum. The residue was purified by flash chromatography (PE:EA=2:1) to afford 2-methyl-1-(phenylsulfonyl)-3-(4,4,5,5-tetramethyl-1,3,2-dioxaborolan-2-yl)-1H-indole-7-carbonitrile 6 (760 mg, 75%). LRMS (M+H$^+$) m/z: calcd 422.31; found 422. $^1$HNMR (300 MHz, CDCl$_3$): δ 8.28 (d, J=3.6 Hz, 1H), 7.97 (t, J=4.8 Hz, 2H), 7.60-7.63 (m, 2H), 7.54 (t, J=5.4 Hz, 2H), 7.30 (t, J=7.8 Hz, 1H), 2.89 (s, 3H), 1.37 (s, 12H). A mixture of 2-methyl-1-(phenylsulfonyl)-3-(4,4,5,5-tetramethyl-1,3,2-dioxaborolan-2-yl)-1H-indole-7-carbonitrile 6 (360 mg, 0.85 mmol), N-benzyl-2-chloro-5,6,7,8-tetrahydroquinazolin-4-amine 7 (232 mg, 0.85 mmol), Pd(PPh$_3$)$_4$ (196 mg, 0.17 mmol) and Na$_2$CO$_3$ (176 mg, 1.7 mmol) in dioxane (10 mL) and H$_2$O (3 mL) was heated at 100° C. for 16 hours under nitrogen atmosphere. The reaction mixture was cooled to room temperature and concentrated under vacuum, The residue was purified by flash chromatography (PE:EA=1:1) to afford 3-(4-(benzylamino)-5,6,7,8-tetrahydroquinazolin-2-yl)-2-methyl-1-(phenylsulfonyl)-1H-indole-7-carbonitrile 8 (217 mg, 48%). LRMS (M+H$^+$) m/z: calcd 533.64; found 533.

To a solution of 3-(4-(benzylamino)-5,6,7,8-tetrahydroquinazolin-2-yl)-2-methyl-1-(phenylsulfonyl)-1H-indole-7-carbonitrile 8 (120 mg, 0.22 mmol) in DMSO (5 mL) was added UHP (165 mg, 1.76 mmol), K$_2$CO$_3$ (15 mg, 0.11 mmol) and water (0.3 mL) at 0° C., and the reaction mixture was stirred at 60° C. overnight. Water (100 mL) was added to the mixture and the solid was crashed out, filtered to give the crude product, which was purified by flash chromatography (DCM:MeOH=20:1) to afford 3-(4-(benzylamino)-5,6,7,8-tetrahydroquinazolin-2-yl)-2-methyl-1H-indole-7-carboxamide 65 mg (72%) FF05. LRMS (M+1-1±) m/z: calcd 411.5; found 411. HPLC purity (214 nm): 97.6%. $^1$HNMR (400 MHz, DMSO): δ 10.97 (s, 1H), 8.52 (d, J=4.0 Hz, 1H), 8.00 (s, 1H), 7.57 (d, J=4.0 Hz, 1H), 7.27-7.35 (m, 5H), 7.18 (t, J=7.2 Hz, 1H), 7.12 (t, J=6.0 Hz, 1H), 6.97 (t, J=8.0 Hz, 1H), 4.73 (d, J=2.8 Hz, 2H), 2.70 (s, 3H), 2.66 (bs, 2H), 2.44 (bs, 2H), 1.81 (bs, 4H).

Synthesis of 1-(4-(benzylamino)-6,7-dihydro-5H-pyrano[2,3-d]pyrimidin-2-yl)-2-methyl-1H-indole-4-carboxamide FF06

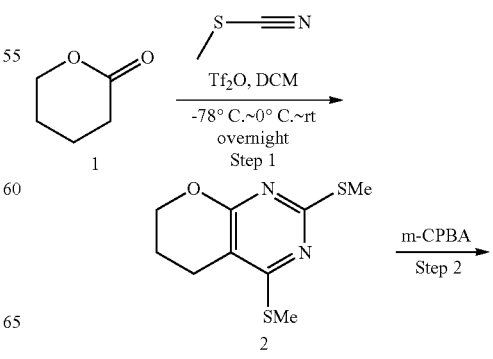

-continued

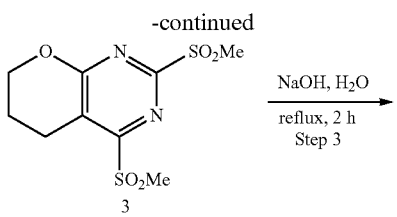
3

NaOH, H₂O
reflux, 2 h
Step 3

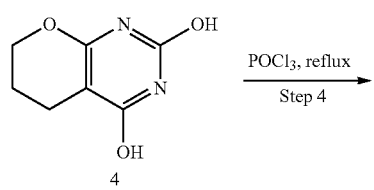
4

POCl₃, reflux
Step 4

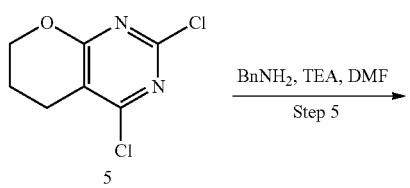
5

BnNH₂, TEA, DMF
Step 5

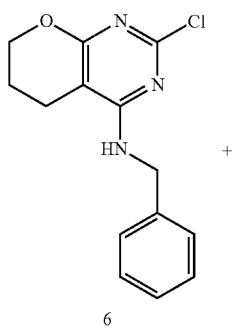
6

+

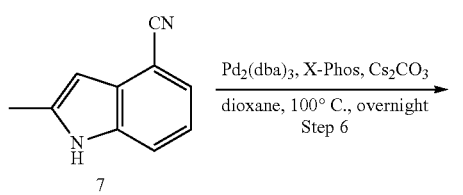
7

Pd₂(dba)₃, X-Phos, Cs₂CO₃
dioxane, 100° C., overnight
Step 6

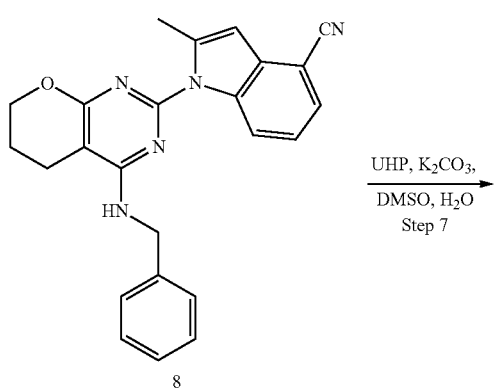
8

UHP, K₂CO₃,
DMSO, H₂O
Step 7

-continued

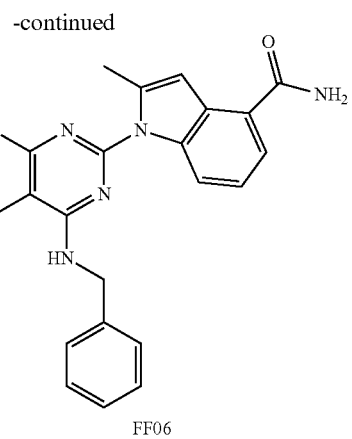
FF06

To a mixture of tetrahydropyran-2-one 1 (1.0 g, 10 mmol) and thiocyanatomethane (2.93 g, 40 mmol) in DCM (25 mL) was added Tf₂O (4.23 g, 15 mmol) in DCM (25 mL) dropwise at −78° C. under nitrogen atmosphere. After the addition, the resulting mixture was stirred at 0° C. for 3 h, and then stirred at room temperature overnight. The volatile phase was removed off under reduced pressure. The residue was dissolved in DCM (40 mL), washed with sodium bicarbonate, brine, dried over sodium sulfate. The organic layer was concentrated under reduced pressure. The residue was applied onto silica gel column eluting with DCM. This resulted in 2,4-bis(methylthio)-6,7-dihydro-5H-pyrano[2,3-d]pyrimidine 2 as white solid (0.4 g. 17.5%). LRMS (M+H⁺) m/z: calcd 229.0; found 229.

To a mixture of 2,4-bis(methylthio)-6,7-dihydro-5H-pyrano[2,3-d]pyrimidine 2 (0.4 g, 1.75 mmol) in DCM (20 mL) was added m-CPBA (2.47 g, 12 mmol) portionwise. The resulting mixture was stirred at room temperature for 5 h. It was quenched with Na₂S₂O₃ (5%, 20 mL), then sat. NaHCO₃ (20 mL) was added carefully. The mixture was stirred for 30 min. The organic layer was separated. The aqueous layer was extracted with DCM (20 mL×2). The organic layers were combined, washed with brine, dried over Na₂SO₄, filtered and concentrated. This resulted in 0.42 g (82%) of 2,4-bis(methylsulfonyl)-6,7-dihydro-5H-pyrano[2,3-d]pyrimidine 3 in white solid. LRMS (M+H⁺) m/z: calcd 293.0; found 293.

A mixture of 2,4-bis(methylsulfonyl)-6,7-dihydro-5H-pyrano[2,3-d]pyrimidine 3 (1.5 g, 5.1 mmol) in 10% NaOH (30 mL) was refluxed for 2 h, then the reaction mixture was acidified with HCl (10%) until pH=2 and the solid was collected by filtration, washed with H₂O. Recrystallization from H₂O to give 0.82 g (95.7%) 6,7-dihydro-5H-pyrano[2,3-d]pyrimidine-2,4-diol 4 in white solid. LRMS (M+H⁺) m/z: calcd 169.0; found 169.

A mixture of 6,7-dihydro-5H-pyrano[2,3-d]pyrimidine-2,4-diol 4 (0.4 g, 2.4 mmol) in POCl₃ (10 mL) was stirred at 100° C. for 4 h. The volatile phase was removed off under reduced pressure. The residue was dissolved in DCM (50 mL), and then was added ice/water, which was washed with NaHCO₃, brine, dried over sodium sulfate, filtered and concentrated. The residue was applied onto silica gel column eluting with PE/EA=4/1. This resulted in 0.25 g (50%) of 2,4-dichloro-6,7-dihydro-5H-pyrano[2,3-d]pyrimidine 5 as white solid. LRMS (M+H⁺) m/z: calcd 205.0; found 205.

A mixture of 2,4-dichloro-6,7-dihydro-5H-pyrano[2,3-d]pyrimidine 5 (0.16 g, 0.8 mmol) and Et₃N (0.24 g, 2.4 mmol) in DMF (15 mL) was stirred at room temperature overnight. It was diluted with ethyl acetate (50 mL), which was washed with water, brine, dried over sodium sulfate, filtered and concentrated. The residue was applied onto silica gel column eluting with PE/EA=2/1. This resulted in 0.16 g (74.5%) of N-benzyl-2-chloro-6,7-dihydro-5H-pyrano[2,3-d]pyrimidin-4-amine 6 as white solid. LRMS (M+H$^+$) m/z: calcd 276.1; found 276.

To a mixture of N-benzyl-2-chloro-6,7-dihydro-5H-pyrano[2,3-d]pyrimidin-4-amine 6 (82 mg, 0.3 mmol), 2-methyl-1H-indole-4-carbonitrile 7 (48 mg, 0.3 mmol), Pd$_2$(dba)$_3$ (55 mg, 0.06 mmol), X-Phos (57 mg, 0.12 mmol) and Cs$_2$CO$_3$ (196 mg, 0.6 mmol) in dioxane (8 mL) was stirred at 100° C. overnight. The volatile phase was removed off under reduced pressure. The residue was applied onto silica gel column eluting with PE/EA=2/1. This resulted in 80 mg (68%) of 1-(4-(benzylamino)-6,7-dihydro-5H-pyrano[2,3-d]pyrimidin-2-yl)-2-methyl-1H-indole-4-carbonitrile 8 as a yellow solid. LRMS (M+H$^+$) m/z: calcd 396.2; found 396.

A mixture of 1-(4-(benzylamino)-6,7-dihydro-5H-pyrano[2,3-d]pyrimidin-2-yl)-2-methyl-1H-indole-4-carbonitrile 8 (72 mg, 0.182 mmol), 1-hydroperoxyurea (112 mg, 1.45 mmol) and K$_2$CO$_3$ (13 mg, 0.09 mmol) in DMSO/H$_2$O (10 mL/1 mL) was stirred at room temperature for 3 h. It was diluted with 50 mL water, which was extracted with ethyl acetate (20 mL×3).

The organic layers were combined, washed with brine, dried over sodium sulfated, filtered and concentrated. The residue was applied onto silica gel column eluting with PE/EA=2/1. This resulted in 50 mg (66%) of 1-(4-(benzylamino)-6,7-dihydro-5H-pyrano[2,3-d]pyrimidin-2-yl)-2-methyl-1H-indole-4-carboxamide FF06 as yellow solid. LRMS (M+Fr) m/z: calcd 414.2; found 414. HPLC purity (214 nm): 97%. $^1$HNMR (400 MHz, DMSO): δ 7.88 (d, J=8.0 Hz, 1H), 7.75-7.71 (m, 1H), 7.69-7.7.65 (m, 1H), 7.45 (d, J=8.0 Hz, 1H), 7.40-7.30 (m, 4H), 7.28-7.20 (m, 2H), 6.94 (t, J=8.0 Hz, 1H), 4.69 (d, J=8.0 Hz, 2H), 4.31 (t, J=4.0 Hz, 2H), 2.52-2.50 (m, 2H), 2.48 (s, 3H), 2.06-2.02 (m, 3H).

Synthesis of 1-(4-(benzylamino)-5,6,7,8-tetrahydro-pyrido[2,3-d]pyrimidin-2-yl)-2-methyl-1H-indole-4-carboxamide FF07

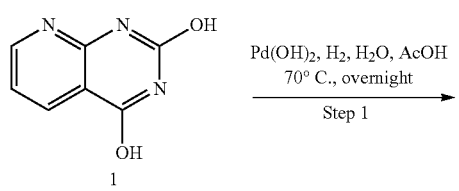

Pd(OH)$_2$, H$_2$, H$_2$O, AcOH
70° C., overnight
Step 1

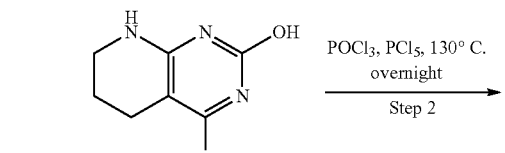

POCl$_3$, PCl$_5$, 130° C.
overnight
Step 2

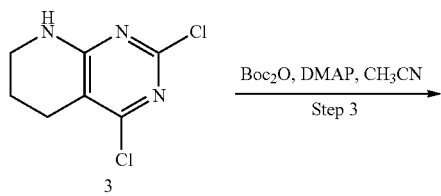

Boc$_2$O, DMAP, CH$_3$CN
Step 3

-continued

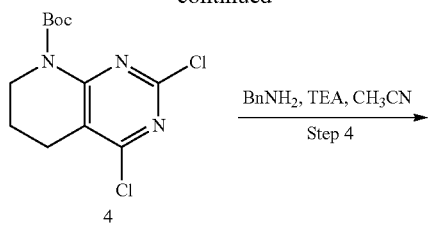

BnNH$_2$, TEA, CH$_3$CN
Step 4

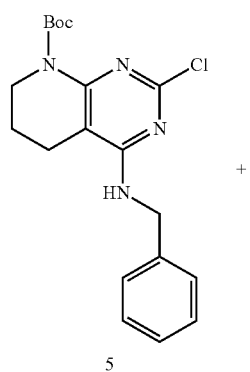

+

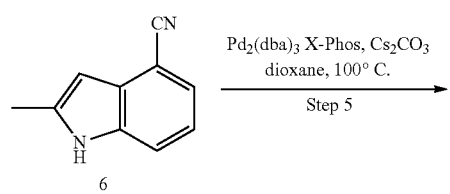

Pd$_2$(dba)$_3$ X-Phos, Cs$_2$CO$_3$
dioxane, 100° C.
Step 5

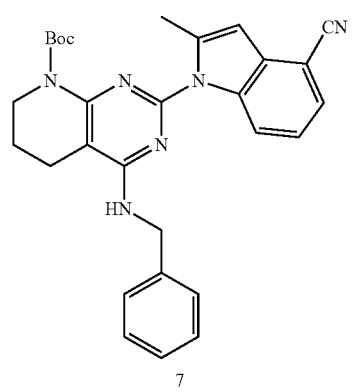

UHP, K$_2$CO$_3$, DMSO
Step 6

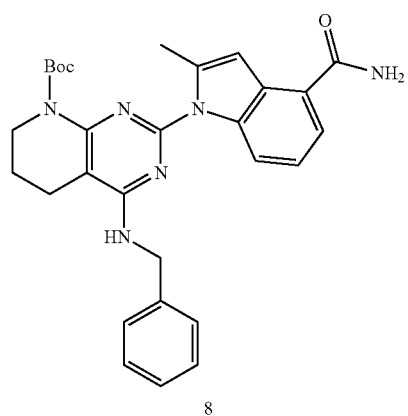

HCl, EA
Step 7

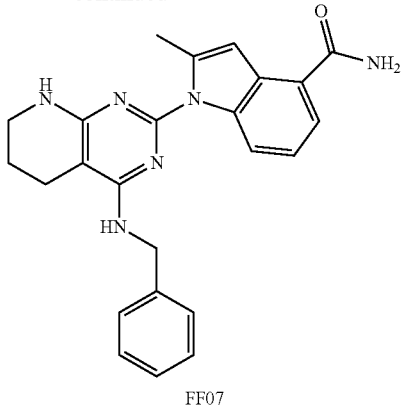

FF07

To a solution of pyrido[2,3-d]pyrimidine-2,4-diol 1 (0.80 g, 4.9 mmol) in AcOH/H₂O (12 mL/8 mL) was added Pd(OH)₂ (0.08 g, 0.57 mmol). The mixture was heated at 70° C. overnight under hydrogen atmosphere. The mixture was filtered to afford 5,6,7,8-tetrahydropyrido[2,3-d]pyrimidine-2,4-diol 2 (0.5 g, 61%). LRMS (M+H⁺) m/z: calcd 168.07; found 168.

A mixture of 5,6,7,8-tetrahydropyrido[2,3-d]pyrimidine-2,4-diol 2 (500 mg, 2.99 mmol) and PCl₅ (300 mg, 1.5 mmol) in POCl₃ (10 mL) was heated at 130° C. overnight. The reaction mixture was cooled to room temperature and concentrated under vacuum, the residue was dissolved in DCM (20 mL) and poured into ice water (20 mL), the oil layer was concentrated under vacuum and the residue was purified by flash chromatography (petroleum:ethyl acetate=5:1) to afford 2,4-dichloro-5,6,7,8-tetrahydropyrido[2,3-d]pyrimidine 3 (150 mg, 25%). LCMS (M+H⁺) m/z: calcd 204.00; found 203.9.

A mixture of 2,4-dichloro-5,6,7,8-tetrahydropyrido[2,3-d]pyrimidine 3 (150 mg, 0.74 mmol), DMAP (91 mg, 0.74 mmol) and Boc₂O (241 mg, 1.1 mmol) in CH₃CN (10 mL) was stirred at room temperature for 0.5 hour. The reaction mixture was concentrated under vacuum, and the residue was purified by flash chromatography (petroleum:ethyl acetate=10:1) to afford tert-butyl 2,4-dichloro-6,7-dihydropyrido[2,3-d]pyrimidine-8(5H)-carboxylate 4 (100 mg, 45%). LRMS (M+H) m/z: calcd 248.05; found 247.9.

To a solution of tert-butyl 2,4-dichloro-6,7-dihydropyrido[2,3-d]pyrimidine-8(5H)-carboxylate 4 (100 mg, 0.33 mmol) and TEA (100 mg, 0.99 mmol) in CH₃CN (10 mL) was added phenylmethanamine (43 mg, 0.39 mmol) stirred at 70° C. overnight. The reaction mixture was cooled to room temperature and concentrated under vacuum, the residue was purified by flash chromatography (petroleum/ethyl acetate) to afford tert-butyl 4-(benzylamino)-2-chloro-6,7-dihydropyrido[2,3-d]pyrimidine-8(5H)-carboxylate 5 (100 mg, 81%). LRMS (M+H⁺) m/z: calcd 375.15; found 375.1.

A mixture of tert-butyl 4-(benzylamino)-2-chloro-6,7-dihydropyrido[2,3-d]pyrimidine-8(5H)-carboxylate 5 (100 mg, 0.27 mmol), 2-methyl-1H-indole-4-carbonitrile 6 (41 mg, 0.32 mmol), tris(dibenzylideneacetone) dipalladium (98 mg, 0.11 mmol), X-phos (26 mg, 0.05 mmol) and Cs₂CO₃ (174 mg, 0.54 mmol) in dioxane (10 mL) was heated at 100° C. for 3 hours under nitrogen atmosphere.

The reaction mixture was cooled to room temperature and concentrated under vacuum, and the residue was purified by flash chromatography (petroleum/ethyl acetate) to afford tert-butyl 4-(benzylamino)-2-(4-cyano-2-methyl-1H-indol-1-yl)-6,7-dihydropyrido[2,3-d]pyrimidine-8(5H)-carboxylate 7 (80 mg, 61%). LCMS (M+H⁺) m/z: calcd 495.24; found 495.2.

To a solution of tert-butyl 4-(benzylamino)-2-(4-cyano-2-methyl-1H-indol-1-yl)-6,7-dihydropyrido[2,3-d]pyrimidine-8(5H)-carboxylate 7 (80 mg, 0.16 mmol) in DMSO (8 mL) was added UHP (123 mg, 1.29 mmol) and K₂CO₃ (12 mg, 0.081 mmol), added water (0.5 mL) and the reaction was stirred at room temperature for 2 hours. Water (100 mL) was added to the mixture and the solid formed was filtered to afford tert-butyl 4-(benzylamino)-2-(4-carbamoyl-2-methyl-1H-indol-1-yl)-6,7-dihydropyrido[2,3-d]pyrimidine-8(5H)-carboxylate 8 (60 mg, 70%). LCMS (M+H⁺) m/z: calcd 513.25; found 513.

To a solution of tert-butyl 4-(benzylamino)-2-(4-carbamoyl-2-methyl-1H-indol-1-yl)-6,7-dihydropyrido[2,3-d]pyrimidine-8(5H)-carboxylate 8 (60 mg, 0.12 mmol) in EtOAc (2 mL) was added HCl/EA (5 mL, 2 N), then stirred at room temperature for 1 hour. The solid formed was filtered to afford 1-(4-(benzylamino)-5,6,7,8-tetrahydropyrido[2,3-d]pyrimidin-2-yl)-2-methyl-1H-indole-4-carboxamide FF07 as a white solid (20 mg, 40%). LCMS (M+H⁺) m/z: calcd 413.2; found 413.1. HPLC purity (214 nm): 100%. ¹HNMR (400 MHz, DMSO): δ 7.79-7.65 (m, 2H), 7.50-7.41 (m, 2H), 7.38-7.19 (m, 7H), 6.97-6.89 (m, 1H), 6.88-6.79 (m, 1H), 4.62-4.59 (m, 2H), 3.33-3.26 (m, 2H), 2.54-2.52 (m, 2H), 2.45 (s, 3H), 1.94-1.86 (m, 2H).

Synthesis of 1-[4-(Benzylamino)-5,6-dihydrofuro[2,3-d]pyrimidin-2-yl]-2-methyl-indole-4-carboxamide FF08

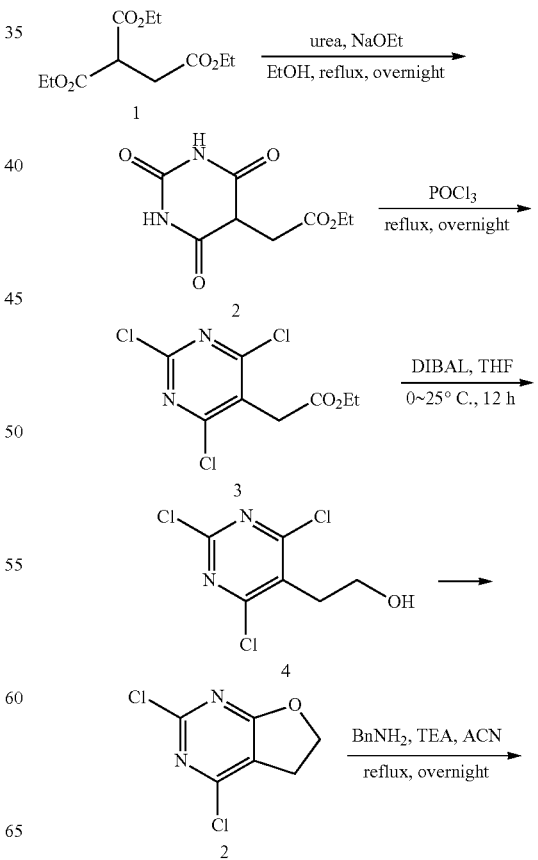

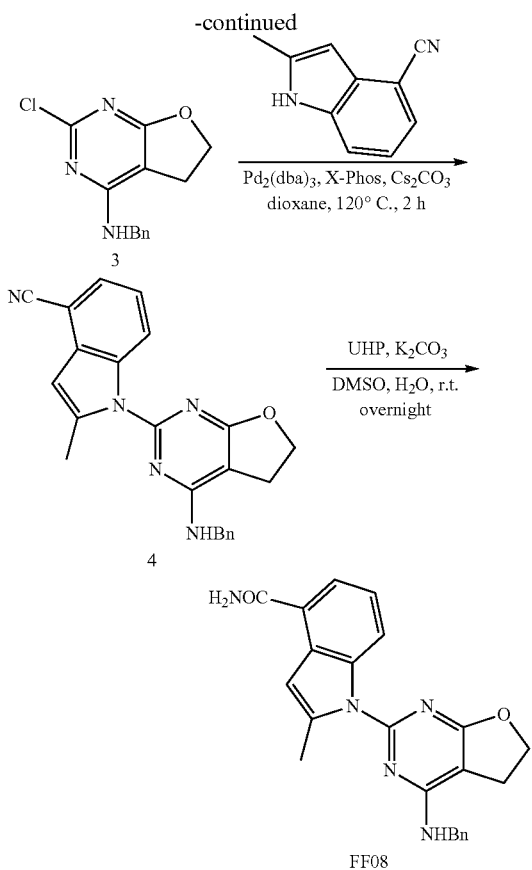

To a solution of EtOH (400 mL) was added Na (2.66 g, 0.12 mol) in portions. After all the sodium was dissolved, triethyl ethane-1,1,2-tricarboxylate (19 g, 77.16 mmol) and urea (5.1 g, 84.87 mmol) were added to the reaction successively. The white suspension was refluxed for 16 h. A lot of white solid formed. TLC showed the reaction was completed. The reaction mixture was filtered and the filter cake was washed with EtOH (200 mL). The filtrate was concentrated in vacuo to give the desired Ethyl 2-(2,4,6-trioxohexahydropyrimidin-5-yl)acetate (15 g, 81.7%) as a white solid which was confirmed at next step. LCMS (M−H$^+$) m/z: Calcd: 213.05; Found: 213.3.

A white suspension of ethyl 2-(2,4,6-trioxohexahydropyrimidin-5-yl)acetate (19 g, 88.71 mmol) in POCl$_3$ (100 mL) was refluxed for 16 h. The color of reaction mixture turned to brown. TLC showed the reaction was completed. The reaction mixture was concentrated in vacuo. The brown residue was purified by column chromatography on silica gel (PE:EA=20:1 to 5:1) to give the desired Ethyl 2-(2,4,6-trichloropyrimidin-5-yl)acetate (1.8 g, 6.8%) as brown oil. LCMS (M+H$^+$) m/z: Calcd: 268.97; Found: 269.0.

To a solution of ethyl 2-(2,4,6-trichloropyrimidin-5-yl)acetate (500 mg, 1.86 mmol) in THF (20 mL) was added DIBAL-H (1 M in toluene, 7.42 mL) drop wise at 0° C. The light yellow solution was stirred at 15° C. for 12 h. TLC showed the reaction was completed. The reaction was quenched by 1 N HCl (20 mL). The resulting mixture was extracted with EA (20 mL*3). The combined organic layers were dried over Na$_2$SO$_4$ and concentrated in vacuo. The residue was purified by column chromatography on silica gel (PE:EA=10:1 to 1:1) to give the desired 2-(2,4,6-Trichloropyrimidin-5-yl)ethanol (0.2 g, 42.7%) as brown solid. LCMS (M+H$^+$) m/z: Calcd: 226.95; Found: 227.0.

To a colorless solution of 2-(2,4,6-trichloropyrimidin-5-yl)ethanol (500 mg, 2.2 mmol) in anhydrous THF (50 mL) was added NaH (131.87 mg, 3.3 mmol, 60% in mineral oil) at r.t. The reaction mixture was stirred at r.t. for overnight. TLC showed the reaction was completed. The reaction was quenched by adding sat. NH$_4$Cl (20 mL) and then extracted with EA (20 mL*3). The combined organic layers were dried over Na$_2$SO$_4$ and concentrated in vacuo. The residual was purified by prep-TLC to give the desired 2,4-Dichloro-5,6-dihydrofuro[2,3-d]pyrimidine (0.1 g, 21.4%) as a white solid. LCMS (M+H$^+$) m/z: Calcd: 190.97; Found: 191.1.

A colorless solution of 2,4-dichloro-5,6-dihydrofuro[2,3-d]pyrimidine (90 mg, 0.47 mmol), phenylmethanamine (55.54 mg, 0.52 mmol) and TEA (57.21 mg, 0.57 mmol) in MeCN (25 mL) was refluxed for 16 h. LCMS showed the reaction was completed. The reaction mixture was concentrated in vacuo and purified by prep-TLC (PE:EA=1:1) to give the desired N-Benzyl-2-chloro-5,6-dihydrofuro[2,3-d]pyrimidin-4-amine (50 mg, 36.5%) as a white solid. $^1$HNMR (400 MHz, CDCl$_3$): δ 7.30 (m, 5H, Ph), 5.50 (s, 1H, NH), 4.63 (m, 4H, NHC$\underline{H}_2$, OC$\underline{H}_2$), 3.18 (m, 2H, PhC$\underline{H}_2$). LRMS (M+H$^+$) m/z: Calcd: 262.07; Found: 262.1. A red suspension of N-benzyl-2-chloro-5,6-dihydrofuro[2,3-d]pyrimidin-4-amine (45 mg, 0.17 mmol), 2-methyl-1H-indole-4-carbonitrile (32.23 mg, 0.21 mmol), Pd$_2$(dba)$_3$ (31.49 mg, 0.03 mmol), K$_2$CO$_3$ (47.53 mg, 0.34 mmol) and X-Phos (16.39 mg, 0.03 mmol) in dioxane (5 mL) was refluxed for 2 h under N$_2$. LCMS showed the reaction was completed. The reaction was filtered and the filtrate was concentrated in vacuo. The crude product was purified by prep-TLC (PE:EA=5:1) to give the desired 1-[4-(Benzylamino)-5,6-dihydrofuro[2,3-d]pyrimidin-2-yl]-2-methyl-indole-4-carbonitrile (50 mg, 68.6%) as light yellow solid. LRMS (M+H$^+$) m/z: Calcd: 382.16; Found: 382.2.

A light yellow solution of 1-[4-(benzylamino)-5,6-dihydrofuro[2,3-d]pyrimidin-2-yl]-2-methyl-indole-4-carbonitrile (45 mg, 0.12 mmol), UHP (55.49 mg, 0.59 mmol) and K$_2$CO$_3$ (16.31 mg, 0.12 mmol) in DMSO (20 mL) and H$_2$O (1 mL) was stirred at 15° C. for 2 h. TLC showed the reaction was completed. EA (20 mL) and brine (20 mL) was added to the reaction. The organic layer was separated and washed with brine (20 mL*3), dried over Na$_2$SO$_4$ and concentrated in vacuo. The yellow residue was purified by prep-TLC to give the desired 1-[4-(Benzylamino)-5,6-dihydrofuro[2,3-d]pyrimidin-2-yl]-2-methyl-indole-4-carboxamide FF08 (30 mg, 63.7%) as a white solid. $^1$HNMR (400 MHz, CDCl$_3$): δ 8.28 (d, 1H, Ph), 7.49 (d, 1H, Ph), 7.43-7.30 (m, 5H, CH$_2$Ph), 7.10 (m, 1H, Ph), 6.83 (s, 1H, 3-H of indole), 6.15 (s, 2H, NH$_2$), 4.98 (s, 1H, NH), 4.81-4.61 (m, 4H, OC$\underline{H}_2$+NHC$\underline{H}_2$), 3.08 (m, 2H, C$\underline{H}_2$), 2.74-2.57 (s, 3H, C$\underline{H}_3$). LRMS (M+H$^+$) m/z: Calcd: 400.18; Found: 400.2.

Synthesis of 1-(4-((3-Fluorobenzyl)amino)-6,7-dihydro-5H-pyrano[2,3-d]pyrimidin-2-yl)-2-methyl-1H-indole-4-carboxamide FF09

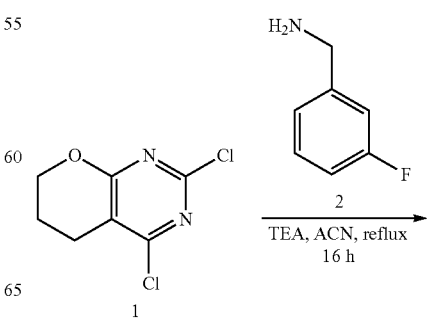

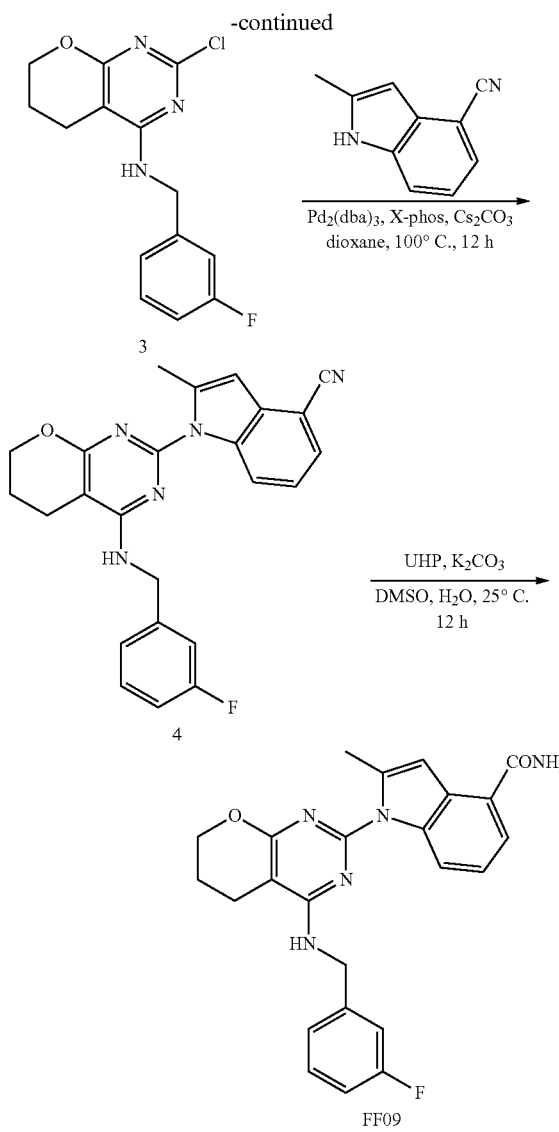

To a mixture of 2,4-dichloro-6,7-dihydro-5H-pyrano[2,3-d]pyrimidine (250 mg, 1 mmol) in ACN (20 mL) was added DIPEA (464 mg, 4 mmol) compound 2 (604 mg, 5 mmol). The reaction mixture was refluxed for 16 h. TLC (PE:EA=2:1) show the reaction was completed. Then the mixture was concentrated and purified by silica gel (PE:EA=6:1 to 3:1) to give the desired 2-chloro-N-(3-fluorobenzyl)-6,7-dihydro-5H-pyrano[2,3-d]pyrimidin-4-amine (240 mg, 67.67%) as a white solid. LCMS (M+H$^+$) m/z: Calcd: 294.07; Found: 294.1.

To a solution of 2-chloro-N-(3-fluorobenzyl)-6,7-dihydro-5H-pyrano[2,3-d]pyrimidin-4-amine (820 mg, 3 mmol) in dioxane (150 mL) were added 2-methyl-1H-indole-4-carbonitrile (654 mg, 4 mmol), Cs$_2$CO$_3$ (1.819 g, 6 mmol), X-Phos (532 mg, 1 mmol) and Pd$_2$(dba)$_3$ (767 mg, 0.838 mmol). The resulting mixture was stirred at 100° C. for 12 h under N$_2$. TLC (PE:EA=1:1) show the reaction was completed. Then the mixture was filtered, the filtrate was concentrated and purified by silica gel (PE:EA=10:1) to give the desired 1-(4-((3-Fluorobenzyl)amino)-6,7-dihydro-5H-pyrano[2,3-d]pyrimidin-2-yl)-2-methyl-1H-indole-4-carbonitrile (600 mg, 52%). LCMS (M+H$^+$) m/z: Calcd: 414.17; Found: 414.2.

To a mixture of 1-(4-((3-fluorobenzyl)amino)-6,7-dihydro-5H-pyrano[2,3-d]pyrimidin-2-yl)-2-methyl-1H-indole-4-carbonitrile (0.6 g, 1 mmol) in DMSO (50 mL) was added UHP (0.697 g, 7 mmol) and K$_2$CO$_3$ (0.1 g, 0.726 mmol). The reaction mixture was stirred for 10 min. Then H$_2$O (5 mL) was added and stirred for 12 h at 25° C. TLC (PE:EA=1:2) show the reaction was completed. Then H$_2$O (500 mL) was added, and then extracted with EA (200 mL*3). The combined organic phase was concentrated and purified by silica gel (PE:EA=5:1 to 1:1) to give crude product which was washed with ACN (10 mL), filtered and concentrated to give the desired 1-(4-((3-Fluorobenzyl)amino)-6,7-dihydro-5H-pyrano[2,3-d]pyrimidin-2-yl)-2-methyl-1H-indole-4-carboxamide FF09 (0.2 g, 31.3%). LCMS (M+H$^+$) m/z: Calcd: 432.18; Found: 432.2. $^1$HNMR (400 MHz, CD$_3$OD): δ 7.73 (d, J=8.4 Hz, 1H, Ph), 7.47 (d, J=7.2 Hz, 1H, Ph), 7.34 (m, 1H, Ph), 7.16-7.14 (d, J=7.2 Hz, 1H, Ph), 7.04 (m, 1H, Ph), 7.00-6.97 (m, 2H, Ph), 6.77 (s, 1H, 3-H of indole), 4.73 (s, 2H, PhCH$_2$NH), 4.40-4.38 (m, 2H, OCH$_2$CH$_2$CH$_2$), 2.61-2.58 (m, 2H, OCH$_2$CH$_2$CH$_2$), 2.46 (s, 3H, NCCH$_3$), 2.17-2.14 (m, 2H, OCH$_2$CH$_2$CH$_2$).

Synthesis of 3-[4-(Benzylamino)-7,8-dihydro-5H-pyrano[4,3-d]pyrimidin-2-yl-2-methyl-1H-indole-7-carboxamide FF10

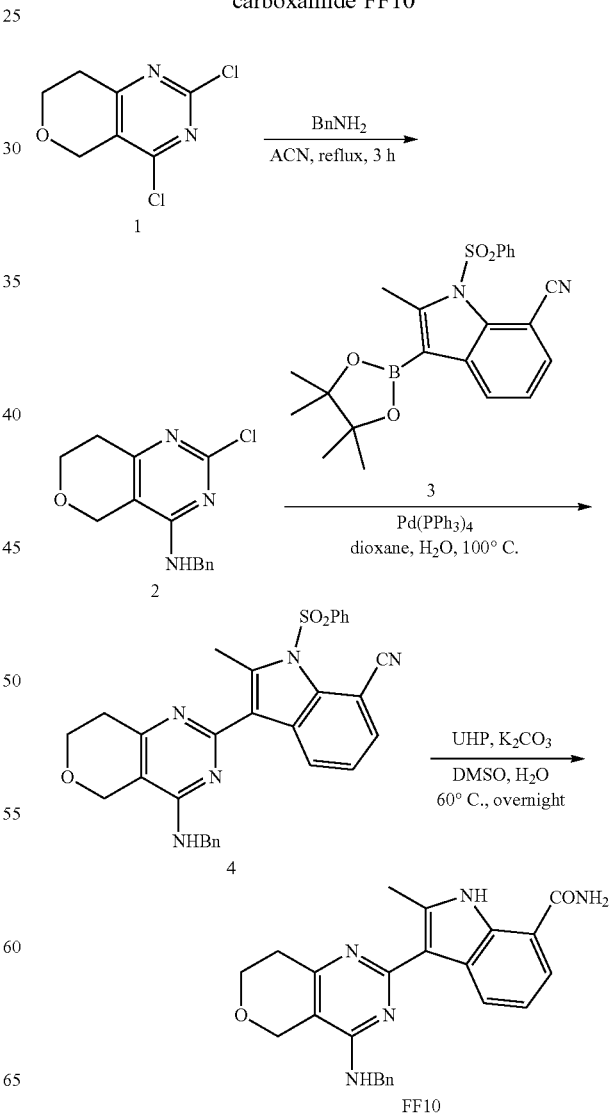

To a solution of 2,4-dichloro-7,8-dihydro-5H-pyrano[4,3-d]pyrimidine (1 g, 4.877 mmol) in ACN (50 ml) was added BnNH₂ (0.78 g, 7.316 mmol). The mixture was stirred at 25° C. for 12 h under N₂. TLC showed the reaction was completed. The reaction was concentrated in vacuo and purified by column chromatography (PE/EA=10/1 to 5/1) to give the desired N-Benzyl-2-chloro-7,8-dihydro-5H-pyrano[4,3-d]pyrimidin-4-amine (0.85 g, 60.5% yield) as a white solid.

To a solution of N-benzyl-2-chloro-7,8-dihydro-5H-pyrano[4,3-d]pyrimidin-4-amine (300 mg, 1.09 mmol) and 1-(benzenesulfonyl)-2-methyl-3-(4,4,5,5-tetramethyl-1,3,2-dioxaborolan-2-yl)indole-7-carbonitrile (551 mg, 1.31 mmol) in dioxane (10 mL) and H₂O (2 mL) were added K₂CO₃ (300 mg, 2.17 mmol) and Pd(PPh₃)₄ (126 mg, 0.11 mmol). The mixture was stirred at 100° C. under N₂ for 3 h. TLC showed the reaction was completed. The mixture was diluted with EA (20 mL) and H₂O (5 mL). The organic phase was separated, dried over Na₂SO₄, concentrated and purified by column chromatography (PE:EA=10:1 to pure EA) to afford the desired 1-(Benzenesulfonyl)-3-[4-(benzylamino)-7,8-dihydro-5H-pyrano[4,3-d]pyrimidin-2-yl]-2-methyl-indole-7-carbonitrile (300 mg, 50.5%) as a white solid. LCMS (M+H⁺) m/z: Calcd: 536.17; Found: 536.2.

To a solution of 1-(benzenesulfonyl)-3-[4-(benzylamino)-7,8-dihydro-5H-pyrano[4,3-d]pyrimidin-2-yl]-2-methyl-indole-7-carbonitrile (150 mg, 280 mmol) in DMSO (10 mL) and H₂O (0.2 mL) were added UHP (130 mg, 1.4 mmol) and K₂CO₃ (19 mg, 140 mmol). The mixture was stirred at 60° C. for 12 h. TLC showed 10% 1-(benzenesulfonyl)-3-[4-(benzylamino)-7,8-dihydro-5H-pyrano[4,3-d]pyrimidin-2-yl]-2-methyl-indole-7-carbonitrile was remained. The mixture was poured into H₂O (100 mL) and then extracted with EA (50 mL*2).

The combined organic layers were washed with brine (20 mL), dried over Na₂SO₄, concentrated in vacuo to dryness and purified by column chromatography (PE:EA=5:1 to 100% EA) to afford the desired 3-[4-(Benzylamino)-7,8-dihydro-5H-pyrano[4,3-d]pyrimidin-2-yl-2-methyl-1H-indole-7-carboxamide FF10 (60 mg, 50.3%). LCMS (M+H⁺) m/z: Calcd: 414.19; Found: 414.3. ¹HNMR (400 MHz, CDCl₃): δ 11.05 (s, 1H, CONH₂), 8.53 (d, J=8.0 Hz, 1H, C₆H₃), 8.02 (s, 1H, CONH₂), 7.57-7.59 (m, 1H, C₆H₃), 7.31-7.35 (m, 5H, C₆H₅), 7.20-7.21 (m, 1H, C₆H₃), 7.14-7.15 (m, 1H, NH), 6.99-7.02 (m, 1H, NH), 4.72-4.73 (d, J=7.2 Hz, 2H, CH₂), 4.55 (s, 2H, CH₂), 3.96 (t, J=5.6 Hz, CH₃), 2.72-2.73 (m, 5H, CH₂, CH3)

Synthesis of 1-(4-((3-fluorobenzyl)amino)-5-methyl-5,6,7,8-tetrahydropyrido[3,2-d]pyrimidin-2-yl)-1H-indazole-4-carboxamide FF11

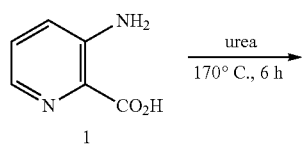

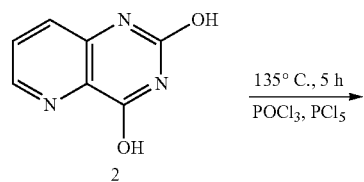

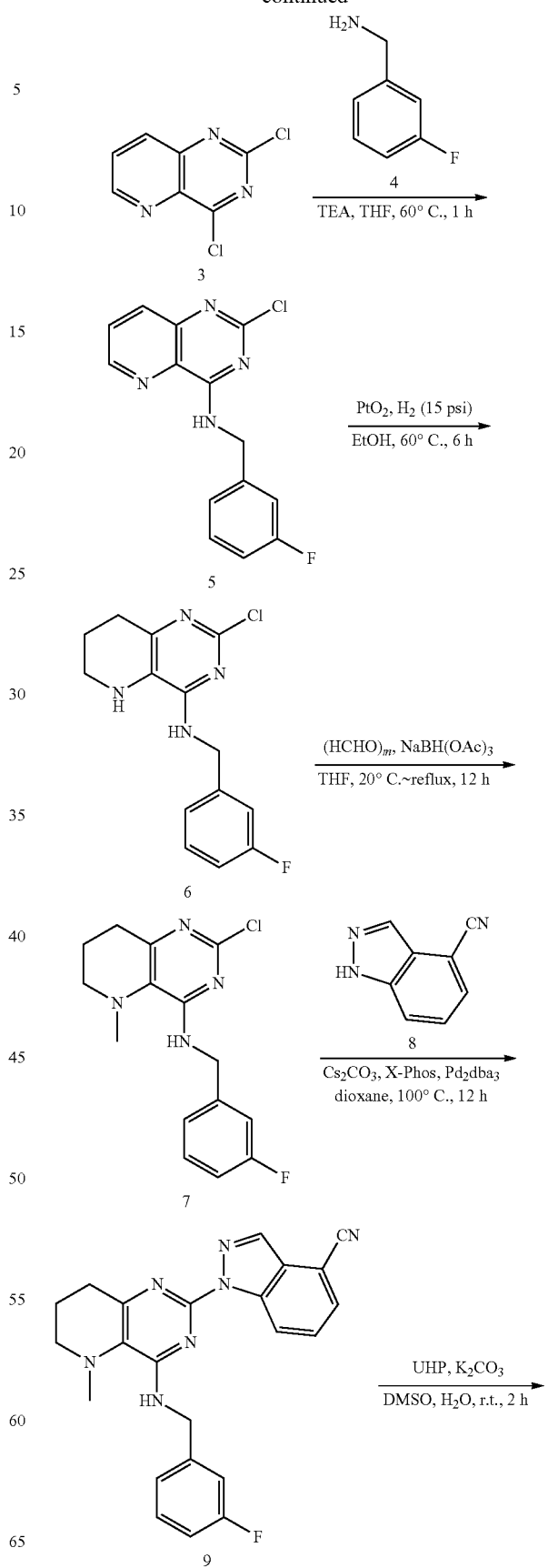

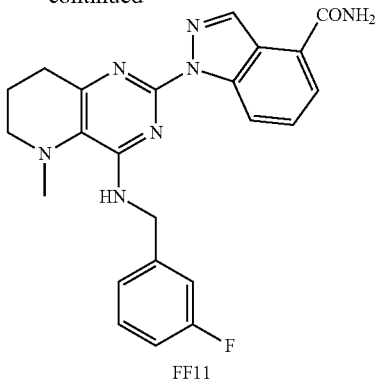

FF11

A mixture of 3-aminopicolinic acid (5.00 g, 36.2 mmol) and urea (10.9 g, 181 mmol) in a 100 mL flask was stirred at 170° C. for 6 h. The reaction mixture was turned from clear solution to suspension. Then the reaction mixture was cooled to 25° C. and filtered. The filter cake was washed with water (50 mL) and dried to give the desired Pyrido[3,2-d]pyrimidine-2,4-diol (3.2 g, 74.5%) as a white solid. $^1$HNMR (400 MHz, CDCl$_3$): δ 11.66 (s, 1H, O$\underline{H}$), 11.16 (s, 1H, O$\underline{H}$), 8.59 (d, J=2.4 Hz, 1H, C$_6\underline{H}_3$), 8.25 (d, J=8.4 Hz, 1H, C$_6\underline{H}_3$), 7.24 (t, J=2.4 Hz, 1H, C$_6\underline{H}_3$).

A mixture of pyrido[3,2-d]pyrimidine-2,4-diol (5.0 g, 0.031 mol), POCl$_3$ (150 mL) and PCl$_5$ (25.5 g, 0.128 mol) was stirred at 130° C. for 3 h. TLC showed the reaction was completed. It was concentrated in vacuo, the residue was dissolved with DCM (1000 mL) and then poured into H$_2$O (400 mL). The organic layer was separated, washed with sat. Na$_2$CO$_3$ (400 mL), dried with Na$_2$SO$_4$, filtered, concentrated in vacuo and purified by column chromatography (PE:EA=10:1 to PE:EA=3:1) to afford pure desired 2,4-dichloropyrido[3,2-d]pyrimidine (3.5 g, 57.4%) as a yellow solid. $^1$HNMR (400 MHz, CDCl$_3$): 9.33 (t, J=2.4 Hz, 1H, C$_6\underline{H}_3$), 8.64 (d, J=7.6 Hz, 1H, C$_6\underline{H}_3$), 7.71-7.75 (m, 1H, C$_6\underline{H}_3$).

To a yellow solution of 2,4-dichloropyrido[3,2-d]pyrimidine (500 mg, 2.5 mmol) in anhydrous THF (30 ml) were added (3-fluorophenyl)methanamine (344 mg, 2.75 mmol) and TEA (379 mg, 3.75 mmol). Then the mixture stirred at 60° C. for 1 h under N$_2$. TLC showed the reaction was completed. The reaction mixture was concentrated to dryness in vacuo to afford crude 2-Chloro-N-[(3-fluorophenyl)methyl]pyrido[3,2-d]pyrimidin-4-amine (0.72 g, 84.8%) as a yellow solid.

To a yellow suspension of 2-chloro-N-[(3-fluorophenyl)methyl]pyrido[3,2-d]pyrimidin-4-amine (0.72 g, 2.5 mmol) in EtOH (50 ml) was added PtO$_2$ (110 mg). Then the mixture was stirred at 60° C. under H$_2$ (15 psi) over 6 h. TLC showed the ratio of product:2-chloro-N-[(3-fluorophenyl)methyl]pyrido[3,2-d]pyrimidin-4-amine=1:1. Catalyst was removed by filtration. The filtrate was concentrated to dryness in vacuo and purified by column chromatography (PE:EA=5:1 to 1:1) to afford the desired 2-chloro-N-[(3-fluorophenyl)methyl]-5,6,7,8-tetrahydropyrido[3,2-d]pyrimidin-4-amine (300 mg, 37%) as a white solid.

To a white suspension of 2-chloro-N-[(3-fluorophenyl)methyl]-5,6,7,8-tetrahydropyrido[3,2-d]pyrimidin-4-amine (250 mg, 0.854 mmol) in anhydrous THF (10 mL) was added paraformalgehyde (153.85 mg, 1.708 mmol) and one drop AcOH. Then the white suspension was stirred at 20° C. for 3 h. NaBH(OAc)$_3$ (362 mg, 1.708 mmol) was added to the above mixture. Then the mixture was stirred at 80° C. for 9 h. LCMS and TLC showed 2-chloro-N-[(3-fluorophenyl)methyl]-5,6,7,8-tetrahydropyrido[3,2-d]pyrimidin-4-amine: Product=1:2. The white suspension was filtered through celitic and the filtrate was concentrated to dryness in vacuo and purified by column chromatography (PE:EA=10:1 to 1:1) to afford the desired 2-chloro-N-[(3-fluorophenyl)methyl]-5-methyl-7,8-dihydro-6H-pyrido[3,2-d]pyrimidin-4-amine (200 mg, 57%) as colorless oil. LCMS (M+H$^+$) m/z: Calcd: 307.11; Found: 307.10. $^1$HNMR (400 MHz, CDCl$_3$): δ 7.32 (t, J=6.0 Hz, 1H, C$_6\underline{H}_4$), 7.13 (d, J=7.6 Hz, 1H, C$_6\underline{H}_4$), 7.06-7.00 (m, 2H, C$_6\underline{H}_4$), 5.67 (s, 1H, N$\underline{H}$), 4.69 (d, J=7.2 Hz, 2H, C$\underline{H}_2$Ph), 2.96-3.02 (m, 2H, C$\underline{H}_2$), 2.71-2.74 (m, 2H, C$\underline{H}_2$), 2.58 (s, 3H, C$\underline{H}_3$), 1.95-1.99 (m, 2H, C$\underline{H}_2$).

To a solution of 2-chloro-N-[(3-fluorophenyl)methyl]-5-methyl-7,8-dihydro-6H-pyrido[3,2-d]pyrimidin-4-amine (50 mg, 0.16 mmol) and 1H-indazole-4-carbonitrile (25.66 mg, 0.18 mmol) in anhydrous dioxane (10 mL) were added X-Phos (15.52 mg, 0.033 mmol), Pd$_2$dba$_3$ (29.83 mg, 0.033 mmol) and Cs$_2$CO$_3$ (106.92 mg, 0.326 mmol). Then the mixture was stirred at 100° C. for 12 under N$_2$. TLC showed Product: 2-chloro-N-[(3-fluorophenyl)methyl]-5-methyl-7,8-dihydro-6H-pyrido[3,2-d]pyrimidin-4-amine=1:1. The mixture was filtered through celitic, concentrated to dryness in vacuo and purified by column chromatography (PE:EA=10:1 to 1:1) to afford the desired 1-[4-[(3-Fluorophenyl)methylamino]-5-methyl-7,8-dihydro-6H-pyrido[3,2-d]pyrimidin-2-yl]indazole-4-carbonitrile (20 mg, 23.7%) as yellow oil. LCMS (M+H$^+$) m/z: Calcd: 414.18; Found: 414.2.

To a yellow solution of 1-[4-[(3-fluorophenyl)methylamino]-5-methyl-7,8-dihydro-6H-pyrido[3,2-d]pyrimidin-2-yl]indazole-4-carbonitrile (20 mg, 0.05 mmol) in DMSO (3 mL) and H$_2$O (0.3 mL) were added UHP (22.74 mg, 0.242 mmol) and K$_2$CO$_3$ (3.338 mg, 0.024 mmol). Then the mixture was stirred at 20° C. for 2 h. TLC showed the reaction was completed. To the above mixture were added H$_2$O (30 ml) and EA (20 mL). The organic phase was separated and the aqueous layer was extracted with EA (10 mL*2). The combined organic layers were washed with brine (15 mL*5), dried over Na$_2$SO$_4$, concentrated to dryness in vacuo and purified by prep-TLC (EA:MeOH=3:1) to afford the desired 1-[4-[(3-Fluorophenyl)methylamino]-5-methyl-7,8-dihydro-6H-pyrido[3,2-d]pyrimidin-2-yl]indazole-4-carboxamide FF11(6 mg, 26.4%) as a white solid. LCMS (M+H$^+$) m/z: Calcd: 432.19; Found: 432.3. $^1$HNMR (400 MHz, CDCl$_3$): δ 8.73 (s, 1H, C$\underline{H}$), 8.55 (d, J=8.0 Hz, 1H, C$_6\underline{H}_4$), 7.34-7.54 (m, 3H, C$_6\underline{H}_4$), 7.01-7.22 (m, 3H, C$_6\underline{H}_3$), 6.12 (s, 2H, CON$\underline{H}_2$), 5.86 (s, 1H, N$\underline{H}$), 3.10 (m, C$\underline{H}_2$), 2.93 (m, C$\underline{H}_2$), 2.69 (s, C$\underline{H}_3$), 1.62 (s, C$\underline{H}_2$).

Synthesis of 1-(4-((3-fluorobenzyl)amino)-5-methyl-5,6,7,8-tetrahydropyrido[3,2-d]pyrimidin-2-yl)-2-methyl-1H-indole-4-carboxamide FF12

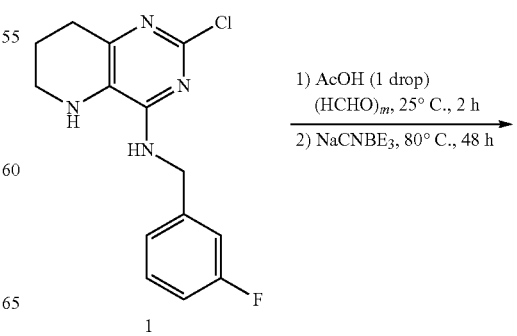

1) AcOH (1 drop)
(HCHO)$_m$, 25° C., 2 h
2) NaCNBE$_3$, 80° C., 48 h

1

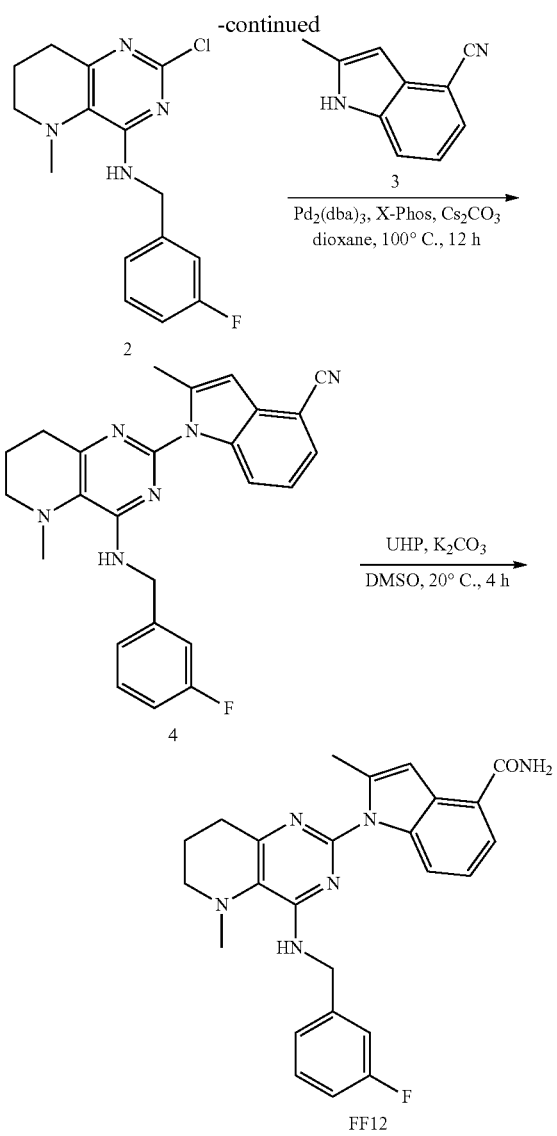

trile (61 mg, 0.392 mmol) in dioxane (10 mL) were added Pd$_2$(dba)$_3$ (60 mg, 0.065 mmol), X-Phos (31 mg, 0.065 mmol) and Cs$_2$CO$_3$ (214 mg, 0.978 mmol). Then the mixture was stirred at 100° C. for 12 h under N$_2$. LCMS showed product: by-product (298)=4:1. The mixture was diluted with H$_2$O (10 mL) and then extracted with EA (10 mL*3). The combined organic layers were washed with brine (10 mL), dried over Na$_2$SO$_4$, concentrated to dryness in vacuo and purified by prep-HPLC (TFA) to afford the desired 1-[4-[(3-fluorophenyl)methylamino]-5-methyl-7,8-dihydro-6H-pyrido[3,2-d]pyrimidin-2-yl]-2-methyl-indole-4-carbonitrile (100 mg, 68.3%) as a white solid. LCMS (M+H$^+$) m/z: Calcd: 427.20; Found: 427.1.

To a solution of 1-[4-[(3-fluorophenyl)methylamino]-5-methyl-7,8-dihydro-6H-pyrido[3,2-d]pyrimidin-2-yl]-2-methyl-indole-4-carbonitrile (90 mg, 0.211 mmol) in DMSO (10 mL) and H$_2$O (1 mL) were added UHP (99 mg, 1.055 mmol) and K$_2$CO$_3$ (15 mg, 0.105 mmol). The mixture was stirred at 20° C. for 4 h. TLC showed the reaction was completed. The mixture was quenched with H$_2$O (20 mL) and then extracted with EA (10 mL*3). The combined organic layers were washed with brine (10 mL*5), dried over Na$_2$SO$_4$, concentrated to dryness in vacuo and purified by prep-TLC (PE:EA=1:3) to afford the desired 1-[4-[(3-fluorophenyl)methylamino]-5-methyl-7,8-dihydro-6H-pyrido[3,2-d]pyrimidin-2-yl]-2-methyl-indole-4-carboxamide FF12 (30 mg, 33.8%) as a white solid. LCMS (M+H$^+$) m/z: Calcd: 445.22; Found: 445.3. $^1$HNMR (400 MHz, CDCl$_3$): δ 8.06 (d, J=8.0 Hz, 1H, C$_6$H$_3$), 7.51 (d, J=7.2 Hz, 1H, C$_6$H$_3$), 7.28-7.33 (m, 1H, C$_6$H$_3$), 7.00-7.14 (m, 4H, C$_6$H$_4$), 6.80 (s, 1H, CH), 6.08 (s, 2H, CONH$_2$), 5.77 (s, 1H, NH), 4.74 (d, J=6.0 Hz, 2H, PhCH$_2$), 3.08-3.12 (m, 2H, CH$_2$), 2.81-2.86 (m, CH$_2$), 2.71 (s, 3H, CH$_3$), 2.59 (s, 3H, CH$_3$), 2.04-2.06 (m, 2H, CH$_2$).

Synthesis of 1-(4-(benzylamino)-6,8-dimethyl-5,6,7,8-tetrahydropyrido[4,3-d]pyrimidin-2-yl)-2-methyl-1H-indole-4-carboxamide FF13

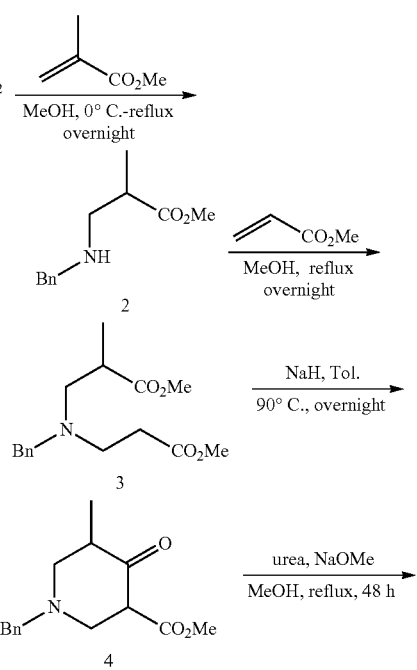

To a solution of 2-chloro-N-[(3-fluorophenyl)methyl]-5,6,7,8-tetrahydropyrido[3,2-d]pyrimidin-4-amine (500 mg, 1.71 mmol) in anhydrous THF (50 mL) were added (HCHO)$_m$ (923 mg, 10.27 mmol) and AcOH (5 drops). Then the mixture was stirred at 25° C. with a drying tube for 8 h. Then NaBH$_3$CN (644 mg, 10.27 mmol) was added. The mixture was stirred at 80° C. for further 48 h. The mixture was quenched with H$_2$O (20 mL) and then extracted with EA (50 mL*3). The combined organic layers were washed with brine (10 mL), dried over Na$_2$SO$_4$, concentrated to dryness in vacuo and purified by column chromatography (PE:EA=10:1 to 5:1) to afford the desired 2-Chloro-N-[(3-fluorophenyl)methyl]-5-methyl-7,8-dihydro-6H-pyrido[3,2-d]pyrimidin-4-amine (340 mg, 60.3%) as red oil. LCMS (M+H$^+$) m/z: Calcd: 307.11; Found: 307.10. $^1$HNMR (400 MHz, CDCl$_3$): δ 7.32 (t, J=6.0 Hz, 1H, C$_6$H$_4$), 7.13 (d, J=7.6 Hz, 1H, C$_6$H$_4$), 7.06-7.00 (m, 2H, C$_6$H$_4$), 5.62 (s, 1H, NH), 4.69 (d, J=7.2 Hz, 2H, CH$_2$Ph), 2.96-3.02 (m, 2H, CH$_2$), 2.71-2.74 (m, 2H, CH$_2$), 2.58 (s, 3H, CH$_3$), 1.93-1.99 (m, 2H, CH2).

To a suspension of 2-chloro-N-[(3-fluorophenyl)methyl]-5-methyl-7,8-dihydro-6H-pyrido[3,2-d]pyrimidin-4-amine (100 mg, 0.326 mmol) and 2-methyl-1H-indole-4-carboni-

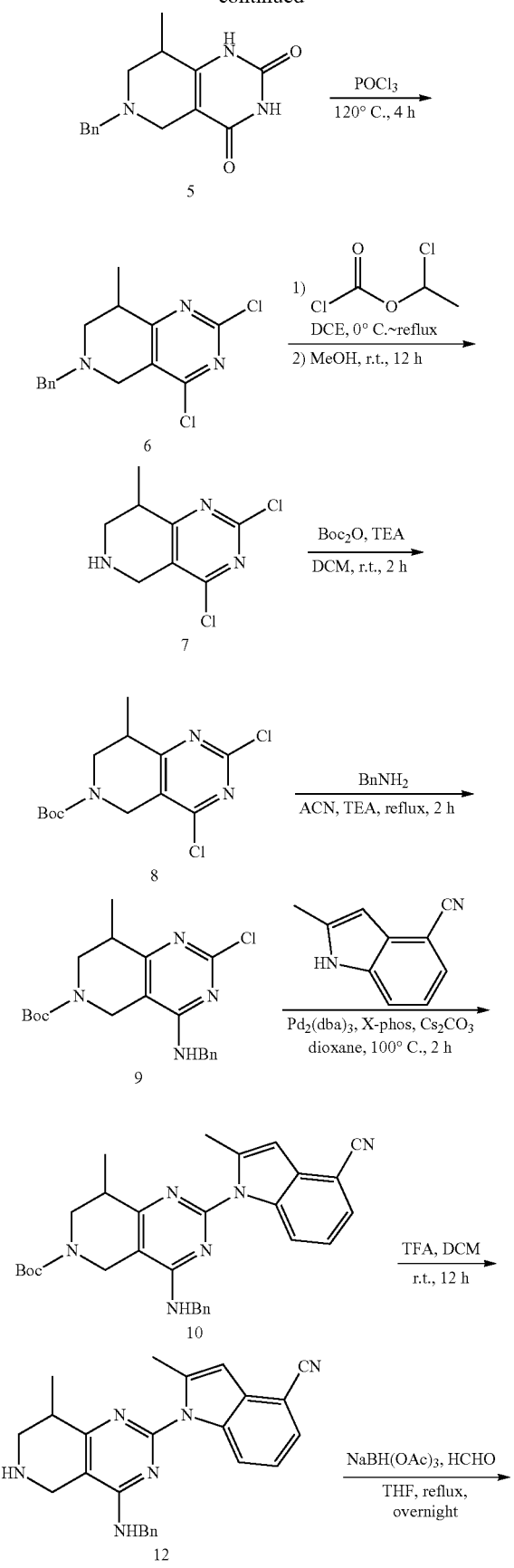

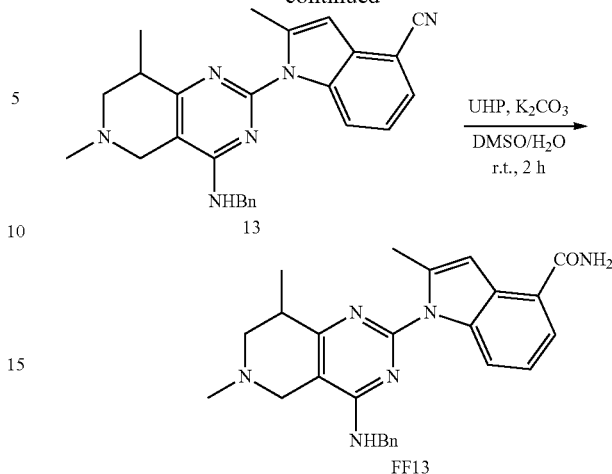

A solution of BnNH₂ (50.0 g, 0.47 mol) and methyl methacrylate (56.04 g, 0.560 mol) in MeOH (1000 mL) was stirred for 5 h at 25° C. under N₂. TLC showed 70% SM was remained. Then the solution was heated to reflux and stirred for overnight. TLC showed the reaction was completed. Then the solution was concentrated in vacuum to give methyl 3-(benzylamino)-2-methylpropanoate 2 (60 g, 62%) as pink oil.

A solution of compound 2 (60.0 g, 0.29 mol) and methyl acrylate (30.0 g, 0.35 mol) in MeOH (800 mL) was heated to reflux and stirred for overnight. TLC showed the reaction was completed. Then the solution was concentrated in vacuum to give crude product of methyl 3-(benzyl(3-methoxy-3-oxopropyl)amino)-2-methylpropanoate 3 (70 g, about 80% purity) as pink oil.

To a solution of compound 3 (20 g, 68.18 mol) in toluene (300 ml), NaH (3.272 g, 81.81 mmol) was added slowly. The mixture was stirred at 90° C. for 12 h under N₂. TLC showed the reaction was completed. After being cooled, the reaction solution was quenched with 100 mL of water, then extracted with EA (200 mL*2). The combined organic phase was concentrated in vacuum and purified by silica gel column chromatography (PE:EA=50:1 to 25:1) to give methyl 1-benzyl-5-methyl-4-oxopiperidine-3-carboxylate 4 (13.6 g, 76.4%) as colorless oil. LCMS (M+H⁺) m/z: Calcd: 262.14; Found: 262.2.

To a solution of compound 4 (15 g, 0.06 mol) in MeOH (200 mL), urea (6.89 g, 0.11 mol) and NaOMe (15.51 g, 0.29 mol) were added slowly. The mixture was stirred at 70° C. for 16 h under N₂. TLC showed the reaction was completed. Then the mixture was cooled to r.t. and then filtered. The filter cake was washed with EtOH (100 mL*2) and dried in vacuum to give the product of 6-benzyl-8-methyl-5,6,7,8-tetrahydropyrido[4,3-d]pyrimidine-2,4(1H,3H)-dione 5 (6.3 g, 40%) as a white solid. LCMS (M+H⁺) m/z: Calcd: 272.14; Found: 272.10.

A solution of compound 5 (3.0 g, 0.011 mol) in POCl₃ (100 mL) was stirred at 120° C. for 4 h. LCMS showed the reaction was completed; the mixture was concentrated in vacuum to give a residue. It was diluted with EA (200 mL) and poured into H₂O (50 mL). The organic layer was separated, dried over Na₂SO₄, filtered and concentrated to give crude compound 6 which was suspended in MTBE (50 mL) and filtered to give pure 6-Benzyl-2,4-dichloro-8-methyl-5,6,7,8-tetrahydropyrido[4,3-d]pyrimidine 6 (2.0 g, 54.58%) as a yellow solid. LCMS (MAT) m/z: Calcd: 308.06; Found: 308.1.

To a solution of compound 6 (4.1 g, 0.013 mol) in DCE (150 mL) at 25° C. under N₂ was added 1-chloroethyl carbonochloridate (38.04 g, 0.266 mol). The mixture was refluxed for 48 h. LCMS showed the reaction was completed; it was concentrated to dryness and dissolved in anhydrous MeOH (150 mL) and stirred at 25° C. for 12 h. LCMS showed the reaction was completed, it was concentrated to dryness in vacuum to afford crude product. It was suspended in EA (5 mL) and filtered to give pure 2,4-dichloro-8-methyl-5,6,7,8-tetrahydropyrido[4,3-d]pyrimidine 7 (2.0 g, 68%) as a yellow solid. LCMS (M+H⁺) m/z: Calcd: 218.02; Found: 218.1.

A mixture of compound 7 (2.0 g, 9.171 mmol), Boc₂O (2.999 g, 13.76 mmol) and Et₃N (1.853 g, 18.34 mmol) in DCM (120 mL) was stirred at 25° C. for 3 h. TLC and LCMS showed the reaction was completed. The reaction mixture was concentrated to give a residue, which was suspended in MTBE (20 mL) and filtered to give pure tert-Butyl 2,4-dichloro-8-methyl-7,8-dihydropyrido[4,3-d]pyrimidine-6(5H)-carboxylate 8 (2.1 g, 72%) as a yellow solid. LCMS (M+H⁺) m/z: Calcd: 318.02; Found: 318.1.

To a solution of compound 8 (1.9 g, 5.971 mmol) and TEA (1.206 g, 11.94 mmol) in ACN (50 mL) was added BnNH₂ (0.768 g, 7.165 mmol). The mixture was stirred at 85° C. for 3.5 h. TLC and LCMS showed the reaction was completed, it was concentrated in vacuum to get a residue, which was purified by column chromatography (PE/EA=10/1 to 5/1) to give tert-butyl 4-(benzylamino)-2-chloro-8-methyl-7,8-dihydropyrido[4,3-d]pyrimidine-6(5H)-carboxylate 9 (1.9 g, 82%) as a yellow solid. LCMS (M+H⁺) m/z: Calcd: 389.17; Found: 389.2.

A mixture of compound 9 (389 mg, 1 mmol), 2-methyl-4-nitrile-indole (0.203 g, 1.3 mmol), Pd₂(dba)₃ (0.275 g, 0.3 mmol), X-Phos (0.187 g, 0.4 mmol) and Cs₂CO₃ (0.652 g, 2 mmol) in dioxane (50 mL) was stirred at 100° C. for 2 h under N₂. TLC showed the reaction was completed. It was concentrated to get a residue, which was purified by column chromatography (PE/EA=5/1) to give tert-butyl 4-(benzylamino)-2-(4-cyano-2-methyl-1H-indol-1-yl)-8-methyl-7,8-dihydropyrido[4,3-d]pyrimidine-6(5H)-carboxylate 10 (0.34 g, 67%) as a yellow solid. LCMS (M+H⁺) m/z: Calcd: 509.27; Found: 509.3.

A solution of compound 10 (0.28 g, 0.551 mmol) in TFA (20 mL, 20% in DCM) was stirred at 25° C. for 12 h. LCMS showed the reaction was completed, it was poured into sat. NaHCO₃ (250 mL) and extracted with EA (100 mL*2). The combined organic phase was dried over Na₂SO₄, filtered and concentrated to give 1-(4-(benzylamino)-8-methyl-5,6,7,8-tetrahydropyrido[4,3-d]pyrimidin-2-yl)-2-methyl-1H-indole-4-carbonitrile 12 (0.13 g, 60%) as a yellow solid. LCMS (M+H⁺) m/z: Calcd: 409.21; Found: 409.3.

A mixture of compound 12 (110 mg, 0.269 mmol), (CH₂O)n (72.71 mg, 0.808 mmol) and three drops of AcOH in THF (40 mL) was stirred at 25° C. for 3 h, then NaBH₃(AcO)₃ (171.26 mg, 0.808 mmol) was added to the mixture. The reaction was stirred at 90° C. for 12 h. LCMS showed the reaction was completed, it was concentrated in vacuum to get a residue, which was purified by prep-TLC to give 1-(4-(benzylamino)-6,8-dimethyl-5,6,7,8-tetrahydropyrido[4,3-d]pyrimidin-2-yl)-2-methyl-1H-indole-4-carbonitrile 13 (0.095 g, 83.5%) as a yellow solid. LCMS (MAT) m/z: Calcd: 423.23; Found: 423.3.

A mixture of compound 13 (95 mg, 0.098 mmol), UHP (0.106 g, 0.001 mol) and K₂CO₃ (0.031 g, 0.225 mmol) in DMSO/H₂O (6.0 mL, V/V, 10/1) was stirred at 25° C. for 12 h. LCMS showed the reaction was completed. It was poured into H₂O (15 mL) and extracted with EA (25 mL*2). The combined organic phase was dried over Na₂SO₄, filtered and concentrated to get a residue. It was purified by prep-TLC to give 1-(4-(Benzylamino)-6,8-dimethyl-5,6,7,8-tetrahydropyrido[4,3-d]pyrimidin-2-yl)-2-methyl-1H-indole-4-carboxamide FF13 (35 mg, 35.3%) as a yellow solid. LCMS (M+H⁺) m/z: Calcd: 441.2; Found: 441.3. ¹HNMR (400 MHz, DMSO-d₆): δ 7.81 (t, J=8.4 Hz, 1H, Ph), 7.68-7.60 (m, 2H, CONH₂), 7.44-7.73 (m, 1H, Ph), 7.34-7.24 (m, 5H, Ph), 6.91-6.84 (m, 2H, Ph), 4.64 (d, J=6.4 Hz, 2H, CH₂Ph), 3.45-3.31 (m, 4H, CH₂NCH₂), 2.87-2.83 (m, 2H, CHCH₃+NH), 2.54 (s, 3H, NCH₃), 2.37 (s, 3H, CH₃), 1.30 (d, J=2.8 Hz, 3H, CH₃CH).

Synthesis of 1-(4-((3-fluorobenzyl)amino)-5,6,7,8-tetrahydroquinazolin-2-yl)-1H-indazole-4-carboxamide FF14

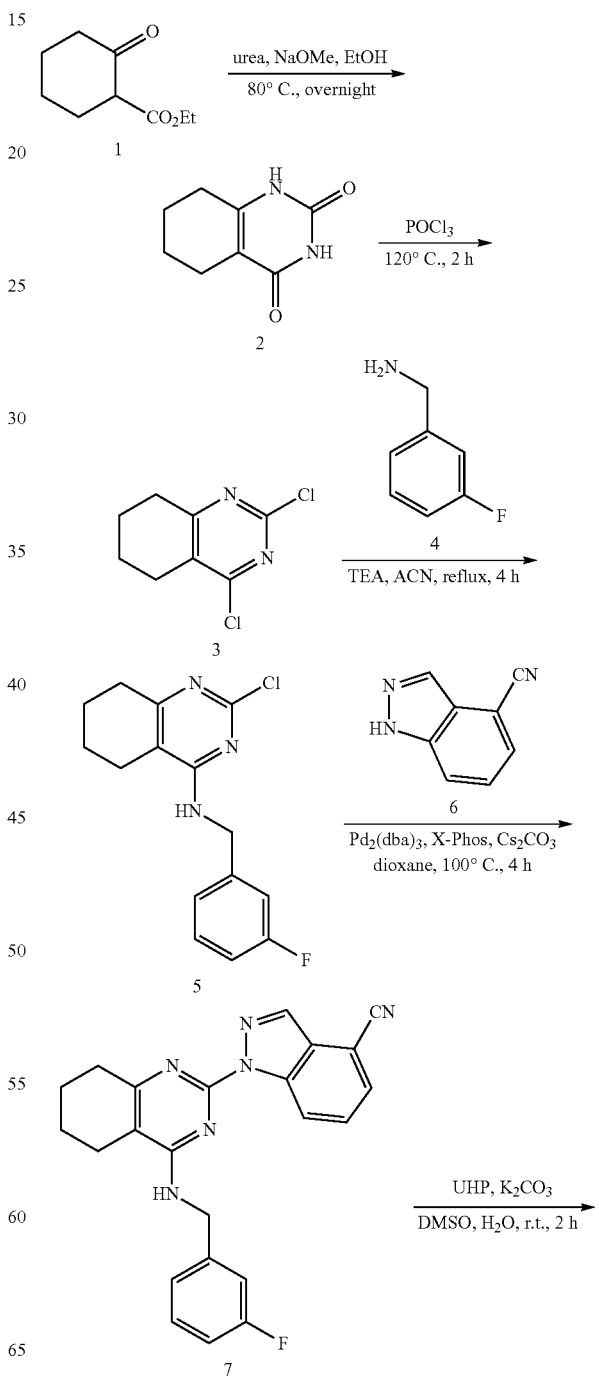

-continued

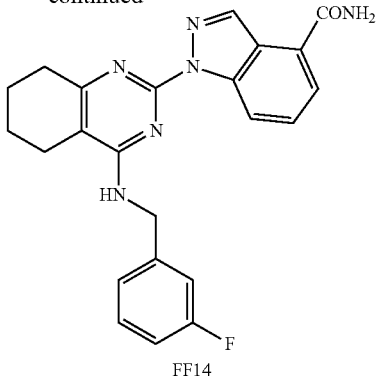

FF14

To a solution of ethyl 2-oxocyclohexane-carboxylate (20.00 g, 117.50 mmol) in EtOH (250.00 mL) was added urea (9.17 g, 152.76 mmol) at r.t. under $N_2$. The solution was stirred at r.t. for 5 min. Then MeONa (12.70 g, 235.01 mmol) in MeOH (200 mL) was added in one portion. The white suspension was heated to 80° C. and stirred for 16 h. White solid was precipitated during stirring. TLC showed the reaction was completed. Then the suspension was filtered. The filter cake was washed with MTBE (50 mL*2) and then dried in vacuo to give the desired 5,6,7,8-tetrahydroquinazoline-2,4(1H,3H)-dione: (14.00 g, 65% yield, 90% $^1$H NMR purity) as a white powder. $^1$HNMR (400 MHz, $CD_3OD$): δ 8.54 (br s, 2H, CON$\underline{H}$), 2.38 (m, 2H, $CH_2C\underline{H}_2$CCONH), 2.30 (m, 2H, $CH_2C\underline{H}_2$CNHCO), 1.71 (m, 4H, $CH_2C\underline{H}_2C\underline{H}_2CH_2$).

A suspension of 5,6,7,8-tetrahydroquinazoline-2,4(1H, 3H)-dione (25.0 g, 0.151 mol) in $POCl_3$ (100 mL) was heated to 120° C. and stirred for 2 h. TLC showed the reaction was complete. Then the mixture was concentrated in vacuo. The residue was dissolved in EtOAC (200 mL) and slowly poured into sat. $NaHCO_3$ (500 mL) at 0° C. Then the organic phase was separated and aqueous phase was extracted with EtOAc (200 mL*2). The combined organic phase was dried over $Na_2SO_4$ and concentrated in vacuo. The residue was purified by silica gel column (PE/EtOAc=20/1 to 10/1) to give 2,4-dichloro-5,6,7,8-tetrahydroquinazoline (10.3 g, 99.9% HPLC purity) as a white powder. $^1$HNMR (300 MHz, $CDCl_3$): δ 2.89 (m, 2H, $CH_2C\underline{H}_2$CCONH), 2.73 (m, 2H, $CH_2C\underline{H}_2$CNHCO), 1.88 (m, 4H, $CH_2C\underline{H}_2C\underline{H}_2CH2$).

A mixture of 2,4-dichloro-5,6,7,8-tetrahydroquinazoline (1.0 g, 4.9 mmol), (3-fluorophenyl)methanamine (796 mg, 6.37 mmol) and TEA (1.48 g, 14.7 mmol) in MeCN (50 ml) was refluxed for 4 h under $N_2$. TLC showed the reaction was almost completed. The reaction was concentrated in vacuum and purified by column chromatography (PE/EA=10/1 to 5/1) to give the desired 2-chloro-N-(3-fluorobenzyl)-5,6,7,8-tetrahydroquinazolin-4-amine (800 mg, 56% yield) as a white solid. LCMS (M+H$^+$) m/z: Calcd: 292.10; Found: 292.1. A mixture of 2-chloro-N-[(3-fluorophenyl)methyl]-5,6,7,8-tetrahydroquinazolin-4-amine (20 mg, 68.5 umol), 1H-indazole-4-carbonitrile (12 mg, 82.3 umol), $Pd_2(dba)_3$ (13 mg, 13.7 umol), $Cs_2CO_3$ (67 mg, 206 umol) and X-Phos (7 mg, 13.7 umol) in dioxane (5 ml) was stirred at 100° C. for 4 h under $N_2$. TLC showed SM:TM=2:1. The reaction mixture was concentrated in vacuum and purified by column chromatography (PE/EA=10/1 to 5/1) to give 1-(4-((3-fluorobenzyl)amino)-5,6,7,8-tetrahydroquinazolin-2-yl)-1H-indazole-4-carbonitrile (20 mg, 73%) as light yellow solid. LCMS (M+H+) m/z: Calcd: 399.17; Found: 399.2.

A mixture of 1-[4-[(3-fluorophenyl)methylamino]-5,6,7,8-tetrahydroquinazolin-2-yl]indazole-4-carbonitrile (90 mg, 0.23 mmol), UHP (21.25 mg, 0.23 mmol) and $K_2CO_3$ (31.22 mg, 0.23 mmol) in DMSO (10 ml) and $H_2O$ (1 mL) was stirred at 20° C. for 16 h under $N_2$. TLC showed the reaction was almost completed. The reaction was concentrated in vacuum and purified by prep-HPLC ($H_2O$, MeCN, HCl) to give the desired 1-(4-((3-Fluorobenzyl)amino)-5,6,7,8-tetrahydroquinazolin-2-yl)-1H-indazole-4-carboxamide FF14 (20 mg, 21.3%) as a white solid. LCMS (M+H$^+$) m/z: Calcd: 417.18; Found: 417.2. $^1$HNMR (400 MHz, DMSO-$d_6$): δ 9.11 (s, 1H, CON$\underline{H}_2$), 8.91 (s, 1H, 3-$\underline{H}$ of pyrazole), 8.30-8.26 (m, 2H, Ph), 7.87-7.85 (m, 1H, Ph), 7.71 (s, 1H, CON$\underline{H}_2$), 7.56-7.54 (m, 1H, Ph), 7.43-7.42 (m, 2H, Ph), 7.09 (m, 1H, $CH_2N\underline{H}$), 4.88-4.87 (m, 2H, $C\underline{H}_2NH$), 2.82 (s, 2H, NCC$\underline{H}_2$), 1.84 (s, 4H, $CH_2C\underline{H}_2C\underline{H}_2CH_2$).

Synthesis of 1-(4-((3-fluorobenzyl)amino)-6,7-dihydro-5H-pyrano[2,3-d]pyrimidin-2-yl)-2-methoxy-1H-benzo[d]imidazole-4-carboxamide FF15

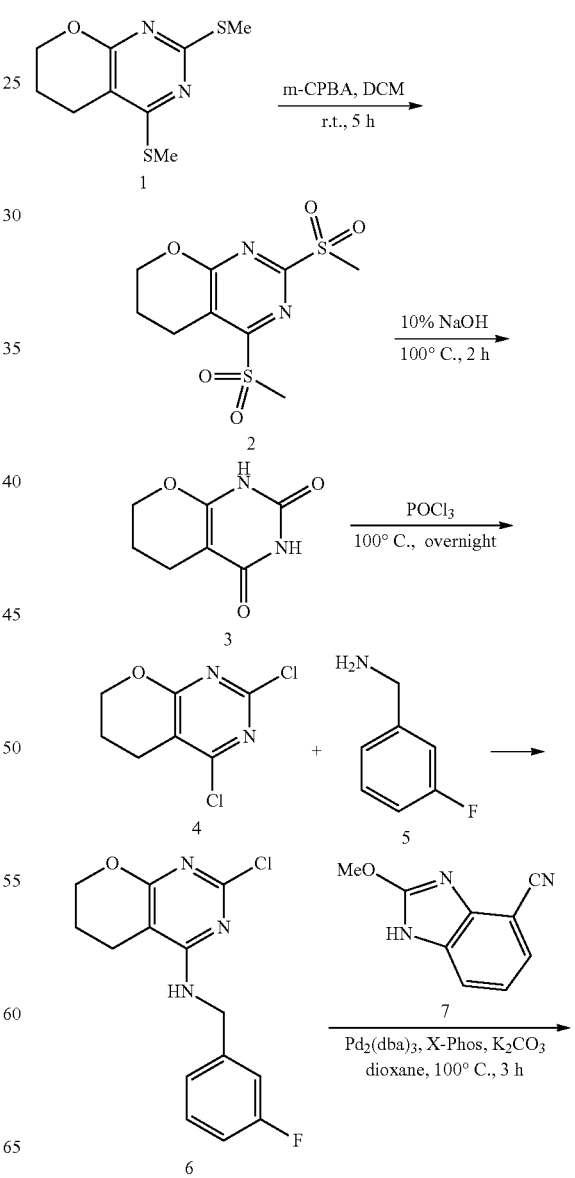

-continued

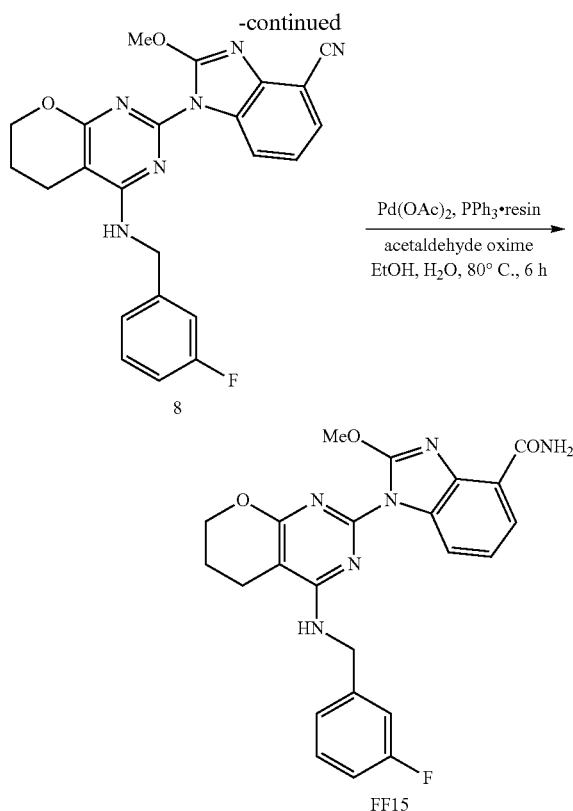

To a mixture of compound 1 (13 g, 0.057 mol) in DCM (650 mL) was added m-CPBA (73.69 g, 0.342 mol) portion wise. The resulting mixture was stirred at r.t. for overnight. LCMS showed the reaction was completed. It was filtered and the filtrate was quenched with 5% $Na_2S_2O_3$ (500 mL), then sat. $NaHCO_3$ (500 mL) was added carefully. The organic phase was separated, washed with brine (300 mL), dried over $Na_2SO_4$, filtered and concentrated to give crude compound 2. It was slurry with EA (100 mL) and filtered to give pure 2,4-bis(methylsulfonyl)-6,7-dihydro-5H-pyrano[2,3-d]pyrimidine 2 (15 g, 72%) as a white solid. LCMS (M+H$^+$) m/z: Calcd: 293.03; Found: 293.0.

A mixture of compound 2 (10.0 g, 0.034 mol) in 10% NaOH (200 mL) was refluxed for 3 h. TLC showed the reaction was completed, it was acidified with HCl (10%) until pH=2 and the solid was collected by filtration to give 6,7-dihydro-1H-pyrano[2,3-d]pyrimidine-2,4(3H,5H)-dione 3 (3.5 g, 60.8%) as a white solid. LCMS (M+H$^+$) m/z: Calcd: 169.06; Found: 169.10.

A mixture of compound 3 (3.5 g, 0.021 mol) in $POCl_3$ (80 mL) was stirred at 100° C. for 12 h. TLC showed the reaction was completed, the mixture was concentrated in vacuum to get a residue, it was diluted with DCM (500 mL) and poured into ice/water (200 mL). The organic layer was separated and washed with sat. $NaHCO_3$ (150 mL), brine (150 mL), dried over $Na_2SO_4$, filtered and concentrated to get a residue. It was purified by column chromatography (PE/EA=10/1) to give 2,4-dichloro-6,7-dihydro-5H-pyrano [2,3-d]pyrimidine 4 (2.2 g, 51.5%) as a white solid. LCMS (M+H$^+$) m/z: Calcd: 204.99; Found: 205.1.

A mixture of intermediate 4 (1.0 g, 0.005 mol), amine 5 (0.671 g, 0.005 mol) and TEA (0.985 g, 0.010 mol) in ACN (50 mL) was stirred at 90° C. for 12 h. LCMS showed 60% of the product was formed, the mixture was concentrated to give a residue which was stirred in EA (10 mL) and filtered to give pure 2-chloro-N-(3-fluorobenzyl)-6,7-dihydro-5H-pyrano[2,3-d]pyrimidin-4-amine 6 (0.4 g, 28%) as a white solid. LCMS (M+H$^+$) m/z: Calcd: 294.08; Found: 294.1. A mixture of intermediate 6 (100 mg, 0.340 mmol), compound 7 (70.75 mg, 0.409 mmol), $Pd_2(dba)_3$ (93.53 mg, 0.102 mmol), X-Phos (63.70 mg, 0.136 mmol) and $K_2CO_3$ (0.094 g, 0.68 mmol) in dioxane (30 mL) was stirred at 100° C. for 2 h under $N_2$. TLC showed the reaction was completed. It was concentrated to get a residue, which was purified by column chromatography (PE/EA=5/1) to give 1-(4-((3-fluorobenzyl)amino)-6,7-dihydro-5H-pyrano[2,3-d]pyrimidin-2-yl)-2-methoxy-1H-benzo[d]imidazole-4-carbonitrile 8 (0.11 g, 75.1%) as a yellow solid. LCMS (M+H$^+$) m/z: Calcd: 431.16; Found: 431.2.

A mixture of compound 7 (90 mg, 0.209 mmol), acetaldehyde oxime (24.67 mg, 0.418 mmol), $PPh_3$-resin (17 mg, 0.042 mmol) and Pd(OAc)$_2$ (9 mg) in EtOH/$H_2O$ (5 mL, V/V=10/1) was stirred at 80° C. for 4 h. LCMS showed the reaction was completed. The reaction mixture was concentrated in vacuum to give a residue which was purified by prep-TLC to give 1-(4-((3-Fluorobenzyl)amino)-6,7-dihydro-5H-pyrano[2,3-d]pyrimidin-2-yl)-2-methoxy-1H-benzo[d]imidazole-4-carboxamide FF15 (0.044 g, 47%) as a white solid. LRMS (M+H$^+$) m/z: Calcd: 449.17; Found: 449.30. $^1$HNMR (400 MHz, DMSO-d$_6$): δ 8.76 (s, 1H, CONH$_2$), 7.82-7.76 (m, 3H, Ph), 7.42-7.40 (m, 2H, Ph, CONH$_2$), 7.18-7.13 (m, 3H, Ph, NH), 7.04-7.02 (m, 1H, Ph), 4.61 (d, J=6.4 Hz, 2H, C$\underline{H}_2$Ph), 4.32-4.30 (m, 2H, OCH$_2$CH2), 4.15 (s, 3H, OC$\underline{H}_3$), 2.02-1.98 (m, 2H, OCH$_2$C$\underline{H}_2$).

Synthesis of 1-(4-((3-fluorobenzyl)amino)-6,7-dihydro-5H-pyrano[2,3-d]pyrimidin-2-yl)-1H-indazole-4-carboxamide FF16

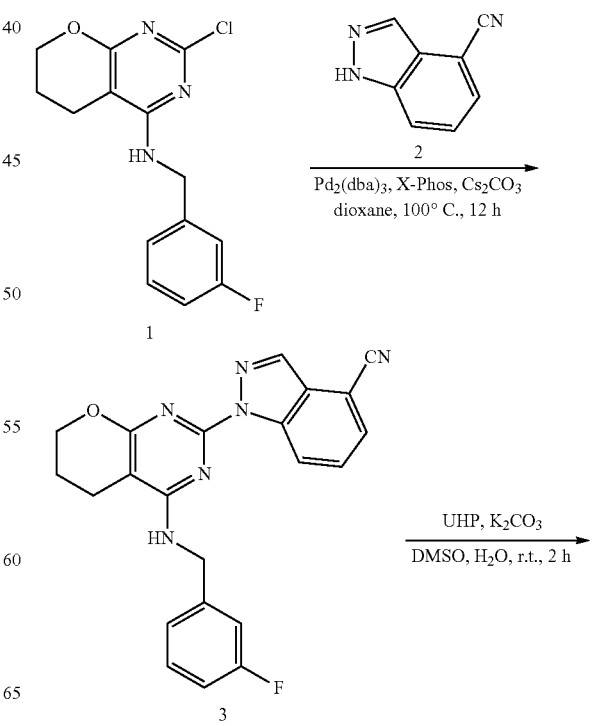

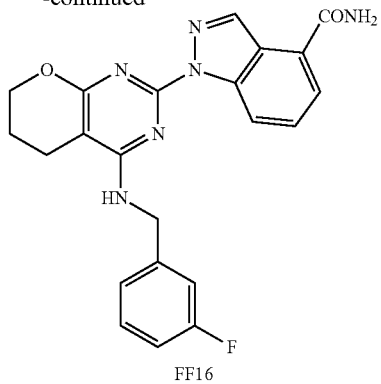

FF16

A mixture of compound 1 (50 mg, 0.170 mmol), compound 2 (29.24 mg, 0.204 mmol), Pd$_2$(dba)$_3$ (46.67 mg, 0.051 mmol), X-Phos (31.85 g, 0.068 mmol) and Cs$_2$CO$_3$ (0.111 g, 0.34 mmol) in dioxane (10 mL) was stirred at 110° C. for 24 h, four same reactions was carried out in parallel. LCMS showed the reaction was completed; four reactions were combined, concentrated to give a residue which was purified by column chromatography (PE/EA=1/1) to give 1-(4-((3-fluorobenzyl)amino)-6,7-dihydro-5H-pyrano[2,3-d]pyrimidin-2-yl)-1H-indazole-4-carbonitrile: 3 (163 mg, 43%) as a white solid. LCMS (M+H$^+$) m/z: Calcd: 401.15; Found: 401.20.

A solution of compound 3 (123 mg, 0.307 mmol), UHP (0.144 g, 0.002 mol) and K$_2$CO$_3$ (0.042 g, 0.307 mmol) in DMSO/H$_2$O (10/1, 7 mL) was stirred at 25° C. for 2 h. TLC and LCMS showed the reaction was completed. The mixture was poured into H$_2$O (30 mL) and extracted with EA (80 mL*2). The combined organic layer was dried over Na$_2$SO$_4$, filtered and concentrated to get a residue which was purified by prep-TLC to give desired 1-(4-((3-Fluorobenzyl)amino)-6,7-dihydro-5H-pyrano[2,3-d]pyrimidin-2-yl)-1H-indazole-4-carboxamide FF16 (53 mg, 41%) as a yellow solid. LCMS (M+H$^+$) m/z: Calcd: 419.2; Found: 419.16. $^1$HNMR (400 MHz, DMSO-d$_6$): δ 8.61 (s, 1H, P$\underline{h}$), 8.40 (d, J=8.4 Hz, 1H, P$\underline{h}$), 8.15-8.10 (m, 1H, CON$\underline{H}_2$), 7.71-7.67 (m, 2H, P$\underline{h}$), 7.53-7.52 (m, 1H, CON$\underline{H}_2$), 7.40-7.36 (m, 2H, P$\underline{h}$), 7.36-7.25 (m, 2H, PhN$\underline{H}$), 7.15-7.05 (m, 1H, P$\underline{h}$), 4.73 (d, J=6.0 Hz, 2H, PhC$\underline{H}_2$), 4.31 (t, J=4.4 Hz, 2H, OC$\underline{H}_2$CH$_2$CH$_2$), 2.02-1.98 (m, 2H, OCH$_2$CH$_2$C$\underline{H}_2$).

Biological Protocols

The in vitro and in vivo biological assays to determine the anti-cancer properties of the fused pyrimidine compounds of the invention are summarized above. The details of these protocols show how the assays are carried out.

P97 Biochemical Assay Protocol

The p97 assay is an initial screening assay used to determine inhibitory activity of the fused pyrimidine compounds of the invention against the p97 complex. As discussed above, inhibition of activity of the p97 proteosome complex can enable apoptosis and cause elimination of neoplastic cells (cancer cells). The method follows that of Christianson in Nat. Cell Biol., (2011) 14:93.

The Reagents Used for the p97 Assay Include:
Assay Buffer is a mixture of 50 mM TRIS pH 7.5, 20 mM MgCl$_2$, 0.02% TX-100, 1 mM DTT and 0.2% (v/v) Glycerol. The well plate is Platetype: Corning 3674, 384w plate. The identification kit is an ADP glo kit (Promega): stop buffer, detection reagent.

The Assay Protocol is Conducted as Follows:
Serial dilute compound in DMSO in a 1:3.33-fold 10 point serial dilution.
in each well of 384w plate add the following reagents:
0.5 μL compound serial diluted in DMSO (Final Conc. 10%)
2 μL ATP (Final Conc.=20 uM, diluted in assay buffer)
2.5 μL p97 (Final Conc.=20 nM, diluted in assay buffer)
Incubate at 37 degC for 15 min.
Add 5 μL of stop buffer, incubate at RT for 40 min.
Add 10 μL of detection reagent, incubate at RT for 30 min.
Read luminescence on Envision plate reader.
Upon obtaining the data from the luminescence reading, the data may be analyzed as follows:
Normalize luminescence data using no enzyme (full inhibition) and no compound (no inhibition) controls. Plot normalized luminescence data against log-transformed concentration values and fit to a sigmoidal curve to determine IC50 values (done in Collaborative Drug Discovery software).

Caco-2 Permeability Assay

This assay is designed as a model to indicate the permeability of a fused pyrimidine compound of this invention through the gut-blood barrier. The result will yield indications of whether or not the fused pyrimidine compound may be efficiently absorbed into the blood stream of a patient. Efficient, effective absorption of an orally administered drug determines in part its bioavailability. For the fused pyrimidine compounds of the invention, this assay is a model to evaluate the bioavailability of the compounds as a result of their ability to pass through biological barriers to entry into the physiological system of the patient.

The experimental goal of the Caco-2 assay is to measure directional Caco-2 permeability of test compounds in cultured Caco-2 monolayer.

The test compounds are the fused pyrimidine compounds of the invention.

Set-Up

Instruments
Tissue culture CO$_2$ incubator with humidity control
Liquid handler
Orbital shaker
EVOM Epithelial Volt-ohmmeter fitted with planar electrodes (World Precision Instruments, Sarasota, Fla.) required for measuring transepithelial electrical resistance (TEER)
Bench top centrifuge with 96-well plate adaptor
Caco-2 cells (Human colorectal adenocarcinoma, ATCC #37-HTB, passage 30-45)
Cells seeded onto PET membranes (1 μm pore size, 0.31 cm$^2$ surface area) inside Falcon HTS multiwell Insert system using 24-well plates (Becton Dickinson plates, Part #351181, Fisher Scientific, Inc.) at a density of 23,000 cells/well. Cells grown 20-23 days with medium changed every 2-3 days Reagents Ringers buffer solution (pH 7.4 at 25° C.)
Ringers buffer with 1% Methanol
Blk solution: Ringers buffer: Methanol=2:1 (v/v); 100% Methanol including internal standard (IS); 10 mM stock dosing solution in DMSO; 100 μM dosing solution in buffer.

Protocol Summary

Caco-2 permeability: 20-23 day/Passage 30-45
24-well format transwell: 0.31 cm2 surface area Donor conc: 100 μM including 1% DMSO
A: 300 μL pH 7.4/B: 1200 μL pH 7.4 Ringers buffer
Directionality: A B and B A (N=4)
Donor side sampling: 20 μL at beginning and end (90 min)
Receiver side sampling: 100 μL at 30, 50, 70, and 90 min
Incubation at 50 oscillations per minute, 37° C., 5% $CO_2$ 95% humidity
Analysis: LC-UV, LC-MS, or LSC
Output: Peff (cm/sec)=(dX/dt)/(A*Co*60), dX/dt: transported amount (nmole) versus time (minute) profile in the receiver chamber; A: surface area ($cm^2$); and Co: initial donor concentration (μM)
Positive control: Atenolol and propranolol
Membrane integrity: TEER>200 $Ocm^2$
Amount required: Approximately 1 mg or 100 μL of 10 mM test compound in DMSO
Instruments: $CO_2$ incubator with humidity control, liquid handler, epithelial volt-ohmmeter for TEER, Caco-2 cells (ATCC #37-HTB), and 24-well insert plates (PET membranes, 1 μm pore size, 0.31 $cm^2$ plates, Part #351181) surface area, Becton Dickinson
Throughput: 6 compounds/2 Caco-2 plates/1 FTE/day

PREPARATION

TABLE 24

| Chemical | Molecular Wt | Concentration | Mass(g) for 1 L | Mass(g) for 2 L | Mass(g) for 4 L |
|---|---|---|---|---|---|
| Preparation of Ringers with Glucose (Isotonic = 290 mOsm/kg), pH 7.4 | | | | | |
| Ca $SO_4$ 2$H_2O$ | 172.2 | 1.25 mM | 0.2152 | 0.4305 | 0.861 |
| $MgSO_4$ 7H2O | 246.5 | 1.1 mM | 0.2712 | 0.5423 | 1.0846 |
| KCl | 74.55 | 5 mM | 0.3728 | 0.7455 | 1.491 |
| $Na_2HPO_4$ | 142.0 | 1.15 mM | 0.1633 | 0.3266 | 0.6532 |
| $NaH_2PO_4$ $H_2O$ | 138.0 | 0.3 mM | 0.0414 | 0.0828 | 0.1656 |
| $NaHCO_3$ | 84.01 | 25 mM | 2.100 | 4.200 | 8.401 |
| Glucose($C_6H_{12}O_6$) | 180.2 | 25 mM | 4.505 | 9.01 | 18.02 |
| NaCl | 58.44 | 110 mM | 6.428 | 12.86 | 25.71 |

Preparation of 4 Solution

1. To 3.5 distilled water, add Calcium Sulfate and Magnesium Sulfate.
   Note: Add Calcium Sulfate and Magnesium Sulfate first due to low solubility and add the remaining ingredients in the order listed in Table 1.
2. Adjust the final volume of the solution to 4 with distilled water, with continuous stirring.
3. Adjust final solution to a pH of 7.4 using 1N HCl or 1N NaOH.
4. Make the buffer iso-osmotic using NaCl. Measure tonicity of the solution using a tonometer. Given that an isotonic solution is equivalent to 0.9% NaCl (290 mOsm/L),
   Y={(290−x)/290}×9 mg×4000 mL, where y=NaCl required (in mg) to make the solution isotonic and x=observed tonicity of solution (reported as mOsm/L).

Preparation of Dosing Solution in 15 Ml PP Tube 1. 100 μM dosing solution in RG: 140 μL 10 mM stock+(14 mL−140 μL) RG Preparation of Calibration in 96 Shallow Well 1. Prepare 10 μM standard: 100 μL of 100 μM dosing solution+0.9 mL Ringers with 1% Methanol.
2. Prepare analytical standard solutions 10, 5, 2, 1, 0.5, 0.2, 0.1, 0.05, 0.02, 0.01, and 0 μM. (See Table 26)

TABLE 25

Preparation of analytical calibration in 96 shallow well

| | 1 | 2 | 3 | 4 | 5 | 6 | 7 | 8 | 9 | 10 | 11 | 12 |
|---|---|---|---|---|---|---|---|---|---|---|---|---|
| | 0 | 20 μL of 0.1 μM | 20 μL of 0.2 μM | 20 μL of 0.5 μM | 20 μL of 1 μM | 20 μL of 2 μM | 20 μL of 5 μM | 20 μL of 10 μM | 40 μL of 10 μM | 100 μL of 10 μM | 200 μL of 10 μM | Source solution 1% MeOH in buffer |
| | 180 μL | 180 μL | 180 μL | 180 μL | 180 μL | 180 μL | 180 μL | 180 μL | 160 μL | 100 μL | 0 | |
| Comp 1 Comp 2 Comp 3 | Blk | 0.01 μM | 0.02 μM | 0.05 μM | 0.1 μM | 0.2 μM | 0.5 μM | 1 μM | 2 μM | 5 μM | 10 μM | |

Transport Studies
Dosing and Sampling
1. Equilibrate both sides of the monolayers for 10 minutes with prewarmed (37° C.) drug-free Ringers buffer (300 μL apical side, 1,200 μL basolateral side) supplemented with glucose (25 mM).
2. Measure TEER under 37° C. water bath conditions.
   Note: The TEER value serves as a quality control check for monolayer integrity. At 21 days post-seeding, each Caco-2 cell monolayer should have a TEER value of greater than or equal to 2000×$cm^2$ and those not meeting this criteria are not suitable for permeability evaluations.
3. When studying A to B transport: Fill basolateral side with 1,200 μL of Ringers buffer. Initiate transport experiments by transferring test drug dosing solution (320 μL) to apical side.
4. When studying B to A transport: Fill apical side with 300 μL of Ringers buffer. Initiate transport experiments by transferring test drug dosing solution (1,220 μL) to basolateral side. Transport studies for each direction (A to B, B to A) are performed in quadruplicate for each test drug.
5. Start timer after dosing last donor well.
6. Remove 20 μL aliquots from the donor wells at 0 minutes ($D_O$) and transfer these aliquots to the donor site of the 96-well plate containing 180 μL buffer with 1% Methanol. This step effectively dilutes the $D_0$ ten times.
7. Initiate transport studies by placing plate on orbital shaker maintained inside a prewarmed (37° C.) and humidified (5% $CO_2$) incubator. Studies are performed under stirring conditions at 50 oscillations per minute.
8. Remove 100 μL aliquots from the receiver side of the monolayer at 30, 50, 70, and 90 minutes postdosing and transfer these aliquots to the corresponding 96-well sample plate (See Table 26). Replace with an equivalent volume of prewarmed buffer.
9. Remove 20 µL aliquots from the donor side of the monolayer at 90 minutes postdosing ($D_f$) and transfer these aliquots to a donor site of a 96-well plate containing 180 µL Ringers buffer with 1% Methanol. This step effectively dilutes the $D_f$ ten times.
10. Replace both sides of monolayer with fresh, drug-free, prewarmed Ringers buffer (300 µL apical side, 1,200 µL basolateral side) and equilibrate for 10 minutes.
11. Measure TEER under 37° C. water bath conditions.

Sample Handling

The following steps refer to 96-well analytical plate for Caco-2, Table 26.
1. Transfer 20 µL of diluted $D_0$ and $D_f$ to corresponding 96-well sample plate with each well containing 80 µL buffer with 1% Methanol. This step effectively dilutes the samples five times further. Therefore, donor samples are diluted 50 times from their initial concentration.
2. Transfer 100 µL of analytical calibration (from 0 to 10 µM) to the sample plate row 1.
3. Add 50 µL Methanol including IS to all sample wells and mix (standards, samples, and $D_0$ and $D_f$).
4. Transfer 150 µL of Blk solution to the analytical plate row 2.
5. Seal the analytical plate with adhesive sealing film and store samples with label at −80° C. for LC-UV or LC-MS analysis.
6. Analyze 20 µL aliquots of the individual permeability samples and the standards using a suitable analytical instrument.
7. Peff=(dX/dt)/(A×$C_0$×60), where $P_{eff}$ is the effective permeability in cm/sec, X=mass transported, A is the surface area (cm)$^2$ available for transport, $C_0$ is the initial donor drug concentration (µM), and dX/dt is the slope of the best fit line through the transported amount (nmole) versus time (min) profile in the receiver chamber.

Mouse Liver Microsome Assay

The liver microsome assay is a model for studying the metabolic stability of the fused pyrimidine compounds of the invention. Metabolic stability is another aspect determining bioavailability. The facility of a compound to be bioabsorbed into the blood stream as shown by the Caco-2 model indicates the degree to which an oral dose of the compound will reach the blood stream. The body efficiently metabolizes substances to rid them from the body and/or to utilize them as nutrients. This aspect of bioavailability can be determined by such model studies as liver microsomal metabolism. Whether by oxidation, conjugation or any other biological pathway, metabolism of a drug determines at least in part the lifetime of the drug in the body.

The mouse liver microsome assay is a model designed to establish drug half-life in vivo. The liver enzymes are responsible to conversion of substances to materials that can be readily excreted by the body. Other routes for such metabolism include kidney metabolism, cellular metabolism and the like.

In this protocol, the compound is combined with a liver microsomal preparation (protein) and NADPH. The mixture is incubated and the rate of disappearance of the compound from the test solution is measured. Measurement is made by screening for the compound concentration at specified times using liquid chromatography in combination with mass spectroscopy.

Concentrations of Reactants Ready for Formulation as the Test Solution:
  Protein: 1.0 mg/ml
  Compound: 1 um
  Organic solvent: 0.4% DMSO
  Medium: 0.1 M Potassium Phosphate (KB)
  1 mM NADPH (sigma N1630, FW 833.3, make freshly)
  Prepare test article (TA, i.e., a compound of the invention) by dissolving solid TA in DMSO to make a 0.25 mM solution

TABLE 26

Analytical Plate for Caco-2 (96-well plate)

| 0 | 0.01 µM | 0.02 µM | 0.05 µM | 0.1 µM | 0.2 µM | 0.5 µM | 1 µM | 2 µM | 5 µM | 10 µM |
|---|---|---|---|---|---|---|---|---|---|---|
| Blk | Blk | Blk | Blk | A to B | | | B to A | Blk | Blk | Blk | Blk |
| 1-30 | 2-30 | 3-30 | 4-30 | | | | | 5-30 | 6-30 | 7-30 | 8-30 |
| 1-50 | 2-50 | 3-50 | 4-50 | | | | | 5-50 | 6-50 | 7-50 | 8-50 |
| 1-70 | 2-70 | 3-70 | 4-70 | | | | | 5-70 | 6-70 | 7-70 | 8-70 |
| 1-90 | 2-90 | 3-90 | 4-90 | | | | | 5-90 | 6-90 | 7-90 | 8-90 |
| 1-Do | 2-Do | 3-Do | 4-Do | | | | | 5-Do | 6-Do | 7-Do | 8-Do |
| 1-Df | 2-Df | 3-Df | 4-Df | | | | | 5-Df | 6-Df | 7-Df | 8-Df |

Positive Control Data

Mean data in Table 27 represent the mean value from 12 separate inter-day experiments.

TABLE 27

$P_{eff}$ (x E-6 cm/sec) in pH 7.4 Caco-2

| | A B | B A |
|---|---|---|
| Atenolol | | |
| Mean | 1.08 | 2.29 |
| Range | 0.69-1.80 | 1.69-2.68 |
| Propranolol | | |
| Mean | 28.53 | 20.91 |
| Range | 18.50-36.80 | 16.30-31.40 |

Amounts of Reactant Solutions to be Combined to Form the Test Solution:

| 423 ul | KB (potassium phosphate) |
| +25 ul | MLM (20 mg/ml) (mouse liver microsomal preparation) |
| 448 ul | |
| +2 ul | Test compound (a fused pyrimidine compound at 0.25 mM DMSO) |
| +50 ul | NADPH stock (10 mM, 10 x) |
| 500 ul | |

Test Protocol for Conducting the Assay
1. Add 423 ul KB to an 8-strip deep well tubes
2. Add 25 ul of MLM for condition 1
3. Place on ice, add 2 ul cmpds (250×stock in DMSO, stock at 0.25 mM)

4. Preincubate the reaction mixture at 37 C for 3 to 5 minutes (shaking at 150 rpm)
5. Initiate reaction by adding 50 ul NADPH for condition 1
6. Add 50 ul KB for condition 2
7. An aliquot of samples of 100 ul were collected at 0, 15, 30, and 60 min time point, and 200 ul of acetonitrile mixture containing IS was added to quench the reaction.
8. Centrifuge for 10 min at 4000 rpm
9. The supernatant were injected for liquid chromatographic tandem mass spectrometry (LC-MS/MS) analysis Procedure of Protein Binding Using 96-Well Equilibrium Dialyzer Non-specific protein binding is another facet affecting bioavailability and effectiveness of a drug. To assay a compound for non-specific binding, the compound is combined with human blood plasma and the solution dialyzed against a membrane constructed to prevent passage of larger molecules such as human plasma proteins but allow passage of small molecules such as the compounds of the invention. Typically, such membranes allow passage of such compounds irrespective of their salt or neutral form. The dialysate (solution passing through the membrane) is examined by liquid chromatography mass spectrometric techniques to determine the identity and concentration of the compound present. The concentration of compound in the dialysate compared with the concentration of compound combined with blood plasma indicates whether or not non-specific protein binding has occurred.

Equipment and Reagent:
96-Well Equilibrium Dialyzer (made by: Harvard Apparatus)
Plate Rotator with DIALYZER plates secured in clamp fixture
Buffer: DPBS (gibco, 1×)
Compound Concentration: 1 µM (~0.5 in µg/mL) in Human Plasma Procedure:
1. Seal the empty Sample Side well on the colored side with cap strips.
2. Invert the plate and carefully pipet a volume of buffer, 200 µL equal to the sample volume into the wells on the Buffer Side (clear frame) without touching the membranes by allowing the liquid to flow along the inner side wall of each well.
3. Gently seal the filled buffer wells with cap strips.
4. Invert the plate and carefully remove the cap strips from the sample side wells. Pipet desired samples, without touching the membranes.
5. Reseal the sample wells with the cap strips.
6. Slide the assembled DIALYZER Plate into a Plate Rotator and hand tighten the snobs. Turn on and allow rotating until equilibrium has been reached (24 hours at 37 C), remove the DIALYZER Plate from the Rotator.
7. After equilibrium has been reached, remove the DIALYZER Plate from the rotator.
8. Carefully remove the cap strips from the Buffer Side of the Plated (clear frame) and slowly pipet out the analysis samples from the wells taking care not to touch or puncture the membranes.

Samples will include control at 4 C and stability at 37 C samples in PBS and plasma.

MS Analysis:
Prepare standard range 5, 10, 50, 100, 500 and 1000 ng/mL in Plasma
Pipet 10 µL each of standard and sample into 40 µL of blank buffer/blank plasma them (ratio: 1 plasma/4 DPBS), mix them.
Add 200 µL of Is (internal standard) in ACN, mix well.
Centrifuge the samples and transfer supernatant solution for LC/MS analysis.

The Cell Assay Protocol

The cellular assay provides information about the antineoplastic activity of the compounds of the invention. The compounds are tested against cultured cancer cells to determine whether or not the compounds of the invention are capable of intersecting with cancer cells to minimize or eliminate such cells. The assay involves establishing colonies of such cells and then treating them with the test compound under specified conditions and analysis regima to determine results.

Day 1, Cell Plating to Establish Colonies of Cancer Cells
Cell Plating:
Seed cells ~16 hrs prior to compound treatment
Plate 25 µL of A549 cells in every well of 384-well plate using multidrop.
Two (2) black plates for IF at 2500 cells/well
Let plate sit at room temp for 10-15 minutes prior to putting in incubator to allow cells to stick in middle of plate.
One (1) white plate for viability at 500 cells/well.
Day 2 Treatment of Cultured Cells with Test Compounds
Treat Cells:
Serial dilute compounds with a 10 point 2-fold serial dilution in DMSO to make 250× stock compound solution
Dilute compounds 1:125 in cell culture media to make a 2× solution Add 25 µl of dilution compounds to cell plates in well duplicates
Put cells back in incubator (6 hr incubation for black plates, 72 hr incubation for white plates).
Fix/Stain Black Plates:
Incubate cells in black plates with compound at 37 degC for 6 hrs. add 15 µL of 16% Paraformaldehyde (PFA) directly into media of each well, incubate at room temp for 5 min, flick plate and wash in 50 µL of PBS block in 50 µL of Blocking Buffer for 30 minutes (can go up to several hours)
Blocking buffer: 1×PBS, 1% BSA, 0.3% Triton-X100, Hoechst (1:10,000) incubate in 25 µL of primary antibody in blocking buffer at 4 degC over night
Primary Antibodies:
Plate A K48-Ub 1:20,000 (millipore 05-1307 Lot 2049282) Rabbit
CHOP/Gadd153 1:2,000 (SC-7351) Mouse
Plate B P53 1:2,000 (SC-6243) Rabbit
p62/SQSTM1 1:2,000 (SC-28359) Mouse overnight at 4 degC
Secondary Antibodies:
AlexaFluor488 Goat anti-Rabbit 1:2,000 (Life Tech A11008)
AlexaFluor555 Goat anti-Mouse 1:2,000 (Life Tech A21422)
Day 3/4
Black Plate Staining (cont):
wash black plates 3× in 50 µL PBS (~5 min each)
incubate in 25 µl of secondary antibody (1:2,000) in blocking buffer for 1-2 hrs at room temp (alexafluor488-anti-Rabbit/alexafluor555-anti-Mouse)
wash 4× in 50 µL PBS (~5 min each)
leave plates in PBS for imaging
clean bottom of plates with 70% EtOH Imaging:
Image plates in high content microscope with 405 nm, 488 nm and 555 nm filters
Data Analysis:
Nuclear counts and cellular intensities of each markers are measured using Hoechst as a nuclear marker with an automated image analysis protocol using Matlab software (Math Works)
Day 5
Viability assay:
Thaw an aliquot of frozen cell titer glo (Promega G7572) at room temperature.

Add 45 mL of NaCl/PBS solution to 5 ml of cell titer glo (10×).
Remove white plates from incubator, leave at room temp for 30 minutes.
Add 25 μl of diluted cell titer glo to each well.
Shake plate for >1 minute.
Incubate plate for >5 minutes to stabilize luminescence.
Luminescence is stable for up to 3 hours.
Read luminescence on plate reader

TABLE II

Biological data for representative compounds of Formula I

| ID | IUPAC name | p97 IC50<br>**** < 30 nM<br>*** < 100 nM<br>** < 300 nM<br>* < 1000 nM | A549 CTG IC50<br>*** < 1 uM<br>** < 3 uM<br>* < 10 uM | A549 K48 IC50<br>*** < 1 uM<br>** < 3 uM<br>* < 10 uM |
|---|---|---|---|---|
| FF03 | 1-(4-(benzylamino)-5,6,7,8-tetrahydroquinazolin-2-yl)-1H-indazole-4-carboxamide | **** | *** | *** |
| FF04 | 1-(4-(benzylamino)-7,8-dihydro-5H-pyrano[4,3-d]pyrimidin-2-yl)-1H-indazole-4-carboxamide | ** | NA | NA |
| FF05 | 3-(4-(benzylamino)-5,6,7,8-tetrahydroquinazolin-2-yl)-2-methyl-1H-indole-7-carboxamide | **** | ** | ** |
| FF06 | 1-(4-(benzylamino)-6,7-dihydro-5H-pyrano[2,3-d]pyrimidin-2-yl)-2-methyl-1H-indole-4-carboxamide | **** | *** | *** |
| FF07 | 1-(4-(benzylamino)-5,6,7,8-tetrahydropyrido[2,3-d]pyrimidin-2-yl)-2-methyl-1H-indole-4-carboxamide | **** | *** | *** |
| FF08 | 1-(4-(benzylamino)-5,6-dihydrofuro[2,3-d]pyrimidin-2-yl)-2-methyl-1H-indole-4-carboxamide | *** | ** | ** |
| FF09 | 1-(4-((3-fluorobenzyl)amino)-6,7-dihydro-5H-pyrano[2,3-d]pyrimidin-2-yl)-2-methyl-1H-indole-4-carboxamide | **** | *** | *** |
| FF10 | 3-(4-(benzylamino)-7,8-dihydro-5H-pyrano[4,3-d]pyrimidin-2-yl)-2-methyl-1H-indole-7-carboxamide | *** | ** | ** |
| FF11 | 1-(4-((3-fluorobenzyl)amino)-5-methyl-5,6,7,8-tetrahydropyrido[3,2-d]pyrimidin-2-yl)-1H-indazole-4-carboxamide | *** | NA | NA |
| FF12 | 1-(4-((3-fluorobenzyl)amino)-5-methyl-5,6,7,8-tetrahydropyrido[3,2-d]pyrimidin-2-yl)-2-methyl-1H-indole-4-carboxamide | **** | *** | ** |
| FF13 | 1-(4-(benzylamino)-6,8-dimethyl-5,6,7,8-tetrahydropyrido[4,3-d]pyrimidin-2-yl)-2-methyl-1H-indole-4-carboxamide | *** | NA | NA |
| FF14 | 1-(4-((3-fluorobenzyl)amino)-5,6,7,8-tetrahydroquinazolin-2-yl)-1H-indazole-4-carboxamide | *** | ** | NA |
| FF15 | 1-(4-((3-fluorobenzyl)amino)-6,7-dihydro-5H-pyrano[2,3-d]pyrimidin-2-yl)-2-methoxy-1H-benzo[d]imidazole-4-carboxamide | **** | ** | NA |
| FF16 | 1-(4-((3-fluorobenzyl)amino)-6,7-dihydro-5H-pyrano[2,3-d]pyrimidin-2-yl)-1H-indazole-4-carboxamide | **** | * | NA |
| FF17 | 1-(4-(benzylamino)-5,6,7,8-tetrahydropyrido[2,3-d]pyrimidin-2-yl)-2-(hydroxymethyl)-1H-indole-4-carboxamide | **** | *** | NA |
| FF18 | 1-(4-(benzylamino)-6,7,8,9-tetrahydro-5H-cyclohepta[d]pyrimidin-2-yl)-2-methyl-1H-indole-4-carboxamide | **** | *** | ** |
| FF19 | 1-(4-(benzylamino)-8-methyl-5,6,7,8-tetrahydropyrido[4,3-d]pyrimidin-2-yl)-2-methyl-1H-indole-4-carboxamide | *** | ** | *** |
| FF20 | 1-(4-(benzylamino)-6,7,8,9-tetrahydro-5H-pyrimido[4,5-d]azepin-2-yl)-2-methyl-1H-indole-4-carboxamide | ** | ** | NA |

TABLE II-continued

Biological data for representative compounds of Formula I

| ID | IUPAC name | p97 IC50<br>**** < 30 nM<br>*** < 100 nM<br>** < 300 nM<br>* < 1000 nM | A549 CTG IC50<br>*** < 1 uM<br>** < 3 uM<br>* < 10 uM | A549 K48 IC50<br>*** < 1 uM<br>** < 3 uM<br>* < 10 uM |
|---|---|---|---|---|
| FF21 | 1-(4-(benzylamino)-5-methyl-5,6,7,8-tetrahydropyrido[3,2-d]pyrimidin-2-yl)-2-methyl-1H-indole-4-carboxamide | **** | *** | *** |
| FF22 | 3-(4-((3-fluorobenzyl)amino)-7,8-dihydro-5H-pyrano[4,3-d]pyrimidin-2-yl)-2-methylbenzofuran-7-carboxamide | * | NA | NA |
| FF23 | 1-(4-(benzylamino)-5,6,7,8-tetrahydropyrido[2,3-d]pyrimidin-2-yl)-2-methoxy-1H-benzo[d]imidazole-4-carboxamide | **** | ** | ** |
| FF24 | 1-(4-(benzylamino)-6,7-dihydro-5H-pyrano[2,3-d]pyrimidin-2-yl)-2-methoxy-1H-benzo[d]imidazole-4-carboxamide | **** | ** | ** |
| FF25 | 1-(4-((3-fluorobenzyl)amino)-5,6,7,8-tetrahydropyrido[3,2-d]pyrimidin-2-yl)-2-methyl-1H-indole-4-carboxamide | **** | ** | ** |
| FF26 | 1-(4-((3-fluorobenzyl)amino)-5,6,7,8-tetrahydropyrido[2,3-d]pyrimidin-2-yl)-2-methyl-1H-indole-4-carboxamide | **** | ** | ** |
| FF27 | 3-(4-(benzylamino)-6,7-dihydro-5H-pyrano[2,3-d]pyrimidin-2-yl)-2-methyl-1H-indole-7-carboxamide | *** | ** | ** |
| FF28 | 1-(4-(benzylamino)-6,7-dihydro-5H-pyrano[2,3-d]pyrimidin-2-yl)-1H-indazole-4-carboxamide | *** | ** | ** |
| FF29 | 1-(4-(benzylamino)-8-methyl-5,6,7,8-tetrahydropyrido[2,3-d]pyrimidin-2-yl)-2-methyl-1H-indole-4-carboxamide | **** | ** | ** |
| FF30 | 1-(4-((3,5-difluorobenzyl)amino)-6,7-dihydro-5H-pyrano[2,3-d]pyrimidin-2-yl)-2-methyl-1H-indole-4-carboxamide | **** | ** | ** |
| FF31 | 2-(4-(aminomethyl)-2-methyl-1H-indol-1-yl)-N-benzyl-6,7-dihydro-5H-pyrano[2,3-d]pyrimidin-4-amine | ** | NA | NA |
| FF32 | 2-(aminomethyl)-1-(4-(benzylamino)-6,7-dihydro-5H-pyrano[2,3-d]pyrimidin-2-yl)-1H-indole-4-carboxamide | *** | * | * |
| FF33 | 1-(4-(benzylamino)-5,6,7,8-tetrahydropyrido[4,3-d]pyrimidin-2-yl)-1H-indazole-4-carboxamide | * | NA | NA |
| FF34 | 1-(4-(benzylamino)-5,6,7,8-tetrahydropyrido[3,2-d]pyrimidin-2-yl)-2-methyl-1H-indole-4-carboxamide | **** | *** | *** |
| FF35 | 3-(4-(benzylamino)-5,6,7,8-tetrahydroquinazolin-2-yl)-2-methylbenzofuran-7-carboxamide | **** | ** | ** |
| FF36 | N-benzyl-2-(2-methyl-1H-indol-3-yl)-5,6,7,8-tetrahydroquinazolin-4-amine | ** | * | * |

Summary Statements

The inventions, examples, biological assays and results described and claimed herein have may attributes and embodiments include, but hot limited to, those set forth or described or referenced in this application.

All patents, publications, scientific articles, web sites and other documents and material references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incoporate into this specification any and all materials and information from any such patent publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any an all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, for example, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

What is claimed is:

1. A compound of Formula I

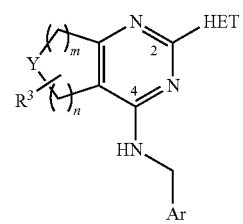

Formula I

Wherein:

Y is $NR^5$ or O;

One of m and n is zero and the other is an integer of 2 or 3 and the sum of m and n is 2 or 3 so that a moiety of Formula I having the Formula Scaffold

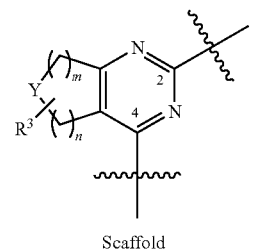

Scaffold is selected from the group consisting of Formulas S1, S3, S6 and S7 and the valence bonds of the Scaffold marked by squiggles are respectively the bond to HET at position 2 and the bond to $NHCH_2Ar$ at position 4;

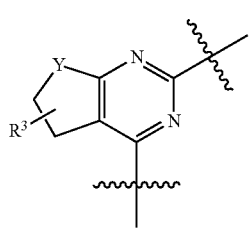

S1

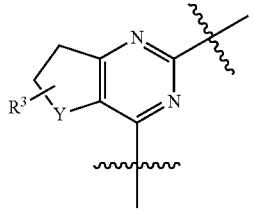

S3

-continued

S6 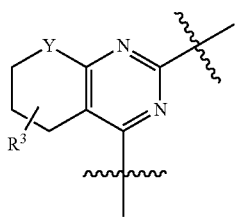

S7 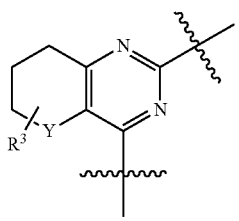

HET is a 5:6 bicyclic aromatic group having one or two nitrogens or one oxygen in the 5 member ring and is selected from the group consisting of Formula H4, Formula H5, Formula H8, Formula H10, Formula H13 and Formula H22

H4 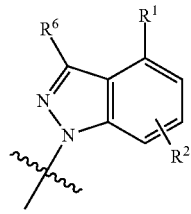

H5 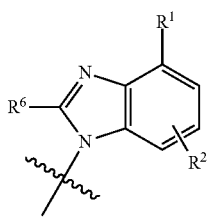

H7 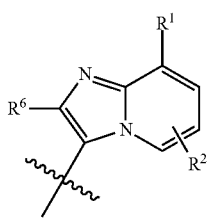

H8 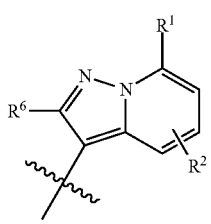

-continued

H10 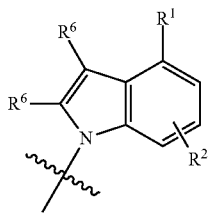

H13 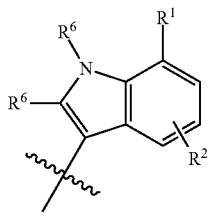

H22 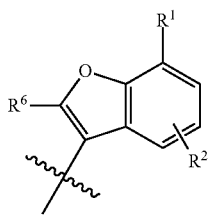

Wherein:
$R^1$ is selected from the group consisting of halogen, carboxyl, carboxamido, —$CH_2NH_2$, sulfonyl hydroxide, sulfonamido, amino, mono, di alkyl amino of 1 to 6 carbons, nitrile, —C(O)NH-alkyl having 1 to 6 carbons in the alkyl group, —$CH_2OH$, and alkoxy of 1 to 6 carbons;
$R^2$ is hydrogen;
$R^3$ is hydrogen or alkyl of 1 to 4 carbons;
$R^5$ is hydrogen or alkyl of 1 to 4 carbons
Each $R^6$ is independently selected from hydrogen, halogen, linear, branched or cyclo alkyl of 1 to 6 carbons, carboxyl, carboxamido, —$CH_2NH_2$, sulfonyl hydroxide, sulfonamido, amino, mono, di alkyl amino of 1 to 6 carbons, nitrile, —C(O)NH-alkyl having 1 to 6 carbons in the alkyl group, perfluoroalkyl of 1 to 3 carbons, or alkoxy of 1 to 6 carbons;
$R^7$ is hydrogen or alkyl of 1 to 4 carbons;
Ar is phenyl or fluorophenyl.

2. The compound according to claim 1 wherein the scaffold is Formula S6 or Formula S7.

3. The compound according to claim 2 wherein the HET is Formula H5 or Formula H10.

4. The compound according to claim 3 wherein $R^1$ is selected from the group consisting of carboxyl, carboxamido, sulfonyl hydroxide, sulfonamido and nitrile.

5. The compound according to claim 4 wherein $R^3$ is hydrogen, $R^5$ is hydrogen or methyl, and $R^6$ is hydrogen, methyl or methoxy.

6. The compound of claim 1 wherein $R^6$ is hydrogen.

7. The compound of claim 1 wherein $R^6$ is methyl.

8. The compound of claim 1 wherein $R^6$ is methoxy.

9. The compound of any one of claims 6-8, 1 wherein Y is $NR^5$ and $R^5$ is hydrogen or methyl.

10. The compound of any one of claims 6-8, 1 wherein Y is O.

11. The compound of any one of claims 6-10, 1 wherein $R^3$ is hydrogen.

12. The compound of claim 1 wherein Ar is phenyl.

13. The compound of claim 1 wherein Ar is fluorophenyl.

14. The compound of any one of claims 6-13, 1 wherein $R^1$ is carboxyl, carboxamido, —$CH_2NH_2$ or —$CH_2OH$.

15. The compound of claim 14 wherein $R^1$ is carboxamido.

16. The compound of claim 1 having any one of the following specific names:

1-(4-((3,5-difluorobenzyl)amino)-6,7-dihydro-5H-pyrano[2,3-d]pyrimidin-2-yl)-2-methyl-1H-indole-4-carboxamide, 1-(4-((3-fluorobenzyl)amino -5,6,7,8-tetrahydropyrido[2,3-d]pyrimidin-2-yl)-1H-indazole-4-carboxamide, 1-(4-((3-fluorobenzyl)amino)-5,6,7,8-tetrahydropyrido[2,3-d]pyrimidin-2-yl)-2-methoxy-1H-benzo[d]imidazole-4-carboxamide, 1-(4-((3-fluorobenzyl)amino)-5,6,7,8-tetrahydropyrido[2,3-d]pyrimidin-2-yl)-2-methyl-1H-indole-4-carboxamide, 1-(4-((3-fluorobenzyl)amino)-5,6,7,8-tetrahydropyrido[2,3-d]pyrimidin-2-yl)-6-fluoro-1H-indazole-4-carboxamide, 1-(4-((3-fluorobenzyl)amino)-5,6,7,8-tetrahydropyrido[2,3-d]pyrimidin-2-yl)-6-fluoro-2-methoxy-1H-benzo[d]imidazole-4-carboxamide, 1-(4-((3-fluorobenzyl)amino)-5,6,7,8-tetrahydropyrido[2,3-d]pyrimidin-2-yl)-6-fluoro-2-methyl-1H-indole-4-carboxamide, 1-(4-((3-fluorobenzyl)amino)-5,6,7,8-tetrahydropyrido[3,2-d]pyrimidin-2-yl)-1H-indazole-4-carboxamide, 1-(4-((3-fluorobenzyl)amino)-5,6,7,8-tetrahydropyrido[3,2-d]pyrimidin-2-yl)-2-methoxy-1H-benzo[d]imidazole-4-carboxamide, 1-(4-((3-fluorobenzyl)amino)-5,6,7,8-tetrahydropyrido[3,2-d]pyrimidin-2-yl)-2-methyl-1H-indole-4-carboxamide, 1-(4-((3-fluorobenzyl)amino)-5,6,7,8-tetrahydropyrido[3,2-d]pyrimidin-2-yl)-6-fluoro-1H-indazole-4-carboxamide, 1-(4-((3-((3-fluorobenzyl)amino)-5,6,7,8-tetrahydropyrido[3,2-d]pyrimidin-2-yl)-6-fluoro-2-methoxy-1H-benzo[d]imidazole-4-carboxamide, 1-(4-((3-fluorobenzyl)amino)-5,6,7,8-tetrahydropyrido[3,2-d]pyrimindin-2-yl)-6-fluoro-2-methyl-1H-indole-4-carboxamide, 1-(4-((3-fluorobenzyl)amino)-5,6-dihydrofuro[2,3-d]pyrimidin-2-yl)-1H-indazole-4-carboxamide, 1-(4-((3-fluorobenzyl)amino)-5,6-dihydrofuro[2,3-d]pyrimidin-2-yl)-2-methoxy-1H-benzo[d]imidazole-4-carboxamide, 1-(4-((3-fluorobenzyl)amino)-5,6-dihydrofuro[2,3-d]pyrimidin-2-yl)-2-methyl-1H-indole-4-carboxamide, 1-(4-((3-fluorobenzyl)amino)-5,6-dihydrofuro[2,3-d]pyrimidin-2-yl)-6-fluoro-1H-indazole-4-carboxamide, 1-(4-((3-fluorobenzyl)amino)-5,6-dihydrofuro[2,3-d]pyrimidin-2-yl)-6-fluoro-2-methoxy-1H-benzo[d]imidazole-4-carboxamide, 1-(4-((3-fluorobenzyl)amino)-5,6-dihydrofuro[2,3-d]pyrimidin-2-yl)-6-fluoro-2-methyl-1H-indole-4-carboxamide, 1-(4-((3-fluorobenzyl)amino)-5-methyl-5,6,7,8-tetrahydropyrido[3,2-d]pyrimidin-2-yl)-1H-indazole-4-carboxamide, 1-(4-((3-fluorobenzyl)amino)-5-methyl-5,6,7,8-tetrahydropyrido[3,2-d]pyrimidin-2-yl)-2-methoxy-1H-benzo[d]imidazole-4-carboxamide, 1-(4-((3-fluorobenzyl)amino)-5-methyl-5,6,7,8-tetrahydropyrido[3,2-d]pyrimidin-2yl)-2-methyl-1H-indole-4-carboxamide, 1-(4-((3-fluorobenzyl)amino)-5-methyl-5,6,7,8-tetrahydropyrido[3,2-d]pyrimidin-2-yl)-6-fluoro-1H-indazole-4-carboxamide, 1-(4-((3-fluorobenzyl)amino)-5-methyl-5,6,7,8-tetrahydropyrido[3,2-d]pyrimidin-2-yl)-6-fluoro-2-methoxy-1H-benzo[d]imidazole-4-carboxamide, 1-(4-((3-fluorobenzyl)amino)-5-methyl-5,6,7,8-tetrahydropyrido[3,2-d]pyrimidin-2-yl)-6-fluoro-2-methyl-1H-indole-4-carboxamide, 1-(4-((3-fluorobenzyl)amino)-5-methyl-6,7-dihydro-5H-pyrrolo[3,2-d]pyrimidin-2-yl)-1H-indazole-4-carboxamide, 1-(4-((3-fluorobenzyl)amino)-5-methyl-6,7-dihydro-5H-pyrrolo[3,2-d]pyrimidin-2-yl)-2-methoxy-1H-benzo[d]imidazole-4-carboxamide, 1-(4-((3-fluorobenzyl)amino)-5-methyl-6,7-dihydro-5H-pyrrolo[3,2-d]pyrimidin-2-yl)-2-methyl-1H-indole-4-carboxamide, 1-(4-((3-fluorobenzyl)amino)-5-methyl-6,7-dihydro-5H-pyrrolo[3,2-d]pyrimidin-2-yl)-6-fluoro-1H-indazole-4-carboxamide, 1-(4-((3-fluorobenzyl)amino)-5-methyl-6,7-dihydro-5H-pyrrolo[3,2-d]pyrimidin-2-yl)-6-fluoro-2-methoxy-1H-benzo[d]imidazole-4-carboxamide, 1-(4-((3-fluorobenzy)amino)-5-methyl-6,7-dihydro-5H-pyrrolo[3,2-d]pyrimidin-2-yl)-6-fluoro-2-methyl-1H-indole-4-carboxamide, 1-(4-((3-fluorobenzyl)amino)-6,7-dihydro-5H-pyrano[2,3-d]pyrimidin-2-yl)-1H-indazole-4-carboxamide, 1-(4-((3-fluorobenzyl)amino)-6,7-dihydro-5H-pyrano[2,3-d]pyrimidin-2-yl)-2-methoxy-1H-benzo[d]imidazole-4-carboxamide, 1-(4-((3-fluorobenzyl)amino)-6,7-dihydro-5H-pyrano[2,3-d]pyrimidin-2-yl)-2-methyl-1H-indole-4-carboxamide, 1-(4-((3-fluorobenzyl)amino)-6,7-dihydro-5H-pyrano[2,3-d]pyrimidin-2-yl)-6-fluoro-1H-indazole-4-carboxamide, 1-(4-((3-fluorobenzyl)amino)-6,7-dihydro-5H-pyrano[2,3-d]pyrimidin-2-yl)-6-fluoro-2-methoxy-1H-benzo[d]imidazole-4-carboxamide, 1-(4-((3-fluorobenzyl)amino)-6,7-dihydro-5H-pyrano[2,3-d]pyrimidin-2-yl)-6-fluoro-2-methyl-1H-indole-4-carboxamide, 1-(4-((3-fluorobenzyl)amino)-6,7-dihydro-5H-pyrrolo[2,3-d]pyrimidin-2yl)-1H-indazole-4-carboxamide, 1-(4-((3-fluorobenzyl)amino)-6,7-dihydro-5H-pyrrolo[2,3-d]pyrimidin-2-yl)-2-methoxy-1H-benzo[d]imidazole-4-carboxamide, 1-(4-((3-fluorobenzyl)amino)-6,7-dihydro-5H-pyrrolo[2,3-d]pyrimidin-2-yl)-2-methyl-1H-indole-4-carboxamide, 1-(4-((3-fluorobenzyl)amino)-6,7-dihydro-5H-pyrrolo[2,3-d]pyrimidin-2-yl)-6-fluoro-1H-indazole-4-carboxamide, 1-(4-((3-fluorobenzyl)amino)-6,7-dihydro-5H-pyrrolo[2,3-d]pyrimidin-2-yl)-6-fluoro-2-methoxy-1H-benzo[d]imidazole-4-carboxamide, 1-(4-((3-fluorobenzyl)amino)-6,7-dihydro-5H-pyrrolo[2,3-d]pyrimidin-2-yl)-6-fluoro-2-methyl-1H-indole-4-carboxamide, 1-(4-((3-fluorobenzyl)amino)-6,7-dihydro-5H-pyrrolo[3,2-d]pyrimidin-2H-indazole-4-carboxamide, 1-(4-((3-fluorobenzyl)amino)-6,7-dihydro-5H-pyrrolo[3,2-d]pyrimidin-2-yl)-2-methoxy-1H-benzo[d]imidazole-4-carboxamide, 1-(4-((3-fluorobenzyl)amino)-6,7-dihydro-5H-pyrrolo[3,2-d]pyrimidin-2-yl)-2-methyl-1H-indole-4-carboxamide, 1-(4-((3-fluorobenzyl)amino)-6,7-dihydro-5H-pyrrolo[3,2-d]pyrimidin-2-yl)-6-fluoro-1H-indazole-4-carboxamide, 1-(4-((3-fluorobenzyl)amino)-6,7-dihydro-5H-pyrrolo[3,2-d]pyrimidin-2-yl)-6-fluoro-2-methoxy-1H-benzo[d]imidazole-4-carboxamide, 1-(4-((3-fluorobenzyl)amino)-6,7-dihydro-5H-pyrrolo[3,2-d]pyrimidin-2-yl)-6-fluoro-2-methyl-1H-indole-4-carboxamide, 1-(4-((3-fluorobenzyl)amino)-7-methyl-6,7-dihydro-5H-pyrrolo[2,3-d]pyrimidin-2-yl)-1H-indazole-4-carboxamide, 1-(4-((3-fluorobenzyl)amino)-7-methyl-6,7-dihydro-5H-pyrrolo[2,3-d]pyrimidin-2-methoxy-1H-benzo[d]imidazole-4-carboxamide, 1-(4-((3-fluorobenzyl)amino)-7-methyl-6,7-dihydro-5H-pyrrolo[2,3-d]pyrimidin-2-yl)-2-methyl-1H-indole-4-carboxamide, 1-(4-((3-fluorobenzyl)amino)-7-methyl-6,7-dihydro-5H-pyrrolo[2,3-d]pyrimidin-2-yl)-6-fluoro-1H-indazole-4-carboxamide, 1-(4-((3-fluorobenzyl)amino)-7-methyl-6,7-dihydro-5H-pyrrolo[2,3-d]pyrimidin-2-yl)-6-fluoro-2-methoxy-1H-benzo[d]imidazole-4-carboxamide, 1-(4-((3-fluorobenzyl)amino)-7-methyl-6,7-dihydro-5H-pyrrolo[2,3-d]pyrimidin-2-yl)-6-fluoro-2-methyl-1H-indole-4-carboxamide, 1-(4-((3-fluorobenzyl)amino)-8-methyl-5,6,7,8-tetrahydropyrido[2,3-d]pyrimidin-2-yl)-1H-indazole-4-carboxamide, 1-(4-((3-fluorobenzyl)amino)-8-methyl-5,6,7,8-tetrahydropyrido[2,3-d]pyrimidin-2-yl)-2-methoxy-1H-benzo[d]imidazole-4-carboxamide, 1-(4-((3-fluorobenzyl)amino)-8-methyl-5,6,7,8-tetrahydropyrido[2,3-d]pyrimidin-2-yl)-2-methyl-1H-indole-4-carboxamide, 1-(4-((3-fluorobenzyl)amino)-8-methyl-5,6,7,8-tetrahydropyrido[2,3-d]pyrimidin-2-yl)-6-fluoro-1H-indazole-4-carboxamide, 1-(4-((3-fluorobenzyl)amino)-8-methyl-5,6,7,8-tetrahydropyrido[2,3-d]pyrimidin-2-yl)-6-fluoro-2-methoxy-1H-benzo[d]imidazole-4-carboxamide, 1-(4-((3-fluorobenzyl)amino)-8-methyl-5,6,7,8-tetrahydropyrido[2,3-d]pyrimidin-2-yl)-6-fluoro-2-methyl-1H-indole-4-carboxamide, 1-(4-(benzylamino)-5,6,7,8-tetrahydropyrido[2,3-d]pyrimidin-2-yl)-1H-indazole-4-carboxamide, 1-(4-(benzylamino)-5,6,7,8-tetrahydropyrido[2,3-d]pyritnidin-2-yl)-2-(hydroxymethyl)-1H-,indole-4-carboxamide, 1-(4-(benzylamino)-5,6,7,8-tetrahydropyrido[2,3-d]pyrimidin-2-yl)-2-methoxy-1H-benzo[d]imidazole-4-carboxamide, 1-(4-(benzylamino)-5,6,7,8-tetrahydropyrido[2,3-d]pyrimidin-2-yl)-2-methyl-1H-indole-4-carboxamide, 1-(4-(benzylamino)-5,6,7,8-tetrahydropyrido[2,3-d]pyrimidin-2-yl)-6-fluoro-1H-indazole-4-carboxamide, 1-(4-(benzylamino)-5,6,7,8-tetrahydropyrido[2,3-d]pyrimidin-2-yl)-6-fluoro-2-methoxy-1H-benzo[d]imidazole-4-carboxamide, 1-(4-(benzylamino)-5,6,7,8-tetrahydropyrido[2,3-d]pyrimidin-2-yl)-6-flouro-2-methyl-1H-indole-4-carboxamide, 1-(4-(benzylamino)-5,6,7,8-tetrahydropyrido[3,2-d]pyrimidin-2-yl)-1H-indazole-4-carboxamide, 1-(4-(benzylamino)-5,6,7,8-tetrahydropyrido[3,2-d]pyrimidin-2-yl)-2-methoxy-1H-benzo[d]imidazole-4-carboxamide, 1-(4-(benzylamino)-5,6,7,8-tetrahydropyrido[3,2-d]pyrimidin-2-yl)-2-methyl-1H-indole-4-carboxamide, 1-(4-(benzylamino)-5,6,7,8-tetrahydropyrido[3,2-d]pyrimidin-2-yl)-6-fluoro-1H-indazole-4-carboxamide, 1-(4-(benzylamino)-5,6,7,8-tetrahydropyrido[3,2-d]pyrimidin-2-yl)-6-fluoro-2-methoxy-1H-benzo[d]imidazole-4-carboxamide, 1-(4-(benzylamino)-5,6,7,8-tetrahydropyrido[3,2-d]pyrimidin-2-yl)-6-fluoro-2-methyl-1H-indole-4-carboxamide, 1-(4-(benzylamino)-5,6-dihydrofuro[2,3-d]pyrimidin-2-yl)-1H-indazole-4-carboxamide, 1-(4-(benzylamino)-5,6-dihydrofuro[2,3-d]pyrimidin-2-yl)-2-methoxy-1H-benzo[d]imidazole-4-carboxamide, 1-(4-(benzylamino)-5,6-dihydrofuro[2,3-d]pyrimidin-2-yl)-2-methyl-1H-indole-4-carboxamide, 1-(4-(benzylamino)-5,6-dihydrofuro[2,3-d]pyrimidin-2-yl)-6-fluoro-1H-indazole-4-carboxamide, 1-(4-(benzylamino)-5,6-dihydrofuro[2,3-d]pyrimidin-2-yl)-6-fluoro-2-methoxy-1H-benzo[d]imidazole-4-carboxamide, 1-(4-(benzylamino)-5,6-dihydrofuro[2,3-d]pyrimidin-2-yl)-6-fluoro-2-methyl-1H-indole-4-carboxamide, 1-(4-(benzylamino)-5-methyl-5,6,7,8-tetrahydropyrido[3,2-d]pyrimidin-2-yl)-1H-indazole-4-carboxamide, 1-(4-(benzylamino)-5-methyl-5,6,7,8-tetrahydropyrido[3,2-d]pyrimidin-2-yl)-2-methoxy-1H-benzo[d]imidazole-4-carboxamide, 1-(4-(benzylamino)-5-methyl-5,6,7,8-tetrahydropyrido[3,2-d]pyrimidin-2-yl)-2-methyl-1H-indole-4-carboxamide, 1-(4-(benzylamino)-5-methyl-5,6,7,8-tetrahydropyrido[3,2-d]pyrimidin-2-yl)-6-fluoro-1H-indazole-4-carboxamide, 1-(4-(benzylamino)-5-methyl-5,6,7,8-tetrahydropyrido[3,2-d]pyrimidin-2-yl)-6-fluoro-2-methoxy-1H-benzo[d]imidazole-4-carboxamide, 1-(4-(benzylamino)-5-methyl-5,6,7,8-tetrahydropyrido[3,2-d]pyrimidin-2-yl)-6-fluoro-2-methyl-1H-indole-4-carboxamide, 1-(4-(benzylamino)-5-methyl-6,7-dihydro-5H-pyrrolo[3,2-d]pyrimidin-2-yl)-1H-indazole-4-carboxamide, 1-(4-(benzylamino)-5-methyl-6,7-dihydro-5H-pyrrolo[3,2-d]pyrimidin-2-yl)-2-methoxy-1H-benzo[d]imidazole-4-carboxamide, 1-(4-(benzylamino)-5-methyl-6,7-dihydro-5H-pyrrolo[3,2-d]pyrimidin-2-yl)-2-methyl-1H-indole-4-carboxamide, 1-(4-(benzylamino)-5-methyl-6,7-dihydro-5H-pyrrolo[3,2-d]pyrimidin-2-yl)-6-fluoro-1H-indazole-4-carboxamide, 1-(4-(benzylamino)-5-methyl-6,7-dihydro-5H-pyrrolo[3,2-d]pyrimidin-2-yl)-6-fluoro-2-methoxy-1H-benzo[d]imidazole-4-carboxamide, 1-(4-(benzylamino)-5-methyl-6,7-dihydro-5H-pyrrolo[3,2-d]pyrimidin-2-yl)-6-fluoro-2-methyl-1H-indole-4-carboxamide, 1-(4-(benzylamino)-6,7-dihydro-5H-pyrano[2,3-d]pyrimidin-2-yl)-1H-indazole-4-carboxamide, 1-(4-(benzylamino)-6,7-dihydro-5H-pyrano[2,3-d]pyrimidin-2-yl)-2-(hydroxymethyl)-1H-indole-4-carboxamide,
1-(4-(benzylamino)-6,7-dihydro-5H-pyrano[2,3-d]pyrimidin-2-yl)-2-methoxy-1H-benzo[d]imidazole-4-carboxamide,
1-(4-(benzylamino)-6,7-dihydro-5H-pyrano[2,3-d]pyrimidin-2-yl)-2-methyl-1H-indole-4-carboxamide,
1-(4-(benzylamino)-6,7-dihydro-5H-pyrano[2,3-d]pyrimidin-2-yl)-6-fluoro-1H-indazole-4-carboxamide,
1-(4-(benzylamino)-6,7-dihydro-5H-pyrano[2,3-d]pyrimidin-2-yl)-6-fluoro-2-methoxy-1H-benzo[d]imidazole-4-carboxamide,
1-(4-(benzylamino)-6,7-dihydro-5H-pyrano[2,3-d]pyrimidin-2-yl)-6-fluoro-2-methyl-1H-indole-4-carboxamide,
1-(4-(benzylamino)-6,7-dihydro-5H-pyrrolo[2,3-d]pyrimidin-2-yl)-1H-indazole-4-carboxamide,
1-(4-(benzylamino)-6,7-dihydro-5H-pyrrolo[2,3-d]pyrimidin-2-yl)-2-methoxy-1H-benzo[d]imidazole-4-carboxamide,
1-(4-(benzylamino)-6,7-dihydro-5H-pyrrolo[2,3-d]pyrimidin-2-yl)-2-methyl-1H-indole-4-carboxamide,
1-(4-(benzylamino)-6,7-dihydro-5H-pyrrolo[2,3-d]pyrimidin-2-yl)-6-fluoro-1H-indazole-4-carboxamide,
1-(4-(benzylamino)-6,7-dihydro-5H-pyrrolo[2,3-d]pyrimidin-2-yl)-6-fluoro-2-methoxy-1H-benzo[d]imidazole-4-carboxamide,
1-(4-(benzylamino)-6,7-dihydro-5H-pyrrolo[2,3-d]pyrimidin-2-yl)-6-fluoro-2-methyl-1H-indole-4-carboxamide,
1-(4-(benzylamino)-6,7-dihydro-5H-pyrrolo[3,2-d]pyrimidin-2-yl)-1H-indazole-4-carboxamide,
1-(4-(benzylamino)-6,7-dihydro-5H-pyrrolo[3,2-d]pyrimidin-2-yl)-2-methoxy-1H-benzo[d]imidazole-4-carboxamide,
1-(4-(benzylamino)-6,7-dihydro-5H-pyrrolo[3,2-d]pyrimidin-2-yl)-2-methyl-1H-indole-4-carboxamide,
1-(4-(benzylamino)-6,7-dihydro-5H-pyrrolo[3,2-d]pyrimidin-2-yl)-6-fluoro-1H-indazole-4-carboxamide,
1-(4-(benzylamino)-6,7-dihydro-5H-pyrrolo[3,2-d]pyrimidin-2-yl)-6-fluoro-2methoxy-2methoxy-1H-benzo[d]imidazole-4-carboxamide,
1-(4-(benzylamino)-6,7-dihydro-5H-pyrrolo[3,2-d]pyrimidin-2-yl)-6-fluoro-2-methyl-1H-indole-4-carboxamide,
1-(4-(benzylamino)-7-methyl-6,7-dihydro-5H-pyrrolo[2,3-d]pyrimidin-2-yl)-1H-indazole-4-carboxamide,
1-(4-(benzylamino)-7-dihydro-5H-pyrrolo[2,3-d]pyrimidin-2-yl)-2-methoxy-1H-benzo[d]imidazole-4-carboxamide,
1-(4-(benzylamino)-7-methyl-6,7-dihydro-5H-pyrrolo[2,3-d]pyrimidin-2-yl)-2-methyl-1H-indole-4-carboxamide,
1-(4-(benzylamino)-7-methyl-6,7-dihydro-5H-pyrrolo[2,3-d]pyrimidin-2-yl)-6-fluoro-1H-indazole-4-carboxamide,
1-(4-(benzylamino)-7-methyl-6,7-dihydro-5H-pyrrolo[2,3-d]pyrimidin-2-yl)-6-fluoro-2-methoxy-1H-benzo[d]imidazole-4-carboxamide,
1-(4-(benzylamino)-7-methyl-6,7-dihydro-5H-pyrrolo[2,3-d]pyrimidin-2-yl)-6-fluoro-2-methyl-1H-indole-4-carboxamide,
1-(4-(benzylamino)-8-methyl-5,6,7,8-tetrahydropyrido[2,3-d]pyrimidin-2-yl)-1H-indazole-4-carboxamide,
1-(4-(benzylamino)-8-methyl-5,6,7,8-tetrahydropyrido[2,3-d]pyrimidin-2-yl)-2-methoxy-1H-benzo[d]imidazole-4-carboxamide,
1-(4-(benzylamino)-8-methyl-5,6,7,8-tetrahydropyrido[2,3-d]pyrimidin-2-yl)-2-methyl-1H-indole-4-carboxamide,
1-(4-(benzylamino)-8-methyl-5,6,7,8-tetrahydropyrido[2,3-d]pyrimidin-2-yl)-6-ftuoro-1H-indazole-4-carboxamide,
1-(4-(benzylamino)-8-methyl-5,6,7,8-tetrahydropyrido[2,3-d]pyrimidin-2-yl)-6-fluoro-2-methoxy-1H-benzo[d]imidazole-4-carboxamide,
1-(4-(benzylamino)-8-methyl-5,6,7,8-tetrahydropyrido[2,3-d]pyrimidin-2-yl)-6-fluoro-2-methyl-1H-indole-4-carboxamide,
2-(4-(aminomethyl)-2-methyl-1H-indol-1-yl)-N-benzyl-6,7-dihydro-5H-pyrano[2,3-d]pyrimidin-4-amine,
2-(aminomethyl)-1-(4-(benzylamino)-6,7-dihydro-5H-pyrano[2,3-d]pyrimidin-2-yl)-1H-indole-4-carboxamide,
3-(4-((3-fluorobenzyl)amino)-5,6,7,8-tetrahydropyrido[2,3-d]pyrimidin-2-yl)-2-methyl-1H-indole-7-carboxamide,
3-(4-((3-fluorobenzyl)amino)-5,6,7,8-tetrahydropyrido[3,2-d]pyrimidin-2-yl)-2-methyl-1H-indole-7-carboxamide,
3-(4-((3-fluorobenzyl)amino)-5,6-dihydrofuro[2,3-d]pyrimidin-2-yl)-2-methyl-1H-indole-7-carboxamide,
3-(4-((3-fluorobenzyl)amino)-5-methyl-5,6,7,8-tetrahydropyrido[3,2-d]pyrimidin-2-yl)-2-methyl-1H-indole-7-carboxamide,
3-(4-((3-fluorobenzyl)amino)-5-methyl-6,7-dihydro-5H-pyrrolo[3,2-d]pyrimidin-2-yl)-2-methyl-1H-indole-7-carboxamide,
3-(4-((3-fluorobenzyl)amino)-6,7-dihydro-5H-pyrano[2,3-d]pyrimidin-2-yl)-2-methyl-1H-indole-7-carboxamide,
3-(4-((3-fluorobenzyl)amino)-6,7-dihydro-5H-pyrrolo[2,3-d]pyrimidin-2-yl)-2-methyl-1H-indole-7-carboxamide,
3-(4-((3-fluorobenzyl)amino)-6,7-dihydro-5H-pyrrolo[3,2-d]pyrimidin-2-yl)-2-methyl-1H-indole-7-carboxamide,
3-(4-((3-fluorobenzyl)amino)-7-methyl-6,7-dihydro-5H-pyrrolo[2,3-d]pyrimidin-2-yl)-2-methyl-1H-indole-7-carboxamide,
3-(4-((3-fluorobenzyl)amino)-8-methyl-5,6,7,8-tetrahydropyrido[2,3-d]pyrimidin-2-yl)-2-methyl-1H-indole-7-carboxamide,
3-(4-(benzylamino)-5,6,7,8-tetrahydropyrido[2,3-d]pyrimidin-2-yl)-2-methyl-1H-indole-7-carboxamide,
3-(4-(benzylamino)-5,6,7,8-tetrahydropyrido[3,2-d]pyrimidin-2-yl)-2-methyl-1H-indole-7-carboxamide,
3-(4-(benzylamino)-5-methyl-5,6,7,8-tetrahydropyrido[3,2-d]pyrimidin-2-yl)-2-methyl-1H-indole-7-carboxamide,
3-(4-(benzylamino)-5-methyl-6,7-dihydro-5H-pyrrolo[3,2-d]pyrimidin-2-yl)-2-methyl-1H-indole-7-carboxamide,
3-(4-(benzylamino)-6,7-dihydro-5H-pyrano[2,3-d]pyrimidin-2-yl)-2-methyl-1H-indole-7-carboxamide,
3-(4-(benzylamino)-6,7-dihydro-5H-pyrrolo[2,3-d]pyrimidin-2-yl)-2-methyl-1H-indole-7-carboxamide,
1-(4-(benzylamino)-6,7-dihydro-5H-pyrrolo[3,2-d]pyrimidin-2-yl)-2-methyl-1H-indole-7-carboxamide, 3-(4-(benzylamino)-7-methyl-6,7-dihydro-5H-pyrrolo[2,3-d]pyrimidin-2-yl)-2-methyl-1H-indole-7-carboxamide, 3-(4-(benzylamino)-8-methyl-5,6,7,8-tetrahydropyrido[2,3-d]pyrimidin-2-yl)-2-methyl-1H-indole-7-carboxamide, 1-(4-((3-fluorobenzyl)amino)-6,7-dihydrofuro[3,2-d]pyrimidin-2-yl)-1H-indazole-4-carboxamide, 1-(4-((3-fluorobenzyl)amino)-6,7-dihydrofuro[3,2-d]pyrimidin-2-yl)-2-methoxy-1H-benzo[d]imidazole-4-carboxamide, 1-(4-((3-fluorobenzyl)amino)-6,7-dihydrofuro[3,2-d]pyrimidin-2-yl)-2-methyl-1H-indole-4-carboxamide, 1-(4-((3-fluorobenzyl)amino)-6,7-dihydrofuro[2,3-d]pyrimidin-2-yl)-6-fluoro-1H-indazole-4-carboxamide, 1-(4-((3-fluorobenzyl)amino)-6,7-dihydrofuro[3,2-d]pyrimidin-2-yl)-6-fluoro-2-methoxy-1H-benzo[d]imidazole-4-carboxamide, 1-(4-((3-fluorobenzyl)amino)-6,7-dihydrofuro[3,2-d]pyrimidin-2-yl)-6-fluoro-2-methyl-1H-indole-4-carboxamide, 1-(4-((3-fluorobenzyl)amino)-7,8-dihydro-6H-pyrano[3,2-d]pyrimidin-2-yl)-1H-indazole-4-carboxamide, 1-(4-((3-fluorobenzyl)amino)-7,8-dihydro-6H-pyrano[3,2-d]pyrimidin-2-yl)-2-methoxy-1H-benzo[d]imidazole-4-carboxamide, 1-(4-((3-fluorobenzyl)amino)-7,8-dihydro-6H-pyrano[3,2-d]pyrimidin-2-yl)-2-methyl-1H-indole-4-carboxamide, 1-(4-((3-fluorobenzyl)amino)-7,8-dihydro-6H-pyrano[3,2-d]pyrimidin-2-yl)-6-fluoro-1-indazole-4-carboxamide, 1-(4-((3-fluorobenzyl)amino)-7,8-dihydro-6H-pyrano[3,2-d]pyrimidin-2-yl)-6-fluoro-2-methoxy-1H-benzo[d]imidazole-4-carboxamide, 1-(4-((3-fluorobenzyl)amino)-7,8-dihydro-6H-pyrano[3,2-d]pyrimidin-2-yl)-6-fluoro-2-methyl-1H-indole-4-carboxamide, 1-(4-(benzylamino)-5,6,7,8-tetrahydropyrido[2,3-d]pyrimidin-2-yl)imidazo[1,5-a]pyridine-5-carboxamide, 1-(4-(benzylamino)-5,6,7,8-tetrahydropyrido[3,2-d]pyrimidin-2-yl)imidazo[1,5-a]pyridine-5-carboxamide, 1-(4-(benzylamino)-6,7-dihydro-5H-pyrano[2,3-d]pyrimidin-2-yl)imidazo[1,5-a]pyridine-5-carboxamide, 1-(4-(benzylamino)-6,7-dihydrofuro[3,2-d]pyrimidin-2-yl)-1H-indazole-4-carboxamide, 1-(4-(benzylamino)-6,7-dihydrofuro[3,2-d]pyrimidin-2-yl)-2-methoxy-1H-benzo[d]imidazole-4-carboxamide, 1-(4-(benzylamino)-6,7-dihydrofuro[3,2-d]pyrimidin-2-yl)-2-methyl-1H-indole-4-carboxamide, 1-(4-(benzylamino)-6,7-dihydrofuro[3,2-d]pyrimidin-2-yl)-6-fluoro-1H-indazole-4-carboxamide, 1-(4-(benzylamino)-6,7-dihydrofuro[3,2-d]pyrimidin-2-yl)-6-fluoro-2-methoxy-1H-benzo[d]imidazole-4-carboxamide, 1-(4-(benzylamino)-6,7-dihydrofuro[3,2-d]pyfmidin-2-yl)-6-fluoro-2-methyl-1H-indole-4-carboxamide, 1-(4-(benzylamino)-7,8-dihydro-6H-pyrano[3,2-d]pyrimidin-2-yl)-1H-indazole-4-carboxamide, 1-(4-(benzylamino)-7,8-dihydro-6H-pyrano[3,2-d]pyrimidin-2-yl)-2-methoxy-1H-benzo[d]imidazole-4-carboxamide, 1-(4-(benzylamino)-7,8-dihydro-6H-pyrano[3,2-d]pyrimidin-2-yl)-2-methyl-1H-indole-4-carboxamide, 1-(4-(benzylamino)-7,8-dihydro-6H-pyrano[3,2-d]pyrimidin-2-yl)-6-fluoro-1H-indazole-4-carboxamide, 1-(4-(benzylamino)-7,8-dihydro-6H-pyrano[3,2-d]pyrimidin-2-yl)-6-fluoro-2-methoxy-1H-benzo[d]imidazole-4-carboxamide, 1-(4-(benzylamino)-7,8-dihydro-6H-pyrano[3,2-d]pyrimidin-2-yl)-6-fluoro-2-methyl-1H-indole-4-carboxamide, 1-(4-(benzylamino)-8-methyl-5,6,7,8-tetrahydropyrido[2,3-d]pyrimidin-2-yl)imidazo[1,5-a]pyridine-5-carboxamide, 3-(4-((3-fluorobenzyl)amino)-5,6,7,8-tetrahydropyrido[2,3-d]pyrimidin-2-yl)-2-methylimidazo[1,2-a]pyridine-8-carboxamide, 3-(4-((3-fluorobenzyl)amino)-5,6,7,8-tetrahydropyrido[2,3-d]pyrimidin-2-yl)imidazo[1,5-a]pyridine-8-carboxamide, 3-(4-((3-fluorobenzyl)amino)-5,6,7,8-tetrahydropyrido[2,3-d]pyrimidin-2-yl)-2-methylimidazo[1,2-a]pyridine-8-carboxamide, 3-(4-((3-fluorobenzyl)amino)-5,6 7,8-tetrahydropyrido[3,2-d]pyritnidin-2-yl)imidazo[1,5-a]pyridine-8-carboxamide, 3-(4((3-fluorobenzyl)amino)-5-methyl-5,6,7,8-tetrahydropyrido[3,2-d]pyrimidin-2-yl)-2-methylimidazo[1,2-a]pyridine-8-carboxamide, 3-(4-((3-fluorobenzyl)amino)-5-methyl-5,6,7,8-tetrahydropyrido[3,2-d]pyrimidin-2-yl)imidazo[1,5-a]pyridine-8-carboxamide, 3-(4-((3-fluorobenzyl)amino)-6,7-dihydro-5H-pyrano[2,3-d]pyrimidin-2-yl)-2-methylimidazo[1,2-a]pyridine-8-carboxamide, 3-(4-((3-fluorobenzyl)amino)-6,7-dihydro-5H-pyrano[2,3-d]pyrimidin-2-yl)imidazo[1,5-a]pyridine-8-carboxamide, 3-(4-((3-fluorobenzyl)amino)-6,7-dihydrofuro[3,2-d]pyrimidin-2-yl)-2-methyl-1H-indole-7-carboxamide, 3-(4-((3-fluorobenzyl)amino)-7,8-dihydro-6H-pyrano[3,2-d]pyrimidin-2-yl)-2-methyl-1H-indole-7-carboxamide, 3-(4-((3-fluorobenzyl)amino)-7,8-dihydro-6H-pyrano[3,2-d]pyrimidin-2-yl)-2-methylimidazo[1,2-a]pyridine-8-carboxamide, 3-(4-((3-fluorobenzyl)amino)-7,8-dihydro-6H-pyrano[3,2-d]pyrimidin-2-yl)imidazo[1,5-a]pyridine-8-carboxamide, 3-(4-((3-fluorobenzyl)amino -8-methyl-5,6,7,8-tetrahydropyrido[2,3-d]pyrimidin-2-yl)-2-methylimidazo[1,2-a]pyridine-8-carboxamide, 3-(4-((3-fluorobenzyl)amino)-8-methyl-5,6,7,8-tetrahydropyrido[2,3-d]pyrimidin-2-yl)imidazo[1,5-a]pyridine-8-carboxamide, 3-(4-(benzylamino)-5,6,7,8-tetrahydropyrido[2,3-d]pyrimidin-2-yl)-2-methylimidazo[1,2-a]pyridine-8-carboxamide, 3-(4-(benzylamino)-5,6,7,8-tetrahydropyrido[2,3-d]pyrimidin-2-yl)-2-methylpyrazolo[1,5-a]pyridine-7-carboxamide, 3-(4-(benzylamino)-5,6,7,8-tetrahydropyrido[2,3-d]pyrimidin-2-yl)imidazo[1,5-a]pyridine-8-carboxamide, 3-(4-(benzylamino)-5,6,7,8-tetrahydropyrido[3,2-d]pyrimidin-2-yl)-2-methylimidazo[1,2-a]pyridine-8-carboxamide, 3-(4-(benzylamino)-5,6,7,8-tetrahydropyrido[3,2-d]pyrimidin-2-yl)-2-methylpyrazolo[1,5-a]pyridine-7-carboxamide, 3-(4-(benzylamino)-5,6,7,8-tetrahydropyrido[3,2-d]pyrimidin-2-yl)imidazo[1,5-a]pyridine-8-carboxamide, 3-(4-(benzylamino)-5-methyl-5,6,7,8-tetrahydropyrido[3,2-d]pyrimidin-2-yl)-2-methylimidazo[1,2-a]pyridine-8-carboxamide,
3-(4-(benzylamino)-5-methyl-5,6,7,8-tetrahydropyrido[3,2-d]pyrimidin-2-yl)-2-methylpyrazolo[1,5-a]pyridine-7-carboxamide,
3-(4-(benzylamino)-5-methyl-5,6,7,8-tetrahydropyrido[3,2-d]pyrimidin-2-yl)imidazo[1,5-a]pyridine-8-carboxamide,
3-(4-(benzylamino)-7,8-dihydro-6H-pyrano[3,2-d]pyrimidin-2-yl)-2-methyl-1H-indole-7-carboxamide,
3-(4-(benzylamino)-7,8-dihydro-6H-pyrano[3,2-d]pyrimidin-2-yl)-2-methylimidazo[1,2-a]pyridine-8-carboxamide,
3-(4-(benzylamino)-7,8-dihydro-6H-pyrano[3,2-d]pyrimidin-2-yl)imidazo[1,5-a]pyridine-8-carboxamide,
3-(4-(benzylamino)-8-methyl-5,6,7,8-tetrahydropyrido[2,3-d]pyrimidin-2-yl)-2-methylimidazo[1,2-a]pyridine-8-carboxamide,
3-(4-(benzylamino)-8-methyl-5,6,7,8-tetrahydropyrido[2,3-d]pyrimidin-2-yl)-2-methylpyrazolo[1,5-a]pyridine-7-carboxamide,
3-(4-(benzylamino)-8-methyl-5,6,7,8-tetrahydropyrido[2,3-d]pyrimidin-2-yl)imidazo[1,5-a]pyridine-8-carboxamide,
1-(4-(benzylamino)-5,6-dihydrofuro[2,3-d]pyrimidin-2-yl)imidazo[1,5-a]pyridine-5-carboxamide,
1-(4-(benzylamino)-5,6-dihydrofuro[2,3-d]pyrimidin-2-yl)isobenzofuran-4-carboxamide,
1-(4-(benzylamino)-5-methyl-5,6,7,8-tetrahydropyrido[3,2-d]pyrimidin-2-yl)isobenzofuran-4-carboxamide,
1-(4-(benzylamino)-5-methyl-6,7-dihydro-5H-pyrrolo[3,2-d]pyrimidin-2-yl)imidazo[1,5-a]pyridine-5-carboxamide,
1-(4-(benzylamino)-5-methyl-6,7-dihydro-5H-pyrrolo[3,2-d]pyrimidin-2-yl)isobenzofuran-4-carboxamide,
1-(4-(benzylamino)-6,7-dihydro-5H-pyrano[2,3-d]pyrimidin-2-yl)isobenzofuran-4-carboxamide,
1-(4-(benzylamino)-6,7-dihydro-5H-pyrrolo[2,3-d]pyrimidin-2-yl)imidazo[1,5-a]pyridine-5-carboxamide,
1-(4-(benzylamino)-6,7-dihydro-5H-pyrrolo[2,3-d]pyrimidin-2-yl)isobenzofuran-4-carboxamide,
1-(4-(benzylamino)-6,7-dihydro-5H-pyrrolo[3,2-d]pyrimidin-2-yl)imidazo[1,5-a]pyridine-5-carboxamide,
1-(4-(benzylamino)-6,7-dihydro-5H-pyrrolo[3,2-d]pyrimidin-2-yl)isobenzofuran-4-carboxamide,
1-(4-(benzylamino)-6,7-dihydrofuro[3,2-d]pyrimidin-2-yl)imidazo[1,5-a]pyridine-5-carboxamide,
1-(4-(benzylamino)-6,7-dihydrofuro[3,2-d]pyrimidin-2-yl)isobenzofuran-4-carboxamide,
1-(4-(benzylamino)-7,8-dihydro-6H-pyrano[3,2-d]pyrimidin-2-yl)imidazo[1,5-a]pyridine-5-carboxamide,
1-(4-(benzylamino)-7,8-dillydro-6H-pyrano[3,2-d]pyrimidin-2-yl)isobenzofuran-4-carboxamide,
1-(4-(benzylamino)-7-methyl-6,7-dihydro-5H-pyrrollo[2,3-d]pyrimidin-2-yl)imidazo[1,5-a]pyridine-5-carboxamide,
1-(4-(benzylamino)-7-methyl-6 7-dihydro-5H-pyrrolo[2,3-d]pyrimidin-2-yl)isobenzofuran-4-carboxamide,
3-(4-((3-fluorobenzyl)amino)-5,6-dihydrofuro[2,3-d]pyrimidin-2-yl)-2-methylimidazo[1,2-a]pyridine-8-carboxamide,
3-(4-((3-fluorobenzyl)amino)-5,6-dihydrofuro[2,3-d]pyrimidin-2-yl)imidazo[1,5-a]pyridine-8-carboxamide,
3-(4-((3-fluorobenzyl)amino)-5-methyl-6,7-dihydro-5H-pyrrolo[3,2-d]pyrimidin-2-yl)-2-methylimidazo[1,2-a]pyridine-8-carboxamide,
3-(4-((3-fluorobenzyl)amino)-5-methyl-6,7-dihydro-5H-pyrrolo[3,2-d]pyrimidin-2-yl)imidazo[1,5-a]pyridine-8-carboxamide,
3-(4-((3-fluorobenzyl)amino)-6,7-dihydro-5H-pyrrolo[2,3-d]pyrimidin-2-yl)-2-methylimidazo[1,2-a]pyridine-8-carboxamide,
3-(4-((3-fluorobenzyl)amino)-6,7-dihydro-5H-pyrrolo[2,3-d]pyrimidin-2-yl)imidazo[1,5-a]pyridine-8-carboxamide,
3-(4-((3-fiuorobenzyl)amino)-6,7-dihydro-5H-pyrrolo[3,2-d]pyrimidin-2-yl)-2-methylimidazo[1,2-a]pyridine-8-carboxamide,
3-(4-((3-fluorobenzyl)amino)-6,7-dihydro-5H-pyrrolo[3,2-d]pyrimidin-2-yl)imidazo[1,5-a]pyridine-8-carboxamide,
3-(4-((3-fluorobenzyl)amino)-6,7-dihydrofuro[3,2-d]pyrimidin-2-yl)-2-methylimidazo[1,2-a]pyridine-8-carboxamide,
3-(4-((3-fluorobenzyl)amino)-6,7-dihydrofuro[3,2-d]pyrimidin-2-yl)imidazo[1,5-a]pyridine-8-carboxamide,
3-(4-((3-fluorobenzyl)amino)-7-methyl-6,7-dihydro-5H-pyrrolo[2,3-d]pyrimidin-2-yl)-2-methylimidazo[1,2-a]pyridine-8-carboxamide,
3-(4-((3-fluorobenzyl)amino)-7-methyl-6,7-dihydro-5H-pyrrolo[2,3-d]pyrimidin-2-yl)imidazo[1,5-a]pyridine-8-carboxamide,
3-(4-(benzylamino)-5,6,7,8-tetrahydropyrido[2,3-d]pyrimidin-2-yl)-1H-indazole-7-carboxamide,
3-(4-(benzylamino)-5,6,7,8-tetrahydropyrido[3,2-d]pyrimidin-2-yl)-1H-indazole-7-carboxamide,
3-(4-(benzylamino)-5,6-dihydrofuro[2,3-d]pyrimidin-2-yl)-2-methylbenzofuran-7-carboxamide,
3-(4-(benzylamino)-5,6-dihydrofuro[2,3-d]pyrimidin-2-yl)-2-methylimidazo[1,2-a]pyridine-8-carboxamide,
3-(4-(benzylamino)-5,6-dihydrofuro[2,3-d]pyrimidin-2-yl)imidazo[1,5-a]pyridine-8-carboxamide,
3-(4-(benzylamino)-5-methyl-6,7-dihydro-5H-pyrrolo[3,2-d]pyrimidin-2-yl)imidazo[1,5-a]pyridine-8-carboxamide,
3-(4-(benzylamino)-6,7-dihydro-5H-pyrano[2,3-d]pyrimidin-2-yl)-2-methylbenzofuran-7-carboxamide,
3-(4-(benzylamino)-6,7-dihydro-5H-pyrrolo[2,3-d]pyrimidin-2-yl)-2-methylbenzo[b]thiophene-7-carboxamide,
3-(4-(benzylamino)-6,7-dihydro-5H-pyrrolo[2,3-d]pyrimidin-2-yl)-2-methylbenzofuran-7-carboxamide,
3-(4-(benzylamino)-6,7-dihydro-5H-pyrrolo[2,3-d]pyrimidin-2-yl)-2-methylimidazo-[1,2-a]pyridine-8-carboxamide,
3-(4-(benzylamino)-6,7-dihydro-5H-pyrrolo[2,3-d]pyrimidin-2-yl)imidazo[1,5-a]pyridine-8-carboxamide,
3-(4-(benzylamino)-6,7-dihydro-5H-pyrrolo[3,2-d]pyrimidin-2-yl)-2-methylbenzofuran-7-carboxamide,
3-(4-(benzylamino)-6,7-dihydro-5H-pyrrolo[-d]pyrimidin-2-yl)-2-methylimidazo[1,2-a]pyridine-8-carboxamide,
3-(4-(benzylamino)-6,7-dihydro-5H-pyrrolo[3,2-d]pyrimidin-2-yl)imidazo[1,5-a]pyridine-8-carboxamide,
3-(4-(benzylamino)-6,7-dihydrofuro[3,2-d]pyrimidin-2-yl)-2-methylbenzofuran-7-carboxamide, or
3-(4-(benzylamino)-6,7-dihydrofuro[3,2-d]pyrimidin-2-yl)-2-methylimidazo[1,2-a]pyridine-8-carboxamide.

17. The compound of claim 16 having the name:
1-(4-((3-fluorobenzyl)amino)-5,6,7,8-tetrahydropyrido[2,3-d]pyrimidin-2-yl)-2-methyl-1H-indole-4-carboxamide, 1-(4-((benzyl)amino)-5,6,7 8-tetrahydropyrido[2,3-d]pyrimidin-2-yl)-2-methyl-1H-indole-4-carboxamide,
1-(4-((3-fluorobenzyl)amino)-5,6,7,8-tetrahydropyrido[2,3-d]pyrimidin-2-yl)-2-methoxy-1H-indole-4-carboxamide,
1-(4-((benzyl)amino)-5,6,7,8-tetrahydropyrido[2,3-d]pyrimidin-2-yl)-2-methoxy-1H-indole-4-carboxamide,
1-(4(3-fluorobenzyl)amino)-5,6,7,8-tetrahydropyrido[3,2-d]pyrimidin-2-yl)-2-methyl-1H-indole-4-carboxamide,
1-(4-((benzyl)amino)-5,6,7,8-tetrahydropyrido[3,2-d]pyrimidin-2-yl)-2-methyl-1H-indole-4-carboxamide,
1-(4-((3-fluorobenzyl)amino)-5,6,7,8-tetrahydropyrido[3,2-d]pyrimidin-2-yl)-2-methoxy-1H-indole-4-carboxamide,
1-(4-((benzyl)amino)-5,6,7,8-tetrahydropyrido[3,2-d]pyrimidin-2-yl)-2-methoxy-1H-indole-4-carboxamide,
1-(4-(benzylamino)-7,8-dihydro-6H-pyrano[3,2-d]pydmidin-2-yl)-2-methyl-1H-indole-4-carboxamide,
1-(4-(benzylamino)-7,8-dihydro-6H-pyrano[3,2-d]pyrimidin-2-yl)-2-methoxy-1H-indole-4-carboxamide,
1-(4-((3florobenzylamino)-7,8-dihydro-6H-pyrano[3,2-d]pyrimidin-2-yl)-2-methyl-1H-indole-4-carboxamide,
1-4-(3-fluorobenzylamino)-7,8-dihydro-6H-pyrano[3,2-d]pyrimidin-2-yl)-2-methoxy-1H-indole-4-carboxamide,
1-(4-(benzylamino)-7,8-dihydro-6H-pyrano[2,3-d]pyrimidin-2-yl)-2-methyl-1H-indole-4-carboxamide,
1-(4-(benzylamino)-7,8-dihydro-6H-pyrano[2,3-d]pyrimidin-2-yl)-2-methoxy-1H-indole-4-carboxamide,
1-(4-(3-fluorobenzylamino)-7,8-dihydro-6H-pyrano[2,3-d]pyrimidin-2-yl)-2-methyl-1H-indole-4-carboxamide, or
1-(4-(3-fluorobenzylamino)-7,8-dihydro-6H-pyrano[2,3-d]pyrimidin-2-yl)-2-methoxy-1H-indole-4-carboxamide.

18. The compound of claim 17 having the name 1-(4-((benzyl)amino)-5,6,7,8-tetrahydropyrido[2,3-d]pyrimidin-2-yl)-2-methyl-1H-indole-4-carboxamide or 1-(4-(benzylamino)-7,8-dihydro-6H-pyrano[2,3-d]pyrimidin-2-yl)-2-methyl-1H-indole-4-carboxamide.

19. The compound of claim 18 having the name 1-(4-((benzyl)amino)-5,6,7,8-tetrahydropyrido[2,3-d]pyrimidin-2-yl)-2-methyl-1H-indole-4-carboxamide.

20. A pharmaceutical composition comprising the compound of claim 1 and a pharmaceutically acceptable carrier.

\* \* \* \* \*